United States Patent
Cerf et al.

(10) Patent No.: US 10,655,143 B2
(45) Date of Patent: May 19, 2020

(54) INSECTICIDAL PROTEINS AND METHODS FOR THEIR USE

(71) Applicant: PIONEER HI-BRED INTERNATIONAL, INC., Johnston, IA (US)

(72) Inventors: David C. Cerf, Palo Alto, CA (US); James J. English, San Ramon, CA (US); Carol A. Hendrick, Des Moines, IA (US); Lu Liu, Palo Alto, CA (US); Jarred K. Oral, Fremont, CA (US); Phillip A. Patten, Portola Valley, CA (US); Barbara A. Rosen, Mountain View, CA (US); Ute Schellenberger, Palo Alto, CA (US); Ingrid Udranszky, Mountain View, CA (US); Jun-Zhi Wei, Palo Alto, CA (US); Genhai Zhu, San Jose, CA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 307 days.

(21) Appl. No.: 15/602,900

(22) Filed: May 23, 2017

(65) Prior Publication Data
US 2017/0327546 A1 Nov. 16, 2017

Related U.S. Application Data

(62) Division of application No. 13/792,861, filed on Mar. 11, 2013, now Pat. No. 9,688,730.

(60) Provisional application No. 61/667,039, filed on Jul. 2, 2012.

(51) Int. Cl.
*C12N 15/82* (2006.01)
*C07K 14/21* (2006.01)

(52) U.S. Cl.
CPC .......... *C12N 15/8286* (2013.01); *C07K 14/21* (2013.01); *C07K 2319/24* (2013.01)

(58) Field of Classification Search
CPC ................................................. C12N 15/8286
See application file for complete search history.

(56) References Cited

U.S. PATENT DOCUMENTS

| 5,965,428 A | 10/1999 | Gilmer et al. |
| 6,172,184 B1 | 1/2001 | Collmer et al. |
| 2006/0168683 A1 | 7/2006 | Hey et al. |
| 2009/0068159 A1 | 3/2009 | Baum et al. |
| 2012/0311745 A1 | 12/2012 | Meade et al. |

FOREIGN PATENT DOCUMENTS

WO WO2011084622 A1 7/2011

OTHER PUBLICATIONS

Opota et al PLoS Pathogens vol. 7, Issue 9, publication e1002259, 13 pages (Year: 2011).*
Li et al Plant Cell, Tissue and Organ Culture vol. 89, pp. 159-168 (Year: 2007).*
Goral, et al.; "Gaupsin, an Insecticidal and Fungicidal Preparation from Strains of Pseudomonas aureofaciens", Applied Biochemistry and Microbiology, vol. 35, No. 5, pp. 530-532 (1999).
Li, et al; "Agrobacterium-mediated genetic transformation of Elymus breviaristatus with Pseudomonas pseudoalcaligenes insecticidal protein gene", Plant Cell Tiss Organ Cult, vol. 89, pp. 159-168 (2007).
Pechy-Tarr, et al. ; "Molecular analysis of a novel gene cluster encoding an insect toxin in plant-associated stains of Pseudomonas flueorescens", Environmental Microbiology, vol. 10, pp. 2368-2386 (2008).
Peix, et al ,"Reclassification of Pseudomonas aurantiaca as a synonym of Pseudomonas chlororaphis and proposal of three subspecies, P. chlororaphis subsp. chlororaphis subsp. nov., P. chlororaphis subsp. aureofaciens subsp. nov., comb. nov. and P. chlororaphis subsp. aurantiaca subsp. nov., comb. nov." International Journal of Systematic and Evolutionary Microbiology, vol. 57, pp. 1286-1290 (2007).
Sezen, et al, "Study of the bacterial flora as a biological control agent of Agelastica alni L. (Coleoptera: Chrysomelidae)" Biologia Bratislava, vol . 59, pp. 327-331 (2004).
Vodovar, et al, "Complete genome sequence of the entomopathogenic and metabolically versatile soil bacterium Pseudomnas entomophila", Nature Biotechnology, vol. 24, No. 6, pp. 673-679 (2006).
Opota, et al , "Monalysin, a Novel B-Pore-Forming Toxin from the Drosophila Pathogen Pseudomonas entomphila, Contributes to Host Intestinal Damage and Lethality", PLoS Pathogens, vol. 7 (9), pp. 1-13 (2011).
GenBank Accession No. ABQ77224.1, (2013).
GenBank Accession No. ABQ77225.1, (2013).
GenBank Accession No. ABQ77225.1, (2013) Duplicate of reference No. 9.
International Search Report for International Application No. PCT/US2013/047760, (2014)_.
Written Opinion for International Application No. PCT/US2013/047760, (2014).

(Continued)

*Primary Examiner* — David H Kruse

(57) ABSTRACT

Compositions and methods for controlling pests are provided. The methods involve transforming organisms with a nucleic acid sequence encoding an insecticidal protein. In particular, the nucleic acid sequences are useful for preparing plants and microorganisms that possess insecticidal activity. Thus, transformed bacteria, plants, plant cells, plant tissues and seeds are provided. Compositions are insecticidal nucleic acids and proteins of bacterial species. The sequences find use in the construction of expression vectors for subsequent transformation into organisms of interest, as probes for the isolation of other homologous (or partially homologous) genes. The insecticidal proteins find use in controlling, inhibiting growth or killing lepidopteran, coleopteran, dipteran, fungal, hemipteran, and nematode pest populations and for producing compositions with insecticidal activity.

11 Claims, 7 Drawing Sheets

Specification includes a Sequence Listing.

(56) References Cited

OTHER PUBLICATIONS

Moura, Novel Insights Into the Digestive Vacuole Biology of the Malarial Parasite Plasmodium Falciparum, Dissertation, Albert Einstein College of Medicine (2008).
Guo et al, Proc. Natl. Acad. Sci. USA vol. 101: 9205-9210 (2004).
Ngo et al. in the Protein Folding Problem and Tertiary Structure Prediction, Merz et al. (ed.) Birkhauser, Boston, MA, pp. 491-495 (1994).
Szczesny et al PLoS One 6(6): e20349 (2011).
Feris et al GenBank accession NZ_ATLP01000030 (2010).
Ness et al, Nature Biotechnology (2002) 20:1251-1255.
Opota et al, PLoS Pathogens (2011) 7(9): 1-13.
Rose et al Nucleic Acids Research (1998) 26:1628-1635.
Opota et al, PLoS Pathogens (2011) 7(9): 1-13 figure S1.
Selvapandiyan et al, Applied and Environmental Microbiology, (2001) 67: 5855-5858.

\* cited by examiner

Fig. 1

```
                            1                                                  50
       PIP-1A       (1)   MPIKEELSQPQSHSIELDDLKSEQGSLRAALTSNFAGNFDQFPTKRGGFA
    PSEEN3174       (1)   MTIKEELGQPQSHSIELDEVSKEAASTRAALTSNLSGRFDQYPTKKGDFA
       PIP-1B       (1)   MTIKEELNQPQSHSIELDDLNSEQGNARAILTSNFAGSFDQFPTKRGGYA
  AECFG-592740      (1)   ------------------MSYNRQCQERAVNIIDSKVEQISYMPEKHGSYE
     Pput_1063      (1)   ------------------------------MTGFERLSPDAFPVLNGSYL
     Pput_1064      (1)   ---------------------------MRSYSMSDLMNEISRYPLKRGSFE BBBBBBBBBBBBBBBBB       BBBBBBBBBBB
                           51                                                 100
       PIP-1A      (51)   IDSYLLDYSAPK--QGCWVDGITVYGDIFIGKQNWGTYTRPVFAYLQYMD
    PSEEN3174      (51)   IDGYLLDYSSPK--QGCWVDGITVYGDIYIGKQNWGTYTRPVFAYLQYVE
       PIP-1B      (51)   IDSYLLDYSAPK--QGCWVDGITVYGDIFIGKQNWGTYTRPVFAYLQYMD
  AECFG-592740     (34)   IDNYLLGETGKSLNPGCWVRGGTIYGDNWIWNQNWGTISVPVFAYLEHVQ
     Pput_1063     (21)   IERYLLSTDEFH--PGCWIEGETVYGGFGFPSGKKKVLTRPVFAYFDYVG
     Pput_1064     (25)   IEQYLIGDQLH---AGCWVDADTTYGDVRCGNYDWATYTRPVFAYLQHVA BBB
                          101                                                 150
       PIP-1A      (99)   TISIPQQVTQTRSYQLTKGHTKTFTTNVSAKYSVGGSIDIVNVGSDISIG
    PSEEN3174      (99)   TISIPQNVTTTLSYQLTKGHTRSFETSVNAKYSVGANIDIVNVGSEISTG
       PIP-1B      (99)   TISIPQQVTQTRSYQLTKGHTKTFTTSVTAKYSVGGSIGIVNVGSDISVG
  AECFG-592740     (84)   TVRIPNATKYTHAVEVTEGFSSSVTQRSEVELSVGGGFVALGAG-GVKLS
     Pput_1063     (69)   TYKTLSAGDCEIDLSRASGHEVWFAHDAEG-FSAPSGIGLVSVKSDLLSG
     Pput_1064     (72)   TIRSNVQTEHEREVVYCEGFSKSFSQGVEFKVGFSADFGPANANAELTAM BBBBBBBBBBB        BBBBBBBBBBBB
                          151                                                 200
       PIP-1A     (149)   FSNSESWSTTQTFSNSTQLTGPGTFIVYQVVMVYAHNATSAGRQNGNAFA
    PSEEN3174     (149)   FTRSESWSTTQSFTDTTEMKGPGTFVTYQVVLVYAHNATSAGRQNANAFA
       PIP-1B     (149)   FSSSESWSTTQTFSESTQLAGPGTFIVYQVVLVYAHNATSAGRQNGNAFA
  AECFG-592740    (133)   SSYTEGVHGSNKRMETFEIQGPGIYNFYQMHMVFAHKATSAG-HLNELFQ
     Pput_1063    (118)   CS-REEWRPLSSVGHTVRVAGAECYVAYQLKLVYAHWVKQQDAQCSELFK
     Pput_1064    (122)   FSVSETVSGSESTKRSLRVKGDGTIMVYQHMVYAHHMTSAG-VLAGYVP BBB
                          201                                                 250
       PIP-1A     (199)   YNKTNTVG-------SRLDLYYLSAITQNSTVIVDSSKAIAPLDWDTVQRN
    PSEEN3174     (199)   YSKTQAVG-------SRVDLYYLSAITQRKRVIVPSSNAVTPLDWDTVQRN
       PIP-1B     (199)   YNKTQTVG-------SRLDLYYLSAITQNSTVIVESSKAIAPLDWDTVQRN
  AECFG-592740    (182)   YSQVATNES------GREDLCPLTSIATDTVVPVAADSSITPLGWHEIQRA
     Pput_1063    (167)   VQPVRVQG-------DNKGVFPLSSVATDLMWVGHGSDNTKAPISRQALYH
     Pput_1064    (171)   YTKSSDIFNDDGRLVRQDITMLSSVVCDQLVPVRNEKSIKPLTWSQVNQA BBBBBBBB      BBBBBBBB
                          251                       279
       PIP-1A     (243)   VLMENYNPGSNSGHFSFDWSAYNDPHRRY
    PSEEN3174     (243)   VLMENYNPGSNSGHFSFDWSAYNDPHRRY
       PIP-1B     (243)   VLMENYNPSSNSGHFSFDWSAYNDPHRRY
  AECFG-592740    (227)   VLMDNYKASDNSGHWLFHSSAYHRPGSRY
     Pput_1063    (211)   LIFNLAYGAAGDAGWSFNDQAASNRFLQY
     Pput_1064    (221)   VLFNQFEKAPGARRWTFDFSVY-------
```

Fig. 3A

```
                                                                            60
AAACCCAAAG ATGTTTGAAC TGAAGAGTTT GATCATGGCT CAGATTGAAC GCTGGCGGCA
                                            GCT CAGATTGAAC GCTGGCGGCA

120
GGCCTAACAC ATGCAAGTCG AGCGGTAGAG AGAAGCTTGC TTCTCTTGAG AGCGGCGGAC
GGCCTAACAC ATGCAAGTCG AGCGGATGAC GGGAGCTTGC TCCTTGATTC AGCGGCGGAC

180
GGGTGAGTAA TGCCTAGGAA TCTGCCTGGT AGTGGGGGAT AACGTCCGGA AACGGACGCT
GGGTGAGTAA TGCCTAGGAA TCTGCCTGGT AGTGGGGGAC AACGTTTCGA AAGGAACGCT

240
AATACCGCAT ACGTCCTACG GGAGAAAGCA GGGGACCTTC GGGCCTTGCG CTATCAGATG
AATACCGCAT ACGTCCTACG GGAGAAAGCA GGGGACCTTC GGGCCTTGCG CTATCARATG

300
AGCCTAGGTC GGATTAGCTA GTTGGTGAGG TAATGGCTCA CCAAGGCGAC GATCCGTAAC
AGCCTAGGTC GGATTAGCTA GTTGGKGGGG TAATGGCTCA CCAAGGCGAC GATCCGTAAC

360
TGGTCTGAGA GGATGATCAG TCACACTGGA ACTGAGACAC GGTCCAGACT CCTACGGGAG
TGGTYTGAGA GGATGATCAG TCACACTGGA ACTGAGACAC GGTCCAGACT CCTACGGGAG

420
GCAGCAGTGG GGAATATTGG ACAATGGGCG AAAGCCTGAT CCAGCCATGC CGCGTGTGTG
GCAGCAGTGG GGAATATTGG ACAATGGGCG AAAGCCTGAT CCAGCCATGC CGCGTGTGTG

480
AAGAAGGTCT TCGGATTGTA AAGCACTTTA AGTTGGGAGG AAGGGTACTT ACCTAATACG
AARAAGGTCT TCGGATTGTA AAGCACTTTA AGTTGGGAGG AAGGGCAGTA AGTTAATACC

540
TGAGTATTTT GACGTTACCG ACAGAATAAG CACCGGCTAA CTCTGTGCCA GCAGCCGCGG
TTGCTGTTTT GACGTTACCG ACAGAATAAG CACCGGCTAA CTCTGTGCCA GCAGCCGCGG

600
TAATACAGAG GGTGCAAGCG TTAATCGGAA TTACTGGGCG TAAAGCGCGC GTAGGTGGTT
TAATACAGAG GGTGCAAGCG TTAATCGGAA TTACTGGGCG TAAAGCGCGC GTAGGTGGTT
```

Fig. 3B

```
                                                                              660
CGTTAAGTTG GATGTGAAAT CCCCGGGCTC AACCTGGGAA CTGCATCCAA AACTGGCGAG
CGTTAAGTTG GATGTGAAAG CCCCGGGCTC AACCTGGGAA CTGCATCCAA AACTGGCGAG

720
CTAGAGTATG GTAGAGGGTG GTGGAATTTC CTGTGTAGCG GTGAAATGCG TAGATATAGG
CTAGAGTATG GTAGAGGGTG GTGGAATTTC CTGTGTAGCG GTGAAATGCG TAGATATAGG

780
AAGGAACACC AGTGGCGAAG GCGACCACCT GGACTGATAC TGACACTGAG GTGCGAAAGC
AAGGAACACC AGTGGCGAAG GCGACCACCT GGACTGATAC TGACACTGAG GTGCGAAAGC

840
GTGGGGAGCA AACAGGATTA GATACCCTGG TAGTCCACGC CGTAAACGAT GTCAACTAGC
GTGGGGAGCA AACAGGATTA GATACCCTGG TAGTCCACGC CGTAAACGAT GTCAACTAGC

900
CGTTGGGAGC CTTGAGCTCT TAGTGGCGCA GCTAACGCAT TAAGTTGACC GCCTGGGGAG
CGTTGGAATC CTTGAGATTT TAGTGGCGCA GCTAACGCAT TAAGTTGACC GCCTGGGGAG

960
TACGGCCGCA AGGTTAAAAC TCAAATGAAT TGACGGGGGC CGCACAAGC GGTGGAGCAT
TACGGCCGCA AGGTTAAAAC TCAAATGAAT TGACGGGGGC CGCACAAGC GGTGGAGCAT

1020
GTGGTTTAAT TCGAAGCAAC GCGAAGAACC TTACCAGGCC TTGACATCCA ATGAACTTTC
GTGGTTTAAT TCGAAGCAAC GCGAAGAACC TTACCAGGCC TTGACATGCA GAGAACTTTC

1080
CAGAGATGGA TTGGTGCCTT CGGGAACATT GAGACAGGTG CTGCATGGCT GTCGTCAGCT
CAGAGATGGA TTGGTGCCTT CGGGAACTCT GACACAGGTG CTGCATGGCT GTCGTCAGCT

1140
CGTGTCGTGA GATGTTGGGT TAAGTCCCGT AACGAGCGCA ACCCTTGTCC TTAGTTACCA
CGTGTCGTGA GATGTTGGGT TAAGTCCCGT AACGAGCGCA ACCCTTGTCC TTAGTTACCA

1200
GCACGTTATG GTGGGCACTC TAAGGAGACT GCCGGTGACA AACCGGAGGA AGGTGGGGAT
GCACGTTATG GTGGGCACTC TAAGGAGACT GCCGGTGACA AACCGGAGGA AGGTGGGGAT
```

Fig. 3C

```
                                                                    1260
GACGTCAAGT CATCATGGCC CTTACGGCCT GGGCTACACA CGTGCTACAA TGGTCGGTAC
GACGTCAAGT CATCATGGCC CTTACGGCCT GGGCTACACA CGTGCTACAA TGGTCGGTAC

1320
AGAGGGTTGC CAAGCCGCGA GGTGGAGCTA ATCCCATAAA ACCGATCGTA GTCCGGATCG
AGAGGGTTGC CAAGCCGCGA GGTGGAGCTA ATCTCACAAA ACCGATCGTA GTCCGGATCG

1380
CAGTCTGCAA CTCGACTGCG TGAAGTCGGA ATCGCTAGTA ATCGCGAATC AGAATGTCGC
CAGTCTGCAA CTCGACTGCG TGAAGTCGGA ATCGCTAGTA ATCGCAAATC AGAATGTTGC

1440
GGTGAATACG TTCCCGGGCC TTGTACACAC CGCCCGTCAC ACCATGGGAG TGGGTTGCAC
GGTGAATACG TTCCCGGGCC TTGTACACAC CGCCCGTCAC ACCATGGGAG TGGGTTGCAC

1500
CAGAAGTAGC TAGTCTAACC TTCGGGAGGA CGGTTACCAC GGTGTGATTC ATGACTGGGG
CAGAAGTAGC TAGTCTAACC TTCGGGGGGA CGGTTACCAC GGTGTGATTC ATGACTGGGG

1560
TGAAGTCGTA ACAAGGTAGC CGTAGGGGAA CCTGCGGCTG GATCACCTCC TTAATCGACG
TGAAGTCGTA ACAAGGTAGC CGTAGGGGAA CCTGCGGCTG GATCACCTCC TT

1620
ACATCAGCTG CTTCATAAGC TCCCACACGA ATTGCTTGAT TCATTGAAGA AGACGATTGG

1680
GTCTGTAGCT CAGTTGGTTA GAGCGCACCC CTGATAAGGG TGAGGTCGGC AGTTCGAATC

1700
TGCCCAGACC CACCAATTAC   SEQ ID NO: 216  P. chlororaphis SS44C4 16S-rDNA
                        SEQ ID NO: 217  P. entomophila-L48 16S-rDNA
```

Fig. 4

Plate 1

|   | 1 | 2 | 3 | 4 | 5 | 6 | 7 | 8 | 9 | 10 | 11 | 12 |
|---|---|---|---|---|---|---|---|---|---|----|----|----|
| A | 0 | 0 |   | 0 | 0 | 2 | 4 | 0 | 3 | 0  |    | 0  |
| B | 0 | 2 | 0 | 0 | 2 | 0 | 0 | 0 |   | 0  | 2  | 0  |
| C | 0 | 0 | 0 | 0 | 0 | 0 | 0 | 0 | 0 |    | 0  | 0  |
| D | 0 | 0 | 0 | 2 | 0 | 0 | 0 | 0 | 0 | 0  | 0  | 0  |
| E | 0 | 0 | 6 | 0 | 0 | 0 | 0 | 0 | 1 | 2  | 0  | 0  |
| F | 0 | 2 | 2 | 0 | 6 | 0 | 0 | 0 | 2 | 0  | 2  | 0  |
| G | 0 | 0 | 3 | 0 | 0 | 0 | 0 | 0 | 0 | 0  | 0  | 0  |
| H | 0 | 0 | 2 | 0 | 0 | 0 | 0 | 2 | 0 | 0  | 4  | 0  |

Plate 2

|   | 1 | 2 | 3 | 4 | 5 | 6 | 7 | 8 | 9 | 10 | 11 | 12 |
|---|---|---|---|---|---|---|---|---|---|----|----|----|
| A | 3 |   | 2 | 1 | 1 | 1 | 1 | 0 | 0 | 0  | 0  | 2  |
| B | 0 | 0 | 0 | 1 | 2 | 0 | 1 | 0 | 4 | 1  | 1  | 1  |
| C | 2 | 1 | 1 | 3 | 2 | 1 | 5 | 0 | 0 | 1  | 0  | 3  |
| D | 1 | 0 | 0 | 5 | 2 | 3 | 0 | 3 | 2 | 2  | 0  | 0  |
| E |   | 0 | 0 | 0 | 0 | 0 | 0 | 2 | 3 | 0  | 0  |    |
| F | 0 | 0 | 1 |   | 4 | 0 | 0 |   | 3 | 0  | 0  | 0  |
| G |   | 1 | 2 | 2 |   |   | 1 | 0 | 0 | 2  | 1  | 0  |
| H | 0 | 0 | 0 | 3 | 1 | 1 | 2 | 3 | 1 | 2  | 1  | 6  |

Plate 3

|   | 1 | 2 | 3 | 4 | 5 | 6 | 7 | 8 | 9 | 10 | 11 | 12 |
|---|---|---|---|---|---|---|---|---|---|----|----|----|
| A | 0 | 5 | 0 | 1 | 1 | 0 | 0 | 0 | 1 |    | 0  | 1  |
| B | 1 | 1 |   | 3 | 0 | 3 | 0 | 3 | 2 | 3  | 3  | 2  |
| C | 0 | 1 | 0 | 0 | 2 | 2 |   | 1 | 0 | 0  | 1  | 0  |
| D | 2 | 0 | 1 | 0 | 0 | 2 | 0 | 3 | 1 | 3  | 1  | 1  |
| E | 1 | 0 |   | 0 | 0 | 0 | 0 | 0 | 1 | 4  | 0  | 3  |
| F |   | 4 | 1 | 6 | 0 | 6 | 0 | 0 | 6 | 0  | 1  |    |
| G | 1 | 1 | 3 | 3 | 2 | 1 |   | 0 | 3 | 1  | 0  | 0  |
| H | 2 | 1 | 0 | 2 | 2 |   | 0 | 2 | 2 | 1  | 1  | 3  |

Fig. 5

```
                  1                                                50
PIP-1A      (1)   MPIKEELSQPQSHSIELDDLKSEQGSLRAALTSNFAGNFDQFPTKRGGFA
PIP-1B      (1)   MTIKEELNQPQSHSIELDDLNSEQGNARAILTSNFAGSFDQFPTKRGGYA
PIP-1C      (1)   MTIKEELGQPQSHSIELDCLNREACSARAALTSNIVGSFDQYPTKHGDFA
PSEEN3174   (1)   MTIKEELGQPQSHSIELDVSKEAASTRAALTSNISGRFDQYPTKRGDFA 51                                               100
PIP-1A      (51)  IDSYLLDYSAPKQGCWVDGITVYGDIFIGKQNWGTYTRPVFAYLQYMDTI
PIP-1B      (51)  IDSYLLDYSAPKQGCWVDGITVYGDIFIGKQNWGTYTRPVFAYLQYMDTI
PIP-1C      (51)  IDSYLLDFSAPKKGCWVDGITVYGDIYIGKQNWGTYTRPVFAYLQYMDTI
PSEEN3174   (51)  IDGYLLDYSSPKQGCWVDGITVYGDIYIGKQNWGTYTRPVFAYLQYMETI 101                                              150
PIP-1A      (101) SIPQQVTQTRSYQLTKGHTKTFFTNVSAKYSVGGSIDIVNVGSDISIGFS
PIP-1B      (101) SIPQQVTQTRSYQLTKGHTKTFTTSVTAKYSVGGSIGIVNVGSDISVGFS
PIP-1C      (101) SIPQQVIQTRSYQLTKGHTQTFETSVSAKYSVGAKIDIVNIDSKISTGFS
PSEEN3174   (101) SIPQNVTTTLSYQLTKGHTRSFETSVNAKYSVGNNIDIVNVGSKISTGFT 151                                              200
PIP-1A      (151) NSESWSTTQTFSNSTQLTGPGTFIVYQVVMVYAHNATSAGRQNGNAFAYN
PIP-1B      (151) SSESWSTTQTFSESTQLAGPGTFIVYQVVLVYAHNATSAGRQNGNAFAYN
PIP-1C      (151) SSESWSTTQTFSESTQLSGPGTFMVYQIVLVYAHNATSAGRQNGNAFAYS
PSEEN3174   (151) RSESWSTTQSFTDTTEMKGPGTFVIYQVVLVYAHNATSAGRQNANAFAYS 201                                              250
PIP-1A      (201) KTNTVGSRLDLYYLSAITQNSTVIVSSSKAIAPLDWDTVQRNVLMENYNP
PIP-1B      (201) KTQTVGSRLDLYYLSAITQNSTVIVESSKAIAPLDWDTVQRNVLMENYNP
PIP-1C      (201) KTQTVDSRVDLYYLSAITQNKTVIVQSGNAIEPLDWDTVQRNVLMDNYNP
PSEEN3174   (201) KTQAVGSRVDLYYLSAITQRKRVIVPSSNAYTPLDWDTVQRNVLMENYNP 251            271
PIP-1A      (251) GSNSGHFSFDWSAYNDPHRRY
PIP-1B      (251) SSNSGHFSFDWSAYNDPHRRY
PIP-1C      (251) ESNNGHFRFDWSAYDNPHRRY
PSEEN3174   (251) GSNSGHFSFDWSAYNDPHRRY
```

INSECTICIDAL PROTEINS AND METHODS FOR THEIR USE

CROSS REFERENCE

This utility application is a divisional of U.S. Non Provisional application Ser. No. 13/792,861 filed Mar. 11, 2013, which claims the benefit U.S. Provisional Application No. 61/667,039, filed Jul. 2, 2012, which is incorporated herein by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named "4208_sequence_listing.txt" created on Mar. 4, 2013, and having a size of 471 kilobytes and is filed concurrently with the specification. The sequence listing contained in this ASCII formatted document is part of the specification and is herein incorporated by reference in its entirety.

FIELD OF THE INVENTION

This disclosure relates to the field of molecular biology. Provided are novel genes that encode pesticidal proteins. These pesticidal proteins and the nucleic acid sequences that encode them are useful in preparing pesticidal formulations and in the production of transgenic pest-resistant plants.

BACKGROUND OF THE INVENTION

Biological control of insect pests of agricultural significance using a microbial agent, such as fungi, bacteria or another species of insect affords an environmentally friendly and commercially attractive alternative to synthetic chemical pesticides. Generally speaking, the use of biopesticides presents a lower risk of pollution and environmental hazards, and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a range of insect pests including Lepidoptera, Diptera, Coleoptera, Hemiptera and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated from strains of Bt. These genetically engineered crops are now widely used in agriculture and have provided the farmer with an environmentally friendly alternative to traditional insect-control methods. While they have proven to be very successful commercially, these genetically engineered, insect-resistant crop plants provide resistance to only a narrow range of the economically important insect pests. In some cases, insects can develop resistance to different insecticidal compounds, which raises the need to identify alternative biological control agents for pest control.

Accordingly, there remains a need for new pesticidal proteins with different ranges of insecticidal activity against insect pests, e.g., insecticidal proteins which are active against a variety of insects in the order Lepidoptera and the order Hemiptera including but not limited to species belonging to the family Pentatomidae, the family Plataspidae and the family Cydnidae. In addition, there remains a need for biopesticides having activity against a variety of insect pests that have developed resistance to existing pesticides.

SUMMARY OF THE INVENTION

Compositions and methods for conferring pesticidal activity to bacteria, plants, plant cells, tissues and seeds are provided. Compositions include nucleic acid molecules encoding sequences for pesticidal and insecticidal polypeptides, vectors comprising those nucleic acid molecules, and host cells comprising the vectors. Compositions also include the pesticidal polypeptide sequences and antibodies to those polypeptides. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues and seeds.

In particular, isolated or recombinant nucleic acid molecules are provided encoding *Pseudomonas* Insecticidal Protein-1 (PIP-1) polypeptides including amino acid substitutions, amino acid deletions, amino acid insertions, and fragments thereof, and combinations thereof. Additionally, amino acid sequences corresponding to the PIP-1 polypeptides are encompassed. Provided are an isolated or recombinant nucleic acid molecule capable of encoding a PIP-1 polypeptide of SEQ ID NO: 2, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 204, 206, 208, 211, 212, 213, 214, 245, 246, 247, 248, 249, 250, 251, 252, 253, 254, 255, 256, 257, 258, 259, 260, 261, 262, 263, 264, 265, 266, 267, 268, 269, 298, 299, 300, 301, 302, 303, 304, 305, 306, 307, 308, 309, 310, 311, 312, 313, 314, 315, 316, 317, 318, 319, 320, 321, 322, 323, 324, and 325 as well as amino acid substitutions, amino acid deletions, amino acid insertions, and fragments thereof, and combinations thereof. In some embodiments exemplary PIP-1 polypeptides comprise a sequence set forth in of SEQ ID NO: 2, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 204, 206, 208, 211, 212, 213, 214, 245, 246, 247, 248, 249, 250, 251, 252, 253, 254, 255, 256, 257, 258, 259, 260, 261, 262, 263, 264, 265, 266, 267, 268, and 269 as well as amino acid substitutions, amino acid deletions, amino acid insertions, and fragments thereof, and combinations thereof.

Also provided are nucleic acid sequences set forth in SEQ ID NO: 1, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 197, 188, 189, 190, 191, 192, 193, 194, 195, 196, 197, 198, 199, 200, 201, 202, 203, 205, 207, 220, 221, 222, 223, 224, 225, 226, 227, 228, 229, 230, 231, 232, 233, 234, 235, 236, 237, 238, 239, 240, 241, 242, 243, 244, 270, 271, 272, 273, 274, 275, 276, 277, 278, 279, 280, 281, 282, 283, 284, 285, 286, 287, 288, 289, 290, 291, 292, 293, 294, 295, 296, and 297 as well as variants and fragments thereof encoding PIP-1 polypeptides.

In some embodiments exemplary nucleic acid molecules comprise a sequence set forth in SEQ ID NO: 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 197, 188, 189, 190, 191, 192, 193, 194, 195, 196, 197, 198, 199, 200, 201, 202, 203, 205, 207, 220, 221, 222, 223, 224, 225, 226, 227, 228, 229, 230, 231, 232, 233, 234, 235, 236, 237, 238, 239, 240, 241, 242, 243, and 244 as well as variants and fragments thereof encoding PIP-1 polypeptides, as well as variants and fragments thereof that encode PIP-1 polypeptides. Nucleic acid sequences that are complementary to a nucleic acid sequence of the embodiments or that hybridize to a sequence of the embodiments are also encompassed.

Methods are provided for producing the polypeptides and for using those polypeptides for controlling, inhibiting growth or killing a Lepidopteran, Coleopteran, nematode, fungi, Hemipteran and/or Dipteran pests. The transgenic plants of the embodiments express one or more of the pesticidal sequences disclosed herein. In various embodiments, the transgenic plant further comprises one or more additional genes for insect resistance, for example, one or more additional genes for controlling coleopteran, lepidopteran, hemipteran or nematode pests. It will be understood by one of skill in the art that the transgenic plant may comprise any gene imparting an agronomic trait of interest.

Methods for detecting the nucleic acids and polypeptides of the embodiments in a sample are also included. A kit for detecting the presence of a PIP-1 polypeptide or detecting the presence of a nucleotide sequence encoding a PIP-1 polypeptide in a sample is provided. A kit for detecting the presence of nucleotide sequence encoding a PIP-1 polypeptide may comprise a nucleic acid probe that comprises at least 20 contiguous nucleotides of the nucleotide sequence encoding the PIP-1 polypeptide or a complement thereof. A kit for detecting the presence of a PIP-1 polypeptide may comprise an antibody that specifically binds to the PIP-1 polypeptide. The kit is provided along with all reagents and control samples necessary for carrying out a method for detecting the intended agent, as well as instructions for use.

The compositions and methods of the embodiments are useful for the production of organisms with enhanced pest resistance or tolerance. These organisms and compositions comprising the organisms are desirable for agricultural purposes. The compositions of the embodiments are also useful for generating altered or improved proteins that have pesticidal activity or for detecting the presence of PIP-1 polypeptides or nucleic acids in products or organisms.

The following embodiments are encompassed by the present disclosure.

1. A recombinant nucleic acid molecule encoding a PIP-1 polypeptide.

2. The recombinant nucleic acid molecule of embodiment 1, wherein the PIP-1 polypeptide is orally active.

3. The recombinant nucleic acid molecule of embodiment 1 or 2, wherein the PIP-1 polypeptide has insecticidal activity against an insect pest in the order Hemiptera.

4. The recombinant nucleic acid molecule of embodiment 1, 2 or 3, wherein the PIP-1 polypeptide has insecticidal activity against an insect pest in the family Pentatomidae.

5. The recombinant nucleic acid molecule of embodiment 1, 2, 3 or 4, wherein the PIP-1 polypeptide has insecticidal activity against an insect pest in the order Lepidoptera.

6. The recombinant nucleic acid molecule of embodiment 1, 2, 3, 4 or 5, wherein the nucleic acid molecule is from a *Pseudomonas chlororaphis* strain.

7. The recombinant nucleic acid molecule of embodiment 1, 2, 3, 4, 5 or 6, wherein the *Pseudomonas chlororaphis* strain comprises a 16S ribosomal DNA having at least about 96.9% identity to SEQ ID NO: 216.

8. The recombinant nucleic acid molecule of embodiment 1, 2, 3, 4, 5, 6 or 7 wherein the *Pseudomonas chlororaphis* strain is SS44C4 deposited under accession # NRRLB-50613.

9. The recombinant nucleic acid molecule of embodiment 1, 2, 3, 4, 5, 6, 7, or 8 wherein the PIP-1 polypeptide comprises an amino acid motif as represented by positions 171-183 of SEQ ID NO: 213.

10. The recombinant nucleic acid molecule of embodiment 1, 2, 3, 4, 5, 6, 7, 8 or 9, wherein the PIP-1 polypeptide further comprises any one or more amino acid motifs as represented by positions 149-159 of SEQ ID NO: 213 and positions 64-79 of SEQ ID NO: 213.

11. The recombinant nucleic acid molecule of embodiment 1, 2, 3, 4, 5, 6, 7, 8, 9 or 10 wherein the PIP-1 polypeptide comprises a polypeptide having at least 80% identity to the amino acid sequence of SEQ ID NO: 2.

12. The recombinant nucleic acid molecule of embodiment 1, 2, 3, 4, 5, 6, 7, 8, 9, 10 or 11, wherein the PIP-1 polypeptide further comprises any one or more amino acid motifs as represented by positions 64-79 of SEQ ID NO: 213, positions 149-159 of SEQ ID NO: 213, and positions 171-183 of SEQ ID NO: 213.

13. The recombinant nucleic acid molecule of embodiment 1, 2, 3, 4, 5, 6, 7, 8, 9, 10, 11 or 12, wherein the PIP-1 polypeptide comprises an amino acid sequence of SEQ ID NO: 211, wherein Xaa at position 2 is Pro or Thr; Xaa at position 8 is Ser, Gly or Asn; Xaa at position 19 is Asp, Glu or Cys; Xaa at position 20 is Leu or Val; Xaa at position 21 is Lys, Ser or Asn; Xaa at position 22 is Ser, Lys or Arg; Xaa at position 24 is Gln or Ala; Xaa at position 25 is Gly or Ala Xaa at position 26 is Ser or Asn; Xaa at position 27 is Leu, Thr or Ala; Xaa at position 30 is Ala or Ile; Xaa at position 35 is Phe or Leu; Xaa at position 36 is Ala, Ser or Val; Xaa at position 38 is Asn, Arg or Ser; Xaa at position 42 is Phe or Tyr; Xaa at position 46 is Arg, Lys or His; Xaa at position 48 is Gly or Asp; Xaa at position 49 is Phe or Tyr; Xaa at position 53 is Ser or Gly; Xaa at position 58 is Tyr or Phe; Xaa at position 60 is Ala or Ser; Xaa at position 63 is Gln or Lys; Xaa at position 77 is Phe or Tyr; Xaa at position 97 is Met or Val; Xaa at position 98 is Asp or Glu; Xaa at position 105 is Gln or Asn; Xaa at position 107 is Thr or Ile; Xaa at position 108 is Gln or Thr; Xaa at position 110 is Arg or Leu; Xaa at position 120 is Lys, Arg or Gln; Xaa at position 121 is Thr or Ser; Xaa at position 123 is Thr or Glu; Xaa at position 125 is Asn or Ser; Xaa at position 127 is Ser, Asn, Thr or Lys; Xaa at position 134 is Gly or Ala; Xaa at position 135 is Ser, Asn or Lys; Xaa at position 137 is Asp or Gly; Xaa at position 141 is Val or Ile; Xaa at position 142 is Gly or Asp; Xaa at position 144 is Asp or Glu; Xaa at position 147 is Ile, Thr or Val; Xaa at position 150 is Ser or Thr; Xaa at position 151 is Asn, Arg or Ser; Xaa at position 160 is Thr or Ser; Xaa at position 162 is Ser or Thr; Xaa at position 163 is Asn, Asp or Glu; Xaa at position 164 is Ser or Thr; Xaa at position 166 is Gln or Glu; Xaa at position 167 is Leu or Met; Xaa at position 168 is Thr, Lys or Ala;

Xaa at position 174 is Ile, Val or Met; Xaa at position 175 is Val or Ile; Xaa at position 180 is Met or Leu; Xaa at position 191 is Arg or Lys; Xaa at position 194 is Gly or Ala; Xaa at position 200 is Asn or Ser; Xaa at position 203 is Asn or Gln; Xaa at position 204 is Thr or Ala; Xaa at position 206 is Gly or Asp; Xaa at position 209 is Leu or Val; Xaa at position 220 is Asn or Arg; Xaa at position 221 is Ser or Lys; Xaa at position 222 is Thr or Arg; Xaa at position 226 is Asp, Pro or Glu; Xaa at position 228 is Ser or Gly; Xaa at position 229 is Lys or Asn; Xaa at position 231 is Ile or Val; Xaa at position 232 is Ala, Thr or Glu; and Xaa at position 251 is Gly, Ser or Glu; Xaa at position 254 is Ser or Asn; Xaa at position 258 is Ser or Arg; Xaa at position 265 is Asn or Asp; and Xaa at position 266 is Asp or Asn; and wherein, 1 to 28 amino acids are optionally deleted from the N-terminus of the polypeptide.

14. The recombinant nucleic acid molecule of embodiment 1, 2, 3, 4, 5, 6, 7, 8, 9, 10, 11 or 12, wherein the PIP-1 polypeptide comprises an amino acid sequence of SEQ ID NO: 212, wherein Xaa at position 2 is Pro or Thr; Xaa at position 3 is Ile or Thr; Xaa at position 6 is Glu or Gly; Xaa at position 8 is Ser, Gly or Asn; Xaa at position 19 is Asp, Glu or Cys; Xaa at position 20 is Leu or Val; Xaa at position 21 is Lys, Ser or Asn; Xaa at position 22 is Ser, Lys or Arg; Xaa at position 24 is Gln or Ala; Xaa at position 25 is Gly or Ala; Xaa at position 26 is Ser or Asn; Xaa at position 27 is Leu, Thr or Ala; Xaa at position 28 is Arg, Ser, Lys, Thr, Val, Gly, Ala, Met, Asp, Trp, Pro, Leu, His, Cys or Gln; Xaa at position 30 is Ala or Ile; Xaa at position 35 is Phe or Leu; Xaa at position 36 is Ala, Ser or Val; Xaa at position 38 is Asn, Arg or Ser; Xaa at position 42 is Phe or Tyr; Xaa at position 43 is Pro, Met, Gly, Gln, Ser, Thr, Arg, Val, Leu, Lys, Asp, Ala, Asn, Phe, Trp, Glu or Cys; Xaa at position 46 is Arg, Lys or His; Xaa at position 48 is Gly or Asp; Xaa at position 49 is Phe, Tyr or Leu; Xaa at position 53 is Ser or Gly; Xaa at position 58 is Tyr or Phe; Xaa at position 60 is Ala or Ser; Xaa at position 63 is Gln or Lys; Xaa at position 66 is Trp, Tyr, Phe, Arg, Lys, His, Ile, Val or Ser; Xaa at position 77 is Phe or Tyr; Xaa at position 89 is Pro, Leu, Gly, Arg, Thr, Ser, Met, Ala, Ile, Asn, Val, Cys or Lys; Xaa at position 93 is Tyr, Cys, Trp, Val, Asp, Asn, Ile, Leu, Met, Phe, Ala or Thr; Xaa at position 97 is Met or Val; Xaa at position 98 is Asp or Glu; Xaa at position 105 is Gln or Asn; Xaa at position 107 is Thr or Ile; Xaa at position 108 is Gln or Thr; Xaa at position 110 is Arg or Leu; Xaa at position 120 is Lys, Arg or Gln; Xaa at position 121 is Thr or Ser; Xaa at position 123 is Thr or Glu; Xaa at position 125 is Asn or Ser; Xaa at position 127 is Ser, Asn, Thr or Lys; Xaa at position 134 is Gly or Ala; Xaa at position 135 is Ser, Asn or Lys; Xaa at position 137 is Asp or Gly; Xaa at position 141 is Val or Ile; Xaa at position 142 is Gly or Asp; Xaa at position 144 is Asp or Glu; Xaa at position 147 is Ile, Thr or Val; Xaa at position 150 is Ser or Thr; Xaa at position 151 is Asn, Arg or Ser; Xaa at position 160 is Thr or Ser; Xaa at position 162 is Ser or Thr; Xaa at position 163 is Asn, Asp or Glu; Xaa at position 164 is Ser or Thr; Xaa at position 166 is Gln or Glu; Xaa at position 167 is Leu or Met; Xaa at position 168 is Thr, Lys or Ala; Xaa at position 171 is Gly, Leu, Gln, Met, Cys, Asn, Asp, Ser or Ala; Xaa at position 172 is Thr, Gly, His, Phe, Glu, Arg, Ser, Asn, Ile, Trp, Lys, Gln, Cys, Val, Ala or Met; Xaa at position 173 is Phe, Gly, His, Leu, Ala, Arg, Asn, Cys, Lys, Trp, Thr, Ser, Tyr or Met; Xaa at position 174 is Ile, Val, Gly, Arg, Asn, Ala, Gln, Met, Cys, Leu, Phe, Tyr, Lys, Glu, Ser, His or Thr; Xaa at position 175 is Val, Ile, Ala, Cys, Glu, Lys, Leu or Met; Xaa at position 176 is Tyr, Met, Phe, Leu or Cys; Xaa at position 177 is Gln, Ile, Met or Pro; Xaa at position 178 is Val, Cys, Thr, Pro, Ala, Met, Gln, Phe, Ile, Ser or Lys; Xaa at position 179 is Val, Phe, Thr, Ile, Cys, Leu, Met, Ser, Ala or Gln; Xaa at position 180 is Met, Leu, Pro, Trp, Asn, Tyr, Gly, Gln, Ala, Val, Phe, Ile, Cys or Ser; Xaa at position 181 is Val, Ala, Leu, Trp, Cys, Thr, Ile or Lys; Xaa at position 182 is Tyr, Phe, Met or His; Xaa at position 183 is Ala, Met, Val, Thr, Asp, Gly, Cys, Ile, Phe, Ser, Gln or Leu; Xaa at position 191 is Arg or Lys; Xaa at position 194 is Gly or Ala; Xaa at position 195 is Asn or Tyr; Xaa at position 200 is Asn or Ser; Xaa at position 203 is Asn or Gln; Xaa at position 204 is Thr or Ala; Xaa at position 206 is Gly or Asp; Xaa at position 209 is Leu or Val; Xaa at position 213 is Tyr or Phe; Xaa at position 220 is Asn or Arg; Xaa at position 221 is Ser or Lys; Xaa at position 222 is Thr or Arg; Xaa at position 226 is Asp, Pro or Glu; Xaa at position 228 is Ser or Gly; Xaa at position 229 is Lys or Asn; Xaa at position 231 is Ile or Val; Xaa at position 232 is Ala, Thr or Glu; Xaa at position 240 is Gln, Arg, Ala, Val, Glu, Met, Gly, Asp, Trp, Asn, Thr, Ile, Ser, Phe, His, Cys or Leu; Xaa at position 241 is Arg, Lys, Glu, Gln, Ser, Ile, Val, Asp, Tyr, Met, Asn, His, Pro, Gly, Leu, Phe, Thr, Ala or Cys; Xaa at position 242 is Asn, Ala, Arg, Lys, His, Ser, Cys, Glu, Pro, Trp, Gln, Thr, Phe, Tyr, Met, Asp, Gly, Leu or Val; Xaa at position 243 is Val, Leu, Ala, Thr, Gly, Cys, Ile, Ser or Met; Xaa at position 244 is Leu, Val, Phe, Ile, Met, Gln, Cys, Trp or Ala; Xaa at position 245 is Met, Ala, Arg, Asp, Glu, Leu, Pro, Ser, Trp, Gly, Val, Lys, Phe, Cys, Thr, His, Ile, Gln, Tyr or Asn; Xaa at position 246 is Glu, Asp, Tyr, Gly, Arg, Val, Ala, Trp, Gln, Ser, Asn, Ile Leu, Met, Cys, Pro, His, Phe, Thr or Lys; Xaa at position 247 is Asn, Leu, Asp, Tyr, Ala, Phe, His, Arg, Lys, Gln, Gly, Val, Ile, Ser, Glu, Pro, Met, Trp, Thr or Cys; Xaa at position 248 is Tyr, Val, Thr, Glu, Phe, Ser, His, Cys, Leu, Trp, Ile, Asp, Gly or Ala; Xaa at position 249 is Asn, Lys, Val, Gly, Met, Asp, Cys, Phe, Arg, Glu, Trp, Tyr, Ser, Ile, Thr, Pro, Leu, Ala, His or Gln; Xaa at position 251 is Gly, Ser or Glu; Xaa at position 254 is Ser or Asn; Xaa at position 258 is Ser or Arg; Xaa at position 259 is Phe, Trp, Tyr, Cys, Met, Leu, Val, Ile or His; Xaa at position 265 is Asn or Asp; and Xaa at position 266 is Asp or Asn; and wherein, 1 to 28 amino acids are optionally deleted from the N-terminus of the polypeptide.

15. The recombinant nucleic acid molecule of embodiment 1, 2, 3, 4, 5, 6, 7, 8, 9, 10, 11 or 12, wherein the PIP-1 polypeptide comprises an amino acid sequence of (SEQ ID NO: 213), wherein Xaa at position 2 is Pro, Thr or Ser; Xaa at position 3 is Ile, Thr, Leu, Val, Met or Ser; Xaa at position 6 is Glu, Gly, Asp or Ala; Xaa at position 8 is Ser, Gly, Asn, Thr or Gln; Xaa at position 19 is Asp, Glu or Cys; Xaa at position 20 is Leu, Val, Ile or Met; Xaa at position 21 is Lys, Ser, Asn, Arg, Thr or Gln; Xaa at position 22 is Ser, Lys, Arg or Thr; Xaa at position 24 is Gln, Gly, Asn or Ala; Xaa at position 25 is Gly or Ala; Xaa at position 26 is Ser, Asn, Thr or Gln; Xaa at position 27 is Leu, Thr, Ala, Ser, Ile, Val or Met; Xaa at position 28 is Arg, Ser, Lys, Thr, Val, Gly, Ala, Met, Asp, Trp, Pro, Leu, His, Cys or Gln; Xaa at position 30 is Ala, Ile, Leu, Val or Met; Xaa at position 35 is Phe, Leu, Ile, Val or Met; Xaa at position 36 is Ala, Ser, Thr, Val, Ile or Leu; Xaa at position 38 is Asn, Arg, Ser, Gln, Lys or Thr; Xaa at position 42 is Phe, Tyr, Trp, Leu, Ile, Val or Met; Xaa at position 43 is Pro, Met, Gly, Gln, Ser, Thr, Arg, Val, Leu, Lys, Asp, Ala, Asn, Phe, Trp, Glu or Cys; Xaa at position 46 is Arg, Lys or His; Xaa at position 48 is Gly, Asp, Ala or Glu; Xaa at position 49 is Phe, Tyr, Trp, Leu, Ile, Val or Met; Xaa at position 53 is Ser, Gly, Ala or Thr; Xaa at position 58 is Tyr or Phe; Xaa at position 60 is Ala, Ser, Gly or Thr; Xaa at position 63 is Gln, Lys, Asn or Arg; Xaa at position 66 is Trp, Tyr, Phe, Arg, Lys, His, Ile, Val or Ser; Xaa at position 77 is Phe, Tyr, Trp, Leu, Ile, Val or Met; Xaa at position 89 is Pro, Leu, Gly, Arg, Thr, Ser, Met, Ala, Ile, Asn, Val, Cys or Lys; Xaa at position 93 is Tyr, Cys, Trp, Val, Asp, Asn, Ile, Leu, Met, Phe, Ala or Thr; Xaa at position 97 is Met, Val, Leu or Ile; Xaa at position 98 is Asp or Glu; Xaa at position 105 is Gln or Asn; Xaa at position 107 is Thr, Ile, Ser, Leu or Val; Xaa at position 108 is Gln, Thr, Ser or Asn; Xaa at position 110 is Arg, Leu, Lys, Ile, Val or Met; Xaa at position 120 is Lys, Arg, Gln or Asn; Xaa at position 121 is Thr or Ser; Xaa at position 123 is Thr, Glu, Ser or Asp; Xaa at position 125 is Asn, Ser, Gln or Thr; Xaa at position 127 is Ser, Asn, Thr, Gln, Lys, Ser or Arg; Xaa at position 134 is Gly or Ala; Xaa at position 135 is Ser, Asn, Thr, Gln, Arg or Lys; Xaa at position 137 is Asp, Gly, Glu or Ala; Xaa at position 141 is Val, Ile or Leu; Xaa at position 142 is Gly, Asp, Ala or Glu; Xaa at position 144 is Asp or Glu; Xaa at position 147 is Ile, Thr, Val, Leu, Met or Ser; Xaa at position 150 is Ser or Thr; Xaa at position 151 is Asn, Arg, Ser, Gln, Lys or Thr; Xaa at position 160 is Thr or Ser; Xaa at position 162 is Ser or Thr; Xaa at position 163 is Asn, Asp, Glu or Gln; Xaa at position 164 is Ser or Thr; Xaa at position 166 is Gln, Glu, Asp or Asn; Xaa at position 167 is Leu, Met, Ile, Val; Xaa at position 168 is Thr, Lys, Ala, Ser, Arg or Gly; Xaa at position 171 is Gly, Leu, Gln, Met, Cys, Asn, Asp, Ser or Ala; Xaa at position 172 is Thr, Gly, His, Phe, Glu, Arg, Ser, Asn, Ile, Trp, Lys, Gln, Cys, Val, Ala or Met; Xaa at position 173 is Phe, Gly, His, Leu, Ala, Arg, Asn, Cys, Lys, Trp, Thr, Ser, Tyr or Met; Xaa at position 174 is Ile, Val, Gly, Arg, Asn, Ala, Gln, Met, Cys, Leu, Phe, Tyr, Lys, Glu, Ser, His or Thr; Xaa at position 175 is Val, Ile, Ala, Cys, Glu, Lys, Leu or Met; Xaa at position 176 is Tyr, Met, Phe, Leu or Cys; Xaa at position 177 is Gln, Ile, Met or Pro; Xaa at position 178 is Val, Cys, Thr, Pro, Ala, Met, Gln, Phe, Ile, Ser or Lys; Xaa at position 179 is Val, Phe, Thr, Ile, Cys, Leu, Met, Ser, Ala or Gln; Xaa at position 180 is Met, Leu; Pro, Trp, Asn, Tyr, Gly, Gln, Ala, Val, Phe, Ile, Cys or Ser; Xaa at position 181 is Val, Ala, Leu, Trp, Cys, Thr, Ile or Lys; Xaa at position 182 is Tyr, Phe, Met or His; Xaa at position 183 is Ala, Met, Val, Thr, Asp, Gly, Cys, Ile, Phe, Ser, Gln or Leu; Xaa at position 191 is Arg or Lys; Xaa at position 194 is Gly or Ala; Xaa at position 195 is Asn, Tyr, Gln or Trp; Xaa at position 200 is Asn, Ser, Thr or Gln; Xaa at position 203 is Asn or Gln; Xaa at position 204 is Thr, Ala, Ser or Gly; Xaa at position 206 is Gly, Asp, Ala or Glu; Xaa at position 209 is Leu, Val, Ile or Met; Xaa at position 213 is Tyr or Phe; Xaa at position 220 is Asn, Arg, Gln or Lys; Xaa at position 221 is Ser, Lys, Thr or Arg; Xaa at position 222 is Thr, Arg, Ser or Lys; Xaa at position 226 is Asp, Pro, Glu or Gln; Xaa at position 228 is Ser or Gly; Xaa at position 229 is Lys, Asn, Arg or Gln; Xaa at position 231 is Ile, Val, Leu or Met; Xaa at position 232 is Ala, Thr, Ser, Gly, Asp or Glu; Xaa at position 240 is Gln, Arg, Ala, Val, Glu, Met, Gly, Asp, Trp, Asn, Thr, Ile, Ser, Phe, His, Cys or Leu; Xaa at position 241 is Arg, Lys, Glu, Gln, Ser, Ile, Val, Asp, Tyr, Met, Asn, His, Pro, Gly, Leu, Phe, Thr, Ala or Cys; Xaa at position 242 is Asn, Ala, Arg, Lys, His, Ser, Cys, Glu, Pro, Trp, Gln, Thr, Phe, Tyr, Met, Asp, Gly, Leu or Val; Xaa at position 243 is Val, Leu, Ala, Thr, Gly, Cys, Ile, Ser or Met; Xaa at position 244 is Leu, Val, Phe, Ile, Met, Gln, Cys, Trp or Ala; Xaa at position 245 is Met, Ala, Arg, Asp, Glu, Leu, Pro, Ser, Trp, Gly, Val, Lys, Phe, Cys, Thr, His, Ile, Gln, Tyr or Asn; Xaa at position 246 is Glu, Asp, Tyr, Gly, Arg, Val, Ala, Trp, Gln, Ser, Asn Ile Leu, Met, Cys, Pro, His, Phe, Thr or Lys; Xaa at position 247 is Asn, Leu, Asp, Tyr, Ala, Phe, His, Arg, Lys, Gln, Gly, Val, Ile, Ser, Glu, Pro, Met, Trp, Thr or Cys; Xaa at position 248 is Tyr, Val, Thr, Glu, Phe, Ser, His, Cys, Leu, Trp, Ile, Asp, Gly or Ala; Xaa at position 249 is Asn, Lys, Val, Gly, Met, Asp, Cys, Phe, Arg, Glu, Trp, Tyr, Ser, Ile, Thr, Pro, Leu, Ala, His or Gln; Xaa at position 251 is Gly, Ser, Thr, Ala, Asp or Glu; Xaa at position 254 is Ser, Asn, Thr or Gln; Xaa at position 258 is Ser, Arg, Thr or Lys; Xaa at position 259 is Phe, Trp, Tyr, Cys, Met, Leu, Val, Ile or His; Xaa at position 265 is Asn, Asp, Gln or Glu; and Xaa at position 266 is Asp, Asn, Gln or Glu; and wherein, 1 to 28 amino acids are optionally deleted from the N-terminus of the polypeptide.

16. The recombinant nucleic acid molecule of embodiment 1, 2, 3, 4, 5, 6, 7, 8, 9, 10, 11, 12, 13, 14 or 15 wherein the recombinant nucleic acid molecule comprises a polynucleotide of SEQ ID NO: 1, a fragment or a complement thereof.

17. The recombinant nucleic acid molecule of embodiment 1, 2, 3, 4, 5, 6, 7, 8, 9, 10, 11, 12, 13, 14 or 15, wherein the PIP-1 polypeptide comprises an amino acid sequence of SEQ ID NO: 2 or a fragment thereof.

18. The recombinant nucleic acid molecule of embodiment 1, 2, 3, 4, 5, 6, 7, 8, 9, 10, 11, 12, 13, 14 or 15, wherein the recombinant nucleic acid molecule hybridizes under stringent conditions to a polynucleotide of SEQ ID NO: 1.

19. The recombinant nucleic acid molecule of embodiment 1, 2, 3, 4, 5, 6, 7, 8, 9, 10, 11, 12, 13, 14 or 15, wherein the recombinant nucleic acid molecule comprises a polynucleotide of SEQ ID NO: 1.

20. A plant or progeny thereof, comprising the recombinant nucleic acid molecule of embodiment 1, 2, 3, 4, 5, 6, 7, 8, 9, 10, 11, 12, 13, 14, 15, 16, 17, 18 or 19.

21. A plant or progeny thereof stably transformed with the recombinant nucleic acid molecule of embodiment 1, 2, 3, 4, 5, 6, 7, 8, 9, 10, 11, 12, 13, 14, 15, 16, 17, 18 or 19.

22. The plant of embodiment 20 or 21, wherein the plant is a monocotyledon.

23. The plant of embodiment 20 or 21, wherein the plant is a dicotyledon.

24. The plant of embodiment 20 or 21, wherein the plant is selected from barley, corn, oat, rice, rye, *sorghum*, turf grass, sugarcane, wheat, alfalfa, banana, broccoli, bean, cabbage, canola, carrot, cassava, cauliflower, celery, *citrus*, cotton, a cucurbit, eucalyptus, flax, garlic, grape, onion, lettuce, pea, peanut, pepper, potato, poplar, pine, sunflower, safflower, soybean, strawberry, sugar beet, sweet potato, tobacco, tomato ornamental, shrub, nut, chickpea, pigeon pea, millets, hops, and pasture grass plant cells.

25. The plant of embodiment 20, 21, 22, 23 or 24, further comprising one or more additional transgenic traits.

26. The plant of embodiment 25, wherein the one or more additional transgenic trait is selected from insect resistance, herbicide resistance, fungal resistance, virus resistance or stress tolerance, disease resistance, male sterility, stalk strength, increased yield, modified starches, improved oil profile, balanced amino acids, high lysine or methionine, increased digestibility, improved fiber quality, and drought tolerance.

27. An expression cassette, comprising the recombinant nucleic acid molecule of embodiment 1, 2, 3, 4, 5, 6, 7, 8, 9, 10, 11, 12, 13, 14, 15, 16, 17, 18 or 19, wherein the nucleic acid is operably linked to one or more regulatory sequences directing expression of the PIP-1 polypeptide.

28. A plant, comprising the expression cassette of embodiment 27.

29. A plant cell, comprising the expression cassette of embodiment 27.

30. A recombinant microbial cell, comprising the expression cassette of embodiment 27.

31. Seed or grain of the plant of embodiment 20, 21, 22, 23, 24, 25 or 26 or a progeny thereof, wherein the seed or grain comprises the recombinant nucleic acid molecule.

32. The seed of embodiment 31, wherein one or more seed treatment has been applied to the seed.

33. The seed of embodiment 32, wherein the one or more seed treatment is selected from a herbicide, an insecticide, a fungicide, a germination inhibitor, a germination enhancer, a plant growth regulator, a bactericide, and a nematocide.

34. A biological sample derived from a tissue or seed of the plant of embodiment 20, 21, 22, 23, 24, 25 or 26.

35. A recombinant microorganism, comprising a recombinant nucleic acid molecule of embodiment 1, 2, 3, 4, 5, 6, 7, 8, 9, 10, 11, 12, 13, 14, 15, 16, 17, 18 or 19.

36. The microorganism of embodiment 35, wherein the microorganism is selected from a bacteria, baculovirus, algae, and fungi.

37. The microorganism of embodiment 36, wherein the bacteria is selected from a *Bacillus*, a *Pseudomonas*, a *Clavibacter*, a *Rhizobium* and *E. coli*.

38. A method for producing a polypeptide with insecticidal activity, comprising culturing the microorganism of embodiment 35, 36 or 37 under conditions in which the nucleic acid molecule encoding the polypeptide is expressed.

39. A method for expressing in a plant a PIP-1 polypeptide, comprising the steps of:
  (a) inserting into the plant cell a nucleic acid sequence comprising in the 5' to 3' direction an operably linked recombinant, double-stranded DNA molecule, wherein the recombinant double-stranded DNA molecule comprises
    (i) a promoter that functions in the plant cell;
    (ii) a nucleic acid molecule encoding a PIP-1 polypeptide as set forth in embodiment 1, 2, 3, 4, 5, 6, 7, 8, 9, 10, 11, 12, 13, 14, 15, 16, 17, 18 or 19; and
    (iii) a 3' non-translated polynucleotide that functions in the cells of the plant to cause termination of transcription;
  (b) obtaining a transformed plant cell comprising the nucleic acid sequence of step (a); and
  (c) generating from the transformed plant cell a plant capable of expressing the PIP-1 polypeptide.

40. A plant produced by the method of embodiment 39.

41. Seed or grain produced by the plant of embodiment 40.

42. The plant of embodiment 40, further comprising one or more additional transgenic traits.

43. The plant of embodiment 42, wherein the one or more additional transgenic trait is selected from insect resistance, herbicide resistance, fungal resistance, viral resistance, stress tolerance, disease resistance, male sterility, stalk strength, increased yield, modified starches, improved oil profile, balanced amino acids, high lysine or methionine, increased digestibility, improved fiber quality, flowering, ear and seed development, enhancement of nitrogen utilization efficiency, altered nitrogen responsiveness, drought resistance or tolerance, cold resistance or tolerance, salt resistance or tolerance, and increased yield under stress.

44. The plant of embodiment 40, 42 or 43, wherein the plant is a monocotyledon.

45. The plant of embodiment 40, 42 or 43, wherein the plant is a dicotyledon.

46. A recombinant PIP-1 polypeptide.

47. The recombinant PIP-1 polypeptide of embodiment 46, wherein the PIP-1 polypeptide is orally active.

48. The recombinant PIP-1 polypeptide of embodiment 46 or 47, wherein the PIP-1 polypeptide has insecticidal activity against an insect pest of the order Hemiptera.

49. The recombinant PIP-1 polypeptide of embodiment 46, 47 or 48, wherein the PIP-1 polypeptide has insecticidal activity against an insect pest of the Pentatomidae family.

50. The recombinant PIP-1 polypeptide of embodiment 49, wherein the PIP-1 polypeptide has insecticidal activity against an insect selected from *Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus, Bagrada hilaris, Megacopta cribraria, Scaptocoris castanea, Helicoverpa zea* Boddie, *Pseudoplusia includens* Walker, and *Anticarsia gemmatalis*.

51. The recombinant PIP-1 polypeptide of embodiment 46, 47, 48, 49 or 50, wherein the PIP-1 polypeptide has insecticidal activity against an insect pest of the order Lepidoptera.

52. The recombinant PIP-1 polypeptide of embodiment 46, 47, 48, 49, 50 or 51, wherein the PIP-1 polypeptide is produced by a *Pseudomonas chlororaphis* strain.

53. The recombinant PIP-1 polypeptide of embodiment 52, wherein the PIP-1 polypeptide is produced by a *Pseudomonas chlororaphis* strain having a 16S ribosomal DNA having at least about 96.9% identity to SEQ ID NO: 216.

54. The recombinant PIP-1 polypeptide of embodiment 52, wherein the *Pseudomonas chlororaphis* strain is SS44C4 deposited under accession # NRRLB-50613.

55. The recombinant PIP-1 polypeptide of embodiment 46, 47, 48, 49, 50, 51, 52, 53 or 54, wherein the PIP-1 polypeptide comprises an amino acid motif as represented by positions 171-183 of SEQ ID NO: 213.

56. The recombinant PIP-1 polypeptide of embodiment 55, further comprising any one or more amino acid motifs as represented by positions 149-159 of SEQ ID NO: 213, and positions 64-79 of SEQ ID NO: 213.

57. The recombinant PIP-1 polypeptide of embodiment 46, 47, 48, 49, 50, 51, 52, 53, 54, 55 or 56, wherein the PIP-1 polypeptide comprises a polypeptide having at least 80% identity to the amino acid sequence of SEQ ID NO: 2.

58. The recombinant PIP-1 polypeptide of embodiment 46, 47, 48, 49, 50, 51, 52, 53, 54, 55, 56 or 57 wherein the PIP-1 polypeptide comprises an amino acid motif as represented by positions 171-183 of SEQ ID NO: 213 and wherein the PIP-1 polypeptide has at least 80% identity to the amino acid sequence of SEQ ID NO: 2.

59. The recombinant PIP-1 polypeptide of embodiment 46, 47, 48, 49, 50, 51, 52, 53, 54, 55, 56, 57 or 58, wherein the PIP-1 polypeptide comprises an amino acid sequence of (SEQ ID NO: 211), wherein
Xaa at position 2 is Pro or Thr; Xaa at position 8 is Ser, Gly or Asn; Xaa at position 19 is Asp, Glu or Cys; Xaa at position 20 is Leu or Val; Xaa at position 21 is Lys, Ser or Asn; Xaa at position 22 is Ser, Lys or Arg; Xaa at position 24 is Gln or Ala; Xaa at position 25 is Gly or Ala Xaa at position 26 is Ser or Asn; Xaa at position 27 is Leu, Thr or Ala; Xaa at position 30 is Ala or Ile; Xaa at position 35 is Phe or Leu; Xaa at position 36 is Ala, Ser or Val; Xaa at position 38 is Asn, Arg or Ser; Xaa at position 42 is Phe or Tyr; Xaa at position 46 is Arg, Lys or His; Xaa at position 48 is Gly or Asp; Xaa at position 49 is Phe or Tyr; Xaa at position 53 is Ser or Gly; Xaa at position 58 is Tyr or Phe; Xaa at position 60 is Ala or Ser; Xaa at position 63 is Gln or Lys; Xaa at position 77 is Phe or Tyr; Xaa at position 97 is Met or Val; Xaa at position 98 is Asp or Glu; Xaa at position 105 is Gln or Asn; Xaa at position 107 is Thr or Ile; Xaa at position 108 is Gln or Thr; Xaa at position 110 is Arg or Leu; Xaa at position 120 is Lys, Arg or Gln; Xaa at position 121 is Thr or Ser; Xaa at position 123 is Thr or Glu; Xaa at position 125 is Asn or Ser; Xaa at position 127 is Ser, Asn, Thr or Lys; Xaa at position 134 is Gly or Ala; Xaa at position 135 is Ser, Asn or Lys; Xaa at position 137 is Asp or Gly; Xaa at position 141 is Val or Ile; Xaa at position 142 is Gly or Asp; Xaa at position 144 is Asp or Glu; Xaa at position 147 is Ile, Thr or Val; Xaa at position 150 is Ser or Thr; Xaa at position 151 is Asn, Arg or Ser; Xaa at position 160 is Thr or Ser; Xaa at position 162 is Ser or Thr; Xaa at position 163 is Asn, Asp or Glu; Xaa at position 164 is Ser or Thr; Xaa at position 166 is Gln or Glu; Xaa at position 167 is Leu or Met; Xaa at position 168 is Thr, Lys or Ala; Xaa at position 174 is Ile, Val or Met; Xaa at position 175 is Val or Ile; Xaa at position 180 is Met or Leu; Xaa at position 191 is Arg or Lys; Xaa at position 194 is Gly or Ala; Xaa at position 200 is Asn or Ser; Xaa at position 203 is Asn or Gln; Xaa at position 204 is Thr or Ala; Xaa at position 206 is Gly or Asp; Xaa at position 209 is Leu or Val; Xaa at position 220 is Asn or Arg; Xaa at position 221 is Ser or Lys; Xaa at position 222 is Thr or Arg; Xaa at position 226 is Asp, Pro or Glu; Xaa at position 228 is Ser or Gly; Xaa at position 229 is Lys or Asn; Xaa at position 231 is Ile or Val; Xaa at position 232 is Ala, Thr or Glu; and Xaa at position 251 is Gly, Ser or Glu; Xaa at position 254 is Ser or Asn; Xaa at position 258 is Ser or Arg; Xaa at position 265 is Asn or Asp; and Xaa at position 266 is Asp or Asn; and wherein, 1 to 28 amino acids are optionally deleted from the N-terminus of the polypeptide.

60. The recombinant PIP-1 polypeptide of embodiment 46, 47, 48, 49, 50, 51, 52, 53, 54, 55, 56, 57 or 58, wherein the PIP-1 polypeptide comprises an amino acid sequence of SEQ ID NO: 212, wherein Xaa at position 2 is Pro or Thr; Xaa at position 3 is Ile or Thr; Xaa at position 6 is Glu or Gly; Xaa at position 8 is Ser, Gly or Asn; Xaa at position 19 is Asp, Glu or Cys; Xaa at position 20 is Leu or Val; Xaa at position 21 is Lys, Ser or Asn; Xaa at position 22 is Ser, Lys or Arg; Xaa at position 24 is Gln or Ala; Xaa at position 25 is Gly or Ala; Xaa at position 26 is Ser or Asn; Xaa at position 27 is Leu, Thr or Ala; Xaa at position 28 is Arg, Ser, Lys, Thr, Val, Gly, Ala, Met, Asp, Trp, Pro, Leu, His, Cys or Gln; Xaa at position 30 is Ala or Ile; Xaa at position 35 is Phe or Leu; Xaa at position 36 is Ala, Ser or Val; Xaa at position 38 is Asn, Arg or Ser; Xaa at position 42 is Phe or Tyr; Xaa at position 43 is Pro, Met, Gly, Gln, Ser, Thr, Arg, Val, Leu, Lys, Asp, Ala, Asn, Phe, Trp, Glu or Cys; Xaa at position 46 is Arg, Lys or His; Xaa at position 48 is Gly or Asp; Xaa at position 49 is Phe, Tyr or Leu; Xaa at position 53 is Ser or Gly; Xaa at position 58 is Tyr or Phe; Xaa at position 60 is Ala or Ser; Xaa at position 63 is Gln or Lys; Xaa at position 66 is Trp, Tyr, Phe, Arg, Lys, His, Ile, Val or Ser; Xaa at position 77 is Phe or Tyr; Xaa at position 89 is Pro, Leu, Gly, Arg, Thr, Ser, Met, Ala, Ile, Asn, Val, Cys or Lys; Xaa at position 93 is Tyr, Cys, Trp, Val, Asp, Asn, Ile, Leu, Met, Phe, Ala or Thr; Xaa at position 97 is Met or Val; Xaa at position 98 is Asp or Glu; Xaa at position 105 is Gln or Asn; Xaa at position 107 is Thr or Ile; Xaa at position 108 is Gln or Thr; Xaa at position 110 is Arg or Leu; Xaa at position 120 is Lys, Arg or Gln; Xaa at position 121 is Thr or Ser; Xaa at position 123 is Thr or Glu; Xaa at position 125 is Asn or Ser; Xaa at position 127 is Ser, Asn, Thr or Lys; Xaa at position 134 is Gly or Ala; Xaa at position 135 is Ser, Asn or Lys; Xaa at position 137 is Asp or Gly; Xaa at position 141 is Val or Ile; Xaa at position 142 is Gly or Asp; Xaa at position 144 is Asp or Glu; Xaa at position 147 is Ile, Thr or Val; Xaa at position 150 is Ser or Thr; Xaa at position 151 is Asn, Arg or Ser; Xaa at position 160 is Thr or Ser; Xaa at position 162 is Ser or Thr; Xaa at position 163 is Asn, Asp or Glu; Xaa at position 164 is Ser or Thr; Xaa at position 166 is Gln or Glu; Xaa at position 167 is Leu or Met; Xaa at position 168 is Thr, Lys or Ala; Xaa at position 171 is Gly, Leu, Gln, Met, Cys, Asn, Asp, Ser or Ala; Xaa at position 172 is Thr, Gly, His, Phe, Glu, Arg, Ser, Asn, Ile, Trp, Lys, Gln, Cys, Val, Ala or Met; Xaa at position 173 is Phe, Gly, His, Leu, Ala, Arg, Asn, Cys, Lys, Trp, Thr, Ser, Tyr or Met; Xaa at position 174 is Ile, Val, Gly, Arg, Asn, Ala, Gln, Met, Cys, Leu, Phe, Tyr, Lys, Glu, Ser, His or Thr; Xaa at position 175 is Val, Ile, Ala, Cys, Glu, Lys, Leu or Met; Xaa at position 176 is Tyr, Met, Phe, Leu or Cys; Xaa at position 177 is Gln, Ile, Met or Pro; Xaa at position 178 is Val, Cys, Thr, Pro, Ala, Met, Gln, Phe, Ile, Ser or Lys; Xaa at position 179 is Val, Phe, Thr, Ile, Cys, Leu, Met, Ser, Ala or Gln; Xaa at position 180 is Met, Leu, Pro, Trp, Asn, Tyr, Gly, Gln, Ala, Val, Phe, Ile, Cys or Ser; Xaa at position 181 is Val, Ala, Leu, Trp, Cys, Thr, Ile or Lys; Xaa at position 182 is Tyr, Phe, Met or His; Xaa at position 183 is Ala, Met, Val, Thr, Asp, Gly, Cys, Ile, Phe, Ser, Gln or Leu; Xaa at position 191 is Arg or Lys; Xaa at position 194 is Gly or Ala; Xaa at position 195 is Asn or Tyr; Xaa at position 200 is Asn or Ser; Xaa at position 203 is Asn or Gln; Xaa at position 204 is Thr or Ala; Xaa at position 206 is Gly or Asp; Xaa at position 209 is Leu or Val; Xaa at position 213 is Tyr or Phe; Xaa at position 220 is Asn or Arg; Xaa at position 221 is Ser or Lys; Xaa at position 222 is Thr or Arg; Xaa at position 226 is Asp, Pro or Glu; Xaa at position 228 is Ser or Gly; Xaa at position 229 is Lys or Asn; Xaa at position 231 is Ile or Val; Xaa at position 232 is Ala, Thr or Glu; Xaa at position 240 is Gln, Arg, Ala, Val, Glu, Met, Gly, Asp, Trp, Asn, Thr, Ile, Ser, Phe, His, Cys or Leu; Xaa at position 241 is Arg, Lys, Glu, Gln, Ser, Ile, Val, Asp, Tyr, Met, Asn, His, Pro, Gly, Leu, Phe, Thr, Ala or Cys; Xaa at position 242 is Asn, Ala, Arg, Lys, His, Ser, Cys, Glu, Pro, Trp, Gln, Thr, Phe, Tyr, Met, Asp, Gly, Leu or Val; Xaa at position 243 is Val, Leu, Ala, Thr, Gly, Cys, Ile, Ser or Met; Xaa at position 244 is Leu, Val, Phe, Ile, Met, Gln, Cys, Trp or Ala; Xaa at position 245 is Met, Ala, Arg, Asp, Glu, Leu, Pro, Ser, Trp, Gly, Val, Lys, Phe, Cys, Thr, His, Ile, Gln, Tyr or Asn; Xaa at position 246 is Glu, Asp, Tyr, Gly, Arg, Val, Ala, Trp, Gln, Ser, Asn, Ile Leu, Met, Cys, Pro, His, Phe, Thr or Lys; Xaa at position 247 is Asn, Leu, Asp, Tyr, Ala, Phe, His, Arg, Lys, Gln, Gly, Val, Ile, Ser, Glu, Pro, Met, Trp, Thr or Cys; Xaa at position 248 is Tyr, Val, Thr, Glu, Phe, Ser, His, Cys, Leu, Trp, Ile, Asp, Gly or Ala; Xaa at position 249 is Asn, Lys, Val, Gly, Met, Asp, Cys, Phe, Arg, Glu, Trp, Tyr, Ser, Ile, Thr, Pro, Leu, Ala, His or Gln; Xaa at position 251 is Gly, Ser or Glu; Xaa at position 254 is Ser or Asn; Xaa at position 258 is Ser or Arg; Xaa at position 259 is Phe, Trp, Tyr, Cys, Met, Leu, Val, Ile or His; Xaa at position 265 is Asn or Asp; and Xaa at position 266 is Asp or Asn; and wherein, 1 to 28 amino acids are optionally deleted from the N-terminus of the polypeptide.

61. The recombinant PIP-1 polypeptide of embodiment 58, wherein the PIP-1 polypeptide comprises an amino acid sequence of SEQ ID NO: 213, wherein Xaa at position 2 is Pro, Thr or Ser; Xaa at position 3 is Ile, Thr, Leu, Val, Met or Ser; Xaa at position 6 is Glu, Gly, Asp or Ala; Xaa at position 8 is Ser, Gly, Asn, Thr or Gln; Xaa at position 19 is Asp, Glu or Cys; Xaa at position 20 is Leu, Val, Ile or Met; Xaa at position 21 is Lys, Ser, Asn, Arg, Thr or Gln; Xaa at position 22 is Ser, Lys, Arg or Thr; Xaa at position 24 is Gln, Gly, Asn or Ala; Xaa at position 25 is Gly or Ala; Xaa at position 26 is Ser, Asn, Thr or Gln; Xaa at position 27 is Leu, Thr, Ala, Ser, Ile, Val or Met; Xaa at position 28 is Arg, Ser, Lys, Thr, Val, Gly, Ala, Met, Asp, Trp, Pro, Leu, His, Cys or Gln; Xaa at position 30 is Ala, Ile, Leu, Val or Met; Xaa at position 35 is Phe, Leu, Ile, Val or Met; Xaa at position 36 is Ala, Ser, Thr, Val, Ile or Leu; Xaa at position 38 is Asn, Arg, Ser, Gln, Lys or Thr; Xaa at position 42 is Phe, Tyr, Trp, Leu, Ile, Val or Met; Xaa at position 43 is Pro, Met, Gly, Gln, Ser, Thr, Arg, Val, Leu, Lys, Asp, Ala, Asn, Phe, Trp, Glu or Cys; Xaa at position 46 is Arg, Lys or His; Xaa at position 48 is Gly, Asp, Ala or Glu; Xaa at position 49 is Phe, Tyr, Trp, Leu, Ile, Val or Met; Xaa at position 53 is Ser, Gly, Ala or Thr; Xaa at position 58 is Tyr or Phe; Xaa at position 60 is Ala, Ser, Gly or Thr; Xaa at position 63 is Gln, Lys, Asn or Arg; Xaa at position 66 is Trp, Tyr, Phe, Arg, Lys, His, Ile, Val or Ser; Xaa at position 77 is Phe, Tyr, Trp, Leu, Ile, Val or Met; Xaa at position 89 is Pro, Leu, Gly, Arg, Thr, Ser, Met, Ala, Ile, Asn, Val, Cys or Lys; Xaa at position 93 is Tyr, Cys, Trp, Val, Asp, Asn, Ile, Leu, Met, Phe, Ala or Thr; Xaa at position 97 is Met, Val, Leu or Ile; Xaa at position 98 is Asp or Glu; Xaa at position 105 is Gln or Asn; Xaa at position 107 is Thr, Ile, Ser, Leu or Val; Xaa at position 108 is Gln, Thr, Ser or Asn; Xaa at position 110 is Arg, Leu, Lys, Ile, Val or Met; Xaa at position 120 is Lys, Arg, Gln or Asn; Xaa at position 121 is Thr or Ser; Xaa at position 123 is Thr, Glu, Ser or Asp; Xaa at position 125 is Asn, Ser, Gln or Thr; Xaa at position 127 is Ser, Asn, Thr, Gln, Lys, Ser or Arg; Xaa at position 134 is Gly or Ala; Xaa at position 135 is Ser, Asn, Thr, Gln, Arg or Lys; Xaa at position 137 is Asp, Gly, Glu or Ala; Xaa at position 141 is Val, Ile or Leu; Xaa at position 142 is Gly, Asp, Ala or Glu; Xaa at position 144 is Asp or Glu; Xaa at position 147 is Ile, Thr, Val, Leu, Met or Ser; Xaa at position 150 is Ser or Thr; Xaa at position 151 is Asn, Arg, Ser, Gln, Lys or Thr; Xaa at position 160 is Thr or Ser; Xaa at position 162 is Ser or Thr; Xaa at position 163 is Asn, Asp, Glu or Gln; Xaa at position 164 is Ser or Thr; Xaa at position 166 is Gln, Glu, Asp or Asn; Xaa at position 167 is Leu, Met, Ile, Val; Xaa at position 168 is Thr, Lys, Ala, Ser, Arg or Gly; Xaa at position 171 is Gly, Leu, Gln, Met, Cys, Asn, Asp, Ser or Ala; Xaa at position 172 is Thr, Gly, His, Phe, Glu, Arg, Ser, Asn, Ile, Trp, Lys, Gln, Cys, Val, Ala or Met; Xaa at position 173 is Phe, Gly, His, Leu, Ala, Arg, Asn, Cys, Lys, Trp, Thr, Ser, Tyr or Met; Xaa at position 174 is Ile, Val, Gly, Arg, Asn, Ala, Gln, Met, Cys, Leu, Phe, Tyr, Lys, Glu, Ser, His or Thr; Xaa at position 175 is Val, Ile, Ala, Cys, Glu, Lys, Leu or Met; Xaa at position 176 is Tyr, Met, Phe, Leu or Cys; Xaa at position 177 is Gln, Ile, Met or Pro; Xaa at position 178 is Val, Cys, Thr, Pro, Ala, Met, Gln, Phe, Ile, Ser or Lys; Xaa at position 179 is Val, Phe, Thr, Ile, Cys, Leu, Met, Ser, Ala or Gln; Xaa at position 180 is Met, Leu; Pro, Trp, Asn, Tyr, Gly, Gln, Ala, Val, Phe, Ile, Cys or Ser; Xaa at position 181 is Val, Ala, Leu, Trp, Cys, Thr, Ile or Lys; Xaa at position 182 is Tyr, Phe, Met or His; Xaa at position 183 is Ala, Met, Val, Thr, Asp, Gly, Cys, Ile, Phe, Ser, Gln or Leu; Xaa at position 191 is Arg or Lys; Xaa at position 194 is Gly or Ala; Xaa at position 195 is Asn, Tyr, Gln or Trp; Xaa at position 200 is Asn, Ser, Thr or Gln; Xaa at position 203 is Asn or Gln; Xaa at position 204 is Thr, Ala, Ser or Gly; Xaa at position 206 is Gly, Asp, Ala or Glu; Xaa at position 209 is Leu, Val, Ile or Met; Xaa at position 213 is Tyr or Phe; Xaa at position 220 is Asn, Arg, Gln or Lys; Xaa at position 221 is Ser, Lys, Thr or Arg; Xaa at position 222 is Thr, Arg, Ser or Lys; Xaa at position 226 is Asp, Pro, Glu or Gln; Xaa at position 228 is Ser or Gly; Xaa at position 229 is Lys, Asn, Arg or Gln; Xaa at position 231 is Ile, Val, Leu or Met; Xaa at position 232 is Ala, Thr, Ser, Gly, Asp or Glu; Xaa at position 240 is Gln, Arg, Ala, Val, Glu, Met, Gly, Asp, Trp, Asn, Thr, Ile, Ser, Phe, His, Cys or Leu; Xaa at position 241 is Arg, Lys, Glu, Gln, Ser, Ile, Val, Asp, Tyr, Met, Asn, His, Pro, Gly, Leu, Phe, Thr, Ala or Cys; Xaa at position 242 is Asn, Ala, Arg, Lys, His, Ser, Cys, Glu, Pro, Trp, Gln, Thr, Phe, Tyr, Met, Asp, Gly, Leu or Val; Xaa at position 243 is Val, Leu, Ala, Thr, Gly, Cys, Ile, Ser or Met; Xaa at position 244 is Leu, Val, Phe, Ile, Met, Gln, Cys, Trp or Ala; Xaa at position 245 is Met, Ala, Arg, Asp, Glu, Leu, Pro, Ser, Trp, Gly, Val, Lys, Phe, Cys, Thr, His, Ile, Gln, Tyr or Asn; Xaa at position 246 is Glu, Asp, Tyr, Gly, Arg, Val, Ala, Trp, Gln, Ser, Asn, Ile Leu, Met, Cys, Pro, His, Phe, Thr or Lys; Xaa at position 247 is Asn, Leu, Asp, Tyr, Ala, Phe, His, Arg, Lys, Gln, Gly, Val, Ile, Ser, Glu, Pro, Met, Trp, Thr or Cys; Xaa at position 248 is Tyr, Val, Thr, Glu, Phe, Ser, His, Cys, Leu, Trp, Ile, Asp, Gly or Ala; Xaa at position 249 is Asn, Lys, Val, Gly, Met, Asp, Cys, Phe, Arg, Glu, Trp, Tyr, Ser, Ile, Thr, Pro, Leu, Ala, His or Gln; Xaa at position 251 is Gly, Ser, Thr, Ala, Asp or Glu; Xaa at position 254 is Ser, Asn, Thr or Gln; Xaa at position 258 is Ser, Arg, Thr or Lys; Xaa at position 259 is Phe, Trp, Tyr, Cys, Met, Leu, Val, Ile or His; Xaa at position 265 is Asn, Asp, Gln or Glu; and Xaa at position 266 is Asp, Asn, Gln or Glu; and wherein, 1 to 28 amino acids are optionally deleted from the N-terminus of the polypeptide.

62. The recombinant PIP-1 polypeptide of embodiment 55, comprising an amino acid sequence of SEQ ID NO: 2 or a fragment thereof.

63. The recombinant PIP-1 polypeptide of embodiment 55, consisting essentially of an amino acid sequence of SEQ ID NO: 2.

64. The recombinant PIP-1 polypeptide of embodiment 55, wherein the PIP-1 polypeptide is encoded by the polynucleotide of SEQ ID NO: 1.

65. The recombinant PIP-1 polypeptide of embodiment 46, comprising one or more properties selected from:
   a) an amino acid motif as represented by positions 64-79 of SEQ ID NO: 213;
   b) an amino acid motif as represented by positions 149-159 of SEQ ID NO: 213;
   c) an amino acid motif as represented by positions 171-183 of SEQ ID NO: 213;
   e) insecticidal activity against an insect pest of the order Hemiptera;
   f) insecticidal activity against an insect pest of the order Lepidoptera;
   g) orally active; and
   h) a calculated molecular weight of between about 15 kD to about 35 kD.

66. A plant capable of expressing the recombinant PIP-1 polypeptide of embodiment 46, 47, 48, 49, 50, 51, 52, 53, 54, 55, 56, 57, 58, 59, 60, 61, 62, 63, 64 or 65.

67. The plant of embodiment 66, wherein the plant is a monocotyledon.

68. The plant of embodiment 66, wherein the plant is a dicotyledon.

69. The plant of embodiment 66, wherein the plant is selected from barley, corn, oat, rice, rye, *sorghum*, turf grass, sugarcane, wheat, alfalfa, banana, broccoli, bean, cabbage, canola, carrot, cassava, cauliflower, celery, *citrus*, cotton, a cucurbit, eucalyptus, flax, garlic, grape, onion, lettuce, pea, peanut, pepper, potato, poplar, pine, sunflower, safflower, soybean, strawberry, sugar beet, sweet potato, tobacco, tomato ornamental, shrub, nut, chickpea, pigeon pea, millets, hops, and pasture grasses.

70. The plant of embodiment 66, 67, 68, 69 or 70 wherein the plant expresses one or more additional transgenic traits.

71. The plant of embodiment 70, wherein the one or more additional transgenic trait is selected insect resistance, herbicide resistance, fungal resistance, viral resistance, stress tolerance, disease resistance, male sterility, stalk strength, increased yield, modified starches, improved oil profile, balanced amino acids, high lysine or methionine, increased digestibility, improved fiber quality, flowering, ear and seed development, enhancement of nitrogen utilization efficiency, altered nitrogen responsiveness, drought resistance or tolerance, cold resistance or tolerance, and salt resistance or tolerance, and increased yield under stress.

72. A composition, comprising an insecticidally-effective amount of the recombinant PIP-1 polypeptide of embodiment 46, 47, 48, 49, 50, 51, 52, 53, 54, 55, 56, 57, 58, 59, 60, 61, 62, 63, 64 or 65.

73. The composition of embodiment 72, further comprising an agriculturally suitable carrier.

74. The composition of embodiment 73, wherein the carrier is selected from a powder, a dust, pellets, granules, spray, emulsion, colloid, and solution.

75. The composition of embodiment 72, 73 or 74, further comprising one or more herbicides, insecticides or fungicides.

76. The composition of embodiment 75, wherein the one or more insecticides are pesticidal proteins.

77. The composition of embodiment 76, wherein the one or more pesticidal proteins are selected from a Cry1 protein, a Cry2 protein, a Cry3 protein, a Cry4 protein, a Cry5 protein, a Cry6 protein, a Cry7 protein, a Cry8 protein, a Cry9 protein, a Cry15 protein, Cry22 protein, a Cry23 protein, a Cry32 protein, a Cry34 protein, a Cry35 protein, a Cry36 protein, a Cry37 protein, a Cry43 protein, a Cry46 protein, a Cry51 protein, a Cry55 protein, a Cry binary toxin, a Cyt protein, a VIP toxin, a SIP protein, an insecticidal lipase, an insecticidal chitinase, and a snake venom protein.

78. A method for controlling an insect pest population, comprising contacting the insect pest population with an insecticidally-effective amount of the recombinant PIP-1 polypeptide of embodiment 46, 47, 48, 49, 50, 51, 52, 53, 54, 55, 56, 57, 58, 59, 60, 61, 62, 63, 64 or 65.

79. A method of inhibiting growth or killing an insect pest, comprising contacting the insect pest with a insecticidally-effective amount of recombinant PIP-1 polypeptide of embodiment 46, 47, 48, 49, 50, 51, 52, 53, 54, 55, 56, 57, 58, 59, 60, 61, 62, 63, 64 or 65.

80. A method for controlling an insect pest population resistant to a pesticidal protein, comprising contacting the resistant insect pest population with a insecticidally-effective amount of the recombinant PIP-1 polypeptide of embodiment 46, 47, 48, 49, 50, 51, 52, 53, 54, 55, 56, 57, 58, 59, 60, 61, 62, 63, 64 or 65.

81. The method of controlling an insect pest population resistant to an pesticidal protein, comprising contacting the population with a insecticidally-effective amount of the recombinant PIP-1 polypeptide of embodiment 46, 47, 48, 49, 50, 51, 52, 53, 54, 55, 56, 57, 58, 59, 60, 61, 62, 63, 64 or 65, wherein the pesticidal protein is selected from Cry1Ac, Cry1Ab, Cry1A.105, Cry1Ac, Cry1F, Cry1Fa2, Cry1F, Cry2Ab, Cry3A, mCry3A, Cry3Bb1, Cry34Ab1, Cry35Ab1, Vip3A, Cry9c, eCry3.1Ab and CBI-Bt.

82. A method for protecting a plant from an insect pest, comprising expressing in the plant or cell thereof a recombinant PIP-1 polypeptide of embodiment 46, 47, 48, 49, 50, 51, 52, 53, 54, 55, 56, 57, 58, 59, 60, 61, 62, 63, 64 or 65.

83. A biologically pure culture of a *Pseudomonas chlororaphis* strain SS44C4 deposited under accession # NRRLB-50613.

84. A method of isolating a polypeptide having insecticidal activity from a *Pseudomonas chlororaphis* strain, comprising
   a) obtaining a protein cell lysate from a bacterial isolate;
   b) screening the protein cell lysate for insecticidal activity; and
   c) isolating an insecticidal protein from the protein cell lysate.

85. A recombinant receptor to the polypeptide of SEQ ID NO: 2, SEQ ID NO: 4, SEQ ID NO: 332 or SEQ ID NO: 6.

86. The recombinant receptor of embodiment 85, wherein the receptor is isolated from a Hemiptera.

87. A method of identifying a PIP-1 polypeptide in a biological sample, comprising contacting the biological sample with the receptor of embodiment 85 or 86.

88. An isolated antibody or antigen-binding portion thereof, wherein the antibody binds specifically to the PIP-1 polypeptide of embodiment 46, 47, 48, 49, 50, 51, 52, 53, 54, 55, 56, 57, 58, 59, 60, 61, 62, 63, 64 or 65.

89. A method of detecting a PIP-1 polypeptide in a biological sample comprising, contacting the protein with the antibody of embodiment 88.

90. A method of isolating a PIP-1 polypeptide in a biological sample comprising, contacting the protein with the antibody of embodiment 88.

91. A method of controlling Lepidoptera and/or Hemiptera insect infestation in a transgenic plant and providing insect resistance management, comprising expressing in the plant at least two different insecticidal proteins having different modes of action.

92. The method of embodiment 91, wherein one of the at least two insecticidal proteins comprises a PIP-1 polypeptide of embodiment 46, 47, 48, 49, 50, 51, 52, 53, 54, 55, 56, 57, 58, 59, 60, 61, 62, 63, 64 or 65 insecticidal to insects in the order Lepidoptera and/or Hemiptera.

93. The method of embodiment 92, wherein one of the at least two insecticidal proteins comprises a Cry protein insecticidal to insects in the order Lepidoptera and/or Hemiptera.

94. A method of reducing likelihood of emergence of Lepidoptera and/or Hemiptera insect resistance to transgenic plants expressing in the plants insecticidal proteins to control the insect species, comprising expressing a PIP-1A polypeptide of embodiment 46, 47, 48, 49, 50, 51, 52, 53, 54, 55, 56, 57, 58, 59, 60, 61, 62, 63, 64 or 65 insecticidal to the insect species in combination with an insecticidal protein to the insect species having a different modes of action compared to the PIP-1A polypeptide.

95. A means for effective Lepidoptera and/or Hemiptera insect resistance management, comprising co-expressing at high levels in transgenic plants two or more insecticidal proteins toxic to Lepidoptera and/or Hemiptera insects but each exhibiting a different mode of effectuating its inhibiting growth or killing activity, wherein the two or more insecticidal proteins comprise a PIP-1 polypeptide of embodiment 46, 47, 48, 49, 50, 51, 52, 53, 54, 55, 56, 57, 58, 59, 60, 61, 62, 63, 64 or 65 and a Cry protein.

96. A method for obtaining regulatory approval for planting or commercialization of plants expressing proteins insecticidal to insects in the order Lepidoptera and/or Hemiptera, comprising the step of referring to, submitting or relying on insect assay binding data showing that the PIP-1 polypeptide of embodiment 46, 47, 48, 49, 50, 51, 52, 53, 54, 55, 56, 57, 58, 59, 60, 61, 62, 63, 64 or 65 does not compete with binding sites for Cry proteins in such insects.

97. A plant or progeny thereof, comprising the recombinant nucleic acid molecule of SEQ ID NO: 3.

98. A plant or progeny thereof stably transformed with the recombinant nucleic acid molecule of SEQ ID NO: 3.

99. The plant or progeny thereof of embodiment 97 or 98, wherein the plant is a monocotyledon.

100. The plant or progeny thereof of embodiment 97 or 98, wherein the plant is a dicotyledon.

101. The plant or progeny thereof of embodiment 97 or 98, wherein the plant is selected from barley, corn, oat, rice, rye, *sorghum*, turf grass, sugarcane, wheat, alfalfa, banana, broccoli, bean, cabbage, canola, carrot, cassava, cauliflower, celery, *citrus*, cotton, a cucurbit, eucalyptus, flax, garlic, grape, onion, lettuce, pea, peanut, pepper, potato, poplar, pine, sunflower, safflower, soybean, strawberry, sugar beet, sweet potato, tobacco, tomato ornamental, shrub, nut, chickpea, pigeon pea, millets, hops, and pasture grasses.

102. The plant or progeny thereof of embodiment 97, 98, 99, 100 or 101, further comprising one or more additional transgenic traits.

103. An expression cassette, comprising the recombinant nucleic acid molecule of SEQ ID NO: 3 or SEQ ID NO: 331, wherein the nucleic acid is operably linked to one or more regulatory sequences directing expression of the polypeptide of SEQ ID NO: 4 or SEQ ID NO: 332.

104. A plant, comprising the expression cassette of embodiment 103.

105. A plant cell, comprising the expression cassette of embodiment 103.

106. A seed or grain of the plant of embodiment 97, 98, 99, 100, 101 or 102, wherein the seed or grain comprises the recombinant nucleic acid molecule of SEQ ID NO: 3.

107. The seed of embodiment 106, wherein one or more seed treatment has been applied to the seed.

108. A method for expressing in a plant a insecticidal protein, comprising
(a) inserting into the plant cell a nucleic acid sequence comprising in the 5' to 3' direction an operably linked recombinant, double-stranded DNA molecule, wherein the recombinant, double-stranded DNA molecule comprises
(i) a promoter that functions in the plant cell;
(ii) a nucleic acid molecule encoding the protein of SEQ ID NO: 4; and
(iii) a 3' non-translated polynucleotide that functions in the cells of the plant to cause termination of transcription;
(b) obtaining a transformed plant cell comprising the nucleic acid sequence of step (a); and
(c) generating from the transformed plant cell a plant capable of expressing the protein of SEQ ID NO: 4.

109. A plant produced by the method of embodiment 108.

110. Seed or grain of the plant of embodiment 109.

111. The method of embodiment 108, wherein the plant further comprises one or more additional transgenic traits.

112. A plant capable of expressing a recombinant protein of SEQ ID NO: 4.

113. A method for controlling an insect pest population, comprising contacting the insect pest population with a insecticidally-effective amount of a recombinant protein of SEQ ID NO: 4.

114. A method of inhibiting growth or killing an insect pest, comprising contacting the insect pest with a insecticidally-effective amount of a recombinant protein of SEQ ID NO: 4.

115. A method for controlling an insect pest population resistant to a pesticidal protein, comprising contacting the insect pest population with a insecticidally-effective amount of a recombinant protein of SEQ ID NO: 4.

116. A method for protecting a plant from an insect pest, comprising expressing in the plant or cell thereof a recombinant insecticidal protein of SEQ ID NO: 4.

117. A recombinant nucleic acid molecule encoding a insecticidal protein comprising a polypeptide having at least 80% identity to the amino acid sequence of SEQ ID NO: 6.

118. The recombinant nucleic acid molecule of embodiment 117, wherein the insecticidal protein is orally active.

119. The recombinant nucleic acid molecule of embodiment 117 or 118, wherein the insecticidal protein has insecticidal activity against an insect pest in the order Hemiptera.

120. The recombinant nucleic acid molecule of embodiment 119, wherein the insecticidal protein has insecticidal activity against an insect pest in the family Pentatomidae.

121. The recombinant nucleic acid molecule of embodiment 117, 118, 119 or 120, wherein the insecticidal protein has insecticidal activity against an insect pest in the order Lepidoptera.

122. The recombinant nucleic acid molecule of embodiment 117, 118, 119, 120 or 121, wherein the nucleic acid molecule is produced by a *Pseudomonas entomophila* strain.

123. The recombinant nucleic acid molecule of embodiment 117, wherein the insecticidal protein comprises an amino acid motif as represented by positions 171-183 of SEQ ID NO: 6 or positions 171-183 of SEQ ID NO: 213.

124. The recombinant nucleic acid molecule of embodiment 123, wherein the insecticidal protein further comprises any one or more amino acid motifs as represented by positions 149-159 of SEQ ID NO: 213 and positions 69-79 of SEQ ID NO: 213.

125. A recombinant insecticidal protein, comprising a polypeptide having at least 80% identity to the amino acid sequence of SEQ ID NO: 6.

126. The recombinant insecticidal protein of embodiment 125, wherein the insecticidal protein is orally active.

127. The recombinant insecticidal protein of embodiment 125 or 126, wherein the insecticidal protein has insecticidal activity against an insect pest in the order Hemiptera.

128. The recombinant insecticidal protein of embodiment 127, wherein the insecticidal protein has insecticidal activity against an insect pest in the family Pentatomidae.

129. The recombinant insecticidal protein of embodiment 125, 126, 127 or 128, wherein the insecticidal protein has insecticidal activity against an insect pest in the order Lepidoptera.

130. The recombinant insecticidal protein of embodiment 125, 126, 127, 128 or 129, wherein the nucleic acid molecule is produced by a *Pseudomonas entomophila* strain.

131. The recombinant insecticidal protein of embodiment 125, wherein the insecticidal protein comprises an amino acid motif as represented by positions 171-183 of SEQ ID NO: 213.

132. The recombinant insecticidal protein of embodiment 131, wherein the insecticidal protein further comprises any one or more amino acid motifs as represented by positions 149-159 of SEQ ID NO: 213, and positions 69-79 of SEQ ID NO: 213.

133. A plant or progeny thereof, comprising the recombinant nucleic acid molecule of embodiment 117, 118, 119, 120, 121, 122, 123 or 124.

134. A plant or progeny thereof stably transformed with the recombinant nucleic acid molecule of embodiment 117, 118, 119, 120, 121, 122, 123 or 124.

135. The plant or progeny thereof of embodiment 133 or 134, wherein the plant is a monocotyledon.

136. The plant or progeny thereof of embodiment 133 or 134, wherein the plant is a dicotyledon.

137. The plant or progeny thereof of embodiment 133 or 134, wherein the plant is selected from barley, corn, oat, rice, rye, sorghum, turf grass, sugarcane, wheat, alfalfa, banana, broccoli, bean, cabbage, canola, carrot, cassava, cauliflower, celery, citrus, cotton, a cucurbit, eucalyptus, flax, garlic, grape, onion, lettuce, pea, peanut, pepper, potato, poplar, pine, sunflower, safflower, soybean, strawberry, sugar beet, sweet potato, tobacco, tomato ornamental, shrub, nut, chickpea, pigeon pea, millets, hops, and pasture grass plant cells.

138. The plant or progeny thereof of embodiment 133, 134, 135, 136 or 137, further comprising one or more additional transgenic traits.

139. An expression cassette, comprising the recombinant nucleic acid molecule encoding the insecticidal protein of embodiment 117, 118, 119, 120, 121, 122, 123 or 124, wherein the nucleic acid is operably linked to one or more regulatory sequences directing expression of the insecticidal protein.

140. A plant, comprising the expression cassette of embodiment 139.

141. A plant cell, comprising the expression cassette of embodiment 139.

142. Seed or grain of the plant of embodiment 133, 134, 135, 136, 137 or 138, wherein the seed or grain comprises the recombinant nucleic acid molecule.

143. The seed of embodiment 142, wherein one or more seed treatment has been applied to the seed.

144. A method for expressing in a plant a insecticidal protein, comprising
(a) inserting into the plant cell a nucleic acid sequence comprising in the 5' to 3' direction an operably linked recombinant, double-stranded DNA molecule, wherein the recombinant, double-stranded DNA molecule comprises
(i) a promoter that functions in the plant cell;
(ii) a nucleic acid molecule encoding the insecticidal protein of embodiment 125, 126, 127, 128, 129, 130, 131 or 132; and
(iii) a 3' non-translated polynucleotide that functions in the cells of the plant to cause termination of transcription;
(b) obtaining a transformed plant cell comprising the nucleic acid sequence of step (a); and
(c) generating from the transformed plant cell a plant capable of expressing the insecticidal protein.

145. A plant produced by the method of embodiment 144.

146. Seed or grain of the plant of embodiment 145.

147. The method of embodiment 144, wherein the plant further comprises one or more additional transgenic traits.

148. A plant capable of expressing a recombinant insecticidal protein of embodiment 125, 126, 127, 128, 129, 130, 131 or 132.

149. A method for controlling an insect pest population, comprising contacting the insect pest population with an insecticidally-effective amount of a recombinant insecticidal protein of embodiment 125, 126, 127, 128, 129, 130, 131 or 132.

150. A method of inhibiting growth or killing an insect pest, comprising contacting the insect pest with a insecticidally-effective amount of a recombinant insecticidal protein of embodiment 125, 126, 127, 128, 129, 130, 131 or 132.

151. A method for controlling an insect pest population resistant to a pesticidal protein, comprising contacting the insect pest population with a pesticidally-effective amount of a recombinant protein of embodiment 125, 126, 127, 128, 129, 130, 131 or 132.

152. A method for protecting a plant from an insect pest, comprising expressing in the plant or cell thereof a recombinant pesticidal protein of embodiment 125, 126, 127, 128, 129, 130, 131 or 132.

153. A method of controlling Lepidoptera and/or Hemiptera insect infestation in a transgenic plant and providing insect resistance management, comprising expressing in the plant at least two different insecticidal proteins having different modes of action, wherein one of the at least two insecticidal proteins comprises a insecticidal protein of embodiment 125, 126, 127, 128, 129, 130, 131 or 132, insecticidal to insects in the order Lepidoptera and/or Hemiptera.

154. The method of embodiment 153, wherein one of the at least two insecticidal proteins comprises a Cry protein insecticidal to insects in the order Lepidoptera and/or Hemiptera.

155. A method of reducing likelihood of emergence of Lepidoptera and/or Hemiptera insect species resistance to transgenic plants expressing in the plants insecticidal proteins to control the insect species, comprising expressing a first insecticidal protein of embodiment 125, 126, 127, 128, 129, 130, 131 or 132, insecticidal to the insect species in combination with a second insecticidal protein insecticidal to the insect species having a different mode of action compared to the first insecticidal protein.

156. A means for effective Lepidoptera and/or Hemiptera insect resistance management, comprising co-expressing at high levels in transgenic plants two or more insecticidal proteins toxic to Lepidoptera and/or Hemiptera insects but each exhibiting a different mode of effectuating its inhibiting growth or killing activity, wherein one of the two or more insecticidal proteins comprise a insecticidal protein of embodiment 125, 126, 127, 128, 129, 130, 131 or 132 and one of the two or more insecticidal proteins comprise a Cry protein.

157. A method for obtaining regulatory approval for planting or commercialization of plants expressing proteins insecticidal to insects in the order Lepidoptera and/or Hemiptera, comprising the step of referring to, submitting or relying on insect assay binding data showing that the insecticidal protein of embodiment 125, 126, 127, 128, 129, 130, 131 or 132 does not compete with binding sites for a Cry protein in the insects.

158. A method of controlling Lepidoptera and/or Hemiptera insect infestation in a transgenic plant and providing insect resistance management, comprising expressing in the plant at least two different insecticidal proteins having different modes of action, wherein one of the at least two insecticidal proteins comprises the amino acid sequence of SEQ ID NO: 4, insecticidal to insects in the order Lepidoptera and/or Hemiptera.

159. The method of embodiment 158, wherein one of the at least two insecticidal proteins comprises a Cry protein insecticidal to insects in the order Lepidoptera and/or Hemiptera.

160. A method of reducing likelihood of emergence of Lepidoptera and/or Hemiptera insect species resistance to transgenic plants expressing in the plants insecticidal proteins to control the insect species, comprising expressing the insecticidal protein of SEQ ID NO: 4 insecticidal to the insect species in combination with an insecticidal protein insecticidal to the insect species having a different modes of action compared to the protein of SEQ ID NO: 4.

161. A means for effective Lepidoptera and/or Hemiptera insect resistance management, comprising co-expressing at high levels in transgenic plants two or more insecticidal proteins toxic to Lepidoptera and/or Hemiptera insects but each exhibiting a different mode of effectuating its inhibiting growth or killing activity, wherein one of the two or more insecticidal proteins comprise the insecticidal protein of SEQ ID NO: 4 and one of the two or more insecticidal proteins comprise a Cry protein.

162. A method for obtaining regulatory approval for planting or commercialization of plants expressing proteins insecticidal to insects in the order Lepidoptera and/or Hemiptera, comprising the step of referring to, submitting or relying on insect assay binding data showing that the insecticidal protein of SEQ ID NO: 4 does not compete with binding sites for a Cry protein in the insects.

BRIEF DESCRIPTION OF THE FIGURES

FIG. 1 shows the alignment of PIP-1A (SEQ ID NO: 2); the active insecticidal protein orthologs PSEEN3174 (SEQ ID NO: 6) and PIP-1B (SEQ ID NO: 4); and the inactive homologs AECFG_592740 (SEQ ID NO: 12); Pput_1063 (SEQ ID NO: 8); and Pput_1064 (SEQ ID NO: 10). The motifs [amino acids 64-79 of SEQ ID NO: 2 (motif 1), amino acids 149-159 of SEQ ID NO: 2 (motif 2), amino acids 171-183 of SEQ ID NO: 2 (motif 3), and amino acids 240-249 of SEQ ID NO: 2 (motif 4)] are indicated in bold and underline in the PIP-1A sequence. The predicted secondary structures of selected beta-sheets are indicated with "B" above the sequence.

FIG. 3A-3C shows the alignment of *Pseudomonas chlororaphis* strain SS44C4 16S ribosomal DNA (SEQ ID NO: 216) and *Pseudomonas entomophila* L48 16S ribosomal DNA (SEQ ID NO: 217) having 96.8% identity. Differences between the sequences are indicated in Bold and Underlined.

FIG. 4 shows the results of the *Lygus* insecticidal activity screening of PIP-1A polypeptide variants having multiple amino acid substitutions at residues 240-249 of SEQ ID NO: 2 (motif 4). The insecticidal activity was scored from 0 to 8 with 8 being the most active.

FIG. 5 shows the sequence alignment of PIP-1A (SEQ ID NO: 2), PIP-1B (SEQ ID NO: 4), PIP-1C (SEQ ID NO: 332) and PSEEN3174 (SEQ ID NO: 6).

DETAILED DESCRIPTION

Figure 2:
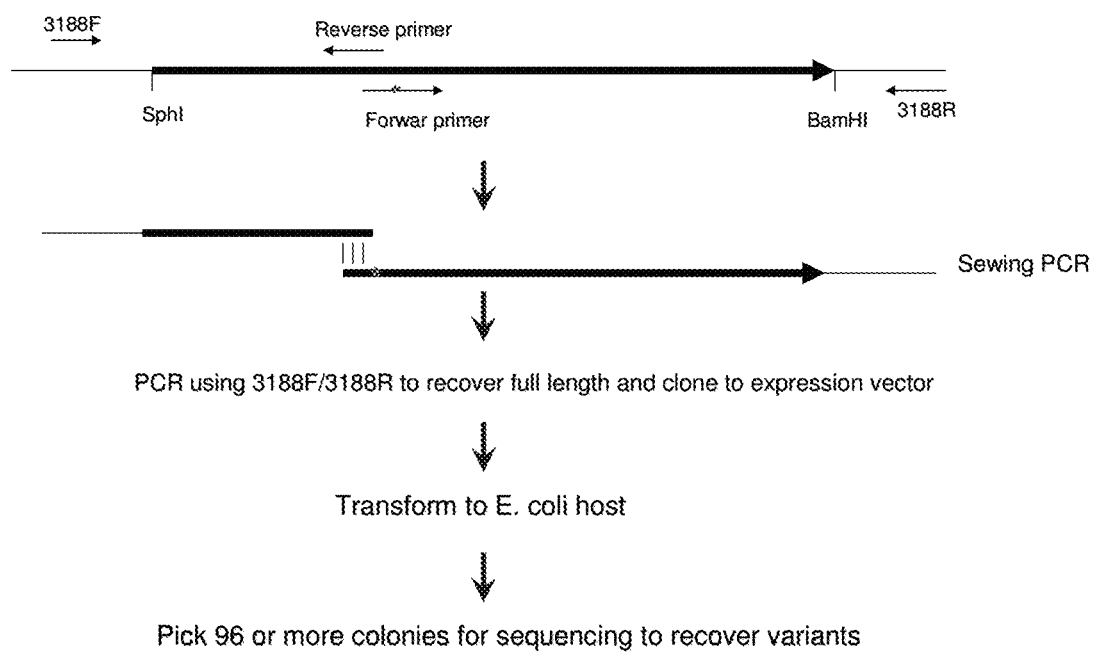
FIG. 2 illustrates a generalized sewing and rescuing PCR mutagenesis strategy using degenerate oligonucleotides to generate partially or fully saturated amino acid substitutions at positions in the PIP-1A protein.

It is to be understood that this invention is not limited to the particular methodology, protocols, cell lines, genera, and reagents described, as such may vary. It is also to be understood that the terminology used herein is for the purpose of describing particular embodiments only, and is not intended to limit the scope of the present invention.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

The present disclosure is drawn to compositions and methods for controlling pests. The methods involve transforming organisms with a nucleic acid sequence encoding a PIP-1 polypeptide. In particular, the nucleic acid sequences of the embodiments are useful for preparing plants and microorganisms that possess pesticidal activity. Thus, transformed bacteria, plants, plant cells, plant tissues and seeds are provided. Compositions are pesticidal nucleic acids and proteins of bacterial species. The nucleic acid sequences find use in the construction of expression vectors for subsequent transformation into organisms of interest, as probes for the isolation of other homologous (or partially homologous) genes, and for the generation of altered PIP-1 polypeptides by methods known in the art, such as site directed mutagenesis, domain swapping or DNA shuffling. The PIP-1 polypeptides find use in controlling, inhibiting growth or killing Lepidopteran, Coleopteran, Dipteran, fungal, Hemipteran, and nematode pest populations and for producing compositions with pesticidal activity. Insect pests of interest include, but are not limited to, the superfamily of stink bugs and other related insects including, but not limited to, species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus*, and *Bagrada hilaris* (Bagrada Bug)), the family Plataspidae (*Megacopta cribraria*—Bean plataspid), and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hübner.

By "pesticidal toxin" or "pesticidal protein" is intended a toxin that has toxic activity against one or more pests, including, but not limited to, members of the Lepidoptera, Diptera, Hemiptera and Coleoptera orders or the Nematoda phylum or a protein that has homology to such a protein. Pesticidal proteins have been isolated from organisms including, for example, *Bacillus* sp., *Pseudomonas* sp., *Photorhabdus* sp., *Xenorhabdus* sp., *Clostridium bifermentans* and *Paenibacillus popilliae*. Pesticidal proteins include but are not limited to: insecticidal proteins from *Pseudomonas* sp. such as PSEEN3174 (Monalysin, (2011) *PLoS Pathogens*, 7:1-13), from *Pseudomonas protegens* strain CHA0 and Pf-5 (previously *fluorescens*) (Pechy-Tarr, (2008) Environmental Microbiology 10:2368-2386: GenBank Accession No. EU400157); from *Pseudomonas Taiwanensis* (Liu, et al., (2010) *J. Agric. Food Chem.* 58:12343-12349) and from *Pseudomonas pseudoalcligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379, 946; and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry 51 and Cry55 classes of δ-endotoxin genes and the *B. thuringiensis* cytolytic Cyt1 and Cyt2 genes. Members of these classes of *B. thuringiensis* insecticidal proteins include, but are not limited to Cry1Aa1 (Accession # Accession # M11250), Cry1Aa2 (Accession # M10917), Cry1Aa3 (Accession # DQ0348), Cry1Aa4 (Accession # X13535), Cry1Aa5 (Accession # D17518), Cry1Aa6 (Accession # U43605), Cry1Aa7 (Accession # AF081790), Cry1Aa8 (Accession #126149), Cry1Aa9 (Accession # AB026261), Cry1Aa10 (Accession # AF154676), Cry1Aa11 (Accession # Y09663), Cry1Aa12 (Accession # AF384211), Cry1Aa13 (Accession # AF510713), Cry1Aa14 (Accession # AY197341), Cry1Aa15 (Accession # DQ062690), Cry1Ab1 (Accession # M13898), Cry1Ab2 (Accession # M12661), Cry1Ab3 (Accession # M15271), Cry1Ab4 (Accession # DQ0117), Cry1Ab5 (Accession # X04698), Cry1Ab6 (Accession # M37263), Cry1Ab7 (Accession # X13233), Cry1Ab8 (Accession # M16463), Cry1Ab9 (Accession # X54939), Cry1Ab10 (Accession # A29125), Cry1Ab11 (Accession #112419), Cry1Ab12 (Accession # AF059670), Cry1Ab13 (Accession # AF254640), Cry1Ab14 (Accession # U94191), Cry1Ab15 (Accession # AF358861), Cry1Ab16 (Accession # AF375608), Cry1Ab17 (Accession # AAT46415), Cry1Ab18 (Accession # AAQ88259), Cry1Ab19 (Accession # AY847289), Cry1Ab20 (Accession # DQ241675), Cry1Ab21 (Accession # EF683163), Cry1Ab22 (Accession # ABW87320), Cry1Ab-like (Accession # AF327924), Cry1Ab-like (Accession # AF327925), Cry1Ab-like (Accession # AF327926), Cry1Ab-like (Accession # DQ781309), Cry1Ac1 (Accession # M11068), Cry1Ac2 (Accession # M35524), Cry1Ac3 (Accession # X54159), Cry1Ac4 (Accession # M73249), Cry1Ac5 (Accession # M73248), Cry1Ac6 (Accession # U43606), Cry1Ac7 (Accession # U87793), Cry1Ac8 (Accession # U87397), Cry1Ac9 (Accession # U89872), Cry1Ac10 (Accession # AJ002514), Cry1Ac11 (Accession # AJ130970), Cry1Ac12 (Accession #112418), Cry1Ac13 (Accession # AF148644), Cry1Ac14 (Accession # AF492767), Cry1Ac15 (Accession # AY122057), Cry1Ac16 (Accession # AY730621), Cry1Ac17 (Accession # AY925090), Cry1Ac18 (Accession # DQ023296), Cry1Ac19 (Accession # DQ195217), Cry1Ac20 (Accession # DQ285666), Cry1Ac21 (Accession # DQ062689), Cry1Ac22 (Accession # EU282379), Cry1Ac23 (Accession # AM949588), Cry1Ac24 (Accession # ABL01535), Cry1Ad1 (Accession # M73250), Cry1Ad2 (Accession # A27531), Cry1Ae1 (Accession # M65252), Cry1Af1 (Accession # U82003), Cry1Ag1 (Accession # AF081248), Cry1Ah1 (Accession # AF281866), Cry1Ah2 (Accession # DQ269474), Cry1Ai1 (Accession # AY174873), Cry1A-like (Accession # AF327927), Cry1Ba1 (Accession # X06711), Cry1Ba2 (Accession # X95704), Cry1Ba3 (Accession # AF368257), Cry1Ba4 (Accession # AF363025), Cry1Ba5 (Accession # AB020894), Cry1Ba6 (Accession # ABL60921), Cry1Bb1 (Accession # L32020), Cry1Bc1 (Accession # Z46442), Cry1Bd1 (Accession # U70726), Cry1Bd2 (Accession # AY138457), Cry1Be1 (Accession # AF077326), Cry1Be2 (Accession # AAQ52387), Cry1Bf1 (Accession # AX189649), Cry1Bf2 (Accession # AAQ52380), Cry1Bg1 (Accession # AY176063), Cry1aCa1 (Accession # X07518), Cry1Ca2 (Accession # X13620), Cry1Ca3 (Accession # M73251), Cry1Ca4 (Accession # A27642), Cry1Ca5 (Accession # X96682), Cry1Ca6 [1] (Accession # AF215647), Cry1Ca7 (Accession # AY015492), Cry1Ca8 (Accession # AF362020), Cry1Ca9 (Accession # AY078160), Cry1aCa10 (Accession # AF540014), Cry1aCa11 (Accession # AY955268), Cry1aCb1 (Accession # M97880), Cry1aCb2 (Accession # AY007686), Cry1Cb3 (Accession # EU679502), Cry1aCb-like (Accession # AAX63901), Cry1Da1 (Accession # X54160), Cry1Da2 (Accession #176415), Cry1Db1 (Accession # Z22511), Cry1Db2 (Accession # AF358862), Cry1Dc1 (Accession # EF059913), Cry1Ea1 (Accession # X53985), Cry1Ea2 (Accession # X56144), Cry1Ea3 (Accession # M73252), Cry1Ea4 (Accession # U94323), Cry1Ea5 (Accession # A15535), Cry1Ea6 (Accession # AF202531), Cry1Ea7 (Accession # AAW72936), Cry1Ea8 (Accession # ABX11258), Cry1Eb1 (Accession # M73253), Cry1 Fa1 (Accession # M63897), Cry1 Fa2 (Accession # M73254), Cry1 Fb1 (Accession # Z22512), Cry1 Fb2 (Accession # AB012288), Cry1 Fb3 (Accession # AF062350), Cry1 Fb4 (Accession #173895), Cry1 Fb5 (Accession # AF336114), Cry1 Fb6 (Accession # EU679500), Cry1 Fb7 (Accession # EU679501), Cry1Ga1 (Accession # Z22510), Cry1Ga2 (Accession # Y09326), Cry1Gb1 (Accession # U70725), Cry1Gb2 (Accession # AF288683), Cry1Gc (Accession # AAQ52381), Cry1Ha1 (Accession # Z22513), Cry1Hb1 (Accession # U35780), Cry1H-like (Accession # AF182196), Cry1Ia1 (Accession # X62821), Cry1Ia2 (Accession # M98544), Cry1Ia3 (Accession # L36338), Cry1Ia4 (Accession # L49391), Cry1Ia5 (Accession # Y08920), Cry1Ia6 (Accession # AF076953), Cry1Ia7 (Accession # AF278797), Cry1Ia8 (Accession # AF373207), Cry1Ia9 (Accession # AF521013), Cry1Ia10 (Accession # AY262167), Cry1Ia11 (Accession # AJ315121), Cry1Ia12 (Accession # AAV53390), Cry1Ia13 (Accession # ABF83202), Cry1Ia14 (Accession # EU887515), Cry1Ib1 (Accession # U07642), Cry1Ib2 (Accession # ABW88019), Cry1Ib3 (Accession # EU677422), Cry1Ic1 (Accession # AF056933), Cry1Ic2 (Accession # AAE71691), Cry1Id1 (Accession # AF047579), Cry1Ie1 (Accession # AF211190), Cry1If1 (Accession # AAQ52382), Cry1I-like (Accession #190732), Cry1I-like (Accession # DQ781310), Cry1Ja1 (Accession # L32019), Cry1Jb1 (Accession # U31527), Cry1Jc1 (Accession #190730), Cry1Jc2 (Accession # AAQ52372), Cry1Jd1 (Accession # AX189651), Cry1Ka1 (Accession # U28801), Cry1La1 (Accession # AAS60191), Cry1-like (Accession #190729), Cry2Aa1 (Accession # M31738), Cry2Aa2 (Accession # M23723), Cry2Aa3 (Accession # D86064), Cry2Aa4 (Accession # AF047038), Cry2Aa5 (Accession # AJ132464), Cry2Aa6 (Accession # AJ132465), Cry2Aa7 (Accession # AJ132463), Cry2Aa8 (Accession # AF252262), Cry2Aa9 (Accession # AF273218), Cry2Aa10 (Accession # AF433645), Cry2Aa11 (Accession # AAQ52384), Cry2Aa12 (Accession # DQ977646), Cry2Aa13 (Accession # ABL01536), Cry2Aa14 (Accession # ACF04939), Cry2Ab1 (Accession # M23724), Cry2Ab2 (Accession # X55416), Cry2Ab3 (Accession # AF164666), Cry2Ab4 (Accession # AF336115), Cry2Ab5 (Accession # AF441855), Cry2Ab6 (Accession # AY297091), Cry2Ab7 (Accession # DQ119823), Cry2Ab8 (Accession # DQ361266), Cry2Ab9 (Accession # DQ341378), Cry2Ab10 (Accession # EF157306), Cry2Ab11 (Accession # AM691748), Cry2Ab12 (Accession # ABM21764), Cry2Ab13 (Accession # EU909454), Cry2Ab14 (Accession # EU909455), Cry2Ac1 (Accession # X57252), Cry2Ac2 (Accession # AY007687), Cry2Ac3 (Accession # AAQ52385), Cry2Ac4 (Accession # DQ361267), Cry2Ac5 (Accession # DQ341379), Cry2Ac6 (Accession # DQ359137), Cry2Ac7 (Accession # AM292031), Cry2Ac8 (Accession # AM421903), Cry2Ac9 (Accession # AM421904), Cry2Ac10 (Accession # BI 877475), Cry2Ac11 (Accession # AM689531), Cry2Ac12 (Accession # AM689532), Cry2Ad1 (Accession # AF200816), Cry2Ad2 (Accession # DQ358053), Cry2Ad3 (Accession # AM268418), Cry2Ad4 (Accession # AM490199), Cry2Ad5 (Accession # AM765844), Cry2Ae1 (Accession # AAQ52362), Cry2Af1 (Accession # EF439818), Cry2Ag (Accession # ACH91610), Cry2Ah (Accession # EU939453), Cry3Aa1 (Accession # M22472), Cry3Aa2

(Accession # J02978), Cry3Aa3 (Accession # Y00420), Cry3Aa4 (Accession # M30503), Cry3Aa5 (Accession # M37207), Cry3Aa6 (Accession # U10985), Cry3Aa7 (Accession # AJ237900), Cry3Aa8 (Accession # AAS79487), Cry3Aa9 (Accession # AAW05659), Cry3Aa10 (Accession # AAU29411), Cry3Aa11 (Accession # AY882576), Cry3Aa12 (Accession # ABY49136), Cry3Ba1 (Accession # X17123), Cry3Ba2 (Accession # A07234), Cry3Bb1 (Accession # M89794), Cry3Bb2 (Accession # U31633), Cry3Bb3 (Accession #I15475), Cry3Ca1 (Accession # X59797), Cry4Aa1 (Accession # Y00423), Cry4Aa2 (Accession # DQ0248), Cry4Aa3 (Accession # AL731825), Cry4A-like (Accession # DQ078744), Cry4Ba1 (Accession # X07423), Cry4Ba2 (Accession # X07082), Cry4Ba3 (Accession # M20242), Cry4Ba4 (Accession # DQ0247), Cry4Ba5 (Accession # AL731825), Cry4Ba-like (Accession # ABC47686), Cry4Ca1 (Accession # EU646202), Cry5Aa1 (Accession # L07025), Cry5Ab1 (Accession # L07026), Cry5Ac1 (Accession #I34543), Cry5Ad1 (Accession # EF219060), Cry5Ba1 (Accession # U19725), Cry5Ba2 (Accession # EU121522), Cry6Aa1 (Accession # L07022), Cry6Aa2 (Accession # AF499736), Cry6Aa3 (Accession # DQ835612), Cry6Ba1 (Accession # L07024), Cry7Aa1 (Accession # M64478), Cry7Ab1 (Accession # U04367), Cry7Ab2 (Accession # U04368), Cry7Ab3 (Accession # BI 1015188), Cry7Ab4 (Accession # EU380678), Cry7Ab5 (Accession # ABX79555), Cry7Ab6 (Accession # FJ194973), Cry7Ba1 (Accession # ABB70817), Cry7Ca1 (Accession # EF486523), Cry8Aa1 (Accession # U04364), Cry8Ab1 (Accession # EU044830), Cry8Ba1 (Accession # U04365), Cry8Bb1 (Accession # AX543924), Cry8Bc1 (Accession # AX543926), Cry8Ca1 (Accession # U04366), Cry8Ca2 (Accession # AAR98783), Cry8Ca3 (Accession # EU625349), Cry8Da1 (Accession # AB089299), Cry8Da2 (Accession # BD133574), Cry8Da3 (Accession # BD133575), Cry8Db1 (Accession # AB303980), Cry8Ea1 (Accession # AY329081), Cry8Ea2 (Accession # EU047597), Cry8Fa1 (Accession # AY551093), Cry8Ga1 (Accession # AY590188), Cry8Ga2 (Accession # DQ318860), Cry8Ga3 (Accession # FJ198072), Cry8Ha1 (Accession # EF465532), Cry8Ia1 (Accession # EU381044), Cry8Ja1 (Accession # EU625348), Cry8 like (Accession # ABS53003), Cry9Aa1 (Accession # X58120), Cry9Aa2 (Accession # X58534), Cry9Aa like (Accession # AAQ52376), Cry9Ba1 (Accession # X75019), Cry9Bb1 (Accession # AY758316), Cry9Ca1 (Accession # Z37527), Cry9Ca2 (Accession # AAQ52375), Cry9Da1 (Accession # D85560), Cry9Da2 (Accession # AF042733), Cry9Db1 (Accession # AY971349), Cry9Ea1 (Accession # AB011496), Cry9Ea2 (Accession # AF358863), Cry9Ea3 (Accession # EF157307), Cry9Ea4 (Accession # EU760456), Cry9Ea5 (Accession # EU789519), Cry9Ea6 (Accession # EU887516), Cry9Eb1 (Accession # AX189653), Cry9Ec1 (Accession # AF093107), Cry9Ed1 (Accession # AY973867), Cry9 like (Accession # AF093107), Cry10Aa1 (Accession # M12662), Cry10Aa2 (Accession # E00614), Cry10Aa3 (Accession # AL731825), Cry10A like (Accession # DQ167578), Cry11Aa1 (Accession # M31737), Cry11Aa2 (Accession # M22860), Cry11Aa3 (Accession # AL731825), Cry11Aa-like (Accession # DQ166531), Cry11Ba1 (Accession # X86902), Cry11Bb1 (Accession # AF017416), Cry12Aa1 (Accession # L07027), Cry13Aa1 (Accession # L07023), Cry14Aa1 (Accession # U13955), Cry15Aa1 (Accession # M76442), Cry16Aa1 (Accession # X94146), Cry17Aa1 (Accession # X99478), Cry18Aa1 (Accession # X99049), Cry18Ba1 (Accession # AF169250), Cry18Ca1 (Accession # AF169251), Cry19Aa1 (Accession # Y07603), Cry19Ba1 (Accession # D88381), Cry20Aa1 (Accession # U82518), Cry21Aa1 (Accession # I32932), Cry21Aa2 (Accession #I66477), Cry21Ba1 (Accession # AB088406), Cry22Aa1 (Accession #I34547), Cry22Aa2 (Accession # AX472772), Cry22Aa3 (Accession # EU715020), Cry22Ab1 (Accession # AAK50456), Cry22Ab2 (Accession # AX472764), Cry22Ba1 (Accession # AX472770), Cry23Aa1 (Accession # AAF76375), Cry24Aa1 (Accession # U88188), Cry24Ba1 (Accession # BAD32657), Cry24Ca1 (Accession # AM158318), Cry25Aa1 (Accession # U88189), Cry26Aa1 (Accession # AF122897), Cry27Aa1 (Accession # AB023293), Cry28Aa1 (Accession # AF132928), Cry28Aa2 (Accession # AF285775), Cry29Aa1 (Accession # AJ251977), Cry30Aa1 (Accession # AJ251978), Cry30Ba1 (Accession # BAD00052), Cry30Ca1 (Accession # BAD67157), Cry30Da1 (Accession # EF095955), Cry30Db1 (Accession # BAE80088), Cry30Ea1 (Accession # EU503140), Cry30Fa1 (Accession # EU751609), Cry30Ga1 (Accession # EU882064), Cry31Aa1 (Accession # AB031065), Cry31Aa2 (Accession # AY081052), Cry31Aa3 (Accession # AB250922), Cry31Aa4 (Accession # AB274826), Cry31Aa5 (Accession # AB274827), Cry31Ab1 (Accession # AB250923), Cry31Ab2 (Accession # AB274825), Cry31Ac1 (Accession # AB276125), Cry32Aa1 (Accession # AY008143), Cry32Ba1 (Accession # BAB78601), Cry32Ca1 (Accession # BAB78602), Cry32Da1 (Accession # BAB78603), Cry33Aa1 (Accession # AAL26871), Cry34Aa1 (Accession # AAG50341), Cry34Aa2 (Accession # AAK64560), Cry34Aa3 (Accession # AY536899), Cry34Aa4 (Accession # AY536897), Cry34Ab1 (Accession # AAG41671), Cry34Ac1 (Accession # AAG50118), Cry34Ac2 (Accession # AAK64562), Cry34Ac3 (Accession # AY536896), Cry34Ba1 (Accession # AAK64565), Cry34Ba2 (Accession # AY536900), Cry34Ba3 (Accession # AY536898), Cry35Aa1 (Accession # AAG50342), Cry35Aa2 (Accession # AAK64561), Cry35Aa3 (Accession # AY536895), Cry35Aa4 (Accession # AY536892), Cry35Ab1 (Accession # AAG41672), Cry35Ab2 (Accession # AAK64563), Cry35Ab3 (Accession # AY536891), Cry35Ac1 (Accession # AAG50117), Cry35Ba1 (Accession # AAK64566), Cry35Ba2 (Accession # AY536894), Cry35Ba3 (Accession # AY536893), Cry36Aa1 (Accession # AAK64558), Cry37Aa1 (Accession # AAF76376), Cry38Aa1 (Accession # AAK64559), Cry39Aa1 (Accession # BAB72016), Cry40Aa1 (Accession # BAB72018), Cry40Ba1 (Accession # BAC77648), Cry40Ca1 (Accession # EU381045), Cry40Da1 (Accession # EU596478), Cry41Aa1 (Accession # AB116649), Cry41Ab1 (Accession # AB116651), Cry42Aa1 (Accession # AB116652), Cry43Aa1 (Accession # AB115422), Cry43Aa2 (Accession # AB176668), Cry43Ba1 (Accession # AB115422), Cry43-like (Accession # AB115422), Cry44Aa (Accession # BAD08532), Cry45Aa (Accession # BAD22577), Cry46Aa (Accession # BAC79010), Cry46Aa2 (Accession # BAG68906), Cry46Ab (Accession # BAD35170), Cry47Aa (Accession # AY950229), Cry48Aa (Accession # AJ841948), Cry48Aa2 (Accession # AM237205), Cry48Aa3 (Accession # AM237206), Cry48Ab (Accession # AM237207), Cry48Ab2 (Accession # AM237208), Cry49Aa (Accession # AJ841948), Cry49Aa2 (Accession # AM237201), Cry49Aa3 (Accession # AM237203), Cry49Aa4 (Accession # AM237204), Cry49Ab1 (Accession # AM237202), Cry50Aa1 (Accession # AB253419), Cry51Aa1 (Accession # DQ836184), Cry52Aa1 (Accession # EF613489), Cry53Aa1 (Accession # EF633476), Cry54Aa1 (Accession # EU339367), Cry55Aa1 (Accession # EU121521), Cry55Aa2 (Accession # AAE33526).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of U.S. Pat. Nos. 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US20090144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to Cry1Ac, Cry1Ac+ Cry2Ab, Cry1Ab, Cry1A.105, Cry1F, Cry1Fa2, Cry1F+ Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus*, *Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus*, *Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

In some embodiments the PIP-1 polypeptides include amino acid sequences deduced from the full-length nucleic acid sequences disclosed herein, and amino acid sequences that are shorter than the full-length sequences, either due to the use of an alternate downstream start site or due to processing that produces a shorter protein having pesticidal activity. Processing may occur in the organism after the protein is expressed in or in the pest after ingestion of the protein.

Thus, provided herein are novel isolated or recombinant nucleic acid sequences encoding polypeptides that confer pesticidal activity. Also provided are the amino acid sequences of PIP-1 polypeptides. The protein resulting from translation of these PIP-1 polypeptide genes allows cells to control or kill pests that ingest it.

Bacterial Strains

One aspect of the invention pertains to bacterial strains that are capable of expressing a PIP-1 polypeptide. In some embodiments the bacterial strain is a *Pseudomonas chlororaphis* strain. In some embodiments the bacterial strain is a biologically pure culture of a *Pseudomonas chlororaphis* strain SS44C4, deposited on Dec. 1, 2011 under Accession Number NRRLB-50613 with the Agricultural Research Service Culture Collection (NRRL). In some embodiments the bacterial strain is a biologically pure culture of a *Pseudomonas chlororaphis* strain having a 16S ribosomal DNA having at least about 96.9%, 97%, 97.1%, 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8% or 99.9% sequence identity compared to SEQ ID NO: 216.

Nucleic Acid Molecules, and Variants and Fragments Thereof

Another aspect of the invention pertains to isolated or recombinant nucleic acid molecules comprising nucleic acid sequences encoding PIP-1 polypeptides and polypeptides or biologically active portions thereof, as well as nucleic acid molecules sufficient for use as hybridization probes to identify nucleic acid molecules encoding proteins with regions of sequence homology. As used herein, the term "nucleic acid molecule" is intended to include DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "recombinant" nucleic acid molecule (or DNA) is used herein to refer to a nucleic acid sequence (or DNA) that is no longer in its natural environment, for example in an in vitro or in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecule encoding a PIP-1 polypeptide can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

A variety of polynucleotides that encode PIP-1 polypeptides or related proteins are contemplated. Such polynucleotides are useful for production of PIP-1 polypeptides in host cells when operably linked to suitable promoter, transcription termination and/or polyadenylation sequences. Such polynucleotides are also useful as probes for isolating homologous or substantially homologous polynucleotides that encode PIP-1 polypeptides or related proteins.

One source of polynucleotides that encode PIP-1 polypeptides or related proteins is a *Pseudomonas chlororaphis* strain which contains the PIP-1A polynucleotide of SEQ ID NO: 1 encoding the PIP-1A polypeptide of SEQ ID NO: 2. This polynucleotide sequence was isolated from a *Pseudomonas chlororaphis* host and is thus suitable for expression of the encoded PIP-1A polypeptide in other bacterial hosts. For example, SEQ ID NO: 1 can be used to express the PIP-1A protein in bacterial hosts that include but are not limited to an *Agrobacterium*, an *Alcaligenes*, a *Bacillus*, an *Escherichia*, a *Salmonella*, a *Pseudomonas* and a *Rhizobium* bacterial host cells. The polynucleotides are also useful as probes for isolating homologous or substantially homologous polynucleotides that encode PIP-1 polypeptides or related proteins. Such probes can be used to identify homologous or substantially homologous polynucleotides derived from *Pseudomonas* or other bacterial strains.

Polynucleotides that encode a PIP-1 polypeptide can also be synthesized de novo from a PIP-1 polypeptide sequence. The sequence of the polynucleotide gene can be deduced from a PIP-1A polypeptide sequence through use of the genetic code. Computer programs such as "BackTranslate" (GCG™ Package, Acclerys, Inc. San Diego, Calif.) can be used to convert a peptide sequence to the corresponding nucleotide sequence encoding the peptide. Examples of PIP-1 polypeptide sequences that can be used to obtain corresponding nucleotide encoding sequences include, but are not limited to, the PIP-1 polypeptide sequence of SEQ ID NO: 2. Furthermore, synthetic PIP-1A polynucleotide sequences of the invention can be designed so that they will be expressed in plants. U.S. Pat. No. 5,500,365 describes a method for synthesizing plant genes to improve the expression level of the protein encoded by the synthesized gene. This method relates to the modification of the structural gene sequences of the exogenous transgene, to cause them to be more efficiently transcribed, processed, translated and expressed by the plant. Features of genes that are expressed well in plants include elimination of sequences that can cause undesired intron splicing or polyadenylation in the coding region of a gene transcript while retaining substantially the amino acid sequence of the toxic portion of the insecticidal protein. A similar method for obtaining enhanced expression of transgenes in monocotyledonous plants is disclosed in U.S. Pat. No. 5,689,052.

In some embodiments the nucleic acid molecule encoding a PIP-1 polypeptide is a polynucleotide having the sequence set forth in SEQ ID NO: 1, 3 or 331 and variants, fragments and complements thereof. By "complement" is intended a nucleic acid sequence that is sufficiently complementary to a given nucleic acid sequence such that it can hybridize to the given nucleic acid sequence to thereby form a stable duplex. In some embodiments the nucleic acid molecule encoding a PIP-1 polypeptide is a nucleic acid molecule having the sequence set forth in SEQ ID NO: 1, 3 or 331.

The corresponding amino acid sequences for the insecticidal protein encoded by these nucleic acid sequences are set forth in SEQ ID NO: 2, 4 and 332.

In some embodiments the nucleic acid molecule encoding a PIP-1 polypeptide is a polynucleotide having a nucleotide sequence encoding a polypeptide comprising an amino acid sequence having at least 80% identity, to the amino acid sequence of SEQ ID NO: 2, SEQ ID NO:4 or SEQ ID NO: 332, wherein the polypeptide has pesticidal activity. In some embodiments the nucleic acid molecule encoding a PIP-1 polypeptide is a polynucleotide having a nucleotide sequence encoding a polypeptide comprising an amino acid sequence having at least 80% identity, to the amino acid sequence of SEQ ID NO: 2, wherein the polypeptide has pesticidal activity. In some embodiments the nucleic acid molecule encoding a PIP-1 polypeptide is a polynucleotide having a nucleotide sequence encoding a polypeptide comprising an amino acid sequence having at least 80% identity, to the amino acid sequence of SEQ ID NO: 4, wherein the polypeptide has pesticidal activity. In some embodiments the nucleic acid molecule encoding a PIP-1 polypeptide is a polynucleotide having a nucleotide sequence encoding a polypeptide comprising an amino acid sequence having at least 80% identity, to the amino acid sequence of SEQ ID NO: 332, wherein the polypeptide has pesticidal activity.

In some embodiments the nucleic acid molecule encoding a PIP-1 polypeptide is a polynucleotide having a nucleotide sequence encoding a polypeptide comprising an amino acid sequence of (SEQ ID NO: 211), wherein Xaa at position 2 is Pro or Thr; Xaa at position 8 is Ser, Gly or Asn; Xaa at position 19 is Asp, Glu or Cys; Xaa at position 20 is Leu or Val; Xaa at position 21 is Lys, Ser or Asn; Xaa at position 22 is Ser, Lys or Arg; Xaa at position 24 is Gln or Ala; Xaa at position 25 is Gly or Ala Xaa at position 26 is Ser or Asn; Xaa at position 27 is Leu, Thr or Ala; Xaa at position 30 is Ala or Ile; Xaa at position 35 is Phe or Leu; Xaa at position 36 is Ala, Ser or Val; Xaa at position 38 is Asn, Arg or Ser; Xaa at position 42 is Phe or Tyr; Xaa at position 46 is Arg, Lys or His; Xaa at position 48 is Gly or Asp; Xaa at position 49 is Phe or Tyr; Xaa at position 53 is Ser or Gly; Xaa at position 58 is Tyr or Phe; Xaa at position 60 is Ala or Ser; Xaa at position 63 is Gln or Lys; Xaa at position 77 is Phe or Tyr; Xaa at position 97 is Met or Val; Xaa at position 98 is Asp or Glu; Xaa at position 105 is Gln or Asn; Xaa at position 107 is Thr or Ile; Xaa at position 108 is Gln or Thr; Xaa at position 110 is Arg or Leu; Xaa at position 120 is Lys, Arg or Gln; Xaa at position 121 is Thr or Ser; Xaa at position 123 is Thr or Glu; Xaa at position 125 is Asn or Ser; Xaa at position 127 is Ser, Asn, Thr or Lys; Xaa at position 134 is Gly or Ala; Xaa at position 135 is Ser, Asn or Lys; Xaa at position 137 is Asp or Gly; Xaa at position 141 is Val or Ile; Xaa at position 142 is Gly or Asp; Xaa at position 144 is Asp or Glu; Xaa at position 147 is Ile, Thr or Val; Xaa at position 150 is Ser or Thr; Xaa at position 151 is Asn, Arg or Ser; Xaa at position 160 is Thr or Ser; Xaa at position 162 is Ser or Thr; Xaa at position 163 is Asn, Asp or Glu; Xaa at position 164 is Ser or Thr; Xaa at position 166 is Gln or Glu; Xaa at position 167 is Leu or Met; Xaa at position 168 is Thr, Lys or Ala; Xaa at position 174 is Ile, Val or Met; Xaa at position 175 is Val or Ile; Xaa at position 180 is Met or Leu; Xaa at position 191 is Arg or Lys; Xaa at position 194 is Gly or Ala; Xaa at position 200 is Asn or Ser; Xaa at position 203 is Asn or Gln; Xaa at position 204 is Thr or Ala; Xaa at position 206 is Gly or Asp; Xaa at position 209 is Leu or Val; Xaa at position 220 is Asn or Arg; Xaa at position 221 is Ser or Lys; Xaa at position 222 is Thr or Arg; Xaa at position 226 is Asp, Pro or Glu; Xaa at position 228 is Ser or Gly; Xaa at position 229 is Lys or Asn; Xaa at position 231 is Ile or Val; Xaa at position 232 is Ala, Thr or Glu; and Xaa at position 251 is Gly, Ser or Glu; Xaa at position 254 is Ser or Asn; Xaa at position 258 is Ser or Arg; Xaa at position 265 is Asn or Asp; and Xaa at position 266 is Asp or Asn; and wherein, 1 to 28 amino acids are optionally deleted from the N-terminus of the polypeptide.

In some embodiments the nucleic acid molecule encoding a PIP-1 polypeptide is a polynucleotide having a nucleotide sequence encoding a polypeptide comprising an amino acid sequence of a sequence of SEQ ID NO: 212, wherein Xaa at position 2 is Pro or Thr; Xaa at position 3 is Ile or Thr; Xaa at position 6 is Glu or Gly; Xaa at position 8 is Ser, Gly or Asn; Xaa at position 19 is Asp, Glu or Cys; Xaa at position 20 is Leu or Val; Xaa at position 21 is Lys, Ser or Asn; Xaa at position 22 is Ser, Lys or Arg; Xaa at position 24 is Gln or Ala; Xaa at position 25 is Gly or Ala; Xaa at position 26 is Ser or Asn; Xaa at position 27 is Leu, Thr or Ala; Xaa at position 28 is Arg, Ser, Lys, Thr, Val, Gly, Ala, Met, Asp, Trp, Pro, Leu, His, Cys or Gln; Xaa at position 30 is Ala or Ile; Xaa at position 35 is Phe or Leu; Xaa at position 36 is Ala, Ser or Val; Xaa at position 38 is Asn, Arg or Ser; Xaa at position 42 is Phe or Tyr; Xaa at position 43 is Pro, Met, Gly, Gln, Ser, Thr, Arg, Val, Leu, Lys, Asp, Ala, Asn, Phe, Trp, Glu or Cys; Xaa at position 46 is Arg, Lys or His; Xaa at position 48 is Gly or Asp; Xaa at position 49 is Phe, Tyr or Leu; Xaa at position 53 is Ser or Gly; Xaa at position 58 is Tyr or Phe; Xaa at position 60 is Ala or Ser; Xaa at position 63 is Gln or Lys; Xaa at position 66 is Trp, Tyr, Phe, Arg, Lys, His, Ile, Val or Ser; Xaa at position 77 is Phe or Tyr; Xaa at position 89 is Pro, Leu, Gly, Arg, Thr, Ser, Met, Ala, Ile, Asn, Val, Cys or Lys; Xaa at position 93 is Tyr, Cys, Trp, Val, Asp, Asn, Ile, Leu, Met, Phe, Ala or Thr; Xaa at position 97 is Met or Val; Xaa at position 98 is Asp or Glu; Xaa at position 105 is Gln or Asn; Xaa at position 107 is Thr or Ile; Xaa at position 108 is Gln or Thr; Xaa at position 110 is Arg or Leu; Xaa at position 120 is Lys, Arg or Gln; Xaa at position 121 is Thr or Ser; Xaa at position 123 is Thr or Glu; Xaa at position 125 is Asn or Ser; Xaa at position 127 is Ser, Asn, Thr or Lys; Xaa at position 134 is Gly or Ala; Xaa at position 135 is Ser, Asn or Lys; Xaa at position 137 is Asp or Gly; Xaa at position 141 is Val or Ile; Xaa at position 142 is Gly or Asp; Xaa at position 144 is Asp or Glu; Xaa at position 147 is Ile, Thr or Val; Xaa at position 150 is Ser or Thr; Xaa at position 151 is Asn, Arg or Ser; Xaa at position 160 is Thr or Ser; Xaa at position 162 is Ser or Thr; Xaa at position 163 is Asn, Asp or Glu; Xaa at position 164 is Ser or Thr; Xaa at position 166 is Gln or Glu; Xaa at position 167 is Leu or Met; Xaa at position 168 is Thr, Lys or Ala; Xaa at position 171 is Gly, Leu, Gln, Met, Cys, Asn, Asp, Ser or Ala; Xaa at position 172 is Thr, Gly, His, Phe, Glu, Arg, Ser, Asn, Ile, Trp, Lys, Gln, Cys, Val, Ala or Met; Xaa at position 173 is Phe, Gly, His, Leu, Ala, Arg, Asn, Cys, Lys, Trp, Thr, Ser, Tyr or Met; Xaa at position 174 is Ile, Val, Gly, Arg, Asn, Ala, Gln, Met, Cys, Leu, Phe, Tyr, Lys, Glu, Ser, His or Thr; Xaa at position 175 is Val, Ile, Ala, Cys, Glu, Lys, Leu or Met; Xaa at position 176 is Tyr, Met, Phe, Leu or Cys; Xaa at position 177 is Gln, Ile, Met or Pro; Xaa at position 178 is Val, Cys, Thr, Pro, Ala, Met, Gln, Phe, Ile, Ser or Lys; Xaa at position 179 is Val, Phe, Thr, Ile, Cys, Leu, Met, Ser, Ala or Gln; Xaa at position 180 is Met, Leu, Pro, Trp, Asn, Tyr, Gly, Gln, Ala, Val, Phe, Ile, Cys or Ser; Xaa at position 181 is Val, Ala, Leu, Trp, Cys, Thr, Ile or Lys; Xaa at position 182 is Tyr, Phe, Met or His; Xaa at position 183 is Ala, Met, Val, Thr, Asp, Gly, Cys, Ile, Phe, Ser, Gln or Leu; Xaa at position 191 is Arg or Lys; Xaa at position 194 is Gly or Ala; Xaa at position 195 is Asn or Tyr;

Xaa at position 200 is Asn or Ser; Xaa at position 203 is Asn or Gln; Xaa at position 204 is Thr or Ala; Xaa at position 206 is Gly or Asp; Xaa at position 209 is Leu or Val; Xaa at position 213 is Tyr or Phe; Xaa at position 220 is Asn or Arg; Xaa at position 221 is Ser or Lys; Xaa at position 222 is Thr or Arg; Xaa at position 226 is Asp, Pro or Glu; Xaa at position 228 is Ser or Gly; Xaa at position 229 is Lys or Asn; Xaa at position 231 is Ile or Val; Xaa at position 232 is Ala, Thr or Glu; Xaa at position 240 is Gln, Arg, Ala, Val, Glu, Met, Gly, Asp, Trp, Asn, Thr, Ile, Ser, Phe, His, Cys or Leu; Xaa at position 241 is Arg, Lys, Glu, Gln, Ser, Ile, Val, Asp, Tyr, Met, Asn, His, Pro, Gly, Leu, Phe, Thr, Ala or Cys; Xaa at position 242 is Asn, Ala, Arg, Lys, His, Ser, Cys, Glu, Pro, Trp, Gln, Thr, Phe, Tyr, Met, Asp, Gly, Leu or Val; Xaa at position 243 is Val, Leu, Ala, Thr, Gly, Cys, Ile, Ser or Met; Xaa at position 244 is Leu, Val, Phe, Ile, Met, Gln, Cys, Trp or Ala; Xaa at position 245 is Met, Ala, Arg, Asp, Glu, Leu, Pro, Ser, Trp, Gly, Val, Lys, Phe, Cys, Thr, His, Ile, Gln, Tyr or Asn; Xaa at position 246 is Glu, Asp, Tyr, Gly, Arg, Val, Ala, Trp, Gln, Ser, Asn, Ile Leu, Met, Cys, Pro, His, Phe, Thr or Lys; Xaa at position 247 is Asn, Leu, Asp, Tyr, Ala, Phe, His, Arg, Lys, Gln, Gly, Val, Ile, Ser, Glu, Pro, Met, Trp, Thr or Cys; Xaa at position 248 is Tyr, Val, Thr, Glu, Phe, Ser, His, Cys, Leu, Trp, Ile, Asp, Gly or Ala; Xaa at position 249 is Asn, Lys, Val, Gly, Met, Asp, Cys, Phe, Arg, Glu, Trp, Tyr, Ser, Ile, Thr, Pro, Leu, Ala, His or Gln; Xaa at position 251 is Gly, Ser or Glu; Xaa at position 254 is Ser or Asn; Xaa at position 258 is Ser or Arg; Xaa at position 259 is Phe, Trp, Tyr, Cys, Met, Leu, Val, Ile or His; Xaa at position 265 is Asn or Asp; and Xaa at position 266 is Asp or Asn.

In some embodiments the nucleic acid molecule encoding a PIP-1 polypeptide is a polynucleotide having a nucleotide sequence encoding a polypeptide comprising an amino acid sequence of a sequence of SEQ ID NO: 213 wherein Xaa at position 2 is Pro, Thr or Ser; Xaa at position 3 is Ile, Thr, Leu, Val, Met or Ser; Xaa at position 6 is Glu, Gly, Asp or Ala; Xaa at position 8 is Ser, Gly, Asn, Thr or Gln; Xaa at position 19 is Asp, Glu or Cys; Xaa at position 20 is Leu, Val, Ile or Met; Xaa at position 21 is Lys, Ser, Asn, Arg, Thr or Gln; Xaa at position 22 is Ser, Lys, Arg or Thr; Xaa at position 24 is Gln, Gly, Asn or Ala; Xaa at position 25 is Gly or Ala; Xaa at position 26 is Ser, Asn, Thr or Gln; Xaa at position 27 is Leu, Thr, Ala, Ser, Ile, Val or Met; Xaa at position 28 is Arg, Ser, Lys, Thr, Val, Gly, Ala, Met, Asp, Trp, Pro, Leu, His, Cys or Gln; Xaa at position 30 is Ala, Ile, Leu, Val or Met; Xaa at position 35 is Phe, Leu, Ile, Val or Met; Xaa at position 36 is Ala, Ser, Thr, Val, Ile or Leu; Xaa at position 38 is Asn, Arg, Ser, Gln, Lys or Thr; Xaa at position 42 is Phe, Tyr, Trp, Leu, Ile, Val or Met; Xaa at position 43 is Pro, Met, Gly, Gln, Ser, Thr, Arg, Val, Leu, Lys, Asp, Ala, Asn, Phe, Trp, Glu or Cys; Xaa at position 46 is Arg, Lys or His; Xaa at position 48 is Gly, Asp, Ala or Glu; Xaa at position 49 is Phe, Tyr, Trp, Leu, Ile, Val or Met; Xaa at position 53 is Ser, Gly, Ala or Thr; Xaa at position 58 is Tyr or Phe; Xaa at position 60 is Ala, Ser, Gly or Thr; Xaa at position 63 is Gln, Lys, Asn or Arg; Xaa at position 66 is Trp, Tyr, Phe, Arg, Lys, His, Ile, Val or Ser; Xaa at position 77 is Phe, Tyr, Trp, Leu, Ile, Val or Met; Xaa at position 89 is Pro, Leu, Gly, Arg, Thr, Ser, Met, Ala, Ile, Asn, Val, Cys or Lys; Xaa at position 93 is Tyr, Cys, Trp, Val, Asp, Asn, Ile, Leu, Met, Phe, Ala or Thr; Xaa at position 97 is Met, Val, Leu or Ile; Xaa at position 98 is Asp or Glu; Xaa at position 105 is Gln or Asn; Xaa at position 107 is Thr, Ile, Ser, Leu or Val; Xaa at position 108 is Gln, Thr, Ser or Asn; Xaa at position 110 is Arg, Leu, Lys, Ile, Val or Met; Xaa at position 120 is Lys, Arg, Gln or Asn; Xaa at position 121 is Thr or Ser; Xaa at position 123 is Thr, Glu, Ser or Asp; Xaa at position 125 is Asn, Ser, Gln or Thr; Xaa at position 127 is Ser, Asn, Thr, Gln, Lys, Ser or Arg; Xaa at position 134 is Gly or Ala; Xaa at position 135 is Ser, Asn, Thr, Gln, Arg or Lys; Xaa at position 137 is Asp, Gly, Glu or Ala; Xaa at position 141 is Val, Ile or Leu; Xaa at position 142 is Gly, Asp, Ala or Glu; Xaa at position 144 is Asp or Glu; Xaa at position 147 is Ile, Thr, Val, Leu, Met or Ser; Xaa at position 150 is Ser or Thr; Xaa at position 151 is Asn, Arg, Ser, Gln, Lys or Thr; Xaa at position 160 is Thr or Ser; Xaa at position 162 is Ser or Thr; Xaa at position 163 is Asn, Asp, Glu or Gln; Xaa at position 164 is Ser or Thr; Xaa at position 166 is Gln, Glu, Asp or Asn; Xaa at position 167 is Leu, Met, Ile, Val; Xaa at position 168 is Thr, Lys, Ala, Ser, Arg or Gly; Xaa at position 171 is Gly, Leu, Gln, Met, Cys, Asn, Asp, Ser or Ala; Xaa at position 172 is Thr, Gly, His, Phe, Glu, Arg, Ser, Asn, Ile, Trp, Lys, Gln, Cys, Val, Ala or Met; Xaa at position 173 is Phe, Gly, His, Leu, Ala, Arg, Asn, Cys, Lys, Trp, Thr, Ser, Tyr or Met; Xaa at position 174 is Ile, Val, Gly, Arg, Asn, Ala, Gln, Met, Cys, Leu, Phe, Tyr, Lys, Glu, Ser, His or Thr; Xaa at position 175 is Val, Ile, Ala, Cys, Glu, Lys, Leu or Met; Xaa at position 176 is Tyr, Met, Phe, Leu or Cys; Xaa at position 177 is Gln, Ile, Met or Pro; Xaa at position 178 is Val, Cys, Thr, Pro, Ala, Met, Gln, Phe, Ile, Ser or Lys; Xaa at position 179 is Val, Phe, Thr, Ile, Cys, Leu, Met, Ser, Ala or Gln; Xaa at position 180 is Met, Leu; Pro, Trp, Asn, Tyr, Gly, Gln, Ala, Val, Phe, Ile, Cys or Ser; Xaa at position 181 is Val, Ala, Leu, Trp, Cys, Thr, Ile or Lys; Xaa at position 182 is Tyr, Phe, Met or His; Xaa at position 183 is Ala, Met, Val, Thr, Asp, Gly, Cys, Ile, Phe, Ser, Gln or Leu; Xaa at position 191 is Arg or Lys; Xaa at position 194 is Gly or Ala; Xaa at position 195 is Asn, Tyr, Gln or Trp; Xaa at position 200 is Asn, Ser, Thr or Gln; Xaa at position 203 is Asn or Gln; Xaa at position 204 is Thr, Ala, Ser or Gly; Xaa at position 206 is Gly, Asp, Ala or Glu; Xaa at position 209 is Leu, Val, Ile or Met; Xaa at position 213 is Tyr or Phe; Xaa at position 220 is Asn, Arg, Gln or Lys; Xaa at position 221 is Ser, Lys, Thr or Arg; Xaa at position 222 is Thr, Arg, Ser or Lys; Xaa at position 226 is Asp, Pro, Glu or Gln; Xaa at position 228 is Ser or Gly; Xaa at position 229 is Lys, Asn, Arg or Gln; Xaa at position 231 is Ile, Val, Leu or Met; Xaa at position 232 is Ala, Thr, Ser, Gly, Asp or Glu; Xaa at position 240 is Gln, Arg, Ala, Val, Glu, Met, Gly, Asp, Trp, Asn, Thr, Ile, Ser, Phe, His, Cys or Leu; Xaa at position 241 is Arg, Lys, Glu, Gln, Ser, Ile, Val, Asp, Tyr, Met, Asn, His, Pro, Gly, Leu, Phe, Thr, Ala or Cys; Xaa at position 242 is Asn, Ala, Arg, Lys, His, Ser, Cys, Glu, Pro, Trp, Gln, Thr, Phe, Tyr, Met, Asp, Gly, Leu or Val; Xaa at position 243 is Val, Leu, Ala, Thr, Gly, Cys, Ile, Ser or Met; Xaa at position 244 is Leu, Val, Phe, Ile, Met, Gln, Cys, Trp or Ala; Xaa at position 245 is Met, Ala, Arg, Asp, Glu, Leu, Pro, Ser, Trp, Gly, Val, Lys, Phe, Cys, Thr, His, Ile, Gln, Tyr or Asn; Xaa at position 246 is Glu, Asp, Tyr, Gly, Arg, Val, Ala, Trp, Gln, Ser, Asn, Ile Leu, Met, Cys, Pro, His, Phe, Thr or Lys; Xaa at position 247 is Asn, Leu, Asp, Tyr, Ala, Phe, His, Arg, Lys, Gln, Gly, Val, Ile, Ser, Glu, Pro, Met, Trp, Thr or Cys; Xaa at position 248 is Tyr, Val, Thr, Glu, Phe, Ser, His, Cys, Leu, Trp, Ile, Asp, Gly or Ala; Xaa at position 249 is Asn, Lys, Val, Gly, Met, Asp, Cys, Phe, Arg, Glu, Trp, Tyr, Ser, Ile, Thr, Pro, Leu, Ala, His or Gln; Xaa at position 251 is Gly, Ser, Thr, Ala, Asp or Glu; Xaa at position 254 is Ser, Asn, Thr or Gln; Xaa at position 258 is Ser, Arg, Thr or Lys; Xaa at position 259 is Phe, Trp, Tyr, Cys, Met, Leu, Val, Ile or His; Xaa at position 265 is Asn, Asp, Gln or Glu; and Xaa at position 266 is Asp, Asn, Gln or Glu.

In some embodiments the nucleic acid molecules encode a PIP-1 polypeptide having a nucleotide sequence encoding a polypeptide comprising one or more amino acid motifs selected from i) amino acids 64-79 of SEQ ID NO: 2, amino acids 64-79 of SEQ ID NO: 211, amino acids 64-79 of SEQ ID NO: 212 or amino acids 64-79 of SEQ ID NO: 213, ii) amino acids 149-159 of SEQ ID NO: 2, amino acids 149-159 of SEQ ID NO: 211, amino acids 149-159 of SEQ ID NO: 212 or amino acids 149-159 of SEQ ID NO: 213, iii) amino acids 171-183 of SEQ ID NO: 2, amino acids 171-183 of SEQ ID NO: 211, amino acids 171-183 of SEQ ID NO: 212 or amino acids 171-183 of SEQ ID NO: 213, and iv) amino acids 240-249 of SEQ ID NO: 2, amino acids 240-249 of SEQ ID NO: 211, amino acids 240-249 of SEQ ID NO: 212 or amino acids 240-249 of SEQ ID NO: 213. In some embodiments the nucleic acid molecules encode a PIP-1 polypeptide having a nucleotide sequence encoding a polypeptide comprising an amino acid as represented by positions 171-183 of SEQ ID NO: 213 wherein at least one amino acid at positions 171-183 of SEQ ID NO: 213 are not identical to amino acids at positions 171-183 of SEQ ID NO: 6.

In some embodiments the nucleic acid molecules encode a PIP-1 polypeptide having a nucleotide sequence encoding a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence set forth in SEQ ID NO: 2, SEQ ID NO: 6 or SEQ ID NO:4 and wherein the polypeptide comprises one or more amino acid motifs selected from i) amino acids 64-79 of SEQ ID NO: 2, amino acids 64-79 of SEQ ID NO: 211, amino acids 64-79 of SEQ ID NO: 212 or amino acids 64-79 of SEQ ID NO: 213, ii) amino acids 149-159 of SEQ ID NO: 2, amino acids 149-159 of SEQ ID NO: 211, amino acids 149-159 of SEQ ID NO: 212 or amino acids 149-159 of SEQ ID NO: 213, iii) amino acids 171-183 of SEQ ID NO: 2, amino acids 171-183 of SEQ ID NO: 211, amino acids 171-183 of SEQ ID NO: 212 or amino acids 171-183 of SEQ ID NO: 213, and iv) amino acids 240-249 of SEQ ID NO: 2, amino acids 240-249 of SEQ ID NO: 211, amino acids 240-249 of SEQ ID NO: 212 or amino acids 240-249 of SEQ ID NO: 213.

In some embodiments the nucleic acid molecules encode a PIP-1 polypeptide having a nucleotide sequence encoding a polypeptide comprising an amino acid sequence having at least 80% identity to the amino acid sequence set forth in SEQ ID NO: 2, SEQ ID NO: 6 or SEQ ID NO:4 and wherein the polypeptide comprises one or more amino acid motifs selected from i) amino acids 64-79 of SEQ ID NO: 2, amino acids 64-79 of SEQ ID NO: 211, amino acids 64-79 of SEQ ID NO: 212 or amino acids 64-79 of SEQ ID NO: 213, ii) amino acids 149-159 of SEQ ID NO: 2, amino acids 149-159 of SEQ ID NO: 211, amino acids 149-159 of SEQ ID NO: 212 or amino acids 149-159 of SEQ ID NO: 213, iii) amino acids 171-183 of SEQ ID NO: 2, amino acids 171-183 of SEQ ID NO: 211, amino acids 171-183 of SEQ ID NO: 212 or amino acids 171-183 of SEQ ID NO: 213, and iv) amino acids 240-249 of SEQ ID NO: 2, amino acids 240-249 of SEQ ID NO: 211, amino acids 240-249 of SEQ ID NO: 212 or amino acids 240-249 of SEQ ID NO: 213.

In some embodiments the nucleic acid molecules encode a PIP-1 polypeptide having a nucleotide sequence encoding a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence set forth in SEQ ID NO: 2 and wherein the polypeptide comprises one or more amino acid motifs selected from i) amino acids 64-79 of SEQ ID NO: 2, amino acids 64-79 of SEQ ID NO: 211, amino acids 64-79 of SEQ ID NO: 212 or amino acids 64-79 of SEQ ID NO: 213, ii) amino acids 149-159 of SEQ ID NO: 2, amino acids 149-159 of SEQ ID NO: 211, amino acids 149-159 of SEQ ID NO: 212 or amino acids 149-159 of SEQ ID NO: 213, iii) amino acids 171-183 of SEQ ID NO: 2, amino acids 171-183 of SEQ ID NO: 211, amino acids 171-183 of SEQ ID NO: 212 or amino acids 171-183 of SEQ ID NO: 213, and iv) amino acids 240-249 of SEQ ID NO: 2, amino acids 240-249 of SEQ ID NO: 211, amino acids 240-249 of SEQ ID NO: 212 or amino acids 240-249 of SEQ ID NO: 213.

In some embodiments the nucleic acid molecules encode a PIP-1 polypeptide having a nucleotide sequence encoding a polypeptide comprising an amino acid sequence having at least 80% identity to the amino acid sequence set forth in SEQ ID NO: 2 and wherein the polypeptide comprises one or more amino acid motifs selected from i) amino acids 64-79 of SEQ ID NO: 2, amino acids 64-79 of SEQ ID NO: 211, amino acids 64-79 of SEQ ID NO: 212 or amino acids 64-79 of SEQ ID NO: 213, ii) amino acids 149-159 of SEQ ID NO: 2, amino acids 149-159 of SEQ ID NO: 211, amino acids 149-159 of SEQ ID NO: 212 or amino acids 149-159 of SEQ ID NO: 213, iii) amino acids 171-183 of SEQ ID NO: 2, amino acids 171-183 of SEQ ID NO: 211, amino acids 171-183 of SEQ ID NO: 212 or amino acids 171-183 of SEQ ID NO: 213, and iv) amino acids 240-249 of SEQ ID NO: 2, amino acids 240-249 of SEQ ID NO: 211, amino acids 240-249 of SEQ ID NO: 212 or amino acids 240-249 of SEQ ID NO: 213.

In some embodiments the nucleic acid molecules encode a PIP-1 polypeptide having a nucleotide sequence encoding a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence set forth in SEQ ID NO: 2, and wherein the polypeptide comprises one or more amino acid motifs selected from i) amino acids 64-79 of SEQ ID NO: 2 or amino acids 64-79 of SEQ ID NO: 213, ii) amino acids 149-159 of SEQ ID NO: 2 or amino acids 149-159 of SEQ ID NO: 213, iii) amino acids 171-183 of SEQ ID NO: 2 or amino acids 171-183 of SEQ ID NO: 213 and iv) amino acids 240-249 of SEQ ID NO: 2 or amino acids 240-249 of SEQ ID NO: 213.

In some embodiments the nucleic acid molecules encode a PIP-1 polypeptide having a nucleotide sequence encoding a polypeptide comprising an amino acid sequence having at least 80% identity to the amino acid sequence set forth in SEQ ID NO: 2, and wherein the polypeptide comprises one or more amino acid motifs selected from i) amino acids 64-79 of SEQ ID NO: 2 or amino acids 64-79 of SEQ ID NO: 213, ii) amino acids 149-159 of SEQ ID NO: 2 or amino acids 149-159 of SEQ ID NO: 213, iii) amino acids 171-183 of SEQ ID NO: 2 or amino acids 171-183 of SEQ ID NO: 213 and iv) amino acids 240-249 of SEQ ID NO: 2 or amino acids 240-249 of SEQ ID NO: 213.

In some embodiments exemplary nucleic acid molecules encode a PIP-1 polypeptide of SEQ ID NO: 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 204, 206, 208, 211, 212, 213, 214, 245, 246, 247, 248, 249, 250, 251, 252, 253, 254, 255, 256, 257, 258, 259, 260, 261, 262, 263, 264, 265, 266, 267, 268, 269, 298, 299, 300, 301, 302, 303, 304, 305, 306, 307, 308, 309, 310, 311, 312, 313, 314, 315, 316, 317, 318, 319, 320, 321, 322, 323, 324, and 325 as well as amino acid substitutions, amino acid deletions, amino acid insertions and fragments thereof and combinations thereof.

In some embodiments exemplary nucleic acid molecules encode a PIP-1 polypeptide of SEQ ID NO: 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 204, 206, 208, 211, 212, 213, 214, 245, 246, 247, 248, 249, 250, 251, 252, 253, 254, 255, 256, 257, 258, 259, 260, 261, 262, 263, 264, 265, 266, 267, 268, and 269 as well as amino acid substitutions, deletions, insertions and fragments thereof and combinations thereof.

In some embodiments exemplary nucleic acid molecules comprise a sequence set forth in SEQ ID NO: 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 197, 188, 189, 190, 191, 192, 193, 194, 195, 196, 197, 198, 199, 200, 201, 202, 203, 205, 207, 220, 221, 222, 223, 224, 225, 226, 227, 228, 229, 230, 231, 232, 233, 234, 235, 236, 237, 238, 239, 240, 241, 242, 243, 244, 270, 271, 272, 273, 274, 275, 276, 277, 278, 279, 280, 281, 282, 283, 284, 285, 286, 287, 288, 289, 290, 291, 292, 293, 294, 295, 296, and 297 as well as variants and fragments thereof encoding PIP-1 polypeptides.

In some embodiments exemplary nucleic acid molecules comprise a sequence set forth in SEQ ID NO: 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 197, 188, 189, 190, 191, 192, 193, 194, 195, 196, 197, 198, 199, 200, 201, 202, 203, 205, 207, 220, 221, 222, 223, 224, 225, 226, 227, 228, 229, 230, 231, 232, 233, 234, 235, 236, 237, 238, 239, 240, 241, 242, 243, and 244 as well as variants and fragments thereof encoding PIP-1 polypeptides.

In some embodiments the nucleic acid molecules encode a PIP-1 polypeptide of Table 4, Table 6, Table 9, Table 12, Table 13, Table 14 and/or Table 16, combinations of the amino acid substitutions thereof and deletions and/or insertions thereof.

Also provided are nucleic acid molecules that encode transcription and/or translation products that are subsequently spliced to ultimately produce functional PIP-1 polypeptide. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate a PIP-1 polypeptide encoding sequence. An example of trans splicing would be where a polynucleotide is encrypted by separating the coding sequence into two or more fragments that can be separately transcribed and then spliced to form the full-length pesticidal encoding sequence. The use of a splicing enhancer sequence, which can be introduced into a construct, can facilitate splicing either in cis or trans-splicing of polypeptides (U.S. Pat. Nos. 6,365,377 and 6,531,316). Thus, in some embodiments the polynucleotides do not directly encode a full-length PIP-1 polypeptide, but rather encode a fragment or fragments of a PIP-1 polypeptide. These polynucleotides can be used to express a functional PIP-1 polypeptide through a mechanism involving splicing, where splicing can occur at the level of polynucleotide (e.g., intron/exon) and/or polypeptide (e.g., intein/extein). This can be useful, for example, in controlling expression of pesticidal activity, since functional pesticidal polypeptide will only be expressed if all required fragments are expressed in an environment that permits splicing processes to generate functional product. In another example, introduction of one or more insertion sequences into a polynucleotide can facilitate recombination with a low homology polynucleotide; use of an intron or intein for the insertion sequence facilitates the removal of the intervening sequence, thereby restoring function of the encoded variant.

Nucleic acid molecules that are fragments of these nucleic acid sequences encoding PIP-1 polypeptides are also encompassed by the embodiments. By "fragment" is intended a portion of the nucleic acid sequence encoding a PIP-1 polypeptide. A fragment of a nucleic acid sequence may encode a biologically active portion of a PIP-1 polypeptide or it may be a fragment that can be used as a hybridization probe or PCR primer using methods disclosed below. Nucleic acid molecules that are fragments of a nucleic acid sequence encoding a PIP-1 polypeptide comprise at least about 50, 100, 200, 300, 400, 500, 600 or 700, contiguous nucleotides or up to the number of nucleotides present in a full-length nucleic acid sequence encoding a PIP-1 polypeptide disclosed herein, depending upon the intended use. By "contiguous" nucleotides is intended nucleotide residues that are immediately adjacent to one another. Fragments of the nucleic acid sequences of the embodiments will encode protein fragments that retain the biological activity of the PIP-1 polypeptide and, hence, retain insecticidal activity. As used herein, the term "pesticidal activity" refers to activity of an organism or a substance (such as, for example, a protein) that can be measured by, but is not limited to, pest mortality, pest weight loss, pest repellency, and other behavioral and physical changes of a pest after feeding and exposure for an appropriate length of time. Thus, an organism or substance having pesticidal activity adversely impacts at least one measurable parameter of pest fitness. For example, "pesticidal proteins" are proteins that display pesticidal activity by themselves or in combination with other proteins. As used herein, the term "insecticidal activity" refers to activity of an organism or a substance (such as, for example, a protein) that can be measured by, but is not limited to, insect mortality, insect weight loss, insect repellency, and other behavioral and physical changes of an insect after feeding and exposure for an appropriate length of time. Thus, an organism or substance having insecticidal activity adversely impacts at least one measurable parameter of insect fitness. For example, "insecticidal proteins" are proteins that display insecticidal activity by themselves or in combination with other proteins.

As used herein, the term "pesticidally effective amount" connotes a quantity of a substance or organism that has pesticidal activity when present in the environment of a pest. For each substance or organism, the pesticidally effective amount is determined empirically for each pest affected in a specific environment. Similarly, an "insecticidally effective amount" may be used to refer to a "pesticidally effective amount" when the pest is an insect pest.

By "retains activity" is intended that the PIP-1A polypeptide has at least about 10%, at least about 30%, at least about 50%, at least about 70%, 80%, 90%, 95% or higher of the insecticidal activity compared to the full-length PIP-1A polypeptide (SEQ ID NO:2). In one embodiment, the insecticidal activity is against a Lepidoptera species. In another embodiment, the insecticidal activity is against a Hemiptera species.

In some embodiments a fragment of a nucleic acid sequence encoding a PIP-1 polypeptide encoding a biologically active portion of a protein will encode at least about 15, 25, 30, 50, 75, 100, 125, 150, 175, 200 or 250, contiguous amino acids or up to the total number of amino acids present in a full-length PIP-1 polypeptide of the embodiments. In some embodiments, the fragment is an N-terminal or a C-terminal truncation of at least about 1, 2, 3, 4, 5, 6, 7, 8, 9, 10, 11, 12, 13, 14, 15, 16, 17, 18, 19, 20, 25 or more amino acids relative to SEQ ID NO: 2, 3 or 4 or variants thereof, e.g., by proteolysis, insertion of a start codon, deletion of the codons encoding the deleted amino acids with the concomitant insertion of a stop codon or by insertion of a stop codon in the coding sequence. In some embodiments, the fragments encompassed herein result from the removal of the N-terminal 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or more amino acids relative to SEQ ID NO: 2, 3 or 4 or variants thereof, e.g., by proteolysis or by insertion of a start codon in the coding sequence.

In some embodiments the PIP-1 polypeptides are encoded by a nucleic acid sequence sufficiently identical to the nucleic acid sequence of SEQ ID NO: 1, 3 or 5. By "sufficiently identical" is intended an amino acid or nucleic acid sequence that has at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to a reference sequence using one of the alignment programs described herein using standard parameters. In some embodiments the sequence homology identity is against the full length sequence of the polynucleotide encoding a PIP-1 polypeptide or against the full length sequence of a PIP-1 polypeptide. In some embodiments the PIP-1 polypeptide has at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, SEQ ID NO: 4, SEQ ID NO: 332 or SEQ ID NO: 6. One of skill in the art will recognize that these values can be appropriately adjusted to determine corresponding identity of proteins encoded by two nucleic acid sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the comparison is across the entirety of the reference sequence (e.g., across the entirety of SEQ ID NO: 1, 331 or 3 or across the entirety of one of SEQ ID NO: 2, 332 or 4). The percent identity between two sequences can be determined using techniques similar to those described below, with or without allowing gaps. In calculating percent identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, (1990) *Proc. Natl. Acad. Sci. USA* 87:2264, modified as in Karlin and Altschul, (1993) *Proc. Natl. Acad. Sci. USA* 90:5873-5877. Such an algorithm is incorporated into the BLASTN and BLASTX programs of Altschul, et al., (1990) *J. Mol. Biol.* 215:403. BLAST nucleotide searches can be performed with the BLASTN program, score=100, wordlength=12, to obtain nucleic acid sequences homologous to pesticidal-like nucleic acid molecules. BLAST protein searches can be performed with the BLASTX program, score=50, wordlength=3, to obtain amino acid sequences homologous to pesticidal protein molecules. To obtain gapped alignments for comparison purposes, Gapped BLAST (in BLAST 2.0) can be utilized as described in Altschul, et al., (1997) *Nucleic Acids Res.* 25:3389. Alternatively, PSI-Blast can be used to perform an iterated search that detects distant relationships between molecules. See, Altschul, et al., (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins, et al., (1994) *Nucleic Acids Res.* 22:4673-4680). ClustalW compares sequences and aligns the entirety of the amino acid or DNA sequence and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller, (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12 and a gap penalty of 4 can be used. Another non-limiting example of a mathematical algorithm utilized for the comparison of sequences is the algorithm of Needleman and Wunsch, (1970) *J. Mol. Biol.* 48(3):443-453, used GAP Version 10 software to determine sequence identity or similarity using the following default parameters: % identity and % similarity for a nucleic acid sequence using GAP Weight of 50 and Length Weight of 3 and the nwsgapdna.cmpii scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The embodiments also encompass nucleic acid molecules encoding variants of PIP-1 polypeptide. "Variants" of the PIP-1 polypeptide encoding nucleic acid sequences include those sequences that encode the PIP-1 polypeptides disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the PIP-1 polypeptides disclosed as discussed below.

The skilled artisan will further appreciate that changes can be introduced by mutation of the nucleic acid sequences thereby leading to changes in the amino acid sequence of the encoded PIP-1 polypeptides, without altering the biological activity of the proteins. Thus, variant nucleic acid molecules can be created by introducing one or more nucleotide substitutions, additions or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present invention.

Alternatively, variant nucleic acid sequences can be made by introducing mutations randomly along all or part of the coding sequence, such as by saturation mutagenesis and the resultant mutants can be screened for ability to confer pesticidal activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional pesticidal polypeptide homologues and fragments thereof with desired properties. A variety of such reactions are known, including those developed by the inventors and their co-workers. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries, and any recombinant polynucleotide produces by such methods. Additionally, such methods optionally comprise selecting a variant polynucleotide from such libraries based on pesticidal activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. pesticidal activity or, such activity at a desired pH, etc. This can include identifying any activity that can be detected, for example, in an automated or automatable format, by any of the assays in the art, see, e.g., discussion of screening of insecticidal activity, infra. A variety of related (or even unrelated) properties can be evaluated, in serial or in parallel, at the discretion of the practitioner.

Descriptions of a variety of diversity generating procedures for generating modified nucleic acid sequences, e.g., those coding for polypeptides having pesticidal activity or fragments thereof, are found in the following publications and the references cited therein: Soong, et al., (2000) *Nat Genet* 25(4):436-439; Stemmer, et al., (1999) *Tumor Targeting* 4:1-4; Ness et al. (1999) *Nat Biotechnol* 17:893-896; Chang et al. (1999) *Nat Biotechnol* 17:793-797; Minshull and Stemmer, (1999) *Curr Opin Chem Biol* 3:284-290; Christians, et al., (1999) *Nat Biotechnol* 17:259-264; Crameri, et al., (1998) *Nature* 391:288-291; Crameri, et al., (1997) *Nat Biotechnol* 15:436-438; Zhang, et al., (1997) *PNAS USA* 94:4504-4509; Patten, et al., (1997) *Curr Opin Biotechnol* 8:724-733; Crameri, et al., (1996) *Nat Med* 2:100-103; Crameri, et al., (1996) *Nat Biotechnol* 14:315-319; Gates, et al., (1996) *J Mol Biol* 255:373-386; Stemmer, (1996) "Sexual PCR and Assembly PCR" In: *The Encyclopedia of Molecular Biology*. VCH Publishers, New York. pp. 447-457; Crameri and Stemmer, (1995) *BioTechniques* 18:194-195; Stemmer, et al., (1995) *Gene,* 164:49-53; Stemmer, (1995) *Science* 270:1510; Stemmer, (1995) *Bio/Technology* 13:549-553; Stemmer, (1994) *Nature* 370:389-391 and Stemmer, (1994) *PNAS USA* 91:10747-10751.

Mutational methods of generating diversity include, for example, site-directed mutagenesis (Ling, et al., (1997) *Anal Biochem* 254(2):157-178; Dale, et al., (1996) *Methods Mol Biol* 57:369-374; Smith, (1985) *Ann Rev Genet* 19:423-462; Botstein and Shortle, (1985) *Science* 229:1193-1201; Carter, (1986) *Biochem J* 237:1-7 and Kunkel, (1987) "The efficiency of oligonucleotide directed mutagenesis" in *Nucleic Acids & Molecular Biology* (Eckstein and Lilley, eds., Springer Verlag, Berlin)); mutagenesis using uracil containing templates (Kunkel, (1985) *PNAS USA* 82:488-492; Kunkel, et al., (1987) *Methods Enzymol* 154:367-382 and Bass, et al., (1988) *Science* 242:240-245); oligonucleotide-directed mutagenesis (Zoller and Smith, (1983) *Methods Enzymol* 100:468-500; Zoller and Smith, (1987) *Methods Enzymol* 154:329-350; Zoller and Smith, (1982) *Nucleic Acids Res* 10:6487-6500), phosphorothioate-modified DNA mutagenesis (Taylor, et al., (1985) *Nucl Acids Res* 13:8749-8764; Taylor, et al., (1985) *Nucl Acids Res* 13:8765-8787 (1985); Nakamaye and Eckstein (1986) *Nucl Acids Res* 14:9679-9698; Sayers, et al., (1988) *Nucl Acids Res* 16:791-802 and Sayers, et al., (1988) *Nucl Acids Res* 16: 803-814); mutagenesis using gapped duplex DNA (Kramer, et al., (1984) *Nucl Acids Res* 12:9441-9456; Kramer and Fritz, (1987) *Methods Enzymol* 154:350-367; Kramer, et al., (1988) *Nucl Acids Res* 16:7207 and Fritz, et al., (1988) *Nucl Acids Res* 16:6987-6999).

Additional suitable methods include point mismatch repair (Kramer, et al., (1984) *Cell* 38:879-887), mutagenesis using repair-deficient host strains (Carter, et al., (1985) *Nucl Acids Res* 13:4431-4443 and Carter, (1987) *Methods in Enzymol* 154:382-403), deletion mutagenesis (Eghtedarzadeh and Henikoff, (1986) *Nucl Acids Res* 14:5115), restriction-selection and restriction-purification (Wells, et al., (1986) *Phil Trans R Soc Lond A* 317:415-423), mutagenesis by total gene synthesis (Nambiar, et al., (1984) *Science* 223:1299-1301; Sakamar and Khorana, (1988) *Nucl Acids Res* 14:6361-6372; Wells, et al., (1985) *Gene* 34:315-323 and Grundström, et al., (1985) *Nucl Acids Res* 13:3305-3316), double-strand break repair (Mandecki, (1986) *PNAS USA,* 83:7177-7181 and Arnold, (1993) *Curr Opin Biotech* 4:450-455). Additional details on many of the above methods can be found in *Methods Enzymol* Volume 154, which also describes useful controls for trouble-shooting problems with various mutagenesis methods.

Additional details regarding various diversity generating methods can be found in the following US Patents, PCT Publications and Applications and EPO Publications: U.S. Pat. Nos. 5,723,323, 5,763,192, 5,814,476, 5,817,483, 5,824,514, 5,976,862, 5,605,793, 5,811,238, 5,830,721, 5,834,252, 5,837,458, WO 1995/22625, WO 1996/33207, WO 1997/20078, WO 1997/35966, WO 1999/41402, WO 1999/41383, WO 1999/41369, WO 1999/41368, EP 752008, EP 0932670, WO 1999/23107, WO 1999/21979, WO 1998/31837, WO 1998/27230, WO 1998/27230, WO 2000/00632, WO 2000/09679, WO 1998/42832, WO 1999/29902, WO 1998/41653, WO 1998/41622, WO 1998/42727, WO 2000/18906, WO 2000/04190, WO 2000/42561, WO 2000/42559, WO 2000/42560, WO 2001/23401, and PCT/US01/06775.

The nucleotide sequences of the embodiments can also be used to isolate corresponding sequences from other organisms, particularly other bacteria, particularly a *Pseudomonas* species and more particularly a *Pseudomonas chlororaphis* strain. In this manner, methods such as PCR, hybridization and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.), hereinafter "Sambrook". See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

To identify potential PIP-1 polypeptides from bacterial collections, the bacterial cell lysates can be screened with antibodies generated against PIP-1A (SEQ ID NO: 2), PSEEN3174 (SEQ ID NO: 6), PIP-1B (SEQ ID NO: 4) and PIP-1C (SEQ ID NO: 332) proteins using Western blotting and/or ELISA methods. This type of assays can be performed in a high throughput fashion. Positive samples can be further analyzed by various techniques such as antibody based protein purification and identification. Methods of generating antibodies are well known in the art as discussed infra.

Alternatively, mass spectrometry based protein identification method can be used to identify homologs of PIP-1A (SEQ ID NO: 2) using protocols in the literatures (Patterson, (1998), 10(22):1-24, Current Protocol in Molecular Biology published by John Wiley & Son Inc). Specifically, LC-MS/MS based protein identification method is used to associate the MS data of given cell lysate or desired molecular weight enriched samples (excised from SDS-PAGE gel of relevant molecular weight bands to PIP-1A protein) with sequence information of PIP-1A (SEQ ID NO: 2) and its homologs. Any match in peptide sequences indicates the potential of having the homologous proteins in the samples. Additional techniques (protein purification and molecular biology) can be used to isolate the protein and identify the sequences of the homologs.

In hybridization methods, all or part of the pesticidal nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides, and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the known PIP-1 polypeptide-encoding nucleic acid sequence disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequence encoding a PIP-1 polypeptide of the disclosure or a fragment or variant thereof. Methods for the preparation of probes for hybridization are generally known in the art and are disclosed in Sambrook and Russell, (2001), supra, herein incorporated by reference.

For example, an entire nucleic acid sequence, encoding a PIP-1 polypeptide, disclosed herein or one or more portions thereof, may be used as a probe capable of specifically hybridizing to corresponding nucleic acid sequences encoding PIP-1 polypeptide-like sequences and messenger RNAs. To achieve specific hybridization under a variety of conditions, such probes include sequences that are unique and are preferably at least about 10 nucleotides in length or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook, et al., (1989) Molecular Cloning: A Laboratory Manual (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the Tm can be approximated from the equation of Meinkoth and Wahl, (1984) *Anal. Biochem.* 138:267-284: Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization, and/or wash conditions can be adjusted to hybridize to sequences of the desired identity. For example, if sequences with 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3 or 4° C. lower than the thermal melting point (Tm); moderately stringent conditions can utilize a hybridization and/or wash at 6, 7, 8, 9 or 10° C. lower than the thermal melting point (Tm); low stringency conditions can utilize a hybridization and/or wash at 11, 12, 13, 14, 15 or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, (1993) Laboratory Techniques in Biochemistry and Molecular Biology—Hybridization with Nucleic Acid Probes, Part I, Chapter 2 (Elsevier, N.Y.); and Ausubel, et al., eds. (1995) Current Protocols in Molecular Biology, Chapter 2 (Greene Publishing and Wiley-Interscience, New York). See, Sambrook, et al., (1989) Molecular Cloning: A Laboratory Manual (2d ed., Cold Spring Harbor Laboratory Press, Cold Spring Harbor, N.Y.).

Proteins and Variants and Fragments Thereof

*Pseudomonas* Insecticidal Protein-1 (PIP-1) polypeptides are also encompassed by the disclosure. By "*Pseudomonas* Insecticidal Protein-1", "PIP-1 polypeptide" or "PIP-1 protein" is intended a polypeptide that retains insecticidal activity against one or more insect pests of the Lepidoptera and/or Hemiptera orders compared to, and including, the protein of SEQ ID NO: 2, and is sufficiently homologous to, and includes, the protein of SEQ ID NO: 2. A variety of PIP-1 polypeptides are contemplated. One source of polypeptides that encode a PIP-1 polypeptide or related proteins is a *Pseudomonas chlororaphis* strain which comprises the polynucleotide of SEQ ID NO: 1 encoding the PIP-1 polypeptide of SEQ ID NO: 2.

As used herein, the terms "protein," "peptide molecule" or "polypeptide" includes any molecule that comprises five or more amino acids. It is well known in the art that protein, peptide or polypeptide molecules may undergo modification, including post-translational modifications, such as, but not limited to, disulfide bond formation, glycosylation, phosphorylation or oligomerization. Thus, as used herein, the terms "protein," "peptide molecule" or "polypeptide" includes any protein that is modified by any biological or non-biological process. The terms "amino acid" and "amino acids" refer to all naturally occurring L-amino acids.

A "recombinant protein" is used to refer to a protein that is no longer in its natural environment, for example in vitro or in a recombinant bacterial or plant host cell. A PIP-1 polypeptide that is substantially free of cellular material includes preparations of protein having less than about 30%, 20%, 10% or 5% or less (by dry weight) of non-pesticidal protein (also referred to herein as a "contaminating protein").

"Fragments" or "biologically active portions" include polypeptide fragments comprising amino acid sequences sufficiently identical to a PIP-1 polypeptide and that exhibit insecticidal activity. "Fragments" or "biologically active portions" include polypeptide fragments comprising amino acid sequences sufficiently identical to the amino acid sequence set forth in SEQ ID NO: 2, 4, 332 and 6 including but not limited to SEQ ID NO: 204, 206 and 208 and that exhibit insecticidal activity. A biologically active portion of a PIP-1 polypeptide can be a polypeptide that is, for example, 10, 25, 50, 100, 150, 200, 250 or more amino acids in length. Such biologically active portions can be prepared by recombinant techniques and evaluated for insecticidal activity. As used here, a fragment comprises at least 8 contiguous amino acids of a PIP-1 polypeptide. In some embodiments a fragment comprises at least 8 contiguous amino acids of SEQ ID NO: 2 or 4. In some embodiments a fragment comprises at least 8 contiguous amino acids of SEQ ID NO: 2. In some embodiments a fragment comprises at least 8 contiguous amino acids of SEQ ID NO: 4. The embodiments encompass other fragments, however, such as any fragment in the protein greater than about 10, 20, 30, 50, 100, 150, 200, 250 or more amino acids.

In some embodiments, the fragment is an N-terminal and/or a C-terminal truncation of at least about 1, 2, 3, 4, 5, 6, 7, 8, 9, 10, 11, 12, 13, 14, 15, 16, 17, 18, 19, 20, 25 or more amino acids relative to SEQ ID NO: 2 or 4 or variants thereof e.g., by proteolysis, by insertion of a start codon, by deletion of the codons encoding the deleted amino acids and concomitant insertion of a start codon and/or insertion of a stop codon. In some embodiments, the fragments encompassed herein result from the removal of the N-terminal 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or more amino acids relative to SEQ ID NO: 2 or 4, and variants thereof (e.g., SEQ ID NO: 204, 206, 208 and 330), e.g., by proteolysis or by insertion of a start codon, by deletion of the codons encoding the deleted amino acids and concomitant insertion of a start codon. In particular embodiments the proteolytic cleavage site is between Ser34 and Asn35 of SEQ ID NO: 2 or variants thereof. In some embodiments the truncation is of the first 34 amino acids of SEQ ID NO: 2 resulting in a PIP-1 polypeptide from amino acids 35-271 of SEQ ID NO: 2. It is well known in the art that polynucleotides encoding the truncated PIP-1 polypeptides can be engineered to add a start codon at the N-terminus such as ATG encoding methionine or methionine followed by an alanine. It is also well known in the art that depending on what host the PIP-1 polypeptide is expressed in the methionine may be partially of completed processed off.

In some embodiments fragments, biologically active portions of SEQ ID NO: 2 or 4, including but not limited to SEQ ID NO: 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 204, 206, 208, 211, 212, 213, 214, 245, 246, 247, 248, 249, 250, 251, 252, 253, 254, 255, 256, 257, 258, 259, 260, 261, 262, 263, 264, 265, 266, 267, 268, and 269, as well as amino acid substitutions, deletions and/or insertions thereof are also provided, and may be used to practice the methods of the disclosure.

By variants is intended proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the parental amino acid sequence. In some embodiments a PIP-1 polypeptide has at least about 60%, 65%, about 70%, 75%, at least about 80%, 81%, 82%, 83%, 84%, 85%, 86%, 87%, 88%, 89%, 90%, 91%, 92%, 93%, 94%, 95%, 96%, 97%, 98% or 99% identity across the entire length of the amino acid sequence of SEQ ID NO: 2, SEQ ID NO: 332 or SEQ ID NO: 4. In some embodiments a PIP-1 polypeptide has at least about 80%, 81%, 82%, 83%, 84%, 85%, 86%, 87%, 88%, 89%, 90%, 91%, 92%, 93%, 94%, 95%, 96%, 97%, 98% or 99% identity across the entire length of the amino acid sequence of SEQ ID NO: 2.

In some embodiments a PIP-1 polypeptide comprises an amino acid sequence having at least 80% identity, to the amino acid sequence of SEQ ID NO: 2, SEQ ID NO: 332 or SEQ ID NO:4, wherein the polypeptide has insecticidal activity. In some embodiments a PIP-1 polypeptide comprises an amino acid sequence having at least 80% identity to the amino acid sequence of SEQ ID NO: 2, SEQ ID NO: 332 or SEQ ID NO: 4, wherein the polypeptide has insecticidal activity. In some embodiments a PIP-1 polypeptide comprises an amino acid sequence having at least 80% identity to the amino acid sequence of SEQ ID NO: 2, wherein the polypeptide has insecticidal activity.

In some embodiments a PIP-1 polypeptide comprises an amino acid sequence of SEQ ID NO: 211, wherein Xaa at position 2 is Pro or Thr; Xaa at position 8 is Ser, Gly or Asn; Xaa at position 19 is Asp, Glu or Cys; Xaa at position 20 is Leu or Val; Xaa at position 21 is Lys, Ser or Asn; Xaa at position 22 is Ser, Lys or Arg; Xaa at position 24 is Gln or Ala; Xaa at position 25 is Gly or Ala Xaa at position 26 is Ser or Asn; Xaa at position 27 is Leu, Thr or Ala; Xaa at position 30 is Ala or Ile; Xaa at position 35 is Phe or Leu; Xaa at position 36 is Ala, Ser or Val; Xaa at position 38 is Asn, Arg or Ser; Xaa at position 42 is Phe or Tyr; Xaa at position 46 is Arg, Lys or His; Xaa at position 48 is Gly or Asp; Xaa at position 49 is Phe or Tyr; Xaa at position 53 is Ser or Gly; Xaa at position 58 is Tyr or Phe; Xaa at position 60 is Ala or Ser; Xaa at position 63 is Gln or Lys; Xaa at position 77 is Phe or Tyr; Xaa at position 97 is Met or Val; Xaa at position 98 is Asp or Glu; Xaa at position 105 is Gln or Asn; Xaa at position 107 is Thr or Ile; Xaa at position 108 is Gln or Thr; Xaa at position 110 is Arg or Leu; Xaa at position 120 is Lys, Arg or Gln; Xaa at position 121 is Thr or Ser; Xaa at position 123 is Thr or Glu; Xaa at position 125 is Asn or Ser; Xaa at position 127 is Ser, Asn, Thr or Lys; Xaa at position 134 is Gly or Ala; Xaa at position 135 is Ser, Asn or Lys; Xaa at position 137 is Asp or Gly; Xaa at position 141 is Val or Ile; Xaa at position 142 is Gly or Asp; Xaa at position 144 is Asp or Glu; Xaa at position 147 is Ile, Thr or Val; Xaa at position 150 is Ser or Thr; Xaa at position 151 is Asn, Arg or Ser; Xaa at position 160 is Thr or Ser; Xaa at position 162 is Ser or Thr; Xaa at position 163 is Asn, Asp or Glu; Xaa at position 164 is Ser or Thr; Xaa at position 166 is Gln or Glu; Xaa at position 167 is Leu or Met; Xaa at position 168 is Thr, Lys or Ala; Xaa at position 174 is Ile, Val or Met; Xaa at position 175 is Val or Ile; Xaa at position 180 is Met or Leu; Xaa at position 191 is Arg or Lys; Xaa at position 194 is Gly or Ala; Xaa at position 200 is Asn or Ser; Xaa at position 203 is Asn or Gln; Xaa at position 204 is Thr or Ala; Xaa at position 206 is Gly or Asp; Xaa at position 209 is Leu or Val; Xaa at position 220 is Asn or Arg; Xaa at position 221 is Ser or Lys; Xaa at position 222 is Thr or Arg; Xaa at position 226 is Asp, Pro or Glu; Xaa at position 228 is Ser or Gly; Xaa at position 229 is Lys or Asn; Xaa at position 231 is Ile or Val; Xaa at position 232 is Ala, Thr or Glu; and Xaa at position 251 is Gly, Ser or Glu; Xaa at position 254 is Ser or Asn; Xaa at position 258 is Ser or Arg; Xaa at position 265 is Asn or Asp; and Xaa at position 266 is Asp or Asn; and amino acid deletions, amino acid insertions, and fragments thereof, and combinations thereof.

In some embodiments a PIP-1 polypeptide comprises an amino acid sequence of SEQ ID NO: 211 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or 61 amino acid substitutions, in any combination, at residues designated by Xaa in SEQ ID NO: 211 compared to the native amino acid at the corresponding position of SEQ ID NO: 2.

In some embodiments a PIP-1 polypeptide comprises an amino acid sequence of SEQ ID NO: 211 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 or 54 amino acid substitutions, in any combination, at residues designated by Xaa in SEQ ID NO: 211 compared to the native amino acid at the corresponding position of SEQ ID NO: 2.

In some embodiments a PIP-1 polypeptide comprises an amino acid sequence of SEQ ID NO: 212, wherein Xaa at position 2 is Pro or Thr; Xaa at position 3 is Ile or Thr; Xaa at position 6 is Glu or Gly; Xaa at position 8 is Ser, Gly or Asn; Xaa at position 19 is Asp, Glu or Cys; Xaa at position 20 is Leu or Val; Xaa at position 21 is Lys, Ser or Asn; Xaa at position 22 is Ser, Lys or Arg; Xaa at position 24 is Gln or Ala; Xaa at position 25 is Gly or Ala; Xaa at position 26 is Ser or Asn; Xaa at position 27 is Leu, Thr or Ala; Xaa at position 28 is Arg, Ser, Lys, Thr, Val, Gly, Ala, Met, Asp, Trp, Pro, Leu, His, Cys or Gln; Xaa at position 30 is Ala or Ile; Xaa at position 35 is Phe or Leu; Xaa at position 36 is Ala, Ser or Val; Xaa at position 38 is Asn, Arg or Ser; Xaa at position 42 is Phe or Tyr; Xaa at position 43 is Pro, Met, Gly, Gln, Ser, Thr, Arg, Val, Leu, Lys, Asp, Ala, Asn, Phe, Trp, Glu or Cys; Xaa at position 46 is Arg, Lys or His; Xaa at position 48 is Gly or Asp; Xaa at position 49 is Phe, Tyr or Leu; Xaa at position 53 is Ser or Gly; Xaa at position 58 is Tyr or Phe; Xaa at position 60 is Ala or Ser; Xaa at position 63 is Gln or Lys; Xaa at position 66 is Trp, Tyr, Phe, Arg, Lys, His, Ile, Val or Ser; Xaa at position 77 is Phe or Tyr; Xaa at position 89 is Pro, Leu, Gly, Arg, Thr, Ser, Met, Ala, Ile, Asn, Val, Cys or Lys; Xaa at position 93 is Tyr, Cys, Trp, Val, Asp, Asn, Ile, Leu, Met, Phe, Ala or Thr; Xaa at position 97 is Met or Val; Xaa at position 98 is Asp or Glu; Xaa at position 105 is Gln or Asn; Xaa at position 107 is Thr or Ile; Xaa at position 108 is Gln or Thr; Xaa at position 110 is Arg or Leu; Xaa at position 120 is Lys, Arg or Gln; Xaa at position 121 is Thr or Ser; Xaa at position 123 is Thr or Glu; Xaa at position 125 is Asn or Ser; Xaa at position 127 is Ser, Asn, Thr or Lys; Xaa at position 134 is Gly or Ala; Xaa at position 135 is Ser, Asn or Lys; Xaa at position 137 is Asp or Gly; Xaa at position 141 is Val or Ile; Xaa at position 142 is Gly or Asp; Xaa at position 144 is Asp or Glu; Xaa at position 147 is Ile, Thr or Val; Xaa at position 150 is Ser or Thr; Xaa at position 151 is Asn, Arg or Ser; Xaa at position 160 is Thr or Ser; Xaa at position 162 is Ser or Thr; Xaa at position 163 is Asn, Asp or Glu; Xaa at position 164 is Ser or Thr; Xaa at position 166 is Gln or Glu; Xaa at position 167 is Leu or Met; Xaa at position 168 is Thr, Lys or Ala; Xaa at position 171 is Gly, Leu, Gln, Met, Cys, Asn, Asp, Ser or Ala; Xaa at position 172 is Thr, Gly, His, Phe, Glu, Arg, Ser, Asn, Ile, Trp, Lys, Gln, Cys, Val, Ala or Met; Xaa at position 173 is Phe, Gly, His, Leu, Ala, Arg, Asn, Cys, Lys, Trp, Thr, Ser, Tyr or Met; Xaa at position 174 is Ile, Val, Gly, Arg, Asn, Ala, Gln, Met, Cys, Leu, Phe, Tyr, Lys, Glu, Ser, His or Thr; Xaa at position 175 is Val, Ile, Ala, Cys, Glu, Lys, Leu or Met; Xaa at position 176 is Tyr, Met, Phe, Leu or Cys; Xaa at position 177 is Gln, Ile, Met or Pro; Xaa at position 178 is Val, Cys, Thr, Pro, Ala, Met, Gln, Phe, Ile, Ser or Lys; Xaa at position 179 is Val, Phe, Thr, Ile, Cys, Leu, Met, Ser, Ala or Gln; Xaa at position 180 is Met, Leu, Pro, Trp, Asn, Tyr, Gly, Gln, Ala, Val, Phe, Ile, Cys or Ser; Xaa at position 181 is Val, Ala, Leu, Trp, Cys, Thr, Ile or Lys; Xaa at position 182 is Tyr, Phe, Met or His; Xaa at position 183 is Ala, Met, Val, Thr, Asp, Gly, Cys, Ile, Phe, Ser, Gln or Leu; Xaa at position 191 is Arg or Lys; Xaa at position 194 is Gly or Ala; Xaa at position 195 is Asn or Tyr; Xaa at position 200 is Asn or Ser; Xaa at position 203 is Asn or Gln; Xaa at position 204 is Thr or Ala; Xaa at position 206 is Gly or Asp; Xaa at position 209 is Leu or Val; Xaa at position 213 is Tyr or Phe; Xaa at position 220 is Asn or Arg; Xaa at position 221 is Ser or Lys; Xaa at position 222 is Thr or Arg; Xaa at position 226 is Asp, Pro or Glu; Xaa at position 228 is Ser or Gly; Xaa at position 229 is Lys or Asn; Xaa at position 231 is Ile or Val; Xaa at position 232 is Ala, Thr or Glu; Xaa at position 240 is Gln, Arg, Ala, Val, Glu, Met, Gly, Asp, Trp, Asn, Thr, Ile, Ser, Phe, His, Cys or Leu; Xaa at position 241 is Arg, Lys, Glu, Gln, Ser, Ile, Val, Asp, Tyr, Met, Asn, His, Pro, Gly, Leu, Phe, Thr, Ala or Cys; Xaa at position 242 is Asn, Ala, Arg, Lys, His, Ser, Cys, Glu, Pro, Trp, Gln, Thr, Phe, Tyr, Met, Asp, Gly, Leu or Val; Xaa at position 243 is Val, Leu, Ala, Thr, Gly, Cys, Ile, Ser or Met; Xaa at position 244 is Leu, Val, Phe, Ile, Met, Gln, Cys, Trp or Ala; Xaa at position 245 is Met, Ala, Arg, Asp, Glu, Leu, Pro, Ser, Trp, Gly, Val, Lys, Phe, Cys, Thr, His, Ile, Gln, Tyr or Asn; Xaa at position 246 is Glu, Asp, Tyr, Gly, Arg, Val, Ala, Trp, Gln, Ser, Asn, Ile Leu, Met, Cys, Pro, His, Phe, Thr or Lys; Xaa at position 247 is Asn, Leu, Asp, Tyr, Ala, Phe, His, Arg, Lys, Gln, Gly, Val, Ile, Ser, Glu, Pro, Met, Trp, Thr or Cys; Xaa at position 248 is Tyr, Val, Thr, Glu, Phe, Ser, His, Cys, Leu, Trp, Ile, Asp, Gly or Ala; Xaa at position 249 is Asn, Lys, Val, Gly, Met, Asp, Cys, Phe, Arg, Glu, Trp, Tyr, Ser, Ile, Thr, Pro, Leu, Ala, His or Gln; Xaa at position 251 is Gly, Ser or Glu; Xaa at position 254 is Ser or Asn; Xaa at position 258 is Ser or Arg; Xaa at position 259 is Phe, Trp, Tyr, Cys, Met, Leu, Val, Ile or His; Xaa at position 265 is Asn or Asp; and Xaa at position 266 is Asp or Asn; and amino acid deletions, amino acid insertions, and fragments thereof, and combinations thereof.

In some embodiments a PIP-1 polypeptide comprises an amino acid sequence of SEQ ID NO: 212 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89 amino acid substitutions, in any combination, at residues designated by Xaa in SEQ ID NO: 212 compared to the native amino acid at the corresponding position of SEQ ID NO: 2.

In some embodiments a PIP-1 polypeptide comprises an amino acid sequence of SEQ ID NO: 212 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 or 54 amino acid substitutions, in any combination, at residues designated by Xaa in SEQ ID NO: 212 compared to the native amino acid at the corresponding position of SEQ ID NO: 2.

In some embodiments a PIP-1 polypeptide comprises an amino acid sequence of SEQ ID NO: 213 wherein Xaa at position 2 is Pro, Thr or Ser; Xaa at position 3 is Ile, Thr, Leu, Val, Met or Ser; Xaa at position 6 is Glu, Gly, Asp or Ala; Xaa at position 8 is Ser, Gly, Asn, Thr or Gln; Xaa at position 19 is Asp, Glu or Cys; Xaa at position 20 is Leu, Val, Ile or Met; Xaa at position 21 is Lys, Ser, Asn, Arg, Thr or Gln; Xaa at position 22 is Ser, Lys, Arg or Thr; Xaa at position 24 is Gln, Gly, Asn or Ala; Xaa at position 25 is Gly or Ala; Xaa at position 26 is Ser, Asn, Thr or Gln; Xaa at position 27 is Leu, Thr, Ala, Ser, Ile, Val or Met; Xaa at position 28 is Arg, Ser, Lys, Thr, Val, Gly, Ala, Met, Asp, Trp, Pro, Leu, His, Cys or Gln; Xaa at position 30 is Ala, Ile, Leu, Val or Met; Xaa at position 35 is Phe, Leu, Ile, Val or Met; Xaa at position 36 is Ala, Ser, Thr, Val, Ile or Leu; Xaa at position 38 is Asn, Arg, Ser, Gln, Lys or Thr; Xaa at position 42 is Phe, Tyr, Trp, Leu, Ile, Val or Met; Xaa at position 43 is Pro, Met, Gly, Gln, Ser, Thr, Arg, Val, Leu, Lys, Asp, Ala, Asn, Phe, Trp, Glu or Cys; Xaa at position 46 is Arg, Lys or His; Xaa at position 48 is Gly, Asp, Ala or Glu; Xaa at position 49 is Phe, Tyr, Trp, Leu, Ile, Val or Met; Xaa at position 53 is Ser, Gly, Ala or Thr; Xaa at position 58 is Tyr or Phe; Xaa at position 60 is Ala, Ser, Gly or Thr; Xaa at position 63 is Gln, Lys, Asn or Arg; Xaa at position 66 is Trp, Tyr, Phe, Arg, Lys, His, Ile, Val or Ser; Xaa at position 77 is Phe, Tyr, Trp, Leu, Ile, Val or Met; Xaa at position 89 is Pro, Leu, Gly, Arg, Thr, Ser, Met, Ala, Ile, Asn, Val, Cys or Lys; Xaa at position 93 is Tyr, Cys, Trp, Val, Asp, Asn, Ile, Leu, Met, Phe, Ala or Thr; Xaa at position 97 is Met, Val, Leu or Ile; Xaa at position 98 is Asp or Glu; Xaa at position 105 is Gln or Asn; Xaa at position 107 is Thr, Ile, Ser, Leu or Val; Xaa at position 108 is Gln, Thr, Ser or Asn; Xaa at position 110 is Arg, Leu, Lys, Ile, Val or Met; Xaa at position 120 is Lys, Arg, Gln or Asn; Xaa at position 121 is Thr or Ser; Xaa at position 123 is Thr, Glu, Ser or Asp; Xaa at position 125 is Asn, Ser, Gln or Thr; Xaa at position 127 is Ser, Asn, Thr, Gln, Lys, Ser or Arg; Xaa at position 134 is Gly or Ala; Xaa at position 135 is Ser, Asn, Thr, Gln, Arg or Lys; Xaa at position 137 is Asp, Gly, Glu or Ala; Xaa at position 141 is Val, Ile or Leu; Xaa at position 142 is Gly, Asp, Ala or Glu; Xaa at position 144 is Asp or Glu; Xaa at position 147 is Ile, Thr, Val, Leu, Met or Ser; Xaa at position 150 is Ser or Thr; Xaa at position 151 is Asn, Arg, Ser, Gln, Lys or Thr; Xaa at position 160 is Thr or Ser; Xaa at position 162 is Ser or Thr; Xaa at position 163 is Asn, Asp, Glu or Gln; Xaa at position 164 is Ser or Thr; Xaa at position 166 is Gln, Glu, Asp or Asn; Xaa at position 167 is Leu, Met, Ile, Val; Xaa at position 168 is Thr, Lys, Ala, Ser, Arg or Gly; Xaa at position 171 is Gly, Leu, Gln, Met, Cys, Asn, Asp, Ser or Ala; Xaa at position 172 is Thr, Gly, His, Phe, Glu, Arg, Ser, Asn, Ile, Trp, Lys, Gln, Cys, Val, Ala or Met; Xaa at position 173 is Phe, Gly, His, Leu, Ala, Arg, Asn, Cys, Lys, Trp, Thr, Ser, Tyr or Met; Xaa at position 174 is Ile, Val, Gly, Arg, Asn, Ala, Gln, Met, Cys, Leu, Phe, Tyr, Lys, Glu, Ser, His or Thr; Xaa at position 175 is Val, Ile, Ala, Cys, Glu, Lys, Leu or Met; Xaa at position 176 is Tyr, Met, Phe, Leu or Cys; Xaa at position 177 is Gln, Ile, Met or Pro; Xaa at position 178 is Val, Cys, Thr, Pro, Ala, Met, Gln, Phe, Ile, Ser or Lys; Xaa at position 179 is Val, Phe, Thr, Ile, Cys, Leu, Met, Ser, Ala or Gln; Xaa at position 180 is Met, Leu; Pro, Trp, Asn, Tyr, Gly, Gln, Ala, Val, Phe, Ile, Cys or Ser; Xaa at position 181 is Val, Ala, Leu, Trp, Cys, Thr, Ile or Lys; Xaa at position 182 is Tyr, Phe, Met or His; Xaa at position 183 is Ala, Met, Val, Thr, Asp, Gly, Cys, Ile, Phe, Ser, Gln or Leu; Xaa at position 191 is Arg or Lys; Xaa at position 194 is Gly or Ala; Xaa at position 195 is Asn, Tyr, Gln or Trp; Xaa at position 200 is Asn, Ser, Thr or Gln; Xaa at position 203 is Asn or Gln; Xaa at position 204 is Thr, Ala, Ser or Gly; Xaa at position 206 is Gly, Asp, Ala or Glu; Xaa at position 209 is Leu, Val, Ile or Met; Xaa at position 213 is Tyr or Phe; Xaa at position 220 is Asn, Arg, Gln or Lys; Xaa at position 221 is Ser, Lys, Thr or Arg; Xaa at position 222 is Thr, Arg, Ser or Lys; Xaa at position 226 is Asp, Pro, Glu or Gln; Xaa at position 228 is Ser or Gly; Xaa at position 229 is Lys, Asn, Arg or Gln; Xaa at position 231 is Ile, Val, Leu or Met; Xaa at position 232 is Ala, Thr, Ser, Gly, Asp or Glu; Xaa at position 240 is Gln, Arg, Ala, Val, Glu, Met, Gly, Asp, Trp, Asn, Thr, Ile, Ser, Phe, His, Cys or Leu; Xaa at position 241 is Arg, Lys, Glu, Gln, Ser, Ile, Val, Asp, Tyr, Met, Asn, His, Pro, Gly, Leu, Phe, Thr, Ala or Cys; Xaa at position 242 is Asn, Ala, Arg, Lys, His, Ser, Cys, Glu, Pro, Trp, Gln, Thr, Phe, Tyr, Met, Asp, Gly, Leu or Val; Xaa at position 243 is Val, Leu, Ala, Thr, Gly, Cys, Ile, Ser or Met; Xaa at position 244 is Leu, Val, Phe, Ile, Met, Gln, Cys, Trp or Ala; Xaa at position 245 is Met, Ala, Arg, Asp, Glu, Leu, Pro, Ser, Trp, Gly, Val, Lys, Phe, Cys, Thr, His, Ile, Gln, Tyr or Asn; Xaa at position 246 is Glu, Asp, Tyr, Gly, Arg, Val, Ala, Trp, Gln, Ser, Asn, Ile Leu, Met, Cys, Pro, His, Phe, Thr or Lys; Xaa at position 247 is Asn, Leu, Asp, Tyr, Ala, Phe, His, Arg, Lys, Gln, Gly, Val, Ile, Ser, Glu, Pro, Met, Trp, Thr or Cys; Xaa at position 248 is Tyr, Val, Thr, Glu, Phe, Ser, His, Cys, Leu, Trp, Ile, Asp, Gly or Ala; Xaa at position 249 is Asn, Lys, Val, Gly, Met, Asp, Cys, Phe, Arg, Glu, Trp, Tyr, Ser, Ile, Thr, Pro, Leu, Ala, His or Gln; Xaa at position 251 is Gly, Ser, Thr, Ala, Asp or Glu; Xaa at position 254 is Ser, Asn, Thr or Gln; Xaa at position 258 is Ser, Arg, Thr or Lys; Xaa at position 259 is Phe, Trp, Tyr, Cys, Met, Leu, Val, Ile or His; Xaa at position 265 is Asn, Asp, Gln or Glu; and Xaa at position 266 is Asp, Asn, Gln or Glu; and amino acid deletions, amino acid insertions and fragments thereof, and combinations thereof.

In some embodiments a PIP-1 polypeptide comprises an amino acid sequence of SEQ ID NO: 213 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88 or 89 amino acid substitutions, in any combination, at residues designated by Xaa in SEQ ID NO: 213 compared to the native amino acid at the corresponding position of SEQ ID NO: 2.

In some embodiments a PIP-1 polypeptide comprises an amino acid sequence of SEQ ID NO: 213 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 or 54 amino acid substitutions, in any combination, at residues designated by Xaa in SEQ ID NO: 213 compared to the native amino acid at the corresponding position of SEQ ID NO: 2.

In some embodiments a PIP-1 polypeptide comprises one or more amino acid motifs selected from i) an amino acid motif represented by amino acids at positions 64-79 of SEQ ID NO: 2, amino acids 64-79 of SEQ ID NO: 211, amino acids 64-79 of SEQ ID NO: 212 or amino acids 64-79 of SEQ ID NO: 213, ii) an amino acid motif represented by amino acids at positions 149-159 of SEQ ID NO: 2, amino acids 149-159 of SEQ ID NO: 211, amino acids 149-159 of SEQ ID NO: 212 or amino acids 149-159 of SEQ ID NO: 213, iii) an amino acid motif represented by amino acids at positions 171-183 of SEQ ID NO: 2, amino acids 171-183 of SEQ ID NO: 211, amino acids 171-183 of SEQ ID NO: 212 or amino acids 171-183 of SEQ ID NO: 213, and iv) an amino acid motif represented by amino acids at positions 240-249 of SEQ ID NO: 2, amino acids 240-249 of SEQ ID NO: 211, amino acids 240-249 of SEQ ID NO: 212 or amino acids 240-249 of SEQ ID NO: 213. In some embodiments the PIP-1 polypeptide comprises an amino acid as represented by positions 171-183 of SEQ ID NO: 213 wherein at least one amino acid at positions 171-183 of SEQ ID NO: 213 are not identical to amino acids at positions 171-183 of SEQ ID NO: 6.

In some embodiments a PIP-1 polypeptide comprises an amino acid sequence having at least 80% identity to the amino acid sequence set forth in SEQ ID NO: 2, SEQ ID NO: 332 or SEQ ID NO: 4 and comprises one or more amino acid motifs selected from i) an amino acid motif represented by amino acids at positions 64-79 of SEQ ID NO: 2, amino acids 64-79 of SEQ ID NO: 211, amino acids 64-79 of SEQ ID NO: 212 or amino acids 64-79 of SEQ ID NO: 213, ii) an amino acid motif represented by amino acids at positions 149-159 of SEQ ID NO: 2, amino acids 149-159 of SEQ ID NO: 211, amino acids 149-159 of SEQ ID NO: 212 or amino acids 149-159 of SEQ ID NO: 213, iii) an amino acid motif represented by amino acids at positions 171-183 of SEQ ID NO: 2, amino acids 171-183 of SEQ ID NO: 211, amino acids 171-183 of SEQ ID NO: 212 or amino acids 171-183 of SEQ ID NO: 213, and iv) an amino acid motif represented by amino acids at positions 240-249 of SEQ ID NO: 2, amino acids 240-249 of SEQ ID NO: 211, amino acids 240-249 of SEQ ID NO: 212 or amino acids 240-249 of SEQ ID NO: 213.

In some embodiments a PIP-1 polypeptide comprises an amino acid sequence having at least 80% identity to the amino acid sequence set forth in SEQ ID NO: 2, SEQ ID NO: 332 or SEQ ID NO: 4 and comprises one or more amino acid motifs selected from i) an amino acid motif represented by amino acids at positions 64-79 of SEQ ID NO: 2, amino acids 64-79 of SEQ ID NO: 211, amino acids 64-79 of SEQ ID NO: 212 or amino acids 64-79 of SEQ ID NO: 213, ii) an amino acid motif represented by amino acids at positions 149-159 of SEQ ID NO: 2, amino acids 149-159 of SEQ ID NO: 211, amino acids 149-159 of SEQ ID NO: 212 or amino acids 149-159 of SEQ ID NO: 213, iii) an amino acid motif represented by amino acids at positions 171-183 of SEQ ID NO: 2, amino acids 171-183 of SEQ ID NO: 211, amino acids 171-183 of SEQ ID NO: 212 or amino acids 171-183 of SEQ ID NO: 213, and iv) amino acids 240-249 of SEQ ID NO: 2, amino acids 240-249 of SEQ ID NO: 211, amino acids 240-249 of SEQ ID NO: 212 or amino acids 240-249 of SEQ ID NO: 213.

In some embodiments the amino acid motifs represented by i) amino acids 64-79 of SEQ ID NO: 2, amino acids 64-79 of SEQ ID NO: 211, amino acids 64-79 of SEQ ID NO: 212 or amino acids 64-79 of SEQ ID NO: 213, ii) amino acids 149-159 of SEQ ID NO: 2, amino acids 149-159 of SEQ ID NO: 211, amino acids 149-159 of SEQ ID NO: 212 or amino acids 149-159 of SEQ ID NO: 213, iii) amino acids 171-183 of SEQ ID NO: 2, amino acids 171-183 of SEQ ID NO: 211, amino acids 171-183 of SEQ ID NO: 212 or amino acids 171-183 of SEQ ID NO: 213, and iv) amino acids 240-249 of SEQ ID NO: 2, amino acids 240-249 of SEQ ID NO: 211, amino acids 240-249 of SEQ ID NO: 212 or amino acids 240-249 of SEQ ID NO: 213, the amino acid motif may optional have a deletion of one or more amino acids within the motif, a insertion of one or more amino acids within the motif or combinations thereof.

In some embodiments exemplary PIP-1 polypeptides are encoded by the polynucleotide sequence set forth in SEQ ID NO: 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 197, 188, 189, 190, 191, 192, 193, 194, 195, 196, 197, 198, 199, 200, 201, 202, 203, 205, 207, 220, 221, 222, 223, 224, 225, 226, 227, 228, 229, 230, 231, 232, 233, 234, 235, 236, 237, 238, 239, 240, 241, 242, 243, 244, 270, 271, 272, 273, 274, 275, 276, 277, 278, 279, 280, 281, 282, 283, 284, 285, 286, 287, 288, 289, 290, 291, 292, 293, 294, 295, 296, and 297 as well as variants and fragments thereof encoding PIP-1 polypeptides.

In some embodiments exemplary nucleic acid molecules comprise a sequence set forth in SEQ ID NO: 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 197, 188, 189, 190, 191, 192, 193, 194, 195, 196, 197, 198, 199, 200, 201, 202, 203, 205, 207, 220, 221, 222, 223, 224, 225, 226, 227, 228, 229, 230, 231, 232, 233, 234, 235, 236, 237, 238, 239, 240, 241, 242, 243, and 244 as well as variants and fragments thereof encoding PIP-1 polypeptides.

In some embodiments a PIP-1 polypeptide includes variants where an amino acid that is part of a proteolytic cleavage site is changed to another amino acid to eliminate or alter the proteolytic cleavage at that site. In some embodiments the proteolytic cleavage is by a protease in the insect gut. In other embodiments the proteolytic cleavage is by a plant protease in the transgenic plant.

In some embodiments exemplary PIP-1 polypeptides are the polypeptides shown in Table 4, Table 6, Table 9, Table 12, Table 13, Table 14 and/or Table 16 and combinations of the amino substitutions thereof as well as deletions, and or insertions and fragments thereof.

In some embodiments a PIP-1 polypeptide does not have the amino acid sequence of SEQ ID NO: 4. In some embodiments a PIP-1 polypeptide does not have the amino acid sequence of SEQ ID NO: 6.

In some embodiments a PIP-1 polypeptide has a calculated molecular weight of between about 15 kD and about 35 kD, between about 19 kD and about 35 kD, between about 21 kD and about 35 kD, between about 23 kD and about 35 kD, between about 25 kD and about 32 kD, between about 27 kD and about 32 kD, between about 28 kD and about 32 kD, between about 29 kD and about 32 kD, between about 30 kD and about 31 kD or about 30.5 kD.

In some embodiments a PIP-1 polypeptide is encoded by a nucleic acid molecule that hybridizes under stringent conditions to the nucleic acid molecule of SEQ ID NO: 1 or 3. Variants include polypeptides that differ in amino acid sequence due to mutagenesis. Variant proteins encompassed by the disclosure are biologically active, that is they continue to possess the desired biological activity (i.e. pesticidal activity) of the native protein. By "retains activity" is intended that the variant will have at least about 30%, at least about 50%, at least about 70% or at least about 80% of the insecticidal activity of the native protein. In some embodiments, the variants may have improved activity over the native protein.

Bacterial genes quite often possess multiple methionine initiation codons in proximity to the start of the open reading frame. Often, translation initiation at one or more of these start codons will lead to generation of a functional protein. These start codons can include ATG codons. For example, SEQ ID NO: 215 represent alternate start site protein encoded by SEQ ID NO: 1. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present disclosure and may be used in the methods of the present disclosure. It will be understood that, when expressed in plants, it will be necessary to alter the alternate start codon to ATG for proper translation.

In another aspect the PIP-1 polypeptide may be expressed as a precursor protein with an intervening sequence that catalyzes multi-step, post translational protein splicing. Protein splicing involves the excision of an intervening sequence from a polypeptide with the concomitant joining of the flanking sequences to yield a new polypeptide (Chong, et al., (1996) *J. Biol. Chem.* 271:22159-22168). This intervening sequence or protein splicing element, referred to as inteins, which catalyze their own excision through three coordinated reactions at the N-terminal and C-terminal splice junctions: an acyl rearrangement of the N-terminal cysteine or Serine; a transesterfication reaction between the two termini to form a branched ester or thioester intermediate and peptide bond cleavage coupled to cyclization of the intein C-terminal asparagine to free the intein (Evans, et al., (2000) *J. Biol. Chem.* 275:9091-9094. The elucidation of the mechanism of protein splicing has led to a number of intein-based applications (Comb, et al., U.S. Pat. No. 5,496, 714; Comb, et al., U.S. Pat. No. 5,834,247; Camarero and Muir, (1999) *J. Amer. Chem. Soc.* 121:5597-5598; Chong, et al., (1997) *Gene* 192:271-281, Chong, et al., (1998) *Nucleic Acids Res.* 26:5109-5115; Chong, et al., (1998) *J. Biol. Chem.* 273:10567-10577; Cotton, et al., (1999) *J. Am. Chem. Soc.* 121:1100-1101; Evans, et al., (1999) *J. Biol. Chem.* 274:18359-18363; Evans, et al., (1999) *J. Biol. Chem.* 274:3923-3926; Evans, et al., (1998) *Protein Sci.* 7:2256-2264; Evans, et al., (2000) J. Biol. Chem. 275:9091-9094; Iwai and Pluckthun, (1999) *FEBS Lett.* 459:166-172; Mathys, et al., (1999) *Gene* 231:1-13; Mills, et al., (1998) *Proc. Natl. Acad. Sci. USA* 95:3543-3548; Muir, et al., (1998) *Proc. Natl. Acad. Sci. USA* 95:6705-6710; Otomo, et al., (1999) *Biochemistry* 38:16040-16044; Otomo, et al., (1999) *J. Biolmol. NMR* 14:105-114; Scott, et al., (1999) *Proc. Natl. Acad. Sci. USA* 96:13638-13643; Severinov and Muir, (1998) *J. Biol. Chem.* 273:16205-16209; Shingledecker, et al., (1998) *Gene* 207:187-195; Southworth, et al., (1998) *EMBO J.* 17:918-926; Southworth, et al., (1999) *Biotechniques* 27:110-120; Wood, et al., (1999) *Nat. Biotechnol.* 17:889-892; Wu, et al., (1998a) *Proc. Natl. Acad. Sci. USA* 95:9226-9231; Wu, et al., (1998b) *Biochim Biophys Acta* 1387:422-432; Xu, et al., (1999) *Proc. Natl. Acad. Sci. USA* 96:388-393; Yamazaki, et al., (1998) *J. Am. Chem. Soc.* 120:5591-5592). For the application of inteins in plant transgenes see Yang, J, et al., (*Transgene Res* 15:583-593 (2006)) and Evans, et al., (*Annu. Rev. Plant Biol.* 56:375-392, (2005)).

In another aspect the PIP-1 polypeptide may be encoded by two separate genes where the intein of the precursor protein comes from the two genes, referred to as a split-intein and the two portions of the precursor are joined by a peptide bond formation. This peptide bond formation is accomplished by intein-mediated trans-splicing. For this purpose, a first and a second expression cassette comprising the two separate genes further code for inteins capable of mediating protein trans-splicing. By trans-splicing, the proteins and polypeptides encoded by the first and second fragments may be linked by peptide bond formation. Trans-splicing inteins may be selected from the nucleolar and organellar genomes of different organisms including eukaryotes, archaebacteria and eubacteria. Inteins that may be used for are listed at neb.com/neb/inteins.html, which can be accessed on the world-wide web using the "www" prefix). The nucleotide sequence coding for an intein may be split into a 5' and a 3' part that code for the 5' and the 3' part of the intein, respectively. Sequence portions not necessary for intein splicing (e.g., homing endonuclease domain) may be deleted. The intein coding sequence is split such that the 5' and the 3' parts are capable of trans-splicing. For selecting a suitable splitting site of the intein coding sequence, the considerations published by Southworth, et al., (1998) *EMBO J.* 17:918-926 may be followed. In constructing the first and the second expression cassette, the 5' intein coding sequence is linked to the 3' end of the first fragment coding for the N-terminal part of the PIP-1 polypeptide and the 3' intein coding sequence is linked to the 5' end of the second fragment coding for the C-terminal part of the PIP-1 polypeptide.

In general, the trans-splicing partners can be designed using any split intein, including any naturally-occurring or artificially-split split intein. Several naturally-occurring split inteins are known, for example: the split intein of the DnaE gene of *Synechocystis* sp. PCC6803 (see, Wu, et al., (1998) *Proc Natl Acad Sci USA* 95(16):9226-31 and Evans, et al., (2000) J Biol Chem 275(13):9091-4 and of the DnaE gene from *Nostoc punctiforme* (see, Iwai, et al., (2006) *FEBS Lett* 580(7):1853-8). Non-split inteins have been artificially split in the laboratory to create new split inteins, for example: the artificially split Ssp DnaB intein (see, Wu, et al., (1998) *Biochim Biophys Acta* 1387:422-32) and split Sce VMA intein (see, Brenzel, et al., (2006) *Biochemistry* 45(6):1571-8) and an artificially split fungal mini-intein (see, Elleuche, et al., (2007) *Biochem Biophys Res Commun* 355(3):830-4). There are also intein databases available that catalogue known inteins (see, for example the online-database available at: bioinformatics.weizmann.ac.ilrpietro/inteins/Intein-stable.html, which can be accessed on the world-wide web using the "www" prefix).

Naturally-occurring non-split inteins may have endonuclease or other enzymatic activities that can typically be removed when designing an artificially-split split intein. Such mini-inteins or minimized split inteins are well known in the art and are typically less than 200 amino acid residues long (see, Wu, et al., (1998) *Biochim Biophys Acta* 1387: 422-32). Suitable split inteins may have other purification enabling polypeptide elements added to their structure, provided that such elements do not inhibit the splicing of the split intein or are added in a manner that allows them to be removed prior to splicing. Protein splicing has been reported using proteins that comprise bacterial intein-like (BIL) domains (see, Amitai, et al., (2003) *Mol Microbiol* 47:61-73) and hedgehog (Hog) auto-processing domains (the latter is combined with inteins when referred to as the Hog/intein superfamily or HINT family (see, Dassa, et al., (2004) *J Biol Chem.* 279 32001-7) and domains such as these may also be used to prepare artificially-split inteins. In particular, non-splicing members of such families may be modified by molecular biology methodologies to introduce or restore splicing activity in such related species. Recent studies demonstrate that splicing can be observed when a N-terminal split intein component is allowed to react with a C-terminal split intein component not found in nature to be its "partner"; for example, splicing has been observed utilizing partners that have as little as 30 to 50% homology with the "natural" splicing partner (see, Dassa, et al., (2007) *Biochemistry* 46(1):322-30). Other such mixtures of disparate split intein partners have been shown to be unreactive one with another (see, Brenzel, et al., 2006 *Biochemistry* 45(6): 1571-8). However, it is within the ability of a person skilled in the relevant art to determine whether a particular pair of polypeptides is able to associate with each other to provide a functional intein, using routine methods and without the exercise of inventive skill.

In another aspect the PIP-1 polypeptide is a circular permuted variant. In certain embodiments the PIP-1 polypeptide is a circular permuted variant of the polypeptide of SEQ ID NO: 2, 4, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 204, 206, 208, 211, 212, 213, 214, 245, 246, 247, 248, 249, 250, 251, 252, 253, 254, 255, 256, 257, 258, 259, 260, 261, 262, 263, 264, 265, 266, 267, 268, 269, 298, 299, 300, 301, 302, 303, 304, 305, 306, 307, 308, 309, 310, 311, 312, 313, 314, 315, 316, 317, 318, 319, 320, 321, 322, 323, 324, 325, and 332. In certain embodiments the PIP-1 polypeptide is a circular permuted variant of the polypeptide of SEQ ID NO: 2, 4, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 204, 206, 208, 211, 212, 213, 214, 245, 246, 247, 248, 249, 250, 251, 252, 253, 254, 255, 256, 257, 258, 259, 260, 261, 262, 263, 264, 265, 266, 267, 268, 269, and 332.

The development of recombinant DNA methods has made it possible to study the effects of sequence transposition on protein folding, structure and function. The approach used in creating new sequences resembles that of naturally occurring pairs of proteins that are related by linear reorganization of their amino acid sequences (Cunningham, et al., (1979) *Proc. Natl. Acad. Sci. U.S.A.* 76:3218-3222; Teather and Erfle, (1990) *J. Bacteriol.* 172:3837-3841; Schimming, et al., (1992) *Eur. J. Biochem.* 204:13-19; Yamiuchi and Minamikawa, (1991) *FEBS Lett.* 260:127-130; MacGregor, et al., (1996) *FEBS Lett.* 378:263-266). The first in vitro application of this type of rearrangement to proteins was described by Goldenberg and Creighton (*J. Mol. Biol.* 165:407-413, 1983). In creating a circular permuted variant a new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion of sequence (linker), to an amino acid that is at or near the original N-terminus and the new sequence continues with the same sequence as the original until it reaches a point that is at or near the amino acid that was N-terminal to the breakpoint site of the original sequence, this residue forming the new C-terminus of the chain. The length of the amino acid sequence of the linker can be selected empirically or with guidance from structural information or by using a combination of the two approaches. When no structural information is available, a small series of linkers can be prepared for testing using a design whose length is varied in order to span a range from 0 to 50 Å and whose sequence is chosen in order to be consistent with surface exposure (hydrophilicity, Hopp and Woods, (1983) *Mol. Immunol.* 20:483-489; Kyte and Doolittle, (1982) *J. Mol. Biol.* 157:105-132; solvent exposed surface area, Lee and Richards, (1971) *J. Mol. Biol.* 55:379-400) and the ability to adopt the necessary conformation without deranging the configuration of the pesticidal polypeptide (conformationally flexible; Karplus and Schulz, (1985) *Naturwissenschaften* 72:212-213. Assuming an average of translation of 2.0 to 3.8 Å per residue, this would mean the length to test would be between 0 to 30 residues, with 0 to 15 residues being the preferred range. Exemplary of such an empirical series would be to construct linkers using a cassette sequence such as Gly-Gly-Gly-Ser repeated n times, where n is 1, 2, 3 or 4. Those skilled in the art will recognize that there are many such sequences that vary in length or composition that can serve as linkers with the primary consideration being that they be neither excessively long nor short (cf., Sandhu, (1992) *Critical Rev. Biotech.* 12:437-462); if they are too long, entropy effects will likely destabilize the three-dimensional fold, and may also make folding kinetically impractical, and if they are too short, they will likely destabilize the molecule because of torsional or steric strain. Those skilled in the analysis of protein structural information will recognize that using the distance between the chain ends, defined as the distance between the c-alpha carbons, can be used to define the length of the sequence to be used or at least to limit the number of possibilities that must be tested in an empirical selection of linkers. They will also recognize that it is sometimes the case that the positions of the ends of the polypeptide chain are ill-defined in structural models derived from x-ray diffraction or nuclear magnetic resonance spectroscopy data, and that when true, this situation will therefore need to be taken into account in order to properly estimate the length of the linker required. From those residues whose positions are well defined are selected two residues that are close in sequence to the chain ends, and the distance between their c-alpha carbons is used to calculate an approximate length for a linker between them. Using the calculated length as a guide, linkers with a range of number of residues (calculated using 2 to 3.8 Å per residue) are then selected. These linkers may be composed of the original sequence, shortened or lengthened as necessary, and when lengthened the additional residues may be chosen to be flexible and hydrophilic as described above; or optionally the original sequence may be substituted for using a series of linkers, one example being the Gly-Gly-Gly-Ser cassette approach mentioned above; or optionally a combination of the original sequence and new sequence having the appropriate total length may be used. Sequences of pesticidal polypeptides capable of folding to biologically active states can be prepared by appropriate selection of the beginning (amino terminus) and ending (carboxyl terminus) positions from within the original polypeptide chain while using the linker sequence as described above. Amino and carboxyl termini are selected from within a common stretch of sequence, referred to as a breakpoint region, using the guidelines described below. A novel amino acid sequence is thus generated by selecting amino and carboxyl termini from within the same breakpoint region. In many cases the selection of the new termini will be such that the original position of the carboxyl terminus immediately preceded that of the amino terminus. However, those skilled in the art will recognize that selections of termini anywhere within the region may function, and that these will effectively lead to either deletions or additions to the amino or carboxyl portions of the new sequence. It is a central tenet of molecular biology that the primary amino acid sequence of a protein dictates folding to the three-dimensional structure necessary for expression of its biological function. Methods are known to those skilled in the art to obtain and interpret three-dimensional structural information using x-ray diffraction of single protein Crystals or nuclear magnetic resonance spectroscopy of protein solutions. Examples of structural information that are relevant to the identification of breakpoint regions include the location and type of protein secondary structure (alpha and 3-10 helices, parallel and anti-parallel beta sheets, chain reversals and turns, and loops; Kabsch and Sander, (1983) *Biopolymers* 22:2577-2637; the degree of solvent exposure of amino acid residues, the extent and type of interactions of residues with one another (Chothia, (1984) *Ann. Rev. Biochem.* 53:537-572) and the static and dynamic distribution of conformations along the polypeptide chain (Alber and Mathews, (1987) *Methods Enzymol.* 154:511-533). In some cases additional information is known about solvent exposure of residues; one example is a site of post-translational attachment of carbohydrate which is necessarily on the surface of the protein. When experimental structural information is not available or is not feasible to obtain, methods are also available to analyze the primary amino acid sequence in order to make predictions of protein tertiary and secondary structure, solvent accessibility and the occurrence of turns and loops. Biochemical methods are also sometimes applicable for empirically determining surface exposure when direct structural methods are not feasible; for example, using the identification of sites of chain scission following limited proteolysis in order to infer surface exposure (Gentile and Salvatore, (1993) *Eur. J. Biochem.* 218:603-621). Thus using either the experimentally derived structural information or predictive methods (e.g., Srinivisan and Rose, (1995) *Proteins: Struct., Fund. & Genetics* 22:81-99) the parental amino acid sequence is inspected to classify regions according to whether or not they are integral to the maintenance of secondary and tertiary structure. The occurrence of sequences within regions that are known to be involved in periodic secondary structure (alpha and 3-10 helices, parallel and anti-parallel beta sheets) are regions that should be avoided. Similarly, regions of amino acid sequence that are observed or predicted to have a low degree of solvent exposure are more likely to be part of the so-called hydrophobic core of the protein and should also be avoided for selection of amino and carboxyl termini. In contrast, those regions that are known or predicted to be in surface turns or loops, and especially those regions that are known not to be required for biological activity, are the preferred sites for location of the extremes of the polypeptide chain. Continuous stretches of amino acid sequence that are preferred based on the above criteria are referred to as a breakpoint region. Polynucleotides encoding circular permuted PIP-1 polypeptides with new N-terminus/C-terminus which contain a linker region separating the original C-terminus and N-terminus can be made essentially following the method described in Mullins, et al., (1994) *J. Am. Chem. Soc.* 116:5529-5533. Multiple steps of polymerase chain reaction (PCR) amplifications are used to rearrange the DNA sequence encoding the primary amino acid sequence of the protein. Polynucleotides encoding circular permuted PIP-1 polypeptides with new N-terminus/C-terminus which contain a linker region separating the original C-terminus and N-terminus can be made based on the tandem-duplication method described in Horlick, et al., (1992) *Protein Eng.* 5:427-431. Polymerase chain reaction (PCR) amplification of the new N-terminus/C-terminus genes is performed using a tandemly duplicated template DNA.

In another aspect fusion proteins are provided that include within its amino acid sequence an amino acid sequence comprising a PIP-1 polypeptide including but not limited to the polypeptide of SEQ ID NO: 2, 4, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 204, 206, 208, 211, 212, 213, 214, 245, 246, 247, 248, 249, 250, 251, 252, 253, 254, 255, 256, 257, 258, 259, 260, 261, 262, 263, 264, 265, 266, 267, 268, 269, 298, 299, 300, 301, 302, 303, 304, 305, 306, 307, 308, 309, 310, 311, 312, 313, 314, 315, 316, 317, 318, 319, 320, 321, 322, 323, 324, 325, and 332.

In some embodiments fusion proteins comprises a PIP-1 polypeptide of SEQ ID NO: 2, 4, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 204, 206, 208, 211, 212, 213, 214, 245, 246, 247, 248, 249, 250, 251, 252, 253, 254, 255, 256, 257, 258, 259, 260, 261, 262, 263, 264, 265, 266, 267, 268, 269, 332, and active fragments thereof.

In another aspect fusion proteins are provided comprising a PIP-1 polypeptide and a second pesticidal polypeptide such a Cry protein. Methods for design and construction of fusion proteins (and polynucleotides encoding same) are known to those of skill in the art. Polynucleotides encoding a PIP-1 polypeptide may be fused to signal sequences which will direct the localization of the PIP-1 polypeptide to particular compartments of a prokaryotic or eukaryotic cell and/or direct the secretion of the PIP-1 polypeptide of the embodiments from a prokaryotic or eukaryotic cell. For example, in *E. coli*, one may wish to direct the expression of the protein to the periplasmic space. Examples of signal sequences or proteins (or fragments thereof) to which the PIP-1 polypeptide may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit, and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, the PIP-1 polypeptide may be fused to the pelB pectate lyase signal sequence to increase the efficiency of expression and purification of such polypeptides in Gram-negative bacteria (see, U.S. Pat. Nos. 5,576,195 and 5,846,818). Plant plastid transit peptide/polypeptide fusions are well known in the art (see, U.S. Pat. No. 7,193,133). Apoplast transit peptides such as rice or barley alpha-amylase secretion signal are also well known in the art. The plastid transit peptide is generally fused N-terminal to the polypeptide to be targeted (e.g., the fusion partner). In one embodiment, the fusion protein consists essentially of the peptide transit plastid and the PIP-1 polypeptide to be targeted. In another embodiment, the fusion protein comprises the peptide transit plastid and the polypeptide to be targeted. In such embodiments, the plastid transit peptide is preferably at the N-terminus of the fusion protein. However, additional amino acid residues may be N-terminal to the plastid transit peptide providing that the fusion protein is at least partially targeted to a plastid. In a specific embodiment, the plastid transit peptide is in the N-terminal half, N-terminal third or N-terminal quarter of the fusion protein. Most or all of the plastid transit peptide is generally cleaved from the fusion protein upon insertion into the plastid. The position of cleavage may vary slightly between plant species, at different plant developmental stages, as a result of specific intercellular conditions or the particular combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins. The plastid transit peptide can be recombinantly fused to a second protein in one of several ways. For example, a restriction endonuclease recognition site can be introduced into the nucleotide sequence of the transit peptide at a position corresponding to its C-terminal end and the same or a compatible site can be engineered into the nucleotide sequence of the protein to be targeted at its N-terminal end. Care must be taken in designing these sites to ensure that the coding sequences of the transit peptide and the second protein are kept “in frame” to allow the synthesis of the desired fusion protein. In some cases, it may be preferable to remove the initiator methionine codon of the second protein when the new restriction site is introduced. The introduction of restriction endonuclease recognition sites on both parent molecules and their subsequent joining through recombinant DNA techniques may result in the addition of one or more extra amino acids between the transit peptide and the second protein. This generally does not affect targeting activity as long as the transit peptide cleavage site remains accessible and the function of the second protein is not altered by the addition of these extra amino acids at its N-terminus. Alternatively, one skilled in the art can create a precise cleavage site between the transit peptide and the second protein (with or without its initiator methionine) using gene synthesis (Stemmer, et al., (1995) *Gene* 164:49-53) or similar methods. In addition, the transit peptide fusion can intentionally include amino acids downstream of the cleavage site. The amino acids at the N-terminus of the mature protein can affect the ability of the transit peptide to target proteins to plastids and/or the efficiency of cleavage following protein import. This may be dependent on the protein to be targeted. See, e.g., Comai, et al., (1988) *J. Biol. Chem.* 263(29):15104-9.

In some embodiments fusion proteins are provide comprising a PIP-1 polypeptide, a pesticidal protein such as a Cry protein, and an amino acid linker.

In some embodiments fusion proteins are provided represented by a formula selected from the group consisting of $R^1$-L-$R^2$, $R^2$-L-$R^1$, $R^1$— $R^2$ or $R^2$— $R^1$ where $R^1$ is a PIP-1 polypeptide, $R^2$ is a pesticidal protein with a different but complementary activity to the PIP-1 polypeptide, including but not limited to Cry proteins; a polypeptide that increases the solubility and/or stability of the PIP-1 polypeptide; or a transit peptide or leader sequence. The $R^1$ polypeptide is fused either directly or through a linker segment to the $R^2$ polypeptide. The term "directly" defines fusions in which the polypeptides are joined without a peptide linker. Thus L represents a chemical bound or polypeptide segment to which both $R^1$ and $R^2$ are fused in frame, most commonly L is a linear peptide to which $R^1$ and $R^2$ are bound by amide bonds linking the carboxy terminus of $R^1$ to the amino terminus of L and carboxy terminus of L to the amino terminus of $R^2$. By "fused in frame" is meant that there is no translation termination or disruption between the reading frames of $R^1$ and $R^2$. The linking group (L) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of $R^1$ and $R^2$ such that $R^1$ and $R^2$ could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

In some embodiments the linkers comprise sequences selected from the group of formulas: $(Gly_3Ser)_n$, $(Gly_4Ser)_n$, $(Gly_5Ser)_n$, $(Gly_nSer)_n$, or $(AlaGlySer)_n$ where n is an integer. One example of a highly-flexible linker is the (GlySer)-rich spacer region present within the pill protein of the filamentous bacteriophages, e.g., bacteriophages M13 or fd (Schaller, et al., 1975). This region provides a long, flexible spacer region between two domains of the pill surface protein. Also included are linkers in which an endopeptidase recognition sequence is included. Such a cleavage site may be valuable to separate the individual components of the fusion to determine if they are properly folded and active in vitro. Examples of various endopeptidases include, but are not limited to, Plasmin, Enterokinase, Kallikerin, Urokinase, Tissue Plasminogen activator, clostripain, Chymosin, Collagenase, Russell's Viper Venom Protease, Postproline cleavage enzyme, V8 protease, Thrombin and factor Xa. In some embodiments the linker comprises the amino acids EEKKN from the multi-gene expression vehicle (MGEV), which is cleaved by vacuolar proteases as disclosed in US 2007/0277263. In other embodiments, peptide linker segments from the hinge region of heavy chain immunoglobulins IgG, IgA, IgM, IgD or IgE provide an angular relationship between the attached polypeptides. Especially useful are those hinge regions where the cysteines are replaced with serines. Preferred linkers of the present invention include sequences derived from murine IgG gamma 2b hinge region in which the cysteines have been changed to serines. The fusion proteins are not limited by the form, size or number of linker sequences employed and the only requirement of the linker is that functionally it does not interfere adversely with the folding and function of the individual molecules of the fusion.

In another aspect chimeric PIP-1 polypeptide are provided that are created through joining two or more portions of genes, which originally encoded separate insecticidal proteins from different species, to create a chimeric gene. The translation of the chimeric gene results in a single chimeric pesticidal polypeptide with regions, motifs or domains derived from each of the original polypeptides. In certain embodiments the chimeric protein comprises portions, motifs or domains of PIP-1A (SEQ ID NO: 2) and orthologs PSEEN3174 (SEQ ID NO: 6), PIP-1C (SEQ ID NO: 332), and PIP-1B (SEQ ID NO: 4) in any combination. In certain embodiments the chimeric insecticidal polypeptide includes but not limited to the polypeptides of SEQ ID NO: 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 204, 206, 208, 211, 212, 213, 214, 245, 246, 247, 248, 249, 250, 251, 252, 253, 254, 255, 256, 257, 258, 259, 260, 261, 262, 263, 264, 265, 266, 267, 268, 269, and 332.

It is recognized that DNA sequences may be altered by various methods, and that these alterations may result in DNA sequences encoding proteins with amino acid sequences different than that encoded by the wild-type (or native) pesticidal protein. These proteins may be altered in various ways including amino acid substitutions, deletions, truncations, and insertions of one or more amino acids, including up to 2, 3, 4, 5, 6, 7, 8, 9, 10, 15, 20, 25, 30, 35, 40 45, 50, about 55, 60, 65, 70, 75, 80, 85, 90, 100, 105, 110, 115, 120, 125, 130, 135, 140, 145, 150, 155 or more amino acid substitutions, deletions and/or insertions or combinations thereof compared to SEQ ID NO: 2 or 4 including but not limited to SEQ ID NO: 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 204, 206, 208, 211, 212, 213, 214, 245, 246, 247, 248, 249, 250, 251, 252, 253, 254, 255, 256, 257, 258, 259, 260, 261, 262, 263, 264, 265, 266, 267, 268, 269, and 332. In some embodiments a PIP-1 polypeptide comprises the deletion of 1, 2, 3, 4, 5, 6, 7, 8, 9, 10, 11, 12, 13, 14, 15, 16, 17, 18, 19, 20, 21, 22, 23, 24, 25, 26, 27, 28 or more amino acids from the N-terminus of the PIP-1 polypeptide relative to the amino acid position of SEQ ID NO: 2. Methods for such manipulations are generally known in the art. For example, amino acid sequence variants of a PIP-1 polypeptide can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a PIP-1 polypeptide to confer pesticidal activity may be improved by the use of such techniques upon the compositions of this disclosure.

For example, conservative amino acid substitutions may be made at one or more, predicted, nonessential amino acid residues. A "nonessential" amino acid residue is a residue that can be altered from the wild-type sequence of a PIP-1 polypeptide without altering the biological activity. A "conservative amino acid substitution" is one in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); polar, negatively charged residues and their amides (e.g., aspartic acid, asparagine, glutamic, acid, glutamine; uncharged polar side chains (e.g., glycine, asparagine, glutamine, serine, threonine, tyrosine, cysteine); small aliphatic, nonpolar or slightly polar residues (e.g., Alanine, serine, threonine, proline, glycine); nonpolar side chains (e.g., alanine, valine, leucine, isoleucine, proline, phenylalanine, methionine, tryptophan); large aliphatic, nonpolar residues (e.g., methionine, leucine, isoleucine, valine, cystine); beta-branched side chains (e.g., threonine, valine, isoleucine); aromatic side chains (e.g., tyrosine, phenylalanine, tryptophan, histidine); large aromatic side chains (e.g., tyrosine, phenylalanine, tryptophan).

Amino acid substitutions may be made in nonconserved regions that retain function. In general, such substitutions would not be made for conserved amino acid residues or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the embodiments (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the embodiments (e.g., residues that have only conservative substitutions between all proteins contained in the alignment homologous proteins). However, one of skill in the art would understand that functional variants may have minor conserved or nonconserved alterations in the conserved residues. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference.

In making such changes, the hydropathic index of amino acids may be considered. The importance of the hydropathic amino acid index in conferring interactive biologic function on a protein is generally understood in the art (Kyte and Doolittle, (1982) *J Mol Biol.* 157(1):105-32). It is accepted that the relative hydropathic character of the amino acid contributes to the secondary structure of the resultant protein, which in turn defines the interaction of the protein with other molecules, for example, enzymes, substrates, receptors, DNA, antibodies, antigens and the like.

It is known in the art that certain amino acids may be substituted by other amino acids having a similar hydropathic index or score and still result in a protein with similar biological activity, i.e., still obtain a biological functionally equivalent protein. Each amino acid has been assigned a hydropathic index on the basis of its hydrophobicity and charge characteristics (Kyte and Doolittle, ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9) and arginine (−4.5). In making such changes, the substitution of amino acids whose hydropathic indices are within +2 is preferred, those which are within +1 are particularly preferred and those within +0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+ 0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Alternatively, alterations may be made to the protein sequence of many proteins at the amino or carboxy terminus without substantially affecting activity. This can include insertions, deletions or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity or epitope to facilitate either protein purification, protein detection or other experimental uses known in the art (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

In some embodiments, the PIP-1 polypeptide comprises an amino acid sequence of SEQ ID NO: 2 having an amino acid substitutions compared to the native amino acid of SEQ ID NO: 2 at one or more residues selected from positions 2, 3, 6, 8, 19, 20, 21, 22, 24, 25, 26, 27, 28, 30, 35, 36, 38, 42, 43, 46, 48, 49, 53, 60, 63, 66, 77, 89, 93, 97, 98, 105, 108, 110, 120, 121, 123, 125, 127, 134, 135, 137, 141, 142, 144, 147, 150, 151, 160, 162, 163, 164, 166, 167, 168, 171, 172, 173, 174, 175, 176, 177, 178, 179, 180, 181, 182, 183, 194, 195, 200, 203, 204, 209, 213, 220, 221, 222, 226, 228, 229, 231, 232, 240, 241, 242, 243, 244, 245, 246, 247, 248, 249, 251, 254, 258, 259, 265 and 266 of SEQ ID NO: 2. In specific embodiments, the substitution is an alanine for the native amino acid at the recited position(s). Also encompassed are the nucleic acid sequence(s) encoding the variant protein or polypeptide.

Variant nucleotide and amino acid sequences of the disclosure also encompass sequences derived from mutagenic and recombinogenic procedures such as DNA shuffling. With such a procedure, one or more different PIP-1 polypeptide coding regions can be used to create a new PIP-1 polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291 and U.S. Pat. Nos. 5,605,793 and 5,837,458.

Domain swapping or shuffling is another mechanism for generating altered PIP-1 polypeptides. Domains may be swapped between PIP-1 polypeptides, resulting in hybrid or chimeric toxins with improved pesticidal activity or target spectrum. Methods for generating recombinant proteins and testing them for pesticidal activity are well known in the art (see, for example, Naimov, et al., (2001) *Appl. Environ. Microbiol.* 67:5328-5330; de Maagd, et al., (1996) *Appl. Environ. Microbiol.* 62:1537-1543; Ge, et al., (1991) *J. Biol. Chem.* 266:17954-17958; Schnepf, et al., (1990) *J. Biol. Chem.* 265:20923-20930; Rang, et al., 91999) *Appl. Environ. Microbiol.* 65:2918-2925).

Both DNA shuffling and site directed mutagenesis were used to define polypeptide sequences that possess pesticidal activity. In Example 8 DNA shuffling was used to generate a library of active variants by recombination of the diversity present in PIP-1A (SEQ ID NO: 2) and PSEEN3174 (SEQ ID NO: 6). The person skilled in the art will be able to use comparisons to other proteins or functional assays to further define motifs. High throughput screening can be used to test variations of those motifs to determine the role of specific residues. Given that knowledge for several motifs, one can then define the requirements for a functional protein. Knowledge of the motifs allows the skilled artisan to design sequence variations that would not impact function.

This line of investigation was pursued in Examples 9-11. Alignment of homologues of SEQ ID NO: 2, 4 and 6 allowed identification of residues that are highly conserved among natural homologues in this family (FIG. 1). In example 9 saturation mutagenesis was used to make and test most or all possible substitutions at each of 6 conserved residues. These mutants were tested for activity and a number of active substitutions not present among the homologues were identified providing an understanding of the functional constraints at these residues. In Example 10 four motifs were identified among the most conserved regions in the alignment of SEQ ID NO: 2, 4 and 6. To further characterize the functional constraints on these sequence motifs, they were compared to a set of three distant homologues (AECFG_592740 (SEQ ID NO: 12), Pput_1063 (SEQ ID NO: 8), and Pput_1064 (SEQ ID NO: 10) that have no detectable insecticidal activity (FIG. 1). These homologues are deemed to fall within the same PFAM as SEQ ID NO: 2, 4 and 6 and thus are likely to share the same overall fold. The sequences corresponding to these four motifs from these distant homologues were swapped into the PIP-1A backbone. The data presented in Example 10 demonstrates that these motifs are under relatively stringent functional constraints, as most of the motif swaps from the distant homologues resulted in loss of function. In Example 11 the functional constraints on two of these motifs were further examined by performing saturation mutagenesis on all residues in motifs 3 and 4.

Antibodies

Antibodies to a PIP-1 polypeptide of the embodiments or to variants or fragments thereof, are also encompassed. Methods for producing antibodies are well known in the art (see, for example, Harlow and Lane, (1988) Antibodies: A Laboratory Manual, Cold Spring Harbor Laboratory, Cold Spring Harbor, N.Y.; U.S. Pat. No. 4,196,265).

A kit for detecting the presence of a PIP-1 polypeptide, or detecting the presence of a nucleotide sequence encoding a PIP-1 polypeptide, in a sample is provided. In one embodiment, the kit provides antibody-based reagents for detecting the presence of a PIP-1 polypeptide in a tissue sample. In another embodiment, the kit provides labeled nucleic acid probes useful for detecting the presence of one or more polynucleotides encoding PIP-1 polypeptide(s). The kit is provided along with appropriate reagents and controls for carrying out a detection method, as well as instructions for use of the kit Receptor Identification and Isolation Receptors to the PIP-1 polypeptide of the embodiments or to variants or fragments thereof, are also encompassed. Methods for identifying receptors are well known in the art (see, Hofmann, et. al., (1988) *Eur. J. Biochem.* 173:85-91; Gill, et al., (1995) *J. Biol. Chem.* 27277-27282) can be employed to identify and isolate the receptor that recognizes the PIP-1 polypeptides using the brush-border membrane vesicles from susceptible insects. In addition to the radioactive labeling method listed in the cited literatures, PIP-1 polypeptide can be labeled with fluorescent dye and other common labels such as streptavidin. Brush-border membrane vesicles (BBMV) of susceptible insects such as soybean looper and stink bugs can be prepared according to the protocols listed in the references and separated on SDS-PAGE gel and blotted on suitable membrane. Labeled PIP-1 polypeptides can be incubated with blotted membrane of BBMV and labeled the PIP-1 polypeptides can be identified with the labeled reporters. Identification of protein band(s) that interact with the PIP-1 polypeptides can be detected by N-terminal amino acid gas phase sequencing or mass spectrometry based protein identification method (Patterson, (1998) 10(22):1-24, *Current Protocol in Molecular Biology* published by John Wiley & Son Inc). Once the protein is identified, the corresponding gene can be cloned from genomic DNA or cDNA library of the susceptible insects and binding affinity can be measured directly with the PIP-1 polypeptides. Receptor function for insecticidal activity by the PIP-1 polypeptides can be verified by accomplished by RNAi type of gene knock out method (Rajagopal, et al., (2002) *J. Biol. Chem.* 277:46849-46851).

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs particularly polynucleotides and oligonucleotides composed of ribonucleotides and combinations of ribonucleotides and deoxyribonucleotides may also be employed in the methods disclosed herein. The nucleotide constructs, nucleic acids, and nucleotide sequences of the embodiments additionally encompass all complementary forms of such constructs, molecules and sequences. Further, the nucleotide constructs, nucleotide molecules and nucleotide sequences of the embodiments encompass all nucleotide constructs, molecules and sequences which can be employed in the methods of the embodiments for transforming plants including, but not limited to, those comprised of deoxyribonucleotides, ribonucleotides and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the PIP-1 polypeptide gene sequence to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct may also include a transcriptional enhancer sequence. As used herein, the term an "enhancer" refers to a DNA sequence which can stimulate promoter activity and may be an innate element of the promoter or a heterologous element inserted to enhance the level or tissue-specificity of a promoter. Various enhancers are known in the art including for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used, each of which is incorporated by reference. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray, et al., supra. Methods are available in the art for synthesizing plant-preferred genes. See, for example, U.S. Pat. Nos. 5,380,831, and 5,436,391 and Murray, et al., (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus), human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256) and maize chlorotic mottle virus leader (MCMV) (Lommel, et al., (1991) *Virology* 81:382-385). See also, Della-Cioppa, et al., (1987) *Plant Physiol.* 84:965-968. Such constructs may also contain a "signal sequence" or "leader sequence" to facilitate co-translational or post-translational transport of the peptide to certain intracellular structures such as the chloroplast (or other plastid), endoplasmic reticulum or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang, (1987) *Methods Enzymol.* 153:507-516). In some embodiments, the signal sequence is located in the native sequence or may be derived from a sequence of the embodiments. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria and the like. Nuclear-encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved in the identification of numerous nuclear-encoded lumen proteins (Kieselbach et al. *FEBS LETT* 480:271-276, 2000; Peltier et al. *Plant Cell* 12:319-341, 2000; Bricker et al. *Biochim. Biophys Acta* 1503:350-356, 2001), the lumen targeting signal peptide of which can potentially be used in accordance with the present invention. About 80 proteins from *Arabidopsis*, as well as homologous proteins from spinach and garden pea, are reported by Kieselbach et al., *Photosynthesis Research*, 78:249-264, 2003. In particular, table 2 of this publication, which is incorporated into the description herewith by reference, discloses 85 proteins from the chloroplast lumen, identified by their accession number (see also US Patent Application Publication 2009/09044298). In addition, the recently published draft version of the rice genome (Goff et al, *Science* 296:92-100, 2002) is a suitable source for lumen targeting signal peptide which may be used in accordance with the present invention.

Suitable chloroplast transit peptides (CTP) are well known to one skilled in the art including chimeric CTPs comprising but not limited to, an N-terminal domain, a central domain or a C-terminal domain from a CTP from *Oryza sativa* 1-deoxy-D xyulose-5-Phosphate Synthase *Oryza sativa*-Superoxide dismutase *Oryza sativa*-soluble starch synthase *Oryza sativa*-NADP-dependent Malic acid enzyme *Oryza sativa*-Phospho-2-dehydro-3-deoxyheptonate Aldolase 2 *Oryza sativa*-L-Ascorbate peroxidase 5 *Oryza sativa*-Phosphoglucan water dikinase, *Zea Mays* ssRUBISCO, *Zea Mays*-beta-glucosidase, *Zea Mays*-Malate dehydrogenase, *Zea Mays* Thioredoxin M-type US Patent Application Publication 2012/0304336).

The PIP-1 polypeptide gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan, (1990) *Ann. Rev. Phytopath.* 28:425-449; Duan, et al., (1996) *Nature Biotechnology* 14:494-498); wun1 and wun2, U.S. Pat. No. 5,428,148; win1 and win2 (Stanford, et al., (1989) *Mol. Gen. Genet.* 215:200-208); systemin (McGurl, et al., (1992) *Science* 225:1570-1573); WIP1 (Rohmeier, et al., (1993) *Plant Mol. Biol.* 22:783-792; Eckelkamp, et al., (1993) *FEBS Letters* 323:73-76); MPI gene (Corderok, et al., (1994) *Plant J.* 6(2):141-150) and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) *Neth. J. Plant Pathol.* 89:245-254; Uknes, et al., (1992) *Plant Cell* 4:645-656 and Van Loon, (1985) *Plant Mol. Virol.* 4:111-116. See also, WO 1999/43819, herein incorporated by reference.

Of interest are promoters that are expressed locally at or near the site of pathogen infection. See, for example, Marineau, et al., (1987) *Plant Mol. Biol.* 9:335-342; Matton, et al., (1989) *Molecular Plant-Microbe Interactions* 2:325-331; Somsisch, et al., (1986) *Proc. Natl. Acad. Sci. USA* 83:2427-2430; Somsisch, et al., (1988) *Mol. Gen. Genet.* 2:93-98 and Yang, (1996) *Proc. Natl. Acad. Sci. USA* 93:14972-14977. See also, Chen, et al., (1996) *Plant J.* 10:955-966; Zhang, et al., (1994) *Proc. Natl. Acad. Sci. USA* 91:2507-2511; Warner, et al., (1993) *Plant J.* 3:191-201; Siebertz, et al., (1989) *Plant Cell* 1:961-968; U.S. Pat. No. 5,750,386 (nematode-inducible) and the references cited therein. Of particular interest is the inducible promoter for the maize PRms gene, whose expression is induced by the pathogen *Fusarium moniliforme* (see, for example, Cordero, et al., (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156), herein incorporated by reference.

Tissue-preferred promoters can be utilized to target enhanced PIP-1 polypeptide expression within a particular plant tissue. Tissue-preferred promoters include those discussed in Yamamoto, et al., (1997) *Plant J.* 12(2)255-265; Kawamata, et al., (1997) *Plant Cell Physiol.* 38(7):792-803; Hansen, et al., (1997) *Mol. Gen Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam, (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for weak expression.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138 and Matsuoka, et al., (1993) *Proc. Natl. Acad. Sci. USA* 90(20):9586-9590.

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2): 343-350). The TR1' gene fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772) and rolB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732 and 5,023,179.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase) (see, U.S. Pat. No. 6,225,529, herein incorporated by reference).

Gamma-zein and Glb-1 are endosperm-specific promoters. For dicots, seed-specific promoters include, but are not limited to, Kunitz trypsin inhibitor 3 (KTi3) (Jofuku, K. D. and Goldberg, R. B. *Plant Cell* 1:1079-1093, 1989), bean β-phaseolin, napin, β-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end1 and end2 genes are disclosed; herein incorporated by reference. In dicots, seed specific promoters include but are not limited to seed coat promoter from *Arabidopsis*, pBAN; and the early seed promoters from *Arabidopsis*, p26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of about $1/1000$ transcripts to about $1/100,000$ transcripts to about $1/500,000$ transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142 and 6,177,611, herein incorporated by reference.

The above list of promoters is not meant to be limiting. Any appropriate promoter can be used in the embodiments.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213 and Meijer, et al., (1991) *Plant Mol. Biol.* 16:807-820); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-136); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518). See generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Sci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin) and Gill, et al., (1988) *Nature* 334:721-724. Such disclosures are herein incorporated by reference.

The above list of selectable marker genes is not meant to be limiting. Any selectable marker gene can be used in the embodiments.

Plant Transformation

The methods of the embodiments involve introducing a polypeptide or polynucleotide into a plant. "Introducing" is intended to mean presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants are known in the art including, but not limited to, stable transformation methods, transient transformation methods and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant. By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ*

Culture: Fundamental Methods, ed. Gamborg and Phillips, (Springer-Verlag, Berlin) and McCabe, et al., (1988) Biotechnology 6:923-926) and Lec1 transformation (WO 2000/28058). For potato transformation see, Tu, et al., (1998) Plant Molecular Biology 37:829-838 and Chong, et al., (2000) Transgenic Research 9:71-78. Additional transformation procedures can be found in Weissinger, et al., (1988) Ann. Rev. Genet. 22:421-477; Sanford, et al., (1987) Particulate Science and Technology 5:27-37 (onion); Christou, et al., (1988) Plant Physiol. 87:671-674 (soybean); McCabe, et al., (1988) Bio/Technology 6:923-926 (soybean); Finer and McMullen, (1991) In Vitro Cell Dev. Biol. 27P:175-182 (soybean); Singh, et al., (1998) Theor. Appl. Genet. 96:319-324 (soybean); Datta, et al., (1990) Biotechnology 8:736-740 (rice); Klein, et al., (1988) Proc. Natl. Acad. Sci. USA 85:4305-4309 (maize); Klein, et al., (1988) Biotechnology 6:559-563 (maize); U.S. Pat. Nos. 5,240,855; 5,322,783 and 5,324,646; Klein, et al, (1988) Plant Physiol. 91:440-444 (maize); Fromm, et al., (1990) Biotechnology 8:833-839 (maize); Hooykaas-Van Slogteren, et al., (1984) Nature (London) 311:763-764; U.S. Pat. No. 5,736,369 (cereals); Bytebier, et al., (1987) Proc. Natl. Acad. Sci. USA 84:5345-5349 (Liliaceae); De Wet, et al., (1985) in The Experimental Manipulation of Ovule Tissues, ed. Chapman, et al., (Longman, New York), pp. 197-209 (pollen); Kaeppler, et al., (1990) Plant Cell Reports 9:415-418 and Kaeppler, et al., (1992) Theor. Appl. Genet. 84:560-566 (whisker-mediated transformation); D'Halluin, et al., (1992) Plant Cell 4:1495-1505 (electroporation); Li, et al., (1993) Plant Cell Reports 12:250-255 and Christou and Ford, (1995) Annals of Botany 75:407-413 (rice); Osjoda, et al., (1996) Nature Biotechnology 14:745-750 (maize via Agrobacterium tumefaciens); all of which are herein incorporated by reference.

In specific embodiments, the sequences of the embodiments can be provided to a plant using a variety of transient transformation methods. Such transient transformation methods include, but are not limited to, the introduction of the PIP-1 polypeptide or variants and fragments thereof directly into the plant or the introduction of the PIP-1 polypeptide transcript into the plant. Such methods include, for example, microinjection or particle bombardment. See, for example, Crossway, et al., (1986) Mol Gen. Genet. 202:179-185; Nomura, et al., (1986) Plant Sci. 44:53-58; Hepler, et al., (1994) Proc. Natl. Acad. Sci. 91:2176-2180 and Hush, et al., (1994) The Journal of Cell Science 107: 775-784, all of which are herein incorporated by reference. Alternatively, the PIP-1 polypeptide polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma # P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO 1999/25821, WO 1999/25854, WO 1999/25840, WO 1999/25855 and WO 1999/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for Agrobacterium-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from Agrobacterium to plant cells. This plasmid often contains the virulence functions (Vir genes) that allow infection of plant cells by Agrobacterium, and transfer of DNA by cleavage at border sequences and vir-mediated DNA transfer, as is understood in the art (Hellens and Mullineaux, (2000) Trends in Plant Science 5:446-451). Several types of Agrobacterium strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) *The Plant Journal* 6:271-282; Ishida, et al., (1996) *Nature Biotechnology* 14:745-750). Explants are typically transferred to a fresh supply of the same medium and cultured routinely. A general description of the techniques and methods for generating transgenic plants are found in Ayres and Park, (1994) *Critical Reviews in Plant Science* 13:219-239 and Bommineni and Jauhar, (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired PIP-1 polypeptide. It is also recognized that such a viral polyprotein, comprising at least a portion of the amino acid sequence of a PIP-1 polypeptide of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules are known in the art. See, for example, U.S. Pat. Nos. 5,889,191; 5,889,190; 5,866,785; 5,589,367 and 5,316,931, herein incorporated by reference.

Methods for transformation of chloroplasts are known in the art. See, for example, Svab, et al., (1990) *Proc. Natl. Acad. Sci. USA* 87:8526-8530; Svab and Maliga, (1993) *Proc. Natl. Acad. Sci. USA* 90:913-917; Svab and Maliga, (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride, et al., (1994) *Proc. Natl. Acad. Sci. USA* 91:7301-7305.

The embodiments further relate to plant-propagating material of a transformed plant of the embodiments including, but not limited to, seeds, tubers, corms, bulbs, leaves, and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*. Conifers that may be employed in practicing the embodiments include, for example, pines such as loblolly pine (*Pinus taeda*), slash pine (*Pinus elliothi*), ponderosa pine (*Pinus ponderosa*), lodgepole pine (*Pinus contorta*) and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annua*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, *sorghum*, rye, millet, etc. Oil-seed plants include cotton, soybean, safflower, sunflower, *Brassica*, maize, alfalfa, palm, coconut, flax, castor, olive etc. Leguminous plants include beans and peas. Beans include guar, locust bean, fenugreek, soybean, garden beans, cowpea, mungbean, lima bean, fava bean, lentils, chickpea, etc.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell, (2001) Molecular Cloning: A Laboratory Manual. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, (2001) supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled 32P target DNA fragment to confirm the integration of introduced gene into the plant genome according to standard techniques (Sambrook and Russell, (2001) supra).

In Northern blot analysis, RNA is isolated from specific tissues of transformant, fractionated in a formaldehyde agarose gel, and blotted onto a nylon filter according to standard procedures that are routinely used in the art (Sambrook and Russell, (2001) supra). Expression of RNA encoded by the pesticidal gene is then tested by hybridizing the filter to a radioactive probe derived from a pesticidal gene, by methods known in the art (Sambrook and Russell, (2001) supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the PIP-1 polypeptide.

Stacking of Traits in Transgenic Plant

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene, and co-transformation of genes into a single plant cell. As used herein, the term "stacked" includes having two or more traits present in the same plant (e.g., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments the polynucleotides encoding the PIP-1 polypeptides disclosed herein, alone or stacked with one or more additional insect resistance traits can be stacked with one or more additional input traits (e.g., herbicide resistance, fungal resistance, virus resistance or stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes useful for stacking include but are not limited to:

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1994) *Science* 266:789 (cloning of the tomato Cf-9 gene for resistance to *Cladosporium fulvum*); Martin, et al., (1993) *Science* 262: 1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*), McDowell and Woffenden, (2003) *Trends Biotechnol.* 21(4):178-83 and Toyoda, et al., (2002) *Transgenic Res.* 11(6):567-82. A plant resistant to a disease is one that is more resistant to a pathogen as compared to the wild type plant.

(B) Genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC™ Accession Numbers 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849, and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin, (2011) *PLoS Pathogens,* 7:1-13), from *Pseudomonas protegens* strain CHA0 and Pf-5 (previously *fluorescens*) (Pechy-Tarr, (2008) Environmental Microbiology 10:2368-2386: GenBank Accession No. EU400157); from *Pseudomonas Taiwanensis* (Liu, et al., (2010) *J. Agric. Food Chem.* 58:12343-12349) and from *Pseudomonas pseudoalcligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379,946; and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry 51 and Cry55 classes of δ-endotoxin genes and the *B. thuringiensis* cytolytic Cyt1 and Cyt2 genes. Members of these classes of *B. thuringiensis* insecticidal proteins include, but are not limited to Cry1Aa1 (Accession # Accession # M11250), Cry1Aa2 (Accession # M10917), Cry1Aa3 (Accession # DQ0348), Cry1Aa4 (Accession # X13535), Cry1Aa5 (Accession # D17518), Cry1Aa6 (Accession # U43605), Cry1Aa7 (Accession # AF081790), Cry1Aa8 (Accession #126149), Cry1Aa9 (Accession # AB026261), Cry1Aa10 (Accession # AF154676), Cry1Aa11 (Accession # Y09663), Cry1Aa12 (Accession # AF384211), Cry1Aa13 (Accession # AF510713), Cry1Aa14 (Accession # AY197341), Cry1Aa15 (Accession # DQ062690), Cry1Ab1 (Accession # M13898), Cry1Ab2 (Accession # M12661), Cry1Ab3 (Accession # M15271), Cry1Ab4 (Accession # DQ0117), Cry1Ab5 (Accession # X04698), Cry1Ab6 (Accession # M37263), Cry1Ab7 (Accession # X13233), Cry1Ab8 (Accession # M16463), Cry1Ab9 (Accession # X54939), Cry1Ab10 (Accession # A29125), Cry1Ab11 (Accession #112419), Cry1Ab12 (Accession # AF059670), Cry1Ab13 (Accession # AF254640), Cry1Ab14 (Accession # U94191), Cry1Ab15 (Accession # AF358861), Cry1Ab16 (Accession # AF375608), Cry1Ab17 (Accession # AAT46415), Cry1Ab18 (Accession # AAQ88259), Cry1Ab19 (Accession # AY847289), Cry1Ab20 (Accession # DQ241675), Cry1Ab21 (Accession # EF683163), Cry1Ab22 (Accession # ABW87320), Cry1Ab-like (Accession # AF327924), Cry1Ab-like (Accession # AF327925), Cry1Ab-like (Accession # AF327926), Cry1Ab-like (Accession # DQ781309), Cry1Ac1 (Accession # M11068), Cry1Ac2 (Accession # M35524), Cry1Ac3 (Accession # X54159), Cry1Ac4 (Accession # M73249), Cry1Ac5 (Accession # M73248), Cry1Ac6 (Accession # U43606), Cry1Ac7 (Accession # U87793), Cry1Ac8 (Accession # U87397), Cry1Ac9 (Accession # U89872), Cry1Ac10 (Accession # AJ002514), Cry1Ac11 (Accession # AJ130970), Cry1Ac12 (Accession #112418), Cry1Ac13 (Accession # AF148644), Cry1Ac14 (Accession # AF492767), Cry1Ac15 (Accession # AY122057), Cry1Ac16 (Accession # AY730621), Cry1Ac17 (Accession # AY925090), Cry1Ac18 (Accession # DQ023296), Cry1Ac19 (Accession # DQ195217), Cry1Ac20 (Accession # DQ285666), Cry1Ac21 (Accession # DQ062689), Cry1Ac22 (Accession # EU282379), Cry1Ac23 (Accession # AM949588), Cry1Ac24 (Accession # ABL01535), Cry1Ad1 (Accession # M73250), Cry1Ad2 (Accession # A27531), Cry1Ae1 (Accession # M65252), Cry1Af1 (Accession # U82003), Cry1Ag1 (Accession # AF081248), Cry1Ah1 (Accession # AF281866), Cry1Ah2 (Accession # DQ269474), Cry1Ai1 (Accession # AY174873), Cry1A-like (Accession # AF327927), Cry1Ba1 (Accession # X06711), Cry1Ba2 (Accession # X95704), Cry1Ba3 (Accession # AF368257), Cry1Ba4 (Accession # AF363025), Cry1Ba5 (Accession # AB020894), Cry1Ba6 (Accession # ABL60921), Cry1Bb1 (Accession # L32020), Cry1Bc1 (Accession # Z46442), Cry1Bd1 (Accession # U70726), Cry1Bd2 (Accession # AY138457), Cry1Be1 (Accession # AF077326), Cry1Be2 (Accession # AAQ52387), Cry1Bf1 (Accession # AX189649), Cry1Bf2 (Accession # AAQ52380), Cry1Bg1 (Accession # AY176063), Cry1Ca1 (Accession # X07518), Cry1Ca2 (Accession # X13620), Cry1Ca3 (Accession # M73251), Cry1Ca4 (Accession # A27642), Cry1Ca5 (Accession # X96682), Cry1Ca6 [1] (Accession # AF215647), Cry1Ca7 (Accession # AY015492), Cry1Ca8 (Accession # AF362020), Cry1Ca9 (Accession # AY078160), Cry1Ca10 (Accession # AF540014), Cry1Ca11 (Accession # AY955268), Cry1Cb1 (Accession # M97880), Cry1Cb2 (Accession # AY007686), Cry1Cb3 (Accession # EU679502), Cry1Cb-like (Accession # AAX63901), Cry1Da1 (Accession # X54160), Cry1Da2 (Accession #176415), Cry1Db1 (Accession # Z22511), Cry1Db2 (Accession # AF358862), Cry1Dc1 (Accession # EF059913), Cry1Ea1 (Accession # X53985), Cry1Ea2 (Accession # X56144), Cry1Ea3 (Accession # M73252), Cry1Ea4 (Accession # U94323), Cry1Ea5 (Accession # A15535), Cry1Ea6 (Accession # AF202531), Cry1Ea7 (Accession # AAW72936), Cry1Ea8 (Accession # ABX11258), Cry1Eb1 (Accession # M73253), Cry1 Fa1 (Accession # M63897), Cry1 Fa2 (Accession # M73254), Cry1 Fb1 (Accession # Z22512), Cry1 Fb2 (Accession # AB012288), Cry1 Fb3 (Accession # AF062350), Cry1 Fb4 (Accession #173895), Cry1 Fb5 (Accession # AF336114), Cry1 Fb6 (Accession # EU679500), Cry1 Fb7 (Accession # EU679501), Cry1Ga1 (Accession # Z22510), Cry1Ga2 (Accession # Y09326), Cry1Gb1 (Accession # U70725), Cry1Gb2 (Accession # AF288683), Cry1Gc (Accession # AAQ52381), Cry1 Ha1 (Accession # Z22513), Cry1Hb1 (Accession # U35780), Cry1H-like (Accession # AF182196), Cry1Ia1 (Accession # X62821), Cry1Ia2 (Accession # M98544), Cry1Ia3 (Accession # L36338), Cry1Ia4 (Accession # L49391), Cry1Ia5 (Accession # Y08920), Cry1Ia6 (Accession # AF076953), Cry1Ia7 (Accession # AF278797), Cry1Ia8 (Accession # AF373207), Cry1Ia9 (Accession # AF521013), Cry1Ia10

(Accession # AY262167), Cry1Ia11 (Accession # AJ315121), Cry1Ia12 (Accession # AAV53390), Cry1Ia13 (Accession # ABF83202), Cry1Ia14 (Accession # EU887515), Cry1Ib1 (Accession # U07642), Cry1Ib2 (Accession # ABW88019), Cry1Ib3 (Accession # EU677422), Cry1Ic1 (Accession # AF056933), Cry1Ic2 (Accession # AAE71691), Cry1Id1 (Accession # AF047579), Cry1Ie1 (Accession # AF211190), Cry1If1 (Accession # AAQ52382), Cry1I-like (Accession #190732), Cry1I-like (Accession # DQ781310), Cry1Ja1 (Accession # L32019), Cry1Jb1 (Accession # U31527), Cry1Jc1 (Accession #190730), Cry1Jc2 (Accession # AAQ52372), Cry1Jd1 (Accession # AX189651), Cry1Ka1 (Accession # U28801), Cry1La1 (Accession # AAS60191), Cry1-like (Accession #190729), Cry2Aa1 (Accession # M31738), Cry2Aa2 (Accession # M23723), Cry2Aa3 (Accession # D86064), Cry2Aa4 (Accession # AF047038), Cry2Aa5 (Accession # AJ132464), Cry2Aa6 (Accession # AJ132465), Cry2Aa7 (Accession # AJ132463), Cry2Aa8 (Accession # AF252262), Cry2Aa9 (Accession # AF273218), Cry2Aa10 (Accession # AF433645), Cry2Aa11 (Accession # AAQ52384), Cry2Aa12 (Accession # DQ977646), Cry2Aa13 (Accession # ABL01536), Cry2Aa14 (Accession # ACF04939), Cry2Ab1 (Accession # M23724), Cry2Ab2 (Accession # X55416), Cry2Ab3 (Accession # AF164666), Cry2Ab4 (Accession # AF336115), Cry2Ab5 (Accession # AF441855), Cry2Ab6 (Accession # AY297091), Cry2Ab7 (Accession # DQ119823), Cry2Ab8 (Accession # DQ361266), Cry2Ab9 (Accession # DQ341378), Cry2Ab10 (Accession # EF157306), Cry2Ab11 (Accession # AM691748), Cry2Ab12 (Accession # ABM21764), Cry2Ab13 (Accession # EU909454), Cry2Ab14 (Accession # EU909455), Cry2Ac1 (Accession # X57252), Cry2Ac2 (Accession # AY007687), Cry2Ac3 (Accession # AAQ52385), Cry2Ac4 (Accession # DQ361267), Cry2Ac5 (Accession # DQ341379), Cry2Ac6 (Accession # DQ359137), Cry2Ac7 (Accession # AM292031), Cry2Ac8 (Accession # AM421903), Cry2Ac9 (Accession # AM421904), Cry2Ac10 (Accession # BI 877475), Cry2Ac11 (Accession # AM689531), Cry2Ac12 (Accession # AM689532), Cry2Ad1 (Accession # AF200816), Cry2Ad2 (Accession # DQ358053), Cry2Ad3 (Accession # AM268418), Cry2Ad4 (Accession # AM490199), Cry2Ad5 (Accession # AM765844), Cry2Ae1 (Accession # AAQ52362), Cry2Af1 (Accession # EF439818), Cry2Ag (Accession # ACH91610), Cry2Ah (Accession # EU939453), Cry3Aa1 (Accession # M22472), Cry3Aa2 (Accession # J02978), Cry3Aa3 (Accession # Y00420), Cry3Aa4 (Accession # M30503), Cry3Aa5 (Accession # M37207), Cry3Aa6 (Accession # U10985), Cry3Aa7 (Accession # AJ237900), Cry3Aa8 (Accession # AAS79487), Cry3Aa9 (Accession # AAW05659), Cry3Aa10 (Accession # AAU29411), Cry3Aa11 (Accession # AY882576), Cry3Aa12 (Accession # ABY49136), Cry3Ba1 (Accession # X17123), Cry3Ba2 (Accession # A07234), Cry3Bb1 (Accession # M89794), Cry3Bb2 (Accession # U31633), Cry3Bb3 (Accession #115475), Cry3Ca1 (Accession # X59797), Cry4Aa1 (Accession # Y00423), Cry4Aa2 (Accession # DQ0248), Cry4Aa3 (Accession # AL731825), Cry4A-like (Accession # DQ078744), Cry4Ba1 (Accession # X07423), Cry4Ba2 (Accession # X07082), Cry4Ba3 (Accession # M20242), Cry4Ba4 (Accession # DQ0247), Cry4Ba5 (Accession # AL731825), Cry4Ba-like (Accession # ABC47686), Cry4Ca1 (Accession # EU646202), Cry5Aa1 (Accession # L07025), Cry5Ab1 (Accession # L07026), Cry5Ac1 (Accession #134543), Cry5Ad1 (Accession # EF219060), Cry5Ba1 (Accession # U19725), Cry5Ba2 (Accession # EU121522), Cry6Aa1 (Accession # L07022), Cry6Aa2 (Accession # AF499736), Cry6Aa3 (Accession # DQ835612), Cry6Ba1 (Accession # L07024), Cry7Aa1 (Accession # M64478), Cry7Ab1 (Accession # U04367), Cry7Ab2 (Accession # U04368), Cry7Ab3 (Accession # BI 1015188), Cry7Ab4 (Accession # EU380678), Cry7Ab5 (Accession # ABX79555), Cry7Ab6 (Accession # FJ194973), Cry7Ba1 (Accession # ABB70817), Cry7Ca1 (Accession # EF486523), Cry8Aa1 (Accession # U04364), Cry8Ab1 (Accession # EU044830), Cry8Ba1 (Accession # U04365), Cry8Bb1 (Accession # AX543924), Cry8Bc1 (Accession # AX543926), Cry8Ca1 (Accession # U04366), Cry8Ca2 (Accession # AAR98783), Cry8Ca3 (Accession # EU625349), Cry8Da1 (Accession # AB089299), Cry8Da2 (Accession # BD133574), Cry8Da3 (Accession # BD133575), Cry8Db1 (Accession # AB303980), Cry8Ea1 (Accession # AY329081), Cry8Ea2 (Accession # EU047597), Cry8Fa1 (Accession # AY551093), Cry8Ga1 (Accession # AY590188), Cry8Ga2 (Accession # DQ318860), Cry8Ga3 (Accession # FJ198072), Cry8Ha1 (Accession # EF465532), Cry8Ia1 (Accession # EU381044), Cry8Ja1 (Accession # EU625348), Cry8 like (Accession # ABS53003), Cry9Aa1 (Accession # X58120), Cry9Aa2 (Accession # X58534), Cry9Aa like (Accession # AAQ52376), Cry9Ba1 (Accession # X75019), Cry9Bb1 (Accession # AY758316), Cry9Ca1 (Accession # Z37527), Cry9Ca2 (Accession # AAQ52375), Cry9Da1 (Accession # D85560), Cry9Da2 (Accession # AF042733), Cry9Db1 (Accession # AY971349), Cry9Ea1 (Accession # AB011496), Cry9Ea2 (Accession # AF358863), Cry9Ea3 (Accession # EF157307), Cry9Ea4 (Accession # EU760456), Cry9Ea5 (Accession # EU789519), Cry9Ea6 (Accession # EU887516), Cry9Eb1 (Accession # AX189653), Cry9Ec1 (Accession # AF093107), Cry9Ed1 (Accession # AY973867), Cry9 like (Accession # AF093107), Cry10Aa1 (Accession # M12662), Cry10Aa2 (Accession # E00614), Cry10Aa3 (Accession # AL731825), Cry10A like (Accession # DQ167578), Cry11Aa1 (Accession # M31737), Cry11Aa2 (Accession # M22860), Cry11Aa3 (Accession # AL731825), Cry11Aa-like (Accession # DQ166531), Cry11Ba1 (Accession # X86902), Cry11Bb1 (Accession # AF017416), Cry12Aa1 (Accession # L07027), Cry13Aa1 (Accession # L07023), Cry14Aa1 (Accession # U13955), Cry15Aa1 (Accession # M76442), Cry16Aa1 (Accession # X94146), Cry17Aa1 (Accession # X99478), Cry18Aa1 (Accession # X99049), Cry18Ba1 (Accession # AF169250), Cry18Ca1 (Accession # AF169251), Cry19Aa1 (Accession # Y07603), Cry19Ba1 (Accession # D88381), Cry20Aa1 (Accession # U82518), Cry21Aa1 (Accession # I32932), Cry21Aa2 (Accession #166477), Cry21Ba1 (Accession # AB088406), Cry22Aa1 (Accession #134547), Cry22Aa2 (Accession # AX472772), Cry22Aa3 (Accession # EU715020), Cry22Ab1 (Accession # AAK50456), Cry22Ab2 (Accession # AX472764), Cry22Ba1 (Accession # AX472770), Cry23Aa1 (Accession # AAF76375), Cry24Aa1 (Accession # U88188), Cry24Ba1 (Accession # BAD32657), Cry24Ca1 (Accession # AM158318), Cry25Aa1 (Accession # U88189), Cry26Aa1 (Accession # AF122897), Cry27Aa1 (Accession # AB023293), Cry28Aa1 (Accession # AF132928), Cry28Aa2 (Accession # AF285775), Cry29Aa1 (Accession # AJ251977), Cry30Aa1 (Accession # AJ251978), Cry30Ba1 (Accession # BAD00052), Cry30Ca1 (Accession # BAD67157), Cry30Da1 (Accession # EF095955), Cry30Db1 (Accession # BAE80088), Cry30Ea1 (Accession # EU503140), Cry30Fa1 (Accession # EU751609), Cry30Ga1 (Accession # EU882064), Cry31Aa1 (Accession # AB031065), Cry31Aa2 (Accession # AY081052), Cry31Aa3 (Accession # AB250922), Cry31Aa4 (Accession # AB274826), Cry31Aa5 (Accession # AB274827), Cry31Ab1 (Accession # AB250923), Cry31Ab2 (Accession # AB274825), Cry31Ac1 (Accession # AB276125), Cry32Aa1 (Accession # AY008143), Cry32Ba1 (Accession # BAB78601), Cry32Ca1 (Accession # BAB78602), Cry32Da1 (Accession # BAB78603), Cry33Aa1 (Accession # AAL26871), Cry34Aa1 (Accession # AAG50341), Cry34Aa2 (Accession # AAK64560), Cry34Aa3 (Accession # AY536899), Cry34Aa4 (Accession # AY536897), Cry34Ab1 (Accession # AAG41671), Cry34Ac1 (Accession # AAG50118), Cry34Ac2 (Accession # AAK64562), Cry34Ac3 (Accession # AY536896), Cry34Ba1 (Accession # AAK64565), Cry34Ba2 (Accession # AY536900), Cry34Ba3 (Accession # AY536898), Cry35Aa1 (Accession # AAG50342), Cry35Aa2 (Accession # AAK64561), Cry35Aa3 (Accession # AY536895), Cry35Aa4 (Accession # AY536892), Cry35Ab1 (Accession # AAG41672), Cry35Ab2 (Accession # AAK64563), Cry35Ab3 (Accession # AY536891), Cry35Ac1 (Accession # AAG50117), Cry35Ba1 (Accession # AAK64566), Cry35Ba2 (Accession # AY536894), Cry35Ba3 (Accession # AY536893), Cry36Aa1 (Accession # AAK64558), Cry37Aa1 (Accession # AAF76376), Cry38Aa1 (Accession # AAK64559), Cry39Aa1 (Accession # BAB72016), Cry40Aa1 (Accession # BAB72018), Cry40Ba1 (Accession # BAC77648), Cry40Ca1 (Accession # EU381045), Cry40Da1 (Accession # EU596478), Cry41Aa1 (Accession # AB116649), Cry41Ab1 (Accession # AB116651), Cry42Aa1 (Accession # AB116652), Cry43Aa1 (Accession # AB115422), Cry43Aa2 (Accession # AB176668), Cry43Ba1 (Accession # AB115422), Cry43-like (Accession # AB115422), Cry44Aa (Accession # BAD08532), Cry45Aa (Accession # BAD22577), Cry46Aa (Accession # BAC79010), Cry46Aa2 (Accession # BAG68906), Cry46Ab (Accession # BAD35170), Cry47Aa (Accession # AY950229), Cry48Aa (Accession # AJ841948), Cry48Aa2 (Accession # AM237205), Cry48Aa3 (Accession # AM237206), Cry48Ab (Accession # AM237207), Cry48Ab2 (Accession # AM237208), Cry49Aa (Accession # AJ841948), Cry49Aa2 (Accession # AM237201), Cry49Aa3 (Accession # AM237203), Cry49Aa4 (Accession # AM237204), Cry49Ab1 (Accession # AM237202), Cry50Aa1 (Accession # AB253419), Cry51Aa1 (Accession # DQ836184), Cry52Aa1 (Accession # EF613489), Cry53Aa1 (Accession # EF633476), Cry54Aa1 (Accession # EU339367), Cry55Aa1 (Accession # EU121521), Cry55Aa2 (Accession # AAE33526).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of U.S. Pat. Nos. 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US20090144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "Bacillus thuringiensis toxin nomenclature" (2011), at lifesci.sussex.ac.uk/home/Neil_Crickmore/Bt/ which can be accessed on the world-wide web using the "www" prefix). The insecticidal activity of Cry proteins is well known to one skilled in the art (for review, see, van Frannkenhuyzen, (2009) *J. Invert. Path.*

101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

(C) A polynucleotide encoding an insect-specific hormone or pheromone such as an ecdysteroid and juvenile hormone, a variant thereof, a mimetic based thereon or an antagonist or agonist thereof. See, for example, the disclosure by Hammock, et al., (1990) *Nature* 344:458, of baculovirus expression of cloned juvenile hormone esterase, an inactivator of juvenile hormone.

(D) A polynucleotide encoding an insect-specific peptide which, upon expression, disrupts the physiology of the affected pest. For example, see the disclosures of Regan, (1994) *J. Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony, (2004) *J Nat Prod* 67(2):300-310; Carlini and Grossi-de-Sa (2002) *Toxicon* 40(11):1515-1539; Ussuf, et al., (2001) *Curr Sci.* 80(7):847-853 and Vasconcelos and Oliveira (2004) *Toxicon* 44(4):385-403. See also, U.S. Pat. No. 5,266,317 to Tomalski, et al., who disclose genes encoding insect-specific toxins.

(E) A polynucleotide encoding an enzyme responsible for a hyperaccumulation of a monterpene, a sesquiterpene, a steroid, hydroxamic acid, a phenylpropanoid derivative or another non-protein molecule with insecticidal activity.

(F) A polynucleotide encoding an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application WO 1993/02197 in the name of Scott, et al., which discloses the nucleotide sequence of a callase gene. DNA molecules which contain chitinase-encoding sequences can be obtained, for example, from the ATCC under Accession Numbers 39637 and 67152. See also, Kramer, et al., (1993) *Insect Biochem. Molec. Biol.* 23:691, who teach the nucleotide sequence of a cDNA encoding tobacco hookworm chitinase and Kawalleck, et al., (1993) *Plant Molec. Biol.* 21:673, who provide the nucleotide sequence of the parsley ubi4-2 polyubiquitin gene and U.S. Pat. Nos. 6,563,020; 7,145,060 and 7,087,810.

(G) A polynucleotide encoding a molecule that stimulates signal transduction. For example, see the disclosure by Botella, et al., (1994) *Plant Molec. Biol.* 24:757, of nucleotide sequences for mung bean calmodulin cDNA clones and Griess, et al., (1994) *Plant Physiol.* 104:1467, who provide the nucleotide sequence of a maize calmodulin cDNA clone.

(H) A polynucleotide encoding a hydrophobic moment peptide. See, PCT Application WO 1995/16776 and U.S. Pat. No. 5,580,852 disclosure of peptide derivatives of Tachyplesin which inhibit fungal plant pathogens) and PCT Application WO 1995/18855 and U.S. Pat. No. 5,607,914 (teaches synthetic antimicrobial peptides that confer disease resistance).

(I) A polynucleotide encoding a membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum*.

(J) A gene encoding a viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) A gene encoding an insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A gene encoding a virus-specific antibody. See, for example, Tavladoraki, et al., (1993) *Nature* 366:469, who show that transgenic plants expressing recombinant antibody genes are protected from virus attack.

(M) A polynucleotide encoding a developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436. The cloning and characterization of a gene which encodes a bean endopolygalacturonase-inhibiting protein is described by Toubart, et al., (1992) *Plant J.* 2:367.

(N) A polynucleotide encoding a developmental-arrestive protein produced in nature by a plant. For example, Logemann, et al., (1992) *Bio/Technology* 10:305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology* 5(2), Pieterse and Van Loon, (2004) *Curr. Opin. Plant Bio.* 7(4):456-64 and Somssich, (2003) *Cell* 113(7):815-6.

(P) Antifungal genes (Cornelissen and Melchers, (1993) *Pl. Physiol.* 101:709-712 and Parijs, et al., (1991) *Planta* 183:258-264 and Bushnell, et al., (1998) *Can. J. of Plant Path.* 20(2):137-149. Also see, U.S. application Ser. Nos. 09/950,933; 11/619,645; 11/657,710; 11/748,994; 11/774, 121 and U.S. Pat. Nos. 6,891,085 and 7,306,946. LysM Receptor-like kinases for the perception of chitin fragments as a first step in plant defense response against fungal pathogens (US 2012/0110696).

(Q) Detoxification genes, such as for fumonisin, beauvericin, moniliformin and zearalenone and their structurally related derivatives. For example, see, U.S. Pat. Nos. 5,716, 820; 5,792,931; 5,798,255; 5,846,812; 6,083,736; 6,538, 177; 6,388,171 and 6,812,380.

(R) A polynucleotide encoding a Cystatin and cysteine proteinase inhibitors. See, U.S. Pat. No. 7,205,453.

(S) Defensin genes. See, WO 2003/000863 and U.S. Pat. Nos. 6,911,577; 6,855,865; 6,777,592 and 7,238,781.

(T) Genes conferring resistance to nematodes. See, e.g., PCT Application Number WO 1996/30517; PCT Application Number WO 1993/19181, WO 2003/033651 and Urwin, et al., (1998) Planta 204:472-479, Williamson, (1999) *Curr Opin Plant Bio.* 2(4):327-31; U.S. Pat. Nos. 6,284,948 and 7,301,069 and miR164 genes (WO 2012/ 058266).

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al., *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035 and incorporated by reference for this purpose.

(W) Genes that confer resistance to *Colletotrichum*, such as described in US Patent Application Publication US 2009/ 0035765 and incorporated by reference for this purpose. This includes the Rcg locus that may be utilized as a single locus conversion.

2. Transgenes that Confer Resistance to a Herbicide, for Example:

(A) A polynucleotide encoding resistance to a herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7:1241 and Miki, et al., (1990) *Theor. Appl. Genet.* 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824; U.S. patent application Ser. No. 11/683,737 and International Publication WO 1996/ 33270.

(B) A polynucleotide encoding a protein for resistance to Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes) and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876 B1; 6,040,497; 5,804,425; 5,633,435; 5,145,783; 4,971,908; 5,312,910; 5,188,642; 5,094,945, 4,940,835; 5,866,775; 6,225,114 B1; 6,130,366; 5,310,667; 4,535,060; 4,769,061; 5,633,448; 5,510,471; Re. 36,449; RE 37,287 E and 5,491, 288 and International Publications EP 1173580; WO 2001/ 66704; EP 1173581 and EP 1173582, which are incorporated herein by reference for this purpose. Glyphosate resistance is also imparted to plants that express a gene encoding a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. Pat. Nos. 7,462,481; 7,405, 074 and US Patent Publication Number US 2008/0234130). A DNA molecule encoding a mutant aroA gene can be obtained under ATCC Accession Number 39256 and the nucleotide sequence of the mutant gene is disclosed in U.S. Pat. No. 4,769,061 to Comai. European Patent Application Number 0 333 033 to Kumada, et al., and U.S. Pat. No. 4,975,374 to Goodman, et al. disclose nucleotide sequences of glutamine synthetase genes which confer resistance to herbicides such as L-phosphinothricin. The nucleotide sequence of a phosphinothricin-acetyltransferase gene is provided in European Patent No. 0 242 246 and 0 242 236 to Leemans, et al. De Greef, et al., (1989) *Bio/Technology* 7:61, describe the production of transgenic plants that express chimeric bar genes coding for phosphinothricin acetyl transferase activity. See also, U.S. Pat. Nos. 5,969, 213; 5,489,520; 5,550,318; 5,874,265; 5,919,675; 5,561, 236; 5,648,477; 5,646,024; 6,177,616 B1 and 5,879,903, which are incorporated herein by reference for this purpose. Exemplary genes conferring resistance to phenoxy proprionic acids and cyclohexones, such as sethoxydim and haloxyfop, are the Acc1-51, Acc1-S2 and Acc1-S3 genes described by Marshall, et al., (1992) *Theor. Appl. Genet.* 83:435.

(C) A polynucleotide encoding a protein for resistance to herbicide that inhibits photosynthesis, such as a triazine (psbA and gs+ genes) and a benzonitrile (nitrilase gene). Przibilla, et al., (1991) Plant Cell 3:169 describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Numbers 53435, 67441 and 67442. Cloning and expression of DNA coding for a glutathione S-transferase is described by Hayes, et al., (1992) *Biochem. J.* 285: 173.

(D) A polynucleotide encoding a protein for resistance to Acetohydroxy acid synthase, which has been found to make plants that express this enzyme resistant to multiple types of herbicides, has been introduced into a variety of plants (see, e.g., Hattori, et al., (1995) *Mol Gen Genet.* 246:419). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol* 106:17), genes for glutathione reductase and superoxide dismutase (Aono, et al., (1995) *Plant Cell Physiol* 36:1687, and genes for various phosphotransferases (Datta, et al., (1992) *Plant Mol Biol* 20:619).

(E) A polynucleotide encoding resistance to a herbicide targeting Protoporphyrinogen oxidase (protox) which is necessary for the production of chlorophyll. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373 and International Publication WO 2001/12825.

(F) The aad-1 gene (originally from *Sphingobium herbicidovorans*) encodes the aryloxyalkanoate dioxygenase (AAD-1) protein. The trait confers tolerance to 2,4-dichlorophenoxyacetic acid and aryloxyphenoxypropionate (commonly referred to as "fop" herbicides such as quizalofop) herbicides. The aad-1 gene, itself, for herbicide tolerance in plants was first disclosed in WO 2005/107437 (see also, US 2009/0093366). The aad-12 gene, derived from *Delftia acidovorans*, which encodes the aryloxyalkanoate dioxygenase (AAD-12) protein that confers tolerance to 2,4-dichlorophenoxyacetic acid and pyridyloxyacetate herbicides by deactivating several herbicides with an aryloxyalkanoate moiety, including phenoxy auxin (e.g., 2,4-D, MCPA), as well as pyridyloxy auxins (e.g., fluroxypyr, triclopyr).

(G) A polynucleotide encoding a herbicide resistant dicamba monooxygenase disclosed in US Patent Application Publication 2003/0135879 for imparting dicamba tolerance;

(H) A polynucleotide molecule encoding bromoxynil nitrilase (Bxn) disclosed in U.S. Pat. No. 4,810,648 for imparting bromoxynil tolerance;

(I) A polynucleotide molecule encoding phytoene (crtI) described in Misawa, et al., (1993) *Plant J.* 4:833-840 and in Misawa, et al., (1994) *Plant J.* 6:481-489 for norflurazon tolerance.

3. Transgenes that Confer or Contribute to an Altered Grain Characteristic, Such as:

(A) Altered fatty acids, for example, by (1) Down-regulation of stearoyl-ACP to increase stearic acid content of the plant. See, Knultzon, et al., (1992) *Proc. Natl. Acad. Sci. USA* 89:2624 and WO 1999/64579 (Genes to Alter Lipid Profiles in Corn), (2) Elevating oleic acid via FAD-2 gene modification and/or decreasing linolenic acid via FAD-3 gene modification (see, U.S. Pat. Nos. 6,063,947; 6,323,392; 6,372,965 and WO 1993/11245), (3) Altering conjugated linolenic or linoleic acid content, such as in WO 2001/12800, (4) Altering LEC1, AGP, Dek1, Superal1, mi1 ps, and various Ipa genes such as Ipa1, Ipa3, hpt or hggt. For example, see, WO 2002/42424, WO 1998/22604, WO 2003/011015, WO 2002/057439, WO 2003/011015, U.S. Pat. Nos. 6,423,886, 6,197,561, 6,825,397 and US Patent Application Publication Numbers US 2003/0079247, US 2003/0204870 and Rivera-Madrid, et al., (1995) *Proc. Natl. Acad. Sci.* 92:5620-5624.

(5) Genes encoding delta-8 desaturase for making long-chain polyunsaturated fatty acids (U.S. Pat. Nos. 8,058,571 and 8,338,152), delta-9 desaturase for lowering saturated fats (U.S. Pat. No. 8,063,269), Primula Δ6-desaturase for improving omega-3 fatty acid profiles.

(6) Isolated nucleic acids and proteins associated with lipid and sugar metabolism regulation, in particular, lipid metabolism protein (LMP) used in methods of producing transgenic plants and modulating levels of seed storage compounds including lipids, fatty acids, starches or seed storage proteins and use in methods of modulating the seed size, seed number, seed weights, root length and leaf size of plants (EP 2404499).

(7) Altering expression of a High-Level Expression of Sugar-Inducible 2 (HSI2) protein in the plant to increase or decrease expression of HSI2 in the plant. Increasing expression of HSI2 increases oil content while decreasing expression of HSI2 decreases abscisic acid sensitivity and/or increases drought resistance (US 2012/0066794).

(8) Expression of cytochrome b5 (Cb5) alone or with FAD2 to modulate oil content in plant seed, particularly to increase the levels of omega-3 fatty acids and improve the ratio of omega-6 to omega-3 fatty acids (US Patent Application Publication Number 2011/0191904).

(9) Nucleic acid molecules encoding wrinkled1-like polypeptides for modulating sugar metabolism (U.S. Pat. No. 8,217,223).

B) Altered phosphorus content, for example, by the (1) Introduction of a phytase-encoding gene would enhance breakdown of phytate, adding more free phosphate to the transformed plant. For example, see Van Hartingsveldt, et al., (1993) *Gene* 127:87, for a disclosure of the nucleotide sequence of an *Aspergillus niger* phytase gene.

(2) Modulating a gene that reduces phytate content. In maize, this, for example, could be accomplished, by cloning and then re-introducing DNA associated with one or more of the alleles, such as the LPA alleles, identified in maize mutants characterized by low levels of phytic acid, such as in WO 2005/113778 and/or by altering inositol kinase activity as in WO 2002/059324, US 2003/0009011, WO 2003/027243, US 2003/0079247, WO 1999/05298, U.S. Pat. Nos. 6,197,561, 6,291,224, 6,391,348, WO 2002/059324, US 2003/0079247, WO 1998/45448, WO 1999/55882, WO 2001/04147.

(C) Altered carbohydrates effected, for example, by altering a gene for an enzyme that affects the branching pattern of starch or, a gene altering thioredoxin such as NTR and/or TRX (see, (see, U.S. Pat. No. 6,531,648 which is incorporated by reference for this purpose) and/or a gamma zein knock out or mutant such as cs27 or TUSC27 or en27 (see, U.S. Pat. No. 6,858,778 and US 2005/0160488, US 2005/0204418; which are incorporated by reference for this purpose). See, Shiroza, et al., (1988) *J. Bacteriol.* 170:810 (nucleotide sequence of *Streptococcus* mutant fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) *J. Biol. Chem.* 268:22480 (site-directed mutagenesis of barley alpha-amylase gene)

and Fisher, et al., (1993) *Plant Physiol.* 102:1045 (maize endosperm starch branching enzyme II), WO 1999/10498 (improved digestibility and/or starch extraction through modification of UDP-D-xylose 4-epimerase, Fragile 1 and 2, Refl, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US 2004/0034886 and WO 2000/68393 involving the manipulation of antioxidant levels and WO 2003/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 1999/40209 (alteration of amino acid compositions in seeds), WO 1999/29882 (methods for altering amino acid content of proteins), U.S. Pat. No. 5,850,016 (alteration of amino acid compositions in seeds), WO 1998/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 1998/56935 (plant amino acid biosynthetic enzymes), WO 1998/45458 (engineered seed protein having higher percentage of essential amino acids), WO 1998/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 1996/01905 (increased threonine), WO 1995/15392 (increased lysine), US 2003/163838, US 2003/0150014, US 2004/0068767, U.S. Pat. No. 6,803,498, WO 2001/79516.

4. Genes that Control Male-Sterility:

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing or turning "on", the promoter, which in turn allows the gene that confers male fertility to be transcribed.

(A) Introduction of a deacetylase gene under the control of a tapetum-specific promoter and with the application of the chemical N-Ac-PPT (WO 01/29237).

(B) Introduction of various stamen-specific promoters (WO 1992/13956, WO 1992/13957).

(C) Introduction of the barnase and the barstar gene (Paul, et al., (1992) *Plant Mol. Biol.* 19:611-622).

For additional examples of nuclear male and female sterility systems and genes, see also, U.S. Pat. Nos. 5,859,341; 6,297,426; 5,478,369; 5,824,524; 5,850,014; and 6,265,640; all of which are hereby incorporated by reference.

5. Genes that Create a Site for Site Specific DNA Integration.

This includes the introduction of FRT sites that may be used in the FLP/FRT system and/or Lox sites that may be used in the Cre/Loxp system. For example, see Lyznik, et al., (2003) *Plant Cell Rep* 21:925-932 and WO 1999/25821, which are hereby incorporated by reference. Other systems that may be used include the Gin recombinase of phage Mu (Maeser, et al., (1991) Vicki Chandler, The Maize Handbook ch. 118 (Springer-Verlag 1994), the Pin recombinase of *E. coli* (Enomoto, et al., 1983) and the R/RS system of the pSRi plasmid (Araki, et al., 1992).

6. Genes that Affect Abiotic Stress Resistance

Including but not limited to flowering, ear and seed development, enhancement of nitrogen utilization efficiency, altered nitrogen responsiveness, drought resistance or tolerance, cold resistance or tolerance, and salt resistance or tolerance, and increased yield under stress.

(A) For example, see, WO 2000/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 199809521;

(B) WO 199938977 describing genes, including CBF genes and transcription factors effective in mitigating the negative effects of freezing, high salinity and drought on plants, as well as conferring other positive effects on plant phenotype;

(C) US 2004/0148654 and WO 2001/36596 where abscisic acid is altered in plants resulting in improved plant phenotype such as increased yield and/or increased tolerance to abiotic stress;

(D) WO 2000/006341, WO 2004/090143, U.S. Pat. Nos. 7,531,723 and 6,992,237 where cytokinin expression is modified resulting in plants with increased stress tolerance, such as drought tolerance, and/or increased yield. Also see, WO 2002/02776, WO 2003/052063, JP 2002/281975, U.S. Pat. No. 6,084,153, WO 200164898, U.S. Pat. Nos. 6,177,275 and 6,107,547 (enhancement of nitrogen utilization and altered nitrogen responsiveness);

(E) For ethylene alteration, see, US 2004/0128719, US 2003/0166197 and WO 2000/32761;

(F) For plant transcription factors or transcriptional regulators of abiotic stress, see e.g., US 2004/0098764 or US 2004/0078852;

(G) Genes that increase expression of vacuolar pyrophosphatase such as AVP1 (U.S. Pat. No. 8,058,515) for increased yield; nucleic acid encoding a HSFA4 or a HSFA5 (Heat Shock Factor of the class A4 or A5) polypeptides, an oligopeptide transporter protein (OPT4-like) polypeptide; a plastochron2-like (PLA2-like) polypeptide or a Wuschel related homeobox 1-like (WOX1-like) polypeptide (US Patent Application Publication Number US 2011/0283420);

(H) Down regulation of polynucleotides encoding poly (ADP-ribose) polymerase (PARP) proteins to modulate programmed cell death (U.S. Pat. No. 8,058,510) for increased vigor;

(I) Polynucleotide encoding DTP21 polypeptides for conferring drought resistance (US Patent Publication Number US 2011/0277181);

(J) Nucleotide sequences encoding ACC Synthase 3 (ACS3) proteins for modulating development, modulating response to stress and modulating stress tolerance (US Patent Pub. No. US20100287669).

(K) Polynucleotides that encode proteins that confer a drought tolerance phenotype (DTP) for conferring drought resistance (WO 2012/058528).

(L) Tocopherol cyclase (TC) genes for conferring drought and salt tolerance (US Patent Application Publication Number 2012/0272352).

(M) CAAX amino terminal family proteins for stress tolerance (U.S. Pat. No. 8,338,661).

(N) Mutations in the SAL1 encoding gene have increased stress tolerance, including increased drought resistant (US Patent Application Publication Number 2010/0257633).

(O) Expression of a nucleic acid sequence encoding a polypeptide selected from the group consisting of: GRF polypeptide, RAA1-like polypeptide, SYR polypeptide, ARKL polypeptide, and YTP polypeptide increasing yield-related traits (US Patent Application Publication Number 2011/0061133).

(P) Modulating expression in a plant of a nucleic acid encoding a Class III Trehalose Phosphate Phosphatase (TPP) polypeptide for enhancing yield-related traits in plants, particularly increasing seed yield (US Patent Application Publication Number 2010/0024067).

Other genes and transcription factors that affect plant growth and agronomic traits such as yield, flowering, plant growth and/or plant structure, can be introduced or introgressed into plants, see e.g., WO 1997/49811 (LHY), WO 1998/56918 (ESD4), WO 1997/10339 and U.S. Pat. No. 6,573,430 (TFL), U.S. Pat. No. 6,713,663 (FT), WO 1996/14414 (CON), WO 1996/38560, WO 2001/21822 (VRN1), WO 2000/44918 (VRN2), WO 1999/49064 (GI), WO 2000/46358 (FR1), WO 1997/29123, U.S. Pat. Nos. 6,794,560, 6,307,126 (GAI), WO 1999/09174 (D8 and Rht), and WO 2004/076638 and WO 2004/031349 (transcription factors).

7. Genes that Confer Increased Yield (A) A transgenic crop plant transformed by a 1-Amino-Cyclopropane-1-Carboxylate Deaminase-like Polypeptide (ACCDP) coding nucleic acid, wherein expression of the nucleic acid sequence in the crop plant results in the plant's increased root growth, and/or increased yield, and/or increased tolerance to environmental stress as compared to a wild type variety of the plant (U.S. Pat. No. 8,097,769).

(B) Over-expression of maize zinc finger protein gene (Zm-ZFP1) using a seed preferred promoter has been shown to enhance plant growth, increase kernel number and total kernel weight per plant (US 2012/0079623).

(C) Constitutive over-expression of maize lateral organ boundaries (LOB) domain protein (Zm-LOBDP1) has been shown to increase kernel number and total kernel weight per plant (2012/0079622).

(D) Enhancing yield-related traits in plants by modulating expression in a plant of a nucleic acid encoding a VIM1 (Variant in Methylation 1)-like polypeptide or a VTC2-like (GDP-L-galactose phosphorylase) polypeptide or a DUF1685 polypeptide or an ARF6-like (Auxin Responsive Factor) polypeptide (WO 2012/038893).

(E) Modulating expression in a plant of a nucleic acid encoding a Ste20-like polypeptide or a homologue thereof gives plants having increased yield relative to control plants (EP 2431472).

(F) Genes encoding nucleoside diphosphatase kinase (NDK) polypeptides and homologs thereof for modifying the plant's root architecture (US Patent Application Publication Number 2009/0064373).

8. Genes that Confer Plant Digestibility.

(A) Altering the level of xylan present in the cell wall of a plant by modulating expression of xylan synthase (U.S. Pat. No. 8,173,866).

In some embodiment the stacked trait may be a trait or event that has received regulatory approval including but not limited to the events in Table 1A-1F.

TABLE 1A

| Triticum aestivum Wheat | | |
|---|---|---|
| Event | Company | Description |
| AP205CL | BASF Inc. | Selection for a mutagenized version of the enzyme acetohydroxyacid synthase (AHAS), also known as acetolactate synthase (ALS) or acetolactate pyruvate-lyase. |
| AP602CL | BASF Inc. | Selection for a mutagenized version of the enzyme acetohydroxyacid synthase (AHAS), also known as acetolactate synthase (ALS) or acetolactate pyruvate-lyase. |
| BW255-2, BW238-3 | BASF Inc. | Selection for a mutagenized version of the enzyme acetohydroxyacid synthase (AHAS), also known as acetolactate synthase (ALS) or acetolactate pyruvate-lyase. |
| BW7 | BASF Inc. | Tolerance to imidazolinone herbicides induced by chemical mutagenesis of the acetohydroxyacid synthase (AHAS) gene using sodium azide. |
| MON71800 | Monsanto Company | Glyphosate tolerant wheat variety produced by inserting a modified 5-enolpyruvylshikimate-3-phosphate synthase (EPSPS) encoding gene from the soil bacterium *Agrobacterium tumefaciens*, strain CP4. |
| SWP965001 | Cyanamid Crop Protection | Selection for a mutagenized version of the enzyme acetohydroxyacid synthase (AHAS), also known as acetolactate synthase (ALS) or acetolactate pyruvate-lyase. |
| Teal 11A | BASF Inc. | Selection for a mutagenized version of the enzyme acetohydroxyacid synthase (AHAS), also known as acetolactate synthase (ALS) or acetolactate pyruvate-lyase. |

TABLE 1B

| Glycine max L. Soybean | | |
|---|---|---|
| Event | Company | Description |
| A2704-12, A2704-21, A5547-35 | Bayer CropScience (Aventis CropScience (AgrEvo)) | Glufosinate ammonium herbicide tolerant soybean produced by inserting a modified phosphinothricin acetyltransferase (PAT) encoding gene from the soil bacterium *Streptomyces viridochromogenes*. |
| A5547-127 | Bayer CropScience (Aventis CropScience (AgrEvo)) | Glufosinate ammonium herbicide tolerant soybean produced by inserting a modified phosphinothricin acetyltransferase (PAT) encoding gene from the soil bacterium *Streptomyces viridochromogenes*. |
| BPS-CV127-9 | BASF Inc. | The introduced csr1-2 gene from *Arabidopsis thaliana* encodes an acetohydroxyacid synthase protein that confers tolerance to imidazolinone herbicides due to a point mutation that results in a single amino acid substitution in which the serine residue at position 653 is replaced by asparagine (S653N). |

TABLE 1B-continued

Glycine max L. Soybean

| Event | Company | Description |
|---|---|---|
| DP-305423 | Pioneer Hi-Bred International Inc. | High oleic acid soybean produced by inserting additional copies of a portion of the omega-6 desaturase encoding gene, gm-fad2-1 resulting in silencing of the endogenous omega-6 desaturase gene (FAD2-1). |
| DP356043 | Pioneer Hi-Bred International Inc. | Soybean event with two herbicide tolerance genes: glyphosate N-acetyltransferase, which detoxifies glyphosate, and a modified acetolactate synthase (ALS) gene which is tolerant to ALS-inhibiting herbicides. |
| G94-1, G94-19, G168 | DuPont Canada Agricultural Products | High oleic acid soybean produced by inserting a second copy of the fatty acid desaturase (GmFad2-1) encoding gene from soybean, which resulted in "silencing" of the endogenous host gene. |
| GTS 40-3-2 | Monsanto Company | Glyphosate tolerant soybean variety produced by inserting a modified 5-enolpyruvylshikimate-3-phosphate synthase (EPSPS) encoding gene from the soil bacterium *Agrobacterium tumefaciens*. |
| GU262 | Bayer CropScience (Aventis CropScience (AgrEvo)) | Glufosinate ammonium herbicide tolerant soybean produced by inserting a modified phosphinothricin acetyltransferase (PAT) encoding gene from the soil bacterium *Streptomyces viridochromogenes*. |
| MON87701 | Monsanto Company | Resistance to lepidopteran pests of soybean including velvetbean caterpillar (*Anticarsia gemmatalis*) and soybean looper (*Pseudoplusia includens*). |
| MON87701 x MON89788 | Monsanto Company | Glyphosate herbicide tolerance through expression of the EPSPS encoding gene from *A. tumefaciens* strain CP4, and resistance to lepidopteran pests of soybean including velvetbean caterpillar (*Anticarsia gemmatalis*) and soybean looper (*Pseudoplusia includens*) via expression of the Cry1Ac encoding gene from *B. thuringiensis*. |
| MON89788 | Monsanto Company | Glyphosate-tolerant soybean produced by inserting a modified 5-enolpyruvylshikimate-3-phosphate synthase (EPSPS) encoding aroA (epsps) gene from *Agrobacterium tumefaciens* CP4. |
| OT96-15 | Agriculture & Agri-Food Canada | Low linolenic acid soybean produced through traditional cross-breeding to incorporate the novel trait from a naturally occurring fan1 gene mutant that was selected for low linolenic acid. |
| W62, W98 | Bayer CropScience (Aventis CropScience (AgrEvo)) | Glufosinate ammonium herbicide tolerant soybean produced by inserting a modified phosphinothricin acetyltransferase (PAT) encoding gene from the soil bacterium *Streptomyces hygroscopicus*. |

TABLE 1C

Helianthus annuus Sunflower

| Event | Company | Description |
|---|---|---|
| X81359 | BASF Inc. | Tolerance to imidazolinone herbicides by selection of a naturally occurring mutant. |

TABLE 1D

Medicago sativa Alfalfa

| Event | Company | Description |
|---|---|---|
| J101, J163 | Monsanto Company and Forage Genetics International | Glyphosate herbicide tolerant alfalfa (lucerne) produced by inserting a gene encoding the enzyme 5-enolypyruvylshikimate-3-phosphate synthase (EPSPS) from the CP4 strain of *Agrobacterium tumefaciens*. |

TABLE 1E

Oryza sativa Rice

| Event | Company | Description |
|---|---|---|
| CL121, CL141, CFX51 | BASF Inc. | Tolerance to the imidazolinone herbicide, imazethapyr, induced by chemical mutagenesis of the acetolactate synthase (ALS) enzyme using ethyl methanesulfonate (EMS). |
| IMINTA-1, IMINTA-4 | BASF Inc. | Tolerance to imidazolinone herbicides induced by chemical mutagenesis of the acetolactate synthase (ALS) enzyme using sodium azide. |
| LLRICE06, LLRICE62 | Aventis CropScience | Glufosinate ammonium herbicide tolerant rice produced by inserting a modified phosphinothricin acetyltransferase (PAT) encoding gene from the soil bacterium *Streptomyces hygroscopicus*). |
| LLRICE601 | Bayer CropScience (Aventis CropScience (AgrEvo)) | Glufosinate ammonium herbicide tolerant rice produced by inserting a modified phosphinothricin acetyltransferase (PAT) encoding gene from the soil bacterium *Streptomyces hygroscopicus*). |
| PWC16 | BASF Inc. | Tolerance to the imidazolinone herbicide, imazethapyr, induced by chemical mutagenesis of the acetolactate synthase (ALS) enzyme using ethyl methanesulfonate (EMS). |

TABLE 1F

Zea mays L. Maize

| Event | Company | Description |
|---|---|---|
| 176 | Syngenta Seeds, Inc. | Insect-resistant maize produced by inserting the Cry1Ab gene from *Bacillus thuringiensis* subsp. *kurstaki*. The genetic modification affords resistance to attack by the European corn borer (ECB). |
| 3751IR | Pioneer Hi-Bred International Inc. | Selection of somaclonal variants by culture of embryos on imidazolinone containing media. |
| 676, 678, 680 | Pioneer Hi-Bred International Inc. | Male-sterile and glufosinate ammonium herbicide tolerant maize produced by inserting genes encoding DNA adenine methylase and phosphinothricin acetyltransferase (PAT) from *Escherichia coli* and *Streptomyces viridochromogenes*, respectively. |
| B16 (DLL25) | Dekalb Genetics Corporation | Glufosinate ammonium herbicide tolerant maize produced by inserting the gene encoding phosphinothricin acetyltransferase (PAT) from *Streptomyces hygroscopicus*. |
| BT11 (X4334CBR, X4734CBR) | Syngenta Seeds, Inc. | Insect-resistant and herbicide tolerant maize produced by inserting the Cry1Ab gene from *Bacillus thuringiensis* subsp. *kurstaki*, and the phosphinothricin N-acetyltransferase |

TABLE 1F-continued

*Zea mays* L. Maize

| Event | Company | Description |
|---|---|---|
| | | (PAT) encoding gene from *S. viridochromogenes*. |
| BT11 x GA21 | Syngenta Seeds, Inc. | Stacked insect resistant and herbicide tolerant maize produced by conventional cross breeding of parental lines BT11 (OECD unique identifier: SYN-BTO11-1) and GA21 (OECD unique identifier: MON-OOO21-9). |
| BT11 x MIR162 | Syngenta Seeds, Inc. | Stacked insect resistant and herbicide tolerant maize produced by conventional cross breeding of parental lines BT11 (OECD unique identifier: SYN-BTO11-1) and MIR162 (OECD unique identifier: SYN-IR162-4). Resistance to the European Corn Borer and tolerance to the herbicide glufosinate ammonium (Liberty) is derived from BT11, which contains the Cry1Ab gene from *Bacillus thuringiensis* subsp. *kurstaki*, and the phosphinothricin N-acetyltransferase (PAT) encoding gene from *S. viridochromogenes*. Resistance to other lepidopteran pests, including *H. zea*, *S. frugiperda*, *A. ipsilon*, and *S. albicosta*, is derived from MIR162, which contains the vip3Aa gene from *Bacillus thuringiensis* strain AB88. |
| BT11 x MIR162 x MIR604 | Syngenta Seeds, Inc. | *Bacillus thuringiensis* Cry1Ab delta-endotoxin protein and the genetic material necessary for its production (via elements of vector pZO1502) in Event Bt11 corn (OECD Unique Identifier: SYN-BTO11-1) x *Bacillus thuringiensis* Vip3Aa20 insecticidal protein and the genetic material necessary for its production (via elements of vector pNOV1300) in Event MIR162 maize (OECD Unique Identifier: SYN-IR162-4) x modified Cry3A protein and the genetic material necessary for its production (via elements of vector pZM26) in Event MIR604 corn (OECD Unique Identifier: SYN-IR6O4-5). |
| BT11 x MIR162 x MIR604 x GA21 | Syngenta Seeds, Inc. | Resistance to coleopteran pests, particularly corn rootworm pests (*Diabrotica* spp.) and several lepidopteran pests of corn, including European corn borer (ECB, *Ostrinia nubilalis*), corn earworm (CEW, *Helicoverpa zea*), fall army worm (FAW, *Spodoptera frugiperda*), and black cutworm (BCW, *Agrotis ipsilon*); tolerance to glyphosate and glufosinate-ammonium containing herbicides. |
| BT11 x MIR604 | Syngenta Seeds, Inc. | Stacked insect resistant and herbicide tolerant maize produced by conventional cross breeding of parental lines BT11 (OECD unique identifier: SYN-BTO11-1) and MIR604 (OECD unique identifier: SYN-IR6O5-5). Resistance to the European Corn Borer and tolerance to the herbicide glufosinate ammonium (Liberty) is derived from BT11, which contains the Cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mCry3A gene from *Bacillus thuringiensis*. |
| BT11 x MIR604 x GA21 | Syngenta Seeds, Inc. | Stacked insect resistant and herbicide tolerant maize produced by conventional cross breeding of parental lines BT11 (OECD unique identifier: SYN-BTO11-1), MIR604 (OECD unique identifier: SYN-IR6O5-5) and GA21 (OECD unique identifier: MON-OOO21-9). Resistance to the European Corn Borer and tolerance to the herbicide glufosinate ammonium (Liberty) is derived from BT11, which contains the Cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mCry3A gene from *Bacillus thuringiensis*. Tolerance to glyphosate herbicide is derived from GA21 which contains a modified EPSPS gene from maize. |
| CBH-351 | Aventis CropScience | Insect-resistant and glufosinate ammonium herbicide tolerant maize developed by inserting genes encoding Cry9C protein from *Bacillus thuringiensis* subsp *tolworthi* and phosphinothricin acetyltransferase (PAT) from *Streptomyces hygroscopicus*. |
| DAS-06275-8 | DOW AgroSciences LLC | Lepidopteran insect resistant and glufosinate ammonium herbicide-tolerant maize variety produced by inserting the Cry1F gene from *Bacillus thuringiensis* var *aizawai* and the phosphinothricin acetyltransferase (PAT) from *Streptomyces hygroscopicus*. |
| DAS-59122-7 | DOW AgroSciences LLC and Pioneer Hi-Bred International Inc. | Corn rootworm-resistant maize produced by inserting the Cry34Ab1 and Cry35Ab1 genes from *Bacillus thuringiensis* strain PS149B1. The PAT encoding gene from *Streptomyces viridochromogenes* was introduced as a selectable marker. |
| DAS-59122-7 x NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) with NK603 (OECD unique identifier: MON-OO6O3-6). Corn rootworm-resistance is derived from DAS-59122-7 which contains the Cry34Ab1 and Cry35Ab1 genes from *Bacillus thuringiensis* strain PS149B1. Tolerance to glyphosate herbicide is derived from NK603. |
| DAS-59122-7 x TC1507 x NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) and TC1507 (OECD unique identifier: DAS-O15O7-1) with NK603 (OECD unique identifier: MON-OO6O3-6). Corn rootworm-resistance is derived from DAS-59122-7 which contains the Cry34Ab1 and Cry35Ab1 genes from *Bacillus thuringiensis* strain PS149B1. Lepidopteran resistance and tolerance to glufosinate ammonium herbicide is derived from TC1507. Tolerance to glyphosate herbicide is derived from NK603. |

TABLE 1F-continued

Zea mays L. Maize

| Event | Company | Description |
|---|---|---|
| DBT418 | Dekalb Genetics Corporation | Insect-resistant and glufosinate ammonium herbicide tolerant maize developed by inserting genes encoding Cry1AC protein from *Bacillus thuringiensis* subsp *kurstaki* and phosphinothricin acetyltransferase (PAT) from *Streptomyces hygroscopicus* |
| DK404SR | BASF Inc. | Somaclonal variants with a modified acetyl-CoA-carboxylase (ACCase) were selected by culture of embryos on sethoxydim enriched medium. |
| Event 3272 | Syngenta Seeds, Inc. | Maize line expressing a heat stable alpha-amylase gene amy797E for use in the dry-grind ethanol process. The phosphomannose isomerase gene from *E. coli* was used as a selectable marker. |
| Event 98140 | Pioneer Hi-Bred International Inc. | Maize event expressing tolerance to glyphosate herbicide, via expression of a modified bacterial glyphosate N-acetlytransferase, and ALS-inhibiting herbicides, vial expression of a modified form of the maize acetolactate synthase enzyme. |
| EXP1910IT | Syngenta Seeds, Inc. (formerly Zeneca Seeds) | Tolerance to the imidazolinone herbicide, imazethapyr, induced by chemical mutagenesis of the acetolactate synthase (ALS) enzyme using ethyl methanesulfonate (EMS). |
| GA21 | Syngenta Seeds, Inc. (formerly Zeneca Seeds) | Introduction, by particle bombardment, of a modified 5-enolpyruvyl shikimate-3-phosphate synthase (EPSPS), an enzyme involved in the shikimate biochemical pathway for the production of the aromatic amino acids. |
| GA21 x MON810 | Monsanto Company | Stacked insect resistant and herbicide tolerant corn hybrid derived from conventional cross-breeding of the parental lines GA21 (OECD identifier: MON-OOO21-9) and MON810 (OECD identifier: MON-OO81O-6). |
| IT | Pioneer Hi-Bred International Inc. | Tolerance to the imidazolinone herbicide, imazethapyr, was obtained by in vitro selection of somaclonal variants. |
| LY038 | Monsanto Company | Altered amino acid composition, specifically elevated levels of lysine, through the introduction of the cordapA gene, derived from *Corynebacterium glutamicum*, encoding the enzyme dihydrodipicolinate synthase (cDHDPS). |
| MIR162 | Syngenta Seeds, Inc. | Insect-resistant maize event expressing a Vip3A protein from *Bacillus thuringiensis* and the *Escherichia coli* PMI selectable marker |
| MIR604 | Syngenta Seeds, Inc. | Corn rootworm resistant maize produced by transformation with a modified Cry3A gene. The phosphomannose isomerase gene from *E. coli* was used as a selectable marker. |
| MIR604 x GA21 | Syngenta Seeds, Inc. | Stacked insect resistant and herbicide tolerant maize produced by conventional cross breeding of parental lines MIR604 (OECD unique identifier: SYN-IR6O5-5) and GA21 (OECD unique identifier: MON-OOO21-9). Corn rootworm-resistance is derived from MIR604 which contains the mCry3A gene from *Bacillus thuringiensis*. Tolerance to glyphosate herbicide is derived from GA21. |
| MON80100 | Monsanto Company | Insect-resistant maize produced by inserting the Cry1Ab gene from *Bacillus thuringiensis* subsp. *kurstaki*. The genetic modification affords resistance to attack by the European corn borer (ECB). |
| MON802 | Monsanto Company | Insect-resistant and glyphosate herbicide tolerant maize produced by inserting the genes encoding the Cry1Ab protein from *Bacillus thuringiensis* and the 5-enolpyruvylshikimate-3-phosphate synthase (EPSPS) from *A. tumefaciens* strain CP4. |
| MON809 | Pioneer Hi-Bred International Inc. | Resistance to European corn borer (*Ostrinia nubilalis*) by introduction of a synthetic Cry1Ab gene. Glyphosate resistance via introduction of the bacterial version of a plant enzyme, 5-enolpyruvyl shikimate-3-phosphate synthase (EPSPS). |
| MON810 | Monsanto Company | Insect-resistant maize produced by inserting a truncated form of the Cry1Ab gene from *Bacillus thuringiensis* subsp. *kurstaki* HD-1. The genetic modification affords resistance to attack by the European corn borer (ECB). |
| MON810 x LY038 | Monsanto Company | Stacked insect resistant and enhanced lysine content maize derived from conventional cross-breeding of the parental lines MON810 (OECD identifier: MON-OO81O-6) and LY038 (OECD identifier: REN-OOO38-3). |
| MON810 x MON88017 | Monsanto Company | Stacked insect resistant and glyphosate tolerant maize derived from conventional cross-breeding of the parental lines MON810 (OECD identifier: MON-OO81O-6) and MON88017 (OECD identifier: MON-88O17-3). European corn borer (ECB) resistance is derived from a truncated form of the Cry1Ab gene from *Bacillus thuringiensis* subsp. *kurstaki* HD-1 present in MON810. Corn rootworm resistance is derived from the Cry3Bb1 gene from *Bacillus thuringiensis* subspecies *kumamotoensis* strain EG4691 present in MON88017. Glyphosate tolerance is derived from a 5-enolpyruvylshikimate-3-phosphate synthase (EPSPS) encoding gene from *Agrobacterium tumefaciens* strain CP4 present in MON88017. |
| MON832 | Monsanto Company | Introduction, by particle bombardment, of glyphosate oxidase (GOX) and a modified 5-enolpyruvyl shikimate-3-phosphate synthase (EPSPS), an enzyme involved in the shikimate biochemical pathway for the production of the aromatic amino acids. |
| MON863 | Monsanto Company | Corn root worm resistant maize produced by inserting the Cry3Bb1 gene from *Bacillus thuringiensis* subsp. *kumamotoensis*. |
| MON863 x MON810 | Monsanto Company | Stacked insect resistant corn hybrid derived from conventional cross-breeding of the parental lines MON863 (OECD identifier: MON-OO863-5) and MON810 (OECD identifier: MON-OO81O-6) |
| MON863 x MON810 x | Monsanto Company | Stacked insect resistant and herbicide tolerant corn hybrid derived from |

TABLE 1F-continued

Zea mays L. Maize

| Event | Company | Description |
|---|---|---|
| NK603 | | conventional cross-breeding of the stacked hybrid MON-OO863-5 x MON-OO81O-6 and NK603 (OECD identifier: MON-OO6O3-6). |
| MON863 x NK603 | Monsanto Company | Stacked insect resistant and herbicide tolerant corn hybrid derived from conventional cross-breeding of the parental lines MON863 (OECD identifier: MON-OO863-5) and NK603 (OECD identifier: MON-OO6O3-6). |
| MON87460 | Monsanto Company | MON 87460 was developed to provide reduced yield loss under water-limited conditions compared to conventional maize. Efficacy in MON 87460 is derived by expression of the inserted *Bacillus subtilis* cold shock protein B (CspB). |
| MON88017 | Monsanto Company | Corn rootworm-resistant maize produced by inserting the Cry3Bb1 gene from *Bacillus thuringiensis* subspecies *kumamotoensis* strain EG4691. Glyphosate tolerance derived by inserting a 5-enolpyruvylshikimate-3-phosphate synthase (EPSPS) encoding gene from *Agrobacterium tumefaciens* strain CP4. |
| MON89034 | Monsanto Company | Maize event expressing two different insecticidal proteins from *Bacillus thuringiensis* providing resistance to number of lepidopteran pests. |
| MON89034 x MON88017 | Monsanto Company | Stacked insect resistant and glyphosate tolerant maize derived from conventional cross-breeding of the parental lines MON89034 (OECD identifier: MON-89O34-3) and MON88017 (OECD identifier: MON-88O17-3). Resistance to Lepidopteran insects is derived from two Cry genes present in MON89043. Corn rootworm resistance is derived from a single Cry genes and glyphosate tolerance is derived from the 5-enolpyruvylshikimate-3-phosphate synthase (EPSPS) encoding gene from *Agrobacterium tumefaciens* present in MON88017. |
| MON89034 x NK603 | Monsanto Company | Stacked insect resistant and herbicide tolerant maize produced by conventional cross breeding of parental lines MON89034 (OECD identifier: MON-89O34-3) with NK603 (OECD unique identifier: MON-OO6O3-6). Resistance to Lepidopteran insects is derived from two Cry genes present in MON89043. Tolerance to glyphosate herbicide is derived from NK603. |
| MON89034 x TC1507 x MON88017 x DAS-59122-7 | Monsanto Company and Mycogen Seeds c/o Dow AgroSciences LLC | Stacked insect resistant and herbicide tolerant maize produced by conventional cross breeding of parental lines: MON89034, TC1507, MON88017, and DAS-59122. Resistance to the above-ground and below-ground insect pests and tolerance to glyphosate and glufosinate-ammonium containing herbicides. |
| MS3 | Bayer CropScience (Aventis CropScience (AgrEvo)) | Male sterility caused by expression of the barnase ribonuclease gene from *Bacillus amyloliquefaciens*; PPT resistance was via PPT-acetyltransferase (PAT). |
| MS6 | Bayer CropScience (Aventis CropScience (AgrEvo)) | Male sterility caused by expression of the barnase ribonuclease gene from *Bacillus amyloliquefaciens*; PPT resistance was via PPT-acetyltransferase (PAT). |
| NK603 | Monsanto Company | Introduction, by particle bombardment, of a modified 5-enolpyruvyl shikimate-3-phosphate synthase (EPSPS), an enzyme involved in the shikimate biochemical pathway for the production of the aromatic amino acids. |
| NK603 x MON810 | Monsanto Company | Stacked insect resistant and herbicide tolerant corn hybrid derived from conventional cross-breeding of the parental lines NK603 (OECD identifier: MON-OO6O3-6) and MON810 (OECD identifier: MON-OO81O-6). |
| NK603 x T25 | Monsanto Company | Stacked glufosinate ammonium and glyphosate herbicide tolerant maize hybrid derived from conventional cross-breeding of the parental lines NK603 (OECD identifier: MON-OO6O3-6) and T25 (OECD identifier: ACS-ZM003-2). |
| T14, T25 | Bayer CropScience (Aventis CropScience (AgrEvo)) | Glufosinate herbicide tolerant maize produced by inserting the phosphinothricin N-acetyltransferase (PAT) encoding gene from the aerobic actinomycete *Streptomyces viridochromogenes*. |
| T25 x MON810 | Bayer CropScience (Aventis CropScience (AgrEvo)) | Stacked insect resistant and herbicide tolerant corn hybrid derived from conventional cross-breeding of the parental lines T25 (OECD identifier: ACS-ZMOO3-2) and MON810 (OECD identifier: MON-OO81O-6). |
| TC1507 | Mycogen (c/o Dow AgroSciences); Pioneer (c/o DuPont) | Insect-resistant and glufosinate ammonium herbicide tolerant maize produced by inserting the Cry1F gene from *Bacillus thuringiensis* var. *aizawai* and the phosphinothricin N-acetyltransferase encoding gene from *Streptomyces viridochromogenes*. |
| TC1507 x DAS-59122-7 | DOW AgroSciences LLC and Pioneer Hi-Bred International Inc. | Stacked insect resistant and herbicide tolerant maize produced by conventional cross breeding of parental lines TC1507 (OECD unique identifier: DAS-O15O7-1) with DAS-59122-7 (OECD unique identifier: DAS-59122-7). Resistance to lepidopteran insects is derived from TC1507 due the presence of the Cry1F gene from *Bacillus thuringiensis* var. *aizawai*. Corn rootworm-resistance is derived from DAS-59122-7 which contains the Cry34Ab1 and Cry35Ab1 genes from *Bacillus thuringiensis* strain PS149B1. Tolerance to glufosinate ammonium herbicide is derived from TC1507 from the phosphinothricin N-acetyltransferase encoding gene from *Streptomyces viridochromogenes*. |
| TC1507 x NK603 | DOW AgroSciences LLC | Stacked insect resistant and herbicide tolerant corn hybrid derived from conventional cross-breeding of the parental lines 1507 (OECD identifier: DAS-O15O7-1) and NK603 (OECD identifier: MON-OO6O3-6). |

Other events with regulatory approval are well known to one skilled in the art and can be found at the Center for Environmental Risk Assessment (cera-gmc.org/?action=gm_crop_database, which can be accessed using the www prefix).

Gene Silencing

In some embodiments the stacked trait may be in the form of silencing of one or more polynucleotides of interest resulting in suppression of one or more target pest polypeptides. In some embodiments the silencing is achieved through the use of a suppression DNA construct.

In some embodiments one or more of the PIP-1, PIP-1A (SEQ ID NO: 2), PSEEN3174 (SEQ ID NO: 6), PIP-1C (SEQ ID NO: 332), and PIP-1B (SEQ ID NO: 4) polypeptides or fragments or variants thereof may be stacked with one or more polynucleotides encoding one or more polypeptides having insecticidal activity or agronomic traits as set forth supra and optionally may further include one or more polynucleotides providing for gene silencing of one or more target polynucleotides as discussed infra.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The term "suppression" includes lower, reduce, decline, decrease, inhibit, eliminate and prevent. "Silencing" or "gene silencing" does not specify mechanism and is inclusive, and not limited to, anti-sense, cosuppression, viral-suppression, hairpin suppression, stem-loop suppression, RNAi-based approaches and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50% or any integer between 51% and 100% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target protein.

"Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns or the coding sequence.

"Cosuppression" refers to the production of sense RNA transcripts capable of suppressing the expression of the target protein. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see, Vaucheret, et al. (1998) Plant J. 16:651-659 and Gura, (2000) Nature 404:804-808).

Another variation describes the use of plant viral sequences to direct the suppression of proximal mRNA encoding sequences (PCT Publication WO 1998/36083).

Recent work has described the use of "hairpin" structures that incorporate all or part, of an mRNA encoding sequence in a complementary orientation that results in a potential "stem-loop" structure for the expressed RNA (PCT Publication Number WO 1999/53050). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression see, Wesley, et al., (2003) Methods in Molecular Biology, Plant Functional Genomics: Methods and Protocols 236:273-286.

A construct where the stem is formed by at least 30 nucleotides from a gene to be suppressed and the loop is formed by a random nucleotide sequence has also effectively been used for suppression (WO 1999/61632).

The use of poly-T and poly-A sequences to generate the stem in the stem-loop structure has also been described (WO 2002/00894).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication Number WO 2002/00904.

RNA interference refers to the process of sequence-specific post-transcriptional gene silencing in animals mediated by short interfering RNAs (siRNAs) (Fire, et al., (1998) Nature 391:806). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire, et al., (1999) Trends Genet. 15:358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein, et al., (2001) Nature 409:363). Short interfering RNAs derived from dicer activity are typically about 21 to about 23 nucleotides in length and comprise about 19 base pair duplexes (Elbashir, et al., (2001) Genes Dev. 15:188). Dicer has also been implicated in the excision of 21- and 22-nucleotide small temporal RNAs (stRNAs) from precursor RNA of conserved structure that are implicated in translational control (Hutvagner, et al., (2001) Science 293: 834). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir, et al., (2001) *Genes Dev.* 15:188). In addition, RNA interference can also involve small RNA (e.g., miRNA) mediated gene silencing, presumably through cellular mechanisms that regulate chromatin structure and thereby prevent transcription of target gene sequences (see, e.g., Allshire, (2002) *Science* 297:1818-1819; Volpe, et al., (2002) *Science* 297: 1833-1837; Jenuwein, (2002) *Science* 297:2215-2218; and Hall, et al., (2002) *Science* 297:2232-2237). As such, miRNA molecules of the invention can be used to mediate gene silencing via interaction with RNA transcripts or alternately by interaction with particular gene sequences, wherein such interaction results in gene silencing either at the transcriptional or post-transcriptional level.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and composition can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, US 2009/0188008.

As used herein, a "suppressor enhancer element" comprises a polynucleotide comprising the target sequence to be suppressed or an active fragment or variant thereof. It is recognize that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element.

It is recognized that multiple suppressor enhancer elements from the same target sequence or from different target sequences or from different regions of the same target sequence can be employed. For example, the suppressor enhancer elements employed can comprise fragments of the target sequence derived from different region of the target sequence (i.e., from the 3'UTR, coding sequence, intron, and/or 5'UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element the systemic production of RNAi occurs throughout the entire plant. In further embodiments, the plant or plant parts of the invention have an improved loading of RNAi into the phloem of the plant than would be observed with the expression of the silencing element construct alone and, thus provide better control of phloem feeding insects by an RNAi approach. In specific embodiments, the plants, plant parts, and plant cells of the invention can further be characterized as allowing for the production of a diversity of RNAi species that can enhance the effectiveness of disrupting target gene expression.

In specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about 60-70%, about 70%-80%, about a 80%-90%, about a 90%-100% or greater increase in the level of RNAi in the plant, plant part, plant cell or phloem when compared to an appropriate control. In other embodiments, the increase in the level of RNAi in the plant, plant part, plant cell or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Examples of combined expression of the silencing element with suppressor enhancer element for the control of Stinkbugs and *Lygus* can be found in US 2011/0301223 and US 2009/0192117.

Some embodiments relate to down-regulation of expression of target genes in insect pest species by interfering ribonucleic acid (RNA) molecules. WO 2007/074405 describes methods of inhibiting expression of target genes in invertebrate pests including Colorado potato beetle. WO 2005/110068 describes methods of inhibiting expression of target genes in invertebrate pests including in particular Western corn rootworm as a means to control insect infestation. Furthermore, WO 2009/091864 describes compositions and methods for the suppression of target genes from insect pest species including pests from the *Lygus* genus. Nucleic acid molecules including RNAi for targeting the vacuolar ATPase H subunit, useful for controlling a coleopteran pest population and infestation as described in US Patent Application Publication 2012/0198586. WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein; and an insect Tbp-1 such as Tat-binding protein. US Patent Application Publications 2012/029750 and 2012/0322660 describe an interfering ribonucleic acid (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubuliln Homologous Sequence.

Use in Pesticidal Control

General methods for employing strains comprising a nucleic acid sequence of the embodiments or a variant thereof, in pesticide control or in engineering other organisms as pesticidal agents are known in the art. See, for example U.S. Pat. No. 5,039,523 and EP 0480762A2.

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the PIP-1 polypeptide, and desirably, provide for improved protection of the pesticide from environmental degradation and inactivation.

Such microorganisms include bacteria, algae, and fungi. Of particular interest are microorganisms such as bacteria, e.g., *Alcaligenes, Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Alcaligenes faecalis, Pseudomonas syringae, Pseudomonas fluorescens, Serratia marcescens, Acetobacter xylinum*, Agrobacteria, *Rhodopseudomonas spheroides, Xanthomonas campestris, Rhizobium melioti, Alcaligenes entrophus, Clavibacter* xyli and *Azotobacter vinelandii* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms. Host organisms of particular interest include yeast, such as *Rhodotorula* spp., *Aureobasidium* spp., *Saccharomyces* spp. (such as *S. cerevisiae*), *Sporobolomyces* spp., phylloplane organisms such as *Pseudomonas* spp. (such as *P. aeruginosa, P. fluorescens, P. chlororaphis*), *Erwinia* spp., and *Flavobacterium* spp., and other such organisms, including *Agrobacterium tumefaciens, E. coli, Bacillus subtilis*, and the like.

Genes encoding the PIP-1 polypeptides of the embodiments can be introduced into microorganisms that multiply on plants (epiphytes) to deliver PIP-1 polypeptides to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman, et al., (1991) *Appl. Environ. Microbiol.* 56:713-718). Genes encoding the PIP-1 polypeptides of the embodiments can be introduced into a root-colonizing *Bacillus cereus* by standard methods known in the art.

Genes encoding PIP-1 polypeptides can be introduced, for example, into the root-colonizing *Bacillus* by means of electro transformation. Specifically, genes encoding the PIP-1 polypeptides can be cloned into a shuttle vector, for example, pHT3101 (Lerecius, et al., (1989) *FEMS Microbiol. Letts.* 60:211-218. The shuttle vector pHT3101 containing the coding sequence for the particular PIP-1 polypeptide gene can, for example, be transformed into the root-colonizing *Bacillus* by means of electroporation (Lerecius, et al., (1989) *FEMS Microbiol. Letts.* 60:211-218).

Expression systems can be designed so that PIP-1 polypeptides are secreted outside the cytoplasm of gram-negative bacteria, such as *E. coli*, for example. Advantages of having PIP-1 polypeptides secreted are: (1) avoidance of potential cytotoxic effects of the PIP-1 polypeptide expressed; and (2) improvement in the efficiency of purification of the PIP-1 polypeptide, including, but not limited to, increased efficiency in the recovery and purification of the protein per volume cell broth and decreased time and/or costs of recovery and purification per unit protein.

PIP-1 polypeptides can be made to be secreted in *E. coli*, for example, by fusing an appropriate *E. coli* signal peptide to the amino-terminal end of the PIP-1 polypeptide. Signal peptides recognized by *E. coli* can be found in proteins already known to be secreted in *E. coli*, for example the OmpA protein (Ghrayeb, et al., (1984) *EMBO J*, 3:2437-2442). OmpA is a major protein of the *E. coli* outer membrane, and thus its signal peptide is thought to be efficient in the translocation process. Also, the OmpA signal peptide does not need to be modified before processing as may be the case for other signal peptides, for example lipoprotein signal peptide (Duffaud, et al., (1987) *Meth. Enzymol.* 153: 492).

PIP-1 polypeptides of the embodiments can be fermented in a bacterial host and the resulting bacteria processed and used as a microbial spray in the same manner that Bt strains have been used as insecticidal sprays. In the case of a PIP-1 polypeptide(s) that is secreted from *Bacillus*, the secretion signal is removed or mutated using procedures known in the art. Such mutations and/or deletions prevent secretion of the PIP-1 polypeptide(s) into the growth medium during the fermentation process. The PIP-1 polypeptides are retained within the cell, and the cells are then processed to yield the encapsulated PIP-1 polypeptides. Any suitable microorganism can be used for this purpose. *Pseudomonas* has been used to express Bt toxins as encapsulated proteins and the resulting cells processed and sprayed as an insecticide (Gaertner, et al., (1993), in: *Advanced Engineered Pesticides*, ed. Kim).

Alternatively, the PIP-1 polypeptides are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated PIP-1 polypeptides may then be formulated in accordance with conventional techniques for application to the environment hosting a target pest, e.g., soil, water, and foliage of plants. See, for example EPA 0192319, and the references cited therein.

Pesticidal Compositions

In some embodiments the active ingredients can be applied in the form of compositions and can be applied to the crop area or plant to be treated, simultaneously or in succession, with other compounds. These compounds can be fertilizers, weed killers, Cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient or an agro-chemical composition that contains at least one of the PIP-1 polypeptides produced by the bacterial strains include leaf application, seed coating and soil application. The number of applications and the rate of application depend on the intensity of infestation by the corresponding pest.

The composition may be formulated as a powder, dust, pellet, granule, spray, emulsion, colloid, solution or such like, and may be prepared by such conventional means as desiccation, lyophilization, homogenation, extraction, filtration, centrifugation, sedimentation or concentration of a culture of cells comprising the polypeptide. In all such compositions that contain at least one such pesticidal polypeptide, the polypeptide may be present in a concentration of from about 1% to about 99% by weight.

Lepidopteran, dipteran, heteropteran, nematode, hemiptera or coleopteran pests may be killed or reduced in numbers in a given area by the methods of the disclosure or may be prophylactically applied to an environmental area to prevent infestation by a susceptible pest. Preferably the pest ingests or is contacted with, a pesticidally-effective amount of the polypeptide. By "pesticidally-effective amount" is intended an amount of the pesticide that is able to bring about death to at least one pest or to noticeably reduce pest growth, feeding or normal physiological development. This amount will vary depending on such factors as, for example, the specific target pests to be controlled, the specific environment, location, plant, crop or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, Crystal and/or spore suspension or isolated protein component with the desired agriculturally-acceptable carrier. The compositions may be formulated prior to administration in an appropriate means such as lyophilized, freeze-dried, desiccated or in an aqueous carrier, medium or suitable diluent, such as saline or other buffer. The formulated compositions may be in the form of a dust or granular material or a suspension in oil (vegetable or mineral) or water or oil/water emulsions or as a wettable powder or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference. The plants can also be treated with one or more chemical compositions, including one or more herbicide, insecticides or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus* thuriengiensis, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, lndoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoximmethyl, Metalaxyl/mefenoxam, Trifloxystrobin, Ethaboxam, Iprovalicarb, Trifloxystrobin, Fenhexamid, Oxpoconazole fumarate, Cyazof amid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, lodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoximmethyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethon-methyl, Pirimicarb, Methiocarb; Maize Herbicides: Atrazine, Alachlor, Bromoxynil, Acetochlor, Dicamba, Clopyralid, (S-) Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumuron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

In some embodiments the herbicide is Atrazine, Bromacil, Diuron, Chlorsulfuron, Metsulfuron, Thifensulfuron Methyl, Tribenuron, Acetochlor, Dicamba, Isoxaflutole, Nicosulfuron, Rimsulfuron, Pyrithiobac-sodium, Flumioxazin, Chlorimuron-Ethyl, Metribuzin, Quizalofop, S-metolachlor, Hexazinne or combinations thereof.

In some embodiments the insecticide is Esfenvalerate, Chlorantraniliprole, Methomyl, lndoxacarb, Oxamyl or combinations thereof.

Pesticidal and Insecticidal Activity

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera orthroptera, Thysanoptera, Dermaptera, Isoptera, Anoplura, Siphonaptera, Trichoptera, etc., particularly Lepidoptera, and Hemiptera.

Those skilled in the art will recognize that not all compounds are equally effective against all pests. Compounds of the embodiments display activity against insect pests, which may include economically important agronomic, forest, greenhouse, nursery ornamentals, food and fiber, public and animal health, domestic and commercial structure, household and stored product pests.

Larvae of the order Lepidoptera include, but are not limited to, armyworms, cutworms, loopers, and heliothines in the family Noctuidae *Spodoptera frugiperda* J E Smith (fall armyworm); *S. exigua* Hübner (beet armyworm); *S. litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira (Xylomyges) curialis* Grote (citrus cutworm); borers, casebearers, webworms, coneworms, and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenee (celery leaftier); and leafrollers, budworms, seed worms, and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rösslerstamm (summer fruit *tortrix* moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermüller (European grape vine moth); *Spilonota ocellana* Denis & Schiffermuller (eyespotted bud moth); *Endopiza viteana* Clemens (grape berry moth); *Eupoecilia ambiguella* Hübner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guerin-Méneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guérin-Méneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenee (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenee; *Malacosoma* spp. and *Orgyia* spp.

Of interest are larvae and adults of the order Coleoptera including weevils from the families Anthribidae, Bruchidae, and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. Oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles, and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith & Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (corn flea beetle); *Colaspis brunnea* Fabricius (grape *colaspis*); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (*sorghum* midge); *Mayetiola destructor* Say (Hessian fly); *Sitodiplosis mosellana* Géhin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly); and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other Brachycera, mosquitoes *Aedes* spp.; *Anopheles* spp.; *Culex* spp.; black flies *Prosimulium* spp.; *Simulium* spp.; biting midges, sand flies, sciarids, and other Nematocera.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, lssidae and Delphacidae, treehoppers from the family Membracidae, psyllids from the family Psyllidae, whiteflies from the family Aleyrodidae, aphids from the family Aphididae, *phylloxera* from the family Phylloxeridae, mealybugs from the family Pseudococcidae, scales from the families Asterolecanidae, Coccidae, Dactylopiidae, Diaspididae, Eriococcidae ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae, and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/ Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black *citrus* aphid); and *T. citricida* Kirkaldy (brown *citrus* aphid); *Adelges* spp. (adelgids); *Phylloxera devastatrix* Pergande (pecan *phylloxera*); *Bemisia tabaci* Gennadius (tobacco whitefly, sweetpotato whitefly); *B. argentifolii* Bellows & Perring (silverleaf whitefly); *Dialeurodes citri* Ashmead (*citrus* whitefly); *Trialeurodes* abutiloneus (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stål (rice leafhopper); *Nilaparvata lugens* Stål (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (*citrus* mealybug); *Pseudococcus* spp. (other mealybug complex); *Cacopsylla pyricola* Foerster (pear *psylla*); *Trioza diospyri* Ashmead (persimmon *psylla*).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schäffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus*

*albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; Coreidae spp.; Pyrrhocoridae spp.; Tinidae spp.; Blostomatidae spp.; Reduviidae spp.; and Cimicidae spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (*citrus* flat mite); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch & Mulaik (brown recluse spider); and the *Latrodectus mactans* Fabricius (black widow spider); and centipedes in the order Scutigeromorpha such as *Scutigera coleoptrata* Linnaeus (house centipede).

Insect pest of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus,* and *Bagrada hilaris* (*Bagrada* Bug)), the family Plataspidae (*Megacopta cribraria*—Bean plataspid), and the family Cydnidae (*Scaptocoris castanea*—Root stink bug); and Lepidoptera species including but not limited to: diamond-back moth, e.g., *Helicoverpa zea* Boddie; soybean looper, e.g., *Pseudoplusia includens* Walker; and velvet bean caterpillar e.g., *Anticarsia gemmatalis* Hübner.

Methods for measuring pesticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477, all of which are herein incorporated by reference in their entirety. Generally, the protein is mixed and used in feeding assays. See, for example Marrone, et al., (1985) *J. of Economic Entomology* 78:290-293. Such assays can include contacting plants with one or more pests and determining the plant's ability to survive and/or cause the death of the pests.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Seed Treatment

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *bacillus* spp. (including one or more of *cereus, firmus, megaterium, pumilis, sphaericus, subtilis* and/or *thuringiensis*), bradyrhizobium spp. (including one or more of *betae, canariense, elkanii, iriomotense, japonicum*, liaonigense, *pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA registration number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Methods for Inhibiting Growth or Killing an Insect Pest and Controlling an Insect Population In some embodiments methods are provided for inhibiting growth or killing an insect pest, comprising contacting the insect pest with an insecticidally-effective amount of a recombinant PIP-1 polypeptide. In some embodiments methods are provided for inhibiting growth or killing an insect pest, comprising contacting the insect pest with an insecticidally-effective amount of a recombinant pesticidal protein of SEQ ID NO: 6 or a variant thereof.

In some embodiments methods are provided for controlling an insect pest population, comprising contacting the insect pest population with an insecticidally-effective amount of a recombinant PIP-1 polypeptide. In some embodiments methods are provided for controlling an insect pest population, comprising contacting the insect pest population with an insecticidally-effective amount of a recombinant pesticidal protein of SEQ ID NO: 6 or a variant thereof. As used herein, by "controlling a pest population" or "controls a pest" is intended any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments methods are provided for controlling an insect pest population resistant to a pesticidal protein, comprising contacting the insect pest population with an insecticidally-effective amount of a recombinant PIP-1 polypeptide. In some embodiments methods are provided for controlling an insect pest population resistant to a pesticidal protein, comprising contacting the insect pest population with an insecticidally-effective amount of a recombinant pesticidal protein of SEQ ID NO: 6 or a variant thereof.

In some embodiments methods are provided for protecting a plant from an insect pest, comprising expressing in the plant or cell thereof a recombinant PIP-1 polypeptide. In some embodiments methods are provided for protecting a plant from an insect pest, comprising expressing in the plant or cell thereof a recombinant pesticidal protein of SEQ ID NO: 6 or variants thereof.

Insect Resistance Management (IRM) Strategies

Expression of *B. thuringiensis* δ-endotoxins in transgenic corn plants has proven to be an effective means of controlling agriculturally important insect pests (Perlak, et al., 1990; 1993). However, insects have evolved that are resistant to *B. thuringiensis* δ-endotoxins expressed in transgenic plants. Such resistance, should it become widespread, would clearly limit the commercial value of germplasm containing genes encoding such *B. thuringiensis* δ-endotoxins.

One way to increasing the effectiveness of the transgenic insecticides against target pests and contemporaneously reducing the development of insecticide-resistant pests is to use provide non-transgenic (i.e., non-insecticidal protein) refuges (a section of non-insecticidal crops/com) for use with transgenic crops producing a single insecticidal protein active against target pests. The United States Environmental Protection Agency (epa.gov/oppbppdl/biopesticides/pips/bt_corn_refuge_2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush for example, outlines two-toxin strategies, also called "pyramiding" or "stacking," for management of insecticidal transgenic crops. (The Royal Society. Phil. Trans. R. Soc. Lond. B. (1998) 353:777-1786). Stacking or pyramiding of two different proteins each effective against the target pests and with little or no cross-resistance can allow for use of a smaller refuge. The U.S. Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments the PIP-1 polypeptides of the disclosure are useful as an insect resistance management strategy in combination (i.e., pyramided) with other pesticidal proteins include but are not limited to Bt toxins, *Xenorhabdus* sp. or *Photorhabdus* sp. insecticidal proteins, and the like.

Provided are methods of controlling Lepidoptera and/or Hemiptera insect infestation(s) in a transgenic plant that promote insect resistance management, comprising expressing in the plant at least two different insecticidal proteins having different modes of action.

In some embodiments the methods of controlling Lepidoptera and/or Hemiptera insect infestation in a transgenic plant and promoting insect resistance management the at least one of the insecticidal proteins comprise a PIP-1 polypeptide insecticidal to insects in the order Lepidoptera and/or Hemiptera.

In some embodiments the methods of controlling Lepidoptera and/or Hemiptera insect infestation in a transgenic plant and promoting insect resistance management the at least one of the insecticidal proteins comprises a protein of SEQ ID NO: 6 or variants thereof, insecticidal to insects in the order Lepidoptera and/or Hemiptera.

In some embodiments the methods of controlling Lepidoptera and/or Hemiptera insect infestation in a transgenic plant and promoting insect resistance management comprise expressing in the transgenic plant a PIP-1 polypeptide and a Cry protein insecticidal to insects in the order Lepidoptera and/or Hemiptera having different modes of action.

In some embodiments the methods of controlling Lepidoptera and/or Hemiptera insect infestation in a transgenic plant and promoting insect resistance management comprise in the transgenic plant a protein of SEQ ID NO: 6 or variants thereof and a Cry protein insecticidal to insects in the order Lepidoptera and/or Hemiptera having different modes of action.

Also provided are methods of reducing likelihood of emergence of Lepidoptera and/or Hemiptera insect resistance to transgenic plants expressing in the plants insecticidal proteins to control the insect species, comprising expression of a PIP-1 polypeptide insecticidal to the insect species in combination with a second insecticidal protein to the insect species having different modes of action.

Also provided are methods of reducing likelihood of emergence of Lepidoptera and/or Hemiptera insect resistance to transgenic plants expressing in the plants insecticidal proteins to control the insect species, comprising expression of a protein of SEQ ID NO: 6 or variants thereof, insecticidal to the insect species in combination with a second insecticidal protein to the insect species having different modes of action.

Also provided are means for effective Lepidoptera and/or Hemiptera insect resistance management of transgenic plants, comprising co-expressing at high levels in the plants two or more insecticidal proteins toxic to Lepidoptera and/or Hemiptera insects but each exhibiting a different mode of effectuating its inhibiting growth or killing activity, wherein the two or more insecticidal proteins comprise a PIP-1 polypeptide and a Cry protein. Also provided are means for effective Lepidoptera and/or Hemiptera insect resistance management of transgenic plants, comprising co-expressing at high levels in the plants two or more insecticidal proteins toxic to Lepidoptera and/or Hemiptera insects but each exhibiting a different mode of effectuating its inhibiting growth or activity, wherein the two or more insecticidal proteins comprise a protein of SEQ ID NO: 6 or variants thereof and a Cry protein.

In addition, methods are provided for obtaining regulatory approval for planting or commercialization of plants expressing proteins insecticidal to insects in the order Lepidoptera and/or Hemiptera, comprising the step of referring to, submitting or relying on insect assay binding data showing that the PIP-1 polypeptide does not compete with binding sites for Cry proteins in such insects. In addition, methods are provided for obtaining regulatory approval for planting or commercialization of plants expressing proteins insecticidal to insects in the order Lepidoptera and/or Hemiptera, comprising the step of referring to, submitting or relying on insect assay binding data showing that the protein of SEQ ID NO: 6 or variant thereof does not compete with binding sites for Cry proteins in such insects.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which the polypeptide has pesticidal activity. In some embodiments, the polypeptide has pesticidal activity against a lepidopteran, coleopteran, dipteran, hemipteran or nematode pest, and the field is infested with a lepidopteran, hemipteran, coleopteran, dipteran or nematode pest.

As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing a PIP-1 polypeptide disclosed herein. Expression of the PIP-1 polypeptide results in a reduced ability of a pest to infest or feed on the plant, thus improving plant yield.

The following examples are offered by way of illustration and not by way of limitation.

EXPERIMENTALS

Example 1: Identification of an Insecticidal Protein Active Against *Lygus* from Strain SS44C4

The *Lygus* active protein PIP-1A was identified by protein purification, N-terminal amino acid sequencing, PCR cloning from *Pseudomonas chlororaphis* strain SS44C4 as follows:

Insecticidal activity against *Lygus* (*Lygus hesperus*) was observed from a cell lysate of SS44C4 grown in Trypticase soy medium (Tryptone 17 g/L, enzymatic digest of soy meal 3 g/L, Dextrose 2.5 g/L, Sodium Chloride 5 g/L, K2HPO4 2.5 g/L) and cultured overnight at 30° C. This insecticidal activity exhibited heat and proteinase sensitivity indicating proteinaceous nature.

*Lygus* (*Lygus hesperus*) bioassays were conducted using the cell lysate samples mixed with insect diet (Bio-Sery F9644B) in each well of a 96 well bioassay plate (BD Falcon™ 353910). A variable number of *Lygus hesperus* second instar nymphs (2 to 7) were placed into each well of a 96 well plate. The assay was run four days at 25° C. and then was scored for insect mortality and stunting of insect growth. A series of concentrations of the purified protein sample was assayed against those insects and concentrations for 50% mortality (LC50) or inhibition of 50% of the individuals (1050) were calculated. The *Lygus* bioassay results for PIP-1A is shown in Table 2.

Genomic DNA was extracted with a Sigma Bacterial Genomic DNA Extraction Kit (Cat # NA2110-KT, Sigma-Aldrich, PO Box 14508, St. Louis, Mo. 63178) according to the manufactures' instructions. The DNA concentration was determined using a NanoDrop Spectrophotometer (Thermo Scientific, 3411 Silverside Road, Bancroft Building, Suite 100, Wilmington, Del. 19810) and the genomic DNA was diluted to 40 ng/ul with sterile water. A 25 ul PCR reaction was set up by combining 80 ng genomic DNA, 2 ul (5 uM) 16S ribosomal DNA primers TACCTTGTTACGACTT (SEQ ID NO: 209) and AGAGTTTGATCMTGGCTCAG (SEQ ID NO: 210), 1 ul 10 cmM dNTP, 1× Phusion™ HF buffer, and 1 unit of Phusion™ High-Fidelity DNA Polymerase (New England Biolabs, Cat # M0530L, 240 County Road, Ipswich, Mass. 01938-2723). The PCR reaction was run in MJ Research PTC-200 Thermo Cycler (Bio-Rad Laboratories, Inc., 1000 Alfred Nobel Drive, Hercules, Calif., 94547, USA) with the following program: 96° C. 1 min; 30 cycles of 96° C. 15 seconds, 52° C. 2 minutes and 72° C. 2 minutes; 72° C. 10 minutes; and hold on 4° C. The PCR products were purified with QiaQuick® DNA purification Kit (Cat #28104, QIAGEN® Inc., 27220 Turnberry Lane, Valencia, Calif. 91355). The purified PCR sample was DNA sequenced and the resulting 16S ribosomal DNA sequence was BLAST searched against the NCBI database which indicated that SS44C4 is a *Pseudomonas chlororaphis* strain. The *Pseudomonas chlororaphis* strain SS44C4 was deposited on Dec. 1, 2011 under accession # NRRLB-50613 with the Agricultural Research Service Culture Collection (NRRL), 1815 North University Street, Peoria, Ill. 61604, (nrrl.ncaur.usda.gov, which can be accessed on the world-wide web using the "www" prefix).

The cell pellet of an overnight culture from a single colony of SS44C4 grown in LB Broth at 30° C. was lyzed in a French Press at ~20,000 psi in a single pass after resuspension with PBS buffer. The lysis product was centrifuged and the soluble fraction retained and stored at 4° C. overnight to allow insoluble chlororaphin products to precipitate. The remaining supernatant was filtered sequentially through 25 um, 8 um, 5 um, 1.2 um and 0.45 um filters to remove the majority of the Crystalline material. The soluble cell lysate was adjusted to 1.2 M ammonium sulfate and loaded onto an Ether column (Toyopearl™ Ether-650 S, Tosoh Bioscience LLC, 3604 Horizon Drive, Suite 100, King of Prussia, Pa. 19406) of appropriate size. A linear gradient was run from 1.2 M ammonium sulfate to 0.6 M ammonium sulfate over 15 column volumes. The elution peak fractions containing protein of interest were then concentrated via a spin concentrator. The concentrate was then buffer exchanged into 25 mM Tris pH 8 to remove ammonium sulfate using a 7000 MWCO Zeba™ desalting column (Thermo Fisher Scientific Inc., 747 Meridian Rd, Rockford, Ill. 61101). The concentrated and desalted protein was then loaded onto a MonoQ™ column (cat #17-5166-01, GE Healthcare). Optimum elution and purity was achieved by application of a linear gradient from 0 to 400 mM NaCl.

The active fraction pool from the MonoQ™ purification was subjected to N-terminal sequencing. The protein pool was run on SDS-PAGE, transferred to a PVDF membrane, and stained with Coomassie™ Blue dye. Four bands were present on the membrane. All were successfully identified by N-terminal sequencing with a single sequence per band. The N-terminal amino acid sequence of two protein bands were BLAST searched against the NCBI database and a hypothetical protein (PSEEN3174) from a genome sequence of *Pseudomonas entomophila* (Vodovar, N et al. (2006) *Nat. Biotechnol.* 24 (6), 673-679) was identified as a homology match (FIG. 1). The PSEEN3174 gene, was cloned by PCR using primers ATACATATGACGATCAAGGAAGAGCTG (SEQ ID NO: 13) and TTGGATCCTCAATAACGGCGAT-GAGGATCGTTGTAG (SEQ ID NO: 14). PCR with the cloning primers (SEQ ID NO: 13 and 14) was performed against the SS44C4 genomic DNA preparation, and a band of the expected molecular weight was isolated.

The resulting PCR product was DNA sequenced and coupled with MS/MS spectra from in-gel digests showed this gene product having the DNA sequence of SEQ ID NO: 1 encoding a protein designated herein as "PIP-1A", having the amino acid sequence of SEQ ID NO: 2. The PSEEN3174 gene has the DNA sequence set forth in SEQ ID NO: 5 and encodes an amino acid sequence having the amino acid sequence set forth in SEQ ID NO: 6. Using the PIP-1A (SEQ ID NO: 2) and PSEEN3174 (SEQ ID NO: 6) sequence information another homologous gene, SPBB_340380 (annotated as a hypothetical protein from *Dendroctonus frontalis* Bacterial community), was identified by BLAST search from the Department of Energy Joint Genomic Institute website (jgi.doe.gov/, which can be accessed on the world wide web using the "www" prefix). The SPBB_340380 coding sequence was generated by back translation of protein sequence using PSEEN3174 (SEQ ID NO: 5) codon usage and the gene was synthesized. The SPBB_340380 coding sequence has the DNA sequence set forth in SEQ ID NO: 3 and encodes an amino acid sequence, designated herein as "PIP-1B", having the amino acid sequence set forth in SEQ ID NO: 4.

Example 2: E. coli Expression of PIP-1A, PSEEN3174 and PIP-1B

The three coding sequences, PIP-1A (SEQ ID NO: 1); PSEEN3174 (SEQ ID NO: 5); & PIP-1B (SEQ ID NO: 3), were subcloned into an *E. coli* expression vector pMAL™ (New England Biolabs, 240 County Road, Ipswich, Mass. 01938-2723) having a 6×His tag added to the Maltose Binding Protein and transformed into *E. coli* for recombinant protein expression. *E. coli* cells transformed with the expression constructs were grown overnight at 37° C. with carbenicillin selection and then inoculated to a fresh 2XYT medium (1:250) and further grown to $OD_{600}$~0.8. IPTG was then added and the cells were grown further at 37° C. for another 6 hours or transferred to 16° C. for overnight growth to induce protein expression. The *E. coli* expressed proteins were purified either by Amylose resin (New England Biolabs, 240 County Road, Ipswich, Mass. 01938-2723) or Ni-NTA agarose (Cat. No. K950-01, Invitrogen, 3175 Staley Road, Grand Island, N.Y. 14072), according to the manufacturer's protocols.

Example 3: Lepidoptera and Coleoptera Assays with Purified Proteins

Insecticidal activity bioassay screens were conducted on the cell lysate to evaluate the effects of the insecticidal proteins on a variety of Lepidoptera species (European corn borer (*Ostrinia nubilalis*), corn earworm (*Helicoverpa zea*), black cutworm (*Agrotis ipsilon*), fall armyworm (*Spodoptera frugiperda*), Soybean looper (*Pseudoplusia includens*) and Velvet bean caterpillar (*Anticarsia gemmatalis*)), a Coleoptera specie (Western corn rootworm (*Diabrotica virgifera*)

Lepidoptera feeding assays were conducted on an artificial diet containing the cell lysates of bacterial strains in a 96 well plate set up. The cell lysate was incorporated with the Lepidopteran-specific artificial diet in a ratio of 1:2 cell lysate to diet mixture. Neonate larvae were placed in each well to feed ad libitum for 5 days. Results were expressed as positive for larvae reactions such as stunting and or mortality. Results were expressed as negative if the larvae were similar to the negative control that is feeding diet to which the above buffer only has been applied. Cell lysates was assayed on European corn borer (*Ostrinia nubilalis*), corn earworm (*Helicoverpa zea*), black cutworm (*Agrotis ipsilon*), fall armyworm (*Spodoptera frugiperda*), Soybean looper (*Pseudoplusia includens*) and Velvet bean caterpillar (*Anticarsia gemmatalis*). A series of concentrations of the purified protein sample was assayed against those insects and concentrations for 50% mortality (LC50) or inhibition of 50% of the individuals (IC50) were calculated. The insecticidal activity for PIP-1A and PSEEN3174 are shown in Table 2.

TABLE 2

| Insect | PIP-1A (SEQ ID NO: 2) | | PSEEN3174 (SEQ ID NO: 6) | |
| --- | --- | --- | --- | --- |
| | dose | effect | dose | effect |
| Lygus | 40 ppm | LC-50 | 40 ppm | LC-50 |
| Brown marmorated stink bug | 150 ppm | LC50 | 100 ppm | LC50 |
| Southern green stink bug, adult | 700 ppm | single dose, 85% mortality at 6 days | 620 ppm | single dose, 75% mortality at 6 days |
| Southern green stink bug, nymphs | 250 ppm | single dose, 99% mortality at 4 days | | not tested |
| Southern green stink bug, nymphs | 100 ppm | LC50 | 100 ppm | LC50 |
| Colorado potato beetle | 875 ppm | inactive | 875 ppm | inactive |
| Diamond back moth | 122 ng/cm$^2$ | LC-50 | 20.5 ng/cm$^2$ | LC-50 |
| Diamond back moth | 66.7 ng/cm$^2$ | IC-50 | 12.8 ng/cm$^2$ | IC50 |
| Diamond back moth-Cry1A resistant | 205 ng/cm$^2$ | LC-50 | 15.9 ng/cm$^2$ | LC-50 |
| Diamond back moth-Cry1A resistant | 59.9 ng/cm$^2$ | IC-50 | 8.7 ng/cm$^2$ | IC50 |
| Western Corn Root Worm | 200 ug/cm$^2$ | mild stunting | 90 ug/cm$^2$ | mild stunting |
| Soy bean looper | 21.3 ppm | LC-50 | 44.8 ppm | LC-50 |
| Soy bean looper | 10.0 ppm | IC-50 | 18.8 ppm | IC-50 |
| Velvet bean caterpillar | 14.0 ppm | LC-50 | 45.8 ppm | LC-50 |
| Velvet bean caterpillar | 3.9 ppm | IC-50 | 11.8 ppm | IC-50 |
| Corn ear worm | ~200 ppm | IC-50 | ~200 ppm | IC-50 |
| Fall army worm | ~200 ppm | IC-50 | ~200 ppm | IC-50 |
| European corn borer | 700 ppm | inactive | >400 ppm | IC-50 |
| Black cut worm | ~300 ppm | IC-50 | ~200 ppm | IC-50 |
| Black bean aphid | inactive | highest dose 200 ppm | inactive | highest dose 200 ppm |
| Pea aphid (oral dose) | 260 ug/ml | LC-50 Day1, 90% mortality on day 2 | 161 ug/ml | LC-50 Day 2, 90% mortality on day 3 |

Coleoptera feeding assays were conducted on an artificial diet containing the cell lysates of bacterial strains. The cell lysate was incorporated with the coleopteran-specific artificial diet in a ratio of 1:5 cell lysate to diet mixture. Western corn rootworm (*Diabrotica virgifera*) neonate larvae were placed in each well to feed ad libitum for 5 days. Results were expressed as positive for larvae reactions such as stunting and or mortality. Results were expressed as negative if the larvae were similar to the negative control that is feeding diet to which the above buffer only has been applied. A series of concentrations of the purified protein sample was assayed against those insects and concentrations for 50% mortality (LC50) or inhibition of 50% of the individuals (1050) were calculated. The results for PIP-1A and PSEEN3174 are shown in Table 2.

Example 4: Aphid Oral Feeding Assays with Purified Proteins

Membrane feeding assays as described (Li, et al., (2011) *Journal of Invertebrate Pathology* 107:69-78) were used to assess the toxicity of PIP-1A and PSEEN3174, formulated in PBS pH 7.4. Briefly, the individual proteins were mixed with filter-sterilized complete artificial diet as described in Febvay, et al., ((1988), *Can. J. Zool*. 66:2449-2453) to a final concentration of up to 1250 micrograms/ml. This diet (100 ul) was placed on stretched parafilm pulled tightly across a 3 cm cell culture plate with a 1 cm hole on one side of the plate. A second layer of stretched parafilm was applied to form a thin film of diet exposed to aphids through the 1 cm hole. Around 30 second instar pea or green peach aphids were transferred to each plate, with three replicates for each toxin. The same number of aphids were fed on diet only, as a control treatment. All plates were incubated at 24° C. with an 18:6 light:dark photoperiod. Mortality was scored every 24 hours and dead aphids were removed. The artificial diet was replaced every 3 days. Data were analyzed by one-way ANOVA. The results for PIP-1A (SEQ ID NO: 2) and PSEEN3174 (SEQ ID NO: 6) are shown in Table 2.

Example 5: Southern Green Stinkbug (*Nezara viridula*) and Brown Marmorated Stinkbuq (*Halvomorpha Haly*) Bioassay with Purified Proteins 40 ul of the cell lysate samples were mixed with 360 ul of the diet (Bio-Sery F9644B). 10 to 15 newly molted instar nymphs were placed in polystyrene Petri dishes (100 mm×20 mm) lined with moist Whatman® filter paper (100 mm diameter). The bioassay was incubated at 25° C. for four days. The bioassay was scored for insect mortality and stunting of growth. To generate IC50 or LC50 data, a series of concentrations of purified proteins were assayed against insects and the concentration at which 50% of insects experienced severe damage was the IC50 and the concentration at which 50% of insects were dead was the LC50. The results for PIP-1A (SEQ ID NO: 2) and PSEEN3174 (SEQ ID NO: 6) are shown in Table 2.

Example 6: Colorado Potato Beetle (*Leptinotarsa decemlineata*) Bioassay with Purified Proteins 20 ul of cell lysate samples were mixed with 75 ul of modified Coleopteran diet (Bio-Sery F9800B) in each well of a 96 well bioassay plate (BD Falcon™ 353910) and allowed to solidify. A single neonate larva was placed in each well and the plate sealed with a Mylar covering. Holes were punched in the Mylar sheet and the plate incubated at 25° C. for four days. The bioassay was scored for insect mortality and stunting of growth. The results for PIP-1A (SEQ ID NO: 2) and PSEEN3174 (SEQ ID NO: 6) are shown in Table 2.

Example 7: Cross-Resistance Test in Diamondback Moth (*Plutella xylostella*) with Purified Proteins A diet overlay assay similar to Wang, et al., ((2007) *Appl. Environ. Microbiol.* 73:1199-1207) was used for testing the LC50 and IC50 of the sample on susceptible and Cry1A-resistant diamondback moth (DBM, *Plutella xylostella*). For neonate bioassays, an aliquot of PIP-1A (SEQ ID NO: 2) sample solution was applied to the surface (~7 cm$^2$) of 5 ml artificial diet (Southland Products Inc.) in a 30-ml insect-rearing cup. Each bioassay included seven 2× consecutive dilutions from 500 ng/cm$^2$ of the PIP-1A (SEQ ID NO: 2) sample and the negative control, with three replications for each concentration. The PIP-1A (SEQ ID NO: 2) protein dilutions were prepared by mixing PIP-1A protein (SEQ ID NO: 2) with appropriate amount of PBS buffer solution (Fisher Scientific Inc). Neonate larvae (<24 h after hatch) were placed in each assaying cup. Mortality and larval growth inhibition (defined as inhibition if larvae did not enter second instar within 4 days) by each sample were scored after 4 days of feeding on the treated diet at 27° C. Concentrations for 50% mortality (LC50) or inhibition of 50% of the individuals (IC50) were calculated based on probit analysis. The results (Table 3) showed no cross-resistance (resistance ratio <2) for PIP-1A (SEQ ID NO: 2) to Cry1A in diamondback moth.

TABLE 3

| DBM strain | LC/IC | ng/cm$^2$ | 95% FL | Resistance Ratio |
|---|---|---|---|---|
| Susceptible | LC | 122.5 | 80.8-172.3 | 1.0 |
|  | IC | 66.71 | 42.20-98.21 | 1.0 |
| Cry1A-Res | LC | 205.3 | 145.7-285.1 | 1.7 |
|  | IC | 59.94 | 36.90-88.64 | 0.90 |

Example 8: Creation and Identification of PIP-1A Variants

Libraries of modified PIP-1A polynucleotides were generated using recursive sequence recombination methods (Crameri, et al., (1998) *Nature.* 391:288-291; Stemmer, (1994) *Proc. Natl. Acad. Sci USA* 91:10747-10751; Ness, et. al., (2002) *Nature Biotechnology* 20:1251-1255), also known as gene shuffling methods. To increase the crossover points between the two genes, codons of PIP-1A (SEQ ID NO: 1) were modified using the codon usage of PSEEN3174 (SEQ ID NO: 5) as the template while the protein sequences are not changed. The modified PIP-1A coding sequence was named as PIP-1A Synth (SEQ ID NO: 15) and was synthesized. The DNA sequence identity between those two genes was increased from 78% to 87% after the modification. To perform the classic gene family shuffling, random DNA fragments of both PIP-1A Synth (SEQ ID NO: 15) and PSEEN3174 (SEQ ID NO: 5) were generated by limited nuclease digestion. DNA fragments with molecular weights of 50 to 200 base pairs of both genes were recovered from agarose gel. The isolated DNA fragments were assembled on a thermo cycler with polymerase and rescued by cloning primers franking both termini. The libraries were cloned as Maltose-Binding-Protein fusions into pMAL®-c2x (NEB) and transformed into *E. coli* cells. Approximately 5000 clones from the shuffled libraries were screened in the *Lygus* assay and approximately 1000 clones expressed a polypeptide at significant levels and were active as clear cell lysates in the *Lygus* bioassay. *Lygus* bioassays were conducted using the cell lysates at 100 ppm concentration of the PIP-1 polypeptide. The concentrations of PIP-1 polypeptides were estimated using densitometry method of SDS-PAGE with BSA as standard using program Phoretix ID (TotalLab Ltd Keel House, Garth Heads, Newcastle upon Tyne NE1 2JE). Of the active clones, 50 were DNA sequenced (SEQ ID NOS: 152-202) and the amino acid sequence (SEQ ID NOS: 101-151) of the encoded PIP-1 polypeptide was determined. Table 4 shows the percent homology of the PIP-1 polypeptides (SEQ ID NOs: 101-151) to PIP-1A (SEQ ID NO: 2). For each of the sequences in Table 4 only those positions and the corresponding amino acids where PIP-1A (SEQ ID NO: 2), PSEEN3174 (SEQ ID NO: 6) and the PIP-1 polypeptide differ are shown. Amino acid substitutions were also identified at positions 3, 6, 49, 213, 249 (shaded) of PIP-1A (SEQ ID NO: 2) which aren't the corresponding amino acid of PSEEN3174 (SEQ ID NO: 6). These results demonstrate a diverse set of PIP-1A polypeptide variants that have insecticidal activity.

TABLE 4

| Sequence Name | % Identity to PIP-1A | 2 | 3 | 6 | 8 | 19 | 20 | 21 | 22 | 24 | 25 | 27 | 35 | 36 | 38 | 42 | 46 | 48 | 49 | 53 | 60 |
|---|---|---|---|---|---|---|---|---|---|---|---|---|---|---|---|---|---|---|---|---|---|
| PIP-1A (SEQ ID NO: 2) | 100 | P | I | E | S | D | L | K | S | Q | G | L | F | A | N | F | R | G | F | S | A |
| D_D0274242 SEQ ID NO: 109 | 97 |   |   |   |   |   |   |   |   |   |   |   |   |   |   |   |   |   |   |   | S |
| D_D0274246 SEQ ID NO: 112 | 97 |   |   |   |   |   |   |   |   |   |   |   |   |   |   |   |   |   |   |   |   |
| D_D0274267 SEQ ID NO: 125 | 97 |   |   |   |   |   |   |   |   |   |   |   |   |   |   | Y | K | D |   |   |   |
| D_D0274273 SEQ ID NO: 127 | 97 |   |   |   |   |   |   |   |   |   |   |   |   |   |   |   |   |   |   |   |   |
| D_D0274276 SEQ ID NO: 128 | 97 |   |   |   |   | E | V | S | K | A | A | T |   |   |   |   |   |   |   |   |   |
| D_D0274308 SEQ ID NO: 143 | 96 |   |   |   |   |   |   |   |   |   |   |   |   |   |   |   |   |   |   |   |   |
| D_D0274234 SEQ ID NO: 102 | 95 |   |   |   |   |   |   |   |   |   |   |   |   |   |   |   |   |   |   |   | S |
| D_D0274322 SEQ ID NO: 148 | 95 |   |   |   |   |   |   |   |   |   |   |   | L | P | R | Y | K | D |   |   |   |
| D_D0274327 SEQ ID NO: 151 | 95 |   |   |   |   |   |   |   |   |   |   |   |   |   |   |   |   |   | L |   |   |
| D_D0274236 SEQ ID NO: 104 | 94 |   |   |   |   |   |   |   |   |   |   |   |   |   |   |   |   |   |   | G | S |
| D_D0274291 SEQ ID NO: 135 | 94 |   |   |   |   | E | V | S | K | A | A | T |   |   |   |   |   |   |   |   |   |
| D_D0274238 SEQ ID NO: 105 | 93 |   |   |   |   |   |   |   |   |   |   |   | L | S | R | Y | K | D |   | G |   |
| D_D0274270 SEQ ID NO: 126 | 92 |   |   |   |   | E | V | S | K | A | A | T | L | S | R | Y | K | D |   | G | S |

TABLE 4-continued

| Sequence Name | % Identity to PIP-1A | | | | | | | | | | | | | | | | | | | | |
|---|---|---|---|---|---|---|---|---|---|---|---|---|---|---|---|---|---|---|---|---|---|
| D_D0274311 SEQ ID NO: 144 | 92 | | | | | | | | | | | | | | | Y | K | D | | G | |
| D_D0274247 SEQ ID NO: 113 | 91 | | | | | E | V | S | K | A | A | T | L | S | R | Y | K | D | | G | |
| D_D0274258 SEQ ID NO: 119 | 91 | | | | | | | | | | | | | | | | | | | | |
| D_D0274264 SEQ ID NO: 123 | 91 | | | | | E | V | S | K | A | A | T | L | S | R | Y | K | D | | G | |
| D_D0274303 SEQ ID NO: 140 | 91 | | | | | | | | | | | | | | | | | | | G | |
| D_D0274235 SEQ ID NO: 103 | 90 | | | | | | | | | | | | L | S | R | | | | | | |
| D_D0274294 SEQ ID NO: 136 | 90 | | | | | E | V | S | K | A | A | T | L | S | R | Y | | | | | |
| D_D0274300 SEQ ID NO: 138 | 90 | | T | | | | | | | | | | | | | | | | | | |
| D_D0274324 SEQ ID NO: 150 | 90 | | | | | | | | | | | | | | | | | | | | |
| D_D0274241 SEQ ID NO: 108 | 89 | | | | | E | V | S | K | A | A | T | L | S | R | | S | E | | | |
| D_D0274244 SEQ ID NO: 111 | 89 | | | | | | | | | | | | L | S | R | Y | K | D | | | |
| D_D0274248 SEQ ID NO: 114 | 89 | | | G | | | | | | | | | | | | | | | | | S |
| D_D0274251 SEQ ID NO: 116 | 89 | | | | | | | | | | | | | | | | K | D | | | S |
| D_D0274262 SEQ ID NO: 122 | 89 | | | | | E | V | S | K | A | A | T | | | | | | | | | |
| PSEEN3174 (SEQ ID NO: 6) | 79 | T | I | E | | G | E | V | S | K | A | A | T | L | S | R | Y | K | D | F | G | S |

| Sequence Name | % Identity to PIP-1A | 77 | 97 | 98 | 105 | 108 | 110 | 120 | 121 | 123 | 125 | 127 | 134 | 135 | 144 | 147 | 150 | 151 | 160 | 162 | 163 | 164 |
|---|---|---|---|---|---|---|---|---|---|---|---|---|---|---|---|---|---|---|---|---|---|---|
| PIP-1A | 100 | F | M | D | Q | Q | R | K | T | T | N | S | G | S | D | I | S | N | T | S | N | S |
| D_D0274242 | 97 | | | | | | | | | | | | | | | | | | S | T | D | T |
| D_D0274246 | 97 | Y | | | | | | | | | | | | | | T | T | R | | | | |
| D_D0274267 | 97 | | | | | | | | | | | | | | | | | | | | | |
| D_D0274273 | 97 | | | | | | | | | | | | | | | | | | S | T | D | T |
| D_D0274276 | 97 | | | | | | | | | | | | | | | | | | | | | |
| D_D0274308 | 96 | | | | | | | | | | | | A | N | | E | T | T | R | | | |
| D_D0274234 | 95 | | | | | | | | | | | | | | | E | T | T | R | S | T | D | T |
| D_D0274322 | 95 | | | E | | | | | | | | | A | N | | | | R | | | | |
| D_D0274327 | 95 | | | | | | | | | | | | A | N | | E | T | T | R | S | T | D | T |
| D_D0274236 | 94 | Y | | | N | | | | | | | | | | | T | R | | | | | |
| D_D0274291 | 94 | | | | | | | | | | | | | | | | | | S | T | D | T |
| D_D0274238 | 93 | Y | | | | | | | | | | | A | N | | | | R | | | | |
| D_D0274270 | 92 | Y | | | | | | | | | | | A | N | | E | T | T | R | | | |
| D_D0274311 | 92 | Y | | | | | | | | | | | A | N | | | | | S | T | D | T |
| D_D0274247 | 91 | | | | | | | | | | | | | | | T | T | R | | | | |
| D_D0274258 | 91 | | V | | E | N | T | L | | | | | | | | | | | S | T | D | T |
| D_D0274264 | 91 | | | | | | | | | | | | | | | E | T | T | R | | | |
| D_D0274303 | 91 | Y | V | | | | | | | | | | | | | | | | S | T | D | T |
| D_D0274235 | 90 | Y | V | | | | | | | | | | | | | | | | S | T | D | T |
| D_D0274294 | 90 | | | | | | | | | | | | | | | | | | S | T | D | T |
| D_D0274300 | 90 | Y | V | E | | | | R | S | E | S | N | A | N | | | | | S | T | D | T |
| D_D0274324 | 90 | | | | | | | R | S | E | S | N | A | N | | E | T | T | R | S | T | D | T |
| D_D0274241 | 89 | | | | | | | | | | | | | | | E | T | T | R | S | T | D | T |
| D_D0274244 | 89 | Y | | | | | | | | | | | | | | E | T | T | R | S | T | D | T |
| D_D0274248 | 89 | Y | | | | | | R | S | E | S | N | A | N | | E | T | T | R | S | T | D | T |
| D_D0274251 | 89 | Y | | | | T | L | R | S | E | S | N | A | N | | E | T | T | R | | | | |
| D_D0274262 | 89 | | | | | | | | | | | | | | | E | T | T | R | S | T | D | T |
| PSEEN3174 | 79 | Y | V | E | N | T | L | R | S | E | S | N | A | N | | E | T | T | R | S | T | D | T |

| Sequence Name | % Identity to PIP-1A | 166 | 167 | 168 | 174 | 175 | 180 | 194 | 195 | 200 | 203 | 204 | 209 | 213 | 220 | 221 | 222 | 226 | 229 | 231 | 232 | 249 |
|---|---|---|---|---|---|---|---|---|---|---|---|---|---|---|---|---|---|---|---|---|---|---|
| PIP-1A | 100 | Q | L | T | I | V | M | G | N | N | T | L | Y | N | S | T | D | K | I | A | N | |
| D_D0274242 | 97 | E | M | K | | | | A | | | | | | | | | | | | | | |
| D_D0274246 | 97 | | | | | | | | S | Q | A | | | | | | | | | | | |
| D_D0274267 | 97 | | | | | L | | | | | | | | | | | | | N | V | T | |
| D_D0274273 | 97 | E | M | K | | | | A | S | | | | | | | | | | | | | |
| D_D0274276 | 97 | | | | | | | | | | | | | | | | | | | | | |
| D_D0274308 | 96 | | | | | | | | S | Q | A | | | | | | | | N | V | T | |
| D_D0274234 | 95 | E | M | K | | | | | | | | | V | | | | | | | | | |
| D_D0274322 | 95 | | | | | | | A | S | Q | A | | V | | | | | | | | | |
| D_D0274327 | 95 | E | M | K | | | | | | | | | V | | | | | | | | | |
| D_D0274236 | 94 | | | | V | I | L | | | | | | | | R | K | R | P | N | V | T | |
| D_D0274291 | 94 | E | M | K | | | | | | | | | | | | | | | N | V | T | |
| D_D0274238 | 93 | | | | | | | L | A | S | Q | A | V | | R | K | R | | | | | |
| D_D0274270 | 92 | | | | | | | A | | | | | | | | | | | | | | |

TABLE 4-continued

| Sequence Name | % Identity to PIP-1A | | | | | | | | | | | | | | | | | | |
|---|---|---|---|---|---|---|---|---|---|---|---|---|---|---|---|---|---|---|---|
| D_D0274311 | 92 | E | H | K | | | | A | | S | Q | A | V | | R | K | R | P | |
| D_D0274247 | 91 | | | | | | | | | | | | | | R | K | R | P | N V T |
| D_D02742S8 | 91 | E | M | K | V | I | L | | | | Q | A | V | | R | K | R | P | N V T |
| D_D0274264 | 91 | | | | V | I | L | A | | S | | | V | | | | | | |
| D_D0274303 | 91 | E | M | K | V | I | L | | | S | Q | A | V | | R | K | R | P | N V T |
| D_D0274235 | 90 | E | M | K | V | I | L | A | | S | Q | A | | | R | K | R | P | N V T |
| D_D0274294 | 90 | E | M | K | | | | A | | S | Q | A | V | | R | K | R | P | |
| D_D0274300 | 90 | E | M | K | V | I | L | | | | | | | | R | K | R | P | N V T |
| D_D0274324 | 90 | E | M | K | | | L | | | | | | | | R | K | R | P | N V T |
| D_D0274241 | 89 | E | M | K | | | | A | | S | | | | | R | K | R | P | |
| D_D0274244 | 89 | E | M | K | V | I | L | A | | S | Q | A | V | | | | | P | N V T |
| D_D0274248 | 89 | E | M | K | V | I | | | | | | | | | R | K | R | P | N V T |
| D_D0274251 | 89 | | | | | | A | | | S | Q | A | V | | R | K | R | P | N V T |
| D_D0274262 | 89 | E | M | K | V | I | L | A | | | | | | | R | K | R | P | N V T |
| PSEEN3174 | 79 | E | M | K | V | I | L | A | N | S | Q | A | V | Y | R | K | R | P | N V T N |

| Sequence Name | % Identity to PIP-1A | 2 | 3 | 6 | 8 | 19 | 20 | 21 | 22 | 24 | 25 | 27 | 35 | 36 | 38 | 42 | 46 | 48 | 49 | 53 | 60 |
|---|---|---|---|---|---|---|---|---|---|---|---|---|---|---|---|---|---|---|---|---|---|
| PIP-1A (SEQ ID NO: 2) | 100 | P | I | E | S | D | L | K | S | Q | G | L | F | A | N | F | R | G | F | S | A |
| D_D0274266 SEQ ID NO: 124 | 89 | | | | | E | V | S | | K | A | A | T | | L | S | R | Y | K D | G | S |
| D_D0274283 SEQ ID NO: 133 | 89 | | | | | | | | | | | | | | | | | | | | |
| D_D0274290 SEQ ID NO: 134 | 89 | | | | | E | V | S | | K | A | A | T | | L | S | R | Y | K D | G | |
| D_D0274233 SEQ ID NO: 101 | 88 | | | | | | | | | | | | | | | | | | | | |
| D_D0274259 SEQ ID NO: 120 | 88 | | | | | | | | | | | | | | | | | | | | |
| D_D0274278 SEQ ID NO: 129 | 88 | | | | | | | | | | | | | | L | S | R | Y | K D | | |
| D_D0274280 SEQ ID NO: 130 | 88 | | | | | | | | | | | | | | | | | | | | |
| D_D0274306 SEQ ID NO: 142 | 88 | | | | | | | | | | | | | | | | | | | | |
| D_D0274316 SEQ ID NO: 146 | 88 | | | | | E | V | S | | K | A | A | T | | L | S | R | Y | | G | S |
| D_D0274323 SEQ ID NO: 149 | 88 | | | | | | | | | | | | | | L | S | R | Y | K D | G | |
| D_D0274239 SEQ ID NO: 106 | 87 | | | | | E | V | S | | K | A | A | T | | L | S | R | Y | K D | | |
| D_D0274260 SEQ ID NO: 121 | 87 | | | | | | | | | | | | | | | | | | | | |
| D_D0274298 SEQ ID NO: 137 | 87 | | | | | E | V | S | | K | A | A | T | | L | S | R | | | G | |
| D_D0274304 SEQ ID NO: 141 | 87 | | | | | | | | | | | | | | | | | | | | |
| D_D0274282 SEQ ID NO: 132 | 86 | | | | | E | V | S | | K | A | A | T | | L | S | R | Y | K D | | |
| D_D0274320 SEQ ID NO: 147 | 86 | | | | | | | | | | | | | | | | | | | | |
| D_D0274302 SEQ ID NO: 139 | 85 | | | | | E | A | S | | K | A | A | T | | L | S | R | Y | K D | G | |
| D_D0274240 SEQ ID NO: 107 | 84 | | | | | E | V | S | | K | A | A | T | | L | S | R | Y | K D | | S |
| D_D0274252 SEQ ID NO: 117 | 84 | | | | | E | V | S | | K | A | A | T | | L | S | R | Y | K D | G | S |
| D_D0274249 SEQ ID NO: 115 | 83 | | | | | E | V | S | | K | A | A | T | | | | | | | | |
| D_D027425S SEQ ID NO: 118 | 83 | | | | | E | V | S | | K | A | A | T | | L | S | | | | | |
| D_D0274243 SEQ ID NO: 110 | 82 | | | | | E | V | S | | K | A | A | T | | L | S | R | Y | | | |
| D_D0274281 SEQ ID NO: 131 | 82 | | | | | E | V | S | | K | A | A | T | | L | S | R | Y | K D | | |
| D_D0274313 SEQ ID NO: 145 | 82 | | | | | E | V | S | | K | A | A | T | | L | S | R | Y | K D | | |
| PSEEN3174 (SEQ ID NO: 6) | 79 | T | I | E | G | E | V | S | | K | A | A | T | | L | S | R | Y | K D | F | G S |

| Sequence Name | % Identity to PIP-1A | 77 | 97 | 98 | 105 | 108 | 110 | 120 | 121 | 123 | 125 | 127 | 134 | 135 | 144 | 147 | 150 | 151 | 160 | 162 | 163 | 164 |
|---|---|---|---|---|---|---|---|---|---|---|---|---|---|---|---|---|---|---|---|---|---|---|
| PIP-1A | 100 | F | M | D | Q | Q | R | K | T | T | N | S | G | S | D | I | S | N | T | S | N | S |
| D_D0274266 | 89 | | | V | E | N | T | L | R | S | E | S | N | | E | T | T | R | | | | |
| D_D0274283 | 89 | | | | | | | | | | | | | | | | | | R | S | T | D | T |
| D_D0274290 | 89 | | V | | | | | | | | | | | | E | T | T | R | | | | |
| D_D0274233 | 88 | Y | | | | | | R | S | E | S | N | A | N | E | T | T | R | S | T | D | T |
| D_D0274259 | 88 | | V | E | N | T | L | R | S | E | S | N | | | | | | | S | T | D | T |
| D_D0274278 | 88 | Y | V | E | N | T | L | R | S | E | S | N | | | | | | | S | T | D | T |

TABLE 4-continued

| Sequence Name | % Identity to PIP-1A | 88 | 89 | 91 | 93 | 104 | 112 | 113 | 114 | 120 | 124 | 125 | 126 | 128 | 132 | 141 | 143 | 149 | 152 | 153 |
|---|---|---|---|---|---|---|---|---|---|---|---|---|---|---|---|---|---|---|---|---|
| D_D0274280 | 88 | Y | V | E | | | R | S | E | S | N | A | N | E | T | T | R | S | T | D | T |
| D_D0274306 | 88 | Y | | | | | R | S | E | S | N | A | N | E | T | T | R | S | T | D | T |
| D_D0274336 | 88 | Y | V | E | | | R | S | E | S | N | A | N | | | | | S | T | | |
| D_D0274323 | 88 | | | | | | R | S | E | S | N | A | N | | | | | S | T | D | T |
| D_D0274239 | 87 | | V | E | | | | | | | | | | E | T | T | R | S | T | D | T |
| D_D0274260 | 87 | | V | E | N | T | L | R | S | E | S | N | A | N | E | T | T | R | S | T | D | T |
| D_D0274298 | 87 | Y | | | | | | | | | | A | N | E | T | T | R | S | T | D | T |
| D_D0274304 | 87 | | V | E | N | T | L | R | S | E | S | N | A | N | | T | T | R | S | T | D | T |
| D_D0274282 | 86 | | | | N | T | L | R | S | E | S | N | A | N | E | T | T | R | S | T | D | T |
| D_D0274320 | 86 | | V | E | N | T | L | R | S | E | S | N | A | N | E | T | T | R | S | T | D | T |
| D_D0274302 | 85 | | V | | | | | | | | | | | E | T | T | R | S | T | D | T |
| D_D0274240 | 84 | | | | | | R | S | E | S | N | A | N | | | | | S | T | D | T |
| D_D0274252 | 84 | Y | | | | | | | | | | A | N | E | T | T | R | S | T | D | T |
| D_D0274249 | 83 | | V | E | N | T | L | R | S | E | S | N | A | N | E | T | T | R | S | T | D | T |
| D_D0274255 | 83 | | V | E | N | T | L | R | S | E | S | N | A | N | E | T | T | R | S | T | D | T |
| D_D0274243 | 82 | Y | V | E | N | T | L | R | S | E | S | N | A | N | E | T | T | R | S | T | D | T |
| D_D0274281 | 82 | Y | V | E | N | T | L | R | S | E | S | N | A | N | | T | R | S | T | D | T |
| D_D0274313 | 82 | | | E | N | T | L | R | S | E | S | N | A | N | | T | T | R | S | T | D | T |
| PSEEN3174 | 79 | Y | V | E | N | T | L | R | S | E | S | N | A | N | E | T | T | R | S | T | D | T |

| Sequence Name | % Identity to PIP-1A | 166 | 167 | 168 | 174 | 175 | 180 | 194 | 195 | 200 | 203 | 204 | 209 | 213 | 220 | 221 | 222 | 226 | 229 | 231 | 232 | 249 |
|---|---|---|---|---|---|---|---|---|---|---|---|---|---|---|---|---|---|---|---|---|---|---|
| PIP-1A | 100 | Q | L | T | I | V | M | G | N | N | T | L | Y | N | S | T | D | K | I | A | N | |
| D_D0274266 | 89 | | | | | | | | | S | Q | A | V | | R | K | R | P | N | V | T | |
| D_D0274283 | 89 | E | M | K | | | | A | | S | Q | A | V | | R | K | R | P | N | V | T | |
| D_D0274290 | 89 | | | | | | | | | S | Q | A | V | | R | K | R | P | N | V | T | |
| D_D0274233 | 88 | E | M | K | V | I | L | A | | | | | V | | R | K | R | P | N | V | T | |
| D_D0274259 | 88 | E | M | K | V | I | L | | | S | Q | A | V | | R | K | R | P | N | V | T | |
| D_D0274278 | 88 | E | M | K | | | | | | | | | | | R | K | R | P | N | V | T | |
| D_D0274280 | 88 | E | M | K | V | I | L | | | | | | | | R | K | R | P | N | V | T | |
| D_D0274306 | 88 | E | H | K | | | | A | Y | | Q | A | V | F | R | K | R | P | N | V | T | |
| D_D0274316 | 88 | | | | V | | | | | | | | | | R | K | R | P | N | V | T | |
| D_D0274323 | 88 | E | M | K | | | | A | | S | Q | A | | | R | K | R | P | N | V | T | |
| D_D0274239 | 87 | E | M | K | | L | | | | | | | | | R | K | R | P | N | V | T | |
| D_D0274260 | 87 | E | M | K | | | L | A | | S | Q | A | V | | R | K | R | P | N | V | T | |
| D_D0274298 | 87 | E | M | K | | | L | | | S | Q | A | V | | R | K | R | P | | | | | |
| D_D0274304 | 87 | E | M | K | V | I | | A | | S | Q | A | V | | R | K | R | P | N | V | T | |
| D_D0274282 | 86 | E | M | K | | | | A | | S | Q | A | V | | | | | | | | | |
| D_D0274320 | 86 | E | M | K | V | I | L | A | | S | Q | A | V | | R | K | R | P | N | V | T | |
| D_D0274302 | 85 | E | M | K | V | I | L | | | S | Q | A | V | | R | K | R | P | N | V | T | |
| D_D0274240 | 84 | E | M | K | | | | A | | S | Q | A | V | | R | K | R | P | N | V | T | S |
| D_D0274252 | 84 | E | M | K | V | I | L | | | S | Q | A | V | | R | K | R | P | N | V | T | |
| D_D0274249 | 83 | E | M | K | V | I | L | A | | S | Q | A | V | | R | K | R | P | N | V | T | |
| D_D0274255 | 83 | E | M | K | V | I | | A | | S | Q | A | | | R | K | R | P | N | V | T | |
| D_D0274243 | 82 | E | M | K | V | I | L | A | | S | Q | A | | | R | K | R | P | N | V | T | |
| D_D0274281 | 82 | E | M | K | V | I | L | A | | S | Q | A | V | | R | K | R | P | N | V | T | |
| D_D0274313 | 82 | E | M | K | V | I | L | A | | S | Q | A | V | | R | K | R | P | N | V | T | |
| PSEEN3174 | 79 | E | M | K | V | I | L | A | N | S | Q | A | V | Y | R | K | R | P | N | V | T | N |

Example 9: Identification of Amino Acid Positions Affecting the Protein Stability and Function BLAST searching the Department of Energy Joint Genomic Institute website (www.jgi.doe.gov/) and NCBI database using the PIP-1A (SEQ ID NO: 2) and PSEEN3174 (SEQ ID NO: 6) sequence revealed information regarding three additional genes having lower homology: AECFG_592740 (2035954615—annotated as a hypothetical protein [Acromyrmex echinatior fungus garden]), Pput_1063 (Accession # ABQ77224; Gene ID:5191350—annotated as a hypothetical protein [Pseudomonas putida F1]) and Pput_1064 (Accession # ABQ77225; Gene ID:5191351—annotated as a hypothetical protein [Pseudomonas putida F1]). The AECFG_592740 coding sequence has the DNA sequence set forth in SEQ ID NO: 11 and encodes a polypeptide, having the amino acid sequence set forth in SEQ ID NO: 12. The Pput_1063 coding sequence has the DNA sequence set forth in SEQ ID NO: 7 and encodes the polypeptide set forth in SEQ ID NO: 8. The Pput_1064 coding sequence has the DNA sequence set forth in SEQ ID NO: 9 and encodes the polypeptide set forth in SEQ ID NO: 10. The AECFG_592740 (SEQ ID NO: 11), Pput_1063 (SEQ ID NO: 7), and Pput_1064 (SEQ ID NO: 9) genes were synthesized, the respective proteins were expressed as Maltose binding protein fusions in E. coli, and cell lysates were tested in the Lygus assay as described previously for PIP-1A (SEQ ID NO: 2). The AECFG_592740 (SEQ ID NO: 12), Pput_1063 (SEQ ID NO: 8), and Pput_1064 (SEQ ID NO: 8) proteins were inactive in the Lygus assay.

The protein sequence alignment of three active homologs, PIP-1A (SEQ ID NO: 2), PSEEN3174 (SEQ ID NO: 6) and PIP-1B (SEQ ID NO: 4), and three inactive orthologs, AECFG_592740 (SEQ ID NO: 12), Pput_1063 (SEQ ID NO: 8) and Pput_1064 (SEQ ID NO: 10) is shown in FIG. 1. Secondary structure features of PIP-1A (SEQ ID NO: 2) were obtained using program Garnier (EMBOSS Explorer) (Garnier, et al., (1978) J. Mol. Biol. 120:97-120) and selected structure features shown above the alignment of FIG. 1. Six positions (P43, W66, P89, Y93, Y176, F259 of SEQ ID NO: 2) were selected for saturated mutagenesis analysis. Mutants were generated using degenerate oligos (Table 5) for each site using sewing and rescuing PCR strategy of two overlapping fragments of N-terminus (no mutation) and C-terminus (with mutations) gene) for each site using sewing and rescuing PCR strategy of two overlapping fragments of N-terminus (no mutation) and C-terminus (with mutations) gene) as illustrated in FIG. 2. The rescued mutant libraries were cloned into the Maltose-Binding-Protein fusions of pMAL®-c2x (NEB). Individual mutations were identified by sequencing 96 clones of each library. The respective variant proteins were expressed in *E. coli*, and cell lysates tested in the *Lygus* assay as described previously for PIP-1A (SEQ ID NO: 2). Table 6 shows for each mutated position the amino acid substitutions identified those substitutions that expressed soluble protein, and those substitutions that were active in the *Lygus* assay and/or the Soy bean looper assay with a minimal score of 4 or greater out of total maximal score of 8. The expression and activity of the substitutions in parenthesis were not determined. Substitutions indicated with an "*" had significantly reduced soluble expression. This data demonstrate that the amino substitutions indicated in Table 6 as "Active mutants" can be made while retaining activity.

TABLE 5

| Residue | Oligo name | Sequence |
|---|---|---|
| P43 | P43r | GAACTGATCGAAGTTGCCAGC SEQ ID NO: 16 |
| | P43f1 | GCTGGCAACTTCGATCAGTTCCDNACTAAGCGTGGTGGCTTTGC SEQ ID NO: 17 |
| | P43f2 | GCTGGCAACTTCGATCAGTTCDNNACTAAGCGTGGTGGCTTTGC SEQ ID NO: 18 |
| W66 | W68r | GCAGCCTTGCTTGGGCGCGCTG SEQ ID NO: 19 |
| | W68f1 | CAGCGCGCCCAAGCAAGGCTGCTNYGTAGATGGCATTACCGTCTACG SEQ ID NO: 20 |
| | W68f2 | CAGCGCGCCCAAGCAAGGCTGCVNNGTAGATGGCATTACCGTCTACG SEQ ID NO: 21 |
| P89 | P91r | GCGAGTGTAGGTGCCCCAATT SEQ ID NO: 22 |
| | P91f | AATTGGGGCACCTACACTCGCNNKGTCTTTGCCTACCTGCAGTACATG SEQ ID NO: 23 |
| Y93 | Y95r | GGCAAAGACCGGGCGAGTGTAGG SEQ ID NO: 24 |
| | Y95f1 | CCTACACTCGCCCGGTCTTTGCCTBBCTGCAGTACATGGACACCATT SEQ ID NO: 25 |
| | Y95f2 | CCTACACTCGCCCGGTCTTTGCCVNNCTGCAGTACATGGACACCATT SEQ ID NO: 26 |
| Y176 | Y178r | CACGATGAAGGTGCCAGGACC SEQ ID NO: 27 |
| | Y178f1 | GGTCCTGGCACCTTCATCGTGTBBCAGGTTGTTATGGTTTATGC SEQ ID NO: 28 |
| | Y178f2 | GGTCCTGGCACCTTCATCGTGVNNCAGGTTGTTATGGTTTATGC SEQ ID NO: 29 |
| F259 | F267r | ACTGAAGTGCCCACTATTGCTG SEQ ID NO: 30 |
| | F267f1 | CAGCAATAGTGGGCACTTCAGTTVNGACTGGAGCGCCTACAACGATC SEQ ID NO: 31 |
| | F267f2 | CAGCAATAGTGGGCACTTCAGTVNNGACTGGAGCGCCTACAACGATC SEQ ID NO: 32 |

TABLE 6

| Residue | Identified mutations | Soluble expressed Mutants | Lygus Active mutants | SBL Active mutants |
|---|---|---|---|---|
| P43 | M, G, Q, S, T, R, V, L, K, D, A, N, F, W, E, C, (I), (Y), (H) | M, G, Q, S, T, R*, V, L, K, D, A, N, F, W, E, C | M, G, Q, S, T, R, V, L, K, D, A, N, F, W, E, C, | M, G, Q, S, T, V, L, K, D, A, N, F, W, E, C, Y |
| W66 | S, F, Y, P, V, K, T, Q, C, M, N, R, L, A, G, E, D, H, I | Y, F, H, K*, R*, M*, L*, A*, I*, C*, V, S | Y, F, K, R, H, I | V, S |
| P89 | L, G, R, Y, T, S, E, Q, M, K, A, W, D, I, N, V, C, (H), (F) | K, A, C, L, G*, V*, I*, T*, S*, Q*, M*, N* | L, G, R, T, S, M, A, I, N, V, C, K | V, C, |
| Y93 | Q, R, M, D, T, V, H, L, K, N, C, A, W, E, I, G, S, P, F | W, M, F, C*, V*, T*, L*, I*, A*, | C, W, V, M, L, I, F, A, T | W, V, D, N, L, I, F, |
| Y176 | S, W, V, T, M, R, Q, L, N, D, C, A, E, G, F, I, P, (H), (K) | M, F, L*, C*, A*, W* | M, F, L | M, L, C |
| F259 | W, C, A, D, R, K, M, E, L, P, V, H, N, T, I, G, S, Q, Y | W, Y, F, M, L, V, I, H*, C*, | W, Y, C, M, L, V, I, H | W, M, L, V, I, Y, |

Example 10: Identification of Motifs for Insecticidal Activity

Four conserved motifs, amino acids 64-79 of SEQ ID NO: 2 (motif 1), amino acids 149-159 of SEQ ID NO: 2 (motif 2), amino acids 171-183 of SEQ ID NO: 2 (motif 3), and amino acids 240-249 of SEQ ID NO: 2 (motif 4) (motifs underlined in FIG. 1) of active proteins (PIP-1A (SEQ ID NO: 2), PSEEN3174 (SEQ ID NO: 6) and PIP-1B (SEQ ID NO: 4) were selected to determine their roles for insecticidal functions. For each selected motif, amino acids 64-79 of SEQ ID NO: 2, amino acids 149-159 of SEQ ID NO: 2, amino acids 171-183 of SEQ ID NO: 2, and amino acids 240-249 of SEQ ID NO: 2, the sequence was replaced with corresponding sequences from three distantly related but functionally inactive proteins AECFG_592740 (SEQ ID NO: 12), PputX_1063 (SEQ ID NO: 8), and Pput_1064 (SEQ ID NO: 10) respectively (Table 7 shows the % identity).

TABLE 7

|  | PIP-1A | PIP-1B | PSEEN3174 | Pput_1063 | AECFG_592740 | Pput_1064 |
|---|---|---|---|---|---|---|
| PIP-1A |  | 93 | 79 | 23 | 37 | 36 |
| PIP-1B |  |  | 79 | 26 | 38 | 35 |
| PSEEN3174 |  |  |  | 24 | 36 | 34 |
| Pput_1063 |  |  |  |  | 22 | 23 |
| AECFG_592740 |  |  |  |  |  | 36 |
| Pput_1064 |  |  |  |  |  |  |

The chimeras were generated using a sewing PCR strategy with fragments of N-terminus and C-terminus of the wild type PIP-1A with overlapping oligonucleotides (Table 8) coding for the replaced sequence of inactive proteins.

The rescued PCR products containing the replacements were cloned into the pMAL expression vector as described above for PIP-1A. The resulting chimeras were expressed and functionally tested in *Lygus* insect bioassays. Table 9 shows the amino acid sequence for each of the four motifs (underlined in FIG. 1) from PIP-1A and the corresponding amino acid sequence based on the alignment (FIG. 1) with AECFG_592740 (SEQ ID NO:12), Pput_1063 (SEQ ID NO: 8), and Pput_1064 (SEQ ID NO: 10) that were substituted. In Table 9 the differences between the respective sequences are in indicated in "bold" and "underlining".

TABLE 8

| Motif | Replaced from | Oligo name | Sequence |
|---|---|---|---|
| 1 | AECFG_592740 | 55Mot1R | CATGTCACCGTAGATGGTACCGCCACGTACCCAGCAGCCTTGCTTGGG SEQ ID NO: 33 |
|  |  | 55Mot1F | GGTACCATCTACGGTGACATGTGGATCTGGAAGCAGAATTGGGGCACCTAC AC SEQ ID NO: 34 |
|  | Pput 1063 | 1063Mot1R | GAAGCCACCGTAGACGGTTTCGCCTTCTATCCAGCAGCCTTGCTTGGGC SEQ ID NO: 35 |
|  |  | 1063Mot1F | GAAACCGTCTACGGTGGCTTCGGTTTCCCCAAGCAGAATTGGGGCACCTAC SEQ ID NO: 36 |
|  | Pput 1064 | 1064Mot1R | ACGGACGTCACCGTAGGTGGTATCGGCATCTACCCAGCAGCCTTGCTTGG SEQ ID NO: 37 |
|  |  | 1064Mot1F | ACCACCTACGGTGACGTCCGTTGCGGCAAGCAGAATTGGGGCACCTAC SEQ ID NO: 38 |
| 2 | AECFG_592740 | 55Mot2R | ACCATGCACGCCTTCAGTGTAACTGGATCCAATTGAGATATCCGAACC SEQ ID NO: 39 |
|  |  | 55Mot2F | TACACTGAAGGCGTGCATGGTTCGAACACGTTCAGCAATAGCACTCAATTG SEQ ID NO: 40 |
|  | Pput 1063 | 1063Mot2R | CAGAGGACGCCATTCTTCAGCACTGCATCCAATTGAGATATCCGAACC SEQ ID NO: 41 |
|  |  | 1063Mot2F | GCTGAAGAATGGCGTCCTCTGTCGACGTTCAGCAATAGCACTCAATTG SEQ ID NO: 42 |
|  | Pput 1064 | 1064Mot2R | CGAACCAGACACGGTTTCACTGACACTGAATCCAATTGAGATATCCG SEQ ID NO: 43 |
|  |  | 1064Mot2F | AGTGAAACCGTGTCTGGTTCGGAGACGTTCAGCAATAGCACTCAATTG SEQ ID NO: 44 |
| 3 | AECFG_592740 | 55Mot3R | ATGCATCTGATAGAAGTTGTAGATGCCAGGACCAGTCAATTGAGTG SEQ ID NO: 45 |
|  |  | 55Mot3F | TACAACTTCTATCAGATGCATATGGTTTTGCGCACAACGCCACTTCTG SEQ ID NO: 46 |
|  | Pput 1063 | 1063Mot3R | CTGATACGCGACGTAGCATTCAGGACCAGTCAATTGAGTGCTATT SEQ ID NO: 47 |

TABLE 8-continued

| Replaced Motif from | Oligo name | Sequence |
|---|---|---|
| | 1063Mot3F | GAATGCTACGTCGCGTATCAGCTTAAACTGGTTTATGCGCACAACGCCACTTC SEQ ID NO: 48 |
| Pput 1064 | 1064Mot3R | ATGAACCTGATACACCATGATGGTGCCAGGACCAGTCAATTGAG SEQ ID NO: 49 |
| | 1064Mot3F | ATCATGGTGTATCAGGTTCATATGGTTTATGCGCACAACGCCAC SEQ ID NO: 50 |
| 4 AECFG_59 2740 | 55Mot4R | GTTGTCCATCAACACAGCGCGCTGAACAGTATCCCAATCCAG SEQ ID NO: 51 |
| | 55Mot4F | CGCGCTGTGTTGATGGACAACTACAAGCCAGGCAGCAATAGTGGGCAC SEQ ID NO: 52 |
| Pput 1063 | 1063Mot4R | GGCCAGGTTGAAGATAAGGTGGTAAACAGTATCCCAATCCAGCGGC SEQ ID NO: 53 |
| | 1063Mot4F | CACCTTATCTTCAACCTGGCCTACGGCCCAGGCAGCAATAGTGGGCACTTC SEQ ID NO: 54 |
| Pput 1064 | 1064Mot4R | CTGGTTGAACAACACAGCCTGGTTAACAGTATCCCAATCCAGCGGC SEQ ID NO: 55 |
| | 1064Mot4F | CAGGCTGTGTTGTTCAACCAGGAGGAGCCAGGCAGCAATAGTGGGCACTTC SEQ ID NO: 56 |

TABLE 9

| Motif | Replaced from | Oligos | PIP-1A WT amino acid sequence | Amino acids replaced | Soluble protein expressed | Activity |
|---|---|---|---|---|---|---|
| 1 | AECFG_59 2740 | 55Mot1R 55Mot1F | GCWVDGITVYGDIFIG a.a. 64-79 of SEQ ID NO: 2 | GCWVRGGTIYGDMWIW a.a. 49-64 of SEQ ID NO: 12 | No | No |
| | Pput1063 | 1063Mot1R 1063Mot1F | | GCWIEGETVYGGFGFP a.a. 34-49 of SEQ ID NO: 8 | No | No |
| | Pput1064 | 1064Mot1R 1064Mot1F | | GCWVADTTYGDVRCG a.a. 37-52 of SEQ ID NO: 10 | No | No |
| 2 | AECFG_59 2740 | 55Mot2R 55Mot2F | FSNSESWSTTQ a.a. 149-159 of SEQ ID NO: 2 | SSYTEGVHGSN a.a. 133-143 of SEQ ID NO: 12 | No | No |
| | Pput1063 | 1063Mot2R 1063Mot2F | | CS-AEEWRPLS a.a. 118-127 of SEQ ID NO: 8 | No | No |
| | Pput1064 | 1064Mot2R 1064Mot2F | | FSVSETVSGSE a.a. 122-132 of SEQ ID NO: 10 | No | No |
| 3 | AECFG_59 2740 | 55Mot3R 55Mot3F | GTFIVYQVVMVYA a.a. 171-183 of SEQ ID NO: 2 | GIYNFYQMHMVFA a.a. 155-167 of SEQ ID NO: 12 | No | No |
| | Pput1063 | 1063Mot3R 1063Mot3F | | ECYVAYQLKLVYA a.a. 139-151 of SEQ ID NO: 8 | No | No |
| | Pput1064 | 1064Mot3R 1064Mot3F | | GTIMVYQVHMVYA a.a. 144-156 of SEQ ID NO: 10 | No | No |
| 4 | AECFG_59 2740 | 55Mot4R 55Mot4F | QRNVLMENYN a.a. 240-249 of SEQ ID NO: 2 | QRAVLMDNYK a.a. 224-233 of SEQ ID NO: 12 | Yes | Yes |
| | Pput1063 | 1063Mot4R 1063Mot4F | | LYHLIFNLAY a.a. 208-217 of SEQ ID NO: 8 | No | No |
| | Pput1064 | 1064Mot4R 1064Mot4F | | NQAVLFNQFE a.a. 217-227 of SEQ ID NO: 10 | No | No |

Table 9 also indicates if the resulting proteins were soluble when expressed as a MAL fusion in *E. coli.* and were active in the *Lygus* assay.

As indicated in Table 9, all but one of these chimeras had reduced expression of soluble protein and was inactive in the bioassay indicating that these four motifs have functional constraints.

Example 11: Saturated Mutagenesis of Motifs to Define Sequence Variations that Retain Insecticidal Activity Two motifs, amino acids 171 to 183 (motif 3) and amino acids 240 to 249 (motif 4) of PIP-1A (SEQ ID NO: 2) were selected to further define the roles of the regions in insecticidal functions. To further define the permitted sequence variation within those two selected motifs, saturated mutagenesis was designed for each position of the motifs using the mutagenesis oligonucleotides as shown in Tables 10 and 11 for motifs 3 and 4 respectively. The variants were generated using a similar strategy as described in Example 9. Tables 12 and 13 show for each mutated position the amino acid substitutions identified, those substitutions that expressed soluble protein, and those substitutions that were active in the *Lygus* assay and/or the Soy bean looper assay with a minimal score of 4 or greater out of total maximal score of 8. This data demonstrate that the amino substitutions indicated in Tables 12 and 13 as "Active mutants" can be made while retaining activity.

TABLE 10

| Motif # | Amino acid Position of PIP-1A (SEQ ID NO: 2) | Oligo name | Sequence |
|---|---|---|---|
| 3 | G171 | G173R | AGGACCAGTCAATTGAGTGCT SEQ ID NO: 57 |
|   |      | G173F | AGCACTCAATTGACTGGTCCTNNKACCTTCATCGTGTATCAGGT SEQ ID NO: 58 |
|   | T172 | T174R | GCCAGGACCAGTCAATTGAGT SEQ ID NO: 59 |
|   |      | T174F | ACTCAATTGACTGGTCCTGGCNNKTTCATCGTGTATCAGGTTG SEQ ID NO: 60 |
|   | F173 | F175R | GGTGCCAGGACCAGTCAATTG SEQ ID NO: 61 |
|   |      | F175F | CAATTGACTGGTCCTGGCACCNNKATCGTGTATCAGGTTGTTATG SEQ ID NO: 62 |
|   | I174 | I176R | GAAGGTGCCAGGACCAGTCAA SEQ ID NO: 63 |
|   |      | I176F | TTGACTGGTCCTGGCACCTTCNNKGTGTATCAGGTTGTTATG SEQ ID NO: 64 |
|   | V175 | V177R | GATGAAGGTGCCAGGACCAGT SEQ ID NO: 65 |
|   |      | V177F | ACTGGTCCTGGCACCTTCATCNNKTATCAGGTTGTTATGGTTTAT SEQ ID NO: 66 |
|   | Q177 | Q179R | ATACACGATGAAGGTGCCAGG SEQ ID NO: 67 |
|   |      | Q179F | CCTGGCACCTTCATCGTGTATNNKGTTGTTATGGTTTATGCGCAC SEQ ID NO: 68 |
|   | V178 | V180R | CTGATACACGATGAAGGTGCC SEQ ID NO: 69 |
|   |      | V180F | GGCACCTTCATCGTGTATCAGNNKGTTATGGTTTATGCGCACAAC SEQ ID NO: 70 |
|   | V179 | V181R | AACCTGATACACGATGAAGGT SEQ ID NO: 71 |
|   |      | V181F | ACCTTCATCGTGTATCAGGTTNNKATGGTTTATGCGCACAACGCC SEQ ID NO: 72 |
|   | M180 | M182R | AACAACCTGATACACGATGAA SEQ ID NO: 73 |
|   |      | M182F | TTCATCGTGTATCAGGTTGTTNNKGTTTATGCGCACAACGCCACT SEQ ID NO: 74 |
|   | V181 | V183R | CATAACAACCTGATACACGAT SEQ ID NO: 75 |
|   |      | V183F | ATCGTGTATCAGGTTGTTATGNNKTATGCGCACAACGCCACTTCT SEQ ID NO: 76 |
|   | Y182 | Y184R | AACCATAACAACCTGATACAC SEQ ID NO: 77 |
|   |      | Y184F | GTGTATCAGGTTGTTATGGTTNNKGCGCACAACGCCACTTCTGCG SEQ ID NO: 78 |
|   | A183 | A185R | ATAAACCATAACAACCTGATA SEQ ID NO: 79 |
|   |      | A185F | TATCAGGTTGTTATGGTTTATNNKCACAACGCCACTTCTGCGGGC SEQ ID NO: 80 |

TABLE 11

| Motif # | Amino acid Position | Oligo name | Sequence |
|---|---|---|---|
| 4 | Q240 | Q247R | AACAGTATCCCAATCCAGCGG SEQ ID NO: 81 |
|   |   | Q247F | CCGCTGGATTGGGATACTGTTNNKCGCAATGTGTTGATGGAGAAC SEQ ID NO: 82 |
|   | R241 | R248R | CTGAACAGTATCCCAATCCAG SEQ ID NO: 83 |
|   |   | R248F | CTGGATTGGGATACTGTTCAGNNKAATGTGTTGATGGAGAACTAC SEQ ID NO: 84 |
|   | N242 | N249R | GCGCTGAACAGTATCCCAATC SEQ ID NO: 85 |
|   |   | N249F | GATTGGGATACTGTTCAGCGCNNKGTGTTGATGGAGAACTACAAC SEQ ID NO: 86 |
|   | V243 | V250R | ATTGCGCTGAACAGTATCCCA SEQ ID NO: 87 |
|   |   | V250F | TGGGATACTGTTCAGCGCAATNNKTTGATGGAGAACTACAACCCA SEQ ID NO: 88 |
|   | L244 | L251R | CACATTGCGCTGAACAGTATC SEQ ID NO: 89 |
|   |   | L251F | GATACTGTTCAGCGCAATGTGNNKATGGAGAACTACAACCCAGG SEQ ID NO: 90 |
|   | M245 | M252R | CAACACATTGCGCTGAACAGT SEQ ID NO: 91 |
|   |   | M252F | ACTGTTCAGCGCAATGTGTTGNNKGAGAACTACAACCCAGGCAGC SEQ ID NO: 92 |
|   | E246 | E253R | CATCAACACATTGCGCTGAAC SEQ ID NO: 93 |
|   |   | E253F | GTTCAGCGCAATGTGTTGATGNNKAACTACAACCCAGGCAGC SEQ ID NO: 94 |
|   | N247 | N254R | CTCCATCAACACATTGCGCTG SEQ ID NO: 95 |
|   |   | N254F | CAGCGCAATGTGTTGATGGAGNNKTACAACCCAGGCAGCAATAG SEQ ID NO: 96 |
|   | Y248 | Y255R | GTTCTCCATCAACACATTGCG SEQ ID NO: 97 |
|   |   | Y255F | CGCAATGTGTTGATGGAGAACNNKAACCCAGGCAGCAATAGTGG SEQ ID NO: 98 |
|   | N249 | N256R | GTAGTTCTCCATCAACACATT SEQ ID NO: 99 |
|   |   | N256F | AATGTGTTGATGGAGAACTACNNKCCAGGCAGCAATAGTGGGCA SEQ ID NO: 100 |

TABLE 12

| Position | Identified mutations | Soluble expressed Mutants | Lygus Active mutants | SBL Active mutants |
|---|---|---|---|---|
| G171 | P, W, R, Q, L, M, A, S, V, Y, C, K, I, T, H, F, N, D, E | S, L, Q, M, Y, W, C, H, T, I, A, K, R, V, D, F, E, N | L, Q, M, C, N, D | S, L, M C, A, N |
| T172 | G, A, L, H, V, F, S, M, R, E, I, N, W, Q, K, P, D, C, Y | G, A, L, H, V, F, S, M, R, E, I, N, W, Q, K, P, D, C, Y | G, H, F, E, R, S, N, I, W, K, Q, C, V | G, H, F R, S, N I, W, K Q, C, V A, M |
| F173 | G, R, P, C, D, A, E, I, L, V, S, K, Q, T, H, W, N, M, Y | G, H, Q, L, A, R, I, N, C, K, W, T, S, Y, M | G, H, L, A, R, N, C, K, W, T, S, Y, M | H, L, A N, C, K W, T, S Y, M |
| I174 | A, K, G, P, W, L, R, C, H, Q, S, V, E, I, Y, M, F, N, T | A, K, G, W, L, R, C, H, Q, S, V, E, I, Y, M, F, N, T | G, R, N, A, Q, M, I, C, L, F, V, Y, K, E, S, H, T | G, R, N A, Q, M I, C, L F, V, Y K, E, S H, T |
| V175 | L, Q, R, G, C, E, W, A, D, F, K, T, P, N, M, I, S, Y, H | A, I, C, E, K, L | A, I, C, E, K, L | A, I, C E, L |
| Y176 | S, W, V, T, M, R, Q, L, N, D, C, A, E, G, F, I, P, H, K | M, F, L, C, A, W | M, F, L | M, L, C |
| Q177 | W, R, L, K, G, S, A, D, P, E, C, M, V, I, H, T, F, Y, N | I, M, P, | I, M, P | M, P |
| V178 | C, T, R, S, Y, D, G, L, P, A, M, Q, W, E, F, H, N, K, I | C, T, R, S, Y, D, L, P, A, M, Q, W, E, F, I, H, | C, T, P, A, M, Q, F, I | C, T, S P, A, M Q, I, K |
| V179 | F, Y, T, P, D, K, I, G, C, R, L, M, S, H, W, Q, E, N, A, | F, Y, T, I, C, L, M, S, H, Q, A | F, T, I, C, L, M, S, A, Q | T, I, C, S, A |
| M180 | K, D, R, P, E, W, N, Y, G, Q, S, L, A, V, F, I, C | K, P, W, N, Y, G, Q, L, A, V, F, I, C | P, W, N, Y, G, Q, L, A, V, F, I, C, S | P, W, N, Y, Q, L, V, F, I, C, S |
| V181 | G, R, A, P, D, L, E, W, C, S, Q, T, I, N, F, Y, H, K, M | A, L, W, C, T, I | A, L, W, C, T, I | A, L, C, T, I, K |

TABLE 12-continued

| Position | Identified mutations | Soluble expressed Mutants | Lygus Active mutants | SBL Active mutants |
|---|---|---|---|---|
| Y182 | V, E, P, K, A, W, R, T, L, F, Q, C, D, N, M, G, H, S, I | F, M, H | F, M, H | F, M |
| A183 | W, M, P, V, T, D, G, C, I, Y, N, F, E, S, Q, L, H, R, K | M, V, T, D, G, C, I, F, S, Q, L | M, V, T, D, G, C, I, F, S, L | M, V, T, D, G, C, I, F, S, L |

TABLE 13

| Position | Identified mutations | Soluble expressed mutants | Active mutants |
|---|---|---|---|
| Q240 | R, A, V, E, M, G, D, W, N, T, I, S, F, H, C, L, Y, P, K | R, A, V, E, M, G, D*, W, N, T, I, S, F, H, C, L, Y, K | R, A, V, E, M, G, D, W, N, T, I, S, F, H, C, L, Y, K |
| R241 | K, E, Q, S, I, V, D, Y, M, N, H, P, G, L, F, T, A, C, W | K, E, Q, S, I, V, D, Y, M, N, H, P, G, L, F, T, A, C, W | K, E, Q, S, I, V, D, Y, M, N, H, P, G, L, F, T, A, C, W |
| N242 | R, K, H, S, C, A, E, P, W, Q, T, F, Y, M, D, V, G, L, I | R, K, H, S, C, A, E, P*, W, Q, T, F, Y, M, D, V, G, L, I | R, K, H, S, C, A, E, P, W, Q, T, F, Y, M, D, G, L, I |
| V243 | P, L, Q, E, A, F, N, Y, T, W, G, C, I, R, S, H, K, M, D | L, A, T, G, C, I, S, M, | L, A, T, G, C, I, S, M, |
| L244 | V, F, I, S, M, Y, W, P, Q, H, T, K, E, A, N, C, R, G, D | V, F, I, M, W, Q, A, C, | V, F, I, M, Q, C, W |
| M245 | A, R, D, E, L, P, S, W, G, V, K, F, C, T, H, I, Q, Y, N | A, R, D, E, L, P, S, W, G, V, K, F, C, T, H, I, Q, Y, N | A, R, D, E, L, P, S, W, G, V, K, F, C, T, H, I, Q, Y, N |
| E246 | G, S, I, A, L, V, H, W, R, Y, C, D, N, Q, P, M, F, T, K | Y, D, G, R, V, A, W, Q, S, N, I, L, M, C, P, H, F, T, K | Y, D, G, R, V, A, W, Q, S, N, I, L, M, C, P, H, F, T, K |
| N247 | L, D, Y, A, F, H, R, K, Q, G, V, I, S, E, P, M, W, T, C | L, D, Y, A, F, H, R, K, Q, G, V, I, S, E, P, M, W, T, C | L, D, Y, A, F, H, R, K, Q, G, V, I, S, E, P, M, W, T, C |
| Y248 | V, T, E, F, S, H, C, N, L, G, K, A, W, R, I, D, P, Q, (M) | V, T, E, F, S, H, C, N, L, G, A, W, I, D, P | V, T, E, F, S, H, C, L, W, I, D, G, A |
| N249 | V, G, M, D, K, C, F, R, E, W, Y, S, I, T, P, L, A, H, Q | V, G, M, D, K, C, F, R, E, W, Y, S, I, T, P, L, A, H, Q | V, G, M, D, K, C, F, R, E, W, Y, S, I, T, P, L, A, |

Example 12: Transient Expression and Insect Bioassay on Transient Leaf Tissues

Both PIP-1A (SEQ ID NO: 2) and PSEEN3174 (SEQ ID NO: 6) as MBP fusions and alone were cloned into a transient expression vector under control of a viral promoter pDMMV (Day, et. al., (1999) Plant Mol. Biol. 40:771-782). The agro-infiltration method of introducing an Agrobacterium cell suspension to plant cells of intact tissues so that reproducible infection and subsequent plant derived transgene expression may be measured or studied is well known in the art (Kapila, et. al., (1997) Plant Science 122:101-108). Briefly, young plantlets of Phaseolus vulgaris or Glycine max, were agro-infiltrated with normalized bacterial cell cultures of test and control strains. Leaf discs were generated and infested with 3 neonates of both Soy Bean Looper (SBL) (Pseudoplusia includes) or Velvet bean caterpillar (VBC) (Velvet Anticarsia gemmatalis) with two control leaf discs generated with Agrobacterium only. The consumption of green leaf tissues was scored after two day's infestation. The transiently expressed PIP-1A (SEQ ID NO: 2) and PSEEN3174 (SEQ ID NO: 6) protected leaf discs from consumption by the infested SBL and VBC insects while the total green tissue consumption was observed for the two negative controls. Transient protein expressions of both PIP-1A (SEQ ID NO: 2) and PSEEN3174 (SEQ ID NO: 6) were confirmed by Mass spectrometry based protein identification method using extracted protein lysates from infiltrate leaf tissues (Patterson, (1998) 10(22):1-24, Current Protocol in Molecular Biology published by John Wiley & Son Inc).

Example 13: Defined Protein Sequences of Fragments Retaining Activity

A series of truncated variants of PIP-1A (SEQ ID NO: 2) are generated in 5 amino acid increments from both ends by PCR cloning for the first and/or last 30 amino acids. The truncated genes are cloned to the same expression system as listed above. Recombinant proteins of those truncated versions of PIP-1A are assayed with insects and minimal length of the protein is defined with the variant still retains detectable insecticidal activity.

Example 14: N-Terminal Truncation Variants

The PIP-1A (SEQ ID NO: 2), PSEEN3174 (SEQ ID NO: 6) and PIP-1B (SEQ ID NO: 4) proteins were digested with a limited Trypsin digestion (1 part of Trypsin vs. 100 parts of purified protein). The resulting N-terminal trypsin truncated variants, PIP-1AT1 (SEQ ID NO: 204), PSEEN3174T1 (SEQ ID NO: 206), PIP-1BT1 (SEQ ID NO: 208), have amino acids 1-28 deleted compared to the respective full length proteins by N-terminal Amino Acid sequencing. The PIP-1AT1 (SEQ ID NO: 204), PSEEN3174T1 (SEQ ID NO: 206), PIP-1BT1 (SEQ ID NO: 208) were assayed in the Lygus assay and found to have substantially the same activity as the respective full length proteins.

Example 15: Proteolytic Cleavage Site Variants

The arginine (R) at position 28 of PIP-1A was mutated to alter the trypsin cleavage site. The variants were generated using a similar strategy as described in Example 9 using the saturation mutagenesis primers R28R (SEQ ID NO: 218), and R28F (SEQ ID NO: 219). Table 14 shows the amino acid substitutions identified, those substitutions that expressed soluble protein, and those substitutions that were active in the Lygus assay with a minimal score of 4 or greater out of total maximal score of 8. This data demonstrate that the amino substitutions indicated in Table 14 as "Active mutants" can be made to eliminate a proteolytic cleavage site while retaining activity.

TABLE 14

| Position | Identified mutations | Soluble expressed Mutants | Lygus Active mutants |
|---|---|---|---|
| R28 | S, K, T, V, G, A, M, D, W, P, L, H, C, Q, | S, K, T, V, G, A, M, D, W, P, L, H, C, Q, | S, K, T, V, G, A, M, D, W, P, L, H, C, Q, |

Example 16: Multiple Residue Motif 4 PIP-1A Variants

To further explore the role of motif 4 (amino acids 240 to 249 of PIP-1A (SEQ ID NO: 2), a series of variants were generated with multiple amino acid substitutions in motif 4. The variants were generated using a similar mutagenesis strategy as described in Example 9 using the mutagenesis primer Motif 4-Comb-F CCGCTGGATTGGGATACTGTT-VWWNGCHAYDTTWTKDTKGRKNAYTWTNAYCCA-GGCAGC AATAGTGGGCACTTC (SEQ ID NO: 326) paired with primer 3188R GGATGTGCTGCAAGGCGAT-TAAG (SEQ ID NO: 327) and Comb-R AACAGTATC-CCAATCCAGCGG (SEQ ID NO: 328) paired with 3188F CAGACTGTCGATGAAGCCCTGAAAG (SEQ ID NO: 329). The mutagenesis primer Motif 4-Comb-F was designed to be partially degenerate at residues 240-249 of PIP-1A (SEQ ID NO: 2) resulting in selected amino acid substitutions at each residues. Table 15 shows the degenerate codon encoding each of residues 240-249 and the possible resulting amino acids. In Table 15 the native amino acid is indicated in bold and underlining.

TABLE 15

| Residue | Degenerate codon | Degeneracy | Resulting amino acids* |
|---|---|---|---|
| 240 | VWW | V = A, G OR C<br>W = A OR T | Gln, Lys, Glu, Asp, Ile, Val, Asn, His and Leu |
| 241 | NGC | N = G, A, T OR C | Arg, Ser, Gly, and Cys |
| 242 | HAY | H = A, C OR T<br>Y = C OR T | Asn, His, and Tyr |
| 243 | DTT | D = A, G OR T | Val, Ile and Phe |
| 244 | WTK | W = A OR T<br>K = G OR T | Leu, Met, Ile and Phe |
| 245 | DTK | D = A, G OR T<br>K = G OR T | Met, Ile, Val, Leu and Phe |
| 246 | GRK | R = A OR G<br>K = G OR T | Glu, Gly and Asp |
| 247 | NAY | N = G, A, T OR C<br>Y = C OR T | Asn, Asp, Tyr and His |
| 248 | TWT | W = A OR T | Tyr and Phe |
| 249 | NAY | N = G, A, T OR C<br>Y = C OR T | Asn, Asp, Tyr and His |

The resulting polynucleotides encoding the PIP-1A variant polypeptides were expressed as MBP fusions in *E. coli* and screened as cleared lysates in a 96 well format (3 plates) for *Lygus* insecticidal activity as described in Example 1 and scored for activity on a scale of 0 to 8 (see FIG. 4). The clones encoding the variant PIP-polypeptides having *Lygus* insecticidal activity ranging from 4 to 8 were DNA sequenced (SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, and SEQ ID NO: 244) to determine the identity of the amino acid substitutions at residues 240-249 of the PIP1A polypeptides of SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, and SEQ ID NO: 269, which are shown in Table 16. The motif 4 amino acid substitutions compared to PIP-1A (SEQ ID NO: 2) are indicated in bold and underlining.

TABLE 16

| Variant | Amino acids seq | # of mutations | Soluble expression |
|---|---|---|---|
| PIP-1A | QRNVLMENYN (a.a. 240-249 of SEQ ID NO: 2) | 0 | Yes |
| 1A3 SEQ ID NO: 245 | NSYVLLDYYY (a.a. 240-249 of SEQ ID NO: 245) | 7 | Yes |
| 1E3 SEQ ID NO: 246 | NCYIFMEYYD (a.a. 240-249 of SEQ ID NO: 246) | 7 | Yes |
| 1F5 SEQ ID NO: 247 | NCYIMMENFD (a.a. 240-249 of SEQ ID NO: 247) | 7 | Yes |
| 1B9 SEQ ID NO: 248 | QCNVLFDNFH (a.a. 240-249 of SEQ ID NO: 248) | 5 | Yes |
| 1C10 SEQ ID NO: 249 | QGYVLVDNFN (a.a. 240-249 of SEQ ID NO: 249) | 5 | Yes |
| 1A11 SEQ ID NO: 250 | NRYVFFGNYD (a.a. 240-249 of SEQ ID NO: 250) | 6 | Yes |
| 2A2 SEQ ID NO: 251 | QCNIMIGYFD (a.a. 240-249 of SEQ ID NO: 251) | 8 | Yes |
| 2G1 SEQ ID NO: 252 | QGNVLMENYN (a.a. 240-249 of SEQ ID NO: 252) | 1 | Yes |
| 2C7 SEQ ID NO: 253 | VSNILVGNFN (a.a. 240-249 of SEQ ID NO: 253) | 6 | Yes |
| 2E1 SEQ ID NO: 254 | NRHVLVDNFY (a.a. 240-249 of SEQ ID NO: 254) | 5 | Yes |
| 2E12 SEQ ID NO: 255 | VSNVLIDDFD (a.a. 240-249 of SEQ ID NO: 255) | 7 | Yes |
| 2F4 SEQ ID NO: 256 | VSHVMMEDYD (a.a. 240-249 of SEQ ID NO: 256) | 6 | Yes |
| 2F8 SEQ ID NO: 257 | NSHILVGNYD (a.a. 240-249 of SEQ ID NO: 257) | 7 | Yes |
| 2G5 SEQ ID NO: 258 | NSYVMIENFY (a.a. 240-249 of SEQ ID NO: 258) | 7 | Yes |
| 2G6 SEQ ID NO: 259 | NCNIIMENYD (a.a. 240-249 of SEQ ID NO: 259) | 5 | Yes |
| 3A2 SEQ ID NO: 260 | IRYIFIDNFD (a.a. 240-249 of SEQ ID NO: 260) | 8 | Yes |
| 3A10 SEQ ID NO: 261 | VRNVLVENYH (a.a. 240-249 of SEQ ID NO: 261) | 3 | Yes |
| 3C7 SEQ ID NO: 262 | QRYVLIDNFY (a.a. 240-249 of SEQ ID NO: 262) | 5 | Yes |
| 3E3 SEQ ID NO: 263 | LSHFMLGNFN (a.a. 240-249 of SEQ ID NO: 263) | 8 | Yes |
| 3F1 SEQ ID NO: 264 | RCNVLMGDFD (a.a. 240-249 of SEQ ID NO: 264) | 6 | Yes |
| 3F2 SEQ ID NO: 265 | IGNVMVGDFD (a.a. 240-249 of SEQ ID NO: 265) | 8 | Yes |
| 3F6 SEQ ID NO: 266 | QCYVLIENFH (a.a. 240-249 of SEQ ID NO: 266) | 5 | Yes |
| 3F12 SEQ ID NO: 267 | VCNVLMEHFY (a.a. 240-249 of SEQ ID NO: 267) | 5 | Yes |
| 3G7 SEQ ID NO: 268 | VRNVFFDYFD (a.a. 240-249 of SEQ ID NO: 268) | 7 | Yes |

TABLE 16-continued

| Variant | Amino acids seq | # of mutations | Soluble expression |
|---|---|---|---|
| 3F4 SEQ ID NO: 269 | VSYILFDNFH (a.a. 240-249 of SEQ ID NO: 269) | 8 | Yes |

The clones encoding the variant PIP-1A polypeptides having *Lygus* insecticidal activity ranging from 0 to 4 were DNA sequenced (SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, and SEQ ID NO: 297), to determine the identity of the amino acid substitutions at residues 240-249 of the PIP-1A polypeptides SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, and SEQ ID NO: 325, which are shown in Table 17. Protein expression analysis by SDS-PAGE (data not shown) revealed that the variant proteins with *Lygus* insecticidal activity from 0 to 4 affect soluble expression (protein folding and solubility) in *E. coli* with the proteins accumulating as insoluble fraction of the cleared lysate. The loss of activity from the multiple substitutions in motif 4 appears to be from the lack of soluble expressed proteins in the *E coli* expression system. Motif 4 appears to be tolerant to multiple amino acid substitution while remaining active.

TABLE 17

| Variants | Amino acids SEQ | # of mutations | Soluble expression |
|---|---|---|---|
| PIP-1A | QRNVLMENYN (a.a. 240-249 of SEQ ID NO: 2) | 0 | yes |
| 1B7 SEQ ID NO: 298 | HSYVFIDNYN (a.a. 240-249 of SEQ ID NO: 298) | 6 | No |
| 1C7 SEQ ID NO: 299 | VCNFFFGDFD (a.a. 240-249 of SEQ ID NO: 299) | 9 | No |
| 1D7 SEQ ID NO: 300 | KRYFMMGYFH (a.a. 240-249 of SEQ ID NO: 300) | 8 | No |
| 1E7 SEQ ID NO: 301 | LCHVFIGYFY (a.a. 240-249 of SEQ ID NO: 301) | 9 | No |
| 1F7 SEQ ID NO: 302 | EGNFFVGNFD (a.a. 240-249 of SEQ ID NO: 302) | 8 | No |
| 1A8 SEQ ID NO: 303 | IRYFILEDYN (a.a. 240-249 of SEQ ID NO: 303) | 6 | No |
| 1B8 SEQ ID NO: 304 | LGYFMVEDFD (a.a. 240-249 of SEQ ID NO: 304) | 9 | No |
| 1C8 SEQ ID NO: 305 | KGNVLVEYYN (a.a. 240-249 of SEQ ID NO: 305) | 4 | No |
| 1D8 SEQ ID NO: 306 | LSNVIMGHFY (a.a. 240-249 of SEQ ID NO: 306) | 7 | No |
| 1E8 SEQ ID NO: 307 | VSYVFFGHFD (a.a. 240-249 of SEQ ID NO: 307) | 9 | No |
| 1G8 SEQ ID NO: 308 | DGYILVGNFD (a.a. 240-249 of SEQ ID NO: 308) | 8 | No |
| 1A9 SEQ ID NO: 309 | NGNIFLDHFD (a.a. 240-249 of SEQ ID NO: 309) | 9 | No |
| 1D9 SEQ ID NO: 310 | ICYIIFDDYH (a.a. 240-249 of SEQ ID NO: 310) | 9 | No |
| 1F9 SEQ ID NO: 311 | NSNFLFENFH (a.a. 240-249 of SEQ ID NO: 311) | 6 | No |
| 1D10 SEQ ID NO: 312 | LCHILIGDYN (a.a. 240-249 of SEQ ID NO: 312) | 7 | No |
| 1E10 SEQ ID NO: 313 | HCNVIVDYYN (a.a. 240-249 of SEQ ID NO: 313) | 6 | No |
| 1F10 SEQ ID NO: 314 | EGYVMFGYFN (a.a. 240-249 of SEQ ID NO: 314) | 8 | No |
| 1B11 SEQ ID NO: 315 | VCYILVEYYH (a.a. 240-249 of SEQ ID NO: 315) | 7 | No |
| 1C11 SEQ ID NO: 316 | LRHVMFGNYY (a.a. 240-249 of SEQ ID NO: 316) | 6 | No |
| 1D11 SEQ ID NO: 317 | NRNIFFDDYY (a.a. 240-249 of SEQ ID NO: 317) | 7 | No |
| 1E11 SEQ ID NO: 318 | KGYVMVGDFN (a.a. 240-249 of SEQ ID NO: 318) | 8 | No |
| 1F11 SEQ ID NO: 319 | LGNFFLGYYN (a.a. 240-249 of SEQ ID NO: 319) | 7 | No |
| 1H11 SEQ ID NO: 320 | LSNVLIDNFY (a.a. 240-249 of SEQ ID NO: 320) | 6 | No |
| 1A12 SEQ ID NO: 321 | NCYFIVDDYN (a.a. 240-249 of SEQ ID NO: 321) | 8 | No |
| 1B12 SEQ ID NO: 322 | ISYVFVEDFH (a.a. 240-249 of SEQ ID NO: 322) | 8 | No |
| 1D12 SEQ ID NO: 323 | NIHIMIEYYH (a.a. 240-249 of SEQ ID NO: 323) | 8 | No |
| 1E12 SEQ ID NO: 324 | IGHFMLDYYH (a.a. 240-249 of SEQ ID NO: 324) | 9 | No |
| 1G12 SEQ ID NO: 325 | ICYVMVGNYH (a.a. 240-249 of SEQ ID NO: 325) | 7 | No |

Example 17: Identification of an Insecticidal Protein Active Against *Lygus* from Strain JH19887-2

A Blast search of a proprietary genomic contig library of a *Pseudomonas Protegens* strain JH19887-2 against the PIP-1 polynucleotide sequence of SEQ ID NO: 1 identified a polynucleotide of SEQ ID NO: 331, encoding a polypeptide of SEQ ID NO: 332 (herein referred to as PIP-1C) having 82% sequence identity to PIP-1A (SEQ ID NO: 2). Table 18 shows the % sequence identity between PIP-1C (SEQ ID NO: 332) and PIP-1A (SEQ ID NO: 2), PIP-1B (SEQ ID NO: 4), and PSEEN3174 (SEQ ID NO: 6). FIG. 5 shows the sequence alignment of PIP-1A (SEQ ID NO: 2), PIP-1B (SEQ ID NO: 4), PIP-1C (SEQ ID NO: 332) and PSEEN3174 (SEQ ID NO: 6). PIP-1C was expressed in *E. coli* in the same way as PIP-1A. The purified PIP-1C was assayed against Soybean looper (SBL) and *lygus* in diet based assays. PIP-1C (SEQ ID NO: 332) demonstrated killing activity against both SBL and *lygus* demonstrating insecticidal spectrum similar to PIP-1A (SEQ ID NO: 2).

TABLE 18

|  | PIP-1A SEQ ID NO: 2 | PIP-1B SEQ ID NO: 4 | PSEEN3174 SEQ ID NO: 6 | PIP-1C SEQ ID NO: 332 |
| --- | --- | --- | --- | --- |
| PIP-1A |  | 93% | 79% | 82% |
| PIP-1B |  |  | 79% | 84% |
| PSEEN3174 |  |  |  | 80% |
| PIP-1C |  |  |  |  |

Example 18: Transformation of Maize by Particle Bombardment and Regeneration of Transgenic Plants Immature maize embryos from greenhouse donor plants are bombarded with a DNA molecule containing the toxin nucleotide sequence (e.g., SEQ ID NO: 1) operably linked to an ubiquitin promoter and the selectable marker gene PAT (Wohlleben, et al., (1988) *Gene* 70: 25-37), which confers resistance to the herbicide Bialaphos. Alternatively, the selectable marker gene is provided on a separate DNA molecule. Transformation is performed as follows. Media recipes follow below.

Preparation of Target Tissue

The ears are husked and surface sterilized in 30% CLOROX™ bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

Preparation of DNA

A plasmid vector comprising a nucleotide sequence (e.g., SEQ ID NO: 1) operably linked to an ubiquitin promoter is made. For example, a suitable transformation vector comprises a UBI1 promoter from *Zea mays*, a 5' UTR from UBI1 and a UBI1 intron, in combination with a PinII terminator. The vector additionally contains a PAT selectable marker gene driven by a CAMV35S promoter and includes a CAMV35S terminator. Optionally, the selectable marker can reside on a separate plasmid. A DNA molecule comprising a toxin nucleotide sequence as well as a PAT selectable marker is precipitated onto 1.1 μm (average diameter) tungsten pellets using a $CaCl_2$ precipitation procedure as follows:

100 μL prepared tungsten particles in water
10 μL (1 μg) DNA in Tris EDTA buffer (1 μg total DNA)
100 μL 2.5 M $CaCl_2$
10 μL 0.1 M spermidine Each reagent is added sequentially to a tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 mL 100% ethanol, and centrifuged for 30 seconds. Again the liquid is removed, and 105 μL 100% ethanol is added to the final tungsten particle pellet. For particle gun bombardment, the tungsten/DNA particles are briefly sonicated and 10 μL spotted onto the center of each macrocarrier and allowed to dry about 2 minutes before bombardment.

Particle Gun Treatment

The sample plates are bombarded at level #4 in particle gun # HE34-1 or # HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for expression of the toxin by assays known in the art or as described above.

Bombardment and Culture Media

Bombardment medium (560Y) comprises 4.0 g/L N6 basal salts (SIGMA C-1416), 1.0 mL/L Eriksson's Vitamin Mix (1000× SIGMA-1511), 0.5 mg/L thiamine HCl, 120.0 g/L sucrose, 1.0 mg/L 2,4-D and 2.88 g/L L-proline (brought to volume with deionized $H_2O$ following adjustment to pH 5.8 with KOH); 2.0 g/L Gelrite™ (added after bringing to volume with dI $H_2O$); and 8.5 mg/L silver nitrate (added after sterilizing the medium and cooling to room temperature). Selection medium (560R) comprises 4.0 g/L N6 basal salts (SIGMA C-1416), 1.0 mL/L Eriksson's Vitamin Mix (1000× SIGMA-1511), 0.5 mg/L thiamine HCl, 30.0 g/L sucrose, and 2.0 mg/L 2,4-D (brought to volume with dI $H_2O$ following adjustment to pH 5.8 with KOH); 3.0 g/L Gelrite™ (added after bringing to volume with dI $H_2O$); and 0.85 mg/L silver nitrate and 3.0 mg/L Bialaphos (both added after sterilizing the medium and cooling to room temperature).

Plant regeneration medium (288J) comprises 4.3 g/L MS salts (GIBCO 11117-074), 5.0 mL/L MS vitamins stock solution (0.100 g nicotinic acid, 0.02 g/L thiamine HCl, 0.10 g/L pyridoxine HCl, and 0.40 g/L Glycine brought to volume with polished D-I $H_2O$) (Murashige and Skoog, (1962) *Physiol. Plant.* 15:473), 100 mg/L myo-inositol, 0.5 mg/L zeatin, 60 g/L sucrose, and 1.0 mL/L of 0.1 mM abscisic acid (brought to volume with polished dI $H_2O$ after adjusting to pH 5.6); 3.0 g/L Gelrite™ (added after bringing to volume with dI $H_2O$); and 1.0 mg/L indoleacetic acid and 3.0 mg/L Bialaphos (added after sterilizing the medium and cooling to 60° C.).

Hormone-free medium (272V) comprises 4.3 g/L MS salts (GIBCO 11117-074), 5.0 mL/L MS vitamins stock solution (0.100 g/L nicotinic acid, 0.02 g/L thiamine HCl, 0.10 g/L pyridoxine HCl, and 0.40 g/L Glycine brought to volume with polished dI $H_2O$), 0.1 g/L myo-inositol, and 40.0 g/L sucrose (brought to volume with polished dI $H_2O$ after adjusting pH to 5.6); and 6 g/L Bacto-agar (added after bringing to volume with polished dI $H_2O$), sterilized and cooled to 60° C.

Example 19: *Agrobacterium*-Mediated Transformation of Maize and Regeneration of Transgenic Plants For *Agrobacterium*-mediated transformation of maize with a toxin nucleotide sequence (e.g., SEQ ID NO: 1), the method of Zhao can be used (U.S. Pat. No. 5,981,840 and PCT Patent Publication Number WO 1998/32326; the contents of which are hereby incorporated by reference). Briefly, immature embryos are isolated from maize and the embryos contacted with a suspension of *Agrobacterium* under conditions whereby the bacteria are capable of transferring the nucleotide sequence (e.g. SEQ ID NO: 1) to at least one cell of at least one of the immature embryos (step 1: the infection step). In this step the immature embryos can be immersed in an *Agrobacterium* suspension for the initiation of inoculation. The embryos are co-cultured for a time with the *Agrobacterium* (step 2: the co-cultivation step). The immature embryos can be cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos can be cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium can be cultured on solid medium to regenerate the plants.

Example 19: Transformation of Soybean Embryos

Soybean embryos are bombarded with a plasmid containing a nucleotide sequence (e.g., SEQ ID NO: 1) operably linked to a pin II promoter as follows. To induce somatic embryos, cotyledons, 3-5 mm in length dissected from surface-sterilized, immature seeds of an appropriate soybean cultivar are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein, et al., (1987) *Nature* (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188), and the 3' region of the nopaline synthase gene from the T-DNA of the Ti plasmid of *Agrobacterium tumefaciens*. The expression cassette comprising a toxin nucleotide sequence (e.g., SEQ ID NO: 1) operably linked to the pinII promoter can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 204 spermidine (0.1M), and 50 µL $CaCl_2$ (2.5M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment the liquid media may be exchanged with fresh media, and eleven to twelve days post-bombardment with fresh media containing 50 mg/mL hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

Although the foregoing disclosure has been described in some detail by way of illustration and example for purposes of clarity of understanding, it will be obvious that certain changes and modifications may be practiced within the scope of the appended claims.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above. The invention may be practiced in ways other than those particularly described in the foregoing description and examples. Numerous modifications and variations of the invention are possible in light of the above teachings and, therefore, are within the scope of the appended claims.

These and other changes may be made to the invention in light of the above detailed description. In general, in the following claims, the terms used should not be construed to limit the invention to the specific embodiments disclosed in the specification and the claims.

Certain teachings related to PIP polynucleotides and polypeptides were disclosed in U.S. Provisional patent application No. 61/667,039, filed Jul. 2, 2012, the disclosure of which is herein incorporated by reference in its entirety.

The entire disclosure of each document cited (including patents, patent applications, journal articles, abstracts, manuals, books, or other disclosures) in the Background of the Invention, Detailed Description, and Examples is herein incorporated by reference in their entireties.

The above examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight; temperature is in degrees centigrade; and pressure is at or near atmospheric.

That which is claimed:

1. A recombinant nucleic acid molecule encoding a *Pseudomonas* Insecticidal Protein-1 (PIP-1) polypeptide having at least 95% identity to the full-length amino acid sequence of SEQ ID NO: 2 and having oral insecticidal activity against an insect pest in the order Hemiptera and/or an insect pest in the order Lepidoptera, wherein the recombinant nucleic acid is operably linked to a heterologous regulatory element.

2. The recombinant nucleic acid molecule of claim 1, wherein the PIP-1 polypeptide comprises an amino acid sequence of SEQ ID NO: 213, wherein;

Xaa at position 2 is Pro, Thr or Ser;

Xaa at position 3 is Ile, Thr, Leu, Val, Met or Ser;

Xaa at position 6 is Glu, Gly, Asp or Ala;

Xaa at position 8 is Ser, Gly, Asn, Thr or Gln;

Xaa at position 19 is Asp, Glu or Cys;

Xaa at position 20 is Leu, Val, Ile or Met;

Xaa at position 21 is Lys, Ser, Asn, Arg, Thr or Gln;

Xaa at position 22 is Ser, Lys, Arg or Thr;
Xaa at position 24 is Gln, Gly, Asn or Ala;
Xaa at position 25 is Gly or Ala;
Xaa at position 26 is Ser, Asn, Thr or Gln;
Xaa at position 27 is Leu, Thr, Ala, Ser, Ile, Val or Met;
Xaa at position 28 is Arg, Ser, Lys, Thr, Val, Gly, Ala, Met, Asp, Trp, Pro, Leu, His, Cys or Gln;
Xaa at position 30 is Ala, Ile, Leu, Val or Met;
Xaa at position 35 is Phe, Leu, Ile, Val or Met;
Xaa at position 36 is Ala, Ser, Thr, Val, Ile or Leu;
Xaa at position 38 is Asn, Arg, Ser, Gln, Lys or Thr;
Xaa at position 42 is Phe, Tyr, Trp, Leu, Ile, Val or Met;
Xaa at position 43 is Pro, Met, Gly, Gln, Ser, Thr, Arg, Val, Leu, Lys, Asp, Ala, Asn, Phe, Trp, Glu or Cys;
Xaa at position 46 is Arg, Lys or His;
Xaa at position 48 is Gly, Asp, Ala or Glu;
Xaa at position 49 is Phe, Tyr, Trp, Leu, Ile, Val or Met;
Xaa at position 53 is Ser, Gly, Ala or Thr;
Xaa at position 58 is Tyr or Phe;
Xaa at position 60 is Ala, Ser, Gly or Thr;
Xaa at position 63 is Gln, Lys, Asn or Arg;
Xaa at position 66 is Trp, Tyr, Phe, Arg, Lys, His, Ile, Val or Ser;
Xaa at position 77 is Phe, Tyr, Trp, Leu, Ile, Val or Met;
Xaa at position 89 is Pro, Leu, Gly, Arg, Thr, Ser, Met, Ala, Ile, Asn, Val, Cys or Lys;
Xaa at position 93 is Tyr, Cys, Trp, Val, Asp, Asn, Ile, Leu, Met, Phe, Ala or Thr;
Xaa at position 97 is Met, Val, Leu or Ile;
Xaa at position 98 is Asp or Glu;
Xaa at position 105 is Gln or Asn;
Xaa at position 107 is Thr, Ile, Ser, Leu or Val;
Xaa at position 108 is Gln, Thr, Ser or Asn;
Xaa at position 110 is Arg, Leu, Lys, Ile, Val or Met;
Xaa at position 120 is Lys, Arg, Gln or Asn;
Xaa at position 121 is Thr or Ser;
Xaa at position 123 is Thr, Glu, Ser or Asp;
Xaa at position 125 is Asn, Ser, Gln or Thr;
Xaa at position 127 is Ser, Asn, Thr, Gln, Lys, Ser or Arg;
Xaa at position 134 is Gly or Ala;
Xaa at position 135 is Ser, Asn, Thr, Gln, Arg or Lys;
Xaa at position 137 is Asp, Gly, Glu or Ala;
Xaa at position 141 is Val, Ile or Leu;
Xaa at position 142 is Gly, Asp, Ala or Glu;
Xaa at position 144 is Asp or Glu;
Xaa at position 147 is Ile, Thr, Val, Leu, Met or Ser;
Xaa at position 150 is Ser or Thr;
Xaa at position 151 is Asn, Arg, Ser, Gln, Lys or Thr;
Xaa at position 160 is Thr or Ser;
Xaa at position 162 is Ser or Thr;
Xaa at position 163 is Asn, Asp, Glu or Gln;
Xaa at position 164 is Ser or Thr;
Xaa at position 166 is Gln, Glu, Asp or Asn;
Xaa at position 167 is Leu, Met, Ile, Val;
Xaa at position 168 is Thr, Lys, Ala, Ser, Arg or Gly;
Xaa at position 171 is Gly, Leu, Gln, Met, Cys, Asn, Asp, Ser or Ala;
Xaa at position 172 is Thr, Gly, His, Phe, Glu, Arg, Ser, Asn, Ile, Trp, Lys, Gln, Cys, Val, Ala or Met;
Xaa at position 173 is Phe, Gly, His, Leu, Ala, Arg, Asn, Cys, Lys, Trp, Thr, Ser, Tyr or Met;
Xaa at position 174 is Ile, Val, Gly, Arg, Asn, Ala, Gln, Met, Cys, Leu, Phe, Tyr, Lys, Glu, Ser, His or Thr;
Xaa at position 175 is Val, Ile, Ala, Cys, Glu, Lys, Leu or Met;
Xaa at position 176 is Tyr, Met, Phe, Leu or Cys;
Xaa at position 177 is Gln, Ile, Met or Pro;
Xaa at position 178 is Val, Cys, Thr, Pro, Ala, Met, Gln, Phe, Ile, Ser or Lys;
Xaa at position 179 is Val, Phe, Thr, Ile, Cys, Leu, Met, Ser, Ala or Gln;
Xaa at position 180 is Met, Leu; Pro, Trp, Asn, Tyr, Gly, Gln, Ala, Val, Phe, Ile, Cys or Ser;
Xaa at position 181 is Val, Ala, Leu, Trp, Cys, Thr, Ile or Lys;
Xaa at position 182 is Tyr, Phe, Met or His;
Xaa at position 183 is Ala, Met, Val, Thr, Asp, Gly, Cys, Ile, Phe, Ser, Gln or Leu;
Xaa at position 191 is Arg or Lys;
Xaa at position 194 is Gly or Ala;
Xaa at position 195 is Asn, Tyr, Gln or Trp;
Xaa at position 200 is Asn, Ser, Thr or Gln;
Xaa at position 203 is Asn or Gln;
Xaa at position 204 is Thr, Ala, Ser or Gly;
Xaa at position 206 is Gly, Asp, Ala or Glu;
Xaa at position 209 is Leu, Val, Ile or Met;
Xaa at position 213 is Tyr or Phe;
Xaa at position 220 is Asn, Arg, Gln or Lys;
Xaa at position 221 is Ser, Lys, Thr or Arg;
Xaa at position 222 is Thr, Arg, Ser or Lys;
Xaa at position 226 is Asp, Pro, Glu or Gln;
Xaa at position 228 is Ser or Gly;
Xaa at position 229 is Lys, Asn, Arg or Gln;
Xaa at position 231 is Ile, Val, Leu or Met;
Xaa at position 232 is Ala, Thr, Ser, Gly, Asp or Glu;
Xaa at position 240 is Gln, Arg, Ala, Val, Glu, Met, Gly, Asp, Trp, Asn, Thr, Ile, Ser, Phe, His, Cys or Leu;
Xaa at position 241 is Arg, Lys, Glu, Gln, Ser, Ile, Val, Asp, Tyr, Met, Asn, His, Pro, Gly, Leu, Phe, Thr, Ala or Cys;
Xaa at position 242 is Asn, Ala, Arg, Lys, His, Ser, Cys, Glu, Pro, Trp, Gln, Thr, Phe, Tyr, Met, Asp, Gly, Leu or Val;
Xaa at position 243 is Val, Leu, Ala, Thr, Gly, Cys, Ile, Ser or Met;
Xaa at position 244 is Leu, Val, Phe, Ile, Met, Gln, Cys, Trp or Ala;
Xaa at position 245 is Met, Ala, Arg, Asp, Glu, Leu, Pro, Ser, Trp, Gly, Val, Lys, Phe, Cys, Thr, His, Ile, Gln, Tyr or Asn;
Xaa at position 246 is Glu, Asp, Tyr, Gly, Arg, Val, Ala, Trp, Gln, Ser, Asn, Ile Leu, Met, Cys, Pro, His, Phe, Thr or Lys;
Xaa at position 247 is Asn, Leu, Asp, Tyr, Ala, Phe, His, Arg, Lys, Gln, Gly, Val, Ile, Ser, Glu, Pro, Met, Trp, Thr or Cys;
Xaa at position 248 is Tyr, Val, Thr, Glu, Phe, Ser, His, Cys, Leu, Trp, Ile, Asp, Gly or Ala;
Xaa at position 249 is Asn, Lys, Val, Gly, Met, Asp, Cys, Phe, Arg, Glu, Trp, Tyr, Ser, Ile, Thr, Pro, Leu, Ala, His or Gln;
Xaa at position 251 is Gly, Ser, Thr, Ala, Asp or Glu;
Xaa at position 254 is Ser, Asn, Thr or Gln;
Xaa at position 258 is Ser, Arg, Thr or Lys;
Xaa at position 259 is Phe, Trp, Tyr, Cys, Met, Leu, Val, Ile or His;
Xaa at position 265 is Asn, Asp, Gln or Glu; and
Xaa at position 266 is Asp, Asn, Gln or Glu;
and wherein, 1 to 28 amino acids are optionally deleted from the N-terminus of the polypeptide.

3. The recombinant nucleic acid molecule of claim 1 selected from:
  a) a recombinant nucleic acid molecule comprises the polynucleotide sequence of SEQ ID NO: 1;

b) a recombinant nucleic acid molecule encoding a PIP-1 polypeptide comprises the amino acid sequence of SEQ ID NO: 2 and
c) a recombinant nucleic acid molecule that hybridizes under stringent conditions to a polynucleotide of SEQ ID NO: 1.

4. An expression cassette, comprising the recombinant nucleic acid molecule of claim 1, 2 or 3, wherein the recombinant nucleic acid molecule is operably linked to one or more regulatory sequences directing expression of the PIP-1 polypeptide.

5. A transgenic plant or progeny thereof stably transformed with the recombinant nucleic acid molecule of claim 1, 2 or 3.

6. The transgenic plant or progeny thereof of claim 5, further comprising one or more additional transgenic traits.

7. Seed, grain or a processed product thereof, of the transgenic plant or progeny thereof of claim 5, wherein the seed or grain comprises the recombinant nucleic acid molecule.

8. The seed of claim 7, wherein one or more seed treatment has been applied to the seed.

9. A recombinant microorganism, comprising the recombinant nucleic acid molecule of claim 1.

10. A transgenic plant transformed with the recombinant nucleic acid molecule of claim 1, 2 or 3 capable of expressing said recombinant nucleic acid molecule.

11. A plant or progeny thereof stably transformed with a recombinant nucleic acid molecule selected from
a) a recombinant nucleic acid molecule comprising the nucleic acid sequence of SEQ ID NO: 3;
b) a recombinant nucleic acid molecule encoding the polypeptide of SEQ ID NO: 4;
c) a recombinant nucleic acid molecule encoding the polypeptide having at least 95% homology to the amino acid sequence of SEQ ID NO: 4;
d) a recombinant nucleic acid molecule comprising the nucleic acid sequence of SEQ ID NO: 5;
e) a recombinant nucleic acid molecule encoding the polypeptide of SEQ ID NO: 6;
f) a recombinant nucleic acid molecule encoding the polypeptide having at least 95% homology to the amino acid sequence of SEQ ID NO: 6;
g) a recombinant nucleic acid molecule comprising the nucleic acid sequence of SEQ ID NO: 331,
h) a recombinant nucleic acid molecule encoding the polypeptide of SEQ ID NO: 332; and
i) a recombinant nucleic acid molecule encoding the polypeptide having at least 95% homology to the amino acid sequence of SEQ ID NO: 332;
wherein the recombinant nucleic acid molecule encodes a polypeptide having insecticidal activity.

* * * * *

SEQUENCE LISTING

<160> NUMBER OF SEQ ID NOS: 332

<210> SEQ ID NO 1
<211> LENGTH: 816
<212> TYPE: DNA
<213> ORGANISM: Pseudomonas chlororaphis

<400> SEQUENCE: 1

```
atgccgatca aggaagagct gagccagcct caaagtcatt cgatcgaact tgacgacctg      60
aaaagtgagc aaggaagtct ccgcgccgct ttgacatcca actttgctgg caacttcgat     120
cagttcccaa ctaagcgtgg tggctttgcg atcgacagct acctgctgga ttacagcgcg     180
cccaagcaag gctgctgggt agatggcatt accgtctacg gtgacatctt tatcggcaag     240
cagaattggg gcacctacac tcgcccggtc tttgcctacc tgcagtacat ggacaccatt     300
tccattccgc agcaggtgac acagactcgc agctatcagt tgactaaggg acacaccaaa     360
acgttcacga ccaatgtcag cgccaaatac agcgttggag gtagtattga catcgtcaac     420
gtcggttcgg atatctcaat tggattcagt aacagtgaat cctggtctac tacgcagacg     480
ttcagcaata gcactcaatt gactggtcct ggcaccttca tcgtgtatca ggttgttatg     540
gtttatgcgc acaacgccac ttctgcgggc aggcagaatg gtaatgcctt cgcctacaac     600
aagaccaata ctgtcggctc gcggctggac ttgtactatt tgtctgccat cactcagaac     660
agtacggtca ttgtcgattc cagcaaggcc atcgcgccgc tggattggga tactgttcag     720
cgcaatgtgt tgatggagaa ctacaaccca ggcagcaata gtgggcactt cagtttcgac     780
tggagcgcct acaacgatcc tcatcgccgt tattga                                816
```

<210> SEQ ID NO 2
<211> LENGTH: 271
<212> TYPE: PRT
<213> ORGANISM: Pseudomonas chlororaphis

<400> SEQUENCE: 2

```
Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80
```

```
Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270
```

```
<210> SEQ ID NO 3
<211> LENGTH: 816
<212> TYPE: DNA
<213> ORGANISM: Dendroctonus frontalis

<400> SEQUENCE: 3
atgaccatca aggaggagct gaaccagccg cagagccata gcatcgagct ggacgacctg    60
aacagcgagc agggcaacgc ccgcgccatc ctgaccagca acttcgccgg cagcttcgac   120
cagttcccga ccaagcgcgg cggctacgcc atcgacagct acctgctgga ctacagcgcc   180
ccgaagcagg gctgctgggt ggacggcatc accgtgtacg cgacatcttc atcggcaag    240 cagaactggg gcacctacac ccgcccggtg ttcgcctacc tgcagtacat ggacaccatc   300
agcatcccgc agcaggtgac ccagacccgc agctaccagc tgaccaaggg ccataccaag   360
accttcacca ccagcgtgac cgccaagtac agcgtgggcg gcagcatcgg catcgtgaac   420
gtgggcagcg acatcagcgt gggcttcagc agcagcgaga gctggagcac cacccagacc   480
ttcagcgaga gcacccagct ggccggcccg ggcaccttca tcgtgtacca ggtggtgctg   540
gtgtacgccc ataacgccac cagcgccggc cgccagaacg gcaacgcctt cgcctacaac   600
aagaccaaca ccgtgggcag ccgcctggac ctgtactacc tgagcgccat cacccagaac   660
agcaccgtga tcgtggagag cagcaaggcc atcgccccgc tggactggga caccgtgcag   720
cgcaacgtgc tgatggagaa ctacaacccg agcagcaaca gcggccattt cagcttcgac   780
tggagcgcct acaacgaccc gcatcgccgc tactaa                              816
```

```
<210> SEQ ID NO 4
<211> LENGTH: 271
<212> TYPE: PRT
<213> ORGANISM: Dendroctonus frontalis

<400> SEQUENCE: 4
```

```
Met Thr Ile Lys Glu Glu Leu Asn Gln Pro Gln Ser His Ser Ile Glu
1               5                   10                  15

Leu Asp Asp Leu Asn Ser Glu Gln Gly Asn Ala Arg Ala Ile Leu Thr
            20                  25                  30

Ser Asn Phe Ala Gly Ser Phe Asp Gln Phe Pro Thr Lys Arg Gly Gly
        35                  40                  45

Tyr Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Ser Val Thr Ala
        115                 120                 125

Lys Tyr Ser Val Gly Gly Ser Ile Gly Ile Val Asn Val Gly Ser Asp
    130                 135                 140

Ile Ser Val Gly Phe Ser Ser Glu Ser Trp Ser Thr Thr Gln Thr
145                 150                 155                 160

Phe Ser Glu Ser Thr Gln Leu Ala Gly Pro Gly Thr Phe Ile Val Tyr
                165                 170                 175

Gln Val Val Leu Val Tyr Ala His Asn Ala Thr Ser Ala Gly Arg Gln
            180                 185                 190

Asn Gly Asn Ala Phe Ala Tyr Asn Lys Thr Gln Thr Val Gly Ser Arg
        195                 200                 205

Leu Asp Leu Tyr Tyr Leu Ser Ala Ile Thr Gln Asn Ser Thr Val Ile
    210                 215                 220

Val Glu Ser Ser Lys Ala Ile Ala Pro Leu Asp Trp Asp Thr Val Gln
225                 230                 235                 240

Arg Asn Val Leu Met Glu Asn Tyr Asn Pro Ser Ser Asn Ser Gly His
                245                 250                 255

Phe Ser Phe Asp Trp Ser Ala Tyr Asn Asp Pro His Arg Tyr
            260                 265                 270

<210> SEQ ID NO 5
<211> LENGTH: 816
<212> TYPE: DNA
<213> ORGANISM: Pseudomonas entomophila

<400> SEQUENCE: 5
atgacgatca aggaagagct gggccagcct caaagccatt cgatcgaact ggacgaggtg      60
agcaaggagg ccgcaagtac gcgggccgcg ttgacttcca acctgtctgg ccgcttcgac     120
cagtacccga ccaagaaggg cgactttgcg atcgatggtt atttgctgga ctacagctca     180
cccaagcaag gttgctgggt ggacggtatc actgtctatg gcgatatcta catcggcaag     240
cagaactggg gcacttatac ccgcccggtg tttgcctacc tacagtatgt ggaaaccatc     300
tccattccac agaatgtgac gaccaccctc agctatcagc tgaccaaggg catacccgt     360 tccttcgaga ccagtgtcaa cgccaagtac agcgttggcg ccaacataga tatcgtcaac     420
gtgggttcgg agatttccac cgggtttacc cgcagcgagt cctggtccac cacgcagtcg     480
ttcaccgata ccaccgagat gaaggggcca gggacgttcg tcatttacca ggtcgtgctg     540
gtgtatgcgc acaacgccac ctcggcaggg cggcagaatg ccaatgcctt cgcctacagc     600
```

```
aaaacccagg cagtgggctc gcgggtggac ttgtactact tgtcggccat tacccagcgc    660
aagcgggtca tcgttccgtc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tattga                              816
```

<210> SEQ ID NO 6
<211> LENGTH: 271
<212> TYPE: PRT
<213> ORGANISM: Pseudomonas entomophila

<400> SEQUENCE: 6

```
Met Thr Ile Lys Glu Glu Leu Gly Gln Pro Gln Ser His Ser Ile Glu
1               5                   10                  15

Leu Asp Glu Val Ser Lys Glu Ala Ala Ser Thr Arg Ala Ala Leu Thr
                20                  25                  30

Ser Asn Leu Ser Gly Arg Phe Asp Gln Tyr Pro Thr Lys Lys Gly Asp
            35                  40                  45

Phe Ala Ile Asp Gly Tyr Leu Leu Asp Tyr Ser Ser Pro Lys Gln Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Asn Val Thr Thr Thr Leu Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Glu
    130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Val Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 7
<211> LENGTH: 720
<212> TYPE: DNA
<213> ORGANISM: Pseudomonas putida

<400> SEQUENCE: 7

```
atgacaggct tcgagcgttt gtcacccgat gcgttccccg ttttaaacgg ttcatacctg     60
attgaaaggt acctgctcag cacggacgag tttcatcctg gatgttggat agaaggtgaa    120
```

-continued

```
accgtctacg gtgggtttgg gtttccttca ggaaaaaaga aggtattgac ccgcccggtt    180
ttcgcctact tcgactacgt gggcacctat aaaacattaa gtgctggaga ctgtgaaatt    240
gatctgtccc gtgccagtgg gcatgaggtc tggtttgcac atgatgccga aggcttttct    300
gcgccgagtg gaattgggct ggtaagcgta aagtcagatc tgctctccgg ctgctctgcc    360
gaagagtggc ggccgttatc atcggttggg cataccgtgc gcgtagcggg agctgaatgc    420
tatgtggcct accagttgaa actggtctat gcgcattggg taaaacaggg cgatgcccag    480
tgctctgagc tgttcaaggt acagcccgtg cgtgtgcaag gcgacaacaa aggcgttttc    540
ttcctttctt ccgtggccac agacctgatg tgggtaggac atggttcgga taacaccaaa    600
gcgccaatat cacgacaggc gttatatcac ctgatattca atcttgctta tggcgcagcg    660
ggtgacgccg gctggagttt taatgatcag gcggccagca accgcttcct gcaatattga    720
```

<210> SEQ ID NO 8
<211> LENGTH: 239
<212> TYPE: PRT
<213> ORGANISM: Pseudomonas putida

<400> SEQUENCE: 8

```
Met Thr Gly Phe Glu Arg Leu Ser Pro Asp Ala Phe Pro Val Leu Asn
1               5                   10                  15

Gly Ser Tyr Leu Ile Glu Arg Tyr Leu Leu Ser Thr Asp Glu Phe His
            20                  25                  30

Pro Gly Cys Trp Ile Glu Gly Glu Thr Val Tyr Gly Gly Phe Gly Phe
        35                  40                  45

Pro Ser Gly Lys Lys Val Leu Thr Arg Pro Val Phe Ala Tyr Phe
    50                  55                  60

Asp Tyr Val Gly Thr Tyr Lys Thr Leu Ser Ala Gly Asp Cys Glu Ile
65                  70                  75                  80

Asp Leu Ser Arg Ala Ser Gly His Glu Val Trp Phe Ala His Asp Ala
                85                  90                  95

Glu Gly Phe Ser Ala Pro Ser Gly Ile Gly Leu Val Ser Val Lys Ser
            100                 105                 110

Asp Leu Leu Ser Gly Cys Ser Ala Glu Glu Trp Arg Pro Leu Ser Ser
        115                 120                 125

Val Gly His Thr Val Arg Val Ala Gly Ala Glu Cys Tyr Val Ala Tyr
    130                 135                 140

Gln Leu Lys Leu Val Tyr Ala His Trp Val Lys Gln Gly Asp Ala Gln
145                 150                 155                 160

Cys Ser Glu Leu Phe Lys Val Gln Pro Val Arg Val Gln Gly Asp Asn
                165                 170                 175

Lys Gly Val Phe Phe Leu Ser Ser Val Ala Thr Asp Leu Met Trp Val
            180                 185                 190

Gly His Gly Ser Asp Asn Thr Lys Ala Pro Ile Ser Arg Gln Ala Leu
        195                 200                 205

Tyr His Leu Ile Phe Asn Leu Ala Tyr Gly Ala Ala Gly Asp Ala Gly
    210                 215                 220

Trp Ser Phe Asn Asp Gln Ala Ala Ser Asn Arg Phe Leu Gln Tyr
225                 230                 235
```

<210> SEQ ID NO 9
<211> LENGTH: 729
<212> TYPE: DNA
<213> ORGANISM: Pseudomonas putida

```
<400> SEQUENCE: 9
atgaggtcat attcaatgag cgatttgatg aatgaaatca gccggtaccc cctgaaaaga        60
gggtctttcg aaatcgagca gtacctgata ggtgatcagt tgcatgccgg ttgctgggtg       120
gatgccgata ccacctacgg tgatgtcagg tgtggtaact atgactgggc cacttacacg       180
cggccagtct ttgcttatct gcaacatgtg gccacgatac gatccaatgt gcaaacggaa       240
cacgagcgcg aagtggtagt ttgcgagggc ttcagcaaga gtttctccca aggcgtcgag       300
tttaaggtag gcttctctgc tgacttcggc ccggcgaatg cgaacgctga actcactgcc       360
atgttttcgg tttctgaaac ggtgagcggt tcggagtcaa ccaagcgctc attgagagtg       420
aagggcgatg ggaccatcat ggtgtatcaa gtgcacatgg tctacgcgca ccacatgaca       480
tccgctggcg tgcttgctgg atacgtaccc tataccaaga gctcagatat attcaatgac       540
gatgggcggc tggtgcggca ggacatcacg atgctttcat cggtggtttg cgatcagctt       600
gttccggtca ggaatgaaaa atcaataaag cctctgacct ggagtcaggt taaccaagcg       660
gtcttgttca atcaatttga gaaagcgcca ggtgccagac gctggacttt tgatttctcg       720
gtattttga                                                              729

<210> SEQ ID NO 10
<211> LENGTH: 242
<212> TYPE: PRT
<213> ORGANISM: Pseudomonas putida

<400> SEQUENCE: 10

Met Arg Ser Tyr Ser Met Ser Asp Leu Met Asn Glu Ile Ser Arg Tyr
1               5                   10                  15

Pro Leu Lys Arg Gly Ser Phe Glu Ile Glu Gln Tyr Leu Ile Gly Asp
            20                  25                  30

Gln Leu His Ala Gly Cys Trp Val Asp Ala Asp Thr Thr Tyr Gly Asp
        35                  40                  45

Val Arg Cys Gly Asn Tyr Asp Trp Ala Thr Tyr Thr Arg Pro Val Phe
    50                  55                  60

Ala Tyr Leu Gln His Val Ala Thr Ile Arg Ser Asn Val Gln Thr Glu
65                  70                  75                  80

His Glu Arg Glu Val Val Val Cys Glu Gly Phe Ser Lys Ser Phe Ser
                85                  90                  95

Gln Gly Val Glu Phe Lys Val Gly Phe Ser Ala Asp Phe Gly Pro Ala
            100                 105                 110

Asn Ala Asn Ala Glu Leu Thr Ala Met Phe Ser Val Ser Glu Thr Val
        115                 120                 125

Ser Gly Ser Glu Ser Thr Lys Arg Ser Leu Arg Val Lys Gly Asp Gly
    130                 135                 140

Thr Ile Met Val Tyr Gln Val His Met Val Tyr Ala His His Met Thr
145                 150                 155                 160

Ser Ala Gly Val Leu Ala Gly Tyr Val Pro Tyr Thr Lys Ser Ser Asp
                165                 170                 175

Ile Phe Asn Asp Asp Gly Arg Leu Val Arg Gln Asp Ile Thr Met Leu
            180                 185                 190

Ser Ser Val Val Cys Asp Gln Leu Val Pro Val Arg Asn Glu Lys Ser
        195                 200                 205

Ile Lys Pro Leu Thr Trp Ser Gln Val Asn Gln Ala Val Leu Phe Asn
    210                 215                 220
```

```
Gln Phe Glu Lys Ala Pro Gly Ala Arg Arg Trp Thr Phe Asp Phe Ser
225                 230                 235                 240

Val Phe

<210> SEQ ID NO 11
<211> LENGTH: 771
<212> TYPE: DNA
<213> ORGANISM: Acromyrmex echinatior

<400> SEQUENCE: 11
atgtcagtaa accgtcaatg ccaggagcgt gcagtgaata taatcgatag caaagttgtt      60
gagcagatta gttatatgcc ggagaaacac ggtagttacg aaattgataa ctatttgctc     120
ggcgaaaccg ggaagtcgct taatcccggc tgctgggtac gaggcgggac catatatggg     180
gacatgtgga tctggaacca gaactgggga acctacagcg taccggtgtt tgcctacctt     240
gaacatgtgc agacggttcg tataccaaac gcgaccaaat acactcacgc cgttgaggtt     300
acggaagggt tcagctcatc tgttacccaa acttcagagg tcgagctgtc tgtaggcggc     360
ggattcgtgg cgctaggcgc tggaggggtg aagctctcta gcagttatac cgaaggcgtt     420
catggatcga acaagcgtat ggagacattt gagattcagg ggccggggat ttataacttc     480
tatcaaatgc acatggtttt tgcgcacaag gctacatctg caggccatct gaatgagctg     540
ttccagtatt cccaagtggc cacgaatgaa agcgggcggg aggatttgtg tttcctcacc     600
tctatagcaa ctgacactgt cgtgccggtc gcggccgatt cttcgataac gccactgggt     660
tggcatgaga tccaaagggc tgtgctgatg gacaattaca aggcttcgga caatagtggc     720
cactggctgt ccattctag cgcataccat cggcccggtt cgcgctattg a               771

<210> SEQ ID NO 12
<211> LENGTH: 255
<212> TYPE: PRT
<213> ORGANISM: Acromyrmex echinatior

<400> SEQUENCE: 12

Met Ser Val Asn Arg Gln Cys Gln Glu Arg Ala Val Asn Ile Ile Asp
1               5                   10                  15

Ser Lys Val Glu Gln Ile Ser Tyr Met Pro Glu Lys His Gly Ser Tyr
            20                  25                  30

Glu Ile Asp Asn Tyr Leu Leu Gly Glu Thr Gly Lys Ser Leu Asn Pro
        35                  40                  45

Gly Cys Trp Val Arg Gly Gly Thr Ile Tyr Gly Asp Met Trp Ile Trp
    50                  55                  60

Asn Gln Asn Trp Gly Thr Tyr Ser Val Pro Val Phe Ala Tyr Leu Glu
65                  70                  75                  80

His Val Gln Thr Val Arg Ile Pro Asn Ala Thr Lys Tyr Thr His Ala
                85                  90                  95

Val Glu Val Thr Glu Gly Phe Ser Ser Ser Val Thr Gln Thr Ser Glu
            100                 105                 110

Val Glu Leu Ser Val Gly Gly Phe Val Ala Leu Gly Ala Gly Gly
        115                 120                 125

Val Lys Leu Ser Ser Ser Tyr Thr Glu Gly Val His Gly Ser Asn Lys
    130                 135                 140

Arg Met Glu Thr Phe Glu Ile Gln Gly Pro Gly Ile Tyr Asn Phe Tyr
145                 150                 155                 160

Gln Met His Met Val Phe Ala His Lys Ala Thr Ser Ala Gly His Leu
                165                 170                 175
```

```
Asn Glu Leu Phe Gln Tyr Ser Gln Val Ala Thr Asn Glu Ser Gly Arg
            180                 185                 190

Glu Asp Leu Cys Phe Leu Thr Ser Ile Ala Thr Asp Thr Val Val Pro
        195                 200                 205

Val Ala Ala Asp Ser Ser Ile Thr Pro Leu Gly Trp His Glu Ile Gln
210                 215                 220

Arg Ala Val Leu Met Asp Asn Tyr Lys Ala Ser Asp Asn Ser Gly His
225                 230                 235                 240

Trp Leu Phe His Ser Ser Ala Tyr His Arg Pro Gly Ser Arg Tyr
                245                 250                 255
```

```
<210> SEQ ID NO 13
<211> LENGTH: 27
<212> TYPE: DNA
<213> ORGANISM: Artificial Sequence
<220> FEATURE:
<223> OTHER INFORMATION: PCR primer

<400> SEQUENCE: 13
atacatatga cgatcaagga agagctg                                          27

<210> SEQ ID NO 14
<211> LENGTH: 36
<212> TYPE: DNA
<213> ORGANISM: Artificial Sequence
<220> FEATURE:
<223> OTHER INFORMATION: PCR primer

<400> SEQUENCE: 14
ttggatcctc aataacggcg atgaggatcg ttgtag                                36

<210> SEQ ID NO 15
<211> LENGTH: 816
<212> TYPE: DNA
<213> ORGANISM: Artificial Sequence
<220> FEATURE:
<223> OTHER INFORMATION: modified codons

<400> SEQUENCE: 15
atgcctatca aggaagagct gagccagcct caaagccatt cgatcgaact ggacgatctg      60
aaaagcgagc agggtagttt acgggccgcg ttgacttcca acttcgctgg caatttcgac     120
cagtttccga ccaagcgtgg cggatttgcg atcgattcct atttgctgga ctacagcgcc     180
cccaagcaag gttgctgggt ggacggtatc actgtctatg cgatatcttc atcggcaag     240 cagaactggg gcacttatac ccgcccggtg tttgcctacc acagtatat ggataccatc      300 tccattccac agcaagtgac gcagacccgt agctatcagc tgaccaaggg gcataccaaa     360
acattcacca ccaacgtctc agccaagtac agcgttggcg gctcaataga tatcgtcaac     420
gtgggttcgg atatttccat ggggttttcc aatagcgagt cctggtccac cacgcagacc     480
ttctccaatt ctacccagtt aacggggcca gggacgttca ttgtctacca ggtcgtgatg     540
gtgtatgcgc acaacgccac ctcggcaggg cggcagaatg taatgccctt cgcctacaat     600
aaaaccaata ccgtgggctc gcggctggac ttgtactact tgtcggccat tcccagaat     660 agtactgtca tcgttgactc gagcaaagcc attgcaccgc tggactggga tacggtgcaa     720
cgcaacgtgc tgatggaaaa ctacaaccca ggcagtaaca gcggacactt cagcttcgac     780
tggagtgcct acaacgatcc tcatcgccgt tattga                               816
```

```
<210> SEQ ID NO 16
<211> LENGTH: 21
<212> TYPE: DNA
<213> ORGANISM: Artificial Sequence
<220> FEATURE:
<223> OTHER INFORMATION: mutagenesis primer

<400> SEQUENCE: 16
gaactgatcg aagttgccag c                                              21

<210> SEQ ID NO 17
<211> LENGTH: 44
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (23)..(23)
<223> OTHER INFORMATION: d is a, g, or t
<220> FEATURE:
<221> NAME/KEY: misc_feature
<222> LOCATION: (24)..(24)
<223> OTHER INFORMATION: n is a, c, g, or t

<400> SEQUENCE: 17
gctggcaact tcgatcagtt ccdnactaag cgtggtggct ttgc                      44

<210> SEQ ID NO 18
<211> LENGTH: 44
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(22)
<223> OTHER INFORMATION: d is a, g, or t
<220> FEATURE:
<221> NAME/KEY: misc_feature
<222> LOCATION: (23)..(24)
<223> OTHER INFORMATION: n is a, c, g, or t

<400> SEQUENCE: 18
gctggcaact tcgatcagtt cdnnactaag cgtggtggct ttgc                      44

<210> SEQ ID NO 19
<211> LENGTH: 22
<212> TYPE: DNA
<213> ORGANISM: Artificial Sequence
<220> FEATURE:
<223> OTHER INFORMATION: mutagenesis primer

<400> SEQUENCE: 19
gcagccttgc ttgggcgcgc tg                                              22

<210> SEQ ID NO 20
<211> LENGTH: 47
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (25)..(25)
<223> OTHER INFORMATION: y is t or c
```

<400> SEQUENCE: 20
cagcgcgccc aagcaaggct gctnygtaga tggcattacc gtctacg        47

<210> SEQ ID NO 21
<211> LENGTH: 47
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (23)..(23)
<223> OTHER INFORMATION: v is a, g, or c
<220> FEATURE:
<221> NAME/KEY: misc_feature
<222> LOCATION: (24)..(25)
<223> OTHER INFORMATION: n is a, c, g, or t

<400> SEQUENCE: 21
cagcgcgccc aagcaaggct gcvnngtaga tggcattacc gtctacg        47

<210> SEQ ID NO 22
<211> LENGTH: 21
<212> TYPE: DNA
<213> ORGANISM: Artificial Sequence
<220> FEATURE:
<223> OTHER INFORMATION: mutagenesis primer

<400> SEQUENCE: 22
gcgagtgtag gtgccccaat t        21

<210> SEQ ID NO 23
<211> LENGTH: 48
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 23
aattggggca cctacactcg cnnkgtcttt gcctacctgc agtacatg        48

<210> SEQ ID NO 24
<211> LENGTH: 23
<212> TYPE: DNA
<213> ORGANISM: Artificial Sequence
<220> FEATURE:
<223> OTHER INFORMATION: mutagenesis primer

<400> SEQUENCE: 24
ggcaaagacc gggcgagtgt agg        23

<210> SEQ ID NO 25
<211> LENGTH: 47
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (25)..(26)
<223> OTHER INFORMATION: b is g, t, or c

```
<400> SEQUENCE: 25
cctacactcg cccggtctttt gcctbbctgc agtacatgga caccatt                47

<210> SEQ ID NO 26
<211> LENGTH: 47
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (24)..(24)
<223> OTHER INFORMATION: v is a, g, or c
<220> FEATURE:
<221> NAME/KEY: misc_feature
<222> LOCATION: (25)..(26)
<223> OTHER INFORMATION: n is a, c, g, or t

<400> SEQUENCE: 26
cctacactcg cccggtctttt gccvnnctgc agtacatgga caccatt                47

<210> SEQ ID NO 27
<211> LENGTH: 21
<212> TYPE: DNA
<213> ORGANISM: Artificial Sequence
<220> FEATURE:
<223> OTHER INFORMATION: mutagenesis primer

<400> SEQUENCE: 27
cacgatgaag gtgccaggac c                                             21

<210> SEQ ID NO 28
<211> LENGTH: 44
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (23)..(24)
<223> OTHER INFORMATION: b is g, c, or t

<400> SEQUENCE: 28
ggtcctggca ccttcatcgt gtbbcaggtt gttatggttt atgc                    44

<210> SEQ ID NO 29
<211> LENGTH: 44
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(22)
<223> OTHER INFORMATION: v is a, g, or c
<220> FEATURE:
<221> NAME/KEY: misc_feature
<222> LOCATION: (23)..(24)
<223> OTHER INFORMATION: n is a, c, g, or t

<400> SEQUENCE: 29
ggtcctggca ccttcatcgt gvnncaggtt gttatggttt atgc                    44

<210> SEQ ID NO 30
<211> LENGTH: 22
<212> TYPE: DNA
<213> ORGANISM: Artificial Sequence
<220> FEATURE:
```

<223> OTHER INFORMATION: mutagenesis primer

<400> SEQUENCE: 30
actgaagtgc ccactattgc tg                                              22

<210> SEQ ID NO 31
<211> LENGTH: 47
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (24)..(24)
<223> OTHER INFORMATION: v is a, g, or c
<220> FEATURE:
<221> NAME/KEY: misc_feature
<222> LOCATION: (25)..(25)
<223> OTHER INFORMATION: n is a, c, g, or t

<400> SEQUENCE: 31
cagcaatagt gggcacttca gttvngactg gagcgcctac aacgatc                   47

<210> SEQ ID NO 32
<211> LENGTH: 47
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (23)..(23)
<223> OTHER INFORMATION: v is a, g, or c
<220> FEATURE:
<221> NAME/KEY: misc_feature
<222> LOCATION: (24)..(24)
<223> OTHER INFORMATION: v is a, g, or c
<220> FEATURE:
<221> NAME/KEY: misc_feature
<222> LOCATION: (25)..(25)
<223> OTHER INFORMATION: n is a, c, g, or t

<400> SEQUENCE: 32
cagcaatagt gggcacttca gtvnngactg gagcgcctac aacgatc                   47

<210> SEQ ID NO 33
<211> LENGTH: 48
<212> TYPE: DNA
<213> ORGANISM: Artificial Sequence
<220> FEATURE:
<223> OTHER INFORMATION: mutagenesis primer

<400> SEQUENCE: 33
catgtcaccg tagatggtac cgccacgtac ccagcagcct tgcttggg                  48

<210> SEQ ID NO 34
<211> LENGTH: 53
<212> TYPE: DNA
<213> ORGANISM: Artificial Sequence
<220> FEATURE:
<223> OTHER INFORMATION: mutagenesis primer

<400> SEQUENCE: 34
ggtaccatct acggtgacat gtggatctgg aagcagaatt ggggcaccta cac            53

<210> SEQ ID NO 35
<211> LENGTH: 49
<212> TYPE: DNA
<213> ORGANISM: Artificial Sequence

```
<220> FEATURE:
<223> OTHER INFORMATION: mutagenesis primer

<400> SEQUENCE: 35
gaagccaccg tagacggttt cgccttctat ccagcagcct tgcttgggc      49

<210> SEQ ID NO 36
<211> LENGTH: 51
<212> TYPE: DNA
<213> ORGANISM: Artificial Sequence
<220> FEATURE:
<223> OTHER INFORMATION: mutagenesis primer

<400> SEQUENCE: 36
gaaaccgtct acggtggctt cggtttcccc aagcagaatt ggggcaccta c    51

<210> SEQ ID NO 37
<211> LENGTH: 50
<212> TYPE: DNA
<213> ORGANISM: Artificial Sequence
<220> FEATURE:
<223> OTHER INFORMATION: mutagenesis primer

<400> SEQUENCE: 37
acggacgtca ccgtaggtgg tatcggcatc tacccagcag ccttgcttgg     50

<210> SEQ ID NO 38
<211> LENGTH: 48
<212> TYPE: DNA
<213> ORGANISM: Artificial Sequence
<220> FEATURE:
<223> OTHER INFORMATION: mutagenesis primer

<400> SEQUENCE: 38
accacctacg gtgacgtccg ttgcggcaag cagaattggg gcacctac       48

<210> SEQ ID NO 39
<211> LENGTH: 48
<212> TYPE: DNA
<213> ORGANISM: Artificial Sequence
<220> FEATURE:
<223> OTHER INFORMATION: mutagenesis primer

<400> SEQUENCE: 39
accatgcacg ccttcagtgt aactggatcc aattgagata tccgaacc       48

<210> SEQ ID NO 40
<211> LENGTH: 51
<212> TYPE: DNA
<213> ORGANISM: Artificial Sequence
<220> FEATURE:
<223> OTHER INFORMATION: mutagenesis primer

<400> SEQUENCE: 40
tacactgaag gcgtgcatgg ttcgaacacg ttcagcaata gcactcaatt g   51

<210> SEQ ID NO 41
<211> LENGTH: 48
<212> TYPE: DNA
<213> ORGANISM: Artificial Sequence
<220> FEATURE:
<223> OTHER INFORMATION: mutagenesis primer

<400> SEQUENCE: 41
cagaggacgc cattcttcag cactgcatcc aattgagata tccgaacc       48
```

```
<210> SEQ ID NO 42
<211> LENGTH: 48
<212> TYPE: DNA
<213> ORGANISM: Artificial Sequence
<220> FEATURE:
<223> OTHER INFORMATION: mutagenesis primer

<400> SEQUENCE: 42
gctgaagaat ggcgtcctct gtcgacgttc agcaatagca ctcaattg              48

<210> SEQ ID NO 43
<211> LENGTH: 47
<212> TYPE: DNA
<213> ORGANISM: Artificial Sequence
<220> FEATURE:
<223> OTHER INFORMATION: mutagenesis primer

<400> SEQUENCE: 43
cgaaccagac acggtttcac tgacactgaa tccaattgag atatccg                47

<210> SEQ ID NO 44
<211> LENGTH: 48
<212> TYPE: DNA
<213> ORGANISM: Artificial Sequence
<220> FEATURE:
<223> OTHER INFORMATION: mutagenesis primer

<400> SEQUENCE: 44
agtgaaaccg tgtctggttc ggagacgttc agcaatagca ctcaattg              48

<210> SEQ ID NO 45
<211> LENGTH: 46
<212> TYPE: DNA
<213> ORGANISM: Artificial Sequence
<220> FEATURE:
<223> OTHER INFORMATION: mutagenesis primer

<400> SEQUENCE: 45
atgcatctga tagaagttgt agatgccagg accagtcaat tgagtg                 46

<210> SEQ ID NO 46
<211> LENGTH: 49
<212> TYPE: DNA
<213> ORGANISM: Artificial Sequence
<220> FEATURE:
<223> OTHER INFORMATION: mutagenesis primer

<400> SEQUENCE: 46
tacaacttct atcagatgca tatggttttt gcgcacaacg ccacttctg             49

<210> SEQ ID NO 47
<211> LENGTH: 45
<212> TYPE: DNA
<213> ORGANISM: Artificial Sequence
<220> FEATURE:
<223> OTHER INFORMATION: mutagenesis primer

<400> SEQUENCE: 47
ctgatacgcg acgtagcatt caggaccagt caattgagtg ctatt                  45

<210> SEQ ID NO 48
<211> LENGTH: 53
<212> TYPE: DNA
<213> ORGANISM: Artificial Sequence
<220> FEATURE:
<223> OTHER INFORMATION: mutagenesis primer
```

```
<400> SEQUENCE: 48
gaatgctacg tcgcgtatca gcttaaactg gtttatgcgc acaacgccac ttc        53

<210> SEQ ID NO 49
<211> LENGTH: 44
<212> TYPE: DNA
<213> ORGANISM: Artificial Sequence
<220> FEATURE:
<223> OTHER INFORMATION: mutagenesis primer

<400> SEQUENCE: 49
atgaacctga tacaccatga tggtgccagg accagtcaat tgag                  44

<210> SEQ ID NO 50
<211> LENGTH: 44
<212> TYPE: DNA
<213> ORGANISM: Artificial Sequence
<220> FEATURE:
<223> OTHER INFORMATION: mutagenesis primer

<400> SEQUENCE: 50
atcatggtgt atcaggttca tatggtttat gcgcacaacg ccac                  44

<210> SEQ ID NO 51
<211> LENGTH: 42
<212> TYPE: DNA
<213> ORGANISM: Artificial Sequence
<220> FEATURE:
<223> OTHER INFORMATION: mutagenesis primer

<400> SEQUENCE: 51
gttgtccatc aacacagcgc gctgaacagt atcccaatcc ag                    42

<210> SEQ ID NO 52
<211> LENGTH: 48
<212> TYPE: DNA
<213> ORGANISM: Artificial Sequence
<220> FEATURE:
<223> OTHER INFORMATION: mutagenesis primer

<400> SEQUENCE: 52
cgcgctgtgt tgatggacaa ctacaagcca ggcagcaata gtgggcac              48

<210> SEQ ID NO 53
<211> LENGTH: 46
<212> TYPE: DNA
<213> ORGANISM: Artificial Sequence
<220> FEATURE:
<223> OTHER INFORMATION: mutagenesis primer

<400> SEQUENCE: 53
ggccaggttg aagataaggt ggtaaacagt atcccaatcc agcggc                46

<210> SEQ ID NO 54
<211> LENGTH: 51
<212> TYPE: DNA
<213> ORGANISM: Artificial Sequence
<220> FEATURE:
<223> OTHER INFORMATION: mutagenesis primer

<400> SEQUENCE: 54
caccttatct tcaacctggc ctacggccca ggcagcaata gtgggcactt c          51

<210> SEQ ID NO 55
```

```
<210> SEQ ID NO 55
<211> LENGTH: 46
<212> TYPE: DNA
<213> ORGANISM: Artificial Sequence
<220> FEATURE:
<223> OTHER INFORMATION: mutagenesis primer

<400> SEQUENCE: 55
ctggttgaac aacacagcct ggttaacagt atcccaatcc agcggc                    46

<210> SEQ ID NO 56
<211> LENGTH: 51
<212> TYPE: DNA
<213> ORGANISM: Artificial Sequence
<220> FEATURE:
<223> OTHER INFORMATION: mutagenesis primer

<400> SEQUENCE: 56
caggctgtgt tgttcaacca ggaggagcca ggcagcaata gtgggcactt c              51

<210> SEQ ID NO 57
<211> LENGTH: 21
<212> TYPE: DNA
<213> ORGANISM: Artificial Sequence
<220> FEATURE:
<223> OTHER INFORMATION: mutagenesis primer

<400> SEQUENCE: 57
aggaccagtc aattgagtgc t                                               21

<210> SEQ ID NO 58
<211> LENGTH: 44
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 58
agcactcaat tgactggtcc tnnkaccttc atcgtgtatc aggt                      44

<210> SEQ ID NO 59
<211> LENGTH: 21
<212> TYPE: DNA
<213> ORGANISM: Artificial Sequence
<220> FEATURE:
<223> OTHER INFORMATION: mutagenesis primer

<400> SEQUENCE: 59
gccaggacca gtcaattgag t                                               21

<210> SEQ ID NO 60
<211> LENGTH: 43
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
```

```
<222> LOCATION: (24)..(24)
<223> OTHER INFORMATION: k is g or t

<400> SEQUENCE: 60
actcaattga ctggtcctgg cnnkttcatc gtgtatcagg ttg                         43

<210> SEQ ID NO 61
<211> LENGTH: 21
<212> TYPE: DNA
<213> ORGANISM: Artificial Sequence
<220> FEATURE:
<223> OTHER INFORMATION: mutagenesis primer

<400> SEQUENCE: 61
ggtgccagga ccagtcaatt g                                                 21

<210> SEQ ID NO 62
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 62
caattgactg gtcctggcac cnnkatcgtg tatcaggttg ttatg                       45

<210> SEQ ID NO 63
<211> LENGTH: 21
<212> TYPE: DNA
<213> ORGANISM: Artificial Sequence
<220> FEATURE:
<223> OTHER INFORMATION: mutagenesis primer

<400> SEQUENCE: 63
gaaggtgcca ggaccagtca a                                                 21

<210> SEQ ID NO 64
<211> LENGTH: 42
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 64
ttgactggtc ctggcacctt cnnkgtgtat caggttgtta tg                          42

<210> SEQ ID NO 65
<211> LENGTH: 21
<212> TYPE: DNA
<213> ORGANISM: Artificial Sequence
<220> FEATURE:
<223> OTHER INFORMATION: mutagenesis primer
```

<400> SEQUENCE: 65
gatgaaggtg ccaggaccag t                                          21

<210> SEQ ID NO 66
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 66
actggtcctg gcaccttcat cnnktatcag gttgttatgg tttat                45

<210> SEQ ID NO 67
<211> LENGTH: 21
<212> TYPE: DNA
<213> ORGANISM: Artificial Sequence
<220> FEATURE:
<223> OTHER INFORMATION: mutagenesis primer

<400> SEQUENCE: 67
atacacgatg aaggtgccag g                                          21

<210> SEQ ID NO 68
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 68
cctggcacct tcatcgtgta tnnkgttgtt atggtttatg cgcac                45

<210> SEQ ID NO 69
<211> LENGTH: 21
<212> TYPE: DNA
<213> ORGANISM: Artificial Sequence
<220> FEATURE:
<223> OTHER INFORMATION: mutagenesis primer

<400> SEQUENCE: 69
ctgatacacg atgaaggtgc c                                          21

<210> SEQ ID NO 70
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t

```
<220> FEATURE:
<221> NAME/KEY: misc_feature
<222> LOCATION: (24)..(24)
<223> OTHER INFORMATION: k is g or t

<400> SEQUENCE: 70
ggcaccttca tcgtgtatca gnnkgttatg gtttatgcgc acaac          45

<210> SEQ ID NO 71
<211> LENGTH: 21
<212> TYPE: DNA
<213> ORGANISM: Artificial Sequence
<220> FEATURE:
<223> OTHER INFORMATION: mutagenesis primer

<400> SEQUENCE: 71
aacctgatac acgatgaagg t                                    21

<210> SEQ ID NO 72
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 72
accttcatcg tgtatcaggt tnnkatggtt tatgcgcaca acgcc          45

<210> SEQ ID NO 73
<211> LENGTH: 21
<212> TYPE: DNA
<213> ORGANISM: Artificial Sequence
<220> FEATURE:
<223> OTHER INFORMATION: mutagenesis primer

<400> SEQUENCE: 73
aacaacctga tacacgatga a                                    21

<210> SEQ ID NO 74
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 74
ttcatcgtgt atcaggttgt tnnkgtttat gcgcacaacg ccact          45

<210> SEQ ID NO 75
<211> LENGTH: 21
<212> TYPE: DNA
<213> ORGANISM: Artificial Sequence
<220> FEATURE:
```

```
<223> OTHER INFORMATION: mutagenesis primer

<400> SEQUENCE: 75
cataacaacc tgatacacga t                                          21

<210> SEQ ID NO 76
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 76
atcgtgtatc aggttgttat gnnktatgcg cacaacgcca cttct               45

<210> SEQ ID NO 77
<211> LENGTH: 21
<212> TYPE: DNA
<213> ORGANISM: Artificial Sequence
<220> FEATURE:
<223> OTHER INFORMATION: mutagenesis primer

<400> SEQUENCE: 77
aaccataaca acctgataca c                                          21

<210> SEQ ID NO 78
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 78
gtgtatcagg ttgttatggt tnnkgcgcac aacgccactt ctgcg               45

<210> SEQ ID NO 79
<211> LENGTH: 21
<212> TYPE: DNA
<213> ORGANISM: Artificial Sequence
<220> FEATURE:
<223> OTHER INFORMATION: mutagenesis primer

<400> SEQUENCE: 79
ataaaccata acaacctgat a                                          21

<210> SEQ ID NO 80
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
```

<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 80
tatcaggttg ttatggttta tnnkcacaac gccacttctg cgggc                45

<210> SEQ ID NO 81
<211> LENGTH: 21
<212> TYPE: DNA
<213> ORGANISM: Artificial Sequence
<220> FEATURE:
<223> OTHER INFORMATION: mutagenesis primer

<400> SEQUENCE: 81
aacagtatcc caatccagcg g                                          21

<210> SEQ ID NO 82
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 82
ccgctggatt gggatactgt tnnkcgcaat gtgttgatgg agaac                45

<210> SEQ ID NO 83
<211> LENGTH: 21
<212> TYPE: DNA
<213> ORGANISM: Artificial Sequence
<220> FEATURE:
<223> OTHER INFORMATION: mutagenesis primer

<400> SEQUENCE: 83
ctgaacagta tcccaatcca g                                          21

<210> SEQ ID NO 84
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 84
ctggattggg atactgttca gnnkaatgtg ttgatggaga actac                45

<210> SEQ ID NO 85
<211> LENGTH: 21
<212> TYPE: DNA

```
<213> ORGANISM: Artificial Sequence
<220> FEATURE:
<223> OTHER INFORMATION: mutagenesis primer

<400> SEQUENCE: 85
gcgctgaaca gtatcccaat c                                           21

<210> SEQ ID NO 86
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 86
gattgggata ctgttcagcg cnnkgtgttg atggagaact acaac                 45

<210> SEQ ID NO 87
<211> LENGTH: 21
<212> TYPE: DNA
<213> ORGANISM: Artificial Sequence
<220> FEATURE:
<223> OTHER INFORMATION: mutagenesis primer

<400> SEQUENCE: 87
attgcgctga acagtatccc a                                           21

<210> SEQ ID NO 88
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 88
tgggatactg ttcagcgcaa tnnkttgatg gagaactaca accca                 45

<210> SEQ ID NO 89
<211> LENGTH: 21
<212> TYPE: DNA
<213> ORGANISM: Artificial Sequence
<220> FEATURE:
<223> OTHER INFORMATION: mutagenesis primer

<400> SEQUENCE: 89
cacattgcgc tgaacagtat c                                           21

<210> SEQ ID NO 90
<211> LENGTH: 44
<212> TYPE: DNA
<213> ORGANISM: Artificial Sequence
<220> FEATURE:
<223> OTHER INFORMATION: mutagenesis primer
```

```
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 90
gatactgttc agcgcaatgt gnnkatggag aactacaacc cagg          44

<210> SEQ ID NO 91
<211> LENGTH: 21
<212> TYPE: DNA
<213> ORGANISM: Artificial Sequence
<220> FEATURE:
<223> OTHER INFORMATION: mutagenesis primer

<400> SEQUENCE: 91
caacacattg cgctgaacag t                                   21

<210> SEQ ID NO 92
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 92
actgttcagc gcaatgtgtt gnnkgagaac tacaacccag gcagc         45

<210> SEQ ID NO 93
<211> LENGTH: 21
<212> TYPE: DNA
<213> ORGANISM: Artificial Sequence
<220> FEATURE:
<223> OTHER INFORMATION: mutagenesis primer

<400> SEQUENCE: 93
catcaacaca ttgcgctgaa c                                   21

<210> SEQ ID NO 94
<211> LENGTH: 42
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 94
gttcagcgca atgtgttgat gnnkaactac aacccaggca gc            42

<210> SEQ ID NO 95
```

```
<211> LENGTH: 21
<212> TYPE: DNA
<213> ORGANISM: Artificial Sequence
<220> FEATURE:
<223> OTHER INFORMATION: mutagenesis primer

<400> SEQUENCE: 95
ctccatcaac acattgcgct g                                              21

<210> SEQ ID NO 96
<211> LENGTH: 44
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 96
cagcgcaatg tgttgatgga gnnktacaac ccaggcagca atag                     44

<210> SEQ ID NO 97
<211> LENGTH: 21
<212> TYPE: DNA
<213> ORGANISM: Artificial Sequence
<220> FEATURE:
<223> OTHER INFORMATION: mutagenesis primer

<400> SEQUENCE: 97
gttctccatc aacacattgc g                                              21

<210> SEQ ID NO 98
<211> LENGTH: 44
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 98
cgcaatgtgt tgatggagaa cnnkaaccca ggcagcaata gtgg                     44

<210> SEQ ID NO 99
<211> LENGTH: 21
<212> TYPE: DNA
<213> ORGANISM: Artificial Sequence
<220> FEATURE:
<223> OTHER INFORMATION: mutagenesis primer

<400> SEQUENCE: 99
gtagttctcc atcaacacat t                                              21

<210> SEQ ID NO 100
<211> LENGTH: 44
<212> TYPE: DNA
<213> ORGANISM: Artificial Sequence
```

-continued

```
<220> FEATURE:
<223> OTHER INFORMATION: mutagenesis primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 100
aatgtgttga tggagaacta cnnkccaggc agcaatagtg ggca                 44

<210> SEQ ID NO 101
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 101
```

Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Glu
    130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Ala Asn Ala Phe Ala Tyr Asn Lys Thr Asn Thr Val Gly Ser Arg
        195                 200                 205

Val Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

```
<210> SEQ ID NO 102
<211> LENGTH: 271
```

<212> TYPE: PRT
<213> ORGANISM: Artificial Sequence
<220> FEATURE:
<223> OTHER INFORMATION: PIP-1A / PSEEN3174 chimera

<400> SEQUENCE: 102

```
Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Glu
    130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Val Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 103
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 103

```
Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Leu Ser Gly Arg Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60
```

-continued

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Val Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
            130                 135                 140

Ile Ser Ile Gly Phe Ser Asn Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
            195                 200                 205

Leu Asp Leu Tyr Tyr Leu Ser Ala Ile Thr Gln Arg Lys Arg Val Ile
            210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 104
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 104

Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
            35                  40                  45

Phe Ala Ile Asp Gly Tyr Leu Leu Asp Tyr Ser Ser Pro Lys Gln Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Asn Val Thr Gln Thr Arg Ser Tyr
            100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
            130                 135                 140

Ile Ser Ile Gly Phe Thr Arg Ser Glu Ser Trp Ser Thr Thr Gln Thr
145                 150                 155                 160

```
Phe Ser Asn Ser Thr Gln Leu Thr Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 105
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 105

Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Leu Ser Gly Arg Phe Asp Gln Tyr Pro Thr Lys Lys Gly Asp
        35                  40                  45

Phe Ala Ile Asp Gly Tyr Leu Leu Asp Tyr Ser Ala Pro Lys Gln Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Ala Asn Ile Asp Ile Val Asn Val Gly Ser Asp
    130                 135                 140

Ile Ser Ile Gly Phe Ser Arg Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Leu Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Val Asp Leu Tyr Tyr Leu Ser Ala Ile Thr Gln Arg Lys Arg Val Ile
    210                 215                 220

Val Asp Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255
```

```
Phe Ser Phe Asp Trp Ser Ala Tyr Asn Asp Pro His Arg Arg Tyr
            260                 265                 270
```

<210> SEQ ID NO 106
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 106

```
Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Leu Ser Gly Arg Phe Asp Gln Tyr Pro Thr Lys Lys Gly Asp
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Glu
    130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Ile Val Tyr
                165                 170                 175

Gln Val Val Leu Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 107
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 107

```
Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
```

```
            20                  25                  30
Ser Asn Leu Ser Gly Arg Phe Asp Gln Tyr Pro Thr Lys Lys Gly Asp
        35                  40                  45
Phe Ala Ile Asp Ser Tyr Leu Leu Asp Tyr Ser Ser Pro Lys Gln Gly
        50                  55                  60
Cys Trp Val Asp Gly Ile Thr Val Tyr Gly Asp Ile Phe Ile Gly Lys
65                  70                  75                  80
Gln Asn Trp Gly Thr Tyr Thr Arg Pro Val Phe Ala Tyr Leu Gln Tyr
                85                  90                  95
Met Asp Thr Ile Ser Ile Pro Gln Gln Val Thr Gln Thr Arg Ser Tyr
            100                 105                 110
Gln Leu Thr Lys Gly His Thr Arg Ser Phe Glu Thr Ser Val Asn Ala
            115                 120                 125
Lys Tyr Ser Val Gly Ala Asn Ile Asp Ile Val Asn Val Gly Ser Asp
            130                 135                 140
Ile Ser Ile Gly Phe Ser Asn Ser Glu Ser Trp Ser Thr Thr Gln Ser
145                 150                 155                 160
Phe Thr Asp Thr Thr Glu Met Lys Gly Pro Gly Thr Phe Ile Val Tyr
                165                 170                 175
Gln Val Val Leu Val Tyr Ala His Asn Ala Thr Ser Ala Gly Arg Gln
            180                 185                 190
Asn Ala Asn Ala Phe Ala Tyr Ser Lys Thr Gln Ala Val Gly Ser Arg
            195                 200                 205
Val Asp Leu Tyr Tyr Leu Ser Ala Ile Thr Gln Arg Lys Arg Val Ile
            210                 215                 220
Val Pro Ser Ser Asn Ala Val Thr Pro Leu Asp Trp Asp Thr Val Gln
225                 230                 235                 240
Arg Asn Val Leu Met Glu Asn Tyr Ser Pro Gly Ser Asn Ser Gly His
                245                 250                 255
Phe Ser Phe Asp Trp Ser Ala Tyr Asn Asp Pro His Arg Arg Tyr
            260                 265                 270

<210> SEQ ID NO 108
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 108

Met Pro Ile Lys Glu Glu Leu Ser Gln Pro Gln Ser His Ser Ile Glu
1               5                   10                  15
Leu Asp Glu Val Ser Lys Glu Ala Ala Ser Thr Arg Ala Ala Leu Thr
            20                  25                  30
Ser Asn Leu Ser Gly Arg Phe Asp Gln Phe Pro Thr Lys Ser Gly Glu
        35                  40                  45
Phe Ala Ile Asp Ser Tyr Leu Leu Asp Tyr Ser Ala Pro Lys Gln Gly
        50                  55                  60
Cys Trp Val Asp Gly Ile Thr Val Tyr Gly Asp Ile Phe Ile Gly Lys
65                  70                  75                  80
Gln Asn Trp Gly Thr Tyr Thr Arg Pro Val Phe Ala Tyr Leu Gln Tyr
                85                  90                  95
Met Asp Thr Ile Ser Ile Pro Gln Gln Val Thr Gln Thr Arg Ser Tyr
            100                 105                 110
Gln Leu Thr Lys Gly His Thr Lys Thr Phe Thr Thr Asn Val Ser Ala
```

```
            115                 120                 125
Lys Tyr Ser Val Gly Gly Ser Ile Asp Ile Val Asn Val Gly Ser Glu
130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Ile Val Tyr
                165                 170                 175

Gln Val Val Met Val Tyr Ala His Asn Ala Thr Ser Ala Gly Arg Gln
                180                 185                 190

Asn Ala Asn Ala Phe Ala Tyr Ser Lys Thr Asn Thr Val Gly Ser Arg
            195                 200                 205

Leu Asp Leu Tyr Tyr Leu Ser Ala Ile Thr Gln Arg Lys Arg Val Ile
            210                 215                 220

Val Pro Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 109
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 109

Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ser Pro Lys Gln Gly
        50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
130                 135                 140

Ile Ser Ile Gly Phe Ser Asn Ser Glu Ser Trp Ser Thr Thr Gln Ser
145                 150                 155                 160

Phe Thr Asp Thr Thr Glu Met Lys Gly Pro Gly Thr Phe Ile Val Tyr
                165                 170                 175

Gln Val Val Met Val Tyr Ala His Asn Ala Thr Ser Ala Gly Arg Gln
                180                 185                 190

Asn Ala Asn Ala Phe Ala Tyr Asn Lys Thr Asn Thr Val Gly Ser Arg
            195                 200                 205

Leu Asp Leu Tyr Tyr Leu Ser Ala Ile Thr Gln Asn Ser Thr Val Ile
```

```
                210                 215                 220
Val Asp Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 110
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 110

Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Leu Ser Gly Arg Phe Asp Gln Tyr Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Asn Val Thr Thr Leu Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Glu
    130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Leu Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 111
<211> LENGTH: 271
<212> TYPE: PRT
<213> ORGANISM: Artificial Sequence
<220> FEATURE:
<223> OTHER INFORMATION: PIP-1A / PSEEN3174 chimera
```

<400> SEQUENCE: 111

```
Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Leu Ser Gly Arg Phe Asp Gln Tyr Pro Thr Lys Lys Gly Asp
            35                  40                  45

Phe Ala Ile Asp Ser Tyr Leu Leu Asp Tyr Ser Ala Pro Lys Gln Gly
        50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Glu
130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Val Asp Leu Tyr Tyr Leu Ser Ala Ile Thr Gln Asn Ser Thr Val Ile
210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 112
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 112

```
Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
        50                  55                  60

Cys Trp Val Asp Gly Ile Thr Val Tyr Gly Asp Ile Tyr Ile Gly Lys
65                  70                  75                  80
```

```
Gln Asn Trp Gly Thr Tyr Thr Arg Pro Val Phe Ala Tyr Leu Gln Tyr
                    85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Thr Gly Phe Thr Arg Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Ser Lys Thr Gln Ala Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 113
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 113

Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Leu Ser Gly Arg Phe Asp Gln Tyr Pro Thr Lys Lys Gly Asp
        35                  40                  45

Phe Ala Ile Asp Gly Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Thr Gly Phe Thr Arg Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175
```

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
            195                 200                 205

Leu Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 114
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 114

Met Pro Ile Lys Glu Gly Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ser Pro Lys Gln Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Glu
    130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 115
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 115

```
Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Asn Val Thr Thr Leu Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Glu
    130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Val Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 116
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 116

```
Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Lys Gly Asp
        35                  40                  45
```

```
Phe Ala Ile Asp Ser Tyr Leu Leu Asp Tyr Ser Ser Pro Lys Gln Gly
        50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Thr Thr Leu Ser Tyr
                100                 105                 110

Gln Leu Thr Lys Gly His Thr Arg Ser Phe Glu Thr Ser Val Asn Ala
            115                 120                 125

Lys Tyr Ser Val Gly Ala Asn Ile Asp Ile Val Asn Val Gly Ser Glu
        130                 135                 140

Ile Ser Thr Gly Phe Thr Arg Ser Glu Ser Trp Ser Thr Thr Gln Thr
145                 150                 155                 160

Phe Ser Asn Ser Thr Gln Leu Thr Gly Pro Gly Thr Phe Ile Ala Tyr
                165                 170                 175

Gln Val Val Met Val Tyr Ala His Asn Ala Thr Ser Ala Gly Arg Gln
                180                 185                 190

Asn Gly Asn Ala Phe Ala Tyr Ser Lys Thr Gln Ala Val Gly Ser Arg
            195                 200                 205

Val Asp Leu Tyr Tyr Leu Ser Ala Ile Thr Gln Arg Lys Arg Val Ile
        210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 117
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 117

Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
                20                  25                  30

Ser Asn Leu Ser Gly Arg Phe Asp Gln Tyr Pro Thr Lys Lys Gly Asp
            35                  40                  45

Phe Ala Ile Asp Gly Tyr Leu Leu Asp Tyr Ser Ser Pro Lys Gln Gly
        50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
            115                 120                 125

Lys Tyr Ser Val Gly Ala Asn Ile Asp Ile Val Asn Val Gly Ser Glu
        130                 135                 140
```

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Gly Asn Ala Phe Ala Tyr Ser Lys Thr Gln Ala Val Gly Ser Arg
        195                 200                 205

Val Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 118
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 118

Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
                20                  25                  30

Ser Asn Leu Ser Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
        50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Asn Val Thr Thr Thr Leu Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Glu
    130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Met Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Leu Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

```
Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
        260                 265                 270

<210> SEQ ID NO 119
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 119

Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Asn Val Thr Thr Thr Leu Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Gly Asn Ala Phe Ala Tyr Asn Lys Thr Gln Ala Val Gly Ser Arg
        195                 200                 205

Val Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
        260                 265                 270

<210> SEQ ID NO 120
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 120

Met Pro Ile Lys Glu Glu Leu Ser Gln Pro Gln Ser His Ser Ile Glu
```

```
  1               5                  10                 15
Leu Asp Asp Leu Lys Ser Glu Gln Gly Ser Leu Arg Ala Ala Leu Thr
            20                 25                 30

Ser Asn Phe Ala Gly Asn Phe Asp Gln Phe Pro Thr Lys Arg Gly Gly
            35                 40                 45

Phe Ala Ile Asp Ser Tyr Leu Leu Asp Tyr Ser Ala Pro Lys Gln Gly
            50                 55                 60

Cys Trp Val Asp Gly Ile Thr Val Tyr Gly Asp Ile Phe Ile Gly Lys
 65                 70                 75                 80

Gln Asn Trp Gly Thr Tyr Thr Arg Pro Val Phe Ala Tyr Leu Gln Tyr
                85                 90                 95

Val Glu Thr Ile Ser Ile Pro Gln Asn Val Thr Thr Thr Leu Ser Tyr
            100                105                110

Gln Leu Thr Lys Gly His Thr Arg Ser Phe Glu Thr Ser Val Asn Ala
            115                120                125

Lys Tyr Ser Val Gly Gly Ser Ile Asp Ile Val Asn Val Gly Ser Asp
            130                135                140

Ile Ser Ile Gly Phe Ser Asn Ser Glu Ser Trp Ser Thr Thr Gln Ser
145                150                155                160

Phe Thr Asp Thr Thr Glu Met Lys Gly Pro Gly Thr Phe Val Ile Tyr
                165                170                175

Gln Val Val Leu Val Tyr Ala His Asn Ala Thr Ser Ala Gly Arg Gln
            180                185                190

Asn Gly Asn Ala Phe Ala Tyr Ser Lys Thr Gln Ala Val Gly Ser Arg
            195                200                205

Val Asp Leu Tyr Tyr Leu Ser Ala Ile Thr Gln Arg Lys Arg Val Ile
            210                215                220

Val Pro Ser Ser Asn Ala Val Thr Pro Leu Asp Trp Asp Thr Val Gln
225                230                235                240

Arg Asn Val Leu Met Glu Asn Tyr Asn Pro Gly Ser Asn Ser Gly His
                245                250                255

Phe Ser Phe Asp Trp Ser Ala Tyr Asn Asp Pro His Arg Arg Tyr
            260                265                270
```

<210> SEQ ID NO 121
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 121

```
Met Pro Ile Lys Glu Glu Leu Ser Gln Pro Gln Ser His Ser Ile Glu
 1               5                  10                 15

Leu Asp Asp Leu Lys Ser Glu Gln Gly Ser Leu Arg Ala Ala Leu Thr
            20                 25                 30

Ser Asn Phe Ala Gly Asn Phe Asp Gln Phe Pro Thr Lys Arg Gly Gly
            35                 40                 45

Phe Ala Ile Asp Ser Tyr Leu Leu Asp Tyr Ser Ala Pro Lys Gln Gly
            50                 55                 60

Cys Trp Val Asp Gly Ile Thr Val Tyr Gly Asp Ile Phe Ile Gly Lys
 65                 70                 75                 80

Gln Asn Trp Gly Thr Tyr Thr Arg Pro Val Phe Ala Tyr Leu Gln Tyr
                85                 90                 95

Val Glu Thr Ile Ser Ile Pro Gln Asn Val Thr Thr Thr Leu Ser Tyr
```

```
                100             105             110
Gln Leu Thr Lys Gly His Thr Arg Ser Phe Glu Thr Ser Val Asn Ala
            115                 120                 125
Lys Tyr Ser Val Gly Ala Asn Ile Asp Ile Val Asn Val Gly Ser Glu
        130                 135                 140
Ile Ser Thr Gly Phe Thr Arg Ser Glu Ser Trp Ser Thr Thr Gln Ser
145                 150                 155                 160
Phe Thr Asp Thr Thr Glu Met Lys Gly Pro Gly Thr Phe Ile Val Tyr
                165                 170                 175
Gln Val Val Leu Val Tyr Ala His Asn Ala Thr Ser Ala Gly Arg Gln
            180                 185                 190
Asn Ala Asn Ala Phe Ala Tyr Ser Lys Thr Gln Ala Val Gly Ser Arg
        195                 200                 205
Val Asp Leu Tyr Tyr Leu Ser Ala Ile Thr Gln Arg Lys Arg Val Ile
        210                 215                 220
Val Pro Ser Ser Asn Ala Val Thr Pro Leu Asp Trp Asp Thr Val Gln
225                 230                 235                 240
Arg Asn Val Leu Met Glu Asn Tyr Asn Pro Gly Ser Asn Ser Gly His
                245                 250                 255
Phe Ser Phe Asp Trp Ser Ala Tyr Asn Asp Pro His Arg Arg Tyr
                260                 265                 270

<210> SEQ ID NO 122
<211> LENGTH: 270
<212> TYPE: PRT
<213> ORGANISM: Artificial Sequence
<220> FEATURE:
<223> OTHER INFORMATION: PIP-1A / PSEEN3174 chimera

<400> SEQUENCE: 122

Met Pro Ile Lys Glu Glu Leu Ser Gln Pro Gln Ser His Ser Ile Glu
1               5                   10                  15
Leu Asp Glu Val Ser Lys Glu Ala Ala Ser Thr Arg Ala Ala Leu Thr
                20                  25                  30
Ser Asn Phe Ala Gly Asn Phe Asp Gln Phe Pro Thr Lys Arg Gly Gly
            35                  40                  45
Phe Ala Ile Asp Ser Tyr Leu Leu Asp Tyr Ser Ala Pro Lys Gln Gly
        50                  55                  60
Cys Trp Val Asp Gly Ile Thr Val Tyr Gly Asp Ile Phe Ile Gly Lys
65                  70                  75                  80
Gln Asn Trp Gly Thr Tyr Thr Arg Pro Val Phe Ala Tyr Leu Gln Tyr
                85                  90                  95
Met Asp Thr Ile Ser Ile Pro Gln Gln Val Thr Gln Thr Arg Ser Tyr
                100                 105                 110
Gln Leu Thr Lys Gly His Thr Lys Thr Phe Thr Thr Asn Val Ser Ala
            115                 120                 125
Lys Tyr Ser Val Gly Gly Ser Ile Asp Ile Val Asn Val Gly Ser Glu
        130                 135                 140
Ile Ser Thr Gly Phe Thr Arg Ser Glu Ser Trp Ser Thr Thr Gln Ser
145                 150                 155                 160
Phe Thr Asp Thr Thr Glu Met Lys Gly Pro Gly Thr Phe Val Ile Tyr
                165                 170                 175
Gln Val Val Leu Val Tyr Ala His Asn Ala Thr Ser Ala Gly Arg Gln
            180                 185                 190
Asn Ala Asn Ala Phe Ala Tyr Asn Lys Thr Asn Thr Val Gly Ser Arg
```

```
              195                 200                 205

Leu Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg
            260                 265                 270

<210> SEQ ID NO 123
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 123

Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Leu Ser Gly Arg Phe Asp Gln Tyr Pro Thr Lys Lys Gly Asp
        35                  40                  45

Phe Ala Ile Asp Gly Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Glu
    130                 135                 140

Ile Ser Thr Gly Phe Thr Arg Ser Glu Ser Trp Ser Thr Thr Gln Thr
145                 150                 155                 160

Phe Ser Asn Ser Thr Gln Leu Thr Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Ala Asn Ala Phe Ala Tyr Ser Lys Thr Asn Thr Val Gly Ser Arg
        195                 200                 205

Val Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 124
<211> LENGTH: 271
<212> TYPE: PRT
```

<213> ORGANISM: Artificial Sequence
<220> FEATURE:
<223> OTHER INFORMATION: PIP-1A / PSEEN3174 chimera

<400> SEQUENCE: 124

```
Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Leu Ser Gly Arg Phe Asp Gln Tyr Pro Thr Lys Lys Gly Asp
        35                  40                  45

Phe Ala Ile Asp Gly Tyr Leu Leu Asp Tyr Ser Ser Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Glu
    130                 135                 140

Ile Ser Thr Gly Phe Thr Arg Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Ser Lys Thr Gln Ala Val Gly Ser Arg
        195                 200                 205

Val Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 125
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 125

```
Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Tyr Pro Thr Lys Lys Gly Asp
        35                  40                  45

Phe Ala Ile Asp Ser Tyr Leu Leu Asp Tyr Ser Ala Pro Lys Gln Gly
    50                  55                  60
```

```
Cys Trp Val Asp Gly Ile Thr Val Tyr Gly Asp Ile Phe Ile Gly Lys
 65                  70                  75                  80

Gln Asn Trp Gly Thr Tyr Thr Arg Pro Val Phe Ala Tyr Leu Gln Tyr
                 85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Leu Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 126
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 126

Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Leu Ser Gly Arg Phe Asp Gln Tyr Pro Thr Lys Lys Gly Asp
        35                  40                  45

Phe Ala Ile Asp Gly Tyr Leu Leu Asp Tyr Ser Ser Pro Lys Gln Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Ala Asn Ile Asp Ile Val Asn Val Gly Ser Glu
    130                 135                 140

Ile Ser Thr Gly Phe Thr Arg Ser Glu Ser Trp Ser Thr Thr Gln Thr
145                 150                 155                 160
```

```
Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Ala Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270
```

<210> SEQ ID NO 127
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 127

```
Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Ser
145                 150                 155                 160

Phe Thr Asp Thr Thr Glu Met Lys Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Ala Asn Ala Phe Ala Tyr Ser Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255
```

```
Phe Ser Phe Asp Trp Ser Ala Tyr Asn Asp Pro His Arg Arg Tyr
            260                 265                 270
```

<210> SEQ ID NO 128
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 128

```
Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
        50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 129
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 129

```
Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30
```

Ser Asn Leu Ser Gly Arg Phe Asp Gln Tyr Pro Thr Lys Lys Gly Asp
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Asn Val Thr Thr Leu Ser Tyr
            100                 105                 110

Gln Leu Thr Lys Gly His Thr Arg Ser Phe Glu Thr Ser Val Asn Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Ser
145                 150                 155                 160

Phe Thr Asp Thr Thr Glu Met Lys Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 130
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 130

Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Gln Val Thr Gln Thr Arg Ser Tyr
            100                 105                 110

Gln Leu Thr Lys Gly His Thr Arg Ser Phe Glu Thr Ser Val Asn Ala
        115                 120                 125

```
Lys Tyr Ser Val Gly Ala Asn Ile Asp Ile Val Asn Val Gly Ser Glu
            130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 131
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 131

Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Leu Ser Gly Arg Phe Asp Gln Tyr Pro Thr Lys Lys Gly Asp
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Asn Val Thr Thr Thr Leu Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Asp
    130                 135                 140

Ile Ser Ile Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Val Asp Leu Tyr Tyr Leu Ser Ala Ile Thr Gln Arg Lys Arg Val Ile
    210                 215                 220
```

-continued

```
Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 132
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 132

```
Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Leu Ser Gly Arg Phe Asp Gln Tyr Pro Thr Lys Lys Gly Asp
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Asn Val Thr Thr Thr Leu Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Glu
    130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Val Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 133
<211> LENGTH: 271
<212> TYPE: PRT
<213> ORGANISM: Artificial Sequence
<220> FEATURE:
<223> OTHER INFORMATION: PIP-1A / PSEEN3174 chimera

```
<400> SEQUENCE: 133

Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Asn Val Thr Thr Leu Ser Tyr
            100                 105                 110

Gln Leu Thr Lys Gly His Thr Arg Ser Phe Glu Thr Ser Val Asn Ala
        115                 120                 125

Lys Tyr Ser Val Gly Gly Ser Ile Asp Ile Val Asn Val Gly Ser Asp
    130                 135                 140

Ile Ser Ile Gly Phe Ser Arg Ser Glu Ser Trp Ser Thr Thr Gln Ser
145                 150                 155                 160

Phe Thr Asp Thr Thr Glu Met Lys Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Val Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 134
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 134

Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Leu Ser Gly Arg Phe Asp Gln Tyr Pro Thr Lys Lys Gly Asp
        35                  40                  45

Phe Ala Ile Asp Gly Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
```

```
                85                  90                  95
Val Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Glu
            130                 135                 140

Ile Ser Thr Gly Phe Thr Arg Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Ser Lys Thr Gln Ala Val Gly Ser Arg
            195                 200                 205

Val Asp Leu Tyr Tyr Leu Ser Ala Ile Thr Gln Arg Lys Arg Val Ile
            210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 135
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 135

Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
            50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
            130                 135                 140

Ile Ser Ile Gly Phe Ser Asn Ser Glu Ser Trp Ser Thr Thr Gln Ser
145                 150                 155                 160

Phe Thr Asp Thr Thr Glu Met Lys Gly Pro Gly Thr Phe Ile Val Tyr
                165                 170                 175

Gln Val Val Met Val Tyr Ala His Asn Ala Thr Ser Ala Gly Arg Gln
```

```
            180              185              190
Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 136
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 136

Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Leu Ser Gly Arg Phe Asp Gln Tyr Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Ser
145                 150                 155                 160

Phe Thr Asp Thr Thr Glu Met Lys Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Val Asp Leu Tyr Tyr Leu Ser Ala Ile Thr Gln Arg Lys Arg Val Ile
    210                 215                 220

Val Pro Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 137
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 137

```
Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Leu Ser Gly Arg Phe Asp Gln Phe Pro Thr Lys Arg Gly Gly
        35                  40                  45

Phe Ala Ile Asp Gly Tyr Leu Leu Asp Tyr Ser Ala Pro Lys Gln Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Ala Asn Ile Asp Ile Val Asn Val Gly Ser Glu
    130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Ile Val Tyr
                165                 170                 175

Gln Val Val Leu Val Tyr Ala His Asn Ala Thr Ser Ala Gly Arg Gln
            180                 185                 190

Asn Gly Asn Ala Phe Ala Tyr Ser Lys Thr Gln Ala Val Gly Ser Arg
        195                 200                 205

Val Asp Leu Tyr Tyr Leu Ser Ala Ile Thr Gln Arg Lys Arg Val Ile
    210                 215                 220

Val Pro Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 138
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 138

```
Met Pro Thr Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45
```

Phe Ala Ile Asp Ser Tyr Leu Leu Asp Tyr Ser Ala Pro Lys Gln Gly
         50                  55                  60

Cys Trp Val Asp Gly Ile Thr Val Tyr Gly Asp Ile Tyr Ile Gly Lys
 65                  70                  75                  80

Gln Asn Trp Gly Thr Tyr Thr Arg Pro Val Phe Ala Tyr Leu Gln Tyr
                 85                  90                  95

Val Glu Thr Ile Ser Ile Pro Gln Gln Val Thr Gln Thr Arg Ser Tyr
                100                 105                 110

Gln Leu Thr Lys Gly His Thr Arg Ser Phe Glu Thr Ser Val Asn Ala
                115                 120                 125

Lys Tyr Ser Val Gly Ala Asn Ile Asp Ile Val Asn Val Gly Ser Asp
        130                 135                 140

Ile Ser Ile Gly Phe Ser Asn Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
                180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Arg Lys Arg Val Ile
210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 139
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 139

Met Pro Ile Lys Glu Glu Leu Ser Gln Pro Gln Ser His Ser Ile Glu
 1               5                  10                  15

Leu Asp Glu Ala Ser Lys Glu Ala Ala Ser Thr Arg Ala Ala Leu Thr
                20                  25                  30

Ser Asn Leu Ser Gly Arg Phe Asp Gln Tyr Pro Thr Lys Leu Gly Asp
        35                  40                  45

Phe Ala Ile Asp Gly Tyr Leu Leu Asp Tyr Ser Ala Pro Lys Gln Gly
         50                 55                  60

Cys Trp Val Asp Gly Ile Thr Val Tyr Gly Asp Ile Phe Ile Gly Lys
 65                  70                  75                  80

Gln Asn Trp Gly Thr Tyr Thr Arg Pro Val Phe Ala Tyr Leu Gln Tyr
                85                  90                  95

Val Asp Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
                115                 120                 125

Lys Tyr Ser Val Gly Gly Ser Ile Asp Ile Val Asn Val Gly Ser Glu
        130                 135                 140

```
Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Gly Asn Ala Phe Ala Tyr Ser Lys Thr Gln Ala Val Gly Ser Arg
            195                 200                 205

Val Asp Leu Tyr Tyr Leu Ser Ala Ile Thr Gln Arg Lys Arg Val Ile
        210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 140
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 140

Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Gly Tyr Leu Leu Asp Tyr Ser Ala Pro Lys Gln Gly
        50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Val Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Gly Asn Ala Phe Ala Tyr Ser Lys Thr Gln Ala Val Gly Ser Arg
            195                 200                 205

Val Asp Leu Tyr Tyr Leu Ser Ala Ile Thr Gln Arg Lys Arg Val Ile
        210                 215                 220

Val Pro Ser Ser Asn Ala Val Thr Pro Leu Asp Trp Asp Thr Val Gln
225                 230                 235                 240
```

```
Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
        260                 265                 270

<210> SEQ ID NO 141
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 141

Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
        50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Asn Val Thr Thr Leu Ser Tyr
                100                 105                 110

Gln Leu Thr Lys Gly His Thr Arg Ser Phe Glu Thr Ser Val Asn Ala
            115                 120                 125

Lys Tyr Ser Val Gly Ala Asn Ile Asp Ile Val Asn Val Gly Ser Asp
        130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Met Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Val Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
        260                 265                 270

<210> SEQ ID NO 142
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 142

Met Pro Ile Lys Glu Glu Leu Ser Gln Pro Gln Ser His Ser Ile Glu
1               5                   10                  15
```

```
Leu Asp Asp Leu Lys Ser Glu Gln Gly Ser Leu Arg Ala Ala Leu Thr
             20                  25                  30

Ser Asn Phe Ala Gly Asn Phe Asp Gln Phe Pro Thr Lys Arg Gly Gly
         35                  40                  45

Phe Ala Ile Asp Ser Tyr Leu Leu Asp Tyr Ser Ala Pro Lys Gln Gly
     50                  55                  60

Cys Trp Val Asp Gly Ile Thr Val Tyr Gly Asp Ile Tyr Ile Gly Lys
 65                  70                  75                  80

Gln Asn Trp Gly Thr Tyr Thr Arg Pro Val Phe Ala Tyr Leu Gln Tyr
                 85                  90                  95

Met Asp Thr Ile Ser Ile Pro Gln Gln Val Thr Gln Thr Arg Ser Tyr
             100                 105                 110

Gln Leu Thr Lys Gly His Thr Arg Ser Phe Glu Thr Ser Val Asn Ala
         115                 120                 125

Lys Tyr Ser Val Gly Ala Asn Ile Asp Ile Val Asn Val Gly Ser Glu
130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Ile Val Tyr
                 165                 170                 175

Gln Val Val Met Val Tyr Ala His Asn Ala Thr Ser Ala Gly Arg Gln
             180                 185                 190

Asn Ala Tyr Ala Phe Ala Tyr Asn Lys Thr Gln Ala Val Gly Ser Arg
         195                 200                 205

Val Asp Leu Tyr Phe Leu Ser Ala Ile Thr Gln Arg Lys Arg Val Ile
     210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                 245                 250                 255

Phe Ser Phe Asp Trp Ser Ala Tyr Asn Asp Pro His Arg Arg Tyr
             260                 265                 270

<210> SEQ ID NO 143
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 143

Met Pro Ile Lys Glu Glu Leu Ser Gln Pro Gln Ser His Ser Ile Glu
 1               5                  10                  15

Leu Asp Asp Leu Lys Ser Glu Gln Gly Ser Leu Arg Ala Ala Leu Thr
             20                  25                  30

Ser Asn Phe Ala Gly Asn Phe Asp Gln Phe Pro Thr Lys Arg Gly Gly
         35                  40                  45

Phe Ala Ile Asp Ser Tyr Leu Leu Asp Tyr Ser Ala Pro Lys Gln Gly
     50                  55                  60

Cys Trp Val Asp Gly Ile Thr Val Tyr Gly Asp Ile Phe Ile Gly Lys
 65                  70                  75                  80

Gln Asn Trp Gly Thr Tyr Thr Arg Pro Val Phe Ala Tyr Leu Gln Tyr
                 85                  90                  95

Met Asp Thr Ile Ser Ile Pro Gln Gln Val Thr Gln Thr Arg Ser Tyr
             100                 105                 110
```

```
Gln Leu Thr Lys Gly His Thr Lys Thr Phe Thr Thr Asn Val Ser Ala
            115                 120                 125
Lys Tyr Ser Val Gly Ala Asn Ile Asp Ile Val Asn Val Gly Ser Glu
        130                 135                 140
Ile Ser Thr Gly Phe Thr Arg Ser Glu Ser Trp Ser Thr Thr Gln Thr
145                 150                 155                 160
Phe Ser Asn Ser Thr Gln Leu Thr Gly Pro Gly Thr Phe Ile Val Tyr
                165                 170                 175
Gln Val Val Met Val Tyr Ala His Asn Ala Thr Ser Ala Gly Arg Gln
            180                 185                 190
Asn Gly Asn Ala Phe Ala Tyr Ser Lys Thr Gln Ala Val Gly Ser Arg
        195                 200                 205
Leu Asp Leu Tyr Tyr Leu Ser Ala Ile Thr Gln Asn Ser Thr Val Ile
    210                 215                 220
Val Asp Ser Ser Asn Ala Val Thr Pro Leu Asp Trp Asp Thr Val Gln
225                 230                 235                 240
Arg Asn Val Leu Met Glu Asn Tyr Asn Pro Gly Ser Asn Ser Gly His
                245                 250                 255
Phe Ser Phe Asp Trp Ser Ala Tyr Asn Asp Pro His Arg Arg Tyr
            260                 265                 270

<210> SEQ ID NO 144
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 144

Met Pro Ile Lys Glu Glu Leu Ser Gln Pro Gln Ser His Ser Ile Glu
1               5                   10                  15
Leu Asp Asp Leu Lys Ser Glu Gln Gly Ser Leu Arg Ala Ala Leu Thr
            20                  25                  30
Ser Asn Phe Ala Gly Asn Phe Asp Gln Tyr Pro Thr Lys Lys Gly Asp
        35                  40                  45
Phe Ala Ile Asp Gly Tyr Leu Leu Asp Tyr Ser Ala Pro Lys Gln Gly
    50                  55                  60
Cys Trp Val Asp Gly Ile Thr Val Tyr Gly Asp Ile Tyr Ile Gly Lys
65                  70                  75                  80
Gln Asn Trp Gly Thr Tyr Thr Arg Pro Val Phe Ala Tyr Leu Gln Tyr
                85                  90                  95
Met Asp Thr Ile Ser Ile Pro Gln Gln Val Thr Gln Thr Arg Ser Tyr
            100                 105                 110
Gln Leu Thr Lys Gly His Thr Lys Thr Phe Thr Thr Asn Val Ser Ala
        115                 120                 125
Lys Tyr Ser Val Gly Ala Asn Ile Asp Ile Val Asn Val Gly Ser Asp
    130                 135                 140
Ile Ser Ile Gly Phe Ser Asn Ser Glu Ser Trp Ser Thr Thr Gln Ser
145                 150                 155                 160
Phe Thr Asp Thr Thr Glu Met Lys Gly Pro Gly Thr Phe Ile Val Tyr
                165                 170                 175
Gln Val Val Met Val Tyr Ala His Asn Ala Thr Ser Ala Gly Arg Gln
            180                 185                 190
Asn Ala Asn Ala Phe Ala Tyr Ser Lys Thr Gln Ala Val Gly Ser Arg
        195                 200                 205
```

Val Asp Leu Tyr Tyr Leu Ser Ala Ile Thr Gln Arg Lys Arg Val Ile
            210                 215                 220

Val Pro Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 145
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 145

Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Leu Ser Gly Arg Phe Asp Gln Tyr Pro Thr Lys Lys Gly Asp
        35                  40                  45

Phe Ala Ile Asp Ser Tyr Leu Leu Asp Tyr Ser Ala Pro Lys Gln Gly
50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Glu Thr Ile Ser Ile Pro Gln Asn Val Thr Thr Leu Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Asp
130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Val Asp Leu Tyr Tyr Leu Ser Ala Ile Thr Gln Arg Lys Arg Val Ile
            210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 146
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 146

Met Pro Ile Lys Glu Glu Leu Ser Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Leu Ser Gly Arg Phe Asp Gln Tyr Pro Thr Lys Arg Gly Gly
        35                  40                  45

Phe Ala Ile Asp Gly Tyr Leu Leu Asp Tyr Ser Ser Pro Lys Gln Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Gln Val Thr Gln Thr Arg Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Asp
    130                 135                 140

Ile Ser Ile Gly Phe Ser Asn Ser Glu Ser Trp Ser Thr Thr Gln Ser
145                 150                 155                 160

Phe Thr Asn Ser Thr Gln Leu Thr Gly Pro Gly Thr Phe Val Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 147
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 147

Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys

```
            65                  70                  75                  80
Gln Asn Trp Gly Thr Tyr Thr Arg Pro Val Phe Ala Tyr Leu Gln Tyr
                    85                  90                  95

Val Glu Thr Ile Ser Ile Pro Gln Asn Val Thr Thr Leu Ser Tyr
                100                 105                 110

Gln Leu Thr Lys Gly His Thr Arg Ser Phe Glu Thr Ser Val Asn Ala
                115                 120                 125

Lys Tyr Ser Val Gly Ala Asn Ile Asp Ile Val Asn Val Gly Ser Glu
            130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                    165                 170                 175

Gln Val Val Leu Val Tyr Ala His Asn Ala Thr Ser Ala Gly Arg Gln
                180                 185                 190

Asn Ala Asn Ala Phe Ala Tyr Ser Lys Thr Gln Ala Val Gly Ser Arg
            195                 200                 205

Val Asp Leu Tyr Tyr Leu Ser Ala Ile Thr Gln Arg Lys Arg Val Ile
        210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                    245                 250                 255

Phe Ser Phe Asp Trp Ser Ala Tyr Asn Asp Pro His Arg Arg Tyr
                260                 265                 270

<210> SEQ ID NO 148
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 148

Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Leu Pro Gly Arg Phe Asp Gln Tyr Pro Thr Lys Lys Gly Asp
            35                  40                  45

Phe Ala Ile Asp Ser Tyr Leu Leu Asp Tyr Ser Ala Pro Lys Gln Gly
        50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                    85                  90                  95

Met Glu Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
            115                 120                 125

Lys Tyr Ser Val Gly Ala Asn Ile Asp Ile Val Asn Val Gly Ser Asp
        130                 135                 140

Ile Ser Ile Gly Phe Ser Arg Ser Glu Ser Trp Ser Thr Thr Gln Thr
145                 150                 155                 160

Phe Ser Asn Ser Thr Gln Leu Thr Gly Pro Gly Thr Phe Ile Val Tyr
```

```
                165                 170                 175
Gln Val Val Met Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 149
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 149

Met Pro Ile Lys Glu Glu Leu Ser Gln Pro Gln Ser His Ser Ile Glu
1               5                  10                  15

Leu Asp Asp Leu Lys Ser Glu Gln Gly Ser Leu Arg Ala Ala Leu Thr
            20                  25                  30

Ser Asn Leu Ser Gly Arg Phe Asp Gln Tyr Pro Thr Lys Lys Gly Asp
        35                  40                  45

Phe Ala Ile Asp Gly Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Asp
    130                 135                 140

Ile Ser Ile Gly Phe Ser Asn Ser Glu Ser Trp Ser Thr Thr Gln Ser
145                 150                 155                 160

Phe Thr Asp Thr Thr Glu Met Lys Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Leu Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
```

<210> SEQ ID NO 150
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 150

Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Glu
    130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Ile Val Tyr
                165                 170                 175

Gln Val Val Leu Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 151
<211> LENGTH: 271
<212> TYPE: PRT
<213> ORGANISM: Artificial Sequence
<220> FEATURE:
<223> OTHER INFORMATION: PIP-1A / PSEEN3174 chimera

<400> SEQUENCE: 151

Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
                 35                  40                  45

Leu Ala Ile Asp Ser Tyr Leu Leu Asp Tyr Ser Ala Pro Lys Gln Gly
 50                  55                  60

Cys Trp Val Asp Gly Ile Thr Val Tyr Gly Asp Ile Phe Ile Gly Lys
 65                  70                  75                  80

Gln Asn Trp Gly Thr Tyr Thr Arg Pro Val Phe Ala Tyr Leu Gln Tyr
                 85                  90                  95

Met Asp Thr Ile Ser Ile Pro Gln Gln Val Thr Gln Thr Arg Ser Tyr
                100                 105                 110

Gln Leu Thr Lys Gly His Thr Lys Thr Phe Thr Asn Val Ser Ala
                115                 120                 125

Lys Tyr Ser Val Gly Gly Ser Ile Asp Ile Val Asn Val Gly Ser Glu
130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Ile Val Tyr
                165                 170                 175

Gln Val Val Met Val Tyr Ala His Asn Ala Thr Ser Ala Gly Arg Gln
                180                 185                 190

Asn Gly Asn Ala Phe Ala Tyr Asn Lys Thr Asn Thr Val Gly Ser Arg
                195                 200                 205

Val Asp Leu Tyr Tyr Leu Ser Ala Ile Thr Gln Asn Ser Thr Val Ile
                210                 215                 220

Val Asp Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 152
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 152
atgccgatca aggaagagct gagccagcct caaagccatt cgatcgaact ggacgatctg     60
aaaagcgagc agggtagttt acgggccgcg ttgacttcca acttcgctgg caatttcgac    120
cagtttccga ccaagcgtgg cggatttgcg atcgattcct atttgctgga ctacagcgcc    180
cccaagcaag gttgctgggt ggacggtatc actgtctatg gcgatatcta catcggcaag    240
cagaactggg gcacttatac ccgcccggtg tttgcctacc tacagtatat ggataccatc    300
tccattccac agcaagtgac gcagacccgt agctatcagc tgaccaaggg catacccgt    360 tccttcgaga ccagtgtcaa cgccaagtac agcgttggcg ccaacataga tatcgtcaac    420
gtgggttcgg agatttccac cgggtttacc cgcagcgagt cctggtccac cacgcagtcg    480
ttcaccgata ccaccgagat gaaggggcca gggacgttcg tcatttacca ggtcgtgctg    540
gtgtatgcgc acaacgccac ctcggcaggg cggcagaatg ccaatgcctt cgcctacaat    600
aaaaccaata ccgtgggctc gcgggtggac ttgtactact tgtcggccat acccagcgc    660 aagcgggtca tcgttccgtc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813

<210> SEQ ID NO 153
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 153
atgccgatca aggaagagct gagccagcct caaagccatt cgatcgaact ggacgatctg     60
aaaagcgagc agggtagttt acgggccgcg ttgacttcca acttcgctgg caatttcgac   120
cagtttccga ccaagcgtgg cggatttgcg atcgattcct atttgctgga ctacagctca   180
cccaagcaag gttgctgggt ggacggtatc actgtctatg cgatatctt catcggcaag    240 cagaactggg gcacttatac ccgcccggtg tttgcctacc tacagtatat ggataccatc   300
tccattccac agcaagtgac gcagacccgt agctatcagc tgaccaaggg catacccaaa   360
acattcacca ccaacgtctc agccaagtac agcgttggcg gctcaataga tatcgtcaac   420
gtgggttcgg agatttccac cgggtttacc cgcagcgagt cctggtccac cacgcagtcg   480
ttcaccgata ccaccgagat gaaggggcca gggacgttca ttgtctacca ggtcgtgatg   540
gtgtatgcgc acaacgccac ctcggcaggg cggcagaatg taatgccctt cgcctacaat   600
aaaaccaata ccgtgggctc gcgggtggac ttgtactact tgtcggccat acccagaat    660 agtactgtca tcgttgactc gagcaaagcc attgcaccgc tggactggga tacggtgcaa   720
cgcaacgtgc tgatggaaaa ctacaaccca ggcagtaaca gcggacactt cagcttcgac    780
tggagtgcct acaacgatcc tcatcgccgt tat                                 813

<210> SEQ ID NO 154
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 154
atgcctatca aggaagagct gagccagcct caaagccatt cgatcgaact ggacgatctg     60
aaaagcgagc agggtagttt acgggccgcg ttgacttcca acctgtctgg ccgcttcgac   120
cagtttccga ccaagcgtgg cggatttgcg atcgattcct atttgctgga ctacagcgcc   180
cccaagcaag gttgctgggt ggacggtatc actgtctatg cgatatcta catcggcaag    240 cagaactggg gcacttatac ccgcccggtg tttgcctacc tacagtatgt ggataccatc   300
tccattccac agcaagtgac gcagacccgt agctatcagc tgaccaaggg catacccaaa   360
acattcacca ccaacgtctc agccaagtac agcgttggcg gctcaataga tatcgtcaac   420
gtgggttcgg atatttccat ggggttttcc aatagcgagt cctggtccac cacgcagtcg   480
ttcaccgata ccaccgagat gaaggggcca gggacgttcg tcatttacca ggtcgtgctg   540
gtgtatgcgc acaacgccac ctcggcaggg cggcagaatg ccaatgcctt cgcctacagc   600
aaaacccagg cagtgggctc gcggctggac ttgtactact tgtcggccat acccagcgc    660 aagcgggtca tcgttccgtc gagcaatgcc gtcacgccgc tggactggga tacggtgcaa   720
cgcaacgtgc tgatggaaaa ctacaaccca ggcagtaaca gcggacactt cagcttcgac    780
tggagtgcct acaacgatcc tcatcgccgt tat                                 813

<210> SEQ ID NO 155
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 155

```
atgccgatca aggaagagct gagccagcct caaagccatt cgatcgaact ggacgatctg      60
aaaagcgagc agggtagttt acgggccgcg ttgacttcca acttcgctgg caatttcgac     120
cagtttccga ccaagcgtgg cggatttgcg atcgatggtt atttgctgga ctacagctca     180
cccaagcaag gttgctgggt ggacggtatc actgtctatg gcgatatcta catcggcaag     240
cagaactggg gcacttatac ccgcccggtg tttgcctacc tacagtatat ggataccatc     300
tccattccac agaatgtgac gcagacccgt agctatcagc tgaccaaggg gcataccaaa     360
acattcacca ccaacgtctc agccaagtac agcgttggcg gctcaataga tatcgtcaac     420
gtgggttcgg atatttccat tgggtttacc cgcagcgagt cctggtccac cacgcagacc     480
ttctccaatt ctacccagtt aacggggcca gggacgttcg tcatttacca ggtcgtgctg     540
gtgtatgcgc acaacgccac ctcggcaggg cggcagaatg gtaatgcctt cgcctacaat     600
aaaaccaata ccgtgggctc gcggctggac ttgtactact tgtcggccat tacccagcgc     660
aagcgggtca tcgttccgtc gagcaatgcc gtcacgccgc tggactggga tacggtgcaa     720
cgcaacgtgc tgatggaaaa ctacaaccca ggcagtaaca gcggacactt cagcttcgac     780
tggagtgcct acaacgatcc tcatcgccgt tat                                  813
```

<210> SEQ ID NO 156
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 156

```
atgccgatca aggaagagct gagccagcct caaagccatt cgatcgaact ggacgatctg      60
aaaagcgagc agggtagttt acgggccgcg ttgacttcca acctgtctgg ccgcttcgac     120
cagtacccga ccaagaaggg cgactttgcg atcgatggtt atttgctgga ctacagcgcc     180
cccaagcaag gttgctgggt ggacggtatc actgtctatg gcgatatcta catcggcaag     240
cagaactggg gcacttatac ccgcccggtg tttgcctacc tacagtatat ggataccatc     300
tccattccac agcaagtgac gcagacccgt agctatcagc tgaccaaggg gcataccaaa     360
acattcacca ccaacgtctc agccaagtac agcgttggcg ccaacataga tatcgtcaac     420
gtgggttcgg atatttccat tgggttttcc cgcagcgagt cctggtccac cacgcagacc     480
ttctccaatt ctacccagtt aacggggcca gggacgttca ttgtctacca ggtcgtgctg     540
gtgtatgcgc acaacgccac ctcggcaggg cggcagaatg ccaatgcctt cgcctacagc     600
aaaacccagg cagtgggctc gcgggtggac ttgtactact tgtcggccat tacccagcgc     660
aagcgggtca tcgttgactc gagcaaagcc attgcaccgc tggactggga tacggtgcaa     720
cgcaacgtgc tgatggaaaa ctacaaccca ggcagtaaca gcggacactt cagcttcgac     780
tggagtgcct acaacgatcc tcatcgccgt tat                                  813
```

<210> SEQ ID NO 157

```
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 157
atgccgatca aggaagagct gagccagcct caaagccatt cgatcgaact ggacgaggtg      60
agcaaggagg ccgcaagtac gcgggccgcg ttgacttcca acctgtctgg ccgcttcgac     120
cagtacccga ccaagaaggg cgactttgcg atcgattcct atttgctgga ctacagcgcc     180
cccaagcaag gttgctgggt ggacggtatc actgtctatg cgatatcttc atcggcaag     240
cagaactggg gcacttatac ccgcccggtg tttgcctacc tacagtatgt ggaaaccatc     300
tccattccac agcaagtgac gcagacccgt agctatcagc tgaccaaggg cataccaaa    360
acattcacca ccaacgtctc agccaagtac agcgttggcg gctcaataga tatcgtcaac     420
gtgggttcgg agatttccac cgggtttacc cgcagcgagt cctggtccac cacgcagtcg     480
ttcaccgata ccaccgagat gaaggggcca gggacgttca ttgtctacca ggtcgtgctg     540
gtgtatgcgc acaacgccac ctcggcaggg cggcagaatg gtaatgcctt cgcctacaat     600
aaaaccaata ccgtgggctc gcggctggac ttgtactact tgtcggccat acccagcgc     660
aagcgggtca tcgttccgtc gagcaatgcc gtcacgccgc tggactggga tacggtgcaa     720
cgcaacgtgc tgatggaaaa ctacaacccg ggcagtaaca gcggacactt cagcttcgac     780
tggagtgcct acaacgatcc tcatcgccgt tat                                   813

<210> SEQ ID NO 158
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 158
atgccgatca aggaagagct gagccagcct caaagccatt cgatcgaact ggacgaggtg      60
agcaaggagg ccgcaagtac gcgggccgcg ttgacttcca acctgtctgg ccgcttcgac     120
cagtacccga ccaagaaggg cgactttgcg atcgattcct atttgctgga ctacagctca     180
cccaagcaag gttgctgggt ggacggtatc actgtctatg cgatatcttc atcggcaag     240
cagaactggg gcacttatac ccgcccggtg tttgcctacc tacagtatat ggataccatc     300
tccattccac agcaagtgac gcagacccgt agctatcagc tgaccaaggg catacccgt     360
tccttcgaga ccagtgtcaa cgccaagtac agcgttggcg ccaacataga tatcgtcaac     420
gtgggttcgg atatttccat tgggttttcc aatagcgagt cctggtccac cacgcagtcg     480
ttcaccgata ccaccgagat gaaggggcca gggacgttca ttgtctacca ggtcgtgctg     540
gtgtatgcgc acaacgccac ctcggcaggg cggcagaatg ccaatgcctt cgcctacagc     600
aaaacccagg cagtgggctc gcgggtggac ttgtactact tgtcggccat acacagcgc     660
aagcgggtca tcgttccgtc gagcaatgcc gtcacgccgc tggactggga tacggtgcaa     720
cgcaacgtgc tgatggaaaa ctacagccca ggcagtaaca gcggacactt cagcttcgac     780
tggagtgcct acaacgatcc tcatcgccgt tat                                   813

<210> SEQ ID NO 159
<211> LENGTH: 813
<212> TYPE: DNA
<213> ORGANISM: Artificial Sequence
```

```
<220> FEATURE:
<223> OTHER INFORMATION: PIP-1A / PSEEN3174 chimera

<400> SEQUENCE: 159
atgcctatca aggaagagct gagccagcct caaagccatt cgatcgaact ggacgaggtg      60
agcaaggagg ccgcaagtac gcgggccgcg ttgacttcca acttgtctgg ccgcttcgac     120
cagttcccga ccaagagtgg cgaatttgcg atcgattcct atttgctgga ctacagcgcc     180
cccaagcaag gttgctgggt ggacggtatc actgtctatg gcgatatctt catcggcaag     240
cagaactggg gcacttatac ccgcccggtg tttgcctacc tacagtatat ggataccatc     300
tccattccac agcaagtgac gcagacccgt agctatcagc tgaccaaggg cataccaaa     360 acattcacca ccaacgtctc agccaagtac agcgttggcg gctcaataga tatcgtcaac     420
gtgggttcgg agatttccac cgggtttacc cgcagcgagt cctggtccac cacgcagtcg     480
ttcaccgata ccaccgagat gaaggggcca gggacgttca ttgtctacca ggtcgtgatg     540
gtgtatgcgc acaacgccac ctcggcaggg cggcagaatg ccaatgcctt cgcctacagc     600
aaaaccaata ccgtgggctc gcggctggac ttgtactact tgtcggccat acccagcgc     660 aagcgggtca tcgttccgtc gagcaaagcc attgcaccgc tggactggga tacggtgcaa     720
cgcaacgtgc tgatggaaaa ctacaaccca ggcagtaaca gcggacactt cagcttcgac     780
tggagtgcct acaacgatcc tcatcgccgt tat                                  813

<210> SEQ ID NO 160
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 160
atgccgatca aggaagagct gagccagcct caaagccatt cgatcgaact ggacgatctg      60
aaaagcgagc agggtagttt acgggccgcg ttgacttcca acttcgctgg caatttcgac     120
cagtttccga ccaagcgtgg cggatttgcg atcgattcct atttgctgga ctacagctca     180
cccaagcaag gttgctgggt ggacggtatc actgtctatg gcgatatctt catcggcaag     240
cagaactggg gcacttatac ccgcccggtg tttgcctacc tacagtatat ggataccatc     300
tccattccac agcaagtgac gcagacccgt agctatcagc tgaccaaggg cataccaaa     360 acattcacca ccaacgtctc agccaagtac agcgttggcg gctcaataga tatcgtcaac     420
gtgggttcgg atatttccat gggttttcc aatagcgagt cctggtccac cacgcagtcg     480
ttcaccgata ccaccgagat gaaggggcca gggacgttca ttgtctacca ggtcgtgatg     540
gtgtatgcgc acaacgccac ctcggcaggg cggcagaatg ccaatgcctt cgcctacaat     600
aaaaccaata ccgtgggctc gcggctggac ttgtactact tgtcggccat acccagaat     660 agtactgtca tcgttgactc gagcaaagcc attgcaccgc tggactggga tacggtgcaa     720
cgcaacgtgc tgatggaaaa ctacaaccca ggcagtaaca gcggacactt cagcttcgac     780
tggagtgcct acaacgatcc tcatcgccgt tat                                  813

<210> SEQ ID NO 161
<211> LENGTH: 813
<212> TYPE: DNA
<213> ORGANISM: Artificial Sequence
<220> FEATURE:
<223> OTHER INFORMATION: PIP-1A / PSEEN3174 chimera
```

<400> SEQUENCE: 161

```
atgccgatca aggaagagct gagccagcct caaagccatt cgatcgaact ggacgaggtg      60
agcaaggagg ccgcaagtac gcgggccgcg ttgacttcca acctgtctgg ccgcttcgac     120
cagtacccga ccaagcgtgg cggatttgcg atcgattcct atttgctgga ctacagcgcc     180
cccaagcaag gttgctgggt ggacggtatc actgtctatg gcgatatcta catcggcaag     240
cagaactggg gcacttatac ccgcccggtg tttgcctacc tacagtatgt ggaaaccatc     300
tccattccac agaatgtgac gaccaccctc agctatcagc tgaccaaggg catacccgt      360
tccttcgaga ccagtgtcaa cgccaagtac agcgttggcg ccaacataga tatcgtcaac     420
gtgggttcgg agatttccac cgggtttacc cgcagcgagt cctggtccac cacgcagtcg     480
ttcaccgata ccaccgagat gaaggggcca gggacgttcg tcatttacca ggtcgtgctg     540
gtgtatgcgc acaacgccac ctcggcaggg cggcagaatg ccaatgcctt cgcctacagc     600
aaaacccagg cagtgggctc gcggctggac ttgtactact tgtcggccat tacccagcgc     660
aagcgggtca tcgttccgtc gagcaatgcc gtcacgccgc tggactggga tacggtgcaa     720
cgcaacgtgc tgatggaaaa ctacaaccca ggcagtaaca gcggacactt cagcttcgac     780
tggagtgcct acaacgatcc tcatcgccgt tat                                  813
```

<210> SEQ ID NO 162
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 162

```
atgcctatca aggaagagct gagccagcct caaagccatt cgatcgaact ggacgatctg      60
aaaagcgagc agggtagttt acgggccgcg ttgacttcca acctgtctgg ccgcttcgac     120
cagtacccga ccaagaaggg cgactttgcg atcgattcct atttgctgga ctacagcgcc     180
cccaagcaag gttgctgggt ggacggtatc actgtctatg gcgatatcta catcggcaag     240
cagaactggg gcacttatac ccgcccggtg tttgcctacc tacagtatat ggataccatc     300
tccattccac agcaagtgac gcagacccgt agctatcagc tgaccaaggg catacccaaa     360
acattcacca ccaacgtctc agccaagtac agcgttggcg gctcaataga tatcgtcaac     420
gtgggttcgg agatttccac cgggtttacc cgcagcgagt cctggtccac cacgcagtcg     480
ttcaccgata ccaccgagat gaaggggcca gggacgttcg tcatttacca ggtcgtgctg     540
gtgtatgcgc acaacgccac ctcggcaggg cggcagaatg ccaatgcctt cgcctacagc     600
aaaacccagg cagtgggctc gcgggtggac ttgtactact tgtcggccat tacccagaat     660
agtactgtca tcgttccgtc gagcaatgcc gtcacgccgc tggactggga tacggtgcaa     720
cgcaacgtgc tgatggaaaa ctacaaccca ggcagtaaca gcggacactt cagcttcgac     780
tggagtgcct acaacgatcc tcatcgccgt tat                                  813
```

<210> SEQ ID NO 163
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 163

```
atgccgatca aggaagagct gagccagcct caaagccatt cgatcgaact ggacgatctg      60
```

```
aaaagcgagc agggtagttt acgggccgcg ttgacttcca acttcgctgg caatttcgac    120
cagtttccga ccaagcgtgg cggatttgcg atcgattcct atttgctgga ctacagcgcc    180
cccaagcaag gttgctgggt ggacggtatc actgtctatg gcgatatcta catcggcaag    240
cagaactggg gcacttatac ccgcccggtg tttgcctacc tacagtatat ggataccatc    300
tccattccac agcaagtgac gcagacccgt agctatcagc tgaccaaggg gcataccaaa    360
acattcacca ccaacgtctc agccaagtac agcgttggcg gctcaataga tatcgtcaac    420
gtgggttcgg atatttccac cgggtttacc cgcagcgagt cctggtccac cacgcagacc    480
ttctccaatt ctacccagtt aacggggcca gggacgttca ttgtctacca ggtcgtgatg    540
gtgtatgcgc acaacgccac ctcggcaggg cggcagaatg gtaatgcctt cgcctacagc    600
aaaacccagg cagtgggctc gcggctggac ttgtactact tgtcggccat acccagaat     660 agtactgtca tcgttgactc gagcaaagcc attgcaccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813
```

<210> SEQ ID NO 164
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 164

```
atgcctatca aggaagagct gagccagcct caaagccatt cgatcgaact ggacgaggtg     60
agcaaggagg ccgcaagtac gcgggccgcg ttgacttcca acctgtctgg ccgcttcgac    120
cagtacccga ccaagaaggg cgactttgcg atcgatggtt atttgctgga ctacagcgcc    180
cccaagcaag gttgctgggt ggacggtatc actgtctatg gcgatatctt catcggcaag    240
cagaactggg gcacttatac ccgcccggtg tttgcctacc tacagtatat ggataccatc    300
tccattccac agcaagtgac gcagacccgt agctatcagc tgaccaaggg gcataccaaa    360
acattcacca ccaacgtctc agccaagtac agcgttggcg gctcaataga tatcgtcaac    420
gtgggttcgg atatttccac cgggtttacc cgcagcgagt cctggtccac cacgcagacc    480
ttctccaatt ctacccagtt aacggggcca gggacgttca ttgtctacca ggtcgtgatg    540
gtgtatgcgc acaacgccac ctcggcaggg cggcagaatg gtaatgcctt cgcctacaat    600
aaaaccaata ccgtgggctc gcggctggac ttgtactact tgtcggccat acccagcgc     660 aagcgggtca tcgttccgtc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813
```

<210> SEQ ID NO 165
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 165

```
atgcctatca aggaagggct gagccagcct caaagccatt cgatcgaact ggacgatctg     60
aaaagcgagc agggtagttt acgggccgcg ttgacttcca acttcgctgg caatttcgac    120
```

| | |
|---|---|
| cagtttccga ccaagcgtgg cggatttgcg atcgattcct atttgctgga ctacagctca | 180 |
| cccaagcaag gttgctgggt ggacggtatc actgtctatg gcgatatcta catcggcaag | 240 |
| cagaactggg gcacttatac ccgcccggtg tttgcctacc tacagtatat ggataccatc | 300 |
| tccattccac agcaagtgac gcagacccgt agctatcagc tgaccaaggg catacccgt | 360 |
| tccttcgaga ccagtgtcaa cgccaagtac agcgttggcg ccaacataga tatcgtcaac | 420 |
| gtgggttcgg agatttccac cgggtttacc cgcagcgagt cctggtccac cacgcagtcg | 480 |
| ttcaccgata ccaccgagat gaaggggcca gggacgttcg tcatttacca ggtcgtgatg | 540 |
| gtgtatgcgc acaacgccac ctcggcaggg cggcagaatg taatgccttc gcctacaat | 600 |
| aaaaccaata ccgtgggctc gcggctggac ttgtactact tgtcggccat acccagcgc | 660 |
| aagcgggtca tcgttccgtc gagcaatgcc gtcacgccgc tggactggga tacggtgcaa | 720 |
| cgcaacgtgc tgatggaaaa ctacaaccca ggcagtaaca gcggacactt cagcttcgac | 780 |
| tggagtgcct acaacgatcc tcatcgccgt tat | 813 |

<210> SEQ ID NO 166
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 166

| | |
|---|---|
| atgcctatca aggaagagct gagccagcct caaagccatt cgatcgaact ggacgaggtg | 60 |
| agcaaggagg ccgcaagtac gcgggccgcg ttgacttcca acttcgctgg caatttcgac | 120 |
| cagtttccga ccaagcgtgg cggatttgcg atcgattcct atttgctgga ctacagcgcc | 180 |
| cccaagcaag gttgctgggt ggacggtatc actgtctatg gcgatatctt catcggcaag | 240 |
| cagaactggg gcacttatac ccgcccggtg tttgcctacc tacagtatgt ggaaaccatc | 300 |
| tccattccac agaatgtgac gaccaccctc agctatcagc tgaccaaggg catacccgt | 360 |
| tccttcgaga ccagtgtcaa cgccaagtac agcgttggcg ccaacataga tatcgtcaac | 420 |
| gtgggttcgg agatttccac cgggtttacc cgcagcgagt cctggtccac cacgcagtcg | 480 |
| ttcaccgata ccaccgagat gaaggggcca gggacgttcg tcatttacca ggtcgtgctg | 540 |
| gtgtatgcgc acaacgccac ctcggcaggg cggcagaatg ccaatgcctt cgcctacagc | 600 |
| aaaacccagg cagtgggctc gcgggtggac ttgtactact tgtcggccat acccagcgc | 660 |
| aagcgggtca tcgttccgtc gagcaatgcc gtcacgccgc tggactggga tacggtgcaa | 720 |
| cgcaacgtgc tgatggaaaa ctacaaccca ggcagtaaca gcggacactt cagcttcgac | 780 |
| tggagtgcct acaacgatcc tcatcgccgt tat | 813 |

<210> SEQ ID NO 167
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 167

| | |
|---|---|
| atgccgatca aggaagagct gagccagcct caaagccatt cgatcgaact ggacgatctg | 60 |
| aaaagcgagc agggtagttt acgggccgcg ttgacttcca acttcgctgg caatttcgac | 120 |
| cagtttccga ccaagaaggg cgactttgcg atcgattcct atttgctgga ctacagctca | 180 |
| cccaagcaag gttgctgggt ggacggtatc actgtctatg gcgatatcta catcggcaag | 240 |

```
cagaactggg gcacttatac ccgcccggtg tttgcctacc tacagtatat ggataccatc    300
tccattccac agcaagtgac gaccaccctc agctatcagc tgaccaaggg gcatacccgt    360
tccttcgaga ccagtgtcaa cgccaagtac agcgttggcg ccaacataga tatcgtcaac    420
gtgggttcgg agatttccac cgggtttacc cgcagcgagt cctggtccac cacgcagacc    480
ttctccaatt ctacccagtt aacggggcca gggacgttca ttgcctacca ggtcgtgatg    540
gtgtatgcgc acaacgccac ctcggcaggg cggcagaatg gtaatgcctt cgcctacagc    600
aaaacccagg cagtgggctc gcgggtggac ttgtactact tgtcggccat acccagcgc    660 aagcgggtca tcgttccgtc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813
```

<210> SEQ ID NO 168
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 168

```
atgccgatca aggaagagct gagccagcct caaagccatt cgatcgaact ggacgaggtg     60
agcaaggagg ccgcaagtac gcgggccgcg ttgacttcca acctgtctgg ccgcttcgac    120 cagtaccccga ccaagaaggg cgactttgcg atcgatggtt atttgctgga ctacagctca   180
cccaagcaag gttgctgggt ggacggtatc actgtctatg gcgatatcta catcggcaag    240
cagaactggg gcacttatac ccgcccggtg tttgcctacc tacagtatat ggataccatc    300
tccattccac agcaagtgac gcagacccgt agctatcagc tgaccaaggg gcataccaaa    360
acattcacca ccaacgtctc agccaagtac agcgttggcg ccaacataga tatcgtcaac    420
gtgggttcgg agatttccac cgggtttacc cgcagcgagt cctggtccac cacgcagtcg    480
ttcaccgata ccaccgagat gaaggggcca gggacgttcg tcatttacca ggtcgtgctg    540
gtgtatgcgc acaacgccac ctcggcaggg cggcagaatg gtaatgcctt cgcctacagc    600
aaaacccagg cagtgggctc gcgggtggac ttgtactact tgtcggccat acccagcgc    660 aagcgggtca tcgttccgtc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813
```

<210> SEQ ID NO 169
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 169

```
atgccgatca aggaagagct gagccagcct caaagccatt cgatcgaact ggacgaggtg     60
agcaaggagg ccgcaagtac gcgggccgcg ttgacttcca acctgtctgg caatttcgac    120
cagtttccga ccaagcgtgg cggatttgcg atcgattcct atttgctgga ctacagcgcc    180
cccaagcaag gttgctgggt ggacggtatc actgtctatg gcgatatctt catcggcaag    240
cagaactggg gcacttatac ccgcccggtg tttgcctacc tacagtatgt ggaaaccatc    300
```

| | |
|---|---|
| tccattccac agaatgtgac gaccaccctc agctatcagc tgaccaaggg gcatacccgt | 360 |
| tccttcgaga ccagtgtcaa cgccaagtac agcgttggcg ccaacataga tatcgtcaac | 420 |
| gtgggttcgg agatttccac cgggtttacc cgcagcgagt cctggtccac cacgcagtcg | 480 |
| ttcaccgata ccaccgagat gaaggggcca gggacgttcg tcatttacca ggtcgtgatg | 540 |
| gtgtatgcgc acaacgccac ctcggcaggg cggcagaatg ccaatgcctt cgcctacagc | 600 |
| aaaacccagg cagtgggctc gcggctggac ttgtactact tgtcggccat acccagcgc | 660 |
| aagcgggtca tcgttccgtc gagcaatgcc gtcacgccgc tggactggga tacggtgcaa | 720 |
| cgcaacgtgc tgatggaaaa ctacaaccca ggcagtaaca gcggacactt cagcttcgac | 780 |
| tggagtgcct acaacgatcc tcatcgccgt tat | 813 |

<210> SEQ ID NO 170
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 170

| | |
|---|---|
| atgccgatca aggaagagct gagccagcct caaagccatt cgatcgaact ggacgatctg | 60 |
| aaaagcgagc agggtagttt acgggccgcg ttgacttcca acttcgctgg caatttcgac | 120 |
| cagtttccga ccaagcgtgg cggatttgcg atcgattcct atttgctgga ctacagcgcc | 180 |
| cccaagcaag gttgctgggt ggacggtatc actgtctatg gcgatatctt catcggcaag | 240 |
| cagaactggg gcacttatac ccgcccggtg tttgcctacc tacagtatgt ggaaaccatc | 300 |
| tccattccac agaatgtgac gaccaccctc agctatcagc tgaccaaggg gcataccaaa | 360 |
| acattcacca ccaacgtctc agccaagtac agcgttggcg gctcaataga tatcgtcaac | 420 |
| gtgggttcgg atatttccat cgggttttcc aatagcgagt cctggtccac cacgcagtcg | 480 |
| ttcaccgata ccaccgagat gaaggggcca gggacgttcg tcatttacca ggtcgtgctg | 540 |
| gtgtatgcgc acaacgccac ctcggcaggg cggcagaatg gtaatgcctt cgcctacaat | 600 |
| aaaacccagg cagtgggctc gcgggtggac ttgtactact tgtcggccat acccagcgc | 660 |
| aagcgggtca tcgttccgtc gagcaatgcc gtcacgccgc tggactggga tacggtgcaa | 720 |
| cgcaacgtgc tgatggaaaa ctacaaccca ggcagtaaca gcggacactt cagcttcgac | 780 |
| tggagtgcct acaacgatcc tcatcgccgt tat | 813 |

<210> SEQ ID NO 171
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 171

| | |
|---|---|
| atgccgatca aggaagagct gagccagcct caaagccatt cgatcgaact ggacgatctg | 60 |
| aaaagcgagc agggtagttt acgggccgcg ttgacttcca acttcgctgg caatttcgac | 120 |
| cagtttccga ccaagcgtgg cggatttgcg atcgattcct atttgctgga ctacagcgcc | 180 |
| cccaagcaag gttgctgggt ggacggtatc actgtctatg gcgatatctt catcggcaag | 240 |
| cagaactggg gcacttatac ccgcccggtg tttgcctacc tacagtatgt ggaaaccatc | 300 |
| tccattccac agaatgtgac gaccaccctc agctatcagc tgaccaaggg gcatacccgt | 360 |
| tccttcgaga ccagtgtcaa cgccaagtac agcgttggcg gctcaataga tatcgtcaac | 420 |

```
gtgggttcgg atatttccat tgggttttcc aatagcgagt cctggtccac cacgcagtcg    480
ttcaccgata ccaccgagat gaaggggcca gggacgttcg tcatttacca ggtcgtgctg    540
gtgtatgcgc acaacgccac ctcggcaggg cggcagaatg gtaatgcctt cgcctacagc    600
aaaacccagg cagtgggctc gcgggtggac ttgtactact tgtcggccat tacccagcgc    660
aagcgggtca tcgttccgtc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813
```

<210> SEQ ID NO 172
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 172

```
atgccgatca aggaagagct gagccagcct caaagccatt cgatcgaact ggacgatctg     60
aaaagcgagc agggtagttt acgggccgcg ttgacttcca acttcgctgg caatttcgac    120
cagtttccga ccaagcgtgg cggatttgcg atcgattcct atttgctgga ctacagcgcc    180
cccaagcaag gttgctgggt ggacggtatc actgtctatg gcgatatctt catcggcaag    240
cagaactggg gcacttatac ccgcccggtg tttgcctacc tacagtatgt ggaaaccatc    300
tccattccac agaatgtgac gaccaccctc agctatcagc tgaccaaggg gcataccgt    360 tccttcgaga ccagtgtcaa cgccaagtac agcgttggcg ccaacataga tatcgtcaac    420
gtgggttcgg agatttccac cgggtttacc cgcagcgagt cctggtccac cacgcagtcg    480
ttcaccgata ccaccgagat gaaggggcca gggacgttca ttgtctacca ggtcgtgctg    540
gtgtatgcgc acaacgccac ctcggcaggg cggcagaatg ccaatgcctt cgcctacagc    600
aaaacccagg cagtgggctc gcgggtggac ttgtactact tgtcggccat tacccagcgc    660
aagcgggtca tcgttccgtc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813
```

<210> SEQ ID NO 173
<211> LENGTH: 812
<212> TYPE: DNA
<213> ORGANISM: Artificial Sequence
<220> FEATURE:
<223> OTHER INFORMATION: PIP-1A / PSEEN3174 chimera

<400> SEQUENCE: 173

```
atgccgatca aggaagagct gagccagcct caaagccatt cgatcgaact ggacgaggtg     60
agcaaggagg ccgcaagtac gcgggccgcg ttgacttcca acttcgctgg caatttcgac    120
cagtttccga ccaagcgtgg cggatttgcg atcgattcct atttgctgga ctacagcgcc    180
cccaagcaag gttgctgggt ggacggtatc actgtctatg gcgatatctt catcggcaag    240
cagaactggg gcacttatac ccgcccggtg tttgcctacc tacagtatat ggataccatc    300
tccattccac agcaagtgac gcagacccgt agctatcagc tgaccaaggg gcataccaaa    360
acattcacca ccaacgtctc agccaagtac agcgttggcg gctcaataga tatcgtcaac    420
gtgggttcgg agatttccac cgggtttacc cgcagcgagt cctggtccac cacgcagtcg    480
```

| | |
|---|---|
| ttcaccgata ccaccgagat gaaggggcca gggacgttcg tcatttacca ggtcgtgctg | 540 |
| gtgtatgcgc acaacgccac ctcggcaggg cggcagaatg ccaatgcctt cgcctacaat | 600 |
| aaaaccaata ccgtgggctc gcggctggac ttgtactact tgtcggccat tacccagcgc | 660 |
| aagcgggtca tcgttccgtc gagcaatgcc gtcacgccgc tggactggga tacggtgcaa | 720 |
| cgcaacgtgc tgatggaaaa ctacaaccca ggcagtaaca gcggacactt cagcttcgac | 780 |
| tggagtgcct acaacgatcc tcatcgccgt ta | 812 |

<210> SEQ ID NO 174
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 174

| | |
|---|---|
| atgcctatca aggaagagct gagccagcct caaagccatt cgatcgaact ggacgaggtg | 60 |
| agcaaggagg ccgcaagtac gcgggccgcg ttgacttcca acctgtctgg ccgcttcgac | 120 |
| cagtacccga ccaagaaggg cgactttgcg atcgatggtt atttgctgga ctacagcgcc | 180 |
| cccaagcaag gttgctgggt ggacggtatc actgtctatg gcgatatctt catcggcaag | 240 |
| cagaactggg gcacttatac ccgcccggtg tttgcctacc tacagtatat ggataccatc | 300 |
| tccattccac agcaagtgac gcagacccgt agctatcagc tgaccaaggg cataccaaa | 360 |
| acattcacca ccaacgtctc agccaagtac agcgttggcg gctcaataga tatcgtcaac | 420 |
| gtgggttcgg agatttccac cgggtttacc cgcagcgagt cctggtccac cacgcagacc | 480 |
| ttctccaatt ctacccagtt aacggggcca gggacgttcg tcatttacca ggtcgtgctg | 540 |
| gtgtatgcgc acaacgccac ctcggcaggg cggcagaatg ccaatgcctt cgcctacagc | 600 |
| aaaaccaata ccgtgggctc gcgggtggac ttgtactact tgtcggccat tacccagaat | 660 |
| agtactgtca tcgttgactc gagcaaagcc attgcaccgc tggactggga tacggtgcaa | 720 |
| cgcaacgtgc tgatggaaaa ctacaaccca ggcagtaaca gcggacactt cagcttcgac | 780 |
| tggagtgcct acaacgatcc tcatcgccgt tat | 813 |

<210> SEQ ID NO 175
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 175

| | |
|---|---|
| atgccgatca aggaagagct gagccagcct caaagccatt cgatcgaact ggacgaggtg | 60 |
| agcaaggagg ccgcaagtac gcgggccgcg ttgacttcca acctgtctgg ccgcttcgac | 120 |
| cagtacccga ccaagaaggg cgactttgcg atcgatggtt atttgttgga ctacagctca | 180 |
| cccaagcaag gttgctgggt ggacggtatc actgtctatg gcgatatctt catcggcaag | 240 |
| cagaactggg gcacttatac ccgcccggtg tttgcctacc tacagtatat ggataccatc | 300 |
| tccattccac agcaagtgac gcagacccgt agctatcagc tgaccaaggg cataccaaa | 360 |
| acattcacca ccaacgtctc agccaagtac agcgttggcg gctcaataga tatcgtcaac | 420 |
| gtgggttcgg agatttccac cgggtttacc cgcagcgagt cctggtccac cacgcagacc | 480 |
| ttctccaatt ctacccagtt aacggggcca gggacgttcg ttgtctacca ggtcgtgatg | 540 |
| gtgtatgcgc acaacgccac ctcggcaggg cggcagaatg gtaatgcctt cgcctacagc | 600 |

```
aaaacccagg cagtgggctc gcgggtggac ttgtactact tgtcggccat acccagcgc    660 aagcgggtca tcgttccgtc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813
```

<210> SEQ ID NO 176
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 176

```
atgcctatca aggaagagct gagccagcct caaagccatt cgatcgaact ggacgatctg     60
aaaagcgagc agggtagttt acgggccgcg ttgacttcca acttcgctgg caatttcgac    120
cagtacccga ccaagaaggg cgactttgcg atcgattcct atttgctgga ctacagcgcc    180
cccaagcaag gttgctgggt ggacggtatc actgtctatg gcgatatctt catcggcaag    240
cagaactggg gcacttatac ccgcccggtg tttgcctacc tacagtatat ggataccatc    300
tccattccac agcaagtgac gcagacccgt agctatcagc tgaccaaggg gcataccaaa    360
acattcacca ccaacgtctc agccaagtac agcgttggcg gctcaataga tatcgtcaac    420
gtgggttcgg atatttccat tgggttttcc aatagcgagt cctggtccac cacgcagacc    480
ttctccaatt ctacccagtt aacggggcca gggacgttca ttgtctacca ggtcgtgctg    540
gtgtatgcgc acaacgccac ctcggcaggg cggcagaatg taatgccttt cgcctacaat    600
aaaaccaata ccgtgggctc gcggctggac ttgtactact tgtcggccat acccagaat    660 agtactgtca tcgttgactc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813
```

<210> SEQ ID NO 177
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 177

```
atgccgatca aggaagagct gagccagcct caaagccatt cgatcgaact ggacgaggtg     60
agcaaggagg ccgcaagtac gcgggccgcg ttgacttcca acctgtctgg ccgcttcgac    120
cagtacccga ccaagaaggg cgactttgcg atcgatggtt atttgctgga ctacagctca    180
cccaagcaag gttgctgggt ggacggtatc actgtctatg gcgatatcta catcggcaag    240
cagaactggg gcacttatac ccgcccggtg tttgcctacc tacagtatat ggataccatc    300
tccattccac agcaagtgac gcagacccgt agctatcagc tgaccaaggg gcataccaaa    360
acattcacca ccaacgtctc agccaagtac agcgttggcg ccaacataga tatcgtcaac    420
gtgggttcgg agatttccac cgggtttacc cgcagcgagt cctggtccac cacgcagacc    480
ttctccaatt ctacccagtt aacggggcca gggacgttca ttgtctacca ggtcgtgatg    540
gtgtatgcgc acaacgccac ctcggcaggg cggcagaatg ccaacgcctt cgcctacaat    600
aaaaccaata ccgtgggctc gcggctggac ttgtactact tgtcggccat acccagaat    660
```

```
agtactgtca tcgttgactc gagcaaagcc attgcaccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813

<210> SEQ ID NO 178
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 178
atgcctatca aggaagagct gagccagcct caaagccatt cgatcgaact ggacgatctg     60
aaaagcgagc agggtagttt acgggccgcg ttgacttcca acttcgctgg caatttcgac    120
cagtttccga ccaagcgtgg cggatttgcg atcgattcct atttgctgga ctacagcgcc    180
cccaagcaag gttgctgggt ggacggtatc actgtctatg cgatatctt catcggcaag     240 cagaactggg gcacttatac ccgcccggtg tttgcctacc tacagtatat ggataccatc    300
tccattccac agcaagtgac gcagacccgt agctatcagc tgaccaaggg cataccaaa    360 acattcacca ccaacgtctc agccaagtac agcgttggcg gctcaataga tatcgtcaac    420
gtgggttcgg atatttccat ggggttttcc aatagcgagt cctggtccac cacgcagtcg    480
ttcaccgata ccaccgagat gaaggggcca gggacgttca ttgtctacca ggtcgtgatg    540
gtgtatgcgc acaacgccac ctcggcaggg cggcagaatg ccaatgcctt cgcctacagc    600
aaaaccaata ccgtgggctc gcggctggac ttgtactact tgtcggccat tacccagaat   660
agtactgtca tcgttgactc gagcaaagcc attgcaccgc tggactggga tacggtgcaa   720
cgcaacgtgc tgatggaaaa ctacaaccca ggcagtaaca gcggacactt cagcttcgac   780
tggagtgcct acaacgatcc tcatcgccgt tat                                 813

<210> SEQ ID NO 179
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 179
atgccgatca aggaagagct gagccagcct caaagccatt cgatcgaact ggacgaggtg     60
agcaaggagg ccgcaagtac gcgggccgcg ttgacttcca acttcgctgg caatttcgac    120
cagtttccga ccaagcgtgg cggatttgcg atcgattcct atttgctgga ctacagcgcc    180
cccaagcaag gttgctgggt ggacggtatc actgtctatg cgatatctt catcggcaag     240 cagaactggg gcacttatac ccgcccggtg tttgcctacc tacagtatat ggataccatc    300
tccattccac agcaagtgac gcagacccgt agctatcagc tgaccaaggg cataccaaa    360 acattcacca ccaacgtctc agccaagtac agcgttggcg gctcaataga tatcgtcaac    420
gtgggttcgg atatttccat ggggttttcc aatagcgagt cctggtccac cacgcagacc    480
ttctccaatt ctacccagtt aacggggcca gggacgttca ttgtctacca ggtcgtgatg    540
gtgtatgcgc acaacgccac ctcggcaggg cggcagaatg gtaatgcctt cgcctacaat    600
aaaaccaata ccgtgggctc gcggctggac ttgtactact tgtcggccat tacccagaat   660
agtactgtca tcgttgactc gagcaaagcc attgcaccgc tggactggga tacggtgcaa   720
cgcaacgtgc tgatggaaaa ctacaaccca ggcagtaaca gcggacactt cagcttcgac   780
```

```
tggagtgcct acaacgatcc tcatcgccgt tat                               813
```

<210> SEQ ID NO 180
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 180

```
atgcctatca aggaagagct gagccagcct caaagccatt cgatcgaact ggacgatctg    60
aaaagcgagc agggtagttt acgggccgcg ttgacttcca acctgtctgg ccgcttcgac   120
cagtacccga ccaagaaggg cgactttgcg atcgattcct atttgctgga ctacagcgcc   180
cccaagcaag gttgctgggt ggacggtatc actgtctatg cgatatcta catcggcaag   240
cagaactggg gcacttatac ccgcccggtg tttgcctacc tacagtatgt ggaaaccatc   300
tccattccac agaatgtgac gaccaccctc agctatcagc tgaccaaggg cataccgt    360
tccttcgaga ccagtgtcaa cgccaagtac agcgttggcg gctcaataga tatcgtcaac   420
gtgggttcgg atatttccat tgggttttcc aatagcgagt cctggtccac cacgcagtcg   480
ttcaccgata ccaccgagat gaaggggcca gggacgttca ttgtctacca ggtcgtgatg   540
gtgtatgcgc acaacgccac ctcggcaggg cggcagaatg gtaatgcctt cgcctacaat   600
aaaaaccaata ccgtgggctc gcggctggac ttgtactact tgtcggccat tacccagcgc   660
aagcgggtca tcgttccgtc gagcaatgcc gtcacgccgc tggactggga tacggtgcaa   720
cgcaacgtgc tgatggaaaa ctacaaccca ggcagtaaca gcggacactt cagcttcgac   780
tggagtgcct acaacgatcc tcatcgccgt tat                               813
```

<210> SEQ ID NO 181
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 181

```
atgcctatca aggaagagct gagccagcct caaagccatt cgatcgaact ggacgatctg    60
aaaagcgagc agggtagttt acgggccgcg ttgacttcca acttcgctgg caatttcgac   120
cagtttccga ccaagcgtgg cggatttgcg atcgattcct atttgctgga ctacagcgcc   180
cccaagcaag gttgctgggt ggacggtatc actgtctatg cgatatcta catcggcaag   240
cagaactggg gcacttatac ccgcccggtg tttgcctacc tacagtatgt ggaaaccatc   300
tccattccac agcaagtgac gcagaccctc agctatcagc tgaccaaggg cataccgt    360
tccttcgaga ccagtgtcaa cgccaagtac agcgttggcg ccaacataga tatcgtcaac   420
gtgggttcgg agatttccac cgggtttacc cgcagcgagt cctggtccac cacgcagtcg   480
ttcaccgata ccaccgagat gaaggggcca gggacgttcg tcatttacca ggtcgtgctg   540
gtgtatgcgc acaacgccac ctcggcaggg cggcagaatg gtaatgcctt cgcctacaat   600
aaaaaccaata ccgtgggctc gcggctggac ttgtactact tgtcggccat tacccagcgc   660
aagcgggtca tcgttccgtc gagcaatgcc gtcacgccgc tggactggga tacggtgcaa   720
cgcaacgtgc tgatggaaaa ctacaaccca ggcagtaaca gcggacactt cagcttcgac   780
tggagtgcct acaacgatcc tcatcgccgt tat                               813
```

<210> SEQ ID NO 182
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 182

| | | | | | |
|---|---|---|---|---|---|
| atgcctatca | aggaagagct | gagccagcct | caaagccatt | cgatcgaact | ggacgaggtg | 60 |
| agcaaggagg | ccgcaagtac | gcgggccgcg | ttgacttcca | acctgtctgg | ccgcttcgac | 120 |
| cagtacccga | ccaagaaggg | cgactttgcg | atcgattcct | atttgctgga | ctacagcgcc | 180 |
| cccaagcaag | gttgctgggt | ggacggtatc | actgtctatg | gcgatatcta | catcggcaag | 240 |
| cagaactggg | gcacttatac | cgcccggtg | tttgcctacc | tacagtatgt | ggaaaccatc | 300 |
| tccattccac | agaatgtgac | gaccaccctc | agctatcagc | tgaccaaggg | gcatacccgt | 360 |
| tccttcgaga | ccagtgtcaa | cgccaagtac | agcgttggcg | ccaacataga | tatcgtcaac | 420 |
| gtgggttcgg | atatttccat | ggggtttacc | cgcagcgagt | cctggtccac | cacgcagtcg | 480 |
| ttcaccgata | ccaccgagat | gaaggggcca | gggacgttcg | tcatttacca | ggtcgtgctg | 540 |
| gtgtatgcgc | acaacgccac | ctcggcaggg | cggcagaatg | ccaatgcctt | cgcctacagc | 600 |
| aaaacccagg | cagtgggctc | gcgggtggac | ttgtactact | tgtcggccat | tacccagcgc | 660 |
| aagcgggtca | tcgttccgtc | gagcaatgcc | gtcacgccgc | tggactggga | tacggtgcaa | 720 |
| cgcaacgtgc | tgatggaaaa | ctacaaccca | ggcagtaaca | gcggacactt | cagcttcgac | 780 |
| tggagtgcct | acaacgatcc | tcatcgccgt | tat | | | 813 |

<210> SEQ ID NO 183
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 183

| | | | | | |
|---|---|---|---|---|---|
| atgccgatca | aggaagagct | gagccagcct | caaagccatt | cgatcgaact | ggacgaggtg | 60 |
| agcaaggagg | ccgcaagtac | gcgggccgcg | ttgacttcca | acctgtctgg | ccgcttcgac | 120 |
| cagtacccga | ccaagaaggg | cgactttgcg | atcgattcct | atttgctgga | ctacagcgcc | 180 |
| cccaagcaag | gttgctgggt | ggacggtatc | actgtctatg | gcgatatctt | catcggcaag | 240 |
| cagaactggg | gcacttatac | cgcccggtg | tttgcctacc | tacagtatat | ggataccatc | 300 |
| tccattccac | agaatgtgac | gaccaccctc | agctatcagc | tgaccaaggg | gcatacccgt | 360 |
| tccttcgaga | ccagtgtcaa | cgccaagtac | agcgttggcg | ccaacataga | tatcgtcaac | 420 |
| gtgggttcgg | agatttccac | cgggtttacc | cgcagcgagt | cctggtccac | cacgcagtcg | 480 |
| ttcaccgata | ccaccgagat | gaaggggcca | gggacgttca | ttgtctacca | ggtcgtgatg | 540 |
| gtgtatgcgc | acaacgccac | ctcggcaggg | cggcagaatg | ccaatgcctt | cgcctacagc | 600 |
| aaaacccagg | cagtgggctc | gcgggtggac | ttgtactact | tgtcggccat | tacccagaat | 660 |
| agtactgtca | tcgttgactc | gagcaaagcc | attgcaccgc | tggactggga | tacggtgcaa | 720 |
| cgcaacgtgc | tgatggaaaa | ctacaaccca | ggcagtaaca | gcggacactt | cagcttcgac | 780 |
| tggagtgcct | acaacgatcc | tcatcgccgt | tat | | | 813 |

<210> SEQ ID NO 184
<211> LENGTH: 813

-continued

```
<212> TYPE: DNA
<213> ORGANISM: Artificial Sequence
<220> FEATURE:
<223> OTHER INFORMATION: PIP-1A / PSEEN3174 chimera

<400> SEQUENCE: 184
atgccgatca aggaagagct gagccagcct caaagccatt cgatcgaact ggacgatctg      60
aaaagcgagc agggtagttt acgggccgcg ttgacttcca acttcgctgg caatttcgac     120
cagtttccga ccaagcgtgg cggatttgcg atcgattcct atttgctgga ctacagcgcc     180
cccaagcaag gttgctgggt ggacggtatc actgtctatg cgatatcttc atcggcaag      240 cagaactggg gcacttatac ccgcccggtg tttgcctacc tacagtatgt ggaaaccatc     300
tccattccac agaatgtgac gaccaccctc agctatcagc tgaccaaggg cataccgt      360 tccttcgaga ccagtgtcaa cgccaagtac agcgttggcg gctcaataga tatcgtcaac     420
gtgggttcgg atatttccat gggttttcc cgcagcgagt cctggtccac cacgcagtcg      480
ttcaccgata ccaccgagat gaaggggcca gggacgttca ttgtctacca ggtcgtgatg     540
gtgtatgcgc acaacgccac ctcggcaggg cggcagaatg ccaatgcctt cgcctacagc     600
aaaacccagg cagtgggctc gcgggtggac ttgtactact tgtcggccat acccagcgc      660 aagcgggtca tcgttccgtc gagcaatgcc gtcacgccgc tggactggga tacggtgcaa     720
cgcaacgtgc tgatggaaaa ctacaaccca ggcagtaaca gcggacactt cagcttcgac     780
tggagtgcgt acaacgatcc tcatcgccgt tat                                  813

<210> SEQ ID NO 185
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 185
atgccgatca aggaagagct gagccagcct caaagccatt cgatcgaact ggacgaggtg      60
agcaaggagg ccgcaagtac gcgggccgcg ttgacttcca acctgtctgg ccgcttcgac     120
cagtacccga ccaagaaggg cgactttgcg atcgatggtt atttgctgga ctacagcgcc     180
cccaagcaag gttgctgggt ggacggtatc actgtctatg cgatatcttc atcggcaag      240 cagaactggg gcacttatac ccgcccggtg tttgcctacc tacagtatgt ggataccatc     300
tccattccac agcaagtgac gcagacccgt agctatcagc tgaccaaggg cataccaaa     360 acattcacca ccaacgtctc agccaagtac agcgttggcg gctcaataga tatcgtcaac     420
gtgggttcgg agatttccac cgggtttacc cgcagcgagt cctggtccac cacgcagacc     480
ttctccaatt ctacccagtt aacggggcca gggacgttca ttgtctacca ggtcgtgatg     540
gtgtatgcgc acaacgccac ctcggcaggg cggcagaatg gtaatgcctt cgcctacagc     600
aaaacccagg cagtgggctc gcgggtggac ttgtactact tgtcggccat acccagcgc      660 aagcgggtca tcgttccgtc gagcaatgcc gtcacgccgc tggactggga tacggtgcaa     720
cgcaacgtgc tgatggaaaa ctacaaccca ggcagtaaca gcggacactt cagcttcgac     780
tggagtgcct acaacgatcc tcatcgccgt tat                                  813

<210> SEQ ID NO 186
<211> LENGTH: 813
<212> TYPE: DNA
<213> ORGANISM: Artificial Sequence
<220> FEATURE:
```

<223> OTHER INFORMATION: PIP-1A / PSEEN3174 chimera

<400> SEQUENCE: 186

| | | | | | |
|---|---|---|---|---|---|
| atgcctatca | aggaagagct | gagccagcct | caaagccatt | cgatcgaact | ggacgaggtg | 60 |
| agcaaggagg | ccgcaagtac | gcgggccgcg | ttgacttcca | acttcgctgg | caatttcgac | 120 |
| cagtttccga | ccaagcgtgg | cggatttgcg | atcgattcct | atttgctgga | ctacagcgcc | 180 |
| cccaagcaag | gttgctgggt | ggacggtatc | actgtctatg | cgatatctt | catcggcaag | 240 |
| cagaactggg | gcacttatac | ccgcccggtg | tttgcctacc | tacagtatat | ggataccatc | 300 |
| tccattccac | agcaagtgac | gcagacccgt | agctatcagc | tgaccaaggg | gcataccaaa | 360 |
| acattcacca | ccaacgtctc | agccaagtac | agcgttggcg | gctcaataga | tatcgtcaac | 420 |
| gtgggttcgg | atatttccat | gggttttcc | aatagcgagt | cctggtccac | cacgcagtcg | 480 |
| ttcaccgata | ccaccgagat | gaaggggcca | gggacgttca | ttgtctacca | ggtcgtgatg | 540 |
| gtgtatgcgc | acaacgccac | ctcggcaggg | cggcagaatg | gtaatgcctt | cgcctacaat | 600 |
| aaaaccaata | ccgtgggctc | gcggctgac | ttgtactact | tgtcggccat | tacccagaat | 660 |
| agtactgtca | tcgttgactc | gagcaatgcc | gtcacgccgc | tggactggga | tacggtgcaa | 720 |
| cgcaacgtgc | tgatggaaaa | ctacaaccca | ggcagtaaca | gcggacactt | cagcttcgac | 780 |
| tggagtgcct | acaacgatcc | tcatcgccgt | tat | | | 813 |

<210> SEQ ID NO 187
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 187

| | | | | | |
|---|---|---|---|---|---|
| atgccgatca | aggaagagct | gagccagcct | caaagccatt | cgatcgaact | ggacgaggtg | 60 |
| agcaaggagg | ccgcaagtac | gcgggccgcg | ttgacttcca | acctgtctgg | ccgcttcgac | 120 |
| cagtacccga | ccaagcgtgg | cggatttgcg | atcgattcct | atttgctgga | ctacagcgcc | 180 |
| cccaagcaag | gttgctgggt | ggacggtatc | actgtctatg | cgatatctt | catcggcaag | 240 |
| cagaactggg | gcacttatac | ccgcccggtg | tttgcctacc | tacagtatat | ggataccatc | 300 |
| tccattccac | agcaagtgac | gcagacccgt | agctatcagc | tgaccaaggg | gcataccaaa | 360 |
| acattcacca | ccaacgtctc | agccaagtac | agcgttggcg | gctcaataga | tatcgtcaac | 420 |
| gtgggttcgg | atatttccat | gggttttcc | aatagcgagt | cctggtccac | cacgcagtcg | 480 |
| ttcaccgata | ccaccgagat | gaaggggcca | gggacgttca | ttgtctacca | ggtcgtgatg | 540 |
| gtgtatgcgc | acaacgccac | ctcggcaggg | cggcagaatg | ccaatgcctt | cgcctacagc | 600 |
| aaaacccagg | cagtgggctc | gcgggtggac | ttgtactact | tgtcggccat | tacccagcgc | 660 |
| aagcgggtca | tcgttccgtc | gagcaaagcc | attgcaccgc | tggactggga | tacggtgcaa | 720 |
| cgcaacgtgc | tgatggaaaa | ctacaaccca | ggcagtaaca | gcggacactt | cagcttcgac | 780 |
| tggagtgcct | acaacgatcc | tcatcgccgt | tat | | | 813 |

<210> SEQ ID NO 188
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 188

```
atgccgatca aggaagagct gagccagcct caaagccatt cgatcgaact ggacgaggtg      60
agcaaggagg ccgcaagtac gcgggccgcg ttgacttcca acctgtctgg ccgcttcgac     120
cagtttccga ccaagcgtgg cggatttgcg atcgatggtt atttgctgga ctacagcgcc     180
cccaagcaag gttgctgggt ggacggtatc actgtctatg gcgatatcta catcggcaag     240
cagaactggg gcacttatac ccgcccggtg tttgcctacc tacagtatat ggataccatc     300
tccattccac agcaagtgac gcagacccgt agctatcagc tgaccaaggg cataccaaa      360 acattcacca ccaacgtctc agccaagtac agcgttggcg ccaacataga tatcgtcaac     420
gtgggttcgg agatttccac cgggtttacc cgcagcgagt cctggtccac cacgcagtcg     480
ttcaccgata ccaccgagat gaaggggcca gggacgttca tcgtctacca ggtcgtgctg     540
gtgtatgcgc acaacgccac ctcggcaggg cggcagaatg gtaatgcctt cgcctacagc     600
aaaacccagg cagtgggctc gcgggtggac ttgtactact tgtcggccat tacccagcgc     660
aagcgggtca tcgttccgtc gagcaaagcc attgcaccgc tggactggga tacggtgcaa     720
cgcaacgtgc tgatggaaaa ctacaaccca ggcagtaaca gcggacactt cagcttcgac     780
tggagtgcct acaacgatcc tcatcgccgt tat                                  813
```

<210> SEQ ID NO 189
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 189

```
atgccgacca aggaagagct gagccagcct caaagccatt cgatcgaact ggacgatctg      60
aaaagcgagc agggtagttt acgggccgcg ttgacttcca acttcgctgg caatttcgac     120
cagtttccga ccaagcgtgg cggatttgcg atcgattcct atttgctgga ctacagcgcc     180
cccaagcaag gttgctgggt ggacggtatc actgtctatg gcgatatcta catcggcaag     240
cagaactggg gcacttatac ccgcccggtg tttgcctacc tacagtatgt ggaaaccatc     300
tccattccac agcaagtgac gcagacccgt agctatcagc tgaccaaggg cataccccgt     360
tccttcgaga ccagtgtcaa cgccaagtac agcgttggcg ccaacataga tatcgtcaac     420
gtgggttcgg atatttccat ggggttttcc aatagcgagt cctggtccac cacgcagtcg     480
ttcaccgata ccaccgagat gaaggggcca gggacgttcg tcatttacca ggtcgtgctg     540
gtgtatgcgc acaacgccac ctcggcaggg cggcagaatg gtaatgcctt cgcctacaat     600
aaaaccaata ccgtgggctc gcggctggac ttgtactact tgtcggccat tacccagcgc     660
aagcgggtca tcgttccgtc gagcaatgcc gtcacgccgc tggactggga tacggtgcaa     720
cgcaacgtgc tgatggaaaa ctacaaccca ggcagtaaca gcggacactt cagcttcgac     780
tggagtgcct acaacgatcc tcatcgccgt tat                                  813
```

<210> SEQ ID NO 190
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 190

```
atgcctatca aggaagagct gagccagcct caaagccatt cgatcgaact ggacgaggcg      60
```

-continued

| | |
|---|---|
| agcaaggagg ccgcaagtac gcgggccgcg ttgacttcca acctgtctgg ccgcttcgac | 120 |
| cagtacccga ccaagaaggg cgactttgcg atcgatggtt atttgctgga ctacagcgcc | 180 |
| cccaagcaag gttgctgggt ggacggtatc actgtctatg gcgatatctt catcggcaag | 240 |
| cagaactggg gcacttatac ccgcccggtg tttgcctacc tacagtatgt ggataccatc | 300 |
| tccattccac agcaagtgac gcagacccgt agctatcagc tgaccaaggg gcataccaaa | 360 |
| acattcacca ccaacgtctc agccaagtac agcgttggcg gctcaataga tatcgtcaac | 420 |
| gtgggttcgg agatttccac cgggtttacc cgcagcgagt cctggtccac cacgcagtcg | 480 |
| ttcaccgata ccaccgagat gaaggggcca gggacgttcg tcatttacca ggtcgtgctg | 540 |
| gtgtatgcgc acaacgccac ctcggcaggg cggcagaatg gtaatgcctt cgcctacagc | 600 |
| aaaacccagg cagtgggctc gcgggtggac ttgtactact tgtcggccat tacccagcgc | 660 |
| aagcgggtca tcgttccgtc gagcaatgcc gtcacgccgc tggactggga tacggtgcaa | 720 |
| cgcaacgtgc tgatggaaaa ctacaaccca ggcagtaaca gcggacactt cagcttcgac | 780 |
| tggagtgcct acaacgatcc tcatcgccgt tat | 813 |

<210> SEQ ID NO 191
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 191

| | |
|---|---|
| atgccgatca aggaagagct gagccagcct caaagccatt cgatcgaact ggacgatctg | 60 |
| aaaagcgagc agggtagttt acgggccgcg ttgacttcca acttcgctgg caatttcgac | 120 |
| cagtttccga ccaagcgtgg cggatttgcg atcgatggtt atttgctgga ctacagcgcc | 180 |
| cccaagcaag gttgctgggt ggacggtatc actgtctatg gcgatatcta catcggcaag | 240 |
| cagaactggg gcacttatac ccgcccggtg tttgcctacc tacagtatgt ggataccatc | 300 |
| tccattccac agcaagtgac gcagacccgt agctatcagc tgaccaaggg gcataccaaa | 360 |
| acattcacca ccaacgtctc agccaagtac agcgttggcg gctcaataga tatcgtcaac | 420 |
| gtgggttcgg atatttccat ggggttttcc aatagcgagt cctggtccac cacgcagtcg | 480 |
| ttcaccgata ccaccgagat gaaggggcca gggacgttcg tcatttacca ggtcgtgctg | 540 |
| gtgtatgcgc acaacgccac ctcggcaggg cggcagaatg gtaatgcctt cgcctacagc | 600 |
| aaaacccagg cagtgggctc gcgggtggac ttgtactact tgtcggccat tacccagcgc | 660 |
| aagcgggtca tcgttccgtc gagcaatgcc gtcacgccgc tggactggga tacggtgcaa | 720 |
| cgcaacgtgc tgatggaaaa ctacaaccca ggcagtaaca gcggacactt cagcttcgac | 780 |
| tggagtgcct acaacgatcc tcatcgccgt tat | 813 |

<210> SEQ ID NO 192
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 192

| | |
|---|---|
| atgccgatca aggaagagct gagccagcct caaagccatt cgatcgaact ggacgatctg | 60 |
| aaaagcgagc agggtagttt acgggccgcg ttgacttcca acttcgctgg caatttcgac | 120 |
| cagtttccga ccaagcgtgg cggatttgcg atcgattcct atttgctgga ctacagcgcc | 180 |

```
cccaagcaag gttgctgggt ggacggtatc actgtctatg gcgatatctt catcggcaag    240
cagaactggg gcacttatac ccgcccggtg tttgcctacc tacagtatgt ggaaaccatc    300
tccattccac agaatgtgac gaccaccctc agctatcagc tgaccaaggg catacccgt     360 tccttcgaga ccagtgtcaa cgccaagtac agcgttggcg ccaacataga tatcgtcaac    420
gtgggttcgg atatttccac cgggtttacc cgcagcgagt cctggtccac cacgcagtcg    480
ttcaccgata ccaccgagat gaaggggcca gggacgttcg tcatttacca ggtcgtgatg    540
gtgtatgcgc acaacgccac ctcggcaggg cggcagaatg ccaatgcctt cgcctacagc    600
aaaacccagg cagtgggctc gcgggtggac ttgtactact tgtcggccat tcccagcgc    660 aagcgggtca tcgttccgtc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813
```

<210> SEQ ID NO 193
<211> LENGTH: 813
<212> TYPE: DNA
<213> ORGANISM: Artificial Sequence
<220> FEATURE:
<223> OTHER INFORMATION: PIP-1A / PSEEN3174 chimera
<400> SEQUENCE: 193

```
atgcctatca aggaagagct gagccagcct caaagccatt cgatcgaact ggacgatctg     60
aaaagcgagc agggtagttt acgggccgcg ttgacttcca acttcgctgg caatttcgac    120
cagtttccga ccaagcgtgg cggatttgcg atcgattcct atttgctgga ctacagcgcc    180
cccaagcaag gttgctgggt ggacggtatc actgtctatg gcgatatcta catcggcaag    240
cagaactggg gcacttatac ccgcccggtg tttgcctacc tacagtatat ggataccatc    300
tccattccac agcaagtgac gcagacccgt agctatcagc tgaccaaggg catacccgt     360 tccttcgaga ccagtgtcaa cgccaagtac agcgttggcg ccaacataga tatcgtcaac    420
gtgggttcgg agatttccac cgggtttacc cgcagcgagt cctggtccac cacgcagtcg    480
ttcaccgata ccaccgagat gaaggggcca gggacgttca ttgtctacca ggtcgtgatg    540
gtgtatgcgc acaacgccac ctcggcaggg cggcagaatg cctatgcctt cgcctacaat    600
aaaacccagg cagtgggctc gcgggtggac ttgtacttct tgtcggccat tcccagcgc    660 aagcgggtca tcgttccgtc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813
```

<210> SEQ ID NO 194
<211> LENGTH: 813
<212> TYPE: DNA
<213> ORGANISM: Artificial Sequence
<220> FEATURE:
<223> OTHER INFORMATION: PIP-1A / PSEEN3174 chimera
<400> SEQUENCE: 194

```
atgcctatca aggaagagct gagccagcct caaagccatt cgatcgaact ggacgatctg     60
aaaagcgagc agggtagttt acgggccgcg ttgacttcca acttcgctgg caatttcgac    120
cagtttccga ccaagcgtgg cggatttgcg atcgattcct atttgctgga ctacagcgcc    180
cccaagcaag gttgctgggt ggacggtatc actgtctatg gcgatatctt catcggcaag    240
```

```
cagaactggg gcacttatac ccgcccggtg tttgcctacc tacagtatat ggataccatc    300
tccattccac agcaagtgac gcagacccgt agctatcagc tgaccaaggg cataccaaa     360
acattcacca ccaacgtctc agccaagtac agcgttggcg ccaacataga tatcgtcaac    420
gtgggttcgg agatttccac cgggtttacc cgcagcgagt cctggtccac cacgcagacc    480
ttctccaatt ctacccagtt aacggggcca gggacgttca ttgtctacca ggtcgtgatg    540
gtgtatgcgc acaacgccac ctcggcaggg cggcagaatg taatgccttc gcctacagc     600
aaaacccagg cagtgggctc gcggctggac ttgtactact tgtcggccat tacccagaat    660
agtactgtca tcgttgactc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813
```

<210> SEQ ID NO 195
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 195

```
atgcctatca aggaagagct gagccagcct caaagccatt cgatcgaact ggacgatctg    60
aaaagcgagc agggtagttt acgggccgcg ttgacttcca acttcgctgg caatttcgac    120
cagtacccga ccaagaaggg cgactttgcg atcgatggtt atttgctgga ctacagcgcc    180
cccaagcaag gttgctgggt ggacggtatc actgtctatg cgatatcta catcggcaag    240
cagaactggg gcacttatac ccgcccggtg tttgcctacc tacagtatat ggataccatc    300
tccattccac agcaagtgac gcagacccgt agctatcagc tgaccaaggg cataccaaa     360
acattcacca ccaacgtctc agccaagtac agcgttggcg ccaacataga tatcgtcaac    420
gtgggttcgg atatttccat tgggtttttcc aatagcgagt cctggtccac cacgcagtcg    480
ttcaccgata ccaccgagat gaaggggcca gggacgttca ttgtctacca ggtcgtgatg    540
gtgtatgcgc acaacgccac ctcggcaggg cggcagaatg ccaatgcctt cgcctacagc    600
aaaacccagg cagtgggctc gcgggtggac ttgtactact tgtcggccat tacccagcgc    660
aagcgggtca tcgttccgtc gagcaaagcc attgcaccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813
```

<210> SEQ ID NO 196
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 196

```
atgccgatca aggaagagct gagccagcct caaagccatt cgatcgaact ggacgaggtg    60
agcaaggagg ccgcaagtac gcgggccgcg ttgacttcca acctgtctgg ccgcttcgac    120
cagtacccga ccaagaaggg cgactttgcg atcgattcct atttgctgga ctacagcgcc    180
cccaagcaag gttgctgggt ggacggtatc actgtctatg cgatatctt catcggcaag    240
cagaactggg gcacttatac ccgcccggtg tttgcctacc tacagtatat ggaaaccatc    300
tccattccac agaatgtgac gaccacccte agctatcagc tgaccaaggg cataccgt      360
```

```
tccttcgaga ccagtgtcaa cgccaagtac agcgttggcg ccaacataga tatcgtcaac    420
gtgggttcgg atatttccac cgggtttacc cgcagcgagt cctggtccac cacgcagtcg    480
ttcaccgata ccaccgagat gaaggggcca gggacgttcg tcatttacca ggtcgtgctg    540
gtgtatgcgc acaacgccac ctcggcaggg cggcagaatg ccaatgcctt cgcctacagc    600
aaaacccagg cagtgggctc gcgggtggac ttgtactact tgtcggccat tacccagcgc    660
aagcgggtca tcgttccgtc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                  813

<210> SEQ ID NO 197
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 197
atgcctatca aggaagagct gagccagcct caaagccatt cgatcgaact ggacgaggtg     60
agcaaggagg ccgcaagtac gcgggccgcg ttgacttcca acctgtctgg ccgcttcgac    120
cagtacccga ccaagcgtgg cggatttgcg atcgatggtt atttgctgga ctacagctca    180
cccaagcaag gttgctgggt ggacggtatc actgtctatg gcgatatcta catcggcaag    240
cagaactggg gcacttatac ccgccccggtg tttgcctacc tacagtatgt ggaaaccatc    300
tccattccac agcaagtgac gcagacccgt agctatcagc tgaccaaggg gcatacccgt    360
tccttcgaga ccagtgtcaa cgccaagtac agcgttggcg ccaacataga tatcgtcaac    420
gtgggttcgg atatttccat gggttttttcc aatagcgagt cctggtccac cacgcagtcg    480
ttcaccaatt ctacccagtt aacggggcca gggacgttcg ttgtctacca ggtcgtgatg    540
gtgtatgcgc acaacgccac ctcggcaggg cggcagaatg gtaatgcctt cgcctacaat    600
aaaaccaata ccgtgggctc gcggctggac ttgtactact tgtcggccat tacccagcgc    660
aagcgggtca tcgttccgtc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                  813

<210> SEQ ID NO 198
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 198
atgccgatca aggaagagct gagccagcct caaagccatt cgatcgaact ggacgatctg     60
aaaagcgagc agggtagttt acgggccgcg ttgacttcca acttcgctgg caatttcgac    120
cagtttccga ccaagcgtgg cggatttgcg atcgattcct atttgctgga ctacagcgcc    180
cccaagcaag gttgctgggt ggacggtatc actgtctatg gcgatatctt catcggcaag    240
cagaactggg gcacttatac ccgccccggtg tttgcctacc tacagtatgt ggaaaccatc    300
tccattccac agaatgtgac gaccacccctc agctatcagc tgaccaaggg gcatacccgt    360
tccttcgaga ccagtgtcaa cgccaagtac agcgttggcg ccaacataga tatcgtcaac    420
```

```
gtgggttcgg agatttccac cgggtttacc cgcagcgagt cctggtccac cacgcagtcg    480
ttcaccgata ccaccgagat gaaggggcca gggacgttcg tcatttacca ggtcgtgctg    540
gtgtatgcgc acaacgccac ctcggcaggg cggcagaatg ccaatgcctt cgcctacagc    600
aaaacccagg cagtgggctc gcgggtggac ttgtactact tgtcggccat tacccagcgc    660
aagcgggtca tcgttccgtc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813

<210> SEQ ID NO 199
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 199
atgccgatca aggaagagct gagccagcct caaagccatt cgatcgaact ggacgatctg     60
aaaagcgagc agggtagttt acgggccgcg ttgacttcca acctgcctgg ccgcttcgac    120
cagtacccga ccaagaaggg cgactttgcg atcgattcct atttgctgga ctacagcgcc    180
cccaagcaag gttgctgggt ggacggtatc actgtctatg gcgatatctt catcggcaag    240
cagaactggg gcacttatac ccgcccggtg tttgcctacc tacagtatat ggaaaccatc    300
tccattccac agcaagtgac gcagacccgt agctatcagc tgaccaaggg gcataccaaa    360
acattcacca ccaacgtctc agccaagtac agcgttggcg ccaacataga tatcgtcaac    420
gtgggttcgg atatttccat gggttttcc cgcagcgagt cctggtccac cacgcagacc    480
ttctccaatt ctacccagtt aacggggcca gggacgttca ttgtctacca ggtcgtgatg    540
gtgtatgcgc acaacgccac ctcggcaggg cggcagaatg ccaatgcctt cgcctacagc    600
aaaacccagg cagtgggctc gcggctggac ttgtactact tgtcggccat tacccagaat    660
agtactgtca tcgttgactc gagcaaagcc attgcaccgc tggactggga tacggtgcaa    720
cgcaacgtgc tgatggaaaa ctacaaccca ggcagtaaca gcggacactt cagtttcgac    780
tggagtgcgt acaacgatcc tcatcgccgt tat                                 813

<210> SEQ ID NO 200
<211> LENGTH: 813
<212> TYPE: DNA
<213> ORGANISM: Artificial Sequence
<220> FEATURE:
<223> OTHER INFORMATION: PIP-1A / PSEEN3174 chimera

<400> SEQUENCE: 200
atgcctatca aggaagagct gagccagcct caaagccatt cgatcgaact ggacgatctg     60
aaaagcgagc agggtagttt acgggccgcg ttgacttcca acctgtctgg ccgcttcgac    120
cagtacccga ccaagaaggg cgactttgcg atcgatggtt atttgctgga ctacagcgcc    180
cccaagcaag gttgctgggt ggacggtatc actgtctatg gcgatatctt catcggcaag    240
cagaactggg gcacttatac ccgcccggtg tttgcctacc tacagtatat ggataccatc    300
tccattccac agcaagtgac gcagacccgt agctatcagc tgaccaaggg gcatacccgt    360
tccttcgaga ccagtgtcaa cgccaagtac agcgttggcg ccaacataga tatcgtcaac    420
gtgggttcgg atatttccat gggttttcc aatagcgagt cctggtccac cacgcagtcg    480
ttcaccgata ccaccgagat gaaggggcca gggacgttca ttgtctacca ggtcgtgatg    540
```

```
gtgtatgcgc acaacgccac ctcggcaggg cggcagaatg ccaatgcctt cgcctacagc    600
aaaacccagg cagtgggctc gcggctggac ttgtactact tgtcggccat tacccagcgc    660
aagcgggtca tcgttccgtc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813
```

<210> SEQ ID NO 201  
<211> LENGTH: 813  
<212> TYPE: DNA  
<213> ORGANISM: Artificial Sequence  
<220> FEATURE:  
<223> OTHER INFORMATION: PIP-1A / PSEEN3174 chimera

<400> SEQUENCE: 201

```
atgccgatca aggaagagct gagccagcct caaagccatt cgatcgaact ggacgatctg     60
aaaagcgagc agggtagttt acgggccgcg ttgacttcca acttcgctgg caatttcgac    120
cagtttccga ccaagcgtgg cggatttgcg atcgattcct atttgctgga ctacagcgcc    180
cccaagcaag gttgctgggt ggacggtatc actgtctatg gcgatatctt catcggcaag    240
cagaactggg gcacttatac ccgcccggtg tttgcctacc tacagtatat ggataccatc    300
tccattccac agcaagtgac gcagacccgt agctatcagc tgaccaaggg catacccgt    360 tccttcgaga ccagtgtcaa cgccaagtac agcgttggcg ccaacataga tatcgtcaac    420
gtgggttcgg agatttccac cgggtttacc cgcagcgagt cctggtccac cacgcagtcg    480
ttcaccgata ccaccgagat gaaggggcca gggacgttca ttgtctacca ggtcgtgctg    540
gtgtatgcgc acaacgccac ctcggcaggg cggcagaatg gtaatgcctt cgcctacaat    600
aaaaccaata ccgtgggctc gcggctggac ttgtactact tgtcggccat tacccagcgc    660
aagcgggtca tcgttccgtc gagcaatgcc gtcacgccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                 813
```

<210> SEQ ID NO 202  
<211> LENGTH: 813  
<212> TYPE: DNA  
<213> ORGANISM: Artificial Sequence  
<220> FEATURE:  
<223> OTHER INFORMATION: PIP-1A / PSEEN3174 chimera

<400> SEQUENCE: 202

```
atgcctatca aggaagagct gagccagcct caaagccatt cgatcgaact ggacgatctg     60
aaaagcgagc agggtagttt acgggccgcg ttgacttcca acttcgctgg caatttcgac    120
cagtttccga ccaagcgtgg cggattggcg atcgattcct atttgctgga ctacagcgcc    180
cccaagcaag gttgctgggt ggacggtatc actgtctatg gcgatatctt catcggcaag    240
cagaactggg gcacttatac ccgcccggtg tttgcctacc tacagtatat ggataccatc    300
tccattccac agcaagtgac gcagacccgt agctatcagc tgaccaaggg cataccaaa    360 acattcacca ccaacgtctc agccaagtac agcgttggcg gctcaataga tatcgtcaac    420
gtgggttcgg agatttccac cgggtttacc cgcagcgagt cctggtccac cacgcagtcg    480
ttcaccgata ccaccgagat gaaggggcca gggacgttca ttgtctacca ggtcgtgatg    540
gtgtatgcgc acaacgccac ctcggcaggg cggcagaatg gtaatgcctt cgcctacaat    600
```

-continued

```
aaaaccaata ccgtgggctc gcgggtggac ttgtactact tgtcggccat tacccagaat    660
agtactgtca tcgttgactc gagcaaagcc attgcaccgc tggactggga tacggtgcaa    720
cgcaacgtgc tgatggaaaa ctacaaccca ggcagtaaca gcggacactt cagcttcgac    780
tggagtgcct acaacgatcc tcatcgccgt tat                                  813
```

<210> SEQ ID NO 203
<211> LENGTH: 732
<212> TYPE: DNA
<213> ORGANISM: Pseudomonas chlororaphis

<400> SEQUENCE: 203

```
gccgctttga catccaactt tgctggcaac ttcgatcagt tcccaactaa gcgtggtggc     60
tttgcgatcg acagctacct gctggattac agcgcgccca agcaaggctg ctgggtagat    120
ggcattaccg tctacggtga catctttatc ggcaagcaga attggggcac ctacactcgc    180
ccggtctttg cctacctgca gtacatggac accatttcca ttccgcagca ggtgacacag    240
actcgcagct atcagttgac taagggacac accaaaacgt tcacgaccaa tgtcagcgcc    300
aaatacagcg ttggaggtag tattgacatc gtcaacgtcg gttcggatat ctcaattgga    360
ttcagtaaca gtgaatcctg gtctactacg cagacgttca gcaatagcac tcaattgact    420
ggtcctggca ccttcatcgt gtatcaggtt gttatggttt atgcgcacaa cgccacttct    480
gcgggcaggc agaatggtaa tgccttcgcc tacaacaaga ccaatactgt cggctcgcgg    540
ctggacttgt actatttgtc tgccatcact cagaacagta cggtcattgt cgattccagc    600
aaggccatcg cgccgctgga ttgggatact gttcagcgca atgtgttgat ggagaactac    660
aacccaggca gcaatagtgg gcacttcagt ttcgactgga gcgcctacaa cgatcctcat    720
cgccgttatt ga                                                        732
```

<210> SEQ ID NO 204
<211> LENGTH: 243
<212> TYPE: PRT
<213> ORGANISM: Pseudomonas chlororaphis

<400> SEQUENCE: 204

```
Ala Ala Leu Thr Ser Asn Phe Ala Gly Asn Phe Asp Gln Phe Pro Thr
  1               5                  10                  15

Lys Arg Gly Gly Phe Ala Ile Asp Ser Tyr Leu Leu Asp Tyr Ser Ala
             20                  25                  30

Pro Lys Gln Gly Cys Trp Val Asp Gly Ile Thr Val Tyr Gly Asp Ile
         35                  40                  45

Phe Ile Gly Lys Gln Asn Trp Gly Thr Tyr Thr Arg Pro Val Phe Ala
     50                  55                  60

Tyr Leu Gln Tyr Met Asp Thr Ile Ser Ile Pro Gln Gln Val Thr Gln
 65                  70                  75                  80

Thr Arg Ser Tyr Gln Leu Thr Lys Gly His Thr Lys Thr Phe Thr Thr
                 85                  90                  95

Asn Val Ser Ala Lys Tyr Ser Val Gly Gly Ser Ile Asp Ile Val Asn
            100                 105                 110

Val Gly Ser Asp Ile Ser Ile Gly Phe Ser Asn Ser Glu Ser Trp Ser
        115                 120                 125

Thr Thr Gln Thr Phe Ser Asn Ser Thr Gln Leu Thr Gly Pro Gly Thr
    130                 135                 140

Phe Ile Val Tyr Gln Val Val Met Val Tyr Ala His Asn Ala Thr Ser
145                 150                 155                 160
```

```
Ala Gly Arg Gln Asn Gly Asn Ala Phe Ala Tyr Asn Lys Thr Asn Thr
            165                 170                 175

Val Gly Ser Arg Leu Asp Leu Tyr Tyr Leu Ser Ala Ile Thr Gln Asn
        180                 185                 190

Ser Thr Val Ile Val Asp Ser Ser Lys Ala Ile Ala Pro Leu Asp Trp
    195                 200                 205

Asp Thr Val Gln Arg Asn Val Leu Met Glu Asn Tyr Asn Pro Gly Ser
    210                 215                 220

Asn Ser Gly His Phe Ser Phe Asp Trp Ser Ala Tyr Asn Asp Pro His
225                 230                 235                 240

Arg Arg Tyr

<210> SEQ ID NO 205
<211> LENGTH: 732
<212> TYPE: DNA
<213> ORGANISM: Pseudomonas entomophila

<400> SEQUENCE: 205
gccgcgttga cttccaacct gtctggccgc ttcgaccagt acccgaccaa gaagggcgac      60
tttgcgatcg atggttattt gctggactac agctcaccca gcaaggttg ctgggtggac     120
ggtatcactg tctatggcga tatctacatc ggcaagcaga actggggcac ttatacccgc     180
ccggtgtttg cctacctaca gtatgtggaa accatctcca ttccacagaa tgtgacgacc     240
accctcagct atcagctgac caaggggcat acccgttcct tcgagaccag tgtcaacgcc     300
aagtacagcg ttggcgccaa catagatatc gtcaacgtgg ttcggagat tccaccgggg     360
tttacccgca gcgagtcctg gtccaccacg cagtcgttca ccgataccac cgagatgaag     420
gggccaggga cgttcgtcat ttaccaggtc gtgctggtgt atgcgcacaa cgccacctcg     480
gcagggcggc agaatgccaa tgccttcgcc tacagcaaaa cccaggcagt gggctcgcgg     540
gtggacttgt actacttgtc ggccattacc agcgcaagc gggtcatcgt tccgtcgagc     600
aatgccgtca cgccgctgga ctgggatacg gtgcaacgca acgtgctgat ggaaaactac     660
aacccaggca gtaacagcgg acacttcagc ttcgactgga gtgcctacaa cgatcctcat     720
cgccgttatt ga                                                         732

<210> SEQ ID NO 206
<211> LENGTH: 243
<212> TYPE: PRT
<213> ORGANISM: Pseudomonas entomophila

<400> SEQUENCE: 206

Ala Ala Leu Thr Ser Asn Leu Ser Gly Arg Phe Asp Gln Tyr Pro Thr
1               5                  10                  15

Lys Lys Gly Asp Phe Ala Ile Asp Gly Tyr Leu Leu Asp Tyr Ser Ser
            20                  25                  30

Pro Lys Gln Gly Cys Trp Val Asp Gly Ile Thr Val Tyr Gly Asp Ile
        35                  40                  45

Tyr Ile Gly Lys Gln Asn Trp Gly Thr Tyr Thr Arg Pro Val Phe Ala
    50                  55                  60

Tyr Leu Gln Tyr Val Glu Thr Ile Ser Ile Pro Gln Asn Val Thr Thr
65                  70                  75                  80

Thr Leu Ser Tyr Gln Leu Thr Lys Gly His Thr Arg Ser Phe Glu Thr
                85                  90                  95

Ser Val Asn Ala Lys Tyr Ser Val Gly Ala Asn Ile Asp Ile Val Asn
```

```
                100               105                110
Val Gly Ser Glu Ile Ser Thr Gly Phe Thr Arg Ser Glu Ser Trp Ser
            115                 120                 125

Thr Thr Gln Ser Phe Thr Asp Thr Thr Glu Met Lys Gly Pro Gly Thr
            130                 135                 140

Phe Val Ile Tyr Gln Val Val Leu Val Tyr Ala His Asn Ala Thr Ser
145                 150                 155                 160

Ala Gly Arg Gln Asn Ala Asn Ala Phe Ala Tyr Ser Lys Thr Gln Ala
                165                 170                 175

Val Gly Ser Arg Val Asp Leu Tyr Tyr Leu Ser Ala Ile Thr Gln Arg
                180                 185                 190

Lys Arg Val Ile Val Pro Ser Ser Asn Ala Val Thr Pro Leu Asp Trp
                195                 200                 205

Asp Thr Val Gln Arg Asn Val Leu Met Glu Asn Tyr Asn Pro Gly Ser
            210                 215                 220

Asn Ser Gly His Phe Ser Phe Asp Trp Ser Ala Tyr Asn Asp Pro His
225                 230                 235                 240

Arg Arg Tyr

<210> SEQ ID NO 207
<211> LENGTH: 732
<212> TYPE: DNA
<213> ORGANISM: Dendroctonus frontalis

<400> SEQUENCE: 207
gccatcctga ccagcaactt cgccggcagc ttcgaccagt tcccgaccaa gcgcggcggc      60
tacgccatcg acagctacct gctggactac agcgccccga agcagggctg ctgggtggac     120
ggcatcaccg tgtacggcga catcttcatc ggcaagcaga actggggcac ctacacccgc     180
ccggtgttcg cctacctgca gtacatggac accatcagca tcccgcagca ggtgacccag     240
acccgcagct accagctgac caagggccat accaagacct tcaccaccag cgtgaccgcc     300
aagtacagcg tgggcggcag catcggcatc gtgaacgtgg gcagcgacat cagcgtgggc     360
ttcagcagca gcgagagctg gagcaccacc cagaccttca gcgagagcac ccagctggcc     420
ggcccgggca ccttcatcgt gtaccaggtg gtgctggtgt acgcccataa cgccaccagc     480 gccgccgcc agaacggcaa cgccttcgcc tacaacaaga cccagaccgt gggcagccgc     540
ctggacctgt actacctgag cgccatcacc cagaacagca ccgtgatcgt ggagagcagc     600
aaggccatcg ccccgctgga ctgggacacc gtgcagcgca acgtgctgat ggagaactac     660
aacccgagca gcaacagcgg ccatttcagc ttcgactgga gcgcctacaa cgacccgcat     720
cgccgctact aa                                                         732

<210> SEQ ID NO 208
<211> LENGTH: 243
<212> TYPE: PRT
<213> ORGANISM: Dendroctonus frontalis

<400> SEQUENCE: 208

Ala Ile Leu Thr Ser Asn Phe Ala Gly Ser Phe Asp Gln Phe Pro Thr
1               5                   10                  15

Lys Arg Gly Gly Tyr Ala Ile Asp Ser Tyr Leu Leu Asp Tyr Ser Ala
            20                  25                  30

Pro Lys Gln Gly Cys Trp Val Asp Gly Ile Thr Val Tyr Gly Asp Ile
        35                  40                  45
```

```
Phe Ile Gly Lys Gln Asn Trp Gly Thr Tyr Thr Arg Pro Val Phe Ala
 50                  55                  60
Tyr Leu Gln Tyr Met Asp Thr Ile Ser Ile Pro Gln Gln Val Thr Gln
 65                  70                  75                  80
Thr Arg Ser Tyr Gln Leu Thr Lys Gly His Thr Lys Thr Phe Thr Thr
                 85                  90                  95
Ser Val Thr Ala Lys Tyr Ser Val Gly Gly Ser Ile Gly Ile Val Asn
             100                 105                 110
Val Gly Ser Asp Ile Ser Val Gly Phe Ser Ser Glu Ser Trp Ser
             115                 120                 125
Thr Thr Gln Thr Phe Ser Glu Ser Thr Gln Leu Ala Gly Pro Gly Thr
130                 135                 140
Phe Ile Val Tyr Gln Val Val Leu Val Tyr Ala His Asn Ala Thr Ser
145                 150                 155                 160
Ala Gly Arg Gln Asn Gly Asn Ala Phe Ala Tyr Asn Lys Thr Gln Thr
                165                 170                 175
Val Gly Ser Arg Leu Asp Leu Tyr Tyr Leu Ser Ala Ile Thr Gln Asn
                180                 185                 190
Ser Thr Val Ile Val Glu Ser Ser Lys Ala Ile Ala Pro Leu Asp Trp
                195                 200                 205
Asp Thr Val Gln Arg Asn Val Leu Met Glu Asn Tyr Asn Pro Ser Ser
210                 215                 220
Asn Ser Gly His Phe Ser Phe Asp Trp Ser Ala Tyr Asn Asp Pro His
225                 230                 235                 240
Arg Arg Tyr

<210> SEQ ID NO 209
<211> LENGTH: 16
<212> TYPE: DNA
<213> ORGANISM: Artificial Sequence
<220> FEATURE:
<223> OTHER INFORMATION: 16S RNA PCR primer

<400> SEQUENCE: 209
taccttgtta cgactt                                                  16

<210> SEQ ID NO 210
<211> LENGTH: 20
<212> TYPE: DNA
<213> ORGANISM: Artificial Sequence
<220> FEATURE:
<223> OTHER INFORMATION: 16S RNA PCR primer
<220> FEATURE:
<221> NAME/KEY: misc_feature
<222> LOCATION: (12)..(12)
<223> OTHER INFORMATION: m is a or c

<400> SEQUENCE: 210
agagtttgat cmtggctcag                                              20

<210> SEQ ID NO 211
<211> LENGTH: 271
<212> TYPE: PRT
<213> ORGANISM: Artificial Sequence
<220> FEATURE:
<223> OTHER INFORMATION: PIP-1A variant
<220> FEATURE:
<221> NAME/KEY: VARIANT
<222> LOCATION: (2)..(2)
<223> OTHER INFORMATION: Xaa at position 2 is Pro, or Thr
<220> FEATURE:
<221> NAME/KEY: VARIANT
```

```
<222> LOCATION: (8)..(8)
<223> OTHER INFORMATION: Xaa at position 8 is Ser, Gly, or Asn
<220> FEATURE:
<221> NAME/KEY: VARIANT
<222> LOCATION: (19)..(19)
<223> OTHER INFORMATION: Xaa at position 19 is Asp, Glu or Cys
<220> FEATURE:
<221> NAME/KEY: VARIANT
<222> LOCATION: (20)..(20)
<223> OTHER INFORMATION: Xaa at position 20 is Leu, or Val
<220> FEATURE:
<221> NAME/KEY: VARIANT
<222> LOCATION: (21)..(21)
<223> OTHER INFORMATION: Xaa at position 21 is Lys, Ser, or Asn
<220> FEATURE:
<221> NAME/KEY: VARIANT
<222> LOCATION: (22)..(22)
<223> OTHER INFORMATION: Xaa at position 22 is Ser, Lys or Arg
<220> FEATURE:
<221> NAME/KEY: VARIANT
<222> LOCATION: (24)..(24)
<223> OTHER INFORMATION: Xaa at position 24 is Gln, or Ala
<220> FEATURE:
<221> NAME/KEY: VARIANT
<222> LOCATION: (25)..(25)
<223> OTHER INFORMATION: Xaa at position 25 is Gly, or Ala
<220> FEATURE:
<221> NAME/KEY: VARIANT
<222> LOCATION: (26)..(26)
<223> OTHER INFORMATION: Xaa at position 26 is Ser, or Asn
<220> FEATURE:
<221> NAME/KEY: VARIANT
<222> LOCATION: (27)..(27)
<223> OTHER INFORMATION: Xaa at position 27 is Leu, Thr, or Ala
<220> FEATURE:
<221> NAME/KEY: VARIANT
<222> LOCATION: (30)..(30)
<223> OTHER INFORMATION: Xaa at position 30 is Ala, or Ile
<220> FEATURE:
<221> NAME/KEY: VARIANT
<222> LOCATION: (35)..(35)
<223> OTHER INFORMATION: Xaa at position 35 is Phe, or Leu
<220> FEATURE:
<221> NAME/KEY: VARIANT
<222> LOCATION: (36)..(36)
<223> OTHER INFORMATION: Xaa at position 36 is Ala, Ser or Val
<220> FEATURE:
<221> NAME/KEY: VARIANT
<222> LOCATION: (38)..(38)
<223> OTHER INFORMATION: Xaa at position 38 is Asn, Arg, or Ser
<220> FEATURE:
<221> NAME/KEY: VARIANT
<222> LOCATION: (42)..(42)
<223> OTHER INFORMATION: Xaa at position 42 is Phe, or Tyr
<220> FEATURE:
<221> NAME/KEY: VARIANT
<222> LOCATION: (46)..(46)
<223> OTHER INFORMATION: Xaa at position 46 is Arg, Lys or His
<220> FEATURE:
<221> NAME/KEY: VARIANT
<222> LOCATION: (48)..(48)
<223> OTHER INFORMATION: Xaa at position 48 is Gly, or Asp
<220> FEATURE:
<221> NAME/KEY: VARIANT
<222> LOCATION: (49)..(49)
<223> OTHER INFORMATION: Xaa at position 49 is Phe, or Tyr
<220> FEATURE:
<221> NAME/KEY: VARIANT
<222> LOCATION: (53)..(53)
<223> OTHER INFORMATION: Xaa at position 53 is Ser, or Gly
<220> FEATURE:
<221> NAME/KEY: VARIANT
<222> LOCATION: (58)..(58)
<223> OTHER INFORMATION: Xaa at position 58 is Tyr or Phe
<220> FEATURE:
<221> NAME/KEY: VARIANT
<222> LOCATION: (60)..(60)
<223> OTHER INFORMATION: Xaa at position 60 is Ala, or Ser
<220> FEATURE:
```

```
<221> NAME/KEY: VARIANT
<222> LOCATION: (63)..(63)
<223> OTHER INFORMATION: Xaa at position 63 is Gln or Lys
<220> FEATURE:
<221> NAME/KEY: VARIANT
<222> LOCATION: (77)..(77)
<223> OTHER INFORMATION: Xaa at position 77 is Phe, or Tyr
<220> FEATURE:
<221> NAME/KEY: VARIANT
<222> LOCATION: (97)..(97)
<223> OTHER INFORMATION: Xaa at position 97 is Met, or Val
<220> FEATURE:
<221> NAME/KEY: VARIANT
<222> LOCATION: (98)..(98)
<223> OTHER INFORMATION: Xaa at position 98 is Asp, or Glu
<220> FEATURE:
<221> NAME/KEY: VARIANT
<222> LOCATION: (105)..(105)
<223> OTHER INFORMATION: Xaa at position 105 is Gln, or Asn
<220> FEATURE:
<221> NAME/KEY: VARIANT
<222> LOCATION: (107)..(107)
<223> OTHER INFORMATION: Xaa at position 107 is Thr, or Ile
<220> FEATURE:
<221> NAME/KEY: VARIANT
<222> LOCATION: (108)..(108)
<223> OTHER INFORMATION: Xaa at position 108 is Gln, or Thr
<220> FEATURE:
<221> NAME/KEY: VARIANT
<222> LOCATION: (110)..(110)
<223> OTHER INFORMATION: Xaa at position 110 is Arg, or Leu
<220> FEATURE:
<221> NAME/KEY: VARIANT
<222> LOCATION: (120)..(120)
<223> OTHER INFORMATION: Xaa at position 120 is Lys, Arg or Gln
<220> FEATURE:
<221> NAME/KEY: VARIANT
<222> LOCATION: (121)..(121)
<223> OTHER INFORMATION: Xaa at position 121 is Thr, or Ser
<220> FEATURE:
<221> NAME/KEY: VARIANT
<222> LOCATION: (123)..(123)
<223> OTHER INFORMATION: Xaa at position 123 is Thr, or Glu
<220> FEATURE:
<221> NAME/KEY: VARIANT
<222> LOCATION: (125)..(125)
<223> OTHER INFORMATION: Xaa at position 125 is Asn, or Ser
<220> FEATURE:
<221> NAME/KEY: VARIANT
<222> LOCATION: (127)..(127)
<223> OTHER INFORMATION: Xaa at position 127 is Ser, Asn, Thr or Lys
<220> FEATURE:
<221> NAME/KEY: VARIANT
<222> LOCATION: (134)..(134)
<223> OTHER INFORMATION: Xaa at position 134 is Gly, or Ala
<220> FEATURE:
<221> NAME/KEY: VARIANT
<222> LOCATION: (135)..(135)
<223> OTHER INFORMATION: Xaa at position 135 is Ser, Asn or Lys
<220> FEATURE:
<221> NAME/KEY: VARIANT
<222> LOCATION: (137)..(137)
<223> OTHER INFORMATION: Xaa at position 137 is Asp, or Gly
<220> FEATURE:
<221> NAME/KEY: VARIANT
<222> LOCATION: (141)..(141)
<223> OTHER INFORMATION: Xaa at position 141 is Val or Ile
<220> FEATURE:
<221> NAME/KEY: VARIANT
<222> LOCATION: (142)..(142)
<223> OTHER INFORMATION: Xaa at position 142 is Gly or Asp
<220> FEATURE:
<221> NAME/KEY: VARIANT
<222> LOCATION: (144)..(144)
<223> OTHER INFORMATION: Xaa at position 144 is Asp, or Glu
<220> FEATURE:
<221> NAME/KEY: VARIANT
<222> LOCATION: (147)..(147)
<223> OTHER INFORMATION: Xaa at position 147 is Ile, Thr, or Val
```

```
<220> FEATURE:
<221> NAME/KEY: VARIANT
<222> LOCATION: (150)..(150)
<223> OTHER INFORMATION: Xaa at position 150 is Ser, or Thr
<220> FEATURE:
<221> NAME/KEY: VARIANT
<222> LOCATION: (151)..(151)
<223> OTHER INFORMATION: Xaa at position 151 is Asn, Arg, or Ser
<220> FEATURE:
<221> NAME/KEY: VARIANT
<222> LOCATION: (160)..(160)
<223> OTHER INFORMATION: Xaa at position 160 is Thr, or Ser
<220> FEATURE:
<221> NAME/KEY: VARIANT
<222> LOCATION: (162)..(162)
<223> OTHER INFORMATION: Xaa at position 162 is Ser, or Thr
<220> FEATURE:
<221> NAME/KEY: VARIANT
<222> LOCATION: (163)..(163)
<223> OTHER INFORMATION: Xaa at position 163 is Asn, Asp, or Glu
<220> FEATURE:
<221> NAME/KEY: VARIANT
<222> LOCATION: (164)..(164)
<223> OTHER INFORMATION: Xaa at position 164 is Ser, or Thr
<220> FEATURE:
<221> NAME/KEY: VARIANT
<222> LOCATION: (166)..(166)
<223> OTHER INFORMATION: Xaa at position 166 is Gln, or Glu
<220> FEATURE:
<221> NAME/KEY: VARIANT
<222> LOCATION: (167)..(167)
<223> OTHER INFORMATION: Xaa at position 167 is Leu, or Met
<220> FEATURE:
<221> NAME/KEY: VARIANT
<222> LOCATION: (168)..(168)
<223> OTHER INFORMATION: Xaa at position 168 is Thr, Lys, or Ala
<220> FEATURE:
<221> NAME/KEY: VARIANT
<222> LOCATION: (174)..(174)
<223> OTHER INFORMATION: Xaa at position 174 is Ile, Val or Met
<220> FEATURE:
<221> NAME/KEY: VARIANT
<222> LOCATION: (175)..(175)
<223> OTHER INFORMATION: Xaa at position 175 is Val, or Ile
<220> FEATURE:
<221> NAME/KEY: VARIANT
<222> LOCATION: (180)..(180)
<223> OTHER INFORMATION: Xaa at position 180 is Met, or Leu
<220> FEATURE:
<221> NAME/KEY: VARIANT
<222> LOCATION: (191)..(191)
<223> OTHER INFORMATION: Xaa at position 191 is Arg or Lys
<220> FEATURE:
<221> NAME/KEY: VARIANT
<222> LOCATION: (194)..(194)
<223> OTHER INFORMATION: Xaa at position 194 is Gly, or Ala
<220> FEATURE:
<221> NAME/KEY: VARIANT
<222> LOCATION: (200)..(200)
<223> OTHER INFORMATION: Xaa at position 200 is Asn, or Ser
<220> FEATURE:
<221> NAME/KEY: VARIANT
<222> LOCATION: (203)..(203)
<223> OTHER INFORMATION: Xaa at position 203 is Asn, or Gln
<220> FEATURE:
<221> NAME/KEY: VARIANT
<222> LOCATION: (204)..(204)
<223> OTHER INFORMATION: Xaa at position 204 is Thr, or Ala
<220> FEATURE:
<221> NAME/KEY: VARIANT
<222> LOCATION: (206)..(206)
<223> OTHER INFORMATION: Xaa at position 206 is Gly or Asp
<220> FEATURE:
<221> NAME/KEY: VARIANT
<222> LOCATION: (209)..(209)
<223> OTHER INFORMATION: Xaa at position 209 is Leu, or Val
<220> FEATURE:
<221> NAME/KEY: VARIANT
<222> LOCATION: (220)..(220)
```

-continued

```
<223> OTHER INFORMATION: Xaa at position 220 is Asn, or Arg
<220> FEATURE:
<221> NAME/KEY: VARIANT
<222> LOCATION: (221)..(221)
<223> OTHER INFORMATION: Xaa at position 221 is Ser, or Lys
<220> FEATURE:
<221> NAME/KEY: VARIANT
<222> LOCATION: (222)..(222)
<223> OTHER INFORMATION: Xaa at position 222 is Thr, or Arg
<220> FEATURE:
<221> NAME/KEY: VARIANT
<222> LOCATION: (226)..(226)
<223> OTHER INFORMATION: Xaa at position 226 is Asp, Pro, or Glu
<220> FEATURE:
<221> NAME/KEY: VARIANT
<222> LOCATION: (229)..(229)
<223> OTHER INFORMATION: Xaa at position 229 is Lys, or Asn
<220> FEATURE:
<221> NAME/KEY: VARIANT
<222> LOCATION: (231)..(231)
<223> OTHER INFORMATION: Xaa at position 231 is Ile, or Val
<220> FEATURE:
<221> NAME/KEY: VARIANT
<222> LOCATION: (232)..(232)
<223> OTHER INFORMATION: Xaa at position 232 is Ala, Thr or Glu
<220> FEATURE:
<221> NAME/KEY: VARIANT
<222> LOCATION: (251)..(251)
<223> OTHER INFORMATION: Xaa at position 251 is Gly, Ser or Glu
<220> FEATURE:
<221> NAME/KEY: VARIANT
<222> LOCATION: (254)..(254)
<223> OTHER INFORMATION: Xaa at position 254 is Ser or Asn
<220> FEATURE:
<221> NAME/KEY: VARIANT
<222> LOCATION: (258)..(258)
<223> OTHER INFORMATION: Xaa at position 258 is Ser or Arg
<220> FEATURE:
<221> NAME/KEY: VARIANT
<222> LOCATION: (265)..(265)
<223> OTHER INFORMATION: Xaa at position 265 is Asn or Asp
<220> FEATURE:
<221> NAME/KEY: VARIANT
<222> LOCATION: (266)..(266)
<223> OTHER INFORMATION: Xaa at position 266 is Asp or Asn

<400> SEQUENCE: 211

Met Xaa Ile Lys Glu Glu Leu Xaa Gln Pro Gln Ser His Ser Ile Glu
1               5                   10                  15

Leu Asp Xaa Xaa Xaa Xaa Glu Xaa Xaa Xaa Xaa Arg Ala Xaa Leu Thr
            20                  25                  30

Ser Asn Xaa Xaa Gly Xaa Phe Asp Gln Xaa Pro Thr Lys Xaa Gly Xaa
        35                  40                  45

Xaa Ala Ile Asp Xaa Tyr Leu Leu Asp Xaa Ser Xaa Pro Lys Xaa Gly
    50                  55                  60

Cys Trp Val Asp Gly Ile Thr Val Tyr Gly Asp Ile Xaa Ile Gly Lys
65                  70                  75                  80

Gln Asn Trp Gly Thr Tyr Thr Arg Pro Val Phe Ala Tyr Leu Gln Tyr
                85                  90                  95

Xaa Xaa Thr Ile Ser Ile Pro Gln Xaa Val Xaa Xaa Thr Xaa Ser Tyr
            100                 105                 110

Gln Leu Thr Lys Gly His Thr Xaa Xaa Phe Xaa Thr Xaa Val Xaa Ala
        115                 120                 125

Lys Tyr Ser Val Gly Xaa Xaa Ile Xaa Ile Val Asn Xaa Xaa Ser Xaa
    130                 135                 140

Ile Ser Xaa Gly Phe Xaa Xaa Ser Glu Ser Trp Ser Thr Thr Gln Xaa
145                 150                 155                 160

Phe Xaa Xaa Xaa Thr Xaa Xaa Xaa Gly Pro Gly Thr Phe Xaa Xaa Tyr
```

```
                    165                 170                 175
Gln Val Val Xaa Val Tyr Ala His Asn Ala Thr Ser Ala Gly Xaa Gln
            180                 185                 190

Asn Xaa Asn Ala Phe Ala Tyr Xaa Lys Thr Xaa Xaa Val Xaa Ser Arg
        195                 200                 205

Xaa Asp Leu Tyr Tyr Leu Ser Ala Ile Thr Gln Xaa Xaa Val Ile
    210                 215                 220

Val Xaa Ser Ser Xaa Ala Xaa Xaa Pro Leu Asp Trp Asp Thr Val Gln
225                 230                 235                 240

Arg Asn Val Leu Met Glu Asn Tyr Asn Pro Xaa Ser Asn Xaa Gly His
                245                 250                 255

Phe Xaa Phe Asp Trp Ser Ala Tyr Xaa Xaa Pro His Arg Arg Tyr
        260                 265                 270

<210> SEQ ID NO 212
<211> LENGTH: 271
<212> TYPE: PRT
<213> ORGANISM: Artificial Sequence
<220> FEATURE:
<223> OTHER INFORMATION: PIP-1A variant
<220> FEATURE:
<221> NAME/KEY: VARIANT
<222> LOCATION: (2)..(2)
<223> OTHER INFORMATION: Xaa at position 2 is Pro, or Thr
<220> FEATURE:
<221> NAME/KEY: VARIANT
<222> LOCATION: (3)..(3)
<223> OTHER INFORMATION: Xaa at position 3 is Ile, or Thr
<220> FEATURE:
<221> NAME/KEY: VARIANT
<222> LOCATION: (6)..(6)
<223> OTHER INFORMATION: Xaa at position 6 is Glu, or Gly
<220> FEATURE:
<221> NAME/KEY: VARIANT
<222> LOCATION: (8)..(8)
<223> OTHER INFORMATION: Xaa at position 8 is Ser, Gly, or Asn
<220> FEATURE:
<221> NAME/KEY: VARIANT
<222> LOCATION: (19)..(19)
<223> OTHER INFORMATION: Xaa at position 19 is Asp, Glu or Cys
<220> FEATURE:
<221> NAME/KEY: VARIANT
<222> LOCATION: (20)..(20)
<223> OTHER INFORMATION: Xaa at position 20 is Leu, or Val
<220> FEATURE:
<221> NAME/KEY: VARIANT
<222> LOCATION: (21)..(21)
<223> OTHER INFORMATION: Xaa at position 21 is Lys, Ser, or Asn
<220> FEATURE:
<221> NAME/KEY: VARIANT
<222> LOCATION: (22)..(22)
<223> OTHER INFORMATION: Xaa at position 22 is Ser, Lys or Arg
<220> FEATURE:
<221> NAME/KEY: VARIANT
<222> LOCATION: (24)..(24)
<223> OTHER INFORMATION: Xaa at position 24 is Gln, or Ala
<220> FEATURE:
<221> NAME/KEY: VARIANT
<222> LOCATION: (25)..(25)
<223> OTHER INFORMATION: Xaa at position 25 is Gly, or Ala
<220> FEATURE:
<221> NAME/KEY: VARIANT
<222> LOCATION: (26)..(26)
<223> OTHER INFORMATION: Xaa at position 26 is Ser, or Asn
<220> FEATURE:
<221> NAME/KEY: VARIANT
<222> LOCATION: (27)..(27)
<223> OTHER INFORMATION: Xaa at position 27 is Leu, Thr, or Ala
<220> FEATURE:
<221> NAME/KEY: VARIANT
<222> LOCATION: (28)..(28)
<223> OTHER INFORMATION: Xaa at position 28 is Arg, Ser, Lys, Thr, Val,
```

-continued

```
      Gly, Ala, Met, Asp, Trp, Pro, Leu, His, Cys, and Gln
<220> FEATURE:
<221> NAME/KEY: VARIANT
<222> LOCATION: (30)..(30)
<223> OTHER INFORMATION: Xaa at position 30 is Ala, or Ile
<220> FEATURE:
<221> NAME/KEY: VARIANT
<222> LOCATION: (35)..(35)
<223> OTHER INFORMATION: Xaa at position 35 is Phe, or Leu
<220> FEATURE:
<221> NAME/KEY: VARIANT
<222> LOCATION: (36)..(36)
<223> OTHER INFORMATION: Xaa at position 36 is Ala, Ser or Val
<220> FEATURE:
<221> NAME/KEY: VARIANT
<222> LOCATION: (38)..(38)
<223> OTHER INFORMATION: Xaa at position 38 is Asn, Arg, or Ser
<220> FEATURE:
<221> NAME/KEY: VARIANT
<222> LOCATION: (42)..(42)
<223> OTHER INFORMATION: Xaa at position 42 is Phe, or Tyr
<220> FEATURE:
<221> NAME/KEY: VARIANT
<222> LOCATION: (43)..(43)
<223> OTHER INFORMATION: Xaa at position 43 is Pro, Met, Gly, Gln, Ser,
      Thr, Arg, Val, Leu, Lys, Asp, Ala, Asn, Phe, Trp, Glu, or Cys
<220> FEATURE:
<221> NAME/KEY: VARIANT
<222> LOCATION: (46)..(46)
<223> OTHER INFORMATION: Xaa at position 46 is Arg, Lys or His
<220> FEATURE:
<221> NAME/KEY: VARIANT
<222> LOCATION: (48)..(48)
<223> OTHER INFORMATION: Xaa at position 48 is Gly, or Asp
<220> FEATURE:
<221> NAME/KEY: VARIANT
<222> LOCATION: (49)..(49)
<223> OTHER INFORMATION: Xaa at position 49 is Phe, Tyr, or Leu
<220> FEATURE:
<221> NAME/KEY: VARIANT
<222> LOCATION: (53)..(53)
<223> OTHER INFORMATION: Xaa at position 53 is Ser, or Gly
<220> FEATURE:
<221> NAME/KEY: VARIANT
<222> LOCATION: (58)..(58)
<223> OTHER INFORMATION: Xaa at position 58 is Tyr or Phe
<220> FEATURE:
<221> NAME/KEY: VARIANT
<222> LOCATION: (60)..(60)
<223> OTHER INFORMATION: Xaa at position 60 is Ala, or Ser
<220> FEATURE:
<221> NAME/KEY: VARIANT
<222> LOCATION: (63)..(63)
<223> OTHER INFORMATION: Xaa at position 63 is Gln or Lys
<220> FEATURE:
<221> NAME/KEY: VARIANT
<222> LOCATION: (66)..(66)
<223> OTHER INFORMATION: Xaa at position 66 is Trp, Tyr, Phe, Arg, Lys,
      His, Ile, Val or Ser
<220> FEATURE:
<221> NAME/KEY: VARIANT
<222> LOCATION: (77)..(77)
<223> OTHER INFORMATION: Xaa at position 77 is Phe, or Tyr
<220> FEATURE:
<221> NAME/KEY: VARIANT
<222> LOCATION: (89)..(89)
<223> OTHER INFORMATION: Xaa at position 89 is Pro, Leu, Gly, Arg, Thr,
      Ser, Met, Ala, Ile, Asn, Val, Cys, or Lys
<220> FEATURE:
<221> NAME/KEY: VARIANT
<222> LOCATION: (93)..(93)
<223> OTHER INFORMATION: Xaa at position 93 is Tyr, Cys, Trp, Val, Ile,
      Leu, Met, Phe, Ala, Thr, Asp or Asn
<220> FEATURE:
<221> NAME/KEY: VARIANT
<222> LOCATION: (97)..(97)
<223> OTHER INFORMATION: Xaa at position 97 is Met, or Val
<220> FEATURE:
<221> NAME/KEY: VARIANT
```

```
<222> LOCATION: (98)..(98)
<223> OTHER INFORMATION: Xaa at position 98 is Asp, or Glu
<220> FEATURE:
<221> NAME/KEY: VARIANT
<222> LOCATION: (105)..(105)
<223> OTHER INFORMATION: Xaa at position 105 is Gln, or Asn
<220> FEATURE:
<221> NAME/KEY: VARIANT
<222> LOCATION: (107)..(107)
<223> OTHER INFORMATION: Xaa at position 107 is Thr, or Ile
<220> FEATURE:
<221> NAME/KEY: VARIANT
<222> LOCATION: (108)..(108)
<223> OTHER INFORMATION: Xaa at position 108 is Gln, or Thr
<220> FEATURE:
<221> NAME/KEY: VARIANT
<222> LOCATION: (110)..(110)
<223> OTHER INFORMATION: Xaa at position 110 is Arg, or Leu
<220> FEATURE:
<221> NAME/KEY: VARIANT
<222> LOCATION: (120)..(120)
<223> OTHER INFORMATION: Xaa at position 120 is Lys, Arg or Gln
<220> FEATURE:
<221> NAME/KEY: VARIANT
<222> LOCATION: (121)..(121)
<223> OTHER INFORMATION: Xaa at position 121 is Thr, or Ser
<220> FEATURE:
<221> NAME/KEY: VARIANT
<222> LOCATION: (123)..(123)
<223> OTHER INFORMATION: Xaa at position 123 is Thr, or Glu
<220> FEATURE:
<221> NAME/KEY: VARIANT
<222> LOCATION: (125)..(125)
<223> OTHER INFORMATION: Xaa at position 125 is Asn, or Ser
<220> FEATURE:
<221> NAME/KEY: VARIANT
<222> LOCATION: (127)..(127)
<223> OTHER INFORMATION: Xaa at position 127 is Ser, Asn, Thr or Lys
<220> FEATURE:
<221> NAME/KEY: VARIANT
<222> LOCATION: (134)..(134)
<223> OTHER INFORMATION: Xaa at position 134 is Gly, or Ala
<220> FEATURE:
<221> NAME/KEY: VARIANT
<222> LOCATION: (135)..(135)
<223> OTHER INFORMATION: Xaa at position 135 is Ser, Asn or Lys
<220> FEATURE:
<221> NAME/KEY: VARIANT
<222> LOCATION: (137)..(137)
<223> OTHER INFORMATION: Xaa at position 137 is Asp, or Gly
<220> FEATURE:
<221> NAME/KEY: VARIANT
<222> LOCATION: (141)..(141)
<223> OTHER INFORMATION: Xaa at position 141 is Val or Ile
<220> FEATURE:
<221> NAME/KEY: VARIANT
<222> LOCATION: (142)..(142)
<223> OTHER INFORMATION: Xaa at position 142 is Gly or Asp
<220> FEATURE:
<221> NAME/KEY: VARIANT
<222> LOCATION: (144)..(144)
<223> OTHER INFORMATION: Xaa at position 144 is Asp, or Glu
<220> FEATURE:
<221> NAME/KEY: VARIANT
<222> LOCATION: (147)..(147)
<223> OTHER INFORMATION: Xaa at position 147 is Ile, Thr, or Val
<220> FEATURE:
<221> NAME/KEY: VARIANT
<222> LOCATION: (150)..(150)
<223> OTHER INFORMATION: Xaa at position 150 is Ser, or Thr
<220> FEATURE:
<221> NAME/KEY: VARIANT
<222> LOCATION: (151)..(151)
<223> OTHER INFORMATION: Xaa at position 151 is Asn, Arg, or Ser
<220> FEATURE:
<221> NAME/KEY: VARIANT
<222> LOCATION: (160)..(160)
<223> OTHER INFORMATION: Xaa at position 160 is Thr, or Ser
<220> FEATURE:
```

```
<221> NAME/KEY: VARIANT
<222> LOCATION: (162)..(162)
<223> OTHER INFORMATION: Xaa at position 162 is Ser, or Thr
<220> FEATURE:
<221> NAME/KEY: VARIANT
<222> LOCATION: (163)..(163)
<223> OTHER INFORMATION: Xaa at position 163 is Asn, Asp, or Glu
<220> FEATURE:
<221> NAME/KEY: VARIANT
<222> LOCATION: (164)..(164)
<223> OTHER INFORMATION: Xaa at position 164 is Ser, or Thr
<220> FEATURE:
<221> NAME/KEY: VARIANT
<222> LOCATION: (166)..(166)
<223> OTHER INFORMATION: Xaa at position 166 is Gln, or Glu
<220> FEATURE:
<221> NAME/KEY: VARIANT
<222> LOCATION: (167)..(167)
<223> OTHER INFORMATION: Xaa at position 167 is Leu, or Met
<220> FEATURE:
<221> NAME/KEY: VARIANT
<222> LOCATION: (168)..(168)
<223> OTHER INFORMATION: Xaa at position 168 is Thr, Lys, or Ala
<220> FEATURE:
<221> NAME/KEY: VARIANT
<222> LOCATION: (171)..(171)
<223> OTHER INFORMATION: Xaa at position 171 is Gly, Leu, Gln, Met, Cys,
      Asn, Asp, Ser or Ala
<220> FEATURE:
<221> NAME/KEY: VARIANT
<222> LOCATION: (172)..(172)
<223> OTHER INFORMATION: Xaa at position 172 is Thr, Gly, His, Phe, Glu,
      Arg, Ser, Asn, Ile, Trp, Lys, Gln, Cys, Val, Ala, or Met
<220> FEATURE:
<221> NAME/KEY: VARIANT
<222> LOCATION: (173)..(173)
<223> OTHER INFORMATION: Xaa at position 173 is Phe, Gly, His, Leu, Ala,
      Arg, Asn, Cys, Lys, Trp, Thr, Ser, Tyr, or Met
<220> FEATURE:
<221> NAME/KEY: VARIANT
<222> LOCATION: (174)..(174)
<223> OTHER INFORMATION: Xaa at position 174 is Ile, Val, Gly, Arg, Asn,
      Ala, Gln, Met, Cys, Leu, Phe, Tyr, Lys, Glu, Ser, His, or Thr
<220> FEATURE:
<221> NAME/KEY: VARIANT
<222> LOCATION: (175)..(175)
<223> OTHER INFORMATION: Xaa at position 175 is Val, Ile, Ala, Cys, Glu,
      Lys, Leu or Met
<220> FEATURE:
<221> NAME/KEY: VARIANT
<222> LOCATION: (176)..(176)
<223> OTHER INFORMATION: Xaa at position 176 is Tyr, Met, Phe, Leu, or
      Cys
<220> FEATURE:
<221> NAME/KEY: VARIANT
<222> LOCATION: (177)..(177)
<223> OTHER INFORMATION: Xaa at position 177 is Gln, Ile, Met, or Pro
<220> FEATURE:
<221> NAME/KEY: VARIANT
<222> LOCATION: (178)..(178)
<223> OTHER INFORMATION: Xaa at position 178 is Val, Cys, Thr, Pro, Ala,
      Met, Gln, Phe, Ile, Ser or Lys
<220> FEATURE:
<221> NAME/KEY: VARIANT
<222> LOCATION: (179)..(179)
<223> OTHER INFORMATION: Xaa at position 179 is Val, Phe, Thr, Ile, Cys,
      Leu, Met, Ser, Ala, or Gln
<220> FEATURE:
<221> NAME/KEY: VARIANT
<222> LOCATION: (180)..(180)
<223> OTHER INFORMATION: Xaa at position 180 is Met, Leu, Pro, Trp, Asn,
      Tyr, Gly, Gln, Ala, Val, Phe, Ile, Cys, or Ser
<220> FEATURE:
<221> NAME/KEY: VARIANT
<222> LOCATION: (181)..(181)
<223> OTHER INFORMATION: Xaa at position 181 is Val, Ala, Leu, Trp, Cys,
      Thr, Ile or Lys
<220> FEATURE:
<221> NAME/KEY: VARIANT
```

-continued

```
<222> LOCATION: (182)..(182)
<223> OTHER INFORMATION: Xaa at position 182 is Tyr, Phe, Met, or His
<220> FEATURE:
<221> NAME/KEY: VARIANT
<222> LOCATION: (183)..(183)
<223> OTHER INFORMATION: Xaa at position 183 is Ala, Met, Val, Thr, Asp,
      Gly, Cys, Ile, Phe, Ser, Gln, or Leu
<220> FEATURE:
<221> NAME/KEY: VARIANT
<222> LOCATION: (191)..(191)
<223> OTHER INFORMATION: Xaa at position 191 is Arg or Lys
<220> FEATURE:
<221> NAME/KEY: VARIANT
<222> LOCATION: (194)..(194)
<223> OTHER INFORMATION: Xaa at position 194 is Gly, or Ala
<220> FEATURE:
<221> NAME/KEY: VARIANT
<222> LOCATION: (195)..(195)
<223> OTHER INFORMATION: Xaa at position 195 is Asn, or Tyr
<220> FEATURE:
<221> NAME/KEY: VARIANT
<222> LOCATION: (200)..(200)
<223> OTHER INFORMATION: Xaa at position 200 is Asn, or Ser
<220> FEATURE:
<221> NAME/KEY: VARIANT
<222> LOCATION: (203)..(203)
<223> OTHER INFORMATION: Xaa at position 203 is Asn, or Gln
<220> FEATURE:
<221> NAME/KEY: VARIANT
<222> LOCATION: (204)..(204)
<223> OTHER INFORMATION: Xaa at position 204 is Thr, or Ala
<220> FEATURE:
<221> NAME/KEY: VARIANT
<222> LOCATION: (206)..(206)
<223> OTHER INFORMATION: Xaa at position 206 is Gly or Asp
<220> FEATURE:
<221> NAME/KEY: VARIANT
<222> LOCATION: (209)..(209)
<223> OTHER INFORMATION: Xaa at position 209 is Leu, or Val
<220> FEATURE:
<221> NAME/KEY: VARIANT
<222> LOCATION: (213)..(213)
<223> OTHER INFORMATION: Xaa at position 213 is Tyr, or Phe
<220> FEATURE:
<221> NAME/KEY: VARIANT
<222> LOCATION: (220)..(220)
<223> OTHER INFORMATION: Xaa at position 220 is Asn, or Arg
<220> FEATURE:
<221> NAME/KEY: VARIANT
<222> LOCATION: (221)..(221)
<223> OTHER INFORMATION: Xaa at position 221 is Ser, or Lys
<220> FEATURE:
<221> NAME/KEY: VARIANT
<222> LOCATION: (222)..(222)
<223> OTHER INFORMATION: Xaa at position 222 is Thr, or Arg
<220> FEATURE:
<221> NAME/KEY: VARIANT
<222> LOCATION: (226)..(226)
<223> OTHER INFORMATION: Xaa at position 226 is Asp, Pro, or Glu
<220> FEATURE:
<221> NAME/KEY: VARIANT
<222> LOCATION: (228)..(228)
<223> OTHER INFORMATION: Xaa at position 228 is Ser or Gly
<220> FEATURE:
<221> NAME/KEY: VARIANT
<222> LOCATION: (229)..(229)
<223> OTHER INFORMATION: Xaa at position 229 is Lys, or Asn
<220> FEATURE:
<221> NAME/KEY: VARIANT
<222> LOCATION: (231)..(231)
<223> OTHER INFORMATION: Xaa at position 231 is Ile, or Val
<220> FEATURE:
<221> NAME/KEY: VARIANT
<222> LOCATION: (232)..(232)
<223> OTHER INFORMATION: Xaa at position 232 is Ala, Thr or Glu
<220> FEATURE:
<221> NAME/KEY: VARIANT
<222> LOCATION: (240)..(240)
<223> OTHER INFORMATION: Xaa at position 240 is Gln, Arg, Ala, Val, Glu,
```

```
      Met, Gly, Asp, Trp, Asn, Thr, Ile, Ser, Phe, His, Cys, or Leu
<220> FEATURE:
<221> NAME/KEY: VARIANT
<222> LOCATION: (241)..(241)
<223> OTHER INFORMATION: Xaa at position 241 is Arg, Lys, Glu, Gln, Ser,
      Ile, Val, Asp, Tyr, Met, Asn, His, Pro, Gly, Leu, Phe, Thr, Ala,
      or Cys
<220> FEATURE:
<221> NAME/KEY: VARIANT
<222> LOCATION: (242)..(242)
<223> OTHER INFORMATION: Xaa at position 242 is Asn, Ala, Arg, Lys, His,
      Ser, Cys, Glu, Pro, Trp, Gln, Thr, Phe, Tyr, Met, Asp, Gly, Leu or
      Val
<220> FEATURE:
<221> NAME/KEY: VARIANT
<222> LOCATION: (243)..(243)
<223> OTHER INFORMATION: Xaa at position 243 is Val, Leu, Ala, Thr, Gly,
      Cys, Ile, Ser, or Met
<220> FEATURE:
<221> NAME/KEY: VARIANT
<222> LOCATION: (244)..(244)
<223> OTHER INFORMATION: Xaa at position 244 is Leu, Val, Phe, Ile, Met,
      Gln, Cys, Trp or Ala
<220> FEATURE:
<221> NAME/KEY: VARIANT
<222> LOCATION: (245)..(245)
<223> OTHER INFORMATION: Xaa at position 245 is Met, Ala, Arg, Asp, Glu,
      Leu, Pro, Ser, Trp, Gly, Val, Lys, Phe, Cys, Thr, His, Ile, Gln,
      Tyr, or Asn
<220> FEATURE:
<221> NAME/KEY: VARIANT
<222> LOCATION: (246)..(246)
<223> OTHER INFORMATION: Xaa at position 246 is Glu, Asp, Tyr, Gly, Arg,
      Val, Ala, Trp, Gln, Ser, Asn, Ile Leu, Met, Cys, Pro, His, Phe,
      Thr, or Lys
<220> FEATURE:
<221> NAME/KEY: VARIANT
<222> LOCATION: (247)..(247)
<223> OTHER INFORMATION: Xaa at position 247 is Asn, Leu, Asp, Tyr, Ala,
      Phe, His, Arg, Lys, Gln, Gly, Val, Ile, Ser, Glu, Pro, Met, Trp,
      Thr, or Cys
<220> FEATURE:
<221> NAME/KEY: VARIANT
<222> LOCATION: (248)..(248)
<223> OTHER INFORMATION: Xaa at position 248 is Tyr, Val, Thr, Glu, Phe,
      Ser, His, Cys, Leu, Trp, Ile, Asp, Gly, or Ala
<220> FEATURE:
<221> NAME/KEY: VARIANT
<222> LOCATION: (249)..(249)
<223> OTHER INFORMATION: Xaa at position 249 is Asn, Lys, Val, Gly, Met,
      Asp, Cys, Phe, Arg, Glu, Trp, Tyr, Ser, Ile, Thr, Pro, Leu, Ala,
      His or Gln
<220> FEATURE:
<221> NAME/KEY: VARIANT
<222> LOCATION: (251)..(251)
<223> OTHER INFORMATION: Xaa at position 251 is Gly, Ser or Glu
<220> FEATURE:
<221> NAME/KEY: VARIANT
<222> LOCATION: (254)..(254)
<223> OTHER INFORMATION: Xaa at position 254 is Ser or Asn
<220> FEATURE:
<221> NAME/KEY: VARIANT
<222> LOCATION: (258)..(258)
<223> OTHER INFORMATION: Xaa at position 258 is Ser or Arg
<220> FEATURE:
<221> NAME/KEY: VARIANT
<222> LOCATION: (259)..(259)
<223> OTHER INFORMATION: Xaa at position 259 is Phe, Trp, Tyr, Cys, Met,
      Leu, Val, Ile, or His
<220> FEATURE:
<221> NAME/KEY: VARIANT
<222> LOCATION: (265)..(265)
<223> OTHER INFORMATION: Xaa at position 265 is Asn or Asp
<220> FEATURE:
<221> NAME/KEY: VARIANT
<222> LOCATION: (266)..(266)
<223> OTHER INFORMATION: Xaa at position 266 is Asp or Asn

<400> SEQUENCE: 212
```

```
Met Xaa Xaa Lys Glu Xaa Leu Xaa Gln Pro Gln Ser His Ser Ile Glu
1               5                   10                  15

Leu Asp Xaa Xaa Xaa Glu Xaa Xaa Xaa Xaa Ala Xaa Leu Thr
            20                  25                  30

Ser Asn Xaa Xaa Gly Xaa Phe Asp Gln Xaa Xaa Thr Lys Xaa Gly Xaa
            35                  40                  45

Xaa Ala Ile Asp Xaa Tyr Leu Leu Asp Xaa Ser Xaa Pro Lys Gln Gly
        50                  55                  60

Cys Xaa Val Asp Gly Ile Thr Val Tyr Gly Asp Ile Xaa Ile Gly Lys
65              70                  75                  80

Gln Asn Trp Gly Thr Tyr Thr Arg Xaa Val Phe Ala Xaa Leu Gln Tyr
                85                  90                  95

Xaa Xaa Thr Ile Ser Ile Pro Gln Xaa Val Xaa Thr Xaa Ser Tyr
            100                 105                 110

Gln Leu Thr Lys Gly His Thr Xaa Xaa Phe Xaa Thr Xaa Val Xaa Ala
            115                 120                 125

Lys Tyr Ser Val Gly Xaa Xaa Ile Xaa Ile Val Asn Xaa Xaa Ser Xaa
        130                 135                 140

Ile Ser Xaa Gly Phe Xaa Xaa Ser Glu Ser Trp Ser Thr Thr Gln Xaa
145                 150                 155                 160

Phe Xaa Xaa Xaa Thr Xaa Xaa Xaa Gly Pro Xaa Xaa Xaa Xaa Xaa Xaa
                165                 170                 175

Xaa Xaa Xaa Xaa Xaa Xaa Xaa His Asn Ala Thr Ser Ala Gly Xaa Gln
            180                 185                 190

Asn Xaa Xaa Ala Phe Ala Tyr Xaa Lys Thr Xaa Xaa Val Xaa Ser Arg
        195                 200                 205

Xaa Asp Leu Tyr Xaa Leu Ser Ala Ile Thr Gln Xaa Xaa Xaa Val Ile
210                 215                 220

Val Xaa Ser Ser Xaa Ala Xaa Xaa Pro Leu Asp Trp Asp Thr Val Xaa
225                 230                 235                 240

Xaa Xaa Xaa Xaa Xaa Xaa Xaa Xaa Pro Xaa Ser Asn Xaa Gly His
            245                 250                 255

Phe Xaa Xaa Asp Trp Ser Ala Tyr Xaa Xaa Pro His Arg Arg Tyr
        260                 265                 270
```

<210> SEQ ID NO 213
<211> LENGTH: 271
<212> TYPE: PRT
<213> ORGANISM: Artificial Sequence
<220> FEATURE:
<223> OTHER INFORMATION: PIP-1A variant
<220> FEATURE:
<221> NAME/KEY: VARIANT
<222> LOCATION: (2)..(2)
<223> OTHER INFORMATION: Xaa at position 2 is Pro, Thr, or Ser
<220> FEATURE:
<221> NAME/KEY: VARIANT
<222> LOCATION: (3)..(3)
<223> OTHER INFORMATION: Xaa at position 3 is Ile, Thr, Leu, Val, Met, or Ser
<220> FEATURE:
<221> NAME/KEY: VARIANT
<222> LOCATION: (6)..(6)
<223> OTHER INFORMATION: Xaa at position 6 is Glu, Gly, Asp, or Ala
<220> FEATURE:
<221> NAME/KEY: VARIANT
<222> LOCATION: (8)..(8)
<223> OTHER INFORMATION: Xaa at position 8 is Ser, Gly, Asn, Thr, or Gln
<220> FEATURE:
<221> NAME/KEY: VARIANT
<222> LOCATION: (19)..(19)

-continued

```
<223> OTHER INFORMATION: Xaa at position 19 is Asp, Glu or Cys;
<220> FEATURE:
<221> NAME/KEY: VARIANT
<222> LOCATION: (20)..(20)
<223> OTHER INFORMATION: Xaa at position 20 is Leu, Val, Ile, or Met
<220> FEATURE:
<221> NAME/KEY: VARIANT
<222> LOCATION: (21)..(21)
<223> OTHER INFORMATION: Xaa at position 21 is Lys, Ser, Asn, Arg, Thr,
      or Gln
<220> FEATURE:
<221> NAME/KEY: VARIANT
<222> LOCATION: (22)..(22)
<223> OTHER INFORMATION: Xaa at position 22 is Ser, Lys, Arg, or Thr
<220> FEATURE:
<221> NAME/KEY: VARIANT
<222> LOCATION: (24)..(24)
<223> OTHER INFORMATION: Xaa at position 24 is Gln, Gly, Asn, or Ala
<220> FEATURE:
<221> NAME/KEY: VARIANT
<222> LOCATION: (25)..(25)
<223> OTHER INFORMATION: Xaa at position 25 is Gly,  or Ala
<220> FEATURE:
<221> NAME/KEY: VARIANT
<222> LOCATION: (26)..(26)
<223> OTHER INFORMATION: Xaa at position 26 is Ser, Asn, Thr, or Gln
<220> FEATURE:
<221> NAME/KEY: VARIANT
<222> LOCATION: (27)..(27)
<223> OTHER INFORMATION: Xaa at position 27 is Leu, Thr, Ala, Ser, Ile,
      Val, or Met
<220> FEATURE:
<221> NAME/KEY: VARIANT
<222> LOCATION: (28)..(28)
<223> OTHER INFORMATION: Xaa at position 28 is Arg, Ser, Lys, Thr, Val,
      Gly, Ala, Met, Asp, Trp, Pro, Leu, His, Cys, and Gln
<220> FEATURE:
<221> NAME/KEY: VARIANT
<222> LOCATION: (30)..(30)
<223> OTHER INFORMATION: Xaa at position 30 is Ala, Ile, Leu, Val, or
      Met
<220> FEATURE:
<221> NAME/KEY: VARIANT
<222> LOCATION: (35)..(35)
<223> OTHER INFORMATION: Xaa at position 35 is Phe, Leu, Ile, Val, or
      Met
<220> FEATURE:
<221> NAME/KEY: VARIANT
<222> LOCATION: (36)..(36)
<223> OTHER INFORMATION: Xaa at position 36 is Ala, Ser, Thr, Val, Ile
      or Leu
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: VARIANT
<222> LOCATION: (42)..(42)
<223> OTHER INFORMATION: Xaa at position 42 is Phe, Tyr, Trp, Leu, Ile,
      Val, or Met
<220> FEATURE:
<221> NAME/KEY: VARIANT
<222> LOCATION: (43)..(43)
<223> OTHER INFORMATION: Xaa at position 43 is Pro, Met, Gly, Gln, Ser,
      Thr, Arg, Val, Leu, Lys, Asp, Ala, Asn, Phe, Trp, Glu, or Cys
<220> FEATURE:
<221> NAME/KEY: VARIANT
<222> LOCATION: (46)..(46)
<223> OTHER INFORMATION: Xaa at position 46 is Arg, Lys or His
<220> FEATURE:
<221> NAME/KEY: VARIANT
<222> LOCATION: (48)..(48)
<223> OTHER INFORMATION: Xaa at position 48 is Gly, Asp, Ala, or Glu
<220> FEATURE:
<221> NAME/KEY: VARIANT
<222> LOCATION: (49)..(49)
<223> OTHER INFORMATION: Xaa at position 49 is Phe, Tyr, Trp, Leu, Ile,
      Val, or Met
<220> FEATURE:
```

-continued

```
<221> NAME/KEY: VARIANT
<222> LOCATION: (53)..(53)
<223> OTHER INFORMATION: Xaa at position 53 is Ser, Gly, Ala, or Thr
<220> FEATURE:
<221> NAME/KEY: VARIANT
<222> LOCATION: (58)..(58)
<223> OTHER INFORMATION: Xaa at position 58 is Tyr or Phe
<220> FEATURE:
<221> NAME/KEY: VARIANT
<222> LOCATION: (60)..(60)
<223> OTHER INFORMATION: Xaa at position 60 is Ala, Ser, Gly, or Thr
<220> FEATURE:
<221> NAME/KEY: VARIANT
<222> LOCATION: (63)..(63)
<223> OTHER INFORMATION: Xaa at position 63 is Gln, Lys, Asn or Arg
<220> FEATURE:
<221> NAME/KEY: VARIANT
<222> LOCATION: (66)..(66)
<223> OTHER INFORMATION: Xaa at position 66 is Trp, Tyr, Phe, Arg, Lys,
      His, Ile, Val or Ser
<220> FEATURE:
<221> NAME/KEY: VARIANT
<222> LOCATION: (77)..(77)
<223> OTHER INFORMATION: Xaa at position 77 is Phe, Tyr, Trp, Leu, Ile,
      Val, or Met
<220> FEATURE:
<221> NAME/KEY: VARIANT
<222> LOCATION: (89)..(89)
<223> OTHER INFORMATION: Xaa at position 89 is Pro, Leu, Gly, Arg, Thr,
      Ser, Met, Ala, Ile, Asn, Val, Cys, or Lys
<220> FEATURE:
<221> NAME/KEY: VARIANT
<222> LOCATION: (93)..(93)
<223> OTHER INFORMATION: Xaa at position 93 is Tyr, Cys, Trp, Val, Ile,
      Leu, Met, Phe, Ala, Thr, Asp or Asn
<220> FEATURE:
<221> NAME/KEY: VARIANT
<222> LOCATION: (97)..(97)
<223> OTHER INFORMATION: Xaa at position 97 is Met, Val, Leu, or Ile
<220> FEATURE:
<221> NAME/KEY: VARIANT
<222> LOCATION: (98)..(98)
<223> OTHER INFORMATION: Xaa at position 98 is Asp, or Glu
<220> FEATURE:
<221> NAME/KEY: VARIANT
<222> LOCATION: (105)..(105)
<223> OTHER INFORMATION: Xaa at position 105 is Gln, or Asn
<220> FEATURE:
<221> NAME/KEY: VARIANT
<222> LOCATION: (107)..(107)
<223> OTHER INFORMATION: Xaa at position 107 is Thr, Ile, Ser, Leu or
      Val
<220> FEATURE:
<221> NAME/KEY: VARIANT
<222> LOCATION: (108)..(108)
<223> OTHER INFORMATION: Xaa at position 108 is Gln, Thr, Ser, or Asn
<220> FEATURE:
<221> NAME/KEY: VARIANT
<222> LOCATION: (110)..(110)
<223> OTHER INFORMATION: Xaa at position 110 is Arg, Leu, Lys, Ile, Val,
      or Met
<220> FEATURE:
<221> NAME/KEY: VARIANT
<222> LOCATION: (120)..(120)
<223> OTHER INFORMATION: Xaa at position 120 is Lys, Arg, Gln or Asn
<220> FEATURE:
<221> NAME/KEY: VARIANT
<222> LOCATION: (121)..(121)
<223> OTHER INFORMATION: Xaa at position 121 is Thr, or Ser
<220> FEATURE:
<221> NAME/KEY: VARIANT
<222> LOCATION: (123)..(123)
<223> OTHER INFORMATION: Xaa at position 123 is Thr, Glu, Ser, or Asp
<220> FEATURE:
<221> NAME/KEY: VARIANT
<222> LOCATION: (125)..(125)
<223> OTHER INFORMATION: Xaa at position 125 is Asn, Ser, Gln, or Thr
<220> FEATURE:
<221> NAME/KEY: VARIANT
```

```
-continued

<222> LOCATION: (127)..(127)
<223> OTHER INFORMATION: Xaa at position 127 is Ser, Asn, Thr, Gln, Lys,
      Ser or Arg
<220> FEATURE:
<221> NAME/KEY: VARIANT
<222> LOCATION: (134)..(134)
<223> OTHER INFORMATION: Xaa at position 134 is Gly, or Ala
<220> FEATURE:
<221> NAME/KEY: VARIANT
<222> LOCATION: (135)..(135)
<223> OTHER INFORMATION: Xaa at position 135 is Ser, Asn, Thr, Gln, Arg
      or Lys
<220> FEATURE:
<221> NAME/KEY: VARIANT
<222> LOCATION: (137)..(137)
<223> OTHER INFORMATION: Xaa at position 137 is Asp, or Gly
<220> FEATURE:
<221> NAME/KEY: VARIANT
<222> LOCATION: (141)..(141)
<223> OTHER INFORMATION: Xaa at position 141 is Val, Ile or Leu
<220> FEATURE:
<221> NAME/KEY: VARIANT
<222> LOCATION: (142)..(142)
<223> OTHER INFORMATION: Xaa at position 142 is Gly, Asp, Ala or Glu
<220> FEATURE:
<221> NAME/KEY: VARIANT
<222> LOCATION: (144)..(144)
<223> OTHER INFORMATION: Xaa at position 144 is Asp, or Glu
<220> FEATURE:
<221> NAME/KEY: VARIANT
<222> LOCATION: (147)..(147)
<223> OTHER INFORMATION: Xaa at position 147 is Ile, Thr, Val, Leu, Met,
      or Ser
<220> FEATURE:
<221> NAME/KEY: VARIANT
<222> LOCATION: (150)..(150)
<223> OTHER INFORMATION: Xaa at position 150 is Ser, or Thr
<220> FEATURE:
<221> NAME/KEY: VARIANT
<222> LOCATION: (151)..(151)
<223> OTHER INFORMATION: Xaa at position 151 is Asn, Arg, Ser, Gln, Lys,
      or Thr
<220> FEATURE:
<221> NAME/KEY: VARIANT
<222> LOCATION: (160)..(160)
<223> OTHER INFORMATION: Xaa at position 160 is Thr, or Ser
<220> FEATURE:
<221> NAME/KEY: VARIANT
<222> LOCATION: (162)..(162)
<223> OTHER INFORMATION: Xaa at position 162 is Ser, or Thr
<220> FEATURE:
<221> NAME/KEY: VARIANT
<222> LOCATION: (163)..(163)
<223> OTHER INFORMATION: Xaa at position 163 is Asn, Asp, Glu, or Gln
<220> FEATURE:
<221> NAME/KEY: VARIANT
<222> LOCATION: (164)..(164)
<223> OTHER INFORMATION: Xaa at position 164 is Ser, or Thr
<220> FEATURE:
<221> NAME/KEY: VARIANT
<222> LOCATION: (166)..(166)
<223> OTHER INFORMATION: Xaa at position 166 is Gln, Glu, Asp, or Asn
<220> FEATURE:
<221> NAME/KEY: VARIANT
<222> LOCATION: (167)..(167)
<223> OTHER INFORMATION: Xaa at position 167 is Leu, Met, Ile, Val
<220> FEATURE:
<221> NAME/KEY: VARIANT
<222> LOCATION: (168)..(168)
<223> OTHER INFORMATION: Xaa at position 168 is Thr, Lys, Ala, Ser, Arg,
      or Gly
<220> FEATURE:
<221> NAME/KEY: VARIANT
<222> LOCATION: (171)..(171)
<223> OTHER INFORMATION: Xaa at position 171 is Gly, Leu, Gln, Met, Cys,
      Asn, Asp, Ser or Ala
<220> FEATURE:
<221> NAME/KEY: VARIANT
<222> LOCATION: (172)..(172)
```

```
<223> OTHER INFORMATION: Xaa at position 172 is Thr, Gly, His, Phe, Glu,
      Arg, Ser, Asn, Ile, Trp, Lys, Gln, Cys, Val, Ala or Met
<220> FEATURE:
<221> NAME/KEY: VARIANT
<222> LOCATION: (173)..(173)
<223> OTHER INFORMATION: Xaa at position 173 is Phe, Gly, His, Leu, Ala,
      Arg, Asn, Cys, Lys, Trp, Thr, Ser, Tyr, or Met
<220> FEATURE:
<221> NAME/KEY: VARIANT
<222> LOCATION: (174)..(174)
<223> OTHER INFORMATION: Xaa at position 174 is Ile, Val, Gly, Arg, Asn,
      Ala, Gln, Met, Cys, Leu, Phe, Tyr, Lys, Glu, Ser, His, or Thr
<220> FEATURE:
<221> NAME/KEY: VARIANT
<222> LOCATION: (175)..(175)
<223> OTHER INFORMATION: Xaa at position 175 is Val, Ile, Ala, Cys, Glu,
      Lys, Leu or Met
<220> FEATURE:
<221> NAME/KEY: VARIANT
<222> LOCATION: (176)..(176)
<223> OTHER INFORMATION: Xaa at position 176 is Tyr, Met, Phe, Leu, or
      Cys
<220> FEATURE:
<221> NAME/KEY: VARIANT
<222> LOCATION: (177)..(177)
<223> OTHER INFORMATION: Xaa at position 177 is Gln, Ile, Met, or Pro
<220> FEATURE:
<221> NAME/KEY: VARIANT
<222> LOCATION: (178)..(178)
<223> OTHER INFORMATION: Xaa at position 178 is Val, Cys, Thr, Pro, Ala,
      Met, Gln, Phe, Ile, Ser or Lys
<220> FEATURE:
<221> NAME/KEY: VARIANT
<222> LOCATION: (179)..(179)
<223> OTHER INFORMATION: Xaa at position 179 is Val, Phe, Thr, Ile, Cys,
      Leu, Met, Ser, Ala, or Gln
<220> FEATURE:
<221> NAME/KEY: VARIANT
<222> LOCATION: (180)..(180)
<223> OTHER INFORMATION: Xaa at position 180 is Met, Leu, Pro, Trp, Asn,
      Tyr, Gly, Gln, Ala, Val, Phe, Ile, Cys, or Ser
<220> FEATURE:
<221> NAME/KEY: VARIANT
<222> LOCATION: (181)..(181)
<223> OTHER INFORMATION: Xaa at position 181 is Val, Ala, Leu, Trp, Cys,
      Thr, Ile or Lys
<220> FEATURE:
<221> NAME/KEY: VARIANT
<222> LOCATION: (182)..(182)
<223> OTHER INFORMATION: Xaa at position 182 is Tyr, Phe, Met, or His
<220> FEATURE:
<221> NAME/KEY: VARIANT
<222> LOCATION: (183)..(183)
<223> OTHER INFORMATION: Xaa at position 183 is Ala, Met, Val, Thr, Asp,
      Gly, Cys, Ile, Phe, Ser, Gln, or Leu
<220> FEATURE:
<221> NAME/KEY: VARIANT
<222> LOCATION: (191)..(191)
<223> OTHER INFORMATION: Xaa at position 191 is Arg or Lys
<220> FEATURE:
<221> NAME/KEY: VARIANT
<222> LOCATION: (194)..(194)
<223> OTHER INFORMATION: Xaa at position 194 is Gly, or Ala
<220> FEATURE:
<221> NAME/KEY: VARIANT
<222> LOCATION: (195)..(195)
<223> OTHER INFORMATION: Xaa at position 195 is Asn, Tyr, Gln, or Trp
<220> FEATURE:
<221> NAME/KEY: VARIANT
<222> LOCATION: (200)..(200)
<223> OTHER INFORMATION: Xaa at position 200 is Asn, Ser, Thr, or Gln
<220> FEATURE:
<221> NAME/KEY: VARIANT
<222> LOCATION: (203)..(203)
<223> OTHER INFORMATION: Xaa at position 203 is Asn, or Gln
<220> FEATURE:
<221> NAME/KEY: VARIANT
<222> LOCATION: (204)..(204)
<223> OTHER INFORMATION: Xaa at position 204 is Thr, Ala, Ser, or Gly
```

```
<220> FEATURE:
<221> NAME/KEY: VARIANT
<222> LOCATION: (206)..(206)
<223> OTHER INFORMATION: Xaa at position 206 is Gly, Asp, Ala or Glu
<220> FEATURE:
<221> NAME/KEY: VARIANT
<222> LOCATION: (209)..(209)
<223> OTHER INFORMATION: Xaa at position 209 is Leu, Val, Ile, or Met
<220> FEATURE:
<221> NAME/KEY: VARIANT
<222> LOCATION: (213)..(213)
<223> OTHER INFORMATION: Xaa at position 213 is Tyr, or Phe
<220> FEATURE:
<221> NAME/KEY: VARIANT
<222> LOCATION: (220)..(220)
<223> OTHER INFORMATION: Xaa at position 220 is Asn, Arg, Gln, or Lys
<220> FEATURE:
<221> NAME/KEY: VARIANT
<222> LOCATION: (221)..(221)
<223> OTHER INFORMATION: Xaa at position 221 is Ser, Lys, Thr, or Arg
<220> FEATURE:
<221> NAME/KEY: VARIANT
<222> LOCATION: (222)..(222)
<223> OTHER INFORMATION: Xaa at position 222 is Thr, Arg, Ser, or Lys
<220> FEATURE:
<221> NAME/KEY: VARIANT
<222> LOCATION: (226)..(226)
<223> OTHER INFORMATION: Xaa at position 226 is Asp, Pro, Glu or Gln
<220> FEATURE:
<221> NAME/KEY: VARIANT
<222> LOCATION: (228)..(228)
<223> OTHER INFORMATION: Xaa at position 228 is Ser or Gly
<220> FEATURE:
<221> NAME/KEY: VARIANT
<222> LOCATION: (229)..(229)
<223> OTHER INFORMATION: Xaa at position 229 is Lys, Asn, Arg, or Gln
<220> FEATURE:
<221> NAME/KEY: VARIANT
<222> LOCATION: (231)..(231)
<223> OTHER INFORMATION: Xaa at position 231 is Ile, Val, Leu, or Met
<220> FEATURE:
<221> NAME/KEY: VARIANT
<222> LOCATION: (232)..(232)
<223> OTHER INFORMATION: Xaa at position 232 is Ala, Thr, Ser, Gly, Asp
      or Glu
<220> FEATURE:
<221> NAME/KEY: VARIANT
<222> LOCATION: (240)..(240)
<223> OTHER INFORMATION: Xaa at position 240 is Gln, Arg, Ala, Val, Glu,
      Met, Gly, Asp, Trp, Asn, Thr, Ile, Ser, Phe, His, Cys, or Leu
<220> FEATURE:
<221> NAME/KEY: VARIANT
<222> LOCATION: (241)..(241)
<223> OTHER INFORMATION: Xaa at position 241 is Arg, Lys, Glu, Gln, Ser,
      Ile, Val, Asp, Tyr, Met, Asn, His, Pro, Gly, Leu, Phe, Thr, Ala,
      or Cys
<220> FEATURE:
<221> NAME/KEY: VARIANT
<222> LOCATION: (242)..(242)
<223> OTHER INFORMATION: Xaa at position 242 is Asn, Ala, Arg, Lys, His,
      Ser, Cys, Glu, Pro, Trp, Gln, Thr, Phe, Tyr, Met, Asp, Gly, Leu,
      or Val
<220> FEATURE:
<221> NAME/KEY: VARIANT
<222> LOCATION: (243)..(243)
<223> OTHER INFORMATION: Xaa at position 243 is Val, Leu, Ala, Thr, Gly,
      Cys, Ile, Ser, or Met
<220> FEATURE:
<221> NAME/KEY: VARIANT
<222> LOCATION: (244)..(244)
<223> OTHER INFORMATION: Xaa at position 244 is Leu, Val, Phe, Ile, Met,
      Gln, Cys, Trp or Ala
<220> FEATURE:
<221> NAME/KEY: VARIANT
<222> LOCATION: (245)..(245)
<223> OTHER INFORMATION: Xaa at position 245 is Met, Ala, Arg, Asp, Glu,
      Leu, Pro, Ser, Trp, Gly, Val, Lys, Phe, Cys, Thr, His, Ile, Gln,
      Tyr, or Asn
<220> FEATURE:
```

```
<221> NAME/KEY: VARIANT
<222> LOCATION: (246)..(246)
<223> OTHER INFORMATION: Xaa at position 246 is Glu, Asp, Tyr, Gly, Arg,
      Val, Ala, Trp, Gln, Ser, Asn, Ile Leu, Met, Cys, Pro, His, Phe,
      Thr, or Lys
<220> FEATURE:
<221> NAME/KEY: VARIANT
<222> LOCATION: (247)..(247)
<223> OTHER INFORMATION: Xaa at position 247 is Asn, Leu, Asp, Tyr, Ala,
      Phe, His, Arg, Lys, Gln, Gly, Val, Ile, Ser, Glu, Pro, Met, Trp,
      Thr, or Cys
<220> FEATURE:
<221> NAME/KEY: VARIANT
<222> LOCATION: (248)..(248)
<223> OTHER INFORMATION: Xaa at position 248 is Tyr, Val, Thr, Glu, Phe,
      Ser, His, Cys, Leu, Trp, Ile, Asp, Gly, or Ala
<220> FEATURE:
<221> NAME/KEY: VARIANT
<222> LOCATION: (249)..(249)
<223> OTHER INFORMATION: Xaa at position 249 is Asn, Lys, Val, Gly, Met,
      Asp, Cys, Phe, Arg, Glu, Trp, Tyr, Ser, Ile, Thr, Pro, Leu, Ala,
      His or Gln
<220> FEATURE:
<221> NAME/KEY: VARIANT
<222> LOCATION: (251)..(251)
<223> OTHER INFORMATION: Xaa at position 251 is Gly, Ser, Thr,  Ala, Asp
      or Glu
<220> FEATURE:
<221> NAME/KEY: VARIANT
<222> LOCATION: (254)..(254)
<223> OTHER INFORMATION: Xaa at position 254 is Ser, Asn, Thr or Gln
<220> FEATURE:
<221> NAME/KEY: VARIANT
<222> LOCATION: (258)..(258)
<223> OTHER INFORMATION: Xaa at position 258 is Ser, Arg, Thr or Lys
<220> FEATURE:
<221> NAME/KEY: VARIANT
<222> LOCATION: (259)..(259)
<223> OTHER INFORMATION: Xaa at position 259 is Phe, Trp, Tyr, Cys, Met,
      Leu, Val, Ile, or His
<220> FEATURE:
<221> NAME/KEY: VARIANT
<222> LOCATION: (265)..(265)
<223> OTHER INFORMATION: Xaa at position 265 is Asn, Asp, Gln or Glu
<220> FEATURE:
<221> NAME/KEY: VARIANT
<222> LOCATION: (266)..(266)
<223> OTHER INFORMATION: Xaa at position 266 is Asp, Asn, Gln or Glu

<400> SEQUENCE: 213

Met Xaa Xaa Lys Glu Xaa Leu Xaa Gln Pro Gln Ser His Ser Ile Glu
1               5                   10                  15

Leu Asp Xaa Xaa Xaa Ser Glu Xaa Xaa Xaa Xaa Xaa Ala Xaa Leu Thr
            20                  25                  30

Ser Asn Xaa Xaa Gly Xaa Phe Asp Gln Xaa Xaa Thr Lys Xaa Gly Xaa
        35                  40                  45

Xaa Ala Ile Asp Xaa Tyr Leu Leu Asp Xaa Ser Xaa Pro Lys Xaa Gly
    50                  55                  60

Cys Xaa Val Asp Gly Ile Thr Val Tyr Gly Asp Ile Xaa Ile Gly Lys
65                  70                  75                  80

Gln Asn Trp Gly Thr Tyr Thr Arg Xaa Val Phe Ala Xaa Leu Gln Tyr
                85                  90                  95

Xaa Xaa Thr Ile Ser Ile Pro Gln Xaa Val Xaa Xaa Thr Xaa Ser Tyr
            100                 105                 110

Gln Leu Thr Lys Gly His Thr Xaa Xaa Phe Xaa Thr Xaa Val Xaa Ala
        115                 120                 125

Lys Tyr Ser Val Gly Xaa Xaa Ile Xaa Ile Val Asn Xaa Xaa Ser Xaa
    130                 135                 140

Ile Ser Xaa Gly Phe Xaa Xaa Ser Glu Ser Trp Ser Thr Thr Gln Xaa
```

```
145                 150                 155                 160
Phe Xaa Xaa Thr Xaa Xaa Xaa Gly Pro Xaa Xaa Xaa Xaa Xaa
                165                 170                 175

Xaa Xaa Xaa Xaa Xaa Xaa Xaa His Asn Ala Thr Ser Ala Gly Xaa Gln
            180                 185                 190

Asn Xaa Xaa Ala Phe Ala Tyr Xaa Lys Thr Xaa Xaa Val Xaa Ser Arg
        195                 200                 205

Xaa Asp Leu Tyr Xaa Leu Ser Ala Ile Thr Gln Xaa Xaa Xaa Val Ile
    210                 215                 220

Val Xaa Ser Xaa Xaa Ala Xaa Xaa Pro Leu Asp Trp Asp Thr Val Xaa
225                 230                 235                 240

Xaa Xaa Xaa Xaa Xaa Xaa Xaa Xaa Pro Xaa Ser Asn Xaa Gly His
                245                 250                 255

Phe Xaa Xaa Asp Trp Ser Ala Tyr Xaa Xaa Pro His Arg Arg Tyr
        260                 265                 270

<210> SEQ ID NO 214
<211> LENGTH: 175
<212> TYPE: PRT
<213> ORGANISM: Pseudomonas chlororaphis

<400> SEQUENCE: 214

Met Asp Thr Ile Ser Ile Pro Gln Gln Val Thr Gln Thr Arg Ser Tyr
1               5                   10                  15

Gln Leu Thr Lys Gly His Thr Lys Thr Phe Thr Thr Asn Val Ser Ala
            20                  25                  30

Lys Tyr Ser Val Gly Gly Ser Ile Asp Ile Val Asn Val Gly Ser Asp
        35                  40                  45

Ile Ser Ile Gly Phe Ser Asn Ser Glu Ser Trp Ser Thr Thr Gln Thr
    50                  55                  60

Phe Ser Asn Ser Thr Gln Leu Thr Gly Pro Gly Thr Phe Ile Val Tyr
65                  70                  75                  80

Gln Val Val Met Val Tyr Ala His Asn Ala Thr Ser Ala Gly Arg Gln
                85                  90                  95

Asn Gly Asn Ala Phe Ala Tyr Asn Lys Thr Asn Thr Val Gly Ser Arg
            100                 105                 110

Leu Asp Leu Tyr Tyr Leu Ser Ala Ile Thr Gln Asn Ser Thr Val Ile
        115                 120                 125

Val Asp Ser Ser Lys Ala Ile Ala Pro Leu Asp Trp Asp Thr Val Gln
    130                 135                 140

Arg Asn Val Leu Met Glu Asn Tyr Asn Pro Gly Ser Asn Ser Gly His
145                 150                 155                 160

Phe Ser Phe Asp Trp Ser Ala Tyr Asn Asp Pro His Arg Arg Tyr
                165                 170                 175

<210> SEQ ID NO 215
<211> LENGTH: 528
<212> TYPE: DNA
<213> ORGANISM: Pseudomonas chlororaphis

<400> SEQUENCE: 215
atggacacca tttccattcc gcagcaggtg acacagactc gcagctatca gttgactaag    60
ggacacacca aaacgttcac gaccaatgtc agcgccaaat acagcgttgg aggtagtatt   120
gacatcgtca acgtcggttc ggatatctca attggattca gtaacagtga atcctggtct   180
actacgcaga cgttcagcaa tagcactcaa ttgactggtc ctggcacctt catcgtgtat   240
```

| caggttgtta | tggtttatgc | gcacaacgcc | acttctgcgg | gcaggcagaa | tggtaatgcc | 300 |
| ttcgcctaca | acaagaccaa | tactgtcggc | tcgcggctgg | acttgtacta | tttgtctgcc | 360 |
| atcactcaga | acagtacggt | cattgtcgat | tccagcaagg | ccatcgcgcc | gctggattgg | 420 |
| gatactgttc | agcgcaatgt | gttgatggag | aactacaacc | caggcagcaa | tagtgggcac | 480 |
| ttcagtttcg | actggagcgc | ctacaacgat | cctcatcgcc | gttattga | | 528 |

<210> SEQ ID NO 216
<211> LENGTH: 1700
<212> TYPE: DNA
<213> ORGANISM: Pseudomonas chlororaphis

<400> SEQUENCE: 216

| aaacccaaag | atgtttgaac | tgaagagttt | gatcatggct | cagattgaac | gctggcggca | 60 |
| ggcctaacac | atgcaagtcg | agcggtagag | agaagcttgc | ttctcttgag | agcggcggac | 120 |
| gggtgagtaa | tgcctaggaa | tctgcctggt | agtgggggat | aacgtccgga | aacgacgct | 180 |
| aataccgcat | acgtcctacg | ggagaaagca | ggggaccttc | gggccttgcg | ctatcagatg | 240 |
| agcctaggtc | ggattagcta | gttggtgagg | taatggctca | ccaaggcgac | gatccgtaac | 300 |
| tggtctgaga | ggatgatcag | tcacactgga | actgagacac | ggtccagact | cctacgggag | 360 |
| gcagcagtgg | ggaatattgg | acaatgggcg | aaagcctgat | ccagccatgc | cgcgtgtgtg | 420 |
| aagaaggtct | tcggattgta | aagcacttta | agttgggagg | aagggtactt | acctaatacg | 480 |
| tgagtatttt | gacgttaccg | acagaataag | caccggctaa | ctctgtgcca | gcagccgcgg | 540 |
| taatacagag | ggtgcaagcg | ttaatcggaa | ttactgggcg | taaagcgcgc | gtaggtggtt | 600 |
| cgttaagttg | gatgtgaaat | ccccgggctc | aacctgggaa | ctgcatccaa | aactggcgag | 660 |
| ctagagtatg | gtagagggtg | gtggaatttc | ctgtgtagcg | gtgaaatgcg | tagatatagg | 720 |
| aaggaacacc | agtggcgaag | gcgaccacct | ggactgatac | tgacactgag | gtgcgaaagc | 780 |
| gtggggagca | aacaggatta | gataccctgg | tagtccacgc | cgtaaacgat | gtcaactagc | 840 |
| cgttgggagc | cttgagctct | tagtggcgca | gctaacgcat | taagttgacc | gcctggggag | 900 |
| tacggccgca | aggttaaaac | tcaaatgaat | tgacggggggc | ccgcacaagc | ggtggagcat | 960 |
| gtggtttaat | tcgaagcaac | gcgaagaacc | ttaccaggcc | ttgacatcca | atgaactttc | 1020 |
| cagagatgga | ttggtgcctt | cgggaacatt | gagacaggtg | ctgcatggct | gtcgtcagct | 1080 |
| cgtgtcgtga | gatgttgggt | taagtcccgt | aacgagcgca | acccttgtcc | ttagttacca | 1140 |
| gcacgttatg | gtgggcactc | taaggagact | gccggtgaca | aaccggagga | aggtggggat | 1200 |
| gacgtcaagt | catcatggcc | cttacggcct | gggctacaca | cgtgctacaa | tggtcggtac | 1260 |
| agagggttgc | caagccgcga | ggtggagcta | atcccataaa | accgatcgta | gtccggatcg | 1320 |
| cagtctgcaa | ctcgactgcg | tgaagtcgga | atcgctagta | atcgcgaatc | agaatgtcgc | 1380 |
| ggtgaatacg | ttcccgggcc | ttgtacacac | cgcccgtcac | accatgggag | tgggttgcac | 1440 |
| cagaagtagc | tagtctaacc | ttcgggagga | cggttaccac | ggtgtgattc | atgactgggg | 1500 |
| tgaagtcgta | acaaggtagc | cgtagggaa | cctgcggctg | gatcacctcc | ttaatcgacg | 1560 |
| acatcagctg | cttcataagc | tcccacacga | attgcttgat | tcattgaaga | agacgattgg | 1620 |
| gtctgtagct | cagttggtta | gagcgcaccc | ctgataaggg | tgaggtcggc | agttcgaatc | 1680 |
| tgcccagacc | caccaattac | | | | | 1700 |

<210> SEQ ID NO 217

```
<211> LENGTH: 1515
<212> TYPE: DNA
<213> ORGANISM: Pseudomonas entomophila

<400> SEQUENCE: 217
gctcagattg aacgctggcg gcaggcctaa cacatgcaag tcgagcggat gacgggagct      60
tgctccttga ttcagcggcg gacgggtgag taatgcctag gaatctgcct ggtagtgggg     120
gacaacgttt cgaaaggaac gctaataccg catacgtcct acgggagaaa gcaggggacc     180
ttcgggcctt gcgctatcar atgagcctag gtcggattag ctagttggkg gggtaatggc     240
tcaccaaggc gacgatccgt aactggtytg agaggatgat cagtcacact ggaactgaga     300
cacggtccag actcctacgg gaggcagcag tggggaatat tggacaatgg gcgaaagcct     360
gatccagcca tgccgcgtgt gtgaaraagg tcttcggatt gtaaagcact ttaagttggg     420
aggaagggca gtaagttaat accttgctgt tttgacgtta ccgacagaat aagcaccggc     480
taactctgtg ccagcagccg cggtaataca gagggtgcaa gcgttaatcg gaattactgg     540
gcgtaaagcg cgcgtaggtg gttcgttaag ttggatgtga aagcccgggg ctcaacctgg     600
gaactgcatc caaaactggc gagctagagt atggtagagg gtggtggaat ttcctgtgta     660
gcggtgaaat gcgtagatat aggaaggaac accagtggcg aaggcgacca cctggactga     720
tactgacact gaggtgcgaa agcgtgggga gcaaacagga ttagataccc tggtagtcca     780
cgccgtaaac gatgtcaact agccgttgga atccttgaga ttttagtggc gcagctaacg     840
cattaagttg accgcctggg gagtacggcc gcaaggttaa aactcaaatg aattgacggg     900
ggcccgcaca agcggtggag catgtggttt aattcgaagc aacgcgaaga accttaccag     960
gccttgacat gcagagaact ttccagagat ggattggtgc cttcgggaac tctgacacag    1020
gtgctgcatg gctgtcgtca gctcgtgtcg tgagatgttg ggttaagtcc cgtaacgagc    1080
gcaaccctttg tccttagtta ccagcacgtt atggtgggca ctctaaggag actgccggtg    1140
acaaaccgga ggaaggtggg gatgacgtca agtcatcatg gcccttacgg cctgggctac    1200
acacgtgcta caatggtcgg tacagagggt tgccaagccg cgaggtggag ctaatctcac    1260
aaaaccgatc gtagtccgga tcgcagtctg caactcgact gcgtgaagtc ggaatcgcta    1320
gtaatcgcaa atcagaatgt tgcggtgaat acgttcccgg gccttgtaca caccgcccgt    1380
cacaccatgg gagtgggttg caccagaagt agctagtcta accttcgggg ggacggttac    1440
cacggtgtga ttcatgactg gggtgaagtc gtaacaaggt agccgtaggg gaacctgcgg    1500
ctggatcacc tcctt                                                    1515

<210> SEQ ID NO 218
<211> LENGTH: 24
<212> TYPE: DNA
<213> ORGANISM: Artificial Sequence
<220> FEATURE:
<223> OTHER INFORMATION: mutagenesis primer

<400> SEQUENCE: 218
gagacttcct tgctcacttt tcag                                            24

<210> SEQ ID NO 219
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
```

```
<222> LOCATION: (25)..(26)
<223> OTHER INFORMATION: n is a, c, g, or t
<220> FEATURE:
<221> NAME/KEY: misc_feature
<222> LOCATION: (27)..(27)
<223> OTHER INFORMATION: k is g or t

<400> SEQUENCE: 219
ctgaaaagtg agcaaggaag tctcnnkgcc gctttgacat ccaac          45

<210> SEQ ID NO 220
<211> LENGTH: 813
<212> TYPE: DNA
<213> ORGANISM: Artificial Sequence
<220> FEATURE:
<223> OTHER INFORMATION: PIP-1A variant

<400> SEQUENCE: 220
atgacgatca aggaagagct gagccagcct caaagtcatt cgatcgaact tgacgacctg     60
aaaagtgagc aaggaagtct ccgcgccgct tgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttaat    720
agctatgttt tgttggatta ctattatcca ggcagcaata gtgggcactt cagtttcgac    780
tggagcgcct acaacgatcc tcatcgccgt tat                                 813

<210> SEQ ID NO 221
<211> LENGTH: 813
<212> TYPE: DNA
<213> ORGANISM: Artificial Sequence
<220> FEATURE:
<223> OTHER INFORMATION: PIP-1A variant

<400> SEQUENCE: 221
atgacgatca aggaagagct gagccagcct caaagtcatt cgatcgaact tgacgacctg     60
aaaagtgagc aaggaagtct ccgcgccgct tgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
```

```
aagaccaata ctgtcggctc gcggctggac ttgtactatt tgtctgccat cactcagaac    660
agtacggtca ttgtcgattc cagcaaggcc atcgcgccgc tggattggga tactgttaat    720
tgctatattt ttatggagta ttatgaccca ggcagcaata gtgggcactt cagtttcgac    780
tggagcgcct acaacgatcc tcatcgccgt tat                                 813
```

<210> SEQ ID NO 222
<211> LENGTH: 813
<212> TYPE: DNA
<213> ORGANISM: Artificial Sequence
<220> FEATURE:
<223> OTHER INFORMATION: PIP-1A variant

<400> SEQUENCE: 222

```
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt gactaaggg acacaccaaa    360 acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttaat    720
tgctatatta tgatggagaa ttttgaccca ggcagcaata gtgggcactt cagtttcgac    780
tggagcgcct acaacgatcc tcatcgccgt tat                                 813
```

<210> SEQ ID NO 223
<211> LENGTH: 813
<212> TYPE: DNA
<213> ORGANISM: Artificial Sequence
<220> FEATURE:
<223> OTHER INFORMATION: PIP-1A variant

<400> SEQUENCE: 223

```
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt gactaaggg acacaccaaa    360 acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttcaa    720
```

```
tgcaacgttt tgtttgataa ttttcatcca ggcagcaata gtgggcactt cagtttcgac    780
tggagcgcct acaacgatcc tcatcgccgt tat                                 813

<210> SEQ ID NO 224
<211> LENGTH: 813
<212> TYPE: DNA
<213> ORGANISM: Artificial Sequence
<220> FEATURE:
<223> OTHER INFORMATION: PIP-1A variant

<400> SEQUENCE: 224
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttcaa    720
ggctacgttt tggttgataa cttttaatcca ggcagcaata gtgggcactt cagtttcgac    780
tggagcgcct acaacgatcc tcatcgccgt tat                                 813

<210> SEQ ID NO 225
<211> LENGTH: 813
<212> TYPE: DNA
<213> ORGANISM: Artificial Sequence
<220> FEATURE:
<223> OTHER INFORMATION: PIP-1A variant

<400> SEQUENCE: 225
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttaat    720
cgctatgttt tttttggtaa ctatgaccca ggcagcaata gtgggcactt cagtttcgac    780
```

<210> SEQ ID NO 226
<211> LENGTH: 813
<212> TYPE: DNA
<213> ORGANISM: Artificial Sequence
<220> FEATURE:
<223> OTHER INFORMATION: PIP-1A variant

<400> SEQUENCE: 226

```
atgacgatca aggaagagct gagccagcct caaagtcatt cgatcgaact tgacgacctg      60
aaaagtgagc aaggaagtct ccgcgccgct ttgacatcca actttgctgg caacttcgat     120
cagttcccaa ctaagcgtgg tggctttgcg atcgacagct acctgctgga ttacagcgcg     180
cccaagcaag gctgctgggt agatggcatt accgtctacg gtgacatctt tatcggcaag     240
cagaattggg gcacctacac tcgcccggtc tttgcctacc tgcagtacat ggacaccatt     300
tccattccgc agcaggtgac acagactcgc agctatcagt tgactaaggg acacaccaaa     360
acgttcacga ccaatgtcag cgccaaatac agcgttggag gtagtattga catcgtcaac     420
gtcggttcgg atatctcaat tggattcagt aacagtgaat cctggtctac tacgcagacg     480
ttcagcaata gcactcaatt gactggtcct ggcaccttca tcgtgtatca ggttgttatg     540
gtttatgcgc acaacgccac ttctgcgggc aggcagaatg gtaatgcctt cgcctacaac     600
aagaccaata ctgtcggctc gcggctggac ttgtactatt tgtctgccat cactcagaac     660
agtacggtca ttgtcgattc cagcaaggcc atcgcgccgc tggattggga tactgttcaa     720
tgcaatatta tgattgggta ctttgatcca ggcagcaata gtgggcactt cagtttcgac     780
tggagcgcct acaacgatcc tcatcgccgt tat                                  813
```

<210> SEQ ID NO 227
<211> LENGTH: 813
<212> TYPE: DNA
<213> ORGANISM: Artificial Sequence
<220> FEATURE:
<223> OTHER INFORMATION: PIP-1A variant

<400> SEQUENCE: 227

```
atgacgatca aggaagagct gagccagcct caaagtcatt cgatcgaact tgacgacctg      60
aaaagtgagc aaggaagtct ccgcgccgct ttgacatcca actttgctgg caacttcgat     120
cagttcccaa ctaagcgtgg tggctttgcg atcgacagct acctgctgga ttacagcgcg     180
cccaagcaag gctgctgggt agatggcatt accgtctacg gtgacatctt tatcggcaag     240
cagaattggg gcacctacac tcgcccggtc tttgcctacc tgcagtacat ggacaccatt     300
tccattccgc agcaggtgac acagactcgc agctatcagt tgactaaggg acacaccaaa     360
acgttcacga ccaatgtcag cgccaaatac agcgttggag gtagtattga catcgtcaac     420
gtcggttcgg atatctcaat tggattcagt aacagtgaat cctggtctac tacgcagacg     480
ttcagcaata gcactcaatt gactggtcct ggcaccttca tcgtgtatca ggttgttatg     540
gtttatgcgc acaacgccac ttctgcgggc aggcagaatg gtaatgcctt cgcctacaac     600
aagaccaata ctgtcggctc gcggctggac ttgtactatt tgtctgccat cactcagaac     660
agtacggtca ttgtcgattc cagcaaggcc atcgcgccgc tggattggga tactgttcag     720
ggcaatgtgt tgatggagaa ctacaaccca ggcagcaata gtgggcactt cagtttcgac     780
tggagcgcct acaacgatcc tcatcgccgt tat                                  813
```

<210> SEQ ID NO 228
<211> LENGTH: 813
<212> TYPE: DNA
<213> ORGANISM: Artificial Sequence
<220> FEATURE:
<223> OTHER INFORMATION: PIP-1A variant

<400> SEQUENCE: 228

```
atgacgatca aggaagagct gagccagcct caaagtcatt cgatcgaact tgacgacctg      60
aaaagtgagc aaggaagtct ccgcgccgct ttgacatcca actttgctgg caacttcgat     120
cagttcccaa ctaagcgtgg tggctttgcg atcgacagct acctgctgga ttacagcgcg     180
cccaagcaag gctgctgggt agatggcatt accgtctacg gtgacatctt tatcggcaag     240
cagaattggg gcacctacac tcgcccggtc tttgcctacc tgcagtacat ggacaccatt     300
tccattccgc agcaggtgac acagactcgc agctatcagt tgactaaggg acacaccaaa     360
acgttcacga ccaatgtcag cgccaaatac agcgttggag gtagtattga catcgtcaac     420
gtcggttcgg atatctcaat tggattcagt aacagtgaat cctggtctac tacgcagacg     480
ttcagcaata gcactcaatt gactggtcct ggcaccttca tcgtgtatca ggttgttatg     540
gtttatgcgc acaacgccac ttctgcgggc aggcagaatg gtaatgcctt cgcctacaac     600
aagaccaata ctgtcggctc gcggctggac ttgtactatt tgtctgccat cactcagaac     660
agtacggtca ttgtcgattc cagcaaggcc atcgcgccgc tggattggga tactgttgta     720
agcaatattt tggtgggtaa ttttaatcca ggcagcaata gtgggcactt cagtttcgac     780
tggagcgcct acaacgatcc tcatcgccgt tat                                  813
```

<210> SEQ ID NO 229
<211> LENGTH: 813
<212> TYPE: DNA
<213> ORGANISM: Artificial Sequence
<220> FEATURE:
<223> OTHER INFORMATION: PIP-1A variant

<400> SEQUENCE: 229

```
atgacgatca aggaagagct gagccagcct caaagtcatt cgatcgaact tgacgacctg      60
aaaagtgagc aaggaagtct ccgcgccgct ttgacatcca actttgctgg caacttcgat     120
cagttcccaa ctaagcgtgg tggctttgcg atcgacagct acctgctgga ttacagcgcg     180
cccaagcaag gctgctgggt agatggcatt accgtctacg gtgacatctt tatcggcaag     240
cagaattggg gcacctacac tcgcccggtc tttgcctacc tgcagtacat ggacaccatt     300
tccattccgc agcaggtgac acagactcgc agctatcagt tgactaaggg acacaccaaa     360
acgttcacga ccaatgtcag cgccaaatac agcgttggag gtagtattga catcgtcaac     420
gtcggttcgg atatctcaat tggattcagt aacagtgaat cctggtctac tacgcagacg     480
ttcagcaata gcactcaatt gactggtcct ggcaccttca tcgtgtatca ggttgttatg     540
gtttatgcgc acaacgccac ttctgcgggc aggcagaatg gtaatgcctt cgcctacaac     600
aagaccaata ctgtcggctc gcggctggac ttgtactatt tgtctgccat cactcagaac     660
agtacggtca ttgtcgattc cagcaaggcc atcgcgccgc tggattggga tactgttaat     720
cgccatgttt ggttgataa cttttatcca ggcagcaata gtgggcactt cagtttcgac     780
tggagcgcct acaacgatcc tcatcgccgt tat                                  813
```

<210> SEQ ID NO 230
<211> LENGTH: 813
<212> TYPE: DNA

<213> ORGANISM: Artificial Sequence
<220> FEATURE:
<223> OTHER INFORMATION: PIP-1A variant

<400> SEQUENCE: 230

| | | | | | |
|---|---|---|---|---|---|
| atgacgatca | aggaagagct | gagccagcct | caaagtcatt | cgatcgaact | tgacgacctg | 60 |
| aaaagtgagc | aaggaagtct | ccgcgccgct | ttgacatcca | actttgctgg | caacttcgat | 120 |
| cagttcccaa | ctaagcgtgg | tggctttgcg | atcgacagct | acctgctgga | ttacagcgcg | 180 |
| cccaagcaag | gctgctgggt | agatggcatt | accgtctacg | gtgacatctt | tatcggcaag | 240 |
| cagaattggg | gcacctacac | tcgcccggtc | tttgcctacc | tgcagtacat | ggacaccatt | 300 |
| tccattccgc | agcaggtgac | acagactcgc | agctatcagt | tgactaaggg | acacaccaaa | 360 |
| acgttcacga | ccaatgtcag | cgccaaatac | agcgttggag | gtagtattga | catcgtcaac | 420 |
| gtcggttcgg | atatctcaat | tggattcagt | aacagtgaat | cctggtctac | tacgcagacg | 480 |
| ttcagcaata | gcactcaatt | gactggtcct | ggcaccttca | tcgtgtatca | ggttgttatg | 540 |
| gtttatgcgc | acaacgccac | ttctgcgggc | aggcagaatg | gtaatgcctt | cgcctacaac | 600 |
| aagaccaata | ctgtcggctc | gcggctggac | ttgtactatt | tgtctgccat | cactcagaac | 660 |
| agtacggtca | ttgtcgattc | cagcaaggcc | atcgcgccgc | tggattggga | tactgttgta | 720 |
| agcaatgttt | tgattgatga | ttttgatcca | ggcagcaata | gtgggcactt | cagtttcgac | 780 |
| tggagcgcct | acaacgatcc | tcatcgccgt | tat | | | 813 |

<210> SEQ ID NO 231
<211> LENGTH: 813
<212> TYPE: DNA
<213> ORGANISM: Artificial Sequence
<220> FEATURE:
<223> OTHER INFORMATION: PIP-1A variant

<400> SEQUENCE: 231

| | | | | | |
|---|---|---|---|---|---|
| atgacgatca | aggaagagct | gagccagcct | caaagtcatt | cgatcgaact | tgacgacctg | 60 |
| aaaagtgagc | aaggaagtct | ccgcgccgct | ttgacatcca | actttgctgg | caacttcgat | 120 |
| cagttcccaa | ctaagcgtgg | tggctttgcg | atcgacagct | acctgctgga | ttacagcgcg | 180 |
| cccaagcaag | gctgctgggt | agatggcatt | accgtctacg | gtgacatctt | tatcggcaag | 240 |
| cagaattggg | gcacctacac | tcgcccggtc | tttgcctacc | tgcagtacat | ggacaccatt | 300 |
| tccattccgc | agcaggtgac | acagactcgc | agctatcagt | tgactaaggg | acacaccaaa | 360 |
| acgttcacga | ccaatgtcag | cgccaaatac | agcgttggag | gtagtattga | catcgtcaac | 420 |
| gtcggttcgg | atatctcaat | tggattcagt | aacagtgaat | cctggtctac | tacgcagacg | 480 |
| ttcagcaata | gcactcaatt | gactggtcct | ggcaccttca | tcgtgtatca | ggttgttatg | 540 |
| gtttatgcgc | acaacgccac | ttctgcgggc | aggcagaatg | gtaatgcctt | cgcctacaac | 600 |
| aagaccaata | ctgtcggctc | gcggctggac | ttgtactatt | tgtctgccat | cactcagaac | 660 |
| agtacggtca | ttgtcgattc | cagcaaggcc | atcgcgccgc | tggattggga | tactgttgta | 720 |
| agccatgtta | tgatggagga | ttatgatcca | ggcagcaata | gtgggcactt | cagtttcgac | 780 |
| tggagcgcct | acaacgatcc | tcatcgccgt | tat | | | 813 |

<210> SEQ ID NO 232
<211> LENGTH: 813
<212> TYPE: DNA
<213> ORGANISM: Artificial Sequence
<220> FEATURE:
<223> OTHER INFORMATION: PIP-1A variant

<400> SEQUENCE: 232

```
atgacgatca aggaagagct gagccagcct caaagtcatt cgatcgaact tgacgacctg      60
aaaagtgagc aaggaagtct ccgcgccgct ttgacatcca actttgctgg caacttcgat     120
cagttcccaa ctaagcgtgg tggctttgcg atcgacagct acctgctgga ttacagcgcg     180
cccaagcaag gctgctgggt agatggcatt accgtctacg gtgacatctt tatcggcaag     240
cagaattggg gcacctacac tcgcccggtc tttgcctacc tgcagtacat ggacaccatt     300
tccattccgc agcaggtgac acagactcgc agctatcagt tgactaaggg acacaccaaa     360
acgttcacga ccaatgtcag cgccaaatac agcgttggag gtagtattga catcgtcaac     420
gtcggttcgg atatctcaat tggattcagt aacagtgaat cctggtctac tacgcagacg     480
ttcagcaata gcactcaatt gactggtcct ggcaccttca tcgtgtatca ggttgttatg     540
gtttatgcgc acaacgccac ttctgcgggc aggcagaatg gtaatgcctt cgcctacaac     600
aagaccaata ctgtcggctc gcggctggac ttgtactatt tgtctgccat cactcagaac     660
agtacggtca ttgtcgattc cagcaaggcc atcgcgccgc tggattggga tactgttaat     720
agccacattt tggttgggaa ctatgatcca ggcagcaata gtgggcactt cagtttcgac     780
tggagcgcct acaacgatcc tcatcgccgt tat                                  813
```

<210> SEQ ID NO 233
<211> LENGTH: 813
<212> TYPE: DNA
<213> ORGANISM: Artificial Sequence
<220> FEATURE:
<223> OTHER INFORMATION: PIP-1A variant

<400> SEQUENCE: 233

```
atgacgatca aggaagagct gagccagcct caaagtcatt cgatcgaact tgacgacctg      60
aaaagtgagc aaggaagtct ccgcgccgct ttgacatcca actttgctgg caacttcgat     120
cagttcccaa ctaagcgtgg tggctttgcg atcgacagct acctgctgga ttacagcgcg     180
cccaagcaag gctgctgggt agatggcatt accgtctacg gtgacatctt tatcggcaag     240
cagaattggg gcacctacac tcgcccggtc tttgcctacc tgcagtacat ggacaccatt     300
tccattccgc agcaggtgac acagactcgc agctatcagt tgactaaggg acacaccaaa     360
acgttcacga ccaatgtcag cgccaaatac agcgttggag gtagtattga catcgtcaac     420
gtcggttcgg atatctcaat tggattcagt aacagtgaat cctggtctac tacgcagacg     480
ttcagcaata gcactcaatt gactggtcct ggcaccttca tcgtgtatca ggttgttatg     540
gtttatgcgc acaacgccac ttctgcgggc aggcagaatg gtaatgcctt cgcctacaac     600
aagaccaata ctgtcggctc gcggctggac ttgtactatt tgtctgccat cactcagaac     660
agtacggtca ttgtcgattc cagcaaggcc atcgcgccgc tggattggga tactgttaat     720
agctacgtta tgattgagaa ttttacccca ggcagcaata gtgggcactt cagtttcgac     780
tggagcgcct acaacgatcc tcatcgccgt tat                                  813
```

<210> SEQ ID NO 234
<211> LENGTH: 813
<212> TYPE: DNA
<213> ORGANISM: Artificial Sequence
<220> FEATURE:
<223> OTHER INFORMATION: PIP-1A variant

<400> SEQUENCE: 234

```
atgacgatca aggaagagct gagccagcct caaagtcatt cgatcgaact tgacgacctg    60
aaaagtgagc aaggaagtct ccgcgccgct ttgacatcca actttgctgg caacttcgat   120
cagttcccaa ctaagcgtgg tggctttgcg atcgacagct acctgctgga ttacagcgcg   180
cccaagcaag gctgctgggt agatggcatt accgtctacg gtgacatctt tatcggcaag   240
cagaattggg gcacctacac tcgcccggtc tttgcctacc tgcagtacat ggacaccatt   300
tccattccgc agcaggtgac acagactcgc agctatcagt tgactaaggg acacaccaaa   360
acgttcacga ccaatgtcag cgccaaatac agcgttggag gtagtattga catcgtcaac   420
gtcggttcgg atatctcaat tggattcagt aacagtgaat cctggtctac tacgcagacg   480
ttcagcaata gcactcaatt gactggtcct ggcaccttca tcgtgtatca ggttgttatg   540
gtttatgcgc acaacgccac ttctgcgggc aggcagaatg gtaatgcctt cgcctacaac   600
aagaccaata ctgtcggctc gcggctggac ttgtactatt tgtctgccat cactcagaac   660
agtacggtca ttgtcgattc cagcaaggcc atcgcgccgc tggattggga tactgttaat   720
tgcaacatta ttatggagaa ttatgatcca ggcagcaata gtgggcactt cagtttcgac   780
tggagcgcct acaacgatcc tcatcgccgt tat                                 813
```

`<210>` SEQ ID NO 235  
`<211>` LENGTH: 813  
`<212>` TYPE: DNA  
`<213>` ORGANISM: Artificial Sequence  
`<220>` FEATURE:  
`<223>` OTHER INFORMATION: PIP-1A variant

`<400>` SEQUENCE: 235

```
atgacgatca aggaagagct gagccagcct caaagtcatt cgatcgaact tgacgacctg    60
aaaagtgagc aaggaagtct ccgcgccgct ttgacatcca actttgctgg caacttcgat   120
cagttcccaa ctaagcgtgg tggctttgcg atcgacagct acctgctgga ttacagcgcg   180
cccaagcaag gctgctgggt agatggcatt accgtctacg gtgacatctt tatcggcaag   240
cagaattggg gcacctacac tcgcccggtc tttgcctacc tgcagtacat ggacaccatt   300
tccattccgc agcaggtgac acagactcgc agctatcagt tgactaaggg acacaccaaa   360
acgttcacga ccaatgtcag cgccaaatac agcgttggag gtagtattga catcgtcaac   420
gtcggttcgg atatctcaat tggattcagt aacagtgaat cctggtctac tacgcagacg   480
ttcagcaata gcactcaatt gactggtcct ggcaccttca tcgtgtatca ggttgttatg   540
gtttatgcgc acaacgccac ttctgcgggc aggcagaatg gtaatgcctt cgcctacaac   600
aagaccaata ctgtcggctc gcggctggac ttgtactatt tgtctgccat cactcagaac   660
agtacggtca ttgtcgattc cagcaaggcc atcgcgccgc tggattggga tactgttatt   720
cgctatattt ttattgataa ttttgatcca ggcagcaata gtgggcactt cagtttcgac   780
tggagcgcct acaacgatcc tcatcgccgt tat                                 813
```

`<210>` SEQ ID NO 236  
`<211>` LENGTH: 813  
`<212>` TYPE: DNA  
`<213>` ORGANISM: Artificial Sequence  
`<220>` FEATURE:  
`<223>` OTHER INFORMATION: PIP-1A variant

`<400>` SEQUENCE: 236

```
atgacgatca aggaagagct gagccagcct caaagtcatt cgatcgaact tgacgacctg    60
aaaagtgagc aaggaagtct ccgcgccgct ttgacatcca actttgctgg caacttcgat   120
```

```
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttgtt    720
cgcaacgttt tggttgagaa ttatcaccca ggcagcaata gtgggcactt cagtttcgac    780
tggagcgcct acaacgatcc tcatcgccgt tat                                  813

<210> SEQ ID NO 237
<211> LENGTH: 813
<212> TYPE: DNA
<213> ORGANISM: Artificial Sequence
<220> FEATURE:
<223> OTHER INFORMATION: PIP-1A variant

<400> SEQUENCE: 237
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttcaa    720
cgctatgttt tgattgataa cttttatcca ggcagcaata gtgggcactt cagtttcgac    780
tggagcgcct acaacgatcc tcatcgccgt tat                                  813

<210> SEQ ID NO 238
<211> LENGTH: 813
<212> TYPE: DNA
<213> ORGANISM: Artificial Sequence
<220> FEATURE:
<223> OTHER INFORMATION: PIP-1A variant

<400> SEQUENCE: 238
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
```

| | |
|---|---|
| cccaagcaag gctgctgggt agatggcatt accgtctacg gtgacatctt tatcggcaag | 240 |
| cagaattggg gcacctacac tcgcccggtc tttgcctacc tgcagtacat ggacaccatt | 300 |
| tccattccgc agcaggtgac acagactcgc agctatcagt tgactaaggg acacaccaaa | 360 |
| acgttcacga ccaatgtcag cgccaaatac agcgttggag gtagtattga catcgtcaac | 420 |
| gtcggttcgg atatctcaat tggattcagt aacagtgaat cctggtctac tacgcagacg | 480 |
| ttcagcaata gcactcaatt gactggtcct ggcaccttca tcgtgtatca ggttgttatg | 540 |
| gtttatgcgc acaacgccac ttctgcgggc aggcagaatg gtaatgcctt cgcctacaac | 600 |
| aagaccaata ctgtcggctc gcggctggac ttgtactatt tgtctgccat cactcagaac | 660 |
| agtacggtca ttgtcgattc cagcaaggcc atcgcgccgc tggattggga tactgttctt | 720 |
| agccacttta tgttgggtaa ttttaaccca ggcagcaata gtgggcactt cagtttcgac | 780 |
| tggagcgcct acaacgatcc tcatcgccgt tat | 813 |

<210> SEQ ID NO 239
<211> LENGTH: 813
<212> TYPE: DNA
<213> ORGANISM: Artificial Sequence
<220> FEATURE:
<223> OTHER INFORMATION: PIP-1A variant

<400> SEQUENCE: 239

| | |
|---|---|
| atgacgatca aggaagagct gagccagcct caaagtcatt cgatcgaact tgacgacctg | 60 |
| aaaagtgagc aaggaagtct ccgcgccgct ttgacatcca actttgctgg caacttcgat | 120 |
| cagttcccaa ctaagcgtgg tggctttgcg atcgacagct acctgctgga ttacagcgcg | 180 |
| cccaagcaag gctgctgggt agatggcatt accgtctacg gtgacatctt tatcggcaag | 240 |
| cagaattggg gcacctacac tcgcccggtc tttgcctacc tgcagtacat ggacaccatt | 300 |
| tccattccgc agcaggtgac acagactcgc agctatcagt tgactaaggg acacaccaaa | 360 |
| acgttcacga ccaatgtcag cgccaaatac agcgttggag gtagtattga catcgtcaac | 420 |
| gtcggttcgg atatctcaat tggattcagt aacagtgaat cctggtctac tacgcagacg | 480 |
| ttcagcaata gcactcaatt gactggtcct ggcaccttca tcgtgtatca ggttgttatg | 540 |
| gtttatgcgc acaacgccac ttctgcgggc aggcagaatg gtaatgcctt cgcctacaac | 600 |
| aagaccaata ctgtcggctc gcggctggac ttgtactatt tgtctgccat cactcagaac | 660 |
| agtacggtca ttgtcgattc cagcaaggcc atcgcgccgc tggattggga tactgttaga | 720 |
| tgcaacgtgt tgatggggga tttcgatcca ggcagcaata gtgggcactt cagtttcgac | 780 |
| tggagcgcct acaacgatcc tcatcgccgt tat | 813 |

<210> SEQ ID NO 240
<211> LENGTH: 813
<212> TYPE: DNA
<213> ORGANISM: Artificial Sequence
<220> FEATURE:
<223> OTHER INFORMATION: PIP-1A variant

<400> SEQUENCE: 240

| | |
|---|---|
| atgacgatca aggaagagct gagccagcct caaagtcatt cgatcgaact tgacgacctg | 60 |
| aaaagtgagc aaggaagtct ccgcgccgct ttgacatcca actttgctgg caacttcgat | 120 |
| cagttcccaa ctaagcgtgg tggctttgcg atcgacagct acctgctgga ttacagcgcg | 180 |
| cccaagcaag gctgctgggt agatggcatt accgtctacg gtgacatctt tatcggcaag | 240 |
| cagaattggg gcacctacac tcgcccggtc tttgcctacc tgcagtacat ggacaccatt | 300 |

```
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttatt    720
ggcaatgtta tggtgggtga ctttgatcca ggcagcaata gtgggcactt cagtttcgac    780
tggagcgcct acaacgatcc tcatcgccgt tat                                 813
```

<210> SEQ ID NO 241
<211> LENGTH: 813
<212> TYPE: DNA
<213> ORGANISM: Artificial Sequence
<220> FEATURE:
<223> OTHER INFORMATION: PIP-1A variant

<400> SEQUENCE: 241

```
atgacgatca aggaagagct gagccagcct caaagtcatt cgatcgaact tgacgacctg    60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttcaa    720
tgctatgttt tgattgagaa ttttcatcca ggcagcaata gtgggcactt cagtttcgac    780
tggagcgcct acaacgatcc tcatcgccgt tat                                 813
```

<210> SEQ ID NO 242
<211> LENGTH: 813
<212> TYPE: DNA
<213> ORGANISM: Artificial Sequence
<220> FEATURE:
<223> OTHER INFORMATION: PIP-1A variant

<400> SEQUENCE: 242

```
atgacgatca aggaagagct gagccagcct caaagtcatt cgatcgaact tgacgacctg    60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
```

-continued

| | |
|---|---|
| acgttcacga ccaatgtcag cgccaaatac agcgttggag gtagtattga catcgtcaac | 420 |
| gtcggttcgg atatctcaat tggattcagt aacagtgaat cctggtctac tacgcagacg | 480 |
| ttcagcaata gcactcaatt gactggtcct ggcaccttca tcgtgtatca ggttgttatg | 540 |
| gtttatgcgc acaacgccac ttctgcgggc aggcagaatg gtaatgcctt cgcctacaac | 600 |
| aagaccaata ctgtcggctc gcggctggac ttgtactatt tgtctgccat cactcagaac | 660 |
| agtacggtca ttgtcgattc cagcaaggcc atcgcgccgc tggattggga tactgttgtt | 720 |
| tgcaatgttt tgatggagca ttttttaccca ggcagcaata gtgggcactt cagtttcgac | 780 |
| tggagcgcct acaacgatcc tcatcgccgt tat | 813 |

<210> SEQ ID NO 243
<211> LENGTH: 813
<212> TYPE: DNA
<213> ORGANISM: Artificial Sequence
<220> FEATURE:
<223> OTHER INFORMATION: PIP-1A variant

<400> SEQUENCE: 243

| | |
|---|---|
| atgacgatca aggaagagct gagccagcct caaagtcatt cgatcgaact tgacgacctg | 60 |
| aaaagtgagc aaggaagtct ccgcgccgct ttgacatcca actttgctgg caacttcgat | 120 |
| cagttcccaa ctaagcgtgg tggctttgcg atcgacagct acctgctgga ttacagcgcg | 180 |
| cccaagcaag gctgctgggt agatggcatt accgtctacg gtgacatctt tatcggcaag | 240 |
| cagaattggg gcacctacac tcgcccggtc tttgcctacc tgcagtacat ggacaccatt | 300 |
| tccattccgc agcaggtgac acagactcgc agctatcagt tgactaaggg acacaccaaa | 360 |
| acgttcacga ccaatgtcag cgccaaatac agcgttggag gtagtattga catcgtcaac | 420 |
| gtcggttcgg atatctcaat tggattcagt aacagtgaat cctggtctac tacgcagacg | 480 |
| ttcagcaata gcactcaatt gactggtcct ggcaccttca tcgtgtatca ggttgttatg | 540 |
| gtttatgcgc acaacgccac ttctgcgggc aggcagaatg gtaatgcctt cgcctacaac | 600 |
| aagaccaata ctgtcggctc gcggctggac ttgtactatt tgtctgccat cactcagaac | 660 |
| agtacggtca ttgtcgattc cagcaaggcc atcgcgccgc tggattggga tactgttgta | 720 |
| cgcaacgttt ttttttgatta ctttgatcca ggcagcaata gtgggcactt cagtttcgac | 780 |
| tggagcgcct acaacgatcc tcatcgccgt tat | 813 |

<210> SEQ ID NO 244
<211> LENGTH: 813
<212> TYPE: DNA
<213> ORGANISM: Artificial Sequence
<220> FEATURE:
<223> OTHER INFORMATION: PIP-1A variant

<400> SEQUENCE: 244

| | |
|---|---|
| atgacgatca aggaagagct gagccagcct caaagtcatt cgatcgaact tgacgacctg | 60 |
| aaaagtgagc aaggaagtct ccgcgccgct ttgacatcca actttgctgg caacttcgat | 120 |
| cagttcccaa ctaagcgtgg tggctttgcg atcgacagct acctgctgga ttacagcgcg | 180 |
| cccaagcaag gctgctgggt agatggcatt accgtctacg gtgacatctt tatcggcaag | 240 |
| cagaattggg gcacctacac tcgcccggtc tttgcctacc tgcagtacat ggacaccatt | 300 |
| tccattccgc agcaggtgac acagactcgc agctatcagt tgactaaggg acacaccaaa | 360 |
| acgttcacga ccaatgtcag cgccaaatac agcgttggag gtagtattga catcgtcaac | 420 |
| gtcggttcgg atatctcaat tggattcagt aacagtgaat cctggtctac tacgcagacg | 480 |

```
ttcagcaata gcactcaatt gactggtcct ggcaccttca tcgtgtatca ggttgttatg      540
gtttatgcgc acaacgccac ttctgcgggc aggcagaatg gtaatgcctt cgcctacaac      600
aagaccaata ctgtcggctc gcggctggac ttgtactatt tgtctgccat cactcagaac      660
agtacggtca ttgtcgattc cagcaaggcc atcgcgccgc tggattggga tactgttgta      720
agctacattt tgtttgataa ctttcatcca ggcagcaata gtgggcactt cagtttcgac      780
tggagcgcct acaacgatcc tcatcgccgt tat                                    813
```

<210> SEQ ID NO 245
<211> LENGTH: 271
<212> TYPE: PRT
<213> ORGANISM: Artificial Sequence
<220> FEATURE:
<223> OTHER INFORMATION: PIP-1A variant

<400> SEQUENCE: 245

```
Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Asn
225                 230                 235                 240

Ser Tyr Val Leu Leu Asp Tyr Tyr Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 246
<211> LENGTH: 271
<212> TYPE: PRT
<213> ORGANISM: Artificial Sequence
<220> FEATURE:
<223> OTHER INFORMATION: PIP-1A variant

<400> SEQUENCE: 246

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Asn
225                 230                 235                 240

Cys Tyr Ile Phe Met Glu Tyr Tyr Asp Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 247
<211> LENGTH: 271
<212> TYPE: PRT
<213> ORGANISM: Artificial Sequence
<220> FEATURE:
<223> OTHER INFORMATION: PIP-1A variant

<400> SEQUENCE: 247

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys

```
            65                  70                  75                  80
Gln Asn Trp Gly Thr Tyr Thr Arg Pro Val Phe Ala Tyr Leu Gln Tyr
                    85                  90                  95

Met Asp Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
        130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Asn
225                 230                 235                 240

Cys Tyr Ile Met Met Glu Asn Phe Asp Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 248
<211> LENGTH: 271
<212> TYPE: PRT
<213> ORGANISM: Artificial Sequence
<220> FEATURE:
<223> OTHER INFORMATION: PIP-1A variant

<400> SEQUENCE: 248

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
        130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
```

```
                    165                 170                 175
Gln Val Val Met Val Tyr Ala His Asn Ala Thr Ser Ala Gly Arg Gln
                180                 185                 190

Asn Gly Asn Ala Phe Ala Tyr Asn Lys Thr Asn Thr Val Gly Ser Arg
            195                 200                 205

Leu Asp Leu Tyr Tyr Leu Ser Ala Ile Thr Gln Asn Ser Thr Val Ile
        210                 215                 220

Val Asp Ser Ser Lys Ala Ile Ala Pro Leu Asp Trp Asp Thr Val Gln
225                 230                 235                 240

Cys Asn Val Leu Phe Asp Asn Phe His Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 249
<211> LENGTH: 271
<212> TYPE: PRT
<213> ORGANISM: Artificial Sequence
<220> FEATURE:
<223> OTHER INFORMATION: PIP-1A variant

<400> SEQUENCE: 249

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Gln
225                 230                 235                 240

Gly Tyr Val Leu Val Asp Asn Phe Asn Pro Gly Ser Asn Ser Gly His
                245                 250                 255

Phe Ser Phe Asp Trp Ser Ala Tyr Asn Asp Pro His Arg Arg Tyr
```

-continued

```
              260                 265                 270
```

<210> SEQ ID NO 250
<211> LENGTH: 271
<212> TYPE: PRT
<213> ORGANISM: Artificial Sequence
<220> FEATURE:
<223> OTHER INFORMATION: PIP-1A variant

<400> SEQUENCE: 250

```
Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Asn
225                 230                 235                 240

Arg Tyr Val Phe Phe Gly Asn Tyr Asp Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 251
<211> LENGTH: 271
<212> TYPE: PRT
<213> ORGANISM: Artificial Sequence
<220> FEATURE:
<223> OTHER INFORMATION: PIP-1A variant

<400> SEQUENCE: 251

```
Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30
```

```
Ser Asn Phe Ala Gly Asn Phe Asp Gln Phe Pro Thr Lys Arg Gly Gly
         35                  40                  45

Phe Ala Ile Asp Ser Tyr Leu Leu Asp Tyr Ser Ala Pro Lys Gln Gly
 50                  55                  60

Cys Trp Val Asp Gly Ile Thr Val Tyr Gly Asp Ile Phe Ile Gly Lys
 65                  70                  75                  80

Gln Asn Trp Gly Thr Tyr Thr Arg Pro Val Phe Ala Tyr Leu Gln Tyr
                 85                  90                  95

Met Asp Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
                115                 120                 125

Lys Tyr Ser Val Gly Gly Ser Ile Asp Ile Val Asn Val Gly Ser Asp
130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
                180                 185                 190

Asn Gly Asn Ala Phe Ala Tyr Asn Lys Thr Asn Thr Val Gly Ser Arg
            195                 200                 205

Leu Asp Leu Tyr Tyr Leu Ser Ala Ile Thr Gln Asn Ser Thr Val Ile
            210                 215                 220

Val Asp Ser Ser Lys Ala Ile Ala Pro Leu Asp Trp Asp Thr Val Gln
225                 230                 235                 240

Cys Asn Ile Met Ile Gly Tyr Phe Asp Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 252
<211> LENGTH: 271
<212> TYPE: PRT
<213> ORGANISM: Artificial Sequence
<220> FEATURE:
<223> OTHER INFORMATION: PIP-1A variant

<400> SEQUENCE: 252

Met Thr Ile Lys Glu Glu Leu Ser Gln Pro Gln Ser His Ser Ile Glu
  1               5                  10                  15

Leu Asp Asp Leu Lys Ser Glu Gln Gly Ser Leu Arg Ala Ala Leu Thr
                 20                  25                  30

Ser Asn Phe Ala Gly Asn Phe Asp Gln Phe Pro Thr Lys Arg Gly Gly
         35                  40                  45

Phe Ala Ile Asp Ser Tyr Leu Leu Asp Tyr Ser Ala Pro Lys Gln Gly
 50                  55                  60

Cys Trp Val Asp Gly Ile Thr Val Tyr Gly Asp Ile Phe Ile Gly Lys
 65                  70                  75                  80

Gln Asn Trp Gly Thr Tyr Thr Arg Pro Val Phe Ala Tyr Leu Gln Tyr
                 85                  90                  95

Met Asp Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
                115                 120                 125
```

```
Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
                180                 185                 190

Asn Gly Asn Ala Phe Ala Tyr Asn Lys Thr Asn Thr Val Gly Ser Arg
            195                 200                 205

Leu Asp Leu Tyr Tyr Leu Ser Ala Ile Thr Gln Asn Ser Thr Val Ile
210                 215                 220

Val Asp Ser Ser Lys Ala Ile Ala Pro Leu Asp Trp Asp Thr Val Gln
225                 230                 235                 240

Gly Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270
```

<210> SEQ ID NO 253
<211> LENGTH: 271
<212> TYPE: PRT
<213> ORGANISM: Artificial Sequence
<220> FEATURE:
<223> OTHER INFORMATION: PIP-1A variant

<400> SEQUENCE: 253

```
Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
                180                 185                 190

Asn Gly Asn Ala Phe Ala Tyr Asn Lys Thr Asn Thr Val Gly Ser Arg
            195                 200                 205

Leu Asp Leu Tyr Tyr Leu Ser Ala Ile Thr Gln Asn Ser Thr Val Ile
210                 215                 220
```

Val Asp Ser Ser Lys Ala Ile Ala Pro Leu Asp Trp Asp Thr Val Val
225                 230                 235                 240

Ser Asn Ile Leu Val Gly Asn Phe Asn Pro Gly Ser Asn Ser Gly His
            245                 250                 255

Phe Ser Phe Asp Trp Ser Ala Tyr Asn Asp Pro His Arg Arg Tyr
        260                 265                 270

<210> SEQ ID NO 254
<211> LENGTH: 271
<212> TYPE: PRT
<213> ORGANISM: Artificial Sequence
<220> FEATURE:
<223> OTHER INFORMATION: PIP-1A variant

<400> SEQUENCE: 254

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Asn
225                 230                 235                 240

Arg His Val Leu Val Asp Asn Phe Tyr Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 255
<211> LENGTH: 271
<212> TYPE: PRT
<213> ORGANISM: Artificial Sequence
<220> FEATURE:
<223> OTHER INFORMATION: PIP-1A variant

<400> SEQUENCE: 255

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
        50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Val
225                 230                 235                 240

Ser Asn Val Leu Ile Asp Asp Phe Asp Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 256
<211> LENGTH: 271
<212> TYPE: PRT
<213> ORGANISM: Artificial Sequence
<220> FEATURE:
<223> OTHER INFORMATION: PIP-1A variant

<400> SEQUENCE: 256

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
        50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

```
Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
            130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
            195                 200                 205

Leu Asp Leu Tyr Tyr Leu Ser Ala Ile Thr Gln Asn Ser Thr Val Ile
            210                 215                 220

Val Asp Ser Ser Lys Ala Ile Ala Pro Leu Asp Trp Asp Thr Val Val
225                 230                 235                 240

Ser His Val Met Met Glu Asp Tyr Asp Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 257
<211> LENGTH: 271
<212> TYPE: PRT
<213> ORGANISM: Artificial Sequence
<220> FEATURE:
<223> OTHER INFORMATION: PIP-1A variant

<400> SEQUENCE: 257

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
        50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
            130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190
```

```
Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Asn
225                 230                 235                 240

Ser His Ile Leu Val Gly Asn Tyr Asp Pro Gly Ser Asn Ser Gly His
            245                 250                 255

Phe Ser Phe Asp Trp Ser Ala Tyr Asn Asp Pro His Arg Arg Tyr
        260                 265                 270

<210> SEQ ID NO 258
<211> LENGTH: 271
<212> TYPE: PRT
<213> ORGANISM: Artificial Sequence
<220> FEATURE:
<223> OTHER INFORMATION: PIP-1A variant

<400> SEQUENCE: 258

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Asn
225                 230                 235                 240

Ser Tyr Val Met Ile Glu Asn Phe Tyr Pro Gly Ser Asn Ser Gly His
                245                 250                 255

Phe Ser Phe Asp Trp Ser Ala Tyr Asn Asp Pro His Arg Arg Tyr
        260                 265                 270

<210> SEQ ID NO 259
```

<211> LENGTH: 271
<212> TYPE: PRT
<213> ORGANISM: Artificial Sequence
<220> FEATURE:
<223> OTHER INFORMATION: PIP-1A variant

<400> SEQUENCE: 259

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
        50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
210                 215                 220

Val Asp Ser Ser Lys Ala Ile Ala Pro Leu Asp Trp Asp Thr Val Asn
225                 230                 235                 240

Cys Asn Ile Ile Met Glu Asn Tyr Asp Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 260
<211> LENGTH: 271
<212> TYPE: PRT
<213> ORGANISM: Artificial Sequence
<220> FEATURE:
<223> OTHER INFORMATION: PIP-1A variant

<400> SEQUENCE: 260

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly

```
                50                  55                  60
Cys Trp Val Asp Gly Ile Thr Val Tyr Gly Asp Ile Phe Ile Gly Lys
 65                  70                  75                  80

Gln Asn Trp Gly Thr Tyr Thr Arg Pro Val Phe Ala Tyr Leu Gln Tyr
                 85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
            130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
            165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
            195                 200                 205

Leu Asp Leu Tyr Tyr Leu Ser Ala Ile Thr Gln Asn Ser Thr Val Ile
210                 215                 220

Val Asp Ser Ser Lys Ala Ile Ala Pro Leu Asp Trp Asp Thr Val Ile
225                 230                 235                 240

Arg Tyr Ile Phe Ile Asp Asn Phe Asp Pro Gly Ser Asn Ser Gly His
            245                 250                 255

Phe Ser Phe Asp Trp Ser Ala Tyr Asn Asp Pro His Arg Arg Tyr
            260                 265                 270

<210> SEQ ID NO 261
<211> LENGTH: 271
<212> TYPE: PRT
<213> ORGANISM: Artificial Sequence
<220> FEATURE:
<223> OTHER INFORMATION: PIP-1A variant

<400> SEQUENCE: 261

Met Thr Ile Lys Glu Glu Leu Ser Gln Pro Gln Ser His Ser Ile Glu
 1               5                  10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
            50                  55                  60

Cys Trp Val Asp Gly Ile Thr Val Tyr Gly Asp Ile Phe Ile Gly Lys
 65                  70                  75                  80

Gln Asn Trp Gly Thr Tyr Thr Arg Pro Val Phe Ala Tyr Leu Gln Tyr
                 85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
            130                 135                 140

Ile Ser Ile Gly Phe Ser Asn Ser Glu Ser Trp Ser Thr Thr Gln Thr
```

```
                145                 150                 155                 160
Phe Ser Asn Ser Thr Gln Leu Thr Gly Pro Gly Thr Phe Ile Val Tyr
                    165                 170                 175
Gln Val Val Met Val Tyr Ala His Asn Ala Thr Ser Ala Gly Arg Gln
                180                 185                 190
Asn Gly Asn Ala Phe Ala Tyr Asn Lys Thr Asn Thr Val Gly Ser Arg
                195                 200                 205
Leu Asp Leu Tyr Tyr Leu Ser Ala Ile Thr Gln Asn Ser Thr Val Ile
                210                 215                 220
Val Asp Ser Ser Lys Ala Ile Ala Pro Leu Asp Trp Asp Thr Val Val
225                 230                 235                 240
Arg Asn Val Leu Val Glu Asn Tyr His Pro Gly Ser Asn Ser Gly His
                    245                 250                 255
Phe Ser Phe Asp Trp Ser Ala Tyr Asn Asp Pro His Arg Arg Tyr
                260                 265                 270

<210> SEQ ID NO 262
<211> LENGTH: 271
<212> TYPE: PRT
<213> ORGANISM: Artificial Sequence
<220> FEATURE:
<223> OTHER INFORMATION: PIP-1A variant

<400> SEQUENCE: 262

Met Thr Ile Lys Glu Glu Leu Ser Gln Pro Gln Ser His Ser Ile Glu
1               5                   10                  15
Leu Asp Asp Leu Lys Ser Glu Gln Gly Ser Leu Arg Ala Ala Leu Thr
                20                  25                  30
Ser Asn Phe Ala Gly Asn Phe Asp Gln Phe Pro Thr Lys Arg Gly Gly
                35                  40                  45
Phe Ala Ile Asp Ser Tyr Leu Leu Asp Tyr Ser Ala Pro Lys Gln Gly
            50                  55                  60
Cys Trp Val Asp Gly Ile Thr Val Tyr Gly Asp Ile Phe Ile Gly Lys
65                  70                  75                  80
Gln Asn Trp Gly Thr Tyr Thr Arg Pro Val Phe Ala Tyr Leu Gln Tyr
                    85                  90                  95
Met Asp Thr Ile Ser Ile Pro Gln Gln Val Thr Gln Thr Arg Ser Tyr
                100                 105                 110
Gln Leu Thr Lys Gly His Thr Lys Thr Phe Thr Thr Asn Val Ser Ala
                115                 120                 125
Lys Tyr Ser Val Gly Gly Ser Ile Asp Ile Val Asn Val Gly Ser Asp
            130                 135                 140
Ile Ser Ile Gly Phe Ser Asn Ser Glu Ser Trp Ser Thr Thr Gln Thr
145                 150                 155                 160
Phe Ser Asn Ser Thr Gln Leu Thr Gly Pro Gly Thr Phe Ile Val Tyr
                    165                 170                 175
Gln Val Val Met Val Tyr Ala His Asn Ala Thr Ser Ala Gly Arg Gln
                180                 185                 190
Asn Gly Asn Ala Phe Ala Tyr Asn Lys Thr Asn Thr Val Gly Ser Arg
                195                 200                 205
Leu Asp Leu Tyr Tyr Leu Ser Ala Ile Thr Gln Asn Ser Thr Val Ile
            210                 215                 220
Val Asp Ser Ser Lys Ala Ile Ala Pro Leu Asp Trp Asp Thr Val Gln
225                 230                 235                 240
Arg Tyr Val Leu Ile Asp Asn Phe Tyr Pro Gly Ser Asn Ser Gly His
```

```
                    245                 250                 255

Phe Ser Phe Asp Trp Ser Ala Tyr Asn Asp Pro His Arg Arg Tyr
            260                 265                 270

<210> SEQ ID NO 263
<211> LENGTH: 271
<212> TYPE: PRT
<213> ORGANISM: Artificial Sequence
<220> FEATURE:
<223> OTHER INFORMATION: PIP-1A variant

<400> SEQUENCE: 263

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Leu
225                 230                 235                 240

Ser His Phe Met Leu Gly Asn Phe Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 264
<211> LENGTH: 271
<212> TYPE: PRT
<213> ORGANISM: Artificial Sequence
<220> FEATURE:
<223> OTHER INFORMATION: PIP-1A variant

<400> SEQUENCE: 264

Met Thr Ile Lys Glu Glu Leu Ser Gln Pro Gln Ser His Ser Ile Glu
1               5                   10                  15
```

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Arg
225                 230                 235                 240

Cys Asn Val Leu Met Gly Asp Phe Asp Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 265
<211> LENGTH: 271
<212> TYPE: PRT
<213> ORGANISM: Artificial Sequence
<220> FEATURE:
<223> OTHER INFORMATION: PIP-1A variant

<400> SEQUENCE: 265

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

```
Gln Leu Thr Lys Gly His Thr Lys Thr Phe Thr Thr Asn Val Ser Ala
            115                 120                 125
Lys Tyr Ser Val Gly Gly Ser Ile Asp Ile Val Asn Val Gly Ser Asp
        130                 135                 140
Ile Ser Ile Gly Phe Ser Asn Ser Glu Ser Trp Ser Thr Thr Gln Thr
145                 150                 155                 160
Phe Ser Asn Ser Thr Gln Leu Thr Gly Pro Gly Thr Phe Ile Val Tyr
                165                 170                 175
Gln Val Val Met Val Tyr Ala His Asn Ala Thr Ser Ala Gly Arg Gln
            180                 185                 190
Asn Gly Asn Ala Phe Ala Tyr Asn Lys Thr Asn Thr Val Gly Ser Arg
        195                 200                 205
Leu Asp Leu Tyr Tyr Leu Ser Ala Ile Thr Gln Asn Ser Thr Val Ile
    210                 215                 220
Val Asp Ser Ser Lys Ala Ile Ala Pro Leu Asp Trp Asp Thr Val Ile
225                 230                 235                 240
Gly Asn Val Met Val Gly Asp Phe Asp Pro Gly Ser Asn Ser Gly His
                245                 250                 255
Phe Ser Phe Asp Trp Ser Ala Tyr Asn Asp Pro His Arg Arg Tyr
                260                 265                 270
```

<210> SEQ ID NO 266
<211> LENGTH: 271
<212> TYPE: PRT
<213> ORGANISM: Artificial Sequence
<220> FEATURE:
<223> OTHER INFORMATION: PIP-1A variant

<400> SEQUENCE: 266

```
Met Thr Ile Lys Glu Glu Leu Ser Gln Pro Gln Ser His Ser Ile Glu
1               5                   10                  15
Leu Asp Asp Leu Lys Ser Glu Gln Gly Ser Leu Arg Ala Ala Leu Thr
            20                  25                  30
Ser Asn Phe Ala Gly Asn Phe Asp Gln Phe Pro Thr Lys Arg Gly Gly
        35                  40                  45
Phe Ala Ile Asp Ser Tyr Leu Leu Asp Tyr Ser Ala Pro Lys Gln Gly
    50                  55                  60
Cys Trp Val Asp Gly Ile Thr Val Tyr Gly Asp Ile Phe Ile Gly Lys
65                  70                  75                  80
Gln Asn Trp Gly Thr Tyr Thr Arg Pro Val Phe Ala Tyr Leu Gln Tyr
                85                  90                  95
Met Asp Thr Ile Ser Ile Pro Gln Gln Val Thr Gln Thr Arg Ser Tyr
            100                 105                 110
Gln Leu Thr Lys Gly His Thr Lys Thr Phe Thr Thr Asn Val Ser Ala
        115                 120                 125
Lys Tyr Ser Val Gly Gly Ser Ile Asp Ile Val Asn Val Gly Ser Asp
    130                 135                 140
Ile Ser Ile Gly Phe Ser Asn Ser Glu Ser Trp Ser Thr Thr Gln Thr
145                 150                 155                 160
Phe Ser Asn Ser Thr Gln Leu Thr Gly Pro Gly Thr Phe Ile Val Tyr
                165                 170                 175
Gln Val Val Met Val Tyr Ala His Asn Ala Thr Ser Ala Gly Arg Gln
            180                 185                 190
Asn Gly Asn Ala Phe Ala Tyr Asn Lys Thr Asn Thr Val Gly Ser Arg
        195                 200                 205
```

```
Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Gln
225                 230                 235                 240

Cys Tyr Val Leu Ile Glu Asn Phe His Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 267
<211> LENGTH: 271
<212> TYPE: PRT
<213> ORGANISM: Artificial Sequence
<220> FEATURE:
<223> OTHER INFORMATION: PIP-1A variant

<400> SEQUENCE: 267

```
Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
        50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
        130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
                180                 185                 190

Asn Gly Asn Ala Phe Ala Tyr Asn Lys Thr Asn Thr Val Gly Ser Arg
            195                 200                 205

Leu Asp Leu Tyr Tyr Leu Ser Ala Ile Thr Gln Asn Ser Thr Val Ile
        210                 215                 220

Val Asp Ser Ser Lys Ala Ile Ala Pro Leu Asp Trp Asp Thr Val Val
225                 230                 235                 240

Cys Asn Val Leu Met Glu His Phe Tyr Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 268
<211> LENGTH: 271
<212> TYPE: PRT
<213> ORGANISM: Artificial Sequence
<220> FEATURE:

<223> OTHER INFORMATION: PIP-1A variant

<400> SEQUENCE: 268

```
Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Val
225                 230                 235                 240

Arg Asn Val Phe Phe Asp Tyr Phe Asp Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 269
<211> LENGTH: 271
<212> TYPE: PRT
<213> ORGANISM: Synthetic Sequence

<400> SEQUENCE: 269

```
Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
```

|  | 85 | | | | 90 | | | | | 95 | | |
|---|---|---|---|---|---|---|---|---|---|---|---|---|

Met Asp Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
        130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Val
225                 230                 235                 240

Ser Tyr Ile Leu Phe Asp Asn Phe His Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 270
<211> LENGTH: 813
<212> TYPE: DNA
<213> ORGANISM: Artificial Sequence
<220> FEATURE:
<223> OTHER INFORMATION: PIP-1A variant

<400> SEQUENCE: 270
atgacgatca aggaagagct gagccagcct caaagtcatt cgatcgaact tgacgacctg      60
aaaagtgagc aaggaagtct ccgcgccgct ttgacatcca actttgctgg caacttcgat     120
cagttcccaa ctaagcgtgg tggctttgcg atcgacagct acctgctgga ttacagcgcg     180
cccaagcaag gctgctgggt agatggcatt accgtctacg gtgacatctt tatcggcaag     240
cagaattggg gcacctacac tcgcccggtc tttgcctacc tgcagtacat ggacaccatt     300
tccattccgc agcaggtgac acagactcgc agctatcagt tgactaaggg cacaccaaa      360 acgttcacga ccaatgtcag cgccaaatac agcgttggag gtagtattga catcgtcaac     420
gtcggttcgg atatctcaat tggattcagt aacagtgaat cctggtctac tacgcagacg     480
ttcagcaata gcactcaatt gactggtcct ggcaccttca tcgtgtatca ggttgttatg     540
gtttatgcgc acaacgccac ttctgcgggc aggcagaatg gtaatgcctt cgcctacaac     600
aagaccaata ctgtcggctc gcggctggac ttgtactatt tgtctgccat cactcagaac     660
agtacggtca ttgtcgattc cagcaaggcc atcgcgccgc tggattggga tactgttcat     720
agctatgttt ttattgataa ctataatcca ggcagcaata gtgggcactt cagtttcgac     780
tggagcgcct acaacgatcc tcatcgccgt tat                                  813

<210> SEQ ID NO 271
<211> LENGTH: 813
<212> TYPE: DNA
<213> ORGANISM: Artificial Sequence
<220> FEATURE:

<223> OTHER INFORMATION: PIP-1A variant

<400> SEQUENCE: 271

```
atgacgatca aggaagagct gagccagcct caaagtcatt cgatcgaact tgacgacctg    60
aaaagtgagc aaggaagtct ccgcgccgct ttgacatcca actttgctgg caacttcgat   120
cagttcccaa ctaagcgtgg tggctttgcg atcgacagct acctgctgga ttacagcgcg   180
cccaagcaag gctgctgggt agatggcatt accgtctacg gtgacatctt tatcggcaag   240
cagaattggg gcacctacac tcgcccggtc tttgcctacc tgcagtacat ggacaccatt   300
tccattccgc agcaggtgac acagactcgc agctatcagt tgactaaggg acacaccaaa   360
acgttcacga ccaatgtcag cgccaaatac agcgttggag gtagtattga catcgtcaac   420
gtcggttcgg atatctcaat tggattcagt aacagtgaat cctggtctac tacgcagacg   480
ttcagcaata gcactcaatt gactggtcct ggcaccttca tcgtgtatca ggttgttatg   540
gtttatgcgc acaacgccac ttctgcgggc aggcagaatg gtaatgcctt cgcctacaac   600
aagaccaata ctgtcggctc gcggctggac ttgtactatt tgtctgccat cactcagaac   660
agtacggtca ttgtcgattc cagcaaggcc atcgcgccgc tggattggga tactgttgtt   720
tgcaatttttt tttttggtga ctttgaccca ggcagcaata gtgggcactt cagtttcgac   780
tggagcgcct acaacgatcc tcatcgccgt tat                                 813
```

<210> SEQ ID NO 272
<211> LENGTH: 813
<212> TYPE: DNA
<213> ORGANISM: Artificial Sequence
<220> FEATURE:
<223> OTHER INFORMATION: PIP-1A variant

<400> SEQUENCE: 272

```
atgacgatca aggaagagct gagccagcct caaagtcatt cgatcgaact tgacgacctg    60
aaaagtgagc aaggaagtct ccgcgccgct ttgacatcca actttgctgg caacttcgat   120
cagttcccaa ctaagcgtgg tggctttgcg atcgacagct acctgctgga ttacagcgcg   180
cccaagcaag gctgctgggt agatggcatt accgtctacg gtgacatctt tatcggcaag   240
cagaattggg gcacctacac tcgcccggtc tttgcctacc tgcagtacat ggacaccatt   300
tccattccgc agcaggtgac acagactcgc agctatcagt tgactaaggg acacaccaaa   360
acgttcacga ccaatgtcag cgccaaatac agcgttggag gtagtattga catcgtcaac   420
gtcggttcgg atatctcaat tggattcagt aacagtgaat cctggtctac tacgcagacg   480
ttcagcaata gcactcaatt gactggtcct ggcaccttca tcgtgtatca ggttgttatg   540
gtttatgcgc acaacgccac ttctgcgggc aggcagaatg gtaatgcctt cgcctacaac   600
aagaccaata ctgtcggctc gcggctggac ttgtactatt tgtctgccat cactcagaac   660
agtacggtca ttgtcgattc cagcaaggcc atcgcgccgc tggattggga tactgttaaa   720
cgctacttta tgatgggtta ttttcatcca ggcagcaata gtgggcactt cagtttcgac   780
tggagcgcct acaacgatcc tcatcgccgt tat                                 813
```

<210> SEQ ID NO 273
<211> LENGTH: 813
<212> TYPE: DNA
<213> ORGANISM: Artificial Sequence
<220> FEATURE:
<223> OTHER INFORMATION: PIP-1A variant

<400> SEQUENCE: 273

```
atgacgatca aggaagagct gagccagcct caaagtcatt cgatcgaact tgacgacctg    60
aaaagtgagc aaggaagtct ccgcgccgct ttgacatcca actttgctgg caacttcgat   120
cagttcccaa ctaagcgtgg tggctttgcg atcgacagct acctgctgga ttacagcgcg   180
cccaagcaag gctgctgggt agatggcatt accgtctacg gtgacatctt tatcggcaag   240
cagaattggg gcacctacac tcgcccggtc tttgcctacc tgcagtacat ggacaccatt   300
tccattccgc agcaggtgac acagactcgc agctatcagt tgactaaggg acacaccaaa   360
acgttcacga ccaatgtcag cgccaaatac agcgttggag gtagtattga catcgtcaac   420
gtcggttcgg atatctcaat tggattcagt aacagtgaat cctggtctac tacgcagacg   480
ttcagcaata gcactcaatt gactggtcct ggcaccttca tcgtgtatca ggttgttatg   540
gtttatgcgc acaacgccac ttctgcgggc aggcagaatg gtaatgcctt cgcctacaac   600
aagaccaata ctgtcggctc gcggctggac ttgtactatt tgtctgccat cactcagaac   660
agtacggtca ttgtcgattc cagcaaggcc atcgcgccgc tggattggga tactgttcta   720
tgccatgttt ttattgggta cttttaccca ggcagcaata gtgggcactt cagtttcgac   780
tggagcgcct acaacgatcc tcatcgccgt tat                                  813
```

<210> SEQ ID NO 274  
<211> LENGTH: 813  
<212> TYPE: DNA  
<213> ORGANISM: Artificial Sequence  
<220> FEATURE:  
<223> OTHER INFORMATION: PIP-1A variant
<400> SEQUENCE: 274

```
atgacgatca aggaagagct gagccagcct caaagtcatt cgatcgaact tgacgacctg    60
aaaagtgagc aaggaagtct ccgcgccgct ttgacatcca actttgctgg caacttcgat   120
cagttcccaa ctaagcgtgg tggctttgcg atcgacagct acctgctgga ttacagcgcg   180
cccaagcaag gctgctgggt agatggcatt accgtctacg gtgacatctt tatcggcaag   240
cagaattggg gcacctacac tcgcccggtc tttgcctacc tgcagtacat ggacaccatt   300
tccattccgc agcaggtgac acagactcgc agctatcagt tgactaaggg acacaccaaa   360
acgttcacga ccaatgtcag cgccaaatac agcgttggag gtagtattga catcgtcaac   420
gtcggttcgg atatctcaat tggattcagt aacagtgaat cctggtctac tacgcagacg   480
ttcagcaata gcactcaatt gactggtcct ggcaccttca tcgtgtatca ggttgttatg   540
gtttatgcgc acaacgccac ttctgcgggc aggcagaatg gtaatgcctt cgcctacaac   600
aagaccaata ctgtcggctc gcggctggac ttgtactatt tgtctgccat cactcagaac   660
agtacggtca ttgtcgattc cagcaaggcc atcgcgccgc tggattggga tactgttgaa   720
ggcaactttt tgtgggtaa ttttgatcca ggcagcaata gtgggcactt cagtttcgac   780
tggagcgcct acaacgatcc tcatcgccgt tat                                  813
```

<210> SEQ ID NO 275  
<211> LENGTH: 813  
<212> TYPE: DNA  
<213> ORGANISM: Artificial Sequence  
<220> FEATURE:  
<223> OTHER INFORMATION: PIP-1A variant
<400> SEQUENCE: 275

```
atgacgatca aggaagagct gagccagcct caaagtcatt cgatcgaact tgacgacctg    60
```

```
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttatt    720
cgctacttta ttttggagga ttataatcca ggcagcaata gtgggcactt cagtttcgac    780
tggagcgcct acaacgatcc tcatcgccgt tat                                 813

<210> SEQ ID NO 276
<211> LENGTH: 813
<212> TYPE: DNA
<213> ORGANISM: Artificial Sequence
<220> FEATURE:
<223> OTHER INFORMATION: PIP-1A variant

<400> SEQUENCE: 276
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttctt    720
ggctatttta tggtggagga ttttgaccca ggcagcaata gtgggcactt cagtttcgac    780
tggagcgcct acaacgatcc tcatcgccgt tat                                 813

<210> SEQ ID NO 277
<211> LENGTH: 813
<212> TYPE: DNA
<213> ORGANISM: Artificial Sequence
<220> FEATURE:
<223> OTHER INFORMATION: PIP-1A variant

<400> SEQUENCE: 277
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
```

```
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttaaa    720
ggcaatgttt tggtggagta ttataatcca ggcagcaata gtgggcactt cagtttcgac    780
tggagcgcct acaacgatcc tcatcgccgt tat                                 813
```

<210> SEQ ID NO 278
<211> LENGTH: 813
<212> TYPE: DNA
<213> ORGANISM: Artificial Sequence
<220> FEATURE:
<223> OTHER INFORMATION: PIP-1A variant

<400> SEQUENCE: 278

```
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttcta    720
agcaatgtta ttatgggtca ctttatcca ggcagcaata gtgggcactt cagtttcgac     780
tggagcgcct acaacgatcc tcatcgccgt tat                                 813
```

<210> SEQ ID NO 279
<211> LENGTH: 813
<212> TYPE: DNA
<213> ORGANISM: Artificial Sequence
<220> FEATURE:
<223> OTHER INFORMATION: PIP-1A variant

<400> SEQUENCE: 279

```
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
```

| | |
|---|---|
| cagaattggg gcacctacac tcgcccggtc tttgcctacc tgcagtacat ggacaccatt | 300 |
| tccattccgc agcaggtgac acagactcgc agctatcagt tgactaaggg acacaccaaa | 360 |
| acgttcacga ccaatgtcag cgccaaatac agcgttggag gtagtattga catcgtcaac | 420 |
| gtcggttcgg atatctcaat tggattcagt aacagtgaat cctggtctac tacgcagacg | 480 |
| ttcagcaata gcactcaatt gactggtcct ggcaccttca tcgtgtatca ggttgttatg | 540 |
| gtttatgcgc acaacgccac ttctgcgggc aggcagaatg gtaatgcctt cgcctacaac | 600 |
| aagaccaata ctgtcggctc gcggctggac ttgtactatt tgtctgccat cactcagaac | 660 |
| agtacggtca ttgtcgattc cagcaaggcc atcgcgccgc tggattggga tactgttgtt | 720 |
| agctacgttt tttttgggca ttttgatcca ggcagcaata gtgggcactt cagtttcgac | 780 |
| tggagcgcct acaacgatcc tcatcgccgt tat | 813 |

```
<210> SEQ ID NO 280
<211> LENGTH: 813
<212> TYPE: DNA
<213> ORGANISM: Artificial Sequence
<220> FEATURE:
<223> OTHER INFORMATION: PIP-1A variant

<400> SEQUENCE: 280
```

| | |
|---|---|
| atgacgatca aggaagagct gagccagcct caaagtcatt cgatcgaact tgacgacctg | 60 |
| aaaagtgagc aaggaagtct ccgcgccgct ttgacatcca actttgctgg caacttcgat | 120 |
| cagttcccaa ctaagcgtgg tggctttgcg atcgacagct acctgctgga ttacagcgcg | 180 |
| cccaagcaag gctgctgggt agatggcatt accgtctacg gtgacatctt tatcggcaag | 240 |
| cagaattggg gcacctacac tcgcccggtc tttgcctacc tgcagtacat ggacaccatt | 300 |
| tccattccgc agcaggtgac acagactcgc agctatcagt tgactaaggg acacaccaaa | 360 |
| acgttcacga ccaatgtcag cgccaaatac agcgttggag gtagtattga catcgtcaac | 420 |
| gtcggttcgg atatctcaat tggattcagt aacagtgaat cctggtctac tacgcagacg | 480 |
| ttcagcaata gcactcaatt gactggtcct ggcaccttca tcgtgtatca ggttgttatg | 540 |
| gtttatgcgc acaacgccac ttctgcgggc aggcagaatg gtaatgcctt cgcctacaac | 600 |
| aagaccaata ctgtcggctc gcggctggac ttgtactatt tgtctgccat cactcagaac | 660 |
| agtacggtca ttgtcgattc cagcaaggcc atcgcgccgc tggattggga tactgttgtt | 720 |
| tgcaatttta ttatggataa ctattaccca ggcagcaata gtgggcactt cagtttcgac | 780 |
| tggagcgcct acaacgatcc tcatcgccgt tat | 813 |

```
<210> SEQ ID NO 281
<211> LENGTH: 813
<212> TYPE: DNA
<213> ORGANISM: Artificial Sequence
<220> FEATURE:
<223> OTHER INFORMATION: PIP-1A variant

<400> SEQUENCE: 281
```

| | |
|---|---|
| atgacgatca aggaagagct gagccagcct caaagtcatt cgatcgaact tgacgacctg | 60 |
| aaaagtgagc aaggaagtct ccgcgccgct ttgacatcca actttgctgg caacttcgat | 120 |
| cagttcccaa ctaagcgtgg tggctttgcg atcgacagct acctgctgga ttacagcgcg | 180 |
| cccaagcaag gctgctgggt agatggcatt accgtctacg gtgacatctt tatcggcaag | 240 |
| cagaattggg gcacctacac tcgcccggtc tttgcctacc tgcagtacat ggacaccatt | 300 |
| tccattccgc agcaggtgac acagactcgc agctatcagt tgactaaggg acacaccaaa | 360 |

```
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttaat    720
ggcaatattt ttttggatca ttttgatcca ggcagcaata gtgggcactt cagtttcgac    780
tggagcgcct acaacgatcc tcatcgccgt tat                                 813
```

<210> SEQ ID NO 282
<211> LENGTH: 813
<212> TYPE: DNA
<213> ORGANISM: Artificial Sequence
<220> FEATURE:
<223> OTHER INFORMATION: PIP-1A variant

<400> SEQUENCE: 282

```
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttatt    720
tgctacatta ttttgatga ttatcaccca ggcagcaata gtgggcactt cagtttcgac    780
tggagcgcct acaacgatcc tcatcgccgt tat                                 813
```

<210> SEQ ID NO 283
<211> LENGTH: 813
<212> TYPE: DNA
<213> ORGANISM: Artificial Sequence
<220> FEATURE:
<223> OTHER INFORMATION: PIP-1A variant

<400> SEQUENCE: 283

```
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
```

```
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttaat    720
agcaattttt tgtttgagaa ttttcaccca ggcagcaata gtgggcactt cagtttcgac    780
tggagcgcct acaacgatcc tcatcgccgt tat                                 813

<210> SEQ ID NO 284
<211> LENGTH: 813
<212> TYPE: DNA
<213> ORGANISM: Artificial Sequence
<220> FEATURE:
<223> OTHER INFORMATION: PIP-1A variant

<400> SEQUENCE: 284
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttctt    720
tgccatattt tgattggtga ttataaccca ggcagcaata gtgggcactt cagtttcgac    780
tggagcgcct acaacgatcc tcatcgccgt tat                                 813

<210> SEQ ID NO 285
<211> LENGTH: 813
<212> TYPE: DNA
<213> ORGANISM: Artificial Sequence
<220> FEATURE:
<223> OTHER INFORMATION: PIP-1A variant

<400> SEQUENCE: 285
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
```

```
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttcat    720
tgcaacgtta ttgtggatta ctataatcca ggcagcaata gtgggcactt cagtttcgac    780
tggagcgcct acaacgatcc tcatcgccgt tat                                  813
```

<210> SEQ ID NO 286
<211> LENGTH: 813
<212> TYPE: DNA
<213> ORGANISM: Artificial Sequence
<220> FEATURE:
<223> OTHER INFORMATION: PIP-1A variant

<400> SEQUENCE: 286

```
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttgaa    720
ggctatgtta tgtttgggta ttttaaccca ggcagcaata gtgggcactt cagtttcgac    780
tggagcgcct acaacgatcc tcatcgccgt tat                                  813
```

<210> SEQ ID NO 287
<211> LENGTH: 813
<212> TYPE: DNA
<213> ORGANISM: Artificial Sequence
<220> FEATURE:
<223> OTHER INFORMATION: PIP-1A variant

<400> SEQUENCE: 287

```
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
```

| | |
|---|---|
| aagaccaata ctgtcggctc gcggctggac ttgtactatt tgtctgccat cactcagaac | 660 |
| agtacggtca ttgtcgattc cagcaaggcc atcgcgccgc tggattggga tactgttgta | 720 |
| tgctatattt tggtggagta ttatcaccca ggcagcaata gtgggcactt cagtttcgac | 780 |
| tggagcgcct acaacgatcc tcatcgccgt tat | 813 |

<210> SEQ ID NO 288
<211> LENGTH: 813
<212> TYPE: DNA
<213> ORGANISM: Artificial Sequence
<220> FEATURE:
<223> OTHER INFORMATION: PIP-1A variant

<400> SEQUENCE: 288

| | |
|---|---|
| atgacgatca aggaagagct gagccagcct caaagtcatt cgatcgaact tgacgacctg | 60 |
| aaaagtgagc aaggaagtct ccgcgccgct ttgacatcca actttgctgg caacttcgat | 120 |
| cagttcccaa ctaagcgtgg tggctttgcg atcgacagct acctgctgga ttacagcgcg | 180 |
| cccaagcaag gctgctgggt agatggcatt accgtctacg gtgacatctt tatcggcaag | 240 |
| cagaattggg gcacctacac tcgcccggtc tttgcctacc tgcagtacat ggacaccatt | 300 |
| tccattccgc agcaggtgac acagactcgc agctatcagt tgactaaggg acacaccaaa | 360 |
| acgttcacga ccaatgtcag cgccaaatac agcgttggag gtagtattga catcgtcaac | 420 |
| gtcggttcgg atatctcaat tggattcagt aacagtgaat cctggtctac tacgcagacg | 480 |
| ttcagcaata gcactcaatt gactggtcct ggcaccttca tcgtgtatca ggttgttatg | 540 |
| gtttatgcgc acaacgccac ttctgcgggc aggcagaatg gtaatgcctt cgcctacaac | 600 |
| aagaccaata ctgtcggctc gcggctggac ttgtactatt tgtctgccat cactcagaac | 660 |
| agtacggtca ttgtcgattc cagcaaggcc atcgcgccgc tggattggga tactgttcta | 720 |
| cgccatgtta tgtttggtaa ttattatcca ggcagcaata gtgggcactt cagtttcgac | 780 |
| tggagcgcct acaacgatcc tcatcgccgt tat | 813 |

<210> SEQ ID NO 289
<211> LENGTH: 813
<212> TYPE: DNA
<213> ORGANISM: Artificial Sequence
<220> FEATURE:
<223> OTHER INFORMATION: PIP-1A variant

<400> SEQUENCE: 289

| | |
|---|---|
| atgacgatca aggaagagct gagccagcct caaagtcatt cgatcgaact tgacgacctg | 60 |
| aaaagtgagc aaggaagtct ccgcgccgct ttgacatcca actttgctgg caacttcgat | 120 |
| cagttcccaa ctaagcgtgg tggctttgcg atcgacagct acctgctgga ttacagcgcg | 180 |
| cccaagcaag gctgctgggt agatggcatt accgtctacg gtgacatctt tatcggcaag | 240 |
| cagaattggg gcacctacac tcgcccggtc tttgcctacc tgcagtacat ggacaccatt | 300 |
| tccattccgc agcaggtgac acagactcgc agctatcagt tgactaaggg acacaccaaa | 360 |
| acgttcacga ccaatgtcag cgccaaatac agcgttggag gtagtattga catcgtcaac | 420 |
| gtcggttcgg atatctcaat tggattcagt aacagtgaat cctggtctac tacgcagacg | 480 |
| ttcagcaata gcactcaatt gactggtcct ggcaccttca tcgtgtatca ggttgttatg | 540 |
| gtttatgcgc acaacgccac ttctgcgggc aggcagaatg gtaatgcctt cgcctacaac | 600 |
| aagaccaata ctgtcggctc gcggctggac ttgtactatt tgtctgccat cactcagaac | 660 |
| agtacggtca ttgtcgattc cagcaaggcc atcgcgccgc tggattggga tactgttaat | 720 |

```
cgcaatattt tttttgatga ttattaccca ggcagcaata gtgggcactt cagtttcgac    780
tggagcgcct acaacgatcc tcatcgccgt tat                                 813

<210> SEQ ID NO 290
<211> LENGTH: 813
<212> TYPE: DNA
<213> ORGANISM: Artificial Sequence
<220> FEATURE:
<223> OTHER INFORMATION: PIP-1A variant

<400> SEQUENCE: 290
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttaaa    720
ggctatgtta tggtgggggga ctttaatcca ggcagcaata gtgggcactt cagtttcgac    780
tggagcgcct acaacgatcc tcatcgccgt tat                                 813

<210> SEQ ID NO 291
<211> LENGTH: 813
<212> TYPE: DNA
<213> ORGANISM: Artificial Sequence
<220> FEATURE:
<223> OTHER INFORMATION: PIP-1A variant

<400> SEQUENCE: 291
atgacgatca aggaagagct gagccagcct caaagtcatt cgatcgaact tgacgacctg     60
aaaagtgagc aaggaagtct ccgcgccgct ttgacatcca actttgctgg caacttcgat    120
cagttcccaa ctaagcgtgg tggctttgcg atcgacagct acctgctgga ttacagcgcg    180
cccaagcaag gctgctgggt agatggcatt accgtctacg gtgacatctt tatcggcaag    240
cagaattggg gcacctacac tcgcccggtc tttgcctacc tgcagtacat ggacaccatt    300
tccattccgc agcaggtgac acagactcgc agctatcagt tgactaaggg acacaccaaa    360
acgttcacga ccaatgtcag cgccaaatac agcgttggag gtagtattga catcgtcaac    420
gtcggttcgg atatctcaat tggattcagt aacagtgaat cctggtctac tacgcagacg    480
ttcagcaata gcactcaatt gactggtcct ggcaccttca tcgtgtatca ggttgttatg    540
gtttatgcgc acaacgccac ttctgcgggc aggcagaatg gtaatgcctt cgcctacaac    600
aagaccaata ctgtcggctc gcggctggac ttgtactatt tgtctgccat cactcagaac    660
agtacggtca ttgtcgattc cagcaaggcc atcgcgccgc tggattggga tactgttcta    720
ggcaattttt ttttggggta ttataaccca ggcagcaata gtgggcactt cagtttcgac    780
```

```
tggagcgcct acaacgatcc tcatcgccgt tat                             813
```

<210> SEQ ID NO 292
<211> LENGTH: 813
<212> TYPE: DNA
<213> ORGANISM: Artificial Sequence
<220> FEATURE:
<223> OTHER INFORMATION: PIP-1A variant

<400> SEQUENCE: 292

```
atgacgatca aggaagagct gagccagcct caaagtcatt cgatcgaact tgacgacctg    60
aaaagtgagc aaggaagtct ccgcgccgct tgacatcca actttgctgg caacttcgat    120
cagttcccaa ctaagcgtgg tggctttgcg atcgacagct acctgctgga ttacagcgcg   180
cccaagcaag gctgctgggt agatggcatt accgtctacg gtgacatctt tatcggcaag   240
cagaattggg gcacctacac tcgcccggtc tttgcctacc tgcagtacat ggacaccatt   300
tccattccgc agcaggtgac acagactcgc agctatcagt tgactaaggg acacaccaaa   360
acgttcacga ccaatgtcag cgccaaatac agcgttggag gtagtattga catcgtcaac   420
gtcggttcgg atatctcaat tggattcagt aacagtgaat cctggtctac tacgcagacg   480
ttcagcaata gcactcaatt gactggtcct ggcaccttca tcgtgtatca ggttgttatg   540
gtttatgcgc acaacgccac ttctgcgggc aggcagaatg gtaatgcctt cgcctacaac   600
aagaccaata ctgtcggctc gcggctggac ttgtactatt tgtctgccat cactcagaac   660
agtacggtca ttgtcgattc cagcaaggcc atcgcgccgc tggattggga tactgttctt   720
agcaatgttt tgattgataa tttttaccca ggcagcaata gtgggcactt cagtttcgac   780
tggagcgcct acaacgatcc tcatcgccgt tat                             813
```

<210> SEQ ID NO 293
<211> LENGTH: 813
<212> TYPE: DNA
<213> ORGANISM: Artificial Sequence
<220> FEATURE:
<223> OTHER INFORMATION: PIP-1A variant

<400> SEQUENCE: 293

```
atgacgatca aggaagagct gagccagcct caaagtcatt cgatcgaact tgacgacctg    60
aaaagtgagc aaggaagtct ccgcgccgct tgacatcca actttgctgg caacttcgat    120
cagttcccaa ctaagcgtgg tggctttgcg atcgacagct acctgctgga ttacagcgcg   180
cccaagcaag gctgctgggt agatggcatt accgtctacg gtgacatctt tatcggcaag   240
cagaattggg gcacctacac tcgcccggtc tttgcctacc tgcagtacat ggacaccatt   300
tccattccgc agcaggtgac acagactcgc agctatcagt tgactaaggg acacaccaaa   360
acgttcacga ccaatgtcag cgccaaatac agcgttggag gtagtattga catcgtcaac   420
gtcggttcgg atatctcaat tggattcagt aacagtgaat cctggtctac tacgcagacg   480
ttcagcaata gcactcaatt gactggtcct ggcaccttca tcgtgtatca ggttgttatg   540
gtttatgcgc acaacgccac ttctgcgggc aggcagaatg gtaatgcctt cgcctacaac   600
aagaccaata ctgtcggctc gcggctggac ttgtactatt tgtctgccat cactcagaac   660
agtacggtca ttgtcgattc cagcaaggcc atcgcgccgc tggattggga tactgttaat   720
tgctacttta ttgtggatga ttataatcca ggcagcaata gtgggcactt cagtttcgac   780
tggagcgcct acaacgatcc tcatcgccgt tat                             813
```

<210> SEQ ID NO 294
<211> LENGTH: 813
<212> TYPE: DNA
<213> ORGANISM: Artificial Sequence
<220> FEATURE:
<223> OTHER INFORMATION: PIP-1A variant

<400> SEQUENCE: 294

```
atgacgatca aggaagagct gagccagcct caaagtcatt cgatcgaact tgacgacctg        60
aaaagtgagc aaggaagtct ccgcgccgct ttgacatcca actttgctgg caacttcgat       120
cagttcccaa ctaagcgtgg tggctttgcg atcgacagct acctgctgga ttacagcgcg       180
cccaagcaag gctgctgggt agatggcatt accgtctacg gtgacatctt tatcggcaag       240
cagaattggg gcacctacac tcgcccggtc tttgcctacc tgcagtacat ggacaccatt       300
tccattccgc agcaggtgac acagactcgc agctatcagt tgactaaggg acacaccaaa       360
acgttcacga ccaatgtcag cgccaaatac agcgttggag gtagtattga catcgtcaac       420
gtcggttcgg atatctcaat tggattcagt aacagtgaat cctggtctac tacgcagacg       480
ttcagcaata gcactcaatt gactggtcct ggcaccttca tcgtgtatca ggttgttatg       540
gtttatgcgc acaacgccac ttctgcgggc aggcagaatg gtaatgcctt cgcctacaac       600
aagaccaata ctgtcggctc gcggctggac ttgtactatt tgtctgccat cactcagaac       660
agtacggtca ttgtcgattc cagcaaggcc atcgcgccgc tggattggga tactgttatt       720
agctatgttt ttgtggagga ttttcaccca ggcagcaata gtgggcactt cagtttcgac       780
tggagcgcct acaacgatcc tcatcgccgt tat                                    813
```

<210> SEQ ID NO 295
<211> LENGTH: 813
<212> TYPE: DNA
<213> ORGANISM: Artificial Sequence
<220> FEATURE:
<223> OTHER INFORMATION: PIP-1A variant

<400> SEQUENCE: 295

```
atgacgatca aggaagagct gagccagcct caaagtcatt cgatcgaact tgacgacctg        60
aaaagtgagc aaggaagtct ccgcgccgct ttgacatcca actttgctgg caacttcgat       120
cagttcccaa ctaagcgtgg tggctttgcg atcgacagct acctgctgga ttacagcgcg       180
cccaagcaag gctgctgggt agatggcatt accgtctacg gtgacatctt tatcggcaag       240
cagaattggg gcacctacac tcgcccggtc tttgcctacc tgcagtacat ggacaccatt       300
tccattccgc agcaggtgac acagactcgc agctatcagt tgactaaggg acacaccaaa       360
acgttcacga ccaatgtcag cgccaaatac agcgttggag gtagtattga catcgtcaac       420
gtcggttcgg atatctcaat tggattcagt aacagtgaat cctggtctac tacgcagacg       480
ttcagcaata gcactcaatt gactggtcct ggcaccttca tcgtgtatca ggttgttatg       540
gtttatgcgc acaacgccac ttctgcgggc aggcagaatg gtaatgcctt cgcctacaac       600
aagaccaata ctgtcggctc gcggctggac ttgtactatt tgtctgccat cactcagaac       660
agtacggtca ttgtcgattc cagcaaggcc atcgcgccgc tggattggga tactgttaat       720
atccatatta tgattgagta ctatcatcca ggcagcaata gtgggcactt cagtttcgac       780
tggagcgcct acaacgatcc tcatcgccgt tat                                    813
```

<210> SEQ ID NO 296
<211> LENGTH: 813
<212> TYPE: DNA

<213> ORGANISM: Artificial Sequence
<220> FEATURE:
<223> OTHER INFORMATION: PIP-1A variant

<400> SEQUENCE: 296

```
atgacgatca aggaagagct gagccagcct caaagtcatt cgatcgaact tgacgacctg      60
aaaagtgagc aaggaagtct ccgcgccgct ttgacatcca actttgctgg caacttcgat     120
cagttcccaa ctaagcgtgg tggctttgcg atcgacagct acctgctgga ttacagcgcg     180
cccaagcaag gctgctgggt agatggcatt accgtctacg gtgacatctt tatcggcaag     240
cagaattggg gcacctacac tcgcccggtc tttgcctacc tgcagtacat ggacaccatt     300
tccattccgc agcaggtgac acagactcgc agctatcagt tgactaaggg acacaccaaa     360
acgttcacga ccaatgtcag cgccaaatac agcgttggag gtagtattga catcgtcaac     420
gtcggttcgg atatctcaat tggattcagt aacagtgaat cctggtctac tacgcagacg     480
ttcagcaata gcactcaatt gactggtcct ggcaccttca tcgtgtatca ggttgttatg     540
gtttatgcgc acaacgccac ttctgcgggc aggcagaatg taatgccttc gcctacaac     600
aagaccaata ctgtcggctc gcggctggac ttgtactatt tgtctgccat cactcagaac     660
agtacggtca ttgtcgattc cagcaaggcc atcgcgccgc tggattggga tactgttatt     720
ggccatttta tgttggatta ttatcatcca ggcagcaata gtgggcactt cagtttcgac     780
tggagcgcct acaacgatcc tcatcgccgt tat                                  813
```

<210> SEQ ID NO 297
<211> LENGTH: 813
<212> TYPE: DNA
<213> ORGANISM: Artificial Sequence
<220> FEATURE:
<223> OTHER INFORMATION: PIP-1A variant

<400> SEQUENCE: 297

```
atgacgatca aggaagagct gagccagcct caaagtcatt cgatcgaact tgacgacctg      60
aaaagtgagc aaggaagtct ccgcgccgct ttgacatcca actttgctgg caacttcgat     120
cagttcccaa ctaagcgtgg tggctttgcg atcgacagct acctgctgga ttacagcgcg     180
cccaagcaag gctgctgggt agatggcatt accgtctacg gtgacatctt tatcggcaag     240
cagaattggg gcacctacac tcgcccggtc tttgcctacc tgcagtacat ggacaccatt     300
tccattccgc agcaggtgac acagactcgc agctatcagt tgactaaggg acacaccaaa     360
acgttcacga ccaatgtcag cgccaaatac agcgttggag gtagtattga catcgtcaac     420
gtcggttcgg atatctcaat tggattcagt aacagtgaat cctggtctac tacgcagacg     480
ttcagcaata gcactcaatt gactggtcct ggcaccttca tcgtgtatca ggttgttatg     540
gtttatgcgc acaacgccac ttctgcgggc aggcagaatg taatgccttc gcctacaac     600
aagaccaata ctgtcggctc gcggctggac ttgtactatt tgtctgccat cactcagaac     660
agtacggtca ttgtcgattc cagcaaggcc atcgcgccgc tggattggga tactgttata     720
tgctatgtta tggtgggtaa ttatcaccca ggcagcaata gtgggcactt cagtttcgac     780
tggagcgcct acaacgatcc tcatcgccgt tat                                  813
```

<210> SEQ ID NO 298
<211> LENGTH: 271
<212> TYPE: PRT
<213> ORGANISM: Artificial Sequence
<220> FEATURE:
<223> OTHER INFORMATION: PIP-1A variant

<400> SEQUENCE: 298

| | | | | | | | | | | | | | | |
|---|---|---|---|---|---|---|---|---|---|---|---|---|---|---|
|Met|Thr|Ile|Lys|Glu|Glu|Leu|Ser|Gln|Pro|Gln|Ser|His|Ser|Ile|Glu
1| | | |5| | | | |10| | | | |15|

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
    195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val His
225                 230                 235                 240

Ser Tyr Val Phe Ile Asp Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 299
<211> LENGTH: 271
<212> TYPE: PRT
<213> ORGANISM: Artificial Sequence
<220> FEATURE:
<223> OTHER INFORMATION: PIP-1A variant

<400> SEQUENCE: 299

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Val
225                 230                 235                 240

Cys Asn Phe Phe Phe Gly Asp Phe Asp Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 300
<211> LENGTH: 271
<212> TYPE: PRT
<213> ORGANISM: Artificial Sequence
<220> FEATURE:
<223> OTHER INFORMATION: PIP-1A variant

<400> SEQUENCE: 300

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

-continued

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Lys
225                 230                 235                 240

Arg Tyr Phe Met Met Gly Tyr Phe His Pro Gly Ser Asn Ser Gly His
                245                 250                 255

Phe Ser Phe Asp Trp Ser Ala Tyr Asn Asp Pro His Arg Arg Tyr
        260                 265                 270

<210> SEQ ID NO 301
<211> LENGTH: 271
<212> TYPE: PRT
<213> ORGANISM: Artificial Sequence
<220> FEATURE:
<223> OTHER INFORMATION: PIP-1A variant

<400> SEQUENCE: 301

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Leu
225                 230                 235                 240

Cys His Val Phe Ile Gly Tyr Phe Tyr Pro Gly Ser Asn Ser Gly His
                245                 250                 255

Phe Ser Phe Asp Trp Ser Ala Tyr Asn Asp Pro His Arg Arg Tyr
        260                 265                 270

<210> SEQ ID NO 302
<211> LENGTH: 271
<212> TYPE: PRT
<213> ORGANISM: Artificial Sequence
<220> FEATURE:
<223> OTHER INFORMATION: PIP-1A variant

<400> SEQUENCE: 302

```
Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Glu
225                 230                 235                 240

Gly Asn Phe Phe Val Gly Asn Phe Asp Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 303
<211> LENGTH: 271
<212> TYPE: PRT
<213> ORGANISM: Artificial Sequence
<220> FEATURE:
<223> OTHER INFORMATION: PIP-1A variant

<400> SEQUENCE: 303

```
Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45
```

```
Phe Ala Ile Asp Ser Tyr Leu Leu Asp Tyr Ser Ala Pro Lys Gln Gly
         50                  55                  60

Cys Trp Val Asp Gly Ile Thr Val Tyr Gly Asp Ile Phe Ile Gly Lys
 65                  70                  75                  80

Gln Asn Trp Gly Thr Tyr Thr Arg Pro Val Phe Ala Tyr Leu Gln Tyr
                 85                  90                  95

Met Asp Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
                180                 185                 190

Asn Gly Asn Ala Phe Ala Tyr Asn Lys Thr Asn Thr Val Gly Ser Arg
            195                 200                 205

Leu Asp Leu Tyr Tyr Leu Ser Ala Ile Thr Gln Asn Ser Thr Val Ile
        210                 215                 220

Val Asp Ser Ser Lys Ala Ile Ala Pro Leu Asp Trp Asp Thr Val Ile
225                 230                 235                 240

Arg Tyr Phe Ile Leu Glu Asp Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 304
<211> LENGTH: 271
<212> TYPE: PRT
<213> ORGANISM: Artificial Sequence
<220> FEATURE:
<223> OTHER INFORMATION: PIP-1A variant

<400> SEQUENCE: 304

Met Thr Ile Lys Glu Glu Leu Ser Gln Pro Gln Ser His Ser Ile Glu
 1               5                  10                  15

Leu Asp Asp Leu Lys Ser Glu Gln Gly Ser Leu Arg Ala Ala Leu Thr
                 20                  25                  30

Ser Asn Phe Ala Gly Asn Phe Asp Gln Phe Pro Thr Lys Arg Gly Gly
             35                  40                  45

Phe Ala Ile Asp Ser Tyr Leu Leu Asp Tyr Ser Ala Pro Lys Gln Gly
         50                  55                  60

Cys Trp Val Asp Gly Ile Thr Val Tyr Gly Asp Ile Phe Ile Gly Lys
 65                  70                  75                  80

Gln Asn Trp Gly Thr Tyr Thr Arg Pro Val Phe Ala Tyr Leu Gln Tyr
                 85                  90                  95

Met Asp Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
130                 135                 140
```

```
Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Leu
225                 230                 235                 240

Gly Tyr Phe Met Val Glu Asp Phe Asp Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 305
<211> LENGTH: 271
<212> TYPE: PRT
<213> ORGANISM: Artificial Sequence
<220> FEATURE:
<223> OTHER INFORMATION: PIP-1A variant

<400> SEQUENCE: 305

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Lys
225                 230                 235                 240
```

```
Gly Asn Val Leu Val Glu Tyr Tyr Asn Pro Gly Ser Asn Ser Gly His
            245                 250                 255

Phe Ser Phe Asp Trp Ser Ala Tyr Asn Asp Pro His Arg Arg Tyr
            260                 265                 270

<210> SEQ ID NO 306
<211> LENGTH: 271
<212> TYPE: PRT
<213> ORGANISM: Artificial Sequence
<220> FEATURE:
<223> OTHER INFORMATION: PIP-1A variant

<400> SEQUENCE: 306

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Leu
225                 230                 235                 240

Ser Asn Val Ile Met Gly His Phe Tyr Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 307
<211> LENGTH: 271
<212> TYPE: PRT
<213> ORGANISM: Artificial Sequence
<220> FEATURE:
<223> OTHER INFORMATION: PIP-1A variant

<400> SEQUENCE: 307

Met Thr Ile Lys Glu Glu Leu Ser Gln Pro Gln Ser His Ser Ile Glu
```

```
  1               5                  10                 15
Leu Asp Asp Leu Lys Ser Glu Gln Gly Ser Leu Arg Ala Ala Leu Thr
             20                  25                 30

Ser Asn Phe Ala Gly Asn Phe Asp Gln Phe Pro Thr Lys Arg Gly Gly
             35                  40                 45

Phe Ala Ile Asp Ser Tyr Leu Leu Asp Tyr Ser Ala Pro Lys Gln Gly
             50                  55                 60

Cys Trp Val Asp Gly Ile Thr Val Tyr Gly Asp Ile Phe Ile Gly Lys
65                       70                 75                 80

Gln Asn Trp Gly Thr Tyr Thr Arg Pro Val Phe Ala Tyr Leu Gln Tyr
                 85                  90                 95

Met Asp Thr Ile Ser Ile Pro Gln Gln Val Thr Gln Thr Arg Ser Tyr
                100                 105                110

Gln Leu Thr Lys Gly His Thr Lys Thr Phe Thr Thr Asn Val Ser Ala
                115                 120                125

Lys Tyr Ser Val Gly Gly Ser Ile Asp Ile Val Asn Val Gly Ser Asp
            130                 135                140

Ile Ser Ile Gly Phe Ser Asn Ser Glu Ser Trp Ser Thr Thr Gln Thr
145                 150                 155                160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
                180                 185                 190

Asn Gly Asn Ala Phe Ala Tyr Asn Lys Thr Asn Thr Val Gly Ser Arg
            195                 200                 205

Leu Asp Leu Tyr Tyr Leu Ser Ala Ile Thr Gln Asn Ser Thr Val Ile
            210                 215                 220

Val Asp Ser Ser Lys Ala Ile Ala Pro Leu Asp Trp Asp Thr Val Val
225                 230                 235                240

Ser Tyr Val Phe Phe Gly His Phe Asp Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 308
<211> LENGTH: 271
<212> TYPE: PRT
<213> ORGANISM: Artificial Sequence
<220> FEATURE:
<223> OTHER INFORMATION: PIP-1A variant

<400> SEQUENCE: 308

Met Thr Ile Lys Glu Glu Leu Ser Gln Pro Gln Ser His Ser Ile Glu
1               5                  10                 15

Leu Asp Asp Leu Lys Ser Glu Gln Gly Ser Leu Arg Ala Ala Leu Thr
             20                  25                 30

Ser Asn Phe Ala Gly Asn Phe Asp Gln Phe Pro Thr Lys Arg Gly Gly
             35                  40                 45

Phe Ala Ile Asp Ser Tyr Leu Leu Asp Tyr Ser Ala Pro Lys Gln Gly
             50                  55                 60

Cys Trp Val Asp Gly Ile Thr Val Tyr Gly Asp Ile Phe Ile Gly Lys
65                       70                 75                 80

Gln Asn Trp Gly Thr Tyr Thr Arg Pro Val Phe Ala Tyr Leu Gln Tyr
                 85                  90                 95

Met Asp Thr Ile Ser Ile Pro Gln Gln Val Thr Gln Thr Arg Ser Tyr
```

```
                100             105             110
Gln Leu Thr Lys Gly His Thr Lys Thr Phe Thr Thr Asn Val Ser Ala
            115                 120                 125
Lys Tyr Ser Val Gly Gly Ser Ile Asp Ile Val Asn Val Gly Ser Asp
        130                 135                 140
Ile Ser Ile Gly Phe Ser Asn Ser Glu Ser Trp Ser Thr Thr Gln Thr
145                 150                 155                 160
Phe Ser Asn Ser Thr Gln Leu Thr Gly Pro Gly Thr Phe Ile Val Tyr
                165                 170                 175
Gln Val Val Met Val Tyr Ala His Asn Ala Thr Ser Ala Gly Arg Gln
            180                 185                 190
Asn Gly Asn Ala Phe Ala Tyr Asn Lys Thr Asn Thr Val Gly Ser Arg
        195                 200                 205
Leu Asp Leu Tyr Tyr Leu Ser Ala Ile Thr Gln Asn Ser Thr Val Ile
    210                 215                 220
Val Asp Ser Ser Lys Ala Ile Ala Pro Leu Asp Trp Asp Thr Val Val
225                 230                 235                 240
Cys Asn Phe Ile Met Asp Asn Tyr Tyr Pro Gly Ser Asn Ser Gly His
                245                 250                 255
Phe Ser Phe Asp Trp Ser Ala Tyr Asn Asp Pro His Arg Arg Tyr
                260                 265                 270

<210> SEQ ID NO 309
<211> LENGTH: 271
<212> TYPE: PRT
<213> ORGANISM: Artificial Sequence
<220> FEATURE:
<223> OTHER INFORMATION: PIP-1A variant

<400> SEQUENCE: 309

Met Thr Ile Lys Glu Glu Leu Ser Gln Pro Gln Ser His Ser Ile Glu
1               5                   10                  15
Leu Asp Asp Leu Lys Ser Glu Gln Gly Ser Leu Arg Ala Ala Leu Thr
            20                  25                  30
Ser Asn Phe Ala Gly Asn Phe Asp Gln Phe Pro Thr Lys Arg Gly Gly
        35                  40                  45
Phe Ala Ile Asp Ser Tyr Leu Leu Asp Tyr Ser Ala Pro Lys Gln Gly
    50                  55                  60
Cys Trp Val Asp Gly Ile Thr Val Tyr Gly Asp Ile Phe Ile Gly Lys
65                  70                  75                  80
Gln Asn Trp Gly Thr Tyr Thr Arg Pro Val Phe Ala Tyr Leu Gln Tyr
                85                  90                  95
Met Asp Thr Ile Ser Ile Pro Gln Gln Val Thr Gln Thr Arg Ser Tyr
                100                 105                 110
Gln Leu Thr Lys Gly His Thr Lys Thr Phe Thr Thr Asn Val Ser Ala
            115                 120                 125
Lys Tyr Ser Val Gly Gly Ser Ile Asp Ile Val Asn Val Gly Ser Asp
        130                 135                 140
Ile Ser Ile Gly Phe Ser Asn Ser Glu Ser Trp Ser Thr Thr Gln Thr
145                 150                 155                 160
Phe Ser Asn Ser Thr Gln Leu Thr Gly Pro Gly Thr Phe Ile Val Tyr
                165                 170                 175
Gln Val Val Met Val Tyr Ala His Asn Ala Thr Ser Ala Gly Arg Gln
            180                 185                 190
Asn Gly Asn Ala Phe Ala Tyr Asn Lys Thr Asn Thr Val Gly Ser Arg
```

```
            195                 200                 205
Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Asn
225                 230                 235                 240

Gly Asn Ile Phe Leu Asp His Phe Asp Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 310
<211> LENGTH: 271
<212> TYPE: PRT
<213> ORGANISM: Artificial Sequence
<220> FEATURE:
<223> OTHER INFORMATION: PIP-1A variant

<400> SEQUENCE: 310

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Ile
225                 230                 235                 240

Cys Tyr Ile Ile Phe Asp Asp Tyr His Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 311
<211> LENGTH: 271
<212> TYPE: PRT
```

<213> ORGANISM: Artificial Sequence
<220> FEATURE:
<223> OTHER INFORMATION: PIP-1A variant

<400> SEQUENCE: 311

```
Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Asn
225                 230                 235                 240

Ser Asn Phe Leu Phe Glu Asn Phe His Pro Gly Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 312
<211> LENGTH: 271
<212> TYPE: PRT
<213> ORGANISM: Artificial Sequence
<220> FEATURE:
<223> OTHER INFORMATION: PIP-1A variant

<400> SEQUENCE: 312

```
Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60
```

```
Cys Trp Val Asp Gly Ile Thr Val Tyr Gly Asp Ile Phe Ile Gly Lys
 65                  70                  75                  80

Gln Asn Trp Gly Thr Tyr Thr Arg Pro Val Phe Ala Tyr Leu Gln Tyr
                 85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
        130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Leu
225                 230                 235                 240

Cys His Ile Leu Ile Gly Asp Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 313
<211> LENGTH: 271
<212> TYPE: PRT
<213> ORGANISM: Artificial Sequence
<220> FEATURE:
<223> OTHER INFORMATION: PIP-1A variant

<400> SEQUENCE: 313

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
 65                  70                  75                  80

Gln Asn Trp Gly Thr Tyr Thr Arg Pro Val Phe Ala Tyr Leu Gln Tyr
                 85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
        130                 135                 140

Ile Ser Ile Gly Phe Ser Asn Ser Glu Ser Trp Ser Thr Thr Gln Thr
145                 150                 155                 160
```

```
Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val His
225                 230                 235                 240

Cys Asn Val Ile Val Asp Tyr Tyr Asn Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 314
<211> LENGTH: 271
<212> TYPE: PRT
<213> ORGANISM: Artificial Sequence
<220> FEATURE:
<223> OTHER INFORMATION: PIP-1A variant

<400> SEQUENCE: 314

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Glu
225                 230                 235                 240

Gly Tyr Val Met Phe Gly Tyr Phe Asn Pro Gly Ser Asn Ser Gly His
                245                 250                 255
```

```
Phe Ser Phe Asp Trp Ser Ala Tyr Asn Asp Pro His Arg Arg Tyr
            260                 265                 270

<210> SEQ ID NO 315
<211> LENGTH: 271
<212> TYPE: PRT
<213> ORGANISM: Artificial Sequence
<220> FEATURE:
<223> OTHER INFORMATION: PIP-1A variant

<400> SEQUENCE: 315

Met Thr Ile Lys Glu Glu Leu Ser Gln Pro Gln Ser His Ser Ile Glu
 1               5                  10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
        50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Val
225                 230                 235                 240

Cys Tyr Ile Leu Val Glu Tyr Tyr His Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 316
<211> LENGTH: 271
<212> TYPE: PRT
<213> ORGANISM: Synthetic Sequence

<400> SEQUENCE: 316

Met Thr Ile Lys Glu Glu Leu Ser Gln Pro Gln Ser His Ser Ile Glu
 1               5                  10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
```

```
                35                  40                  45
Phe Ala Ile Asp Ser Tyr Leu Leu Asp Tyr Ser Ala Pro Lys Gln Gly
 50                  55                  60
Cys Trp Val Asp Gly Ile Thr Val Tyr Gly Asp Ile Phe Ile Gly Lys
65                  70                  75                  80
Gln Asn Trp Gly Thr Tyr Thr Arg Pro Val Phe Ala Tyr Leu Gln Tyr
                85                  90                  95
Met Asp Thr Ile Ser Ile Pro Gln Gln Val Thr Gln Thr Arg Ser Tyr
                100                 105                 110
Gln Leu Thr Lys Gly His Thr Lys Thr Phe Thr Thr Asn Val Ser Ala
                115                 120                 125
Lys Tyr Ser Val Gly Gly Ser Ile Asp Ile Val Asn Val Gly Ser Asp
    130                 135                 140
Ile Ser Ile Gly Phe Ser Asn Ser Glu Ser Trp Ser Thr Thr Gln Thr
145                 150                 155                 160
Phe Ser Asn Ser Thr Gln Leu Thr Gly Pro Gly Thr Phe Ile Val Tyr
                165                 170                 175
Gln Val Val Met Val Tyr Ala His Asn Ala Thr Ser Ala Gly Arg Gln
                180                 185                 190
Asn Gly Asn Ala Phe Ala Tyr Asn Lys Thr Asn Thr Val Gly Ser Arg
            195                 200                 205
Leu Asp Leu Tyr Tyr Leu Ser Ala Ile Thr Gln Asn Ser Thr Val Ile
    210                 215                 220
Val Asp Ser Ser Lys Ala Ile Ala Pro Leu Asp Trp Asp Thr Val Leu
225                 230                 235                 240
Arg His Val Met Phe Gly Asn Tyr Tyr Pro Gly Ser Asn Ser Gly His
                245                 250                 255
Phe Ser Phe Asp Trp Ser Ala Tyr Asn Asp Pro His Arg Arg Tyr
                260                 265                 270
```

<210> SEQ ID NO 317
<211> LENGTH: 271
<212> TYPE: PRT
<213> ORGANISM: Artificial Sequence
<220> FEATURE:
<223> OTHER INFORMATION: PIP-1A variant

<400> SEQUENCE: 317

```
Met Thr Ile Lys Glu Glu Leu Ser Gln Pro Gln Ser His Ser Ile Glu
1               5                   10                  15
Leu Asp Asp Leu Lys Ser Glu Gln Gly Ser Leu Arg Ala Ala Leu Thr
                20                  25                  30
Ser Asn Phe Ala Gly Asn Phe Asp Gln Phe Pro Thr Lys Arg Gly Gly
            35                  40                  45
Phe Ala Ile Asp Ser Tyr Leu Leu Asp Tyr Ser Ala Pro Lys Gln Gly
 50                  55                  60
Cys Trp Val Asp Gly Ile Thr Val Tyr Gly Asp Ile Phe Ile Gly Lys
65                  70                  75                  80
Gln Asn Trp Gly Thr Tyr Thr Arg Pro Val Phe Ala Tyr Leu Gln Tyr
                85                  90                  95
Met Asp Thr Ile Ser Ile Pro Gln Gln Val Thr Gln Thr Arg Ser Tyr
                100                 105                 110
Gln Leu Thr Lys Gly His Thr Lys Thr Phe Thr Thr Asn Val Ser Ala
                115                 120                 125
Lys Tyr Ser Val Gly Gly Ser Ile Asp Ile Val Asn Val Gly Ser Asp
```

```
            130                 135                 140
Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
                180                 185                 190

Asn Gly Asn Ala Phe Ala Tyr Asn Lys Thr Asn Thr Val Gly Ser Arg
                195                 200                 205

Leu Asp Leu Tyr Tyr Leu Ser Ala Ile Thr Gln Asn Ser Thr Val Ile
                210                 215                 220

Val Asp Ser Ser Lys Ala Ile Ala Pro Leu Asp Trp Asp Thr Val Asn
225                 230                 235                 240

Arg Asn Ile Phe Phe Asp Asp Tyr Tyr Pro Gly Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 318
<211> LENGTH: 271
<212> TYPE: PRT
<213> ORGANISM: Artificial Sequence
<220> FEATURE:
<223> OTHER INFORMATION: PIP-1A variant

<400> SEQUENCE: 318

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
        50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
        130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
                180                 185                 190

Asn Gly Asn Ala Phe Ala Tyr Asn Lys Thr Asn Thr Val Gly Ser Arg
                195                 200                 205

Leu Asp Leu Tyr Tyr Leu Ser Ala Ile Thr Gln Asn Ser Thr Val Ile
                210                 215                 220

Val Asp Ser Ser Lys Ala Ile Ala Pro Leu Asp Trp Asp Thr Val Lys
```

```
                 225                 230                 235                 240

Gly Tyr Val Met Val Gly Asp Phe Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 319
<211> LENGTH: 271
<212> TYPE: PRT
<213> ORGANISM: Artificial Sequence
<220> FEATURE:
<223> OTHER INFORMATION: PIP-1A variant

<400> SEQUENCE: 319

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
        50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
130                 135                 140

Ile Ser Ile Gly Phe Ser Asn Ser Glu Ser Trp Ser Thr Thr Gln Thr
                145                 150                 155                 160

Phe Ser Asn Ser Thr Gln Leu Thr Gly Pro Gly Thr Phe Ile Val Tyr
            165                 170                 175

Gln Val Val Met Val Tyr Ala His Asn Ala Thr Ser Ala Gly Arg Gln
        180                 185                 190

Asn Gly Asn Ala Phe Ala Tyr Asn Lys Thr Asn Thr Val Gly Ser Arg
    195                 200                 205

Leu Asp Leu Tyr Tyr Leu Ser Ala Ile Thr Gln Asn Ser Thr Val Ile
210                 215                 220

Val Asp Ser Ser Lys Ala Ile Ala Pro Leu Asp Trp Asp Thr Val Leu
225                 230                 235                 240

Gly Asn Phe Phe Leu Gly Tyr Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 320
<211> LENGTH: 271
<212> TYPE: PRT
<213> ORGANISM: Artificial Sequence
<220> FEATURE:
<223> OTHER INFORMATION: PIP-1A variant

<400> SEQUENCE: 320
```

```
Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
                35                  40                  45

Phe Ala Ile Asp Ser Tyr Leu Leu Asp Tyr Ser Ala Pro Lys Gln Gly
                50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Val Thr Gln Thr Arg Ser Tyr
                100                 105                 110

Gln Leu Thr Lys Gly His Thr Lys Thr Phe Thr Thr Asn Val Ser Ala
                115                 120                 125

Lys Tyr Ser Val Gly Gly Ser Ile Asp Ile Val Asn Val Gly Ser Asp
                130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
                180                 185                 190

Asn Gly Asn Ala Phe Ala Tyr Asn Lys Thr Asn Thr Val Gly Ser Arg
                195                 200                 205

Leu Asp Leu Tyr Tyr Leu Ser Ala Ile Thr Gln Asn Ser Thr Val Ile
                210                 215                 220

Val Asp Ser Ser Lys Ala Ile Ala Pro Leu Asp Trp Asp Thr Val Leu
225                 230                 235                 240

Ser Asn Val Leu Ile Asp Asn Phe Tyr Pro Gly Ser Asn Ser Gly His
                245                 250                 255

Phe Ser Phe Asp Trp Ser Ala Tyr Asn Asp Pro His Arg Arg Tyr
                260                 265                 270
```

<210> SEQ ID NO 321
<211> LENGTH: 271
<212> TYPE: PRT
<213> ORGANISM: Artificial Sequence
<220> FEATURE:
<223> OTHER INFORMATION: PIP-1A variant

<400> SEQUENCE: 321

```
Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
                35                  40                  45

Phe Ala Ile Asp Ser Tyr Leu Leu Asp Tyr Ser Ala Pro Lys Gln Gly
                50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95
```

-continued

```
Met Asp Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
            115                 120                 125

Lys Tyr Ser Val Gly Gly Ser Ile Asp Ile Val Asn Val Gly Ser Asp
        130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Asn
225                 230                 235                 240

Cys Tyr Phe Ile Val Asp Asp Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 322
<211> LENGTH: 271
<212> TYPE: PRT
<213> ORGANISM: Artificial Sequence
<220> FEATURE:
<223> OTHER INFORMATION: PIP-1A variant

<400> SEQUENCE: 322

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190
```

```
Asn Gly Asn Ala Phe Ala Tyr Asn Lys Thr Asn Thr Val Gly Ser Arg
            195                 200                 205

Leu Asp Leu Tyr Tyr Leu Ser Ala Ile Thr Gln Asn Ser Thr Val Ile
            210                 215                 220

Val Asp Ser Ser Lys Ala Ile Ala Pro Leu Asp Trp Asp Thr Val Ile
225                 230                 235                 240

Ser Tyr Val Phe Val Glu Asp Phe His Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 323
<211> LENGTH: 271
<212> TYPE: PRT
<213> ORGANISM: Artificial Sequence
<220> FEATURE:
<223> OTHER INFORMATION: PIP-1A variant

<400> SEQUENCE: 323

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
            195                 200                 205

Leu Asp Leu Tyr Tyr Leu Ser Ala Ile Thr Gln Asn Ser Thr Val Ile
            210                 215                 220

Val Asp Ser Ser Lys Ala Ile Ala Pro Leu Asp Trp Asp Thr Val Asn
225                 230                 235                 240

Ile His Ile Met Ile Glu Tyr Tyr His Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 324
<211> LENGTH: 271
```

```
<212> TYPE: PRT
<213> ORGANISM: Artificial Sequence
<220> FEATURE:
<223> OTHER INFORMATION: PIP-1A variant

<400> SEQUENCE: 324

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Ile
225                 230                 235                 240

Gly His Phe Met Leu Asp Tyr Tyr His Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 325
<211> LENGTH: 271
<212> TYPE: PRT
<213> ORGANISM: Artificial Sequence
<220> FEATURE:
<223> OTHER INFORMATION: PIP-1A variant

<400> SEQUENCE: 325

Met Thr Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60
```

-continued

```
Cys Trp Val Asp Gly Ile Thr Val Tyr Gly Asp Ile Phe Ile Gly Lys
 65                  70                  75                  80

Gln Asn Trp Gly Thr Tyr Thr Arg Pro Val Phe Ala Tyr Leu Gln Tyr
                 85                  90                  95

Met Asp Thr Ile Ser Ile Pro Gln Gln Val Gln Thr Arg Ser Tyr
            100                 105                 110

Gln Leu Thr Lys Gly His Thr Lys Thr Phe Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220

Val Asp Ser Ser Lys Ala Ile Ala Pro Leu Asp Trp Asp Thr Val Ile
225                 230                 235                 240

Cys Tyr Val Met Val Gly Asn Tyr His Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 326
<211> LENGTH: 75
<212> TYPE: DNA
<213> ORGANISM: Artificial Sequence
<220> FEATURE:
<223> OTHER INFORMATION: Mutagenesis Primer
<220> FEATURE:
<221> NAME/KEY: misc_feature
<222> LOCATION: (22)..(22)
<223> OTHER INFORMATION: v is a, g, or c
<220> FEATURE:
<221> NAME/KEY: misc_feature
<222> LOCATION: (23)..(23)
<223> OTHER INFORMATION: w is a or t
<220> FEATURE:
<221> NAME/KEY: misc_feature
<222> LOCATION: (24)..(24)
<223> OTHER INFORMATION: w is a or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: h is a, c, or t
<220> FEATURE:
<221> NAME/KEY: misc_feature
<222> LOCATION: (30)..(30)
<223> OTHER INFORMATION: y is c or t
<220> FEATURE:
<221> NAME/KEY: misc_feature
<222> LOCATION: (31)..(31)
<223> OTHER INFORMATION: d is a, g, or t
<220> FEATURE:
<221> NAME/KEY: misc_feature
<222> LOCATION: (34)..(34)
<223> OTHER INFORMATION: w is a or t
```

```
<220> FEATURE:
<221> NAME/KEY: misc_feature
<222> LOCATION: (36)..(36)
<223> OTHER INFORMATION: k is g or t
<220> FEATURE:
<221> NAME/KEY: misc_feature
<222> LOCATION: (37)..(37)
<223> OTHER INFORMATION: d is a, g, or t
<220> FEATURE:
<221> NAME/KEY: misc_feature
<222> LOCATION: (39)..(39)
<223> OTHER INFORMATION: k is g or t
<220> FEATURE:
<221> NAME/KEY: misc_feature
<222> LOCATION: (41)..(41)
<223> OTHER INFORMATION: r is a or g
<220> FEATURE:
<221> NAME/KEY: misc_feature
<222> LOCATION: (42)..(42)
<223> OTHER INFORMATION: k is g or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (45)..(45)
<223> OTHER INFORMATION: y is c or t
<220> FEATURE:
<221> NAME/KEY: misc_feature
<222> LOCATION: (47)..(47)
<223> OTHER INFORMATION: w is a or t
<220> FEATURE:
<221> NAME/KEY: misc_feature
<222> LOCATION: (47)..(47)
<223> OTHER INFORMATION: w is a or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (51)..(51)
<223> OTHER INFORMATION: y is c or t

<400> SEQUENCE: 326
ccgctggatt gggatactgt tvwwngchay dttwtkdtkg rknaytwtna yccaggcagc    60
aatagtgggc acttc                                                    75

<210> SEQ ID NO 327
<211> LENGTH: 23
<212> TYPE: DNA
<213> ORGANISM: Artificial Sequence
<220> FEATURE:
<223> OTHER INFORMATION: Mutagenesis Primer

<400> SEQUENCE: 327
ggatgtgctg caaggcgatt aag                                           23

<210> SEQ ID NO 328
<211> LENGTH: 21
<212> TYPE: DNA
<213> ORGANISM: Artificial Sequence
<220> FEATURE:
<223> OTHER INFORMATION: Mutagenesis Primer

<400> SEQUENCE: 328
aacagtatcc caatccagcg g                                             21

<210> SEQ ID NO 329
<211> LENGTH: 25
<212> TYPE: DNA
```

<213> ORGANISM: Artificial Sequence
<220> FEATURE:
<223> OTHER INFORMATION: Mutagenesis Primer

<400> SEQUENCE: 329
cagactgtcg atgaagccct gaaag         25

<210> SEQ ID NO 330
<211> LENGTH: 175
<212> TYPE: PRT
<213> ORGANISM: Artificial Sequence
<220> FEATURE:
<223> OTHER INFORMATION: PIP-1A variant

<400> SEQUENCE: 330

```
Met Asp Thr Ile Ser Ile Pro Gln Gln Val Thr Gln Thr Arg Ser Tyr
1               5                   10                  15

Gln Leu Thr Lys Gly His Thr Lys Thr Phe Thr Thr Asn Val Ser Ala
            20                  25                  30

Lys Tyr Ser Val Gly Gly Ser Ile Asp Ile Val Asn Val Gly Ser Asp
        35                  40                  45

Ile Ser Ile Gly Phe Ser Asn Ser Glu Ser Trp Ser Thr Thr Gln Thr
    50                  55                  60

Phe Ser Asn Ser Thr Gln Leu Thr Gly Pro Gly Thr Phe Ile Val Tyr
65                  70                  75                  80

Gln Val Val Met Val Tyr Ala His Asn Ala Thr Ser Ala Gly Arg Gln
                85                  90                  95

Asn Gly Asn Ala Phe Ala Tyr Asn Lys Thr Asn Thr Val Gly Ser Arg
            100                 105                 110

Leu Asp Leu Tyr Tyr Leu Ser Ala Ile Thr Gln Asn Ser Thr Val Ile
        115                 120                 125

Val Asp Ser Ser Lys Ala Ile Ala Pro Leu Asp Trp Asp Thr Val Gln
    130                 135                 140

Arg Asn Val Leu Met Glu Asn Tyr Asn Pro Gly Ser Asn Ser Gly His
145                 150                 155                 160

Phe Ser Phe Asp Trp Ser Ala Tyr Asn Asp Pro His Arg Arg Tyr
                165                 170                 175
```

<210> SEQ ID NO 331
<211> LENGTH: 816
<212> TYPE: DNA
<213> ORGANISM: Pseudomonas Protegens

<400> SEQUENCE: 331
atgactatca aggaagagct gggtcagccc caaagccatt cgatcgaact tgactgtttg         60
aacagggagg cgggaagtgc tcgcgccgct ttgacatcca accttgtcgg aagcttcgat        120
cagtacccga ccaagcatgg tgactttgcg attgacagct acctgctgga cttcagtgca        180
cccaaaaaag gttgctgggt ggacggtatc accgtttacg gtgatatcta tattggcaag        240
cagaactggg gtacctacac gcgtccggtc tttgcctacc tgcaatatat ggacaccatt        300
tccatcccgc agcaggtgat ccagacccgc agctatcagc tgacaaaggg tcacacccaa        360
acattcgaga ccagtgtcag cgccaaatac agcgttgggg ccaagatcga tatcgtcaac        420
atcgactcgg agatctccac tggattcagc agcagtgagt cctggtctac tacgcagaca        480
ttcagcgaaa gcacccaatt gagcggccct ggcaccttca tggtctatca gatcgtgctt        540
gtctatgcac acaatgccac ctcggcgggc aagcagaatg gcaatgcctt tgcctacagc        600

```
aagacccaga cggtggactc gcgagtggac ctgtactacc tgtcggccat cacccagaac    660
aagacggtca ttgtccagtc cggcaatgcc atcgagccac tggactggga tacggtgcaa    720
cgcaatgtgt tgatggacaa ctacaaccca gaaagcaata acgggcactt ccgtttcgac    780
tggagcgcct acgacaatcc tcatcgccgc tactga                              816
```

<210> SEQ ID NO 332
<211> LENGTH: 271
<212> TYPE: PRT
<213> ORGANISM: Pseudomonas Protegens

<400> SEQUENCE: 332

```
Met Thr Ile Lys Glu Glu Leu Gly Gln Pro Gln Ser His Ser Ile Glu
1               5                   10                  15

Leu Asp Cys Leu Asn Arg Glu Ala Gly Ser Ala Arg Ala Ala Leu Thr
            20                  25                  30

Ser Asn Leu Val Gly Ser Phe Asp Gln Tyr Pro Thr Lys His Gly Asp
        35                  40                  45

Phe Ala Ile Asp Ser Tyr Leu Leu Asp Phe Ser Ala Pro Lys Lys Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Ile Gln Thr Arg Ser Tyr
            100                 105                 110

Gln Leu Thr Lys Gly His Thr Gln Thr Phe Glu Thr Ser Val Ser Ala
        115                 120                 125

Lys Tyr Ser Val Gly Ala Lys Ile Asp Ile Val Asn Ile Asp Ser Glu
    130                 135                 140

Ile Ser Thr Gly Phe Ser Ser Ser Glu Ser Trp Ser Thr Thr Gln Thr
145                 150                 155                 160

Phe Ser Glu Ser Thr Gln Leu Ser Gly Pro Gly Thr Phe Met Val Tyr
                165                 170                 175

Gln Ile Val Leu Val Tyr Ala His Asn Ala Thr Ser Ala Gly Lys Gln
            180                 185                 190

Asn Gly Asn Ala Phe Ala Tyr Ser Lys Thr Gln Thr Val Asp Ser Arg
        195                 200                 205

Val Asp Leu Tyr Tyr Leu Ser Ala Ile Thr Gln Asn Lys Thr Val Ile
    210                 215                 220

Val Gln Ser Gly Asn Ala Ile Glu Pro Leu Asp Trp Asp Thr Val Gln
225                 230                 235                 240

Arg Asn Val Leu Met Asp Asn Tyr Asn Pro Glu Ser Asn Asn Gly His
                245                 250                 255

Phe Arg Phe Asp Trp Ser Ala Tyr Asp Asn Pro His Arg Arg Tyr
            260                 265                 270
```